US009932290B2

(12) United States Patent
Petrie et al.

(10) Patent No.: US 9,932,290 B2
(45) **Date of Patent: *Apr. 3, 2018**

(54) PROCESS FOR PRODUCING ETHYL ESTERS OF POLYUNSATURATED FATTY ACIDS

(71) Applicants: Commonwealth Scientific and Industrial Research Organisation, Acton (AU); Grains Research and Development Corporation, Barton (AU); Nuseed Pty. Ltd., Laverton North (AU)

(72) Inventors: James Robertson Petrie, Goulburn (AU); Surinder Pal Singh, Downer (AU); Robert Charles de Feyter, Monash (AU)

(73) Assignees: COMMONWEALTH SCIENTIFIC AND INDUSTRIAL RESEARCH ORGANISATION, Acton (AU); GRAINS RESEARCH AND DEVELOPMENT CORPORATION, Barton (AU); NUSEED PTY LTD, Laverton North (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/678,005

(22) Filed: Aug. 15, 2017

(65) Prior Publication Data

US 2017/0349526 A1 Dec. 7, 2017

Related U.S. Application Data

(63) Continuation of application No. 15/400,532, filed on Jan. 6, 2017, which is a continuation of application (Continued)

(51) Int. Cl.
*C07C 67/02* (2006.01)
*C11B 1/10* (2006.01)
(Continued)

(52) U.S. Cl.
CPC .............. *C07C 67/02* (2013.01); *A23L 33/12* (2016.08); *C11B 1/00* (2013.01); *C11B 1/10* (2013.01);
(Continued)

(58) Field of Classification Search
CPC ..... C11B 1/00; C11B 1/04; C11B 1/10; C11C 3/04; C07C 67/02; C07C 67/03
See application file for complete search history.

(56) References Cited

U.S. PATENT DOCUMENTS 5,004,863 A 4/1991 Umbeck
5,159,135 A 10/1992 Umbeck
(Continued)

FOREIGN PATENT DOCUMENTS

AU 2005901673 4/2005
EP 256223 2/1988
(Continued)

OTHER PUBLICATIONS

U.S. Appl. No. 15/400,532, filed Jan. 6, 2017, Petrie.
(Continued)

*Primary Examiner* — Yate' K Cutliff
(74) *Attorney, Agent, or Firm* — John P. White; Gary J. Gershik; Cooper & Dunham LLP

(57) ABSTRACT

The present invention relates to a process for producing ethyl esters of polyunsaturated fatty acids, comprising trans-esterifying triacylglycerols in extracted plant lipid.

28 Claims, 21 Drawing Sheets

Related U.S. Application Data

Figure 1:
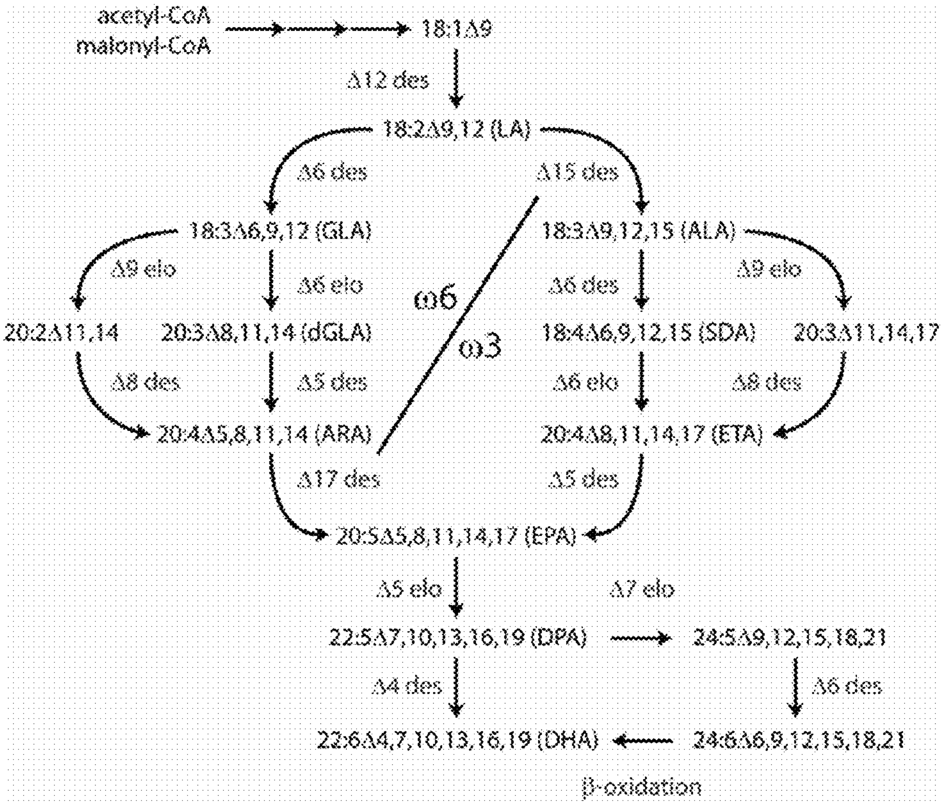

No. 14/600,653, filed on Jan. 20, 2015, now Pat. No. 9,556,102, which is a continuation of application No. 13/918,392, filed on Jun. 14, 2013, now Pat. No. 8,946,460.

(60) Provisional application No. 61/782,680, filed on Mar. 14, 2013, provisional application No. 61/697,676, filed on Sep. 6, 2012, provisional application No. 61/663,344, filed on Jun. 22, 2012, provisional application No. 61/660,392, filed on Jun. 15, 2012.

(51) Int. Cl.

| | |
|---|---|
| ***C11B 1/00*** | (2006.01) |
| ***C11C 3/00*** | (2006.01) |
| ***C11C 3/06*** | (2006.01) |
| ***A23L 33/12*** | (2016.01) |

(52) U.S. Cl.

CPC ................ *C11C 3/00* (2013.01); *C11C 3/003* (2013.01); *C11C 3/06* (2013.01)

(56) References Cited

U.S. PATENT DOCUMENTS

| | | | | |
|---|---|---|---|---|
| 5,177,010 | A | 1/1993 | Goldman | |
| 5,362,865 | A | 11/1994 | Austin | |
| 5,451,513 | A | 9/1995 | Maliga | |
| 5,504,200 | A | 4/1996 | Hall | |
| 5,545,818 | A | 8/1996 | McBride | |
| 5,608,152 | A | 3/1997 | Kridl | |
| 5,859,347 | A | 1/1999 | Brown | |
| 5,869,617 | A | 2/1999 | Fischer | |
| 5,877,402 | A | 3/1999 | Maliga | |
| 5,912,416 | A | 6/1999 | Weisker | |
| 5,932,479 | A | 8/1999 | Daniell | |
| 5,952,544 | A | 9/1999 | Browse | |
| 6,566,583 | B1 | 5/2003 | Facciotti | |
| 6,620,986 | B1 | 9/2003 | McKeon | |
| 7,211,656 | B2 | 5/2007 | Mukerji | |
| 7,550,286 | B2 | 6/2009 | Damude | |
| 7,572,464 | B2 * | 8/2009 | Chandler | C11B 1/10 424/522 |
| 7,589,253 | B2 | 9/2009 | Green | |
| 7,619,105 | B2 | 11/2009 | Green | |
| 7,659,247 | B2 | 2/2010 | Kretschmar | |
| 7,807,849 | B2 | 10/2010 | Singh | |
| 7,834,248 | B2 | 11/2010 | Green | |
| 7,834,250 | B2 | 11/2010 | Singh | |
| 7,879,591 | B2 | 2/2011 | Damude | |
| 7,932,438 | B2 | 4/2011 | Singh | |
| 8,013,216 | B2 | 9/2011 | Napier | |
| 8,071,341 | B2 | 12/2011 | Singh | |
| 8,106,226 | B2 | 1/2012 | Singh | |
| 8,119,861 | B2 | 2/2012 | Napier | |
| 8,134,046 | B2 | 3/2012 | Cirpus | |
| 8,158,392 | B1 | 4/2012 | Singh | |
| 8,192,964 | B2 | 6/2012 | Knauf | |
| 8,288,572 | B2 | 10/2012 | Singh | |
| 8,318,914 | B2 | 11/2012 | Bauer | |
| 8,455,035 | B2 | 6/2013 | Rein | |
| 8,535,917 | B2 | 9/2013 | Singh | |
| 8,575,377 | B2 | 11/2013 | Singh | |
| 8,609,875 | B2 | 12/2013 | Bezelgues | |
| 8,716,555 | B2 | 5/2014 | Liu | |
| 8,778,644 | B2 | 7/2014 | Singh | |
| 8,785,163 | B2 | 7/2014 | Senger | |
| 8,785,727 | B2 | 7/2014 | Bauer | |
| 8,809,559 | B2 | 8/2014 | Petrie | |
| 8,816,106 | B2 | 8/2014 | Damcevski | |
| 8,816,111 | B2 * | 8/2014 | Petrie | C11B 1/00 554/224 |
| 8,822,662 | B2 | 9/2014 | Senger | |
| 8,853,383 | B2 | 10/2014 | Bauer | |
| 8,853,432 | B2 | 10/2014 | Singh | |
| 8,901,374 | B2 | 12/2014 | Bauer | |
| 8,921,652 | B2 | 12/2014 | Liu | |
| 8,946,460 | B2 | 2/2015 | Petrie | |
| 9,090,902 | B2 | 7/2015 | Bauer | |
| 9,212,371 | B2 | 12/2015 | Senger | |
| 9,347,049 | B2 | 5/2016 | Bauer et al. | |
| 9,388,436 | B2 | 7/2016 | Bauer et al. | |
| 9,428,757 | B2 | 8/2016 | Senger | |
| 9,453,183 | B2 | 9/2016 | Singh | |
| 9,458,410 | B2 | 10/2016 | Singh | |
| 9,458,477 | B2 | 10/2016 | Senger et al. | |
| 9,493,520 | B2 | 11/2016 | Bauer | |
| 9,550,718 | B2 * | 1/2017 | Petrie | C11B 1/00 |
| 9,556,102 | B2 | 1/2017 | Petrie | |
| 9,718,759 | B2 | 8/2017 | Petrie | |
| 9,725,399 | B2 | 8/2017 | Petrie | |
| 2003/0159173 | A1 | 8/2003 | Wolter | |
| 2004/0132654 | A1 | 7/2004 | Kumpe | |
| 2004/0195512 | A1 | 10/2004 | Crosetto | |
| 2004/0221335 | A1 | 11/2004 | Shewmaker | |
| 2005/0239171 | A1 | 10/2005 | Mitterer | |
| 2005/0262588 | A1 | 11/2005 | Dehesh | |
| 2005/0273885 | A1 | 12/2005 | Singh | |
| 2006/0246556 | A1 | 11/2006 | Napier | |
| 2007/0192902 | A1 | 8/2007 | Qiu | |
| 2007/0224661 | A1 | 9/2007 | Cirpus | |
| 2008/0076164 | A1 | 3/2008 | Cirpus | |
| 2010/0088776 | A1 | 4/2010 | Bauer | |
| 2011/0039010 | A1 * | 2/2011 | Rein | A23D 9/00 426/607 |
| 2011/0201683 | A1 * | 8/2011 | Bezelgues | C11B 1/06 514/560 |
| 2011/0218348 | A1 | 9/2011 | Zhou | |
| 2011/0314725 | A1 | 12/2011 | Petrie | |
| 2013/0309772 | A1 | 11/2013 | Sakaguchi | |
| 2015/0018571 | A1 | 1/2015 | Petrie | |
| 2015/0203826 | A1 | 7/2015 | Marty et al. | |
| 2015/0216828 | A1 | 8/2015 | Napier | |
| 2015/0275243 | A1 | 10/2015 | Napier | |
| 2015/0353863 | A1 | 12/2015 | Petrie | |
| 2016/0177220 | A1 | 6/2016 | Petrie | |
| 2017/0058304 | A1 | 3/2017 | Singh | |
| 2017/0073712 | A1 | 3/2017 | Singh | |
| 2017/0211013 | A1 | 7/2017 | Petrie | |
| 2017/0305834 | A1 | 10/2017 | Petrie | |
| 2017/0320806 | A1 | 11/2017 | Petrie | |
| 2017/0321234 | A1 | 11/2017 | Singh | |
| 2017/0327767 | A1 | 11/2017 | Petrie | |
| 2017/0327852 | A1 | 11/2017 | Singh | |

FOREIGN PATENT DOCUMENTS

| | | |
|---|---|---|
| EP | 275957 | 7/1988 |
| GB | 1206483.8 | 4/2012 |
| GB | 1222184.2 | 4/2012 |
| WO | WO 1987/005327 | 9/1987 |
| WO | WO 1991/002071 | 2/1991 |
| WO | WO 1991/013980 | 9/1991 |
| WO | WO 1995/015389 | 6/1995 |
| WO | WO 1995/023230 | 8/1995 |
| WO | WO 1997/006269 | 2/1997 |
| WO | WO 1998/045461 | 10/1998 |
| WO | WO 1999/005265 | 2/1999 |
| WO | WO 1999/016890 | 4/1999 |
| WO | WO 1999/49050 A2 | 9/1999 |
| WO | WO 2001/14538 A2 | 3/2001 |
| WO | WO 2001/03852 | 5/2001 |
| WO | WO 2002/90493 A2 | 11/2002 |
| WO | WO 2003/099216 | 12/2003 |
| WO | WO 2004/057001 | 7/2004 |
| WO | WO 2004/71467 A2 | 8/2004 |
| WO | WO 2004/101757 | 11/2004 |
| WO | WO 2005/012316 | 2/2005 |
| WO | WO 2005/83093 A2 | 9/2005 |
| WO | WO 2005/103253 * | 11/2005 |
| WO | WO 2006/019192 | 2/2006 |
| WO | WO 2006/127789 | 11/2006 |
| WO | WO 2007/042510 | 4/2007 |

(56) References Cited

FOREIGN PATENT DOCUMENTS

| | | | |
|---|---|---|---|
| WO | WO 2007/133425 | | 11/2007 |
| WO | WO 2008/009600 | A1 | 1/2008 |
| WO | WO 2008/022963 | | 2/2008 |
| WO | WO 2009/016202 | | 2/2009 |
| WO | WO 2009/017821 | | 2/2009 |
| WO | WO 2009/130291 | | 10/2009 |
| WO | WO 2010/023202 | | 3/2010 |
| WO | WO 2010/057246 | | 5/2010 |
| WO | WO 2010/147900 | | 12/2010 |
| WO | WO 2011/146524 | | 11/2011 |
| WO | WO 2013/016546 | * | 1/2013 |
| WO | WO 2013/153404 | | 10/2013 |
| WO | WO 2013/185184 | | 12/2013 |
| WO | WO 2015/089587 | | 7/2015 |

OTHER PUBLICATIONS

U.S. Appl. No. 15/642,207, filed Jul. 5, 2017, Singh.
U.S. Appl. No. 15/642,223, filed Jul. 5, 2017, Petrie.
U.S. Appl. No. 15/644,635, filed Jul. 7, 2017, Petrie.
U.S. Appl. No. 15/661,697, filed Jul. 27, 2017, Petrie.
U.S. Appl. No. 15/661,768, filed Jul. 27, 2017, Singh.
U.S. Appl. No. 15/678,002, filed Aug. 15, 2017, Petrie.
U.S. Appl. No. 15/678,008, filed Aug. 15, 2017, Petrie.
U.S. Appl. No. 15/678,009, filed Aug. 15, 2017, Petrie.
U.S. Appl. No. 60/564,627, filed Apr. 22, 2004, Singh.
U.S. Appl. No. 60/613,861, filed Sep. 27, 2004, Singh.
U.S. Appl. No. 60/668,705, filed Aug. 30, 2005, Singh.
Abbadi, A., et al., (2001) "Transgenic Oilseeds as Sustainable Source of Nutritionally Relevant C20 and C22 Polyunsaturated Fatty Acids?" European Journal of Lipid Science and Technology, 103(2): 106-113.
Abbadi, A., et al., (2004) "Biosynthesis of Very-Long-Chain Polyunsaturated Fatty Acids in Transgenic Oilseeds: Constraints on Their Accumulation," The Plant Cell, 16(10): 2734-2748.
Abdullah, R., Cocking, E. C., & Thompson, J. A. (Dec. 1986). Efficient plant regeneration from rice protoplasts through somatic embryogenesis. *Biotechnology,* 4, 1087-1090.
Agaba, M., et al., (2004) "Zebrafish cDNA Encoding Multifunctional Fatty Acid Elongase Involved in Production of Eicosapentaenoic (20:5n-3) and Docosahexaenoic (22:6n-3) Acids," Marine Biotechnology, 6(3): 251-261.
Alvarez et al. (2000) "Silencing of HMW glutenins in transgenic wheat expressing extra HMW subunits" Theor Appl Genet 100:319-327.
Ando, Y., & Kobayashi, S. (2004). Positional distribution of docosahexaenoic acid in triacyl-sn-glycerols of rotifers Brachionus plicatilis enriched with fish oil fatty acid ethyl esters. Aquaculture research, 35(14), 1391-1394.
Ando, Y., Kotake, M., & Ota, T. (1997). Lipids and fatty acids in Artemia nauplii enriched with fish oil triacylglycerols containing docosahexaenoic acid in different positional distribution patterns. Fisheries science, 63(4), 605-609.
Armbrust et al. (2004) the genome of the diatom Thalassiosira pseudonana: ecology, evolution, and metabolism, Science 306:79-86.
Baumberger et al. (2007) "The Polerovirus Silencing Suppressor P0 Targets ARGONAUTE Proteins for Degradation" Curr. Biol. 17:1609-1614.
Bäumlein, H., et al., (1991) "A Novel Seed Protein Gene From Vicia faba is Developmentally Regulated in Transgenic Tobacco and *Arabidopsis* Plants," Molecular and General Genetics, 225(3): 459-467.
Bäumlein, H., et al., (1992) "Cis-Analysis of a Seed Protein Gene Promoter: The Conservative RY Repeat CATGCATC Within the Legumin Box Is Essential for Tissue-Specific Expression of a Legumin Gene," The Plant Journal, 2(2): 233-239.
Beaudoin, et al., (2000) "Production of C20 polyunsaturated fatty acids (PUFAs) by pathway engineering: identification of a PUFA elongase component from Caenorhabditis elegans", Biochemical Society Transactions, vol. 28, Part 6, p. 661-663.
Beaudoin, F., et al., (2000) "Heterologous Reconstitution in Yeast of the Polyunsaturated Fatty Acid Biosynthetic Pathway," Proceedings of the National Academy of Sciences of the United States of America, 97(12): 6421-6426.
Beclin et al. (2002) "A Branched Pathway for Transgene-Induced RNA Silencing in Plants" Curr. Biol. 12:684-688.
Berberich, T., et al., (1998) "Two Maize Genes Encoding Omega-3 Fatty Acid Desaturase and Their Differential Expression to Temperature," Plant Molecular Biology, 36(2): 297-306.
Bortolamiol et al. (2007) The Polerovirus F box protein P0 targets ARGONAUTE1 to suppress RNA silencing. Curr. Biol. 17(18):1615-162.
Broun, P., et al., (1998) "A Bifunctional oleate 12-Hydroxylase: Desaturase From *Lesquerella fendleri,*" The Plant Journal, 13(2): 201-210.
Brown et al. (2002) Limnanthes douglasii lysophosphatidic acid acyltransferases: immunological quantification, acyl selectivity and functional replacement of the *Escherichia coli* pisC gene, Biochem J. 364:795-805.
Cahoon, E. B., Marillia, E., Stecca, K. L., Hall, S. E., Taylor, D. C., & Kinney, A. J. (2000). Production of fatty acid components of meadowfoam oil in somatic soybean embryos. *Plant Physiology,* 124, 243-251.
Chapman et al. (2004) Transgenic Cotton Plants with Increased Seed Oleic Acid Content. Gen. Dev. 18:1179-1186.
Chen et al. (2010) "MISSA Is a Highly Efficient in Vivo DNA Assembly Method for Plant Multiple-Gene Transformation" Plant Physiology, vol. 153, pp. 41-51.
Cheng et al. (2010) Towards the production of high levels of eicosapentaenoic acid in transgenic plants: the effects of different host species, genes and promoters, Transgenic Res 19: 221-229.
Cheng, M., Jarret, R. L., Li, Z., Xing, A., & Demski, J. W. (1996). Production of fertile transgenic peanut (*Arachis hypogaea* L.) plants using *Agrobacterium tumefaciens. Plant Cell Reports,* 15, 653-657.
Chikwamba et al. (2003) "Localization of a bacterial protein in starch granules of transgenic maize kernels" Proc. Natl. Acad. Sci. U.S.A. 100:11127-11132.
Cho, H.P., et al., (1999) "Cloning, Expression, and Fatty Acid Regulation of the Human Δ-5 Desaturase," The Journal of Biological Chemistry, 274(52): 37335-37339.
Cho, H.P., et al., (1999) "Cloning, Expression, and Nutritional Regulation of the Mammalian Δ-6 Desaturase," The Journal of Biological Chemistry, 274(1): 471-477.
Clough, S.J. and Bent, A.F., (1998) "Floral Dip: A Simplified Method for Agrobacterium-Mediated Transformation of *Arabidopsis thaliana,*" 16(6); 735-743.
Coutu et al. (2007) "pORE: a modular binary vector series suited for both monocot and dicot plant transformation" Transgenic Res. 16: 771-781.
Damude et al. (2006). "Identification of bifunctional delta12/omega3 fatty acid desaturases for improving the ratio of omega3 to omega6 fatty acids in microbes and plants.", Proc Natl Acad Sci USA 103: 9446-9451.
Das et al. (2000) "Polyunsaturated fatty acid-specific elongation enzymes", Biochemical Society Transactions 28(6):658-660.
Denic and Weissman (2007) A molecular caliper mechanism for determining very long-chain fatty acid length, Cell 130:663-677.
Domergue et al., (2003), Acyl Carriers Used as Substrates by the Desaturases and Elongases Involved in Very Long-chian Polyunsaturated Fatty Acids Biosynthesis Reconstituted in Yeast, J. Biol. Chem. 278; 35115-35126.
Domergue, et al. (2005) "In vivo characterization of the first acyl-CoA Δ6 desaturase from a member of the plant kingdom, the microalga *Ostreococcus tauri*" Biochem. J., vol. 389, p. 483-490.
Domergue, F., et al., (2002) "Cloning and Functional Characterization of Phaeodactylum Tricornutum Front-End Desaturases Involved in Eicosapentaenoic Acid Biosynthesis," European Journal of Biochemistry, 269(16):4105-4113.
Dunoyer et al, (2004) "Probing the MicroRNA and Small Interfering RNA Pathways with Virus-Encoded Suppressors of RNA Silencing" The Plant Cell 16:1235-1250.

(56) References Cited

OTHER PUBLICATIONS

Edgar B. Cahoon, Elizabeth-France Marillia, Kevin L. Stecca, Sarah E. Hall, David C. Taylor, and Anthony J. Kinney "Production of Fatty Acid Components of Meadowfoam Oil in Somatic Soybean Embryos" Plant Physiol. Sep. 2000 124(1): 243-251.

Ellerstrom et al. (1996) "Functional dissection of a napin gene promoter: identification of promoter elements required for embryo and endosperm specific transcription", Plant Mol. Biol. 32:1019-1027.

Fujimura et al. (1985) "Regeneration of Rice Plants from Protoplasts" Plant Tissue Culture Lett. 2:74.

Fukunaga (2009) "dsRNA with 5' overhangs contributes to endogenous and antiviral RNA silencing pathways in plants", EMBO J. 28(5):545-55.

Gámez-Meza et al. (2003) "Concentration of eicosapentaenoic acid and docosahexaenoic acid from fish oil by hydrolysis and urea complexation", Food Research International 36:721-27.

Garcia-Maroto, F., et al., (2002) "Cloning and Molecular Characterization of the Δ6-Desaturase From Two Echium Plant Species: Production of GLA by Heterologous Expression in Yeast and Tobacco," Lipids, 37(4): 417-426.

Girke, T., et al., (1998) "Identification of a Novel Δ6-Acyl-Group Desaturase by Targeted Gene Disruption in Physcomitrella patens," The Plant Journal, 15(1): 39-48.

Glick et al. (2008) "Interaction with host SGS3 is required for suppression of RNA silencing by tomato yellow leaf curl virus V2 protein" Proc. Natl. Acad. Sci U.S.A. 105:157-161.

Graham, et al. (2004) "The use of very long chain polyunsaturated fatty acids to ameliorate metabolic syndrome: transgenic plants as an alternative sustainable source to fish oils" Nutrition Bulletin, vol. 29, p. 228-233.

Grant, J. E., Cooper, P. A., McAra, A. E., & Frew, T. J. (1995). Transformation of peas (*Pisum sativum* L.) using immature cotyledons. *Plant Cell Reports,* 15, 254-258.

Gul et al. (2006) Sterols and the phytosterol content of oil seed rape (*Brassica napus* L.). Journal of Cell and Molecular Biology, vol. 5, pp. 71-79.

Gunston, F., Rapseed (Canola) Oil, 2013, American Oil Chemists' Society, Lipid Library, abstract, 2 pages (Year: 2013).

Hall et al. (1991) "Nuclear scaffolds and scaffold-attachment regions in higher plants", Proc. Natl. Acad. Sci. USA 88:9320-24.

Hamilton and Baulcombe (1999) "A Species of Small Antisense RNA in Posttranscriptional Gene Silencing in Plants" Science 286:950-952.

Harayama, S. (1998). Artificial evolution by DNA shuffling. *Trends in Biotechnology,* 16(2), 76-82.

Hastings et al. (2001) "A vertebrate fatty acid desaturase with delta 5 and delta 6 activities", Proc. Natl. Acad. Sci. U.S.A. 98(25):14304-14309.

Heinz (2002). "Docosahexaenoic acid (DHA) in transgenic oilseeds: which approach will be successful first?" European Journal of Lipid Science and Technology 2002, 104:1-2.

Hinchee et al. (1988) "Production of Transgenic Soybean Plants Using Agrobacterium-Mediated DNA Transfer", Biotechnology 6:915-922.

Hoffman et al., (2008) "Metabolic Engineering of ω3—Very Long Chain Polyunsaturated Fatty Acid Production by an Exclusively Acyl-CoA-dependent Pathway", The Journal of Biological Chemistry, 283:22352-22362.

Hong, H., et al., (2002) "Isolation and Characterization of a Δ5 FA Desaturase From Pythium irregulare by Heterologous Expression in *Saccharomyces cerevisiae* and Oilseed Crops," Lipids, 37(9): 863-868.

Horiguchi, G., et al., (1998) "Developmental Regulation of Genes for Microsome and Plastid Omega-3 Fatty Acid Desaturases in Wheat (*Triticum aestivum* L.)," Plant and Cell Physiology, 39(5): 540-544.

Horvath et al. (2000) "The production of recombinant proteins in transgenic barley grains" Proc. Natl. Acad. Sci. U.S.A. 97:1914-1919.

Hu et al. (2008) "Microalgal triacylglycerols as feedstocks for biofuel production: perspectives and advances" The Plant Journal, 54, 621-639.

Huang Y. S., Pereira S. L., Leonard A. E. (2004) "Enzymes for transgenic biosynthesis of long-chain polyunsaturated fatty acids" Biochimie, vol. 86, No. 11, p. 793-798.

Huang, Y., et al., (1999) "Cloning of Δ12- and Δ6-Desaturases From Mortierella alpina and Recombinant Production of γ-Linolenic Acid in *Saccharomyces cerevisiae,*" Lipids, 34(7): 649-659.

Inagaki, K., et al., (2002) "Identification and Expression of a Rat Fatty Acid Elongase Involved in the Biosynthesis of C18 Fatty Acids," Bioscience, Biotechnology, and Biochemistry, 66(3): 613-621.

Jiang et al. (2014) Isolation and Characterization of the Diatom Phaeodactylum Δ5-Elongase Gene for Transgenic LC-PUFA Production in *Pichia pastoris.* Mar. Drugs, 12, 1317-1334.

Johansen and Carrington (2001) "Silencing on the Spot. Induction and Suppression of RNA Silencing in the Agrobacterium-Mediated Transient Expression System" Plant Physiol. 126-930-938.

Kajikawa et al. (2006) Isolation and functional characterization of fatty acid delta5-elongase gene from the liverwort *Marchantia polymorpha* L, FEBS Lett 580:149-154.

Kajikawa, M., et al., (2004) "Isolation and Characterization of Δ6-Desaturase, An ELO-Like Enzyme and Δ5-Desaturase From the Liverwort *Marchantia polymorpha* and Production of Arachidonic and Eicosapentaenoic Acids in the Methylotrophic Yeast *Pichia pastoris,*" Plant Molecular Biology, 54: 335-352.

Kim et al. (2005) "Ubiquitous and endoplasmic reticulum-located lysophosphatidyl acyltransferase, LPAT2, is essential for female but not for male gametophyte development in *Arabidopsis*" Plant Cell. 17:1073-89.

Kinney AJ, Cahoon EB, Hitz WD. "Manipulating desaturase activities in transgenic crop plants." Biochem Soc Trans. Nov. 30, 2002(Pt 6):1099-103.

Knutzon, D.S., et al., (1998) "Identification of Δ5-Desaturase From Mortierella alpine by Heterologous Expression in Bakers' Yeast and Canola," The Journal of Biological Chemistry, 273(45): 29360-29366.

Koziel et al. (1996) "Optimizing expression of transgenes with an emphasis on posttranscriptional events" Plant Mol. Biol. 32:393-405.

Lessner (1995) Lysophosphatidic acid acyltransferase from meadowfoam mediates insertion of erucic acid at the sn-2 position of triacylglycerol in transgenic rapeseed oil, Plant Physiol. 109:1389-94.

Lenihan-Geels et al. (2013) "Alternative Sources of Omega-3 Fats: Can We Find a Sustainable Substitute for Fish?" Nutrients, 5, 1301-1315.

Leonard et al. (2004) "Elongation of long-chain fatty acids", Progress in Lipid Research 43:36-54.

Leonard, A.E., et al., (2000) "cDNA Cloning and Characterization of Human Δ5-Desaturase Involved in the Biosynthesis of Arachidonic Acid," The Biochemical Journal, 347(Pt 3): 719-724.

Leonard, A.E., et al., (2000) "Cloning of a Human cDNA Encoding a Novel Enzyme Involved in the Elongation of Long-Chain Polyunsaturated Fatty Acids," The Biochemical Journal, 350(Pt 3): 765-770.

Leonard, A.E., et al., (2002) "Identification and Expression of Mammalian Long-Chain PUFA Elongation Enzymes," Lipids, 37(8): 733-740.

Lewsey et al. (2007) "Selective targeting of miRNA-regulated plant development by a viral counter-silencing protein" Plant J. 50:240-252.

Lin et al, (2003) "Efficient linking and transfer of multiple genes by a multigene assembly and transformation vector system" PNAS, 100(10): 5962-5967.

List of documents cited by CSIRO and BASF as of Jan. 16, 2017, in connection Opposition to European Patent No. EP1756280 (Application No. EP05733657.0).

Lo, J., et al., (2003) "15,000 Unique Zebrafish EST Clusters and Their Future Use in Microarray for Profiling Gene Expression Patterns During Embryogenesis," Genome Research Letter, 13(3): 455-466.

(56) References Cited

OTHER PUBLICATIONS

Lu and Kang (2008) "Generation of transgenic plants of a potential oilseed crop *Camelina sativa* by Agrobacterium-mediated transformation", Plant Cell Rep. 27(2):273-8.
Mallory et al (2002) "The amplicon-plus system for high-level expression of transgenes in plants" Nat. Biotech. 20:622-625.
Marangoni and Rousseau (1995) "Engineering triacylglycerols: The role of interesterification" Trends in Food Science & Technology 6, 329-335.
Marekov et al. (2009) Sterol composite of rapeseed varieties introduced in Bulgaria. Bulgarian Journal of Agricultural Science, 15(2): 119-122.
Meesapyodsuk et al. (2007) Primary structure, regioselectivity, and evolution of the membrane-bound fatty acid desaturases of Claviceps purpurea, J Biol Chem 282: 20191-20199.
Meng et al. (2008) "Hibiscus chlorotic ringspot virus coat protein inhibits trans-acting small interfering RNA biogenesis in *Arabidopsis*" J. Gen. Virol. 89:2349-2358.
Meyer, A., et al., (2003) "Biosynthesis of Docosahexaenoic Acid in Euglena gracilis: Biochemical and Molecular Evidence for the Involvement of a Δ4-Fatty Acyl Group Desaturase," Biochemistry, 42(32): 9779-9788.
Meyer, A., et al., (2004) "Novel Fatty Acid Elongases and Their Use for the Reconstitution of Docosahexaenoic Acid Biosynthesis," Journal of Lipid Research, 45(10): 1899-1909.
Michaelson, L.V., et al., (1998) "Functional Identification of a Fatty Acid Δ5 Desaturase Gene From Caenorhabditis elegans," Federation of European Biochemical Societies Letters, 439(3): 215-218.
Michaelson, L.V., et al., (1998) "Isolation of a Δ5-Fatty Acid Desaturase Gene From Mortirella alpine," The Journal of Biological Chemistry, 273(30): 19055-19059.
Murashige and Skoog (1962) "A Revised Medium for Rapid Growth and Bio Assays with Tobacco Tissue Cultures", Physiologic Plantarum 15(3):473-97.
Napier JA, Beaudoin F, Michaelson LV, Sayanova O. (2004) "The production of long chain polyunsaturated fatty acids in transgenic plants by reverse-engineering." Biochimie. Nov. 2004 86(11):785-92.
Napier JA, Beaudoin F, Sayanova O. (2005) "Reverse engineering of long-chain polyunsaturated fatty acid biosynthesis into transgenic plants" European Journal of Lipid Science and Technology 107(4):249-255.
Napier, J.A., et al., (1998) "Identification of a Caenorhabditis elegans Δ6-Fatty-Acid-Desaturase by Heterologous Expression in *Saccharomyces cerevisiae*," The Biochemical Journal, 330(Pt 2): 611-614.
Needleman, S. B., & Wunsch, C. D. (1970). A general method applicable to the search for similarities in the amino acid sequence of two proteins. *J. Mol. Biol.*, 48, 443-453.
Niedz et al (1995) "Green fluorescent protein: an in vivo reporter of plant gene expression" Plant Cell Reports 14:403-406.
Ohlrogge and Browse (1995) "Lipid Biosynthesis" Plant Cell 7:957-970.
Opsahl-Ferstad et al. (2003) "Biotechnological approaches to modify rapeseed oil composition for applications in aquaculture" Plant Science 165: 349-357.
Ortega-García, Jesús, et al. "Refining of high oleic safflower oil: effect on the sterols and tocopherols content." European Food Research and Technology 223.6 (2006): 775-779.
Ow et al. (1986) "Transient and Stable Expression of the Firefly Luciferase Gene in Plant Cells and Transgenic Plants" Science 234:856-859.
Parker-Barnes, J.M., et al., (2000) "Identification and Characterization of an Enzyme Involved in the Elongation of n-6 and n-3 Polyunsaturated Fatty Acids," Proceedings of the National Academy of Sciences of the United States of America, 97(15): 8284-8289.
Pereira et al. (2004b) Identification of two novel microalgal enzymes involved in the conversion of the omega3-fatty acid, eicosapentaenoic acid, into docosahexaenoic acid, Biochem. J. 384:357-366.
Pereira, S.L., et al., (2004) "A Novel omega3-Fatty Acid Desaturase Involved in the Biosynthesis of Eicosapentaenoic Acid," The Biochemical Journal, 378 (Pt 2): 665-671.
Petrie et al. (2010) "Rapid expression of transgenes driven by seed-specific constructs in leaf tissue: DHA production" Plant Methods 6:8 (pp. 1-6).
Petrie et al. (2010a) Metabolic engineering of omega-3 long-chain polyunsaturated fatty acids in plants using an acyl-CoA Delta6-desaturase with omega3-preference from the marine microalga *Micromonas pusilla,* Metab. Eng. 12:233-240.
Petrie et al. (2011) "Expanding the docosahexaenoic acid food web for sustainable production: engineering lower plant pathways into higher plants" AoB Plants Article plr011 (doi:10.1093/aobpla/plr011).
Petrie et al. (2012) "Metabolic Engineering Plant Seeds with Fish Oil-Like Levels of DHA" PLoS ONE, vol. 7, No. 11, e49165.
Petrie et al. (2012) Transgenic production of arachidonic acid in oilseeds, Transgenic Res. 21:139-147.
Petrie et al. (2014) Metabolic Engineering Camelina sativa with Fish Oil-Like Levels of DHA. PLoS One 9(1): e85061.
Potenza et al. (2004) "Targeting Transgene Expression in Research, Agricultural, and Environmental Applications: Promoters Used in Plant Transformation" In Vitro Cell Dev Biol—Plant 40:1-22.
Qi, B., et al., (2002) "Identification of a cDNA Encoding a Novel C18-Δ9 Polyunsaturated Fatty Acid-Specific Elongating Activity From the Docosahexaenoic Acid (DHA)-Producing Microalga, *Isochrysis galbana,*" Federation of European Biochemical Societies Letters, 510(3): 159-165.
Qi, et al., (2004) "Production of Very Long Chain Polyunsaturated Omega-3 and Omega-6 Fatty Acids in Plants", Nature Biotechnology 22:739-745 (published online May 16, 2004).
Qiu, X., et al., (2001) "Identification of a Δ4 Fatty Acid Desaturase From *Thraustochytrium* sp. Involved in the Biosynthesis of Docosahexanoic Acid by Heterologous Expression in *Saccharomyces cerevisiae* and *Brassica juncea,*" The Journal of Biological Chemistry, 276(34): 31561-31566.
Reddy, A.S., et al., (1993) "Isolation of a Δ6 -Desaturase Gene From the *Cyanobadterium synechocystis* sp. Strain PCC6803 by Gain-Of-Function Expression in *Anabaena* sp. Strain PCC7120," Plant Molecular Biology, 27: 293-300.
Robert et al. (2009) Isolation and characterisation of a delta5-fatty acid elongase from the marine microalga *Pavlova salina,* Marine Biotech 11:410-418.
Robert et al., Metabolic engineering of *Arabidopsis* to produce nutritionally important DHA in seed oil, Functional Plant Biology, 2005, vol. 32, p. 473-479.
Ruiz-Lopez et al. (2012) "Enhancing the accumulation of omega-3 long chain polyunsaturated fatty acids in transgenic *Arabidopsis thaliana* via iterative metabolic engineering and genetic crossing" Transgenic Res, 21:1233-1243.
Ryckebosch et al. (2012) "Microalgae as an alternative source of omega-3 long chain polyunsaturated fatty acids" Lipid Technology, 24(6): 128-130.
Saha et al. (2006) "Cytosolic Triacylglycerol Biosynthetic Pathway in Oilseeds. Molecular Cloning and Expression of Peanut Cytosolic Diacylglycerol Acyltransferase" Plant Physiol. 141:1533-1543.
Saito, T., et al., (2000) "A Second FunctionalΔ5 Fatty Acid Desaturase in the Cellular Slime Mould Dictyostelium discoideum," European Journal of Biochemistry, 267(6): 1813-1818.
Sakuradani et al (2005) "A novel fungal ω3-desaturase with wide substrate specificity from arachidonic acid-producing Mortierella alpina 1S-4" Appl Microbiol Biotechnol 66: 648-654.
Sakuradani, E., et al., (1999) "Δ6-Fatty Acid Desaturase From an Arachidonic Acid-Producing Mortierella Fungus. Gene Cloning and Its Heterologous Expression in a Fungus, *Aspergillus,*" Gene, 238(2): 445-453.
Sato et al. (2004) Production of gamma-Linolenic Acid Stearidonic Acid in Seeds of Marker-Free Transgenic Soybean, Crop Sci. 44: 646-652.

(56) References Cited

OTHER PUBLICATIONS

Sayanova et al. (2006) A bifunctional Delta12,Delta15-desaturase from Acanthamoeba castellanii directs the synthesis of highly unusual n-1 series unsaturated fatty acids, J Biol Chem 281: 36533-36541.
Sayanova et al. (2006) Identification of Primula "front-end" desaturases with distinct n-6 or n-3 substrate preferences, Planta 224:1269-1277.
Sayanova et al. (2007) "Cloning and characterization of unusual fatty acid desaturases from Anemone leveillei: identification of an acyl-coenzyme A C20 Δ5-desaturase responsible for the synthesis of sciadonic acid. Plant Physiology", 144:455-67.
Sayanova, O.V. and Napier, J.A., (2004) "Eicosapentaenoic Acid: Biosynthetic Routes and the Potential for Synthesis in Transgenic Plants," Phytochemistry, 65(2): 147-158.
Sayanova, O.V., et al., (1997) "Expression of a Borage Desaturase cDNA Containing an N-Terminal Cytochrome b5 Domain Results in the Accumulation of High Levels of Δ6-Desaturated Fatty Acids in Transgenic Tobacco," Proceedings of the National Academy of Sciences of the United States of America, 94(8): 4211-4216.
Sayanova, O.V., et al., (2003) "Identification of Primula Fatty Acid Δ6-Desaturases with n-3 Substrate Preferences," Federation of European Biochemical Societies, 542: 100-104.
Singh et al. (2005) Metabolic engineering of new fatty acids in plants, Curr. Opin. in Plant Biol. 8:197-203.
Speranza and Macedo (2012) "Lipase-mediated production of specific lipids with improved biological and physicochemical properties" Process Biochemistry 47, 1699-1706.
Sperling et al. (2001) Functional identification of a delta8-sphingolipid desaturase from Borago officinalis, Arch. Biochm. Biophys. 388:293-8.
Sperling, P. and Heinz, E., (2001) "Desaturases Fused to Their Electron Donor," European Journal of Lipid Science and Technology, 103(3): 158-180.
Sperling, P., et al., (2000) "A Bifunctional Δ6-Fatty Acyl Acetylenase/Desaturase From the Moss Ceratodon purpureus," European Journal of Biochemistry, 267(12): 3801-3811.
Sprecher, H., et al., (1995) "Reevaluation of the Pathways for the Biosynthesis of Polyunsaturated Fatty Acids," Journal of Lipid Research, 36(12): 2471-2477.
Spychalla, J.P., et al., (1997) "Identification of an animal omega-3 Fatty Acid Desaturase by Heterologous Expression in *Arabidopsis,*" Proceedings of the National Academy of Sciences of the United States of America, 94(4): 1142-1147.
Stalker et al (1988) "Purification and Properties of a Nitrilase Specific for the Herbicide Bromoxynil and Corresponding Nucleotide Sequence Analysis of the bxn Gene" J. Biol. Chem. 263:6310-6314.
Surinder Singh (2010) "Engineering Complex Fatty Acid Pathways in Seeds: The EPA/DHA Example", submitted as "D31" subsequently renumbered as "D34" in connection with Opposition to European Patent No. EP1756280 (Application No. EP05733657.0).
Thillet et al (1988) "Site-directed Mutagenesis of Mouse Dihydrofolate Reductase" J. Biol. Chem 263:12500-12508.
Tonon, T., et al., (2003) "Identification of a Very Long Chain Polyunsaturated Fatty Acid Δ4-Desaturase From the Microalga *Pavlova lutheri,*" Federation of European biochemical Societies, 553(3): 440-444.
Toriyama et al., Haploid and diploid plant regeneration from protoplasts of anther callus in rice. Theor Appl Genet, 1986, 73:16-19.
Trautwein, E.A., (2001) "n-3 Fatty Acids—Physiological and Technical Aspects for Their Use in Food," European Journal of Lipid Science and Technology, 103(1): 45-55.
Tvrdik, P., et al., (2000) "Role of a New Mammalian Gene Family in the Biosynthesis of Very Long Chain Fatty Acids and Sphingolipids," The Journal of Cell Biology, 149(3): 707-718.
Untergasser et al. (2012) "One-Step Agrobacterium Mediated Transformation of Eight Genes Essential for Rhizobium Symbiotic Signaling Using the Novel Binary Vector System pHUGE" PLoS ONE, vol. 7, No. 10, e47885.
Venegas-Calerón et al (2010) "An alternative to fish oils: Metabolic engineering of oil-seed crops to produce omega-3 long chain polyunsaturated fatty acids" Progress in Lipid Research 49, 108-119.
Voelker T1, Kinney AJ. "Variations in the Biosynthesis of Seed-Storage Lipids." Annu Rev Plant Physiol Plant Mol Biol. Jun. 2001 52:335-361.
Voinnet et al., (2003) "An enhanced transient expression system in plants based on suppression of gene silencing by the p19 protein of tomato bushy stunt virus" Plant J. 33:949-956.
Wallis, J.G. and Browse, J., (1999) "The Δ8-Desaturase of Euglena gracilis: An Alternate Pathway for Synthesis of 20-Carbon Polyunsaturated Fatty Acids," Archives of Biochemistry and Biophysics, 365(2): 307-316.
Watts, L., and Browse, J. "A palmitoyl-CoA-specific Δ9 fatty acid desaturase from Caenorhabditis elegans." Biochemical and biophysical research communications 272, No. 1 (2000): 263-269.
Whitney et al (2003) "Functional characterisation of two cytochrome b5-fusion desaturases from Anemone leveillei : the unexpected identification of a fatty acid Δ6-desaturase" Planta 217: 983-992.
Winans et al. (1988) "Transcriptional regulation of the virA and virG genes of Agrobacterium tumefaciens", Journal of Bacteriology 170(9):4047-54.
Wood (2009) A leaf-based assay using interchangeable design principles to rapidly assemble multistep recombinant pathways, Plant Biotechnol J. 7:914-24.
Wu et al. (2005) Stepwise engineering to produce high yields of very long-chain polyunsaturated fatty acids in plants, Nat. Biotech. 23:1013-1017.
Yang et al. (2003) "Expression and localization of human lysozyme in the endosperm of transgenic rice" Planta 216:597-603.
Zank, T.K., et al., (2002) "Cloning and Functional Characterization of an Enzyme Involved in the Elongation of Δ6-Polyunsaturated Fatty Acids From the Moss *Physcomitrella patens,*" The Plant Journal, 31(3): 255-268.
Zhang et al. (2006) "Cucumber mosaic virus-encoded 2b suppressor inhibits *Arabidopsis* Argonaute1 cleavage activity to counter plant defense" Genes & Development 20:3255-3268.
Zhang et al. (2007a) Identification of a novel bifunctional delta12/delta15 fatty acid desaturase from a basidiomycete, Coprinus cinereus TD#822-2, FEBS Letters 581: 315-319.
Zhang et al. (2008) Identification and characterization of a novel yeast omega3-fatty acid desaturase acting on long-chain n-6 fatty acid substrates from *Pichia pastoris,* Yeast 25: 21-27.
Zhang, Q., et al., (2004) "Identification and Characterization of a Novel Δ6-Fatty Acid Desaturase Gene From Rhizopus arrhizus," Federation of European Biochemical Societies Letters, 556(1-3): 81-85.
Zhou et al (2008) "Isolation and functional characterization of two independently-evolved fatty acid Δ12-desaturase genes from insects" Insect Molecular Biology 17(6), 667-676.
Zhou et al: (2007) "Isolation and characterization of genes from the marine microalga *Pavlova salina* encoding three front-end desaturases involved in docosahexaenoic acid biosynthesis" Phytochemistry 68, 785-796.
Zou et al, (1997) "Modification of seed oil content and acyl composition in the Brassicaceae by expression of a yeast sn-2 acyltransferase gene", The Plant Cell 9(6):909-23.
Dec. 6, 2013 International Search Report, issued in connection with PCT International Patent Application No. PCT/AU2013/000639.
Dec. 6, 2013 Written Opinion of the International Searching Authority, issued in connection with PCT International Patent Application No. PCT/AU2013/000639.
May 13, 2014 International Preliminary Report on Patentability, issued in connection with PCT International Patent Application No. PCT/AU2013/000639.

(56) References Cited

OTHER PUBLICATIONS

Apr. 15, 2014 Demand for International Preliminary Examination, including substitute claim pp. 164-186, filed in connection with PCT International Patent Application No. PCT/AU2013/000639.
Communication Pursuant to Article 94(3) EPC dated Jun. 1, 2016 in connection with European Patent Application No. 13803782.5.
Feb. 23, 2016 Communication, issued in connection with European Patent Application No. 13803782.5.
May 12, 2016 Response to the Feb. 23, 2016 Rule 70(2) and 70a(2) Communication, filed in connection with European Patent Application No. 13803782.5.
Oct. 11, 2016 Response filed in connection with European Patent Application No. 13803782.5.
Supplementary European Search Report, dated Feb. 5, 2016 in connection with European Patent Application No. 13803782.5.
Sep. 25, 2017 Extended European Search Report, issued in connection with European Patent Application No. 17168626.4.
Oct. 26, 2016 Australian Examination Report issued in connection with Australian Patent Application No. 2013273934.
Mar. 18, 2017 Office Action, issued in connection with Eurasian Patent Application No. 201590026, including English language translation.
May 8, 2015 Response to Office Action, filed in connection with Vietnamese Patent Application No. 1-2015-00134.
English language translation of an Office Action, issued in connection with Chilean Patent Application No. 3402-2014.
Dec. 5, 2016 Chinese First Office Action issued in connection with Chinese Patent Application No. 201380033472.0, including English language translation.
Sep. 13, 2016 First Office Action, issued in connection with Chinese Patent Application No. 201380042832.3, including English language translation.
English language translation of the Response to the First Office Action, dated Sep. 13, 2016, as filed in connection with Chinese Patent Application No. 201380042832.3.
Aug. 1, 2017 Second Office Action, issued in connection with Chinese Patent Application No. 201380042832.3, including English language translation.
English language translation of Mar. 24, 2017 Office Action, issued in connection with Japanese Patent Application No. 2015-516383.
Feb. 6, 2017 First Written Opinion, issued in connection with Singapore Patent Application No. 11201408362S.
May 4, 2017 Response to First Written Opinion, filed in connection with Singapore Patent Application No. 11201408362S.
May 23, 2017 Notice and the Supplementary Examination Report, issued in connection with Singapore patent application 11201408362S.
Jul. 20, 2017 Response as filed to the Supplementary Examination Report, issued in connection with Singapore Patent Application No. 112014088362S.
Oct. 4, 2017 Office Action, issued in connection with Ukrainian Patent Application No. 201500277, including English language translation.
Apr. 13, 2017 Complaint for Declaratory Judgment, filed by BASF in connection with U.S. Pat. No. 7,807,849, issued Oct. 5, 2010 (Singh et al.); U.S. Pat. No. 7,834,250, issued Nov. 16, 2010 (Singh et al.); U.S. Pat. No. 8,106,226, issued Jan. 31, 2012 (Singh et al.); U.S. Pat. No. 8,288,572, issued Oct. 16, 2012 (Singh et al.); U.S. Pat. No. 8,575,377, issued Nov. 5, 2013 (Singh et al.); U.S. Pat. No. 8,809,559, issued Aug. 19, 2014 (Petrie et al.); U.S. Pat. No. 8,853,432, issued Oct. 7, 2014 (Singh et al.); and U.S. Pat. No. 9,458,410, issued Oct. 4, 2016 (Singh et al.), in the United States District Court of the District of Delaware, Civil Action No. 17-421.
Aug. 22, 2017 Memorandum granting Nuseed America's Motion to Dismiss the Complaint for Declaratory Judgment, filed by BASF in connection with U.S. Pat. No. 7,807,849, issued Oct. 5, 2010 (Singh et al.); U.S. Pat. No. 7,834,250, issued Nov. 16, 2010 (Singh et al.); U.S. Pat. No. 8,106,226, issued Jan. 31, 2012 (Singh et al.); U.S. Pat. No. 8,288,572, issued Oct. 16, 2012 (Singh et al.); U.S. Pat. No. 8,575,377, issued Nov. 5, 2013 (Singh et al.); U.S. Pat. No. 8,809,559, issued Aug. 19, 2014 (Petrie et a).); U.S. Pat. No. 8,853,432, issued Oct. 7, 2014 (Singh et al.); and U.S. Pat. No. 9,458,410, issued Oct. 4, 2016 (Singh et al.), in the United States District Court of the District of Delaware, Civil Action No. 17-421.
Complaint for Declaratory Judgment, filed by BASF Plant Science, LP, on Sep. 19, 2017, in the United States District Court for the Eastern District of Virginia Alexandria Division, in connection with "*BASF Plant Science, LP* v. *Commonwealth Scientific and Industrial Research Organisation, Grains Research and Development Corporation, and Nuseed Pty, Ltd*", Case No. 2:17-cv-00503.
Aug. 20, 2015 Communication of a Notice of Opposition, issued in connection with Opposition to European Patent No. EP1756280, including a list of documents cited by the Opponent.
Sequence alignment demonstrating that the amino acid sequence of GenBank accession No. AY055117 was found to have the same length as protein SEQ ID No. 64 of WO 2005/103253, filed as "D18" in connection with Opposition to European Patent No. EP1756280 (Application No. EP05733657.0).
Sequence alignment demonstrating that the amino acid sequence of GenBank accession No. AY055118 was found to have the same length as protein SEQ ID No. 64 of WO 2005/103253, filed as "D19" in connection with Opposition to European Patent No. EP1756280 (Application No. EP05733657.0).
Reference formula used for the calculation of the melting temperature as regards sequences hybridizing under high stringency conditions, filed as "D20" in connection with Opposition to European Patent No. EP1756280 (Application No. EP05733657.0).
Mar. 29, 2016 Response to the Notice of Opposition, filed by CSIRO in connection with Opposition to European Patent No. EP1756280 (Application No. EP05733657.0).
Jul. 18, 2016 EPO Communication providing Summons to attend Oral Proceedings and Preliminary Opinion, issued in connection with Opposition to European Patent No. EP1756280 (Application No. EP05733657.0).
Jan. 9, 2017 Written Submissions under Rule 116 EPC filed in response to the Summons to Oral Proceedings, filed by CSIRO in connection with Opposition to European Patent No. EP1756280 (Application No. EP05733657.0).
Auxiliary Request I claims, filed with Jan. 9, 2017 Written Submissions under Rule 116 EPC, in response to the Summons to Oral Proceedings, in connection with Opposition to European Patent No. EP1756280 (Application No. EP05733657.0).
Jan. 9, 2017 Written Submissions under Rule 116 EPC filed in response to the Summons to Oral Proceedings, filed by BASF in connection with European Patent Application No. EP05733657.0.
Materials and methods, results and conclusions for experimental data provided by the Opponent. The Opponent's experiments repeated and expanded on the experiment described in Example 5 of the opposed patent EP 1756280 (Annex A); Data table depicting the fatty acid composition of segregating T2 or T1 seeds from *Arabidopsis* or *Brassica napus* (canola) (Annex B); Media used in *Brassica napus* transformation (Annex C), filed by BASF in connection with Opposition to European Patent No. EP1756280 (Application No. EP05733657.0).
Feb. 21, 2017 Additional Submissions, including list of all documents cited to date and documents "D36", "D37" and "D38" filed in connection with Opposition to European Patent No. EP1756280 (Application No. EP05733657.0).
Mar. 9, 2017 Information about the result of Oral Proceedings, filed in connection with Opposition to European Patent No. EP1756280 (Application No. EP05733657.0).
Aug. 23, 2017 Appeal Brief, filed by BASF in connection with Opposition to European Patent No. EP1756280.
Aug. 30, 2017 Correction to Aug. 23, 2017 Appeal Brief, filed by BASF in connection with Opposition to European Patent No. EP1756280.
Feature-structured claim 1, submitted as "D39" by BASF with Aug. 23, 2017 Appeal Brief, filed by BASF in connection with Opposition to European Patent No. EP1756280.
Presentation "Engineering of LCPUFA biosynthesis" presented by Prof. Heinz at the 1st European Symposium on Plant Lipids held Sep. 10-13, 2003 in Aachen, submitted as "D44" by BASF with

(56) References Cited

OTHER PUBLICATIONS

Aug. 23, 2017 Appeal Brief, filed by BASF in connection with Opposition to European Patent No. EP1756280.
Evidence of the publication date of D44, submitted as “D44a” by BASF with Aug. 23, 2017 Appeal Brief, filed by BASF in connection with Opposition to European Patent No. EP1756280.
Expert declaration from Dr. Domergue, submitted as “D47” by BASF with Aug. 28, 2017 Appeal Brief, filed by BASF in connection with Opposition to European Patent No. EP1756280.
Experimental data relating to EPA production in different plants, including experimental details, results, a discussion and conclusion, submitted as “D49” by BASF with Aug. 23, 2017 Appeal Brief, filed by BASF in connection with Opposition to European Patent No. EP1756280 including Attachment 1 of D49 (“D52”).
Media used in Brassica transformation described in D49, submitted as “D49a” by BASF with Aug. 23, 2017 Appeal Brief, filed by BASF in connection with Opposition to European Patent No. EP1756280.
Experimental data on EPA production of segregating seeds, submitted as “D50” by BASF with Aug. 23, 2017 Appeal Brief, filed by BASF in connection with Opposition to European Patent No. EP1756280.
Experimental data on EPA production of homozygous seeds, submitted as “D51” by BASF with Aug. 23, 2017 Appeal Brief, filed by BASF in connection with Opposition to European Patent No. EP1756280.
Gunstone (2005). Bailey’s Industrial Oil and Fat Products, Sixth Edition.
Altschul, S. F., Madden, T. L., Schäffer, A. A., Zhang, J., Zhang, Z., Miller, W., & Lipman, D. J. (1997). Gapped BLAST and PSI-BLAST: a new generation of protein database search programs. *Nucleic Acids Research,* 25(17), 3389-3402.
Aug. 2, 2012 presentation at the UniGateway, Business breakfast series at Melbourne, Australia, entitled “Trends and sustainability of LC omega-3 oils from wild and farmed fish, and Progress with new land plant sources” presented by Peter Nichols, first author, Peter Nichols, 10 slides.
Badami, R. C., & Patil, K. B. (1980). Structure and occurrence of unusual fatty acids in minor seed oils. *Prog. Lipid Res.,* 19, 119-153.
Cahoon, E. B., Ripp, K. G., Hall, S. E., & Kinney, A. J. (2001). Formation of conjugated Δ8,Δ10-double bonds by Δ12—oleic-acid desaturase-related enzymes. *The Journal of Biological Chemistry,* 276(4), 2637-2643.
Cahoon, E. B., Shanklin, J., & Ohlrogge, J. B. (1992). Expression of a coriander desaturase results in petroselinic acid production in transgenic tobacco. *Proc. Natl. Acad. Sci. USA,* 89, 11184-11188.
Chapman et al. (2001) “Transgenic Cotton Plants with Increased Seed Oleic Acid Content” Journal of American Chemists’ Chemistry; vol. 78 No. 9, 941-947.
Clapp et al., The 16-Kilodalton N-Terminal Fragment of Human Prolactin is a Potent Inhibitor of Angiogenesis. Endocrinology, 1993, 133(3):1292-1299.
Cripps, C., Borgeson, C., Blomquist, G. J., & de Renobales, M. (1990). The Δ12-desaturase from the house cricket, *Acheta domesticus* (orthoptera: gryllidae): characterization and form of the substrate. Archives of Biochemistry and Biophysics, 278(1), 46-51.
Crombie, L., & Holloway, S. J. (1984). Origins of conjugated triene fatty acids. The biosynthesis of calendic acid by *Calendula officinalis. J. Chem. Soc., Chem. Commun.,* 15, 953-955.
Crombie, L., & Holloway, S. J. (1985). The biosynthesis of calendic acid, octadeca-(8E,10E,12Z)-trienoic acid, by developing marigold seeds: origins of (E,E,Z) and (Z,E,Z) conjugated triene acids in higher plants. *J. Chem. Soc. Perkin Trans.* 1, 2425-2434.
Cuperus, F. P., & Derksen, J. T. P. (1996). High value-added applications from vernolic acid. In J. Janick (Ed.), *Progress in new crops* (pp. 354-356). Alexandria, VA: ASHS Press.
de Renobales, M., Cripps, C., Stanley-Samuelson, D. W., Jurenka, R. A., & Blomquist, G. J. (1987). Biosynthesis of linoleic acid in insects. *Trends in Biochemical Sciences,* 12, 364-366.
Dobson, G., & Christie, W. W. (2002). Mass spectrometry of fatty acid derivatives. *Eur. J. Lipid Sci. Technol.,* 104, 36-43.
Fay, L., & Richli, U. (1991). Location of double bonds in polyunsaturated fatty acids by gas chromatography-mass spectrometry after 4,4-dimethyloxazoline derivatization. *Journal of Chromatography,* 541, 89-98.
Fritsche, K., Hornung, E., Peitzsch, N., Renz, A., & Feussner, I. (1999). Isolation and characterization of a calendic acid producing (8,11)-linoleoyl desaturase. *FEBS Letters,* 462, 249-253.
GenBank accession CAL55414, (2012).
Green, D. et al., “Measurement of hemostatic factors in EDTA plasma” Am. J. Clin. Pathol., 2008, 130(5): 811-815.
Hao, G., Liu, W., O’Conner, M., & Roelofs, W. L. (2002). Acyl-CoA Z9- and Z10-desaturase genes from a New Zealand leafroller moth species, *Planotortrix octo. Insect Biochemistry and Molecular Biology,* 32, 961-966.
James Petrie, Jul. 13, 2012 presentation at the 20th International conference on plant lipids at Seville, Spain, entitled “Metabolic engineering plant seeds with fish oil-like levels of DNA”, first author, James Petrie, 41 slides.
James Petrie, Nov. 14, 2012 presentation at the Novel sources of omega-3, Copenhagen 2012 at Copenhagen, Denmark, entitled “Metabolic engineering plant seeds with fish oil-like levels of DHA”, first author, James Petrie, 35 slides.
Kleiman, R., & Spencer, G. F. (Jan. 1982). Search for new industrial oils: XVI. umbelliflorae—seed oils rich in petroselinic acid. *Journal of the American Oil Chemists’ Society,* 59(1), 29-38.
Knipple, D. C., Rosenfield, C., Nielsen, R., You, K. M., & Jeong, S. E. (2002). Evolution of the integral membrane desaturase gene family in moths and flies. *Genetics,* 162, 1737-1752.
Lewis, T., Nichols, P. D., & McMeekin, T. A. (2000). Evaluation of extraction methods for recovery of fatty acids from lipid-producing microheterotrophs. *Journal of Microbiological Methods,* 43, 107-116.
Morimoto et al. (2005) Hot Topic: Endogenous Production of n-3 and n-6 Fatty Acids in Mammalian Cells. J. Dairy Sci., 88:1142-1146.
Mortimer, R. K., & Johnston, J. R. (1986). Genealogy of principal strains of the yeast genetic stock center. *Genetics,* 113, 35-43.
Moto, K., Suzuki, M. G., Hull, J. J., Kurata, R., Takahashi, S., Yamamoto, M., . . . Matsumoto, S. (2004). Involvement of a bifunctional fatty-acyl desaturase in the biosynthesis of the silkmoth, *Bombyx mori,* sex pheromone, *PNAS,* 101(23), 8631-8636.
Murata, N., & Wada, H. (1995). Acyl-lipid desaturases and their importance in the tolerance and acclimatization to cold of cyanobacteria. *Biochem. J.,* 308, 1-8.
Peter Nichols, Jul. 16, 2012 presentation at the Australian Institute of Food Science and Technology, Annual Meeting, 2012 at Adelaide, Australia, entitled “New sustainable land plant sources of long-chain omega-3 oils”, first author, Peter Nichols, 26 slides.
Peter Nichols, Jul. 2, 2012 presentation at the Australian Marine Scientists Association, Annual Meeting, 2012 at Hobart, Australia, entitled “New Land Plants With Long-Chain Omega-3 Oils: A journey from marine gene discovery to sustainable sources of health-benefitting oils”, first author, Peter Nichols, 21 slides.
Peter Nichols, Jun. 8, 2012 presentation at the GOED Exchange at Boston, MA, entitled “An Update from Australia: A Global Leader in Long-Chain Omega-3”, first author, Peter Nichols, 34 slides.
Peter Nichols, Mar. 13, 2013 presentation at the Invited seminar, The Biological Club, Hobart at Hobart, Australia, entitled “The Omega-3 Oils story—Sources of Long-chain Omega-3: A Sustainable Future”, first author, Peter Nichols, 39 slides.
Peter Nichols, Mar. 7, 2012 presentation at the CSIRO Marine and Atmospheric Research. Science Forum, Hobart (poster presentation) at Hobart, Australia, entitled “New Land Plants Containing Long-chain Omega-3 Oils”, first author, Peter Nichols.
Peter Nichols, Oct. 9, 2012 presentation at the Invited seminar, Department of Plant Science, University of Tasmania at Hobart, Australia, entitled “The Omega-3 Oils story—Sources of Long-chain Omega-3: A Sustainable Future”, first author, Peter Nichols, 39 slides.

(56) References Cited

OTHER PUBLICATIONS

Peter Nichols, Sep. 26, 2012 presentation at the ComBio—Plants and Human Nutrition Symposium, 2012 at Adelaide, Australia, entitled "Creating Land Plant-Based Sustainable Sources of Essential Long Chain Omega-3 Fatty Acids", first author, James Petrie, 24 slides.
Petrie et al. (2013) "Engineered oilseed crops with fish oil DHA levels" Inform, 24(10):648-652.
Peyou-Ndi et al. (2000) Identification and Characterization of an Animal Δ12 Fatty Acid Desaturase Gene by Heterologous Expression in *Saccharomyces cerevisiae.* Archives of Biochemistry and Biophysics, vol. 376, No. 2, pp. 399-408.
Plant Triacylglycerol Synthesis. AOCS Lipid Library. Nov. 4, 2010. Retrieved Feb. 18, 2016.
Qiu, X., Reed, D. W., Hong, H., MacKenzie, S. L., & Covello, P. S. (2001). Identification and analysis of a gene from *Calendula officinalis* encoding a fatty acid conjugase. *Plant Physiology,* 125, 847-855.
Rodríguez, S., Hao, G., Liu, W., Piña, B., Rooney, A. P., Camps, F., . . . Fabriàs, G. (2004). Expression and evolution of Δ9 and Δ11 desaturase genes in the moth *Spodoptera littoralis. Insect Biochemistry and Molecular Biology,* 34, 1315-1328.
Sayanova et al., the role of delta (6)-desaturase acyl-carrier specificity in the efficient synthesis of long-chain polyunsaturated fatty acids in transgenic plants. Plant Biotechnology Journal, (2012) 10:195-206.
Serra, M., Gauthier, L. T., Fabrias, G., & Buist, P. H. (2006). Δ11 desaturases of *Trichoplusia ni* and *Spodoptera littoralis* exhibit dual catalytic behaviour. *Insect Biochemistry and Molecular Biology,* 36, 822-825.
Smith, C. R., Jr. (1971). Occurrence of unusual fatty acids in plants. *Progress in the Chemistry of Fats and Other Lipids,* 11, 137, 139-177.
Smith, M. A., Moon, H., Chowrira, G., & Kunst, L. (2003). Heterologous expression of a fatty acid hydroxylase gene in developing seeds of *Arabidopsis thaliana. Planta,* 217, 507-516.
Stanley-Samuelson et al (1998) "Fatty Acids in Insects: Composition, Metabolism, and Biological Significance" Archives of Insect Biochemistry and Physiology 9:1-33.
Stukey, J. E., McDonough, V. M., & Martin, C. E. (1990). The OLE1 gene of *Saccharomyces cerevisiae* encodes the Δ9 fatty acid desaturase and can be functionally replaced by the rat stearoyl-CoA desaturase gene. The Journal of Biological Chemistry, 265(33), 20144-20149.
Stymne, S., & Appelqvist, L. (1978). The biosynthesis of linoleate from oleoyl-CoA via oleoyl-phosphatidylcholine in microsomes of developing safflower seeds. *Eur. J. Biochem,* 90, 223-229.
Thompson, J. D., Gibson, T. J., Plewniak, F., Jeanmougin, F., & Higgins, D. G. (1997). The CLUSTAL_X windows interface: flexible strategies for multiple sequence alignment aided by quality analysis tools. *Nucleic Acids Research,* 25(24), 4876-4882.
Whittle, E., Cahoon, E. B., Subrahmanyam, S., & Shanklin, J. (2005). A multifunctional acyl-acyl carrier protein desaturase from *Hedera helix* L. (English ivy) can synthesize 16- and 18-carbon monoene and diene products. The Journal of Biological Chemistry, 280(31), 28169-28176.
Zhou, X., Robert, S., Singh, S., & Green, A. (2005). Heterologous production of GLA and SDA by expression of an Echium plantagineum Δ6-desaturase gene. *Plant Science,* 170, 665-673.
Jan. 4, 2018 Response of Commonwealth Scientific and Industrial Research Organisation (Patentee) to Statement of Appeal by BASF SE (Opponent) in connection with Opposition to European Patent No. EP1756280, including copies of Argument, Main Request and six Auxiliary Requests.
Jan. 4, 2018 Response of BASF SE to Grounds of Appeal filed by Commonwealth Scientific and Industrial Research Organisation dated Aug. 22, 2017 in connection with Opposition to European Patent No. EP1756280.
Connor, W. E. (2000). Importance of n-3 fatty acids in health and disease. The American journal of clinical nutrition, 71(1), 171S-175S.

* cited by examiner

A)

5α-cholestan-3β-ol

B)

campesterol sitosterol brassicasterol stigmasterol avenasterol

PROCESS FOR PRODUCING ETHYL ESTERS OF POLYUNSATURATED FATTY ACIDS

CROSS-REFERENCE TO RELATED APPLICATIONS

This application is a continuation of U.S. Ser. No. 15/400,532, filed Jan. 6, 2017, which is a continuation of U.S. Ser. No. 14/600,653, filed Jan. 20, 2015, now U.S. Pat. No. 9,556,102, issued Jan. 31, 2017, which is a continuation of U.S. Ser. No. 13/918,392, filed Jun. 14, 2013, now U.S. Pat. No. 8,946,460, issued Feb. 3, 2015, claiming the benefit of U.S. Provisional Patent Applications Nos. 61/782,680, filed Mar. 14, 2013, 61/697,676, filed Sep. 6, 2012, 61/663,344, filed Jun. 22, 2012, and 61/660,392, filed Jun. 15, 2012, the entire contents of each of which are hereby incorporated by reference into the subject application.

REFERENCE TO SEQUENCE LISTING

This application incorporates-by-reference nucleotide and/or amino acid sequences which are present in the file named "170815_84199-BAAA_Substitute_Sequence_Listing_DH.txt," which is 369 kilobytes in size, and which was created Aug. 15, 2017 in the IBM-PC machine format, having an operating system compatibility with MS-Windows, which is contained in the text file filed Aug. 15, 2017 as part of this application.

FIELD OF THE INVENTION

The present invention relates to a process for producing ethyl esters of polyunsaturated fatty acids, comprising transesterifying triacylglycerols in extracted plant lipid.

BACKGROUND OF THE INVENTION

Omega-3 long-chain polyunsaturated fatty acids (LC-PUFA) are now widely recognized as important compounds for human and animal health. These fatty acids may be obtained from dietary sources or by conversion of linoleic (LA, 18:2ω6) or α-linolenic (ALA, 18:3ω3) fatty acids, both of which are regarded as essential fatty acids in the human diet. While humans and many other vertebrate animals are able to convert LA or ALA, obtained from plant sources to C22 they carry out this conversion at a very low rate. Moreover, most modern societies have imbalanced diets in which at least 90% of polyunsaturated fatty acids (PUFA) are of the ω6 fatty acids, instead of the 4:1 ratio or less for ω6:ω3 fatty acids that is regarded as ideal (Trautwein, 2001). The immediate dietary source of LC-PUFAs such as eicosapentaenoic acid (EPA, 20:5ω3) and docosahexaenoic acid (DHA, 22:6ω3) for humans is mostly from fish or fish oil. Health professionals have therefore recommended the regular inclusion of fish containing significant levels of LC-PUFA into the human diet. Increasingly, fish-derived LC-PUFA oils are being incorporated into food products and in infant formula, for example. However, due to a decline in global and national fisheries, alternative sources of these beneficial health-enhancing oils are needed.

Flowering plants, in contrast to animals, lack the capacity to synthesise polyunsaturated fatty acids with chain lengths longer than 18 carbons. In particular, crop and horticultural plants along with other angiosperms do not have the enzymes needed to synthesize the longer chain ω3 fatty acids such as EPA, docosapentaenoic acid (DPA, 22:5ω3) and DHA that are derived from ALA. An important goal in plant biotechnology is therefore the engineering of crop plants which produce substantial quantities of LC-PUFA, thus providing an alternative source of these compounds.

LC-PUFA Biosynthesis Pathways

Biosynthesis of LC-PUFAs in organisms such as microalgae, mosses and fungi usually occurs as a series of oxygen-dependent desaturation and elongation reactions (FIG. 1). The most common pathway that produces EPA in these organisms includes a Δ6-desaturation, Δ6-elongation and Δ5-desaturation (termed the Δ6-desaturation pathway) whilst a less common pathway uses a Δ9-elongation, Δ8-desaturation and Δ5-desaturation (termed the Δ9-desaturation pathway). These consecutive desaturation and elongation reactions can begin with either the ω6 fatty acid substrate LA, shown schematically as the upper left part of FIG. 1 (ω6) or the ω3 substrate ALA through to EPA, shown as the lower right part of FIG. 1 (ω3). If the initial Δ6-desaturation is performed on the ω6 substrate LA, the LC-PUFA product of the series of three enzymes will be the ω6 fatty acid ARA. LC-PUFA synthesising organisms may convert ω6 fatty acids to ω3 fatty acids using an ω3-desaturase, shown as the Δ17-desaturase step in FIG. 1 for conversion of arachidonic acid (ARA, 20:4ω6) to EPA. Some members of the ω3-desaturase family can act on a variety of substrates ranging from LA to ARA. Plant ω3-desaturases often specifically catalyse the Δ15-desaturation of LA to ALA, while fungal and yeast ω3-desaturases may be specific for the Δ17-desaturation of ARA to EPA (Pereira et al., 2004a; Zank et al., 2005). Some reports suggest that non-specific ω3-desaturases may exist which can convert a wide variety of ω6 substrates to their corresponding ω3 products (Zhang et al., 2008).

The conversion of EPA to DHA in these organisms occurs by a Δ5-elongation of EPA to produce DPA, followed by a Δ4-desaturation to produce DHA (FIG. 1). In contrast, mammals use the so-called "Sprecher" pathway which converts DPA to DHA by three separate reactions that are independent of a Δ4-desaturase (Sprecher et al., 1995).

The front-end desaturases generally found in plants, mosses, microalgae, and lower animals such as *Caenorhabditis elegans* predominantly accept fatty acid substrates esterified to the sn-2 position of a phosphatidylcholine (PC) substrate. These desaturases are therefore known as acyl-PC, lipid-linked, front-end desaturases (Domergue et al., 2003). In contrast, higher animal front-end desaturases generally accept acyl-CoA substrates where the fatty acid substrate is linked to CoA rather than PC (Domergue et al., 2005). Some microalgal desaturases and one plant desaturase are known to use fatty acid substrates esterified to CoA (Table 2).

Each PUFA elongation reaction consists of four steps catalysed by a multi-component protein complex: first, a condensation reaction results in the addition of a 2C unit from malonyl-CoA to the fatty acid, resulting in the formation of a β-ketoacyl intermediate. This is then reduced by NADPH, followed by a dehydration to yield an enoyl intermediate. This intermediate is finally reduced a second time to produce the elongated fatty acid. It is generally thought that the condensation step of these four reactions is substrate specific whilst the other steps are not. In practice, this means that native plant elongation machinery is capable of elongating PUFA providing that the condensation enzyme (typically called an 'elongase') specific to the PUFA is introduced, although the efficiency of the native plant elongation machinery in elongating the non-native PUFA substrates may be low. In 2007 the identification and characterisation of the yeast elongation cycle dehydratase was published (Denic and Weissman, 2007).

PUFA desaturation in plants, mosses and microalgae naturally occurs to fatty acid substrates predominantly in the acyl-PC pool whilst elongation occurs to substrates in the acyl-CoA pool. Transfer of fatty acids from acyl-PC molecules to a CoA carrier is performed by phospholipases (PLAs) whilst the transfer of acyl-CoA fatty acids to a PC carrier is performed by lysophosphatidyl-choline acyltransferases (LPCATs) (FIG. 21) (Singh et al., 2005).

Engineered Production of LC-PUFA

Most LC-PUFA metabolic engineering has been performed using the aerobic Δ6-desaturation/elongation pathway. The biosynthesis of γ-linolenic acid (GLA, 18:3ω6) in tobacco was first reported in 1996 using a Δ6-desaturase from the cyanobacterium *Synechocystis* (Reddy and Thomas, 1996). More recently, GLA has been produced in crop plants such as safflower (73% GLA in seedoil; Knauf et al., 2006) and soybean (28% GLA; Sato et al., 2004). The production of LC-PUFA such as EPA and DHA involves more complicated engineering due to the increased number of desaturation and elongation steps involved. EPA production in a land plant was first reported by Qi et al. (2004) who introduced genes encoding a Δ9-elongase from *Isochrysis galbana*, a Δ8-desaturase from *Euglena gracilis* and a Δ5-desaturase from *Mortierella alpina* into *Arabidopsis* yielding up to 3% EPA. This work was followed by Abbadi et al. (2004) who reported the production of up to 0.8% EPA in flax seed using genes encoding a Δ6-desaturase and Δ6-elongase from *Physcomitrella patens* and a Δ5-desaturase from *Phaeodactylum tricornutum.*

The first report of DHA production, and to date the highest levels of VLC-PUFA production reported, was in WO 04/017467 where the production of 3% DHA in soybean embryos is described, but not seed, by introducing genes encoding the *Saprolegnia diclina* Δ6-desaturase, *Mortierella alpina* Δ6-desaturase, *Mortierella alpina* Δ5-desaturase, *Saprolegnia diclina* Δ4-desaturase, *Saprolegnia diclina* Δ17-desaturase, *Mortierella alpina* Δ6-elongase and *Pavlova lutheri* Δ5-elongase. The maximal EPA level in embryos also producing DHA was 19.6%, indicating that the efficiency of conversion of EPA to DHA was poor (WO 2004/071467). This finding was similar to that published by Robert et al. (2005), where the flux from EPA to DHA was low, with the production of 3% EPA and 0.5% DHA in *Arabidopsis* using the *Danio rerio* Δ5/6-desaturase, the *Caenorhabditis elegans* Δ6-elongase, and the *Pavlova salina* Δ5-elongase and Δ4-desaturase. Also in 2005, Wu et al. published the production of 25% ARA, 15% EPA, and 1.5% DHA in *Brassica juncea* using the *Pythium irregulare* Δ6-desaturase, a *Thraustochytrid* Δ5-desaturase, the *Physcomitrella patens* Δ6-elongase, the *Calendula officianalis* Δ12-desaturase, a *Thraustochytrid* Δ5-elongase, the *Phytophthora infestans* Δ17-desaturase, the *Oncorhyncus mykiss* LC-PUFA elongase, a *Thraustochytrid* Δ4-desaturase and a *Thraustochytrid* LPCAT (Wu et al., 2005). Summaries of efforts to produce oil-seed crops which synthesize ω3 LC-PUFAs is provided in Venegas-Caleron et al. (2010) and Ruiz-Lopez et al. (2012). As indicated by Ruiz-Lopez et al. (2012), results obtained to date for the production of DHA in transgenic plants has been no where near the levels seen in fish oils.

There therefore remains a need for more efficient production of LC-PUFA in recombinant cells, in particular of DHA in seeds of oilseed plants.

SUMMARY OF THE INVENTION

The present inventors have identified methods and plants for producing lipid with high levels of DHA.

In a first aspect, the present invention provides extracted plant lipid, comprising fatty acids in an esterified form, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of stearidonic acid (SDA), eicosapentaenoic acid (EPA), docosapentaenoic acid (DPA) and eicosatetraenoic acid (ETA), wherein the level of DHA in the total fatty acid content of the extracted lipid is about 7% to 20%.

In an embodiment, the extracted lipid has one or more or all of the following features i) the level of palmitic acid in the total fatty acid content of the extracted lipid is between about 2% and 18%, between about 2% and 16%, or between about 2% and 15%, ii) the level of myristic acid (C14:0) in the total fatty acid content of the extracted lipid is less than about 6%, less than about 3%, less than about 2%, or less than about 1%, iii) the level of oleic acid in the total fatty acid content of the extracted lipid is between about 1% and about 30%, between about 3% and about 30%, between about 6% and about 30%, between 1% and about 20%, between about 30% and about 60%, between about 45% to about 60%, or is about 30%, iv) the level of linoleic acid (LA) in the total fatty acid content of the extracted lipid is between about 4% and about 35%, between about 4% and about 20%, or between about 4% and 17%, v) the level of α-linolenic acid (ALA) in the total fatty acid content of the extracted lipid is between about 4% and about 40%, between about 7% and about 40%, between about 10% and about 35%, between about 20% and about 35%, between about 4% and about 16%, or between about 2% and about 16%, vi) the level of γ-linolenic acid (GLA) in the total fatty acid content of the extracted lipid is less than about 4%, less than about 3%, less than about 2%, less than about 1%, less than about 0.5%, between 0.05% and about 7%, between 0.05% and about 4%, between 0.05% and about 3%, or between 0.05% and about 2%, vii) the level of stearidonic acid (SDA) in the total fatty acid content of the extracted lipid is less than about 7%, less than about 6%, less than about 4%, less than about 3%, between about 0.05% and about 7%, between about 0.05% and about 6%, between about 0.05% and about 4%, between about 0.05% and about 3%, or between 0.05% and about 2%, viii) the level of eicosatetraenoic acid (ETA) in the total fatty acid content of the extracted lipid is less than about 6%, less than about 5%, less than about 4%, less than about 1%, less than about 0.5%, between about 0.05% and about 6%, between about 0.05% and about 5%, between about 0.05% and about 4%, between about 0.05% and about 3%, or between about 0.05% and about 2%, ix) the level of eicosatrienoic acid (ETrA) in the total fatty acid content of the extracted lipid is less than about 4%, less than about 2%, less than about 1%, between about 0.05% and about 4%, between about 0.05% and about 3%, between about 0.05% and about 2%, or between about 0.05% and about 1%, x) the level of eicosapentaenoic acid (EPA) in the total fatty acid content of the extracted lipid is less than about 4%, less than about 3%, less than about 2%, between about 0.05% and about 10%, between about 0.05% and about 5%, between about 0.05% and about 3%, or between about 0.05% and about 2%, xi) the level of docosapentaenoic acid (DPA) in the total fatty acid content of the extracted lipid is less than about 4%, less than about 3%, less than about 2%, between about 0.05% and about 8%, between about 0.05% and about 5%, between about 0.05% and about 3%, or between about 0.05% and about 2%, xii) the level of DHA in the total fatty acid content of the extracted lipid is about 8%, about 9%, about 10%, about 11%, about 12%, about 13%, about 14%, about 15%, about 16%, about 17%, about 18%, between about 8% and 20%, between about 10% and 20%, between about 11% and 20%, between about 10% and about 16%, or between about 14% and 20%, xiii) the lipid comprises ω6-docosapentaenoic acid ($22{:}5^{\Delta4,7,10,13,16}$) in its fatty acid content, xiv) the lipid is essentially free of ω6-docosapentaenoic acid ($22{:}5^{\Delta4,7,10,13,16}$) in its fatty acid content, xv) the lipid is essentially free of SDA, EPA and ETA in its fatty acid content, xvi) the level of total saturated fatty acids in the total fatty acid content of the extracted lipid is between about 4% and about 25%, between about 4% and about 20%, between about 6% and about 20%, between about 4% and about 60%, between about 30% and about 60%, or between about 45% and about 60%, xvii) the level of total monounsaturated fatty acids in the total fatty acid content of the extracted lipid is between about 4% and about 35%, between about 8% and about 25%, or between 8% and about 22%, xviii) the level of total polyunsaturated fatty acids in the total fatty acid content of the extracted lipid is between about 20% and about 75%, between about 50% and about 75%, or between about 60% and about 75%, xix) the level of total ω6 fatty acids in the total fatty acid content of the extracted lipid is between about 35% and about 50%, between about 20% and about 35%, between about 6% and 20%, less than about 20%, less than about 16%, less than about 10%, between about 1% and about 16%, between about 2% and about 10%, or between about 4% and about 10%, xx) the level of new ω6 fatty acids in the total fatty acid content of the extracted lipid is less than about 10%, less than about 8%, less than about 6%, less than 4%, between about 1% and about 20%, between about 1% and about 10%, between about 0.5% and about 8%, or between about 0.5% and 4%, xxi) the level of total ω3 fatty acids in the total fatty acid content of the extracted lipid is between 36% and about 65%, between about 40% and about 60%, between about 20% and about 35%, between about 10% and about 20%, about 25%, about 30%, about 35% or about 40%, xxii) the level of new ω3 fatty acids in the total fatty acid content of the extracted lipid is between about 9% and about 33%, between about 10% and about 20%, between about 20% and about 30%, between about 12% and about 25%, about 13%, about 15%, about 17% or about 20%, xxiii) the ratio of total ω6 fatty acids:total ω3 fatty acids in the fatty acid content of the extracted lipid is between about 1.0 and about 3.0, between about 0.1 and about 1, between about 0.1 and about 0.5, less than about 0.50, less than about 0.40, less than about 0.30, less than about 0.20, less than about 0.15, about 1.0, about 0.1 or about 0.2, xxiv) the ratio of new ω6 fatty acids:new ω3 fatty acids in the fatty acid content of the extracted lipid is between about 1.0 and about 3.0, between about 0.1 and about 1, between about 0.1 and about 0.5, less than about 0.50, less than about 0.40, less than about 0.30, less than about 0.20, less than about 0.15, about 0.1, about 0.2 or about 1.0, xxv) the fatty acid composition of the lipid is based on an efficiency of conversion of oleic acid to LA by Δ12-desaturase of at least about 60%, at least about 70%, at least about 80%, between about 60% and about 98%, between about 70% and about 95%, or between about 75% and about 90%, xxvi) the fatty acid composition of the lipid is based on an efficiency of conversion of ALA to SDA by Δ6-desaturase of at least about 30%, at least about 40%, at least about 50%, at least about 60%, at least about 70%, between about 30% and about 70%, between about 35% and about 60%, or between about 50% and about 70%, xxvii) the fatty acid composition of the lipid is based on an efficiency of conversion of SDA to ETA acid by Δ6-elongase of at least about 60%, at least about 70%, at least about 75%, between about 60% and about 95%, between about 70% and about 88%, or between about 75% and about 85%, xxviii) the fatty acid composition of the lipid is based on an efficiency of conversion of ETA to EPA by Δ5-desaturase of at least about 60%, at least about 70%, at least about 75%, between about 60% and about 99%, between about 70% and about 99%, or between about 75% and about 98%, xxix) the fatty acid composition of the lipid is based on an efficiency of conversion of EPA to DPA by Δ5-elongase of at least about 80%, at least about 85%, at least about 90%, between about 50% and about 95%, or between about 85% and about 95%, xxx) the fatty acid composition of the lipid is based on an efficiency of conversion of DPA to DHA by Δ4-desaturase of at least about 80%, at least about 90%, at least about 93%, between about 50% and about 95%, between about 80% and about 95%, or between about 85% and about 95%, xxxi) the fatty acid composition of the lipid is based on an efficiency of conversion of oleic acid to DHA of at least about 10%, at least about 15%, at least about 20%, between about 10% and about 50%, between about 10% and about 30%, or between about 10% and about 25%, xxxii) the fatty acid composition of the lipid is based on an efficiency of conversion of LA to DHA of at least about 15%, at least about 20%, at least about 22%, at least about 25%, between about 15% and about 50%, between about 20% and about 40%, or between about 20% and about 30/%, xxxiii) the fatty acid composition of the lipid is based on an efficiency of conversion of ALA to DHA of at least about 17%, at least about 22%, at least about 24%, between about 17% and about 55%, between about 22% and about 35%, or between about 24% and about 35%, xxxiv) the total fatty acid in the extracted lipid has less than 1% C20:1, xxxv) the triacylglycerol (TAG) content of the lipid is at least about 70%, at least about 80%, at least about 90%, at least 95%, between about 70% and about 99%, or between about 90% and about 99%, xxxvi) the lipid comprises diacylglycerol (DAG), xxxvii) the lipid comprises less than about 10%, less than about 5%, less than about 1%, or between about 0.001% and about 5%, free (non-esterified) fatty acids and/or phospholipid, or is essentially free thereof, xxxviii) at least 70%, or at least 80%, of the DHA esterified in the form of TAG is in the sn-1 or sn-3 position of the TAG, xxxix) the most abundant DHA-containing TAG species in the lipid is DHA/18:3/18:3 (TAG 58:12), and xl) the lipid comprises tri-DHA TAG (TAG 66:18).

In another embodiment, the extracted lipid is in the form of an oil, wherein at least about 90%, or least about 95%, at least about 98%, or between about 95% and about 98%, by weight of the oil is the lipid.

In a preferred embodiment, the lipid or oil, preferably a seedoil, has the following features: in the total fatty acid content of the lipid or oil, the level of DHA is between about 7% and 20%, the level of palmitic acid is between about 2% and about 16%, the level of myristic acid is less than about 6%, the level of oleic acid is between about 1% and about 30%, the level of LA is between about 4% and about 35%, ALA is present, GLA is present, the level of SDA is between about 0.05% and about 7%, the level of ETA is less than about 4%, the level of EPA is between about 0.05% and about 10%, the level of DPA is between about 0.05% and about 8%, the level of total saturated fatty acids in the total fatty acid content of the extracted lipid is between about 4% and about 25%, the level of total monounsaturated fatty acids in the total fatty acid content of the extracted lipid is between about 4% and about 35%, the level of total polyunsaturated fatty acids in the total fatty acid content of the extracted lipid is between about 20% and about 75%, the ratio of total ω6 fatty acids:total ω3 fatty acids in the fatty acid content of the extracted lipid is between about 0.05 and about 3.0, the ratio of new ω6 fatty acids:new ω3 fatty acids in the fatty acid content of the extracted lipid is between about 0.03 and about 3.0, preferably less than about 0.50, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of EPA to DPA by Δ5-elongase of between about 50% and about 95%, an efficiency of conversion of DPA to DHA by Δ4-desaturase of between about 50% and about 95%, an efficiency of conversion of oleic acid to DHA of at least about 10%, and the triacylglycerol (TAG) content of the lipid is at least about 70%, and optionally the lipid is essentially free of cholesterol and/or the lipid comprises tri-DHA TAG (TAG 66:18).

In a more preferred embodiment, the lipid or oil, preferably a seedoil, has the following features: in the total fatty acid content of the lipid, the level of DHA is between about 7% and 20%, the level of palmitic acid is between about 2% and about 16%, the level of myristic acid is less than about 2%, the level of oleic acid is between about 1% and about 30%, the level of LA is between about 4% and about 35%, the level of ALA is between about 7% and about 40%, the level of GLA is less than about 4%, the level of SDA is between about 0.05% and about 7%, the level of ETA is less than about 4%, the level of ETrA is between about 0.05% and about 4%, the level of EPA is between about 0.05% and about 10%, the level of DPA is between about 0.05% and about 8%, the level of total saturated fatty acids in the total fatty acid content of the extracted lipid is between about 4% and about 25%, the level of total monounsaturated fatty acids in the total fatty acid content of the extracted lipid is between about 4% and about 35%, the level of total polyunsaturated fatty acids in the total fatty acid content of the extracted lipid is between about 20% and about 75%, the level of new ω6 fatty acids in the total fatty acid content of the extracted lipid is between about 0.5% and about 10%, the level of total ω3 fatty acids in the total fatty acid content of the extracted lipid is between 36% and about 75%, the level of new ω3 fatty acids in the total fatty acid content of the extracted lipid is between about 9% and about 33%, the ratio of total ω6 fatty acids:total ω3 fatty acids in the fatty acid content of the extracted lipid is between about 0.05 and about 3.0, the ratio of new ω6 fatty acids:new ω3 fatty acids in the fatty acid content of the extracted lipid is between about 0.03 and about 3.0, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of ETA to EPA by Δ5-desaturase of at least about 60%, an efficiency of conversion of EPA to DPA by Δ5-elongase of between about 50% and about 95%, an efficiency of conversion of DPA to DHA by Δ4-desaturase of between about 50% and about 95%, an efficiency of conversion of oleic acid to DHA of at least about 10%, an efficiency of conversion of LA to DHA of at least about 15%, an efficiency of conversion of ALA to DHA of at least about 17%, and the total fatty acid content in the extracted lipid has less than 1% C20:1, the triacylglycerol (TAG) content of the lipid is at least about 70%, the lipid is essentially free of cholesterol, and the lipid comprises tri-DHA TAG (TAG 66:18). Preferably, the lipid or oil is canola oil and/or has not been treated with a transesterification process after it was extracted from the plant or plant part. In a particular embodiment, the lipid or canola oil may subsequently be treated to convert the fatty acids in the oil to alkyl esters such as methyl or ethyl esters. Further treatment may be applied to enrich the lipid or oil for the DHA.

In an embodiment, the lipid or oil, preferably a seedoil, has the following features: in the total fatty acid content of the lipid, the level of DHA is between about 7% and 20%, the level of palmitic acid is between about 2% and about 16%, the level of myristic acid is less than about 2%, the level of oleic acid is between about 30% and about 60%, preferably between about 45% and about 60%, the level of LA is between about 4% and about 20%, the level of ALA is between about 2% and about 16%, the level of GLA is less than about 3%, the level of SDA is less than about 3%, the level of ETA is less than about 4%, the level of ETrA less than about 2%, the level of EPA is less than about 4%, the level of DPA is less than about 4%, the level of total saturated fatty acids in the total fatty acid content of the extracted lipid is between about 4% and about 25%, the level of total monounsaturated fatty acids in the total fatty acid content of the extracted lipid is between about 30% and about 60%, or between about 40% and about 60%, the level of total polyunsaturated fatty acids in the total fatty acid content of the extracted lipid is between about 20% and about 75%, the level of new ω6 fatty acids in the total fatty acid content of the extracted lipid is between about 0.5% and about 10%, the level of total ω3 fatty acids in the total fatty acid content of the extracted lipid is between about 10% and about 20%, the level of new ω3 fatty acids in the total fatty acid content of the extracted lipid is between about 9% and about 20%, the ratio of total ω6 fatty acids:total ω3 fatty acids in the fatty acid content of the extracted lipid is between about 0.05 and about 3.0, preferably less than about 0.50, the ratio of new ω6 fatty acids:new ω3 fatty acids in the fatty acid content of the extracted lipid is between about 0.03 and about 3.0, the triacylglycerol (TAG) content of the lipid is at least about 70%, the lipid is essentially free of cholesterol, and the lipid comprises tri-DHA TAG (TAG 66:18). Preferably, the lipid or oil is essentially free of SDA, EPA and ETA and/or is canola oil and/or has not been treated with a transesterification process after it was extracted from the plant or plant part. In a particular embodiment, the lipid or canola oil may subsequently be treated to convert the fatty acids in the oil to alkyl esters such as methyl or ethyl esters. Further treatment may be applied to enrich the lipid or oil for the DHA.

In a further preferred embodiment, the lipid or oil, preferably a seedoil, has the following features: in the total fatty acid content of the lipid or oil, the level of DHA is between about 7% and 20%, the level of palmitic acid is between about 2% and about 16%, the level of myristic acid is less than about 6%, the level of oleic acid is between about 1% and about 30%, the level of LA is between about 4% and about 35%, ALA is present, GLA is present, the level of SDA is between about 0.05% and about 7%, the level of ETA is less than about 6%, the level of EPA is between about 0.05% and about 10%, the level of DPA is between about 0.05% and about 8%.

In a further embodiment, the extracted lipid further comprises one or more sterols, preferably plant sterols.

In another embodiment, the extracted lipid is in the form of an oil, and comprises less than about 10 mg of sterols/g of oil, less than about 7 mg of sterols/g of oil, between about 1.5 mg and about 10 mg of sterols/g of oil, or between about 1.5 mg and about 7 mg of sterols/g of oil.

Examples of sterols which can be in the extracted lipid include, but are not necessarily limited to, one or more or all of campesterol/24-methylcholesterol, Δ5-stigmasterol, eburicol, β-sitosterol/24-ethylcholesterol, Δ5-avenasterol/isofucosterol, Δ7-stigmasterol/stigmast-7-en-33-ol, and Δ7-avenasterol.

In an embodiment, the plant species is one listed in Table 26, such as canola, and the level of sterols are about the same as that listed in Table 26 for that particular plant species.

In an embodiment, the extracted lipid comprises less than about 0.5 mg of cholesterol/g of oil, less than about 0.25 mg of cholesterol/g of oil, between about 0 mg and about 0.5 mg of cholesterol/g of oil, or between about 0 mg and about 0.25 mg of cholesterol/g of oil, or which is essentially free of cholesterol.

In a further embodiment, the lipid is an oil, preferably oil from an oilseed. Examples of such oils include, but are not limited to, *Brassica* sp. oil such as canola oil. *Gossypium hirsutum* oil, *Linum usitatissimum* oil, *Helianthus* sp. oil, *Carthamus tinctorius* oil, *Glycine max* oil, *Zea mays* oil, *Arabidopsis thaliana* oil, *Sorghum bicolor* oil, *Sorghum vulgare* oil, *Avena sativa* oil, *Trifolium* sp. oil, *Elaesis guineenis* oil, *Nicotiana benthamiana* oil, *Hordeum vulgare* oil, *Lupinus angustifolius* oil, *Oryza sativa* oil, *Oryza glaberrima* oil, *Camelina sativa* oil, *Crambe abyssinica* oil, *Miscanthus×giganteus* oil, or *Miscanthus sinensis* oil.

Also provided is extracted plant lipid, preferably extracted canola seedoil, comprising fatty acids in an esterified form, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of stearidonic acid (SDA), eicosapentaenoic acid (EPA), docosapentaenoic acid (DPA) and eicosatetraenoic acid (ETA), wherein lipid has the following features in the total fatty acid content of the lipid;

i) the level of DHA is about 3%, about 4%, about 5%, about 6% or about 7%,
ii) the level of palmitic acid is between about 2% and about 16%,
iii) the level of myristic acid is less than about 2%,
iv) the level of oleic acid is between about 30% and about 60%, preferably between about 45% and about 60%,
v) the level of LA is between about 4% and about 20%,
vi) the level of ALA is between about 2% and about 16%,
vii) the level of GLA is less than about 4%,
viii) the level of SDA is less than about 6%, or less than about 4%,
ix) the level of ETA is less than about 6%, or less than about 4%,
x) the level of ETrA less than about 1%,
xi) the level of EPA is less than about 10% and/or the level of EPA is 0.5-2.0 fold the level of DHA,
xii) the level of DPA is less than about 4%,
xiii) the level of total saturated fatty acids in the total fatty acid content of the extracted lipid is between about 4% and about 25%,
xiv) the level of total monounsaturated fatty acids in the total fatty acid content of the extracted lipid is between about 30% and about 70%,
xv) the level of total polyunsaturated fatty acids in the total fatty acid content of the extracted lipid is between about 15% and about 75%, preferably between about 15% and about 30%,
xvi) the level of new ω6 fatty acids in the total fatty acid content of the extracted lipid is between about 0.5% and about 10%,
xvii) the level of total ω3 fatty acids in the total fatty acid content of the extracted lipid is between about 10% and about 20%,
xviii) the level of new ω3 fatty acids in the total fatty acid content of the extracted lipid is between about 3% and about 20%,
xix) the ratio of total ω6 fatty acids:total ω3 fatty acids in the fatty acid content of the extracted lipid is between about 0.05 and about 3.0, preferably less than about 0.50,
xx) the ratio of new ω6 fatty acids:new ω3 fatty acids in the fatty acid content of the extracted lipid is between about 0.03 and about 3.0,
xxi) the triacylglycerol (TAG) content of the lipid is at least about 70%, and
xxii) the lipid is essentially free of cholesterol. In an embodiment, the lipid comprises tri-DHA TAG (TAG 66:18). More preferably, the lipid is essentially free of SDA and ETA, and/or has not been treated with a transesterification process after it was extracted from the plant or plant part.

In another aspect, provided is extracted plant lipid, comprising fatty acids in an esterified form, the fatty acids comprising oleic acid, palmitic acid, ω6 fatty acids which comprise linoleic acid (LA), ω3 fatty acids which comprise α-linolenic acid (ALA) and docosahexaenoic acid (DHA), and one or more of stearidonic acid (SDA), eicosapentaenoic acid (EPA), docosapentaenoic acid (DPA) and eicosatetraenoic acid (ETA), wherein (i) the level of DHA in the total fatty acid content of the extracted lipid is between 7% and 20%, (ii) the level of palmitic acid in the total fatty acid content of the extracted lipid is between 2% and 16%, (iii) the level of myristic acid (C14:0) in the total fatty acid content of the extracted lipid is less than 6%, (iv) the level of oleic acid in the total fatty acid content of the extracted lipid is between 1% and 30% or between 30% and 60%, (v)

the level of linoleic acid (LA) in the total fatty acid content of the extracted lipid is between 4% and 35%, (vi) the level of α-linolenic acid (ALA) in the total fatty acid content of the extracted lipid is between 4% and 40%, (vii) the level of eicosatrienoic acid (ETrA) in the total fatty acid content of the extracted lipid is less than 4%, (viii) the level of total saturated fatty acids in the total fatty acid content of the extracted lipid is between 4% and 25%, (ix) the ratio of total ω6 fatty acids:total ω3 fatty acids in the fatty acid content of the extracted lipid is between 1.0 and 3.0 or between 0.1 and 1, (x) the triacylglycerol (TAG) content of the lipid is at least 70%, and (xi) at least 70% of the DHA esterified in the form of TAG is in the sn-1 or sn-3 position of the TAG. In an embodiment, one or more or all of the following features i) the level of palmitic acid in the total fatty acid content of the extracted lipid is between 2% and 15%, ii) the level of myristic acid (C14:0) in the total fatty acid content of the extracted lipid is less than 1%, iii) the level of oleic acid in the total fatty acid content of the extracted lipid is between about 3% and about 30%, between about 6% and about 30%, between 1% and about 20%, between about 45% and about 60%, or is about 30%, iv) the level of linoleic acid (LA) in the total fatty acid content of the extracted lipid is between about 4% and about 20%, or between about 4% and 17%, v) the level of α-linolenic acid (ALA) in the total fatty acid content of the extracted lipid is between about 7% and about 40%, between about 10% and about 35%, between about 20% and about 35%, or between about 4% and 16%, vi) the level of γ-linolenic acid (GLA) in the total fatty acid content of the extracted lipid is less than 4%, less than about 3%, less than about 2%, less than about 1%, less than about 0.5%, between 0.05% and 7%, between 0.05% and 4%, or between 0.05% and about 3%, or between 0.05% and about 2%, vii) the level of stearidonic acid (SDA) in the total fatty acid content of the extracted lipid is less than about 4%, less than about 3%, between about 0.05% and about 7%, between about 0.05% and about 4%, between about 0.05% and about 3%, or between 0.05% and about 2%, viii) the level of eicosatetraenoic acid (ETA) in the total fatty acid content of the extracted lipid is less than about 4%, less than about 1%, less than about 0.5%, between about 0.05% and about 5%, between about 0.05% and about 4%, between about 0.05% and about 3%, or between about 0.05% and about 2%, ix) the level of eicosatrienoic acid (ETrA) in the total fatty acid content of the extracted lipid is less than about 2%, less than about 1%, between 0.05% and 4%, between 0.05% and 3%, or between 0.05% and about 2%, or between 0.05% and about 1%, x) the level of eicosapentaenoic acid (EPA) in the total fatty acid content of the extracted lipid is less than 4%, less than about 3%, less than about 2%, between 0.05% and 10%, between 0.05% and 5%, or between 0.05% and about 3%, or between 0.05% and about 2%, xi) the level of docosapentaenoic acid (DPA) in the total fatty acid content of the extracted lipid is less than 4%, less than about 3%, less than about 2%, between 0.05% and 8%, between 0.05% and 5%, or between 0.05% and about 3%, or between 0.05% and about 2%, xii) the level of DHA in the total fatty acid content of the extracted lipid is about 8%, about 9%, about 10%, about 11%, about 12%, about 13%, about 14%, about 15%, about 16%, about 17%, about 18%, between about 8% and 20%, between about 10% and 20%, between about 11% and 20%, between about 10% and about 16%, or between about 14% and 20%, xiii) the lipid comprises ω6-docosapentaenoic acid ($22{:}5^{\Delta 4,7,10,13,16}$) in its fatty acid content, xiv) the lipid is essentially free of ω6-docosapentaenoic acid ($22{:}5^{\Delta 4,7,10,13,16}$) in its fatty acid content, xv) the lipid is essentially free of SDA, EPA and ETA in its fatty acid content, xvi) the level of total saturated fatty acids in the total fatty acid content of the extracted lipid is between about 4% and about 20%, or between about 6% and about 20%, xvii) the level of total monounsaturated fatty acids in the total fatty acid content of the extracted lipid is between about 4% and about 35%, between about 8% and about 25%, or between 8% and about 22%, xviii) the level of total polyunsaturated fatty acids in the total fatty acid content of the extracted lipid is between about 20% and about 75%, between about 50% and about 75%, or between about 60% and about 75%, xix) the level of total ω6 fatty acids in the total fatty acid content of the extracted lipid is between about 35% and about 50%, between about 20% and about 35%, between about 6% and 20%, less than 20%, less than about 16%, less than about 10%, between about 1% and about 16%, between about 2% and about 10%, or between about 4% and about 10%, xx) the level of new ω6 fatty acids in the total fatty acid content of the extracted lipid is less than about 10%, less than about 8%, less than about 6%, less than 4%, between about 1% and about 20%, between about 1% and about 10%, between about 0.5% and about 8%, or between about 0.5% and 4%, xxi) the level of total ω3 fatty acids in the total fatty acid content of the extracted lipid is between 36% and about 65%, between 40% and about 60%, between about 20% and about 35%, between about 10% and about 20%, about 25%, about 30%, about 35% or about 40%, xxii) the level of new ω3 fatty acids in the total fatty acid content of the extracted lipid is between 9% and about 33%, between about 10% and about 20%, between about 20% and about 30%, between about 12% and about 25%, about 13%, about 15%, about 17% or about 20%, xxiii) the ratio of total ω6 fatty acids:total ω3 fatty acids in the fatty acid content of the extracted lipid is between about 0.1 and about 0.5, less than about 0.50, less than about 0.40, less than about 0.30, less than about 0.20, less than about 0.15, about 1.0, about 0.1 or about 0.2, xxiv) the ratio of new ω6 fatty acids:new ω3 fatty acids in the fatty acid content of the extracted lipid is between about 1.0 and about 3.0, between about 0.1 and about 1, between about 0.1 and about 0.5, less than about 0.50, less than about 0.40, less than about 0.30, less than about 0.20, less than about 0.15, about 0.1, about 0.2 or about 1.0, xxv) the fatty acid composition of the lipid is based on an efficiency of conversion of oleic acid to DHA of at least about 10%, at least about 15%, at least about 20%, between about 10% and about 50%, between about 10% and about 30%, or between about 10% and about 25%, xxvi) the fatty acid composition of the lipid is based on an efficiency of conversion of LA to DHA of at least about 15%, at least about 20%, at least about 22%, at least about 25%, between about 15% and about 50%, between about 20% and about 40%, or between about 20% and about 30%, xxvii) the fatty acid composition of the lipid is based on an efficiency of conversion of ALA to DHA of at least about 17%, at least about 22%, at least about 24%, between about 17% and about 55%, between about 22% and about 35%, or between about 24% and about 35%, xxviii) the total fatty acid in the extracted lipid has less than 1% C20:1, xxix) the triacylglycerol (TAG) content of the lipid is at least about 80%, at least about 90%, at least 95%, between about 70% and about 99%, or between about 90% and about 99%, xxx) the lipid comprises diacylglycerol (DAG), xxxi) the lipid comprises less than about 10%, less than about 5%, less than about 1%, or between about 0.001% and about 5%, free (non-esterified) fatty acids and/or phospholipid, or is essentially free thereof, xxxii) at least 80%, of the DHA esterified in the form of TAG is in the sn-1 or sn-3 position of the TAG, xxxiii) the most abundant DHA-containing TAG species in the lipid is DHA/18:3/18:3 (TAG 58:12), and xxxiv) the lipid comprises tri-DHA TAG (TAG 66:18).

With specific regard to the above aspect, in an embodiment i) the lipid is in the form of an oil, wherein the oil comprises one or more sterols such as one or more or all of campesterol, Δ5-stigmasterol, eburicol, β-sitosterol, Δ5-avenasterol, Δ7-stigmasterol and Δ7-avenasterol, and optionally the oil comprises less than 10 mg of sterols/g of oil and/or the oil is essentially free of cholesterol, and/or ii) the lipid is in the form of an oil from an oilseed such as oilseed is a *Brassica* sp oilseed or canola seed.

In another aspect, the present invention provides a process for producing extracted plant lipid, comprising the steps of i) obtaining a plant part comprising lipid, the lipid comprising fatty acids in an esterified form, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of eicosapentaenoic acid (EPA), stearidonic acid (SDA), docosapentaenoic acid (DPA) and eicosatetraenoic acid (ETA), wherein the level of DHA in the total fatty acid content of extractable lipid in the plant part is about 7% to 20%, and ii) extracting lipid from the plant part, wherein the level of DHA in the total fatty acid content of the extracted lipid is about 7% to 20%.

In a preferred embodiment, the extracted lipid has one or more of the features defined above.

In an embodiment, wherein the plant part is a seed, preferably an oilseed. Examples of such seeds include, but are not limited to, *Brassica* sp., *Gossypium hirsutum, Linum usitatissimum, Helianthus* sp., *Carthamus tinctorius, Glycine max, Zea mays, Arabidopsis thaliana, Sorghum bicolor, Sorghum vulgare, Avena sativa, Trifolium* sp., *Elaesis guineenis, Nicotiana benthamiana, Hordeum vulgare, Lupinus angustifolius, Oryza sativa, Oryza glaberrima, Camelina sativa*, or *Crambe abyssinica*, preferably a *Brassica napus. B. juncea* or *C. sativa* seed.

In another embodiment, the seed comprises at least about 18 mg, at least about 22 mg, at least about 26 mg, between about 18 mg and about 100 mg, between about 22 mg and about 70 mg, or between about 24 mg and about 50 mg, of DHA per gram of seed.

In a further embodiment, the plant part comprises exogenous polynucleotides encoding one of the following sets of enzymes;

i) an ω3-desaturase, a Δ6-desaturase, a Δ5-desaturase, a Δ4-desaturase, a Δ6-elongase and a Δ5-elongase, ii) a Δ15-desaturase, a Δ6-desaturase, a Δ5-desaturase, a Δ4-desaturase, a Δ6-elongase and a Δ5-elongase, iii) a Δ12-desaturase, a Δ6-desaturase, a Δ5-desaturase, a Δ4-desaturase, a Δ6-elongase and an Δ5-elongase, iv) a Δ12-desaturase, a ω3-desaturase or a Δ15-desaturase, a Δ6-desaturase, a Δ5-desaturase, a Δ4-desaturase, a Δ6-elongase and an Δ5-elongase, v) an ω3-desaturase, a Δ8-desaturase, a Δ5-desaturase, a Δ4-desaturase, a Δ9-elongase and an Δ5-elongase, vi) a Δ15-desaturase, a Δ8-desaturase, a Δ5-desaturase, a Δ4-desaturase, a Δ9-elongase and a Δ5-elongase, vii) a Δ12-desaturase, a Δ8-desaturase, a Δ5-desaturase, a Δ4-desaturase, a Δ9-elongase and an Δ5-elongase, or viii) a Δ12-desaturase, a ω3-desaturase or a Δ15-desaturase, a Δ8-desaturase, a Δ5-desaturase, a Δ4-desaturase, a Δ9-elongase and an Δ5-elongase, and wherein each polynucleotide is operably linked to one or more promoters that are capable of directing expression of said polynucleotides in a cell of the plant part.

In yet a further embodiment, the plant part has one or more or all of the following features i) the Δ12-desaturase converts oleic acid to linoleic acid in one or more cells of the plant with an efficiency of at least about 60%, at least about 70%, at least about 80%, between about 60% and about 98%, between about 70% and about 95%, or between about 75% and about 90%, ii) the ω3-desaturase converts ω6 fatty acids to ω3 fatty acids in one or more cells of the plant with an efficiency of at least about 65%, at least about 75%, at least about 85%, between about 65% and about 95%, between about 75% and about 95%, or between about 80% and about 95%, iii) the Δ6-desaturase converts ALA to SDA in one or more cells of the plant with an efficiency of at least about 30%, at least about 40%, at least about 50%, at least about 60%, at least about 70%, between about 30% and about 70%, between about 35% and about 60%, or between about 50% and about 70%, iv) the Δ6-desaturase converts linoleic acid to γ-linolenic acid in one or more cells of the plant with an efficiency of less than about 5%, less than about 2.5%, less than about 1%, between about 0.1% and about 5%, between about 0.5% and about 2.5%, or between about 0.5% and about 1%, v) the Δ6-elongase converts SDA to ETA in one or more cells of the plant with an efficiency of at least about 60%, at least about 70%, at least about 75%, between about 60% and about 95%, between about 70% and about 88%, or between about 75% and about 85%, vi) the Δ5-desaturase converts ETA to EPA in one or more cells of the plant with an efficiency of at least about 60%, at least about 70%, at least about 75%, at least about 80%, at least about 90%, between about 60% and about 99%, between about 70% and about 99%, or between about 75% and about 98%, vii) the Δ5-elongase converts EPA to DPA in one or more cells of the plant with an efficiency of at least about 80%, at least about 85%, at least about 90%, between about 50% and about 95%, or between about 85% and about 95%, viii) the Δ4-desaturase converts DPA to DHA in one or more cells of the plant with an efficiency of at least about 80%, at least about 90%, at least about 93%, between about 50% and about 95%, between about 80% and about 95%, or between about 85% and about 95%, ix) the efficiency of conversion of oleic acid to DHA in one or more cells of the plant part is at least about 10%, at least about 15%, at least about 20%, between about 10% and about 50%, between about 10% and about 30%, or between about 10% and about 25%, x) the efficiency of conversion of LA to DHA in one or more cells of the plant part is at least about 15%, at least about 20%, at least about 22%, at least about 25%, between about 15% and about 50%, between about 20% and about 40%, or between about 20% and about 30%, xi) the efficiency of conversion of ALA to DHA in one or more cells of the plant part is at least about 17%, at least about 22%, at least about 24%, between about 17% and about 55%, between about 22% and about 35%, or between about 24% and about 35%, xii) one or more cells of the plant part comprise at least about 15%, at least about 20%, between about 15% and about 30%, or between about 22.5% and about 27.5%, more ω3 fatty acids than corresponding cells lacking the exogenous polynucleotides, xiii) the Δ6-desaturase preferentially desaturates α-linolenic acid (ALA) relative to linoleic acid (LA), xiv) the Δ6-elongase also has Δ9-elongase activity, xv) the Δ12-desaturase also has Δ15-desaturase activity, xvi) the Δ6-desaturase also has Δ8-desaturase activity, xvii) the Δ8-desaturase also has Δ6-desaturase activity or does not have Δ6-desaturase activity, xviii) the Δ15-desaturase also has ω3-desaturase activity on GLA, xix) the ω3-desaturase also has Δ15-desaturase activity on LA, xx) the ω3-desaturase desaturates both LA and/or GLA, xxi) the ω3-desaturase preferentially desaturates GLA relative to LA, xxii) the level of DHA in the plant part is based on an efficiency of conversion of oleic acid to DHA in the plant part of at least about 10%, at least about 15%, at least about 20%, between about 10% and about 50%, between about 15% and about 30%, or between about 20% and about 25%, xxiii) the level of DHA in the plant part is based on an efficiency of conversion of LA to DHA in the plant part of at least about 15%, at least about 20%, at least about 22%, between about 15% and about 60%, between about 20% and about 40%, or between about 22% and about 30%, xxiv) the level of DHA in the plant part is based on an efficiency of conversion of ALA to DHA in the plant part of at least about 17%, at least about 22%, at least about 24%, between about 17% and about 65%, between about 22% and about 35%, or between about 24% and about 35% xxx) one or more or all of the desaturases have greater activity on an acyl-CoA substrate than a corresponding acyl-PC substrate, xxxi) the Δ6-desaturase has greater Δ6-desaturase activity on ALA than LA as fatty acid substrate, xxxii) the Δ6-desaturase has greater Δ6-desaturase activity on ALA-CoA as fatty acid substrate than on ALA joined to the sn-2 position of PC as fatty acid substrate, xxxiii) the Δ6-desaturase has at least about a 2-fold greater Δ6-desaturase activity, at least 3-fold greater activity, at least 4-fold greater activity, or at least 5-fold greater activity, on ALA as a substrate compared to LA, xxxiv) the Δ6-desaturase has greater activity on ALA-CoA as fatty acid substrate than on ALA joined to the sn-2 position of PC as fatty acid substrate, xxxv) the Δ6-desaturase has at least about a 5-fold greater Δ6-desaturase activity or at least 10-fold greater activity, on ALA-CoA as fatty acid substrate than on ALA joined to the sn-2 position of PC as fatty acid substrate, xxxvi) the desaturase is a front-end desaturase, xxxvii) the Δ6-desaturase has no detectable Δ5-desaturase activity on ETA.

In yet a further embodiment, the plant part has one or more or all of the following features i) the Δ12-desaturase comprises amino acids having a sequence as provided in SEQ ID NO:10, a biologically active fragment thereof, or an amino acid sequence which is at least 50% identical to SEQ ID NO: 10, ii) the ω3-desaturase comprises amino acids having a sequence as provided in SEQ ID NO:12, a biologically active fragment thereof, or an amino acid sequence which is at least 50% identical to SEQ ID NO: 12, iii) the Δ6-desaturase comprises amino acids having a sequence as provided in SEQ ID NO:16, a biologically active fragment thereof, or an amino acid sequence which is at least 50% identical to SEQ ID NO: 16, iv) the Δ6-elongase comprises amino acids having a sequence as provided in SEQ ID NO:25, a biologically active fragment thereof such as SEQ ID NO:26, or an amino acid sequence which is at least 50% identical to SEQ ID NO:25 and/or SEQ ID NO:26, v) the Δ5-desaturase comprises amino acids having a sequence as provided in SEQ ID NO:30, a biologically active fragment thereof, or an amino acid sequence which is at least 50% identical to SEQ ID NO:30, vi) the Δ5-elongase comprises amino acids having a sequence as provided in SEQ ID NO:37, a biologically active fragment thereof, or an amino acid sequence which is at least 50% identical to SEQ ID NO:37, vii) the Δ4-desaturase comprises amino acids having a sequence as provided in SEQ ID NO:41, a biologically active fragment thereof, or an amino acid sequence which is at least 50% identical to SEQ ID NO:41.

In an embodiment, the plant part further comprises an exogenous polynucleotide encoding a diacylglycerol acyltransferase (DGAT), monoacylglycerol acyltransferase (MGAT), glycerol-3-phosphate acyltransferase (GPAT), 1-acyl-glycerol-3-phosphate acyltransferase (LPAAT) preferably an LPAAT which can use a C22 polyunsaturated fatty acyl-CoA substrate, acyl-CoA:lysophosphatidylcholine acyltransferase (LPCAT), phospholipase $A_2$ ($PLA_2$), phospholipase C (PLC), phospholipase D (PLD), CDP-choline diacylglycerol choline phosphotransferase (CPT), phoshatidylcholine diacylglycerol acyltransferase (PDAT), phosphatidylcholine:diacylglycerol choline phosphotransferase (PDCT), acyl-CoA synthase (ACS), or a combination of two or more thereof.

In another embodiment, the plant part further comprises an introduced mutation or an exogenous polynucleotide which down regulates the production and/or activity of an endogenous enzyme in a cell of the plant part selected from FAE1, DGAT, MGAT, GPAT, LPAAT, LPCAT, $PLA_2$, PLC, PLD, CPT, PDAT, a thioesterase such as FATB, or a Δ12-desaturase, or a combination of two or more thereof.

In a further embodiment, at least one, or all, of the promoters are seed specific promoters. In an embodiment, at least one, or all, of the promoters have been obtained from oil biosynthesis or accumulation genes such as oleosin, or from seed storage protein genes such as conlinin.

In another embodiment, the promoter(s) directing expression of the exogenous polynucleotides encoding the Δ4-desaturase and the Δ5-elongase initiate expression of the polynucleotides in developing seed of the plant part before, or reach peak expression before, the promoter(s) directing expression of the exogenous polynucleotides encoding the Δ12-desaturase and the ω3-desaturase.

In a further embodiment, the exogenous polynucleotides are covalently linked in a DNA molecule, preferably a T-DNA molecule, integrated into the genome of cells of the plant part and preferably where the number of such DNA molecules integrated into the genome of the cells of the plant part is not more than one, two or three, or is two or three.

In yet another embodiment, the plant comprises at least two different, exogenous polynucleotides each encoding a Δ6-desaturase which have the same or different amino acid sequences.

In a further embodiment, the total oil content of the plant part comprising the exogenous polynucleotides is at least about 40%, or at least about 50%, or at least about 60%, or at least about 70%, or between about 50% and about 80% of the total oil content of a corresponding plant part lacking the exogenous polynucleotides. In these embodiments, the maximum oil content may be about 100% of the oil content of a corresponding wild-type plant part.

In another embodiment, the lipid is in the form of an oil, preferably a seedoil from an oilseed, and wherein at least about 90%, or about least 95%, at least about 98%, or between about 95% and about 98%, by weight of the lipid is triacylglycerols.

In a further embodiment, the process further comprises treating the lipid to increase the level of DHA as a percentage of the total fatty acid content. For example, the treatment is transesterification. For example, the lipid such as canola oil may be treated to convert the fatty acids in the oil to alkyl esters such as methyl or ethyl esters, which may then be fractionated to enrich the lipid or oil for the DHA.

Further, provided is a process for producing extracted plant lipid, comprising the steps of i) obtaining a plant part, preferably canola seed, comprising lipid, the lipid comprising fatty acids in an esterified form, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of eicosapentaenoic acid (EPA), stearidonic acid (SDA), docosapentaenoic acid (DPA) and eicosatetraenoic acid (ETA), wherein the level of DHA in the total fatty acid content of extractable lipid in the plant part is about 3%, about 4%, about 5%, about 6% or about 7%, and ii) extracting lipid from the plant part, wherein the extracted lipid has the following features in the total fatty acid content of the lipid;

i) the level of DHA is about 3%, about 4%, about 5%, about 6% or about 7%, ii) the level of palmitic acid is between about 2% and about 16%, iii) the level of myristic acid is less than about 2%, iv) the level of oleic acid is between about 30% and about 60%, preferably between about 45% and about 60%, v) the level of LA is between about 4% and about 20%, vi) the level of ALA is between about 2% and about 16%, vii) the level of GLA is less than about 4%, viii) the level of SDA is less than about 6%, or less than about 4%, ix) the level of ETA is less than about 6%, or less than about 4%, x) the level of ETrA less than about 1%, xi) the level of EPA is less than about 10% and/or the level of EPA is 0.5-2.0 fold the level of DHA, xii) the level of DPA is less than about 4%, xiii) the level of total saturated fatty acids in the total fatty acid content of the extracted lipid is between about 4% and about 25%, xiv) the level of total monounsaturated fatty acids in the total fatty acid content of the extracted lipid is between about 30% and about 70%, xv) the level of total polyunsaturated fatty acids in the total fatty acid content of the extracted lipid is between about 15% and about 75%, preferably between about 15% and about 30%, xvi) the level of new ω6 fatty acids in the total fatty acid content of the extracted lipid is between about 0.5% and about 10%, xvii) the level of total ω3 fatty acids in the total fatty acid content of the extracted lipid is between about 10% and about 20%, xviii) the level of new ω3 fatty acids in the total fatty acid content of the extracted lipid is between about 3% and about 20%, xix) the ratio of total ω6 fatty acids:total ω3 fatty acids in the fatty acid content of the extracted lipid is between about 0.05 and about 3.0, preferably less than about 0.50, xx) the ratio of new ω6 fatty acids:new ω3 fatty acids in the fatty acid content of the extracted lipid is between about 0.03 and about 3.0, xxi) the triacylglycerol (TAG) content of the lipid is at least about 70%, and xxii) the lipid is essentially free of cholesterol. In an embodiment, the lipid comprises tri-DHA TAG (TAG 66:18). More preferably, the lipid is essentially free of SDA and ETA, and/or has not been treated with a transesterification process after it was extracted from the plant or plant part.

Also provided is a process for producing extracted plant lipid, comprising the steps of i) obtaining a plant part comprising lipid, the lipid comprising fatty acids in an esterified form, the fatty acids comprising oleic acid, palmitic acid, ω6 fatty acids which comprise linoleic acid (LA), ω3 fatty acids which comprise α-linolenic acid (ALA) and docosahexaenoic acid (DHA), and one or more of stearidonic acid (SDA), eicosapentaenoic acid (EPA), docosapentaenoic acid (DPA) and eicosatetraenoic acid (ETA), wherein (i) the level of DHA in the total fatty acid content of the extracted lipid is between 7% and 20%, (ii) the level of palmitic acid in the total fatty acid content of the extracted lipid is between 2% and 16%, (iii) the level of myristic acid (C14:0) in the total fatty acid content of the extracted lipid is less than 6%, (iv) the level of oleic acid in the total fatty acid content of the extracted lipid is between 1% and 30% or between 30% and 60%, (v) the level of linoleic acid (LA) in the total fatty acid content of the extracted lipid is between 4% and 35%, (vi) the level of α-linolenic acid (ALA) in the total fatty acid content of the extracted lipid is between 4% and 40%, (vii) the level of eicosatrienoic acid (ETrA) in the total fatty acid content of the extracted lipid is less than 4%, (viii) the level of total saturated fatty acids in the total fatty acid content of the extracted lipid is between 4% and 25%, (ix) the ratio of total ω6 fatty acids:total ω3 fatty acids in the fatty acid content of the extracted lipid is between 1.0 and 3.0 or between 0.1 and 1, (x) the triacylglycerol (TAG) content of the lipid is at least 70%, and (xi) at least 70% of the DHA esterified in the form of TAG is in the sn-1 or sn-3 position of the TAG. %, and ii) extracting lipid from the plant part, wherein the level of DHA in the total fatty acid content of the extracted lipid is about 7% to 20%.

Also provided is lipid, or oil comprising the lipid, produced using a process of the invention.

In another aspect, the present invention provides a process for producing ethyl esters of polyunsaturated fatty acids, the process comprising transesterifying triacylglycerols in extracted plant lipid, wherein the extracted plant lipid comprises fatty acids esterified in the form, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of stearidonic acid (SDA), eicosapentaenoic acid (EPA), docosapentaenoic acid (DPA) and eicosatetraenoic acid (ETA), wherein the level of DHA in the total fatty acid content of the extracted lipid is about 7% to 20%, thereby producing the ethyl esters.

In a preferred embodiment, the extracted lipid has one or more of the features defined above.

In another aspect, the present invention provides a process for producing ethyl esters of polyunsaturated fatty acids, the process comprising transesterifying triacylglycerols in extracted plant lipid, wherein the extracted plant lipid comprises fatty acids esterified in the form of the triacylglycerols, the fatty acids comprising oleic acid, palmitic acid, ω6 fatty acids which comprise linoleic acid (LA), ω3 fatty acids which comprise α-linolenic acid (ALA) and docosahexaenoic acid (DHA), and one or more of stearidonic acid (SDA), eicosapentaenoic acid (EPA), docosapentaenoic acid (DPA) and eicosatetraenoic acid (ETA), wherein (i) the level of DHA in the total fatty acid content of the extracted lipid is about 3%, about 4%, about 5%, about 6% or between 7% and 20%, (ii) the level of palmitic acid in the total fatty acid content of the extracted lipid is between 2% and 16%, (iii) the level of myristic acid (C14:0) in the total fatty acid content of the extracted lipid is less than 6%, (iv) the level of oleic acid in the total fatty acid content of the extracted lipid is between 1% and 30% or between 30% and 60%, (v) the level of linoleic acid (LA) in the total fatty acid content of the extracted lipid is between 4% and 35%, (vi) the level of α-linolenic acid (ALA) in the total fatty acid content of the extracted lipid is between 4% and 40%, (vii) the level of eicosatrienoic acid (ETrA) in the total fatty acid content of the extracted lipid is less than 4%, (viii) the level of total saturated fatty acids in the total fatty acid content of the extracted lipid is between 4% and 25%, (ix) the ratio of total ω6 fatty acids:total ω3 fatty acids in the fatty acid content of the extracted lipid is between 1.0 and 3.0 or between 0.1 and 1, (x) the triacylglycerol (TAG) content of the lipid is at least 70%, and (xi) at least 70% of the DHA esterified in the form of TAG is in the sn-1 or sn-3 position of the TAG, thereby producing the ethyl esters. In an embodiment, the extracted plant lipid has one or more or all of the following features i) the level of palmitic acid in the total fatty acid content of the extracted lipid is between 2% and 15%, ii) the level of myristic acid (C14:0) in the total fatty acid content of the extracted lipid is less than 1%, xxxv) the level of oleic acid in the total fatty acid content of the extracted lipid is between about 3% and about 30%, between about 6% and about 30%, between 1% and about 20%, between about 45% and about 60%, or is about 30%, xxxvi) the level of linoleic acid (LA) in the total fatty acid content of the extracted lipid is between about 4% and about 20%, or between about 4% and 17%, xxxvii) the level of α-linolenic acid (ALA) in the total fatty acid content of the extracted lipid is between about 7% and about 40%, between about 10% and about 35%, between about 20% and about 35%, or between about 4% and 16%, xxxviii) the level of γ-linolenic acid (GLA) in the total fatty acid content of the extracted lipid is less than 4%, less than about 3%, less than about 2%, less than about 1%, less than about 0.5%, between 0.05% and 7%, between 0.05% and 4%, or between 0.05% and about 3%, or between 0.05% and about 2%, xxxix) the level of stearidonic acid (SDA) in the total fatty acid content of the extracted lipid is less than about 4%, less than about 3%, between about 0.05% and about 7%, between about 0.05% and about 4%, between about 0.05% and about 3%, or between 0.05% and about 2%, xl) the level of eicosatetraenoic acid (ETA) in the total fatty acid content of the extracted lipid is less than about 4%, less than about 1%, less than about 0.5%, between about 0.05% and about 5%, between about 0.05% and about 4%, between about 0.05% and about 3%, or between about 0.05% and about 2%, xli) the level of eicosatrienoic acid (ETrA) in the total fatty acid content of the extracted lipid is less than about 2%, less than about 1%, between 0.05% and 4%, between 0.05% and 3%, or between 0.05% and about 2%, or between 0.05% and about 1%, xlii) the level of eicosapentaenoic acid (EPA) in the total fatty acid content of the extracted lipid is less than 4%, less than about 3%, less than about 2%, between 0.05% and 10%, between 0.05% and 5%, or between 0.05% and about 3%, or between 0.05% and about 2%, xliii) the level of docosapentaenoic acid (DPA) in the total fatty acid content of the extracted lipid is less than 4%, less than about 3%, less than about 2%, between 0.05% and 8%, between 0.05% and 5%, or between 0.05% and about 3%, or between 0.05% and about 2%, xliv) the level of DHA in the total fatty acid content of the extracted lipid is about 8%, about 9%, about 10%, about 11%, about 12%, about 13%, about 14%, about 15%, about 16%, about 17%, about 18%, between about 8% and 20%, between about 10% and 20%, between about 11% and 20%, between about 10% and about 16%, or between about 14% and 20%, xlv) the lipid comprises ω6-docosapentaenoic acid ($22{:}5^{\Delta4,7,10,13,16}$) in its fatty acid content, xlvi) the lipid is essentially free of ω6-docosapentaenoic acid ($22{:}5^{\Delta4,7,10,13,16}$) in its fatty acid content, xlvii) the lipid is essentially free of SDA, EPA and ETA in its fatty acid content, xlviii) the level of total saturated fatty acids in the total fatty acid content of the extracted lipid is between about 4% and about 20%, or between about 6% and about 20%, xlix) the level of total monounsaturated fatty acids in the total fatty acid content of the extracted lipid is between about 4% and about 35%, between about 8% and about 25%, or between 8% and about 22%, l) the level of total polyunsaturated fatty acids in the total fatty acid content of the extracted lipid is between about 20% and about 75%, between about 50% and about 75%, or between about 60% and about 75%, li) the level of total ω6 fatty acids in the total fatty acid content of the extracted lipid is between about 35% and about 50%, between about 20% and about 35%, between about 6% and 20%, less than 20%, less than about 16%, less than about 10%, between about 1% and about 16%, between about 2% and about 10%, or between about 4% and about 10%, lii) the level of new ω6 fatty acids in the total fatty acid content of the extracted lipid is less than about 10%, less than about 8%, less than about 6%, less than 4%, between about 1% and about 20%, between about 1% and about 10%, between about 0.5% and about 8%, or between about 0.5% and 4%, liii) the level of total ω3 fatty acids in the total fatty acid content of the extracted lipid is between 36% and about 65%, between 40% and about 60%, between about 20% and about 35%, between about 10% and about 20%, about 25%, about 30%, about 35% or about 40%, liv) the level of new ω3 fatty acids in the total fatty acid content of the extracted lipid is between 9% and about 33%, between about 10% and about 20%, between about 20% and about 30%, between about 12% and about 25%, about 13%, about 15%, about 17% or about 20%, lv) the ratio of total ω6 fatty acids:total ω3 fatty acids in the fatty acid content of the extracted lipid is between about 0.1 and about 0.5, less than about 0.50, less than about 0.40, less than about 0.30, less than about 0.20, less than about 0.15, about 1.0, about 0.1 or about 0.2, lvi) the ratio of new ω6 fatty acids:new ω3 fatty acids in the fatty acid content of the extracted lipid is between about 1.0 and about 3.0, between about 0.1 and about 1, between about 0.1 and about 0.5, less than about 0.50, less than about 0.40, less than about 0.30, less than about 0.20, less than about 0.15, about 0.1, about 0.2 or about 1.0, lvii) the fatty acid composition of the lipid is based on an efficiency of conversion of oleic acid to DHA of at least about 10%, at least about 15%, at least about 20%, between about 10% and about 50%, between about 10% and about 30%, or between about 10% and about 25%, lviii) the fatty acid composition of the lipid is based on an efficiency of conversion of LA to DHA of at least about 15%, at least about 20%, at least about 22%, at least about 25%, between about 15% and about 50%, between about 20% and about 40%, or between about 20% and about 30%, lix) the fatty acid composition of the lipid is based on an efficiency of conversion of ALA to DHA of at least about 17%, at least about 22%, at least about 24%, between about 17% and about 55%, between about 22% and about 35%, or between about 24% and about 35%, lx) the total fatty acid in the extracted lipid has less than 1% C20:1, lxi) the triacylglycerol (TAG) content of the lipid is at least about 80%, at least about 90%, at least 95%, between about 70% and about 99%, or between about 90% and about 99%, lxii) the lipid comprises diacylglycerol (DAG), lxiii) the lipid comprises less than about 10%, less than about 5%, less than about 1%, or between about 0.001% and about 5%, free (non-esterified) fatty acids and/or phospholipid, or is essentially free thereof, lxiv) at least 80%, of the DHA esterified in the form of TAG is in the sn-1 or sn-3 position of the TAG, lxv) the most abundant DHA-containing TAG species in the lipid is DHA/18:3/18:3 (TAG 58:12), and lxvi) the lipid comprises tri-DHA TAG (TAG 66:18).

With specific regard to the above aspect, in an embodiment one or more or all of the following apply i) the lipid is in the form of an oil, wherein the oil comprises one or more sterols such as one or more or all of campesterol, Δ5-stigmasterol, eburicol, β-sitosterol, Δ5-avenasterol, Δ7-stigmasterol and Δ7-avenasterol, and optionally the oil comprises less than 10 mg of sterols/g of oil and/or the oil is essentially free of cholesterol, ii) the lipid is in the form of an oil from an oilseed such as oilseed is a *Brassica* sp oilseed or canola seed, iii) the level of DHA in the total fatty acid content of the extracted plant lipid is about 3%, about 4%, about 5%, about 6%, or is between 7% and 20%.

In a further aspect, the present invention provides a chimeric genetic construct comprising in order a first gene, a second gene, a third gene, a fourth gene, a fifth gene and a sixth gene which are all covalently linked on a single DNA molecule, wherein the first, second and third genes are joined together as a first gene cluster and the fourth, fifth and sixth genes are joined together as a second gene cluster, wherein each gene comprises a promoter, a coding region and a transcription terminator and/or polyadenylation region such that each promoter is operably linked to the coding region and transcription terminator and/or polyadenylation region, wherein each promoter is independently identical or different to the other promoters such that the DNA molecule comprises three, four, five or six different promoters, wherein one or more or all of the promoters are heterologous with respect to the coding region to which it is operably linked, wherein the direction of transcription of the first gene is away from the third gene and opposite to the direction of transcription of the third gene, wherein the direction of transcription of the fourth gene is away from the sixth gene and opposite to the direction of transcription of the sixth gene, wherein the direction of transcription of the second gene is the same as for the first gene or the third gene, wherein the direction of transcription of the fifth gene is the same as for the fourth gene or the sixth gene, wherein the transcription terminator and/or polyadenylation region of the second gene is spaced apart from the promoter of the first or third genes, whichever is closer, by a first spacer region of between about 0.2 and about 3.0 kilobases, wherein the first gene cluster is spaced apart from the second gene cluster by a second spacer region of between about 1.0 and about 10.0 kilobases, and wherein the transcription terminator and/or polyadenylation region of the fifth gene is spaced apart from the promoter of the fourth or sixth genes, whichever is closer, by a third spacer region of between about 0.2 and about 3.0 kilobases.

In an embodiment, the DNA molecule comprises a seventh gene which is spaced apart from the first gene cluster or the second gene cluster, whichever is closer, by a spacer region of between about 1.0 and about 10.0 kilobases.

In another embodiment, the DNA molecule comprises two or more different transcription terminator and/or polyadenylation regions.

In yet a further embodiment, at least one of the spacer regions comprises a matrix attachment region (MAR).

In a further embodiment, the DNA molecule comprises right and left border regions flanking the genes and is a T-DNA molecule.

In another embodiment, the genetic construct is in an *Agrobacterium* cell or is integrated into the genome of a plant cell.

In a preferred embodiment, at least one of the genes encodes a fatty acid desaturase or a fatty acid elongase.

In another embodiment, the genetic construct comprises genes encoding a set of enzymes as defined herein, and/or wherein one or more of the genes encode an enzyme as defined herein.

In a further aspect, the present invention provides an isolated and/or exogenous polynucleotide comprising:

i) a sequence of nucleotides selected from any one of SEQ ID NOs: 1 to 9, 11, 14, 18, 22, 23, 28, 34, 35, 39 or 45, and/or ii) a sequence of nucleotides which are at least 95% identical or 99% identical to one or more of the sequences set forth in SEQ ID NOs: 1 to 9, 11, 14, 18, 22, 23, 28, 34, 35, 39 or 45.

In a particularly preferred embodiment, the isolated and/or exogenous polynucleotide comprises:

i) a sequence of nucleotides of SEQ ID NO: 2, and/or ii) a sequence of nucleotides which are at least 95% identical or 99% identical to the sequence set forth in SEQ ID NO: 2.

In another aspect, the present invention provides a vector or genetic construct comprising the polynucleotide of the invention and/or the genetic construct of the invention.

In an embodiment, the sequence of nucleotides selected from any one of SEQ ID NOs: 11, 14, 18, 22, 23, 28, 34, 35, 39 or 45, or the sequence of nucleotides which is at least 95% identical or 99% identical to one or more of the sequences set forth in SEQ ID NOs: 11, 14, 18, 22, 23, 28, 34, 35, 39 or 45, is operably linked to a promoter.

In a further aspect, the present invention provides a host cell comprising exogenous polynucleotides encoding one of the following sets of enzymes;

i) an ω3-desaturase, a Δ6-desaturase, a Δ5-desaturase, a Δ4-desaturase, a Δ6-elongase and a Δ5-elongase, ii) a Δ15-desaturase, a Δ6-desaturase, a Δ5-desaturase, a Δ4-desaturase, a Δ6-elongase and a Δ5-elongase, iii) a Δ12-desaturase, a Δ6-desaturase, a Δ5-desaturase, a Δ4-desaturase, a Δ6-elongase and an Δ5-elongase, iv) a Δ12-desaturase, a ω3-desaturase or a Δ15-desaturase, a Δ6-desaturase, a Δ5-desaturase, a Δ4-desaturase, a Δ6-elongase and an Δ5-elongase, v) an ω3-desaturase, a Δ8-desaturase, a Δ5-desaturase, a Δ4-desaturase, a Δ9-elongase and an Δ5-elongase, vi) a Δ15-desaturase, a Δ8-desaturase, a Δ5-desaturase, a Δ4-desaturase, a Δ9-elongase and a Δ5-elongase, vii) a Δ12-desaturase, a Δ8-desaturase, a Δ5-desaturase, a Δ4-desaturase, a Δ9-elongase and an Δ5-elongase, or viii) a Δ12-desaturase, a (ω3-desaturase or a Δ15-desaturase, a Δ8-desaturase, a Δ5-desaturase, a Δ4-desaturase, a Δ9-elongase and an Δ5-elongase, and wherein each polynucleotide is operably linked to one or more promoters that are capable of directing expression of said polynucleotides in the cell.

In an embodiment, the cell comprises lipid as defined above, or wherein one or more or all of the desaturases or elongases have one or more of the features as defined above.

In another aspect, the present invention provides a host cell comprising i) a first exogenous polynucleotide encoding a Δ12-desaturase which comprises amino acids having a sequence as provided in SEQ ID NO:10, a biologically active fragment thereof, or an amino acid sequence which is at least 50% identical to SEQ ID NO:10, and ii) a second exogenous polynucleotide encoding a ω3-desaturase which comprises amino acids having a sequence as provided in SEQ ID NO: 12, a biologically active fragment thereof, or an amino acid sequence which is at least 50% identical to SEQ ID NO:12, wherein each polynucleotide is operably linked to one or more promoters that are capable of directing expression of said polynucleotides in the cell.

In a further aspect, the present invention provides a host cell comprising one or more of the polynucleotide of the invention, the genetic construct of the invention, or the vector or genetic construct of the invention.

In an embodiment, the cell is in a plant, in a plant part and/or is a mature plant seed cell.

In an embodiment, the plant or plant seed is an oilseed plant or an oilseed, respectively.

Also provided is a transgenic non-human organism comprising a cell of the invention. Preferably, the transgenic non-human organism is a transgenic plant, preferably an oilseed plant or *Arabidopsis thaliana*. In an embodiment, the plant is a *Brassica* plant, preferably *B. napus* or *B. juncea*, or a plant other than *Arabidopsis thaliana*.

In another aspect, the present invention provides an oilseed plant comprising a) lipid in its seed, the lipid comprising fatty acids in an esterified form, and b) exogenous polynucleotides encoding one of the following sets of enzymes;

i) a Δ12-desaturase, a fungal ω3-desaturase and/or fungal Δ15-desaturase, a Δ6-desaturase, a Δ5-desaturase, a Δ4-desaturase, a Δ6-elongase and an Δ5-elongase, or ii) a Δ12-desaturase, a fungal ω3-desaturase and/or fungal Δ15-desaturase, a Δ8-desaturase, a Δ5-desaturase, a Δ4-desaturase, a Δ9-elongase and an Δ5-elongase, wherein each polynucleotide is operably linked to one or more seed-specific promoters that are capable of directing expression of said polynucleotides in developing seed of the plant, wherein the fatty acids comprise oleic acid, palmitic acid, ω6 fatty acids which comprise linoleic acid (LA) and 7-linolenic acid (GLA), ω3 fatty acids which comprise α-linolenic acid (ALA), stearidonic acid (SDA), docosapentaenoic acid (DPA) and docosahexaenoic acid (DHA), and optionally eicosapentaenoic acid (EPA) and/or eicosatetraenoic acid (ETA), and wherein the level of DHA in the total fatty acid content of the lipid is about 7% to 20%.

Examples of oilseed plants include, but are not limited to, *Brassica* sp., *Gossypium hirsutum, Linum usitatissimum, Helianthus* sp., *Carthamus tinctorius, Glycine max, Zea mays, Arabidopsis thaliana, Sorghum bicolor, Sorghum vulgare, Avena sativa, Trifolium* sp., *Elaesis guineenis, Nicotiana benthamiana, Hordeum vulgare, Lupinus angustifolius, Oryza sativa, Oryza glaberrima, Camelina sativa*, or *Crambe abyssinica*. In an embodiment, the oilseed plant is a canola, *Glycine max, Camelina sativa* or *Arabidopsis thaliana* plant. In an alternate embodiment, the oilseed plant is other than *A. thaliana.*

In an embodiment, one or more of the desaturases is capable of using an acyl-CoA substrate. In a preferred embodiment, one or more of the Δ6-desaturase, Δ5-desaturase, Δ4-desaturase and Δ8-desaturase, if present, is capable of using an acyl-CoA substrate, preferably each of the i) Δ6-desaturase, Δ5-desaturase and Δ4-desaturase or ii) Δ5-desaturase, Δ4-desaturase and Δ8-desaturase is capable of using an acyl-CoA substrate. In an embodiment, a Δ12-desaturase and/or an ω3-desaturase is capable of using an acyl-CoA substrate. The acyl-CoA substrate is preferably an ALA-CoA, ETA-CoA, DPA-CoA, ETrA-CoA, LA-CoA, GLA-CoA, or ARA-CoA.

In an embodiment, mature, harvested seed of the plant has a DHA content of at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed. The maximum DHA content may be about 80 to about 100 mg per gram seed, or about 80 mg or about 100 mg per gram seed.

In a further aspect, the present invention provides a *Brassica napus, B. juncea* or *Camelina sativa* plant which is capable of producing seed comprising DHA, wherein mature, harvested seed of the plant has a DHA content of at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed. The maximum DHA content may be about 80 to about 100 mg per gram seed, or about 80 mg or about 100 mg per gram seed.

In another aspect, the present invention provides plant cell of a plant of the invention comprising the exogenous polynucleotides.

Also provided is a plant part, preferably a seed, which has one or more of the following features i) is from a plant of the invention, ii) comprises lipid as defined herein, iii) can be used in a process of the invention, iv) comprises a genetic construct of the invention, or v) comprises a set of exogenous polynucleotides as defined herein.

In yet another aspect, the present invention provides mature, harvested *Brassica napus, B. juncea* or *Camelina sativa* seed comprising DHA and a moisture content of between about 4% and about 15% by weight, wherein the DHA content of the seed at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed. The maximum DHA content may be about 80 to about 100 mg per gram seed, or about 80 mg or about 100 mg per gram seed.

In an embodiment, the cell of the invention, the transgenic organism of the invention, the oilseed plant of the invention, the *Brassica napus, B. juncea* or *Camelina sativa* plant of the invention, the plant part of the invention, or the seed of the invention, which can be used to produce extracted lipid comprising one or more or all of the features defined herein.

In yet a further aspect, the present invention provides a method of producing a cell of the invention, the method comprising a) introducing into the cell, preferably a cell which is not capable of synthesising a LC-PUFA, the gene construct of the invention, the isolated and/or exogenous polynucleotide of the invention, the vector or genetic construct of the invention, one or more of the combinations of exogenous polynucleotides defined herein, b) optionally, expressing the genes or polynucleotide(s) in the cell;

c) optionally, analysing the fatty acid composition of the cell, and d) optionally, selecting a cell which express the genes or polynucleotide(s).

In an embodiment, the lipid in the cell has one or more of the features defined herein.

In another embodiment, the gene construct, the isolated and/or exogenous polynucleotide, the vector, the genetic construct or combinations of exogenous polynucleotides, become stably integrated into the genome of the cell.

In a further embodiment, the cell is a plant cell, and the method further comprises the step of regenerating a transformed plant from the cell of step a).

In another embodiment, the genes and/or exogenous polynucleotide(s) are expressed transiently in the cell.

Also provided is a cell produced using a method of the invention.

In another aspect, the present invention provides a method of producing seed, the method comprising, a) growing a plant of the invention, or a plant which produces a part as defined herein, preferably in a field as part of a population of at least 1000 such plants or in an area of at least 1 hectare planted at a standard planting density, b) harvesting seed from the plant or plants, and c) optionally, extracting lipid from the seed, preferably to produce oil with a total DHA yield of at least 60 kg DHA/hectare.

In an embodiment, the plant, plant cell, plant part or seed of the invention has one or more of the following features i) the oil is as defined herein, ii) the plant part or seed is capable of being used in a process of the invention, iii) the exogenous polynucleotides are comprised in a genetic construct of the invention, iv) the exogenous polynucleotides comprise an exogenous polynucleotide of the invention, v) the plant cell is a cell of the invention, and vi) the seed was produced according to the method of the invention.

In another aspect, the present invention provides a method of producing one or more fatty acid desaturases and/or fatty acid elongases, or one or more fatty acid desaturases and one or more fatty acid elongases, the method comprising expressing in a cell or cell free expression system the gene construct of the invention, the isolated and/or exogenous polynucleotide of the invention, the vector or genetic construct of the invention, one or more of the combinations of exogenous polynucleotides defined herein, preferably in a developing oilseed in an oilseed plant in the field.

In a further aspect, the present invention provides lipid, or oil, produced by, or obtained from, using the process of the invention, the cell of the invention, the transgenic organism of the invention, the oilseed plant of the invention, the *Brassica napus, B. juncea* or *Camelina sativa* plant of the invention, the plant part of the invention, the seed of the invention, or the plant, plant cell, plant part or seed of the invention.

In an embodiment, the lipid or oil is obtained by extraction of oil from an oilseed. Examples of oil from oilseeds include, but are not limited to, canola oil (*Brassica napus. Brassica rapa* ssp.), mustard oil (*Brassica juncea*), other *Brassica* oil, sunflower oil (*Helianthus annus*), linseed oil (*Linum usitatissimum*), soybean oil (*Glycine max*), safflower oil (*Carthamus tinctorius*), corn oil (*Zea mays*), tobacco oil (*Nicotiana tabacum*), peanut oil (*Arachis hypogaea*), palm oil, cottonseed oil (*Gossypium hirsutum*), coconut oil (*Cocos nucifera*), avocado oil (*Persea americana*), olive oil (*Olea europaea*), cashew oil (*Anacardium occidentale*), *macadamia* oil (*Macadamia intergrifolia*), almond oil (*Prunus amygdalus*) or *Arabidopsis* seed oil (*Arabidopsis thaliana*).

In a further aspect, the present invention provides fatty acid produced by, or obtained from, using the process of the invention, the cell of the invention, the transgenic organism of the invention, the oilseed plant of the invention, the *Brassica napus, B. juncea* or *Camelina sativa* plant of the invention, the plant part of the invention, the seed of the invention, or the plant, plant cell, plant part or seed of the invention. Preferably the fatty acid is DHA. The fatty acid may be in a mixture of fatty acids having a fatty acid composition as described herein. In an embodiment, the fatty acid is non-esterified.

Also provided is seedmeal obtained from seed of the invention. Preferred seedmeal includes, but not necessarily limited to, *Brassica napus, B. juncea, Camelina sativa* or *Glycine max* seedmeal. In an embodiment, the seedmeal comprises an exogenous polynucleotide(s) and/or genentic constructs as defined herein.

In another aspect, the present invention provides a composition comprising one or more of a lipid or oil of the invention, the fatty acid of the invention, the genetic construct of the invention, the isolated and/or exogenous polynucleotide of the invention, the vector or genetic construct of the invention, the cell according of the invention, the transgenic organism of the invention, the oilseed plant of the invention, the *Brassica napus, B. juncea* or *Camelina sativa* plant of the invention, the plant part of the invention, the seed of the invention, the plant, plant cell, plant part or seed of the invention, or the seedmeal of the invention. In embodiments, the composition comprises a carrier suitable for pharmaceutical, food or agricultural use, a seed treatment compound, a fertiliser, another food or feed ingredient, or added protein or vitamins.

Also provided is feedstuffs, cosmetics or chemicals comprising one or more of the lipid or oil of the invention, the fatty acid of the invention, the genetic construct of the invention, the isolated and/or exogenous polynucleotide of the invention, the vector or genetic construct of the invention, the cell according of the invention, the transgenic organism of the invention, the oilseed plant of the invention, the *Brassica napus, B. juncea* or *Camelina sativa* plant of the invention, the plant part of the invention, the seed of the invention, the plant, plant cell, plant part or seed of the invention, the seedmeal of the invention, or the composition of the invention.

In another aspect, the present invention provides a method of producing a feedstuff, the method comprising mixing one or more of the lipid or oil of the invention, the fatty acid of the invention, the genetic construct of the invention, the isolated and/or exogenous polynucleotide of the invention, the vector or genetic construct of the invention, the cell according of the invention, the transgenic organism of the invention, the oilseed plant of the invention, the *Brassica napus, B. juncea* or *Camelina sativa* plant of the invention, the plant part of the invention, the seed of the invention, the plant, plant cell, plant part or seed of the invention, the seedmeal of the invention, or the composition of the invention, with at least one other food ingredient.

In another aspect, the present invention provides a method of treating or preventing a condition which would benefit from a PUFA, the method comprising administering to a subject one or more of the lipid or oil of the invention, the fatty acid of the invention, the genetic construct of the invention, the isolated and/or exogenous polynucleotide of the invention, the vector or genetic construct of the invention, the cell according of the invention, the transgenic organism of the invention, the oilseed plant of the invention, the *Brassica napus, B. juncea* or *Camelina sativa* plant of the invention, the plant part of the invention, the seed of the invention, the plant, plant cell, plant part or seed of the invention, the seedmeal of the invention, the composition of the invention, or the feedstuff of the invention.

Examples of conditions which would benefit from a PUFA include, but are not limited to, cardiac arrhythmia's, angioplasty, inflammation, asthma, psoriasis, osteoporosis, kidney stones, AIDS, multiple sclerosis, rheumatoid arthritis, Crohn's disease, schizophrenia, cancer, foetal alcohol syndrome, attention deficient hyperactivity disorder, cystic fibrosis, phenylketonuria, unipolar depression, aggressive hostility, adrenoleukodystophy, coronary heart disease, hypertension, diabetes, obesity, Alzheimer's disease, chronic obstructive pulmonary disease, ulcerative colitis, restenosis after angioplasty, eczema, high blood pressure, platelet aggregation, gastrointestinal bleeding, endometriosis, premenstrual syndrome, myalgic encephalomyelitis, chronic fatigue after viral infections or an ocular disease.

Also provided is the use of one or more of the lipid or oil of the invention, the fatty acid of the invention, the genetic construct of the invention, the isolated and/or exogenous polynucleotide of the invention, the vector or genetic construct of the invention, the cell according of the invention, the transgenic organism of the invention, the oilseed plant of the invention, the *Brassica napus, B. juncea* or *Camelina sativa* plant of the invention, the plant part of the invention, the seed of the invention, the plant, plant cell, plant part or seed of the invention, the seedmeal of the invention, the composition of the invention, or the feedstuff of the invention for the manufacture of a medicament for treating or preventing a condition which would benefit from a PUFA. The production of the medicament may comprise mixing the oil of the invention with a pharmaceutically acceptable carrier, for treatment of a condition as described herein. The method may comprise firstly purifying the oil and/or transesterification, and/or fractionation of the oil to increase the level of DHA. In a particular embodiment, the method comprises treating the lipid or oil such as canola oil to convert the fatty acids in the oil to alkyl esters such as methyl or ethyl esters. Further treatment such as fractionation or distillation may be applied to enrich the lipid or oil for the DHA. In a preferred embodiment, the medicament comprises ethyl esters of DHA. In an even more preferred embodiment, the level of ethyl esters of DHA in the medicament is between 30% and 50%. The medicament may further comprise ethyl esters of EPA, such as between 30% and 50% of the total fatty acid content in the medicament. Such medicaments are suitable for administration to human or animal subjects for treatment of medical conditions as described herein.

In another aspect, the present invention provides a method of trading seed, comprising obtaining seed of the invention, and trading the obtained seed for pecuniary gain.

In an embodiment, obtaining the seed comprises cultivating plants of the invention and/or harvesting the seed from the plants.

In another embodiment, obtaining the seed further comprises placing the seed in a container and/or storing the seed.

In a further embodiment, obtaining the seed further comprises transporting the seed to a different location.

In yet another embodiment, the method further comprises transporting the seed to a different location after the seed is traded.

In a further embodiment, the trading is conducted using electronic means such as a computer.

In yet a further aspect, the present invention provides a process of producing bins of seed comprising:

a) swathing, windrowing and/or or reaping above-ground parts of plants comprising seed of the invention, b) threshing and/or winnowing the parts of the plants to separate the seed from the remainder of the plant parts, and c) sifting and/or sorting the seed separated in step b), and loading the sifted and/or sorted seed into bins, thereby producing bins of seed.

In an embodiment, where relevant, the lipid or oil, preferably seedoil, of, or useful for, the invention has fatty levels about those provided in a Table in the Examples section, such as seed 14 of Table 16.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Aerobic DHA biosynthesis pathways.

Figure 2:
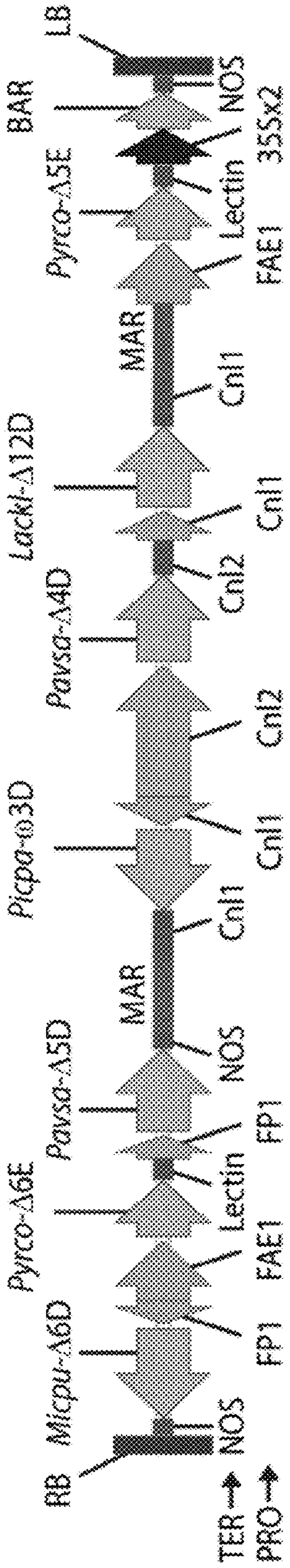

FIG. 2. Map of the T-DNA insertion region between the left and right borders of pJP3416-GA7. RB denotes right border; LB, left border; TER, transcription terminator/polyadenylation region; PRO, promoter; Coding regions are indicated above the arrows, promoters and terminators below the arrows. Micpu-Δ6D, *Micromonas pusilla* Δ6-desaturase; Pyrco-Δ6E, *Pyramimonas cordata* Δ6-elongase; Pavsa-Δ5D, *Pavlova salina* Δ5-desaturase; Picpa-ω3D, *Pichia pastoris* ω3-desaturase; Pavsa-Δ4D, *P. salina* Δ4-desaturase; Lackl-Δ12D, *Lachancea kluyveri* Δ12-desaturase; Pyrco-Δ5E, *Pyramimonas cordata* Δ5-elongase. NOS denotes the *Agrobacterium tumefaciens* nopaline synthase transcription terminator/polyadenylation region; FP1, *Brassica napus* truncated napin promoter; FAE1, *Arabidopsis thaliana* FAE1 promoter; Lectin, *Glycine max* lectin transcription terminator/polyadenylation region; Cnl1 and Cnl2 denotes the *Linum usitatissimum* conlinin1 or conlinin2 promoter or terminator. MAR denotes the Rb7 matrix attachment region from *Nicotiana tabacum.*

Figure 3:
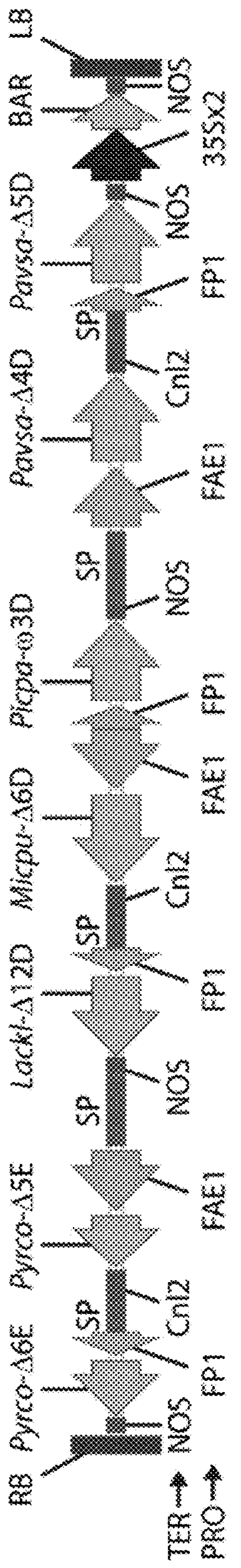

FIG. 3. Map of the T-DNA insertion region between the left and right borders of pJP3404. Labels are as in FIG. 2.

Figure 4:
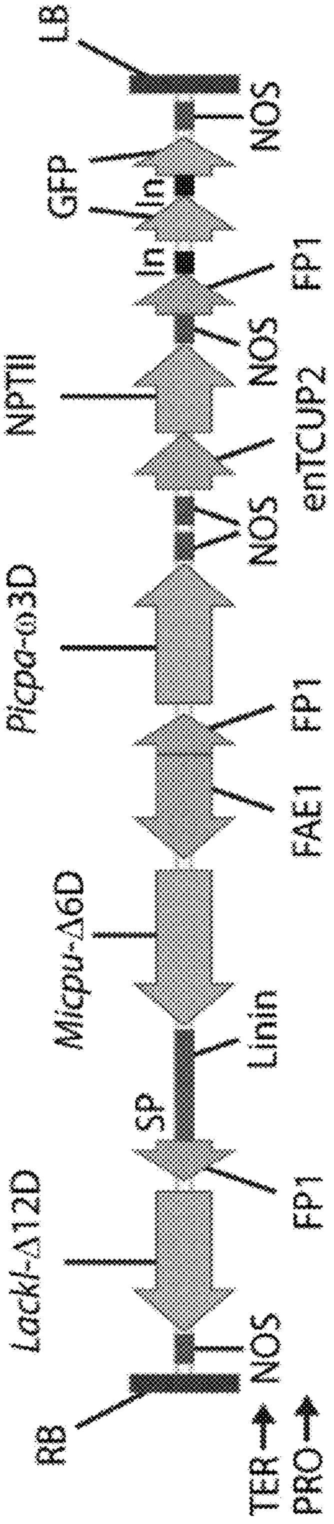

FIG. 4. Map of the insertion region between the left and right borders of pJP3367. Labels are as in FIG. 2.

Figure 5:
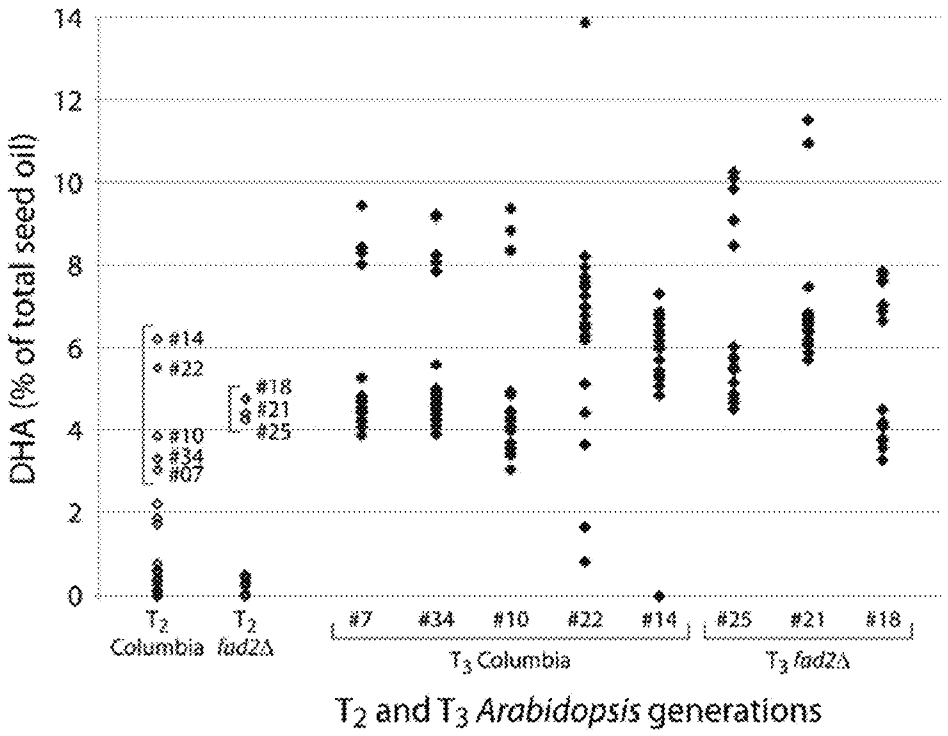

FIG. 5. DHA levels as a percentage of total fatty acids in seed lipid from multiple independent transgenic *Arabidopsis thaliana* seeds in both the $T_2$ and $T_3$ generations. The bracketed $T_2$ events were taken to $T_3$. Events from both the Columbia and fad2 mutant *A. thaliana* backgrounds are shown.

Figure 6:
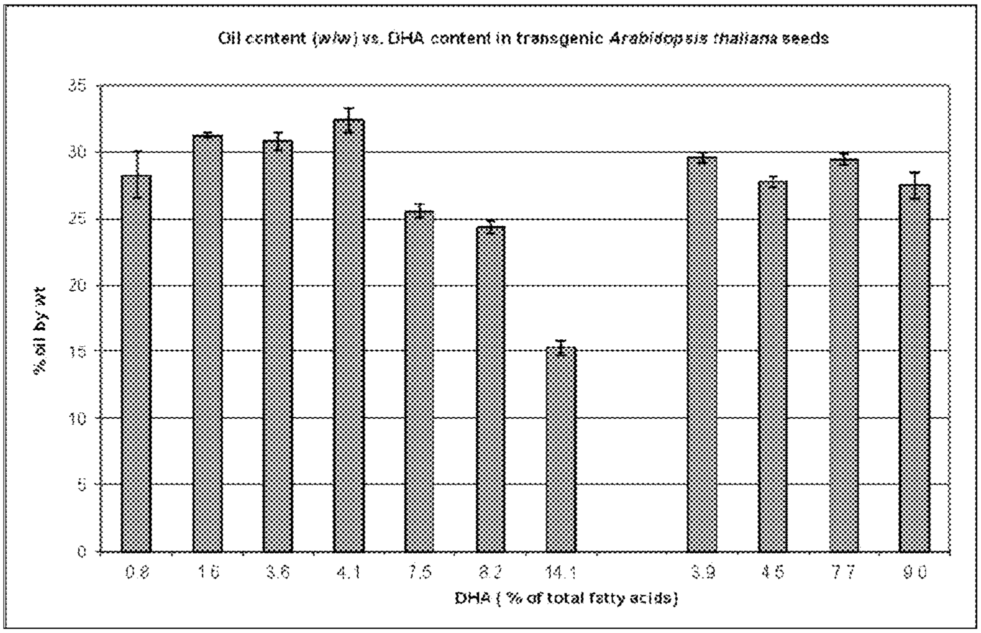

FIG. 6. Oil content (w/w) vs. DHA content, as a percentage of total fatty acid content of lipid from transgenic *Arabidopsis thaliana* seeds.

Figure 7:
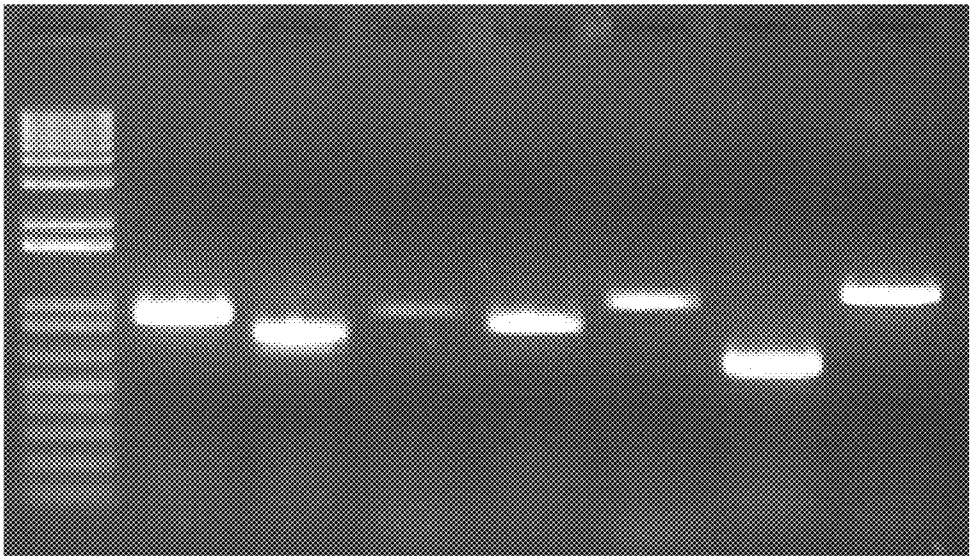

FIG. 7. Representative RT-PCR gel showing the low expression of the Δ6-desaturase gene relative to the other transgenes in the T-DNA of *B. napus* embryos transformed using pJP3416-GA7. Lanes from the left show RT-PCR products: 1, DNA size markers; lane 2, Δ12 desaturase; lane 3, ω3-desaturase; lane 4, Δ6-desaturase (low expression); lane 5, Δ6-elongase; lane 6, Δ5-desaturase; lane 7, Δ5-elongase; lane 8, Δ4-desaturase.

Figure 8:
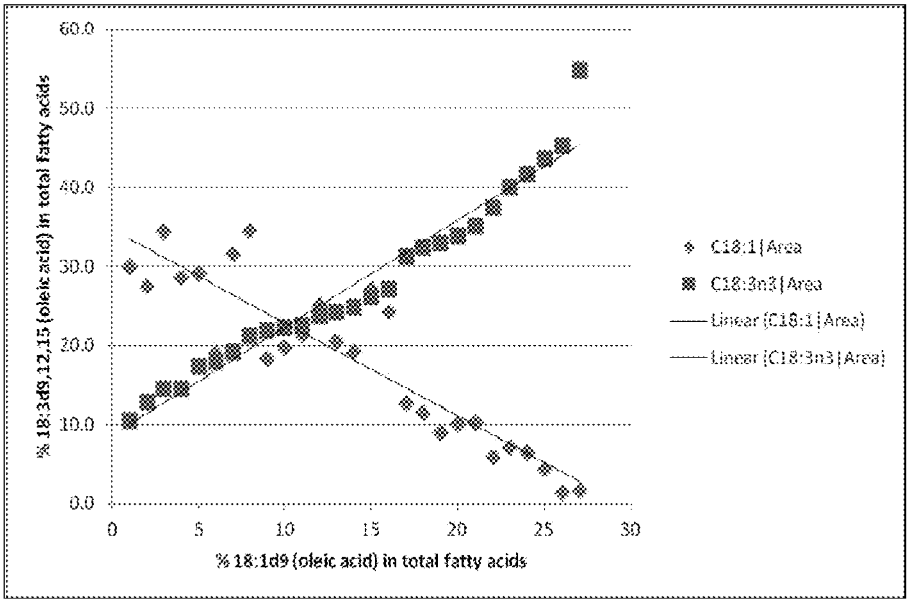

FIG. 8. Percentage of ALA plotted against percentage of oleic acid, each as a percentage of total fatty acids in lipid obtained from transgenic 35S:LEC2 *Brassica napus* somatic embryos.

Figure 9:
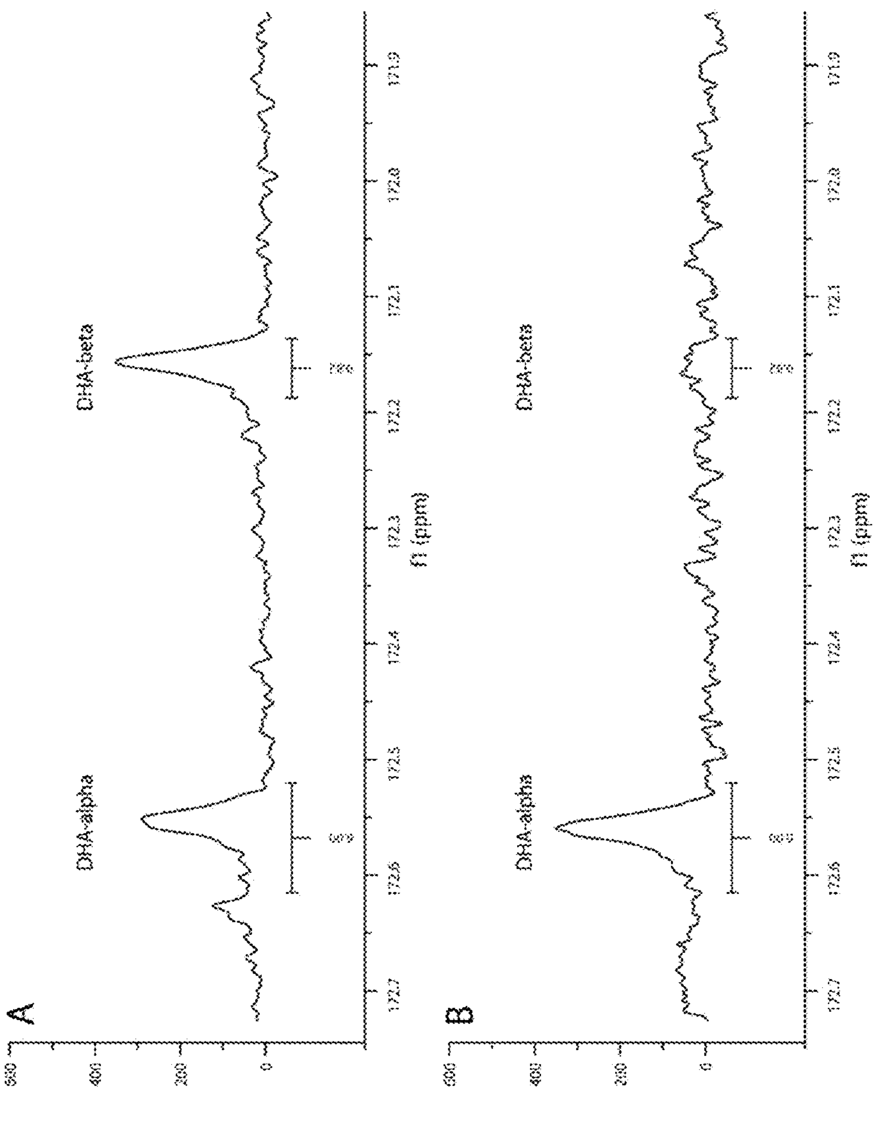

FIG. 9. Positional distribution analysis by NMR on A) Tuna oil and, B) transgenic DHA *Arabidopsis* seed oil. The peaks labelled 'DHA-alpha' represent the amount of DHA present at the sn-1 and sn-3 positions of TAG (with no positional preference this would equal 66% of total DHA) whilst the peaks labelled 'DHA-beta' represent the amount of DHA present at the sn-2 position of TAG (with no preference this would equal 33% of DHA).

Figure 10:
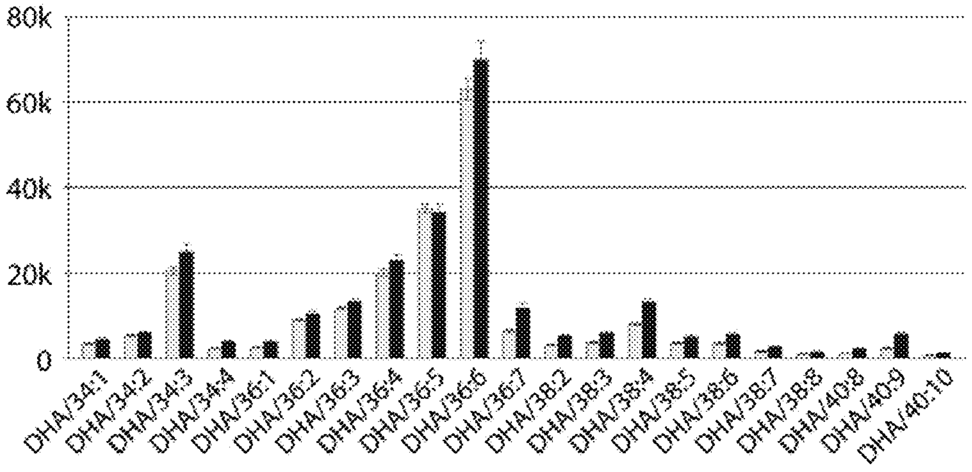

FIG. 10. LC-MS analysis of major DHA-containing triacylglycerol species in transgenic *A. thaliana* developing (grey) and mature (black) seeds. The number following the DHA denotes the total number of carbon atoms and total number of double bonds in the other two fatty acids. Therefore DHA/34:1 can also be designated TAG 56:7, etc.

Figure 11:
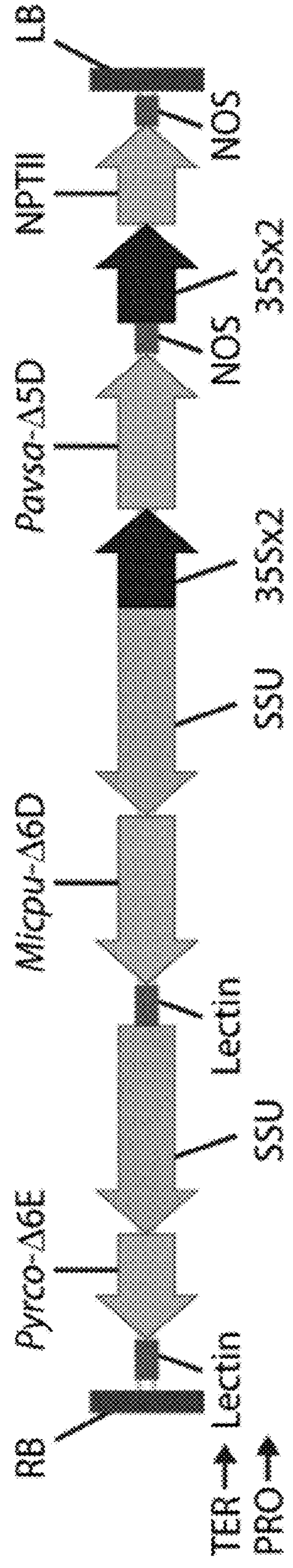

FIG. 11. Map of the T-DNA insertion region between the left and right borders of pORE04+11ABGBEC_Cowpea_EPA_insert. Labels are as in FIG. 2; SSU, *Arabidopsis thaliana* rubisco small subunit promoter.

Figure 12:
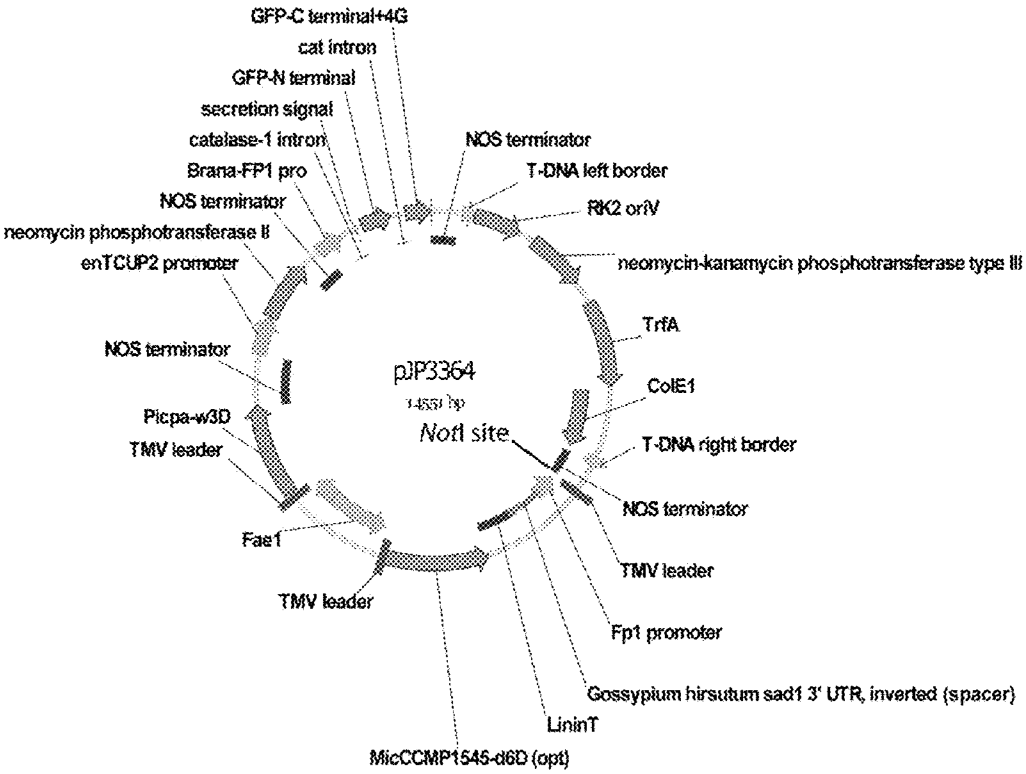

FIG. 12. Map of the binary vector pJP3364 showing the NotI restriction site into which the candidate Δ12-desaturases were cloned.

Figure 13:
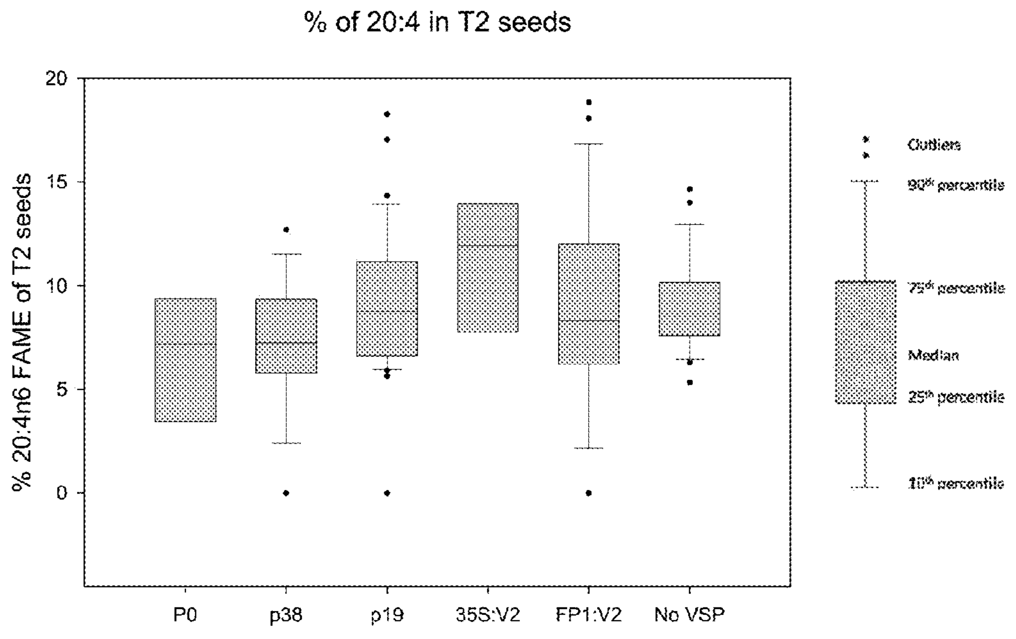

FIG. 13. BoxPlot generated using SigmaPlot showing the percentage of fatty acid 20:4ω6 (ARA) in seed lipid of *Arabidopsis* T2 seed populations transformed with pFN045-pFN050. The boundary of each box closest to zero indicates the 25th percentile, a line within each box marks the median, and the boundary of each box farthest from zero indicates the 75th percentile. Error bars shown above and below each box indicate the 90th and 10th percentiles.

Figure 14:
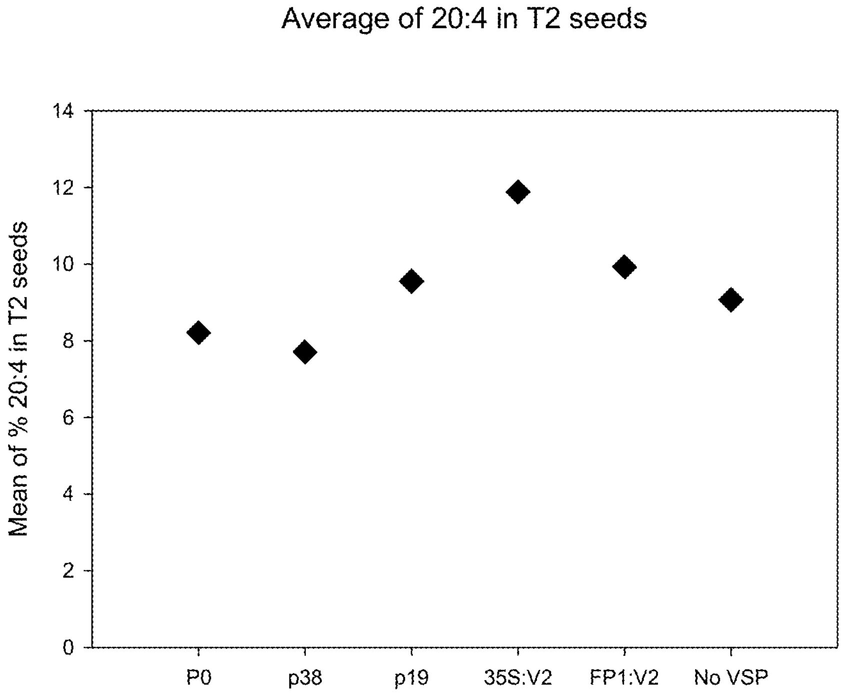

FIG. 14. Average level of ARA as a percentage of the total fatty acid content in seed lipid of *Arabidopsis* T2 seed transformed with pFN045-pFN050.

Figure 15:
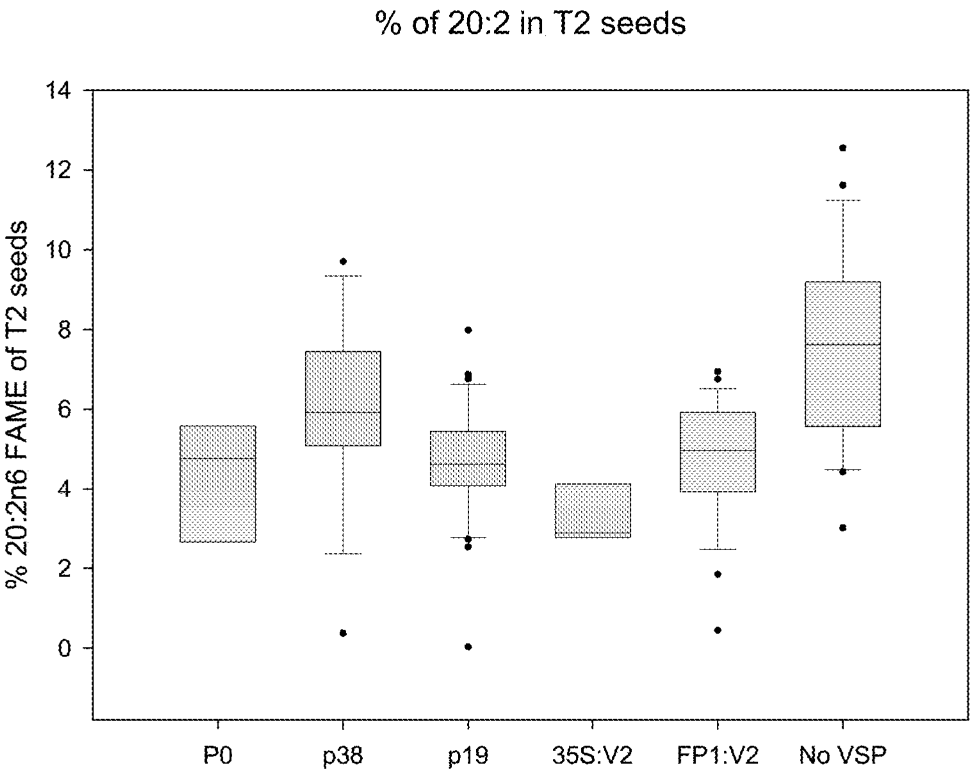

FIG. 15. BoxPlot showing the percentage of fatty acid 20:2ω6 (EDA) in seed lipid of *Arabidopsis* T2 seed populations transformed with pFN045-pFN050. The BoxPlot represents values as described in FIG. 13.

Figure 16:
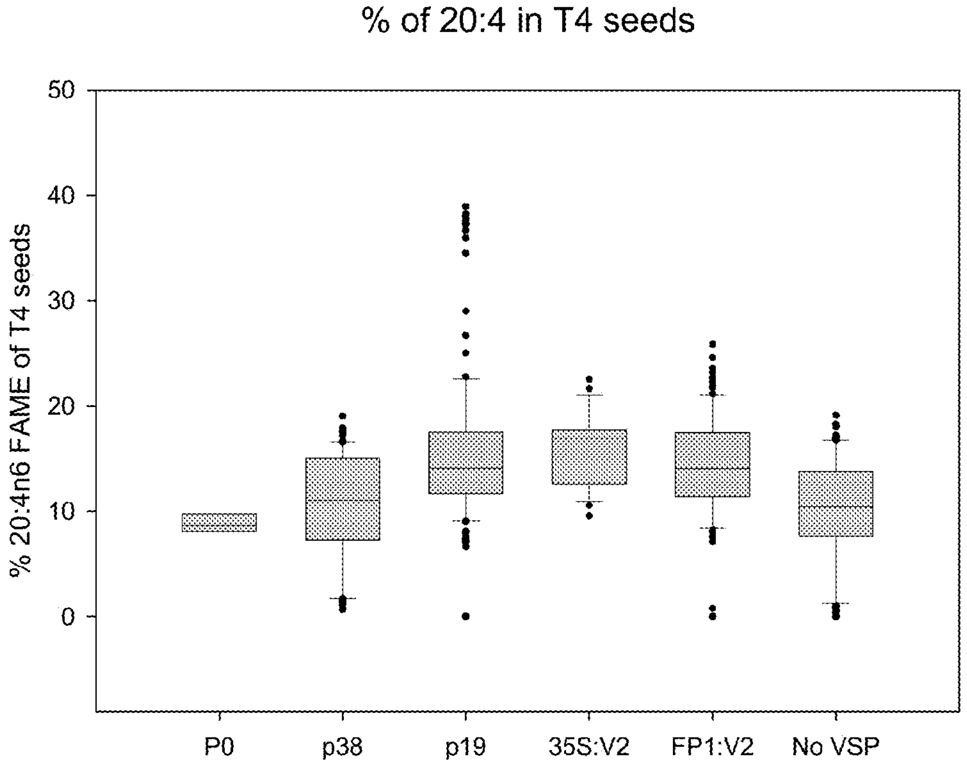

FIG. 16. BoxPlot showing the percentage of ARA in seed lipid of *Arabidopsis* T4 seed populations transformed with pFN045-pFN050. The BoxPlot represents values as described in FIG. 13.

Figure 17:
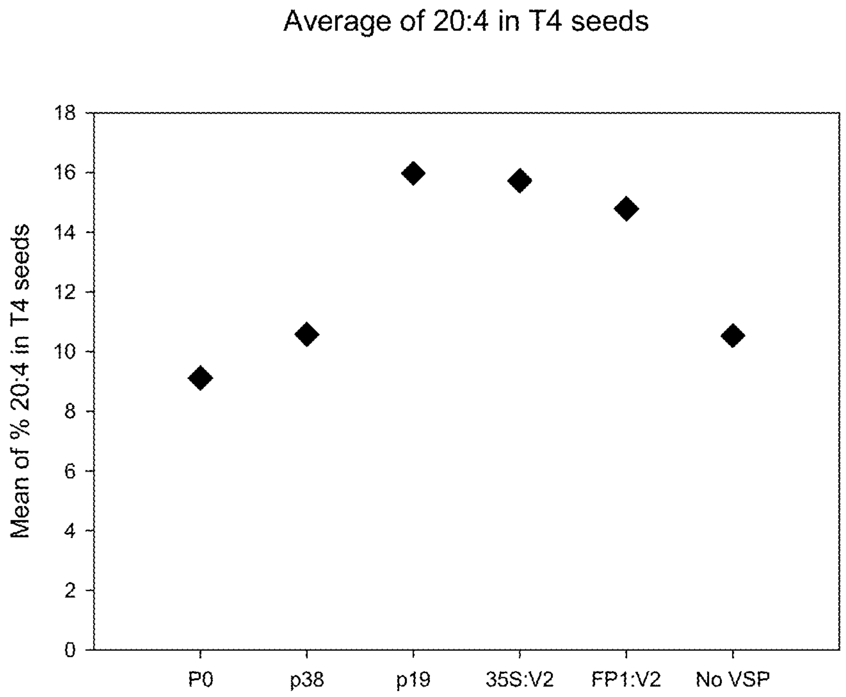

FIG. 17. Average level of ARA as a percentage of the total fatty acid content in seed lipid of *Arabidopsis* T4 seed populations transformed with pFN045-pFN050.

Figure 18:
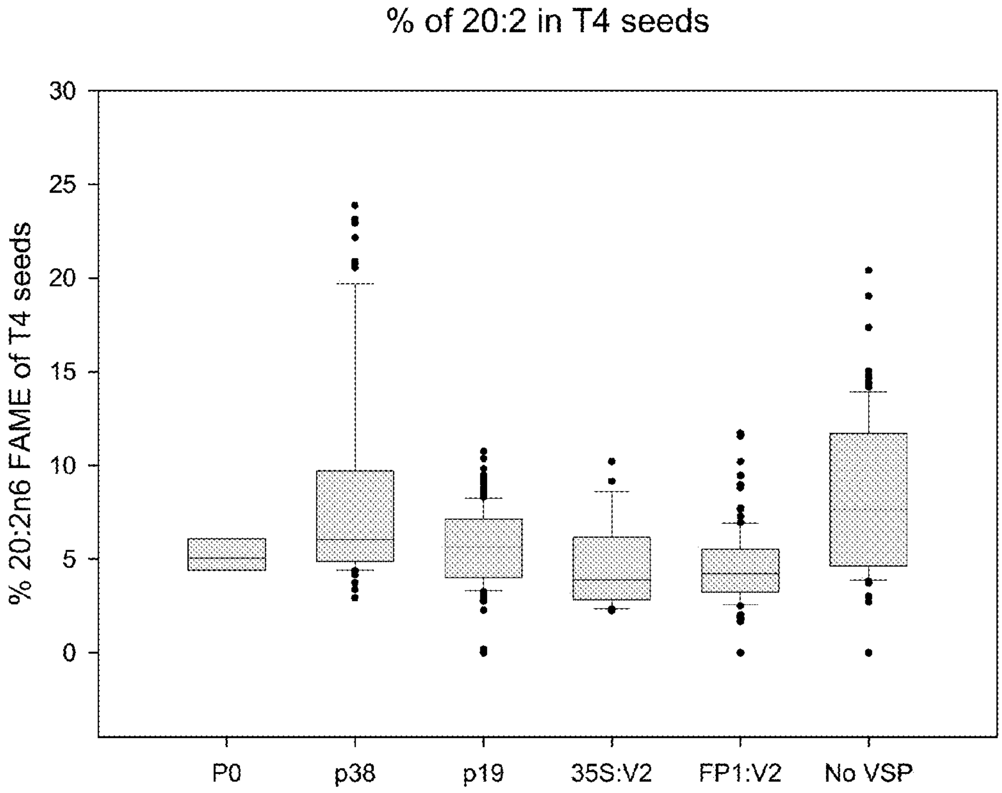

FIG. 18. BoxPlot showing the percentage of EDA in seed lipid of *Arabidopsis* T4 seed populations transformed with pFN045-pFN050. The BoxPlot represents values as described in FIG. 13.

Figure 19:
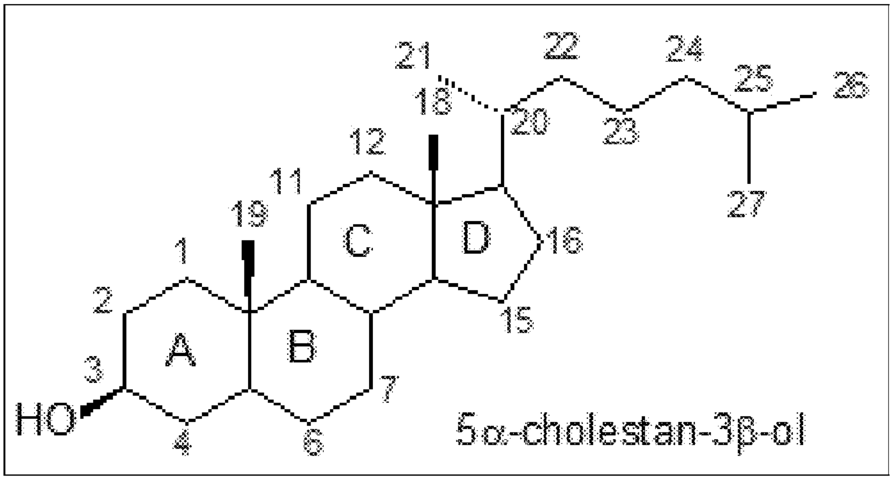
Figure 19:
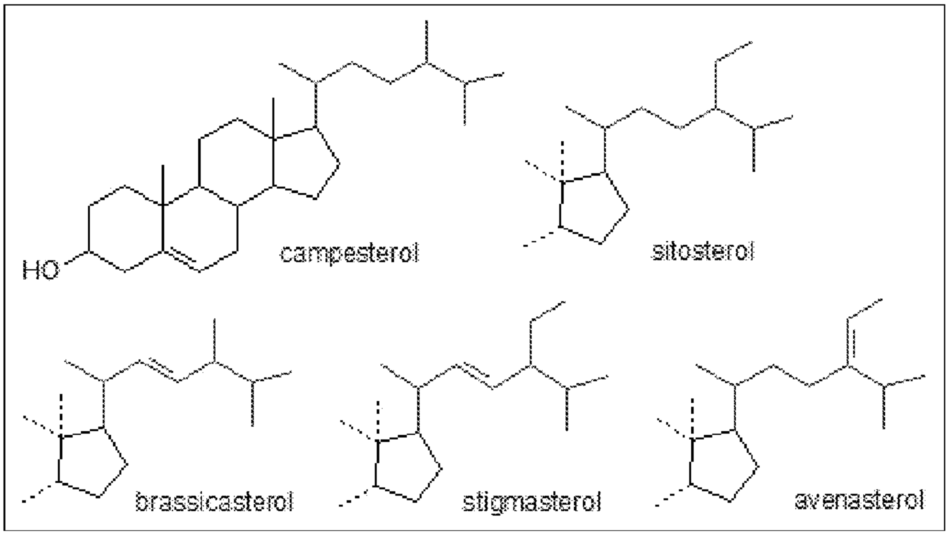

FIG. 19. (A) Basic phytosterol structure with ring and side chain numbering. (B) Chemical structures of some of the phytosterols.

Figure 20:
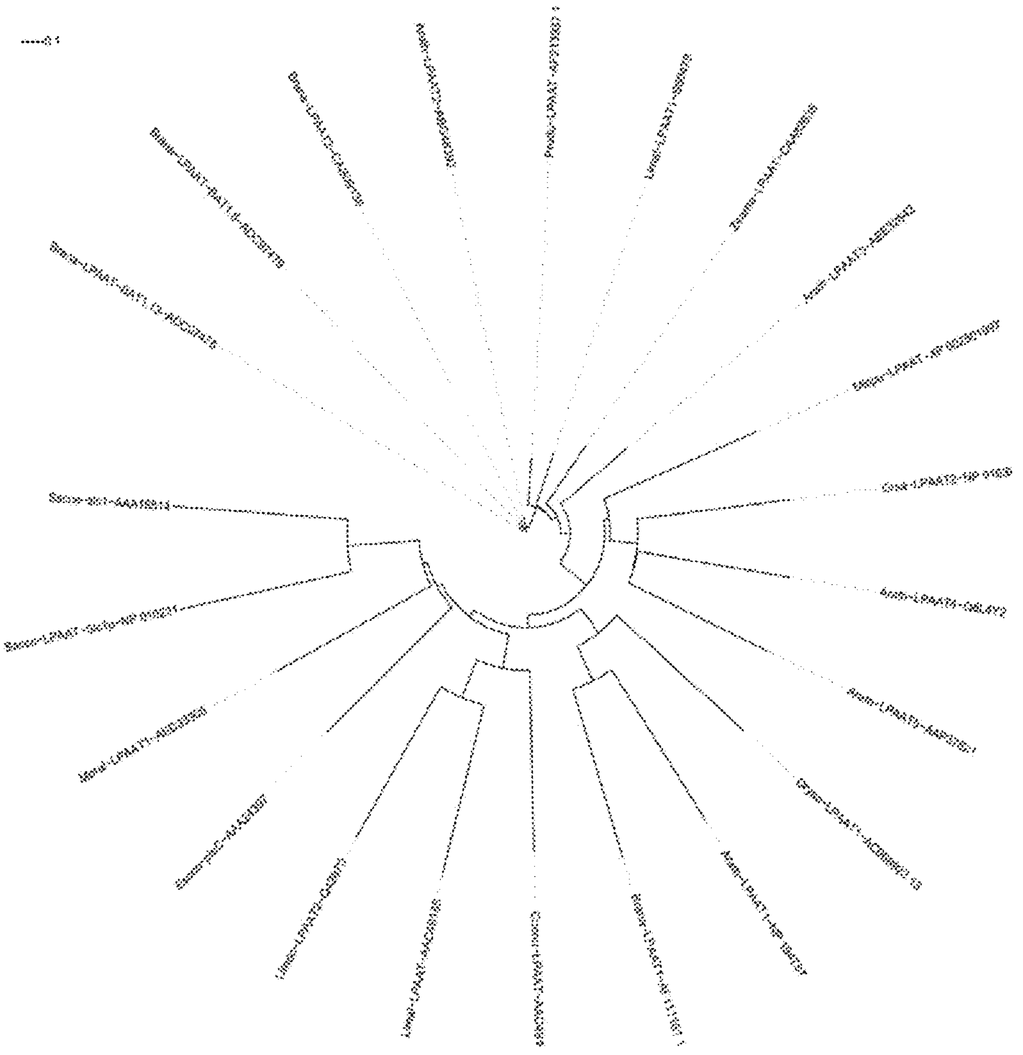

FIG. 20. Phylogenetic tree of known LPAATs.

Figure 21:
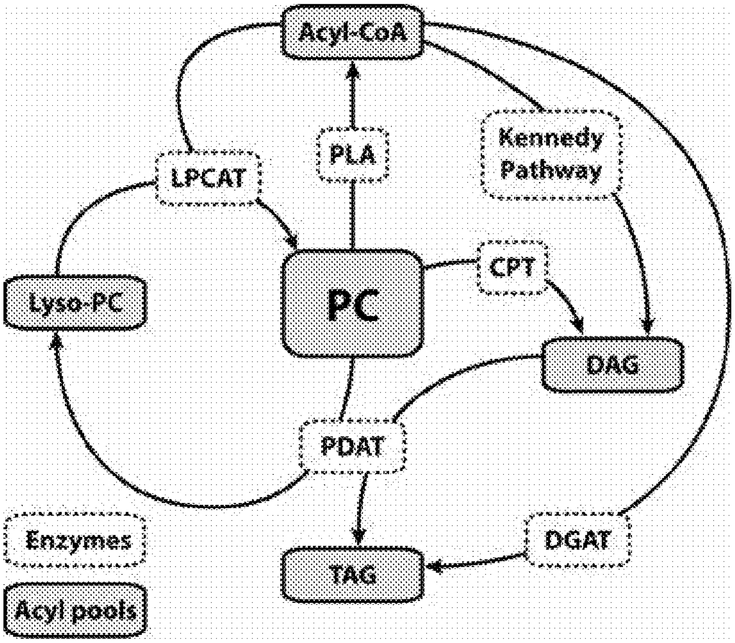

FIG. 21. The various acyl exchange enzymes which transfer fatty acids between PC, CoA pools, and TAG pools. Adapted from Singh et al. (2005).

KEY TO THE SEQUENCE LISTING

SEQ ID NO:1—pJP3416-GA7 nucleotide sequence.

SEQ ID NO:2—pGA7-mod_B nucleotide sequence.

SEQ ID NO:3—pGA7-mod_C nucleotide sequence.

SEQ ID NO:4—pGA7-mod_D nucleotide sequence.

SEQ ID NO:5—pGA7-mod_E nucleotide sequence.

SEQ ID NO:6—pGA7-mod_F nucleotide sequence.

SEQ ID NO:7—pGA7-mod_G nucleotide sequence.

SEQ ID NO:8—pORE04+11ABGBEC_Cowpea_EPA_insert nucleotide sequence. SEQ ID NO:9—Codon-optimized open reading frame for expression of *Lachancea kluyveri* Δ12 desaturase in plants.

SEQ ID NO: 10—*Lachancea kluyveri* Δ12-desaturase.

SEQ ID NO:11—Codon-optimized open reading frame for expression of *Pichia pastoris* ω3 desaturase in plants.

SEQ ID NO: 12—*Pichia pastoris* ω3 desaturase.

SEQ ID NO: 13—Open reading frame encoding *Micromonas pusilla* Δ6-desaturase.

SEQ ID NO: 14—Codon-optimized open reading frame for expression of *Micromonas pusilla* Δ6-desaturase in plants (version 1).

SEQ ID NO: 15—Codon-optimized open reading frame for expression of *Micromonas pusilla* Δ6-desaturase in plants (version 2).

SEQ ID NO: 16—*Micromonas pusilla* Δ6-desaturase.

SEQ ID NO:17—Open reading frame encoding *Ostreococcus lucimarinus* Δ6-desaturase.

SEQ ID NO: 18—Codon-optimized open reading frame for expression of *Ostreococcus lucimarinus* Δ6-desaturase in plants.

SEQ ID NO: 19—*Ostreococcus lucimarinus* Δ6-desaturase.

SEQ ID NO:20—*Ostreococcus tauri* Δ6-desaturase.

SEQ ID NO:21—Open reading frame encoding *Pyramimonas cordata* Δ6-elongase.

SEQ ID NO:22—Codon-optimized open reading frame for expression of *Pyramimonas cordata* Δ6-elongase in plants (truncated at 3' end and encoding functional elongase) (version 1).

SEQ ID NO:23—Codon-optimized open reading frame for expression of *Pyramimonas cordata* Δ6-elongase in plants (truncated at 3' end and encoding functional elongase) (version 2).

SEQ ID NO:24—Codon-optimized open reading frame for expression of *Pyramimonas cordata* Δ6-elongase in plants (truncated at 3' end and encoding functional elongase) (version 3).

SEQ ID NO:25—*Pyramimonas cordata* Δ6-elongase.

SEQ ID NO:26—Truncated *Pyramimonas cordata* Δ6-elongase.

SEQ ID NO:27—Open reading frame encoding *Pavlova salina* Δ5-desaturase.

SEQ ID NO:28—Codon-optimized open reading frame for expression of Pavlova *salina* Δ5-desaturase in plants (version 1).

SEQ ID NO:29—Codon-optimized open reading frame for expression of Pavlova *salina* Δ5-desaturase in plants (version 2).

SEQ ID NO:30—Pavlova *salina* Δ5-desaturase.

SEQ ID NO:31—Open reading frame encoding *Pyramimonas cordata* Δ5-desaturase.

SEQ ID NO:32—*Pyramimonas cordata* Δ5-desaturase.

SEQ ID NO:33—Open reading frame encoding *Pyramimonas cordata* Δ5-elongase.

SEQ ID NO:34—Codon-optimized open reading frame for expression of *Pyramimonas cordata* Δ5-elongase in plants (version 1).

SEQ ID NO:35—Codon-optimized open reading frame for expression of *Pyramimonas cordata* Δ5-elongase in plants (version 2).

SEQ ID NO:36—Codon-optimized open reading frame for expression of *Pyramimonas cordata* Δ5-elongase in plants (version 3).

SEQ ID NO:37—*Pyramimonas cordata* Δ5-elongase.

SEQ ID NO:38—Open reading frame encoding *Pavlova salina* Δ4-desaturase.

SEQ ID NO:39—Codon-optimized open reading frame for expression of *Pavlova salina* Δ4-desaturase in plants (version 1).

SEQ ID NO:40—Codon-optimized open reading frame for expression of *Pavlova salina* Δ4-desaturase in plants (version 2).

SEQ ID NO:41—*Pavlova salina* Δ4-desaturase.

SEQ ID NO:42—Open reading frame encoding *Isochrysis galbana* Δ9-elongase.

SEQ ID NO:43—*Isochrysis galbana* Δ9-elongase.

SEQ ID NO:44—Open reading frame encoding *Emiliania huxleyi* CCMP1516 Δ9-elongase.

SEQ ID NO:45—Codon-optimized open reading frame for expression of *Emiliania huxleyi* Δ9-elongase in plants.

SEQ ID NO:46—*Emiliania huxleyi* CCMP1516 Δ9-elongase.

SEQ ID NO:47—Open reading frame encoding *Pavlova pinguis* Δ9-elongase.

SEQ ID NO:48—*Pavlova pinguis* Δ9-elongase.

SEQ ID NO:49—Open reading frame encoding *Pavlova salina* Δ9-elongase.

SEQ ID NO:50—*Pavlova salina* Δ9-elongase.

SEQ ID NO:51—Open reading frame encoding *Pavlova salina* Δ8-desaturase.

SEQ ID NO:52—*Pavlova salina* Δ8-desaturase.

SEQ ID NO:53—P19 viral suppressor.

SEQ ID NO:54—V2 viral suppressor.

SEQ ID NO:55—P38 viral suppressor.

SEQ ID NO:56—Pe-P0 viral suppressor.

SEQ ID NO:57—RPV-P0 viral suppressor.

SEQ ID NO:58—Open reading frame encoding P19 viral suppressor.

SEQ ID NO:59—Open reading frame encoding V2 viral suppressor.

SEQ ID NO:60—Open reading frame encoding P38 viral suppressor.

SEQ ID NO:61—Open reading frame encoding Pe-P0 viral suppressor.

SEQ ID NO:62—Open reading frame encoding RPV-P0 viral suppressor.

SEQ ID NO: 63—*Arabidopsis thaliana* LPAAT2.

SEQ ID NO: 64—*Limnanthes alba* LPAAT.

SEQ ID NO: 65—*Saccharomyces cerevisiae* LPAAT.

SEQ ID NO: 66—*Micromonas pusilla* LPAAT.

SEQ ID NO: 67—*Mortierella alpina* LPAAT.

SEQ ID NO: 68—*Braccisa napus* LPAAT.

SEQ ID NO: 69—*Brassica napus* LPAAT.

SEQ ID NO: 70—*Phytophthora infestans* ω3 desaturase.

SEQ ID NO: 71—*Thalassiosira pseudonana* ω3 desaturase.

SEQ ID NO: 72—*Pythium irregulare* ω3 desaturase.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, fatty acid synthesis, transgenic plants, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al. (editors), Current Protocols in Molecular Biology, Greene Pub. Associates and Wiley-Interscience (1988, including all updates until present), Ed Harlow and David Lane (editors), Antibodies: A Laboratory Manual, Cold Spring Harbour Laboratory, (1988), and J. E. Coligan et al. (editors), Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10%, more preferably +/−5%, more preferably +/−1% of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

As used herein, the terms "extracted plant lipid" and "isolated plant lipid" refer to a lipid composition which has been extracted from, for example by crushing, a plant or part thereof such as seed. The extracted lipid can be a relatively crude composition obtained by, for example, crushing a plant seed, or a more purified composition where most, if not all, of one or more or each of the water, nucleic acids, proteins and carbohydrates derived from the plant material have been removed. Examples of purification methods are described below. In an embodiment, the extracted or isolated plant lipid comprises at least about 60%, at least about 70%, at least about 80%, at least about 90%, or at least about 95% (w/w) lipid by weight of the composition. The lipid may be solid or liquid at room temperature, when liquid it is considered to be an oil. In an embodiment, extracted lipid of the invention has not been blended with another lipid such as DHA not produced by another source (for example, DHA from fish oil). In an embodiment, following extraction the ratio of one or more or all of, oleic acid to DHA, palmitic acid to DHA, linoleic acid to DHA, and total ω6 fatty acids: total ω3 fatty acids, has not been significantly altered (for example, no greater than a 10% or 5% alteration) when compared to the ratio in the intact seed or cell. In an another embodiment, the extracted plant lipid has not been exposed to a procedure, such as hydrogenation or fractionation, which may alter the ratio of one or more or all of, oleic acid to DHA, palmitic acid to DHA, linoleic acid to DHA, and total ω6 fatty acids: total ω3 fatty acids, when compared to the ratio in the intact seed or cell. When the extracted plant lipid of the invention is comprised in an oil, the oil may further comprise non-fatty acid molecules such as sterols.

As used herein, the terms "extracted plant oil" and "isolated plant oil" refer to a substance or composition comprising extracted plant lipid or isolated plant lipid and which is a liquid at room temperature. The oil is obtained from a plant or part thereof such as seed. The extracted or isolated oil can be a relatively crude composition obtained by, for example, crushing a plant seed, or a more purified composition where most, if not all, of one or more or each of the water, nucleic acids, proteins and carbohydrates derived from the plant material have been removed. The composition may comprise other components which may be lipid or non-lipid. In an embodiment, the oil composition comprises at least about 60%, at least about 70%, at least about 80%, at least about 90%, or at least about 95% (w/w) extracted plant lipid. In an embodiment, extracted oil of the invention has not been blended with another oil such as DHA not produced by another source (for example, DHA from fish oil). In an embodiment, following extraction, the ratio of one or more or all of, oleic acid to DHA, palmitic acid to DHA, linoleic acid to DHA, and total ω6 fatty acids: total ω3 fatty acids, has not been significantly altered (for example, no greater than a 10% or 5% alteration) when compared to the ratio in the intact seed or cell. In an another embodiment, the extracted plant oil has not been exposed to a procedure, such as hydrogenation or fractionation, which may alter the ratio of one or more or all of, oleic acid to DHA, palmitic acid to DHA, linoleic acid to DHA, and total ω6 fatty acids: total ω3 fatty acids, when compared to the ratio in the intact seed or cell. Extracted plant oil of the invention may comprise non-fatty acid molecules such as sterols.

As used herein, an "oil" is a composition comprising predominantly lipid and which is a liquid at room temperature. For instance, oil of the invention preferably comprises at least 75%, at least 80%, at least 85% or at least 90% lipid by weight. Typically, a purified oil comprises at least 90% triacylglycerols (TAG) by weight of the lipid in the oil. Minor components of an oil such as diacylglycerols (DAG), free fatty acids (FFA), phospholipid and sterols may be present as described herein.

As used herein, the term "fatty acid" refers to a carboxylic acid (or organic acid), often with a long aliphatic tail, either saturated or unsaturated. Typically fatty acids have a carbon-carbon bonded chain of at least 8 carbon atoms in length, more preferably at least 12 carbons in length. Most naturally occurring fatty acids have an even number of carbon atoms because their biosynthesis involves acetate which has two carbon atoms. The fatty acids may be in a free state (non-esterified) or in an esterified form such as part of a triglyceride, diacylglyceride, monoacylglyceride, acyl-CoA (thio-ester) bound or other bound form. The fatty acid may be esterified as a phospholipid such as a phosphatidylcholine, phosphatidylethanolamine, phosphatidylserine, phosphatidylglycerol, phosphatidylinositol or diphosphatidylglycerol forms.

"Saturated fatty acids" do not contain any double bonds or other functional groups along the chain. The term "saturated" refers to hydrogen, in that all carbons (apart from the carboxylic acid [—COOH] group) contain as many hydrogens as possible. In other words, the omega (ω) end contains 3 hydrogens (CH3-) and each carbon within the chain contains 2 hydrogens (—CH2-).

"Unsaturated fatty acids" are of similar form to saturated fatty acids, except that one or more alkene functional groups exist along the chain, with each alkene substituting a singly-bonded "—CH2-CH2-" part of the chain with a doubly-bonded "—CH═CH—" portion (that is, a carbon double bonded to another carbon). The two next carbon atoms in the chain that are bound to either side of the double bond can occur in a cis or trans configuration.

As used herein, the term "monounsaturated fatty acid" refers to a fatty acid which comprises at least 12 carbon atoms in its carbon chain and only one alkene group (carbon-carbon double bond) in the chain. As used herein, the terms "polyunsaturated fatty acid" or "PUFA" refer to a fatty acid which comprises at least 12 carbon atoms in its carbon chain and at least two alkene groups (carbon-carbon double bonds).

As used herein, the terms "long-chain polyunsaturated fatty acid" and "LC-PUFA" refer to a fatty acid which comprises at least 20 carbon atoms in its carbon chain and at least two carbon-carbon double bonds, and hence include VLC-PUFAs.

As used herein, the terms "very long-chain polyunsaturated fatty acid" and "VLC-PUFA" refer to a fatty acid which comprises at least 22 carbon atoms in its carbon chain and at least three carbon-carbon double bonds. Ordinarily, the number of carbon atoms in the carbon chain of the fatty acids refers to an unbranched carbon chain. If the carbon chain is branched, the number of carbon atoms excludes those in sidegroups. In one embodiment, the long-chain polyunsaturated fatty acid is an ω3 fatty acid, that is, having a desaturation (carbon-carbon double bond) in the third carbon-carbon bond from the methyl end of the fatty acid. In another embodiment, the long-chain polyunsaturated fatty acid is an ω6 fatty acid, that is, having a desaturation (carbon-carbon double bond) in the sixth carbon-carbon bond from the methyl end of the fatty acid. In a further embodiment, the long-chain polyunsaturated fatty acid is selected from the group consisting of; arachidonic acid (ARA, 20:4Δ5,8,11,14; ω6), eicosatetraenoic acid (ETA, 20:4Δ8,11,14,17, ω3), eicosapentaenoic acid (EPA, 20:5Δ5,8,11,14,17; ω3), docosapentaenoic acid (DPA, 22:5Δ7,10,13,16,19, ω3), or docosahexaenoic acid (DHA, 22:6Δ4,7,10,13,16,19, ω3). The LC-PUFA may also be dihomo-γ-linoleic acid (DGLA) or eicosatrienoic acid (ETrA, 20:3Δ11,14,17, ω3). It would readily be apparent that the LC-PUFA that is produced according to the invention may be a mixture of any or all of the above and may include other LC-PUFA or derivatives of any of these LC-PUFA. In a preferred embodiment, the ω3 fatty acids are at least DHA, preferably, DPA and DHA, or EPA, DPA and DHA.

Furthermore, as used herein the terms "long-chain polyunsaturated fatty acid" and "very long-chain polyunsaturated fatty acid" refer to the fatty acid being in a free state (non-esterified) or in an esterified form such as part of a triglyceride, diacylglyceride, monoacylglyceride, acyl-CoA bound or other bound form. The fatty acid may be esterified as a phospholipid such as a phosphatidylcholine (PC), phosphatidylethanolamine, phosphatidylserine, phosphatidylglycerol, phosphatidylinositol or diphosphatidylglycerol forms. Thus, the LC-PUFA may be present as a mixture of forms in the lipid of a cell or a purified oil or lipid extracted from cells, tissues or organisms. In preferred embodiments, the invention provides oil comprising at least 75% or at least 85% triacylglycerols, with the remainder present as other forms of lipid such as those mentioned, with at least said triacylglycerols comprising the LC-PUFA. The oil may subsequently be further purified or treated, for example by hydrolysis with a strong base to release the free fatty acids, or by distillation or the like.

As used herein, "total ω6 fatty acids" or "total ω6 fatty acid content" or the like refers to the sum of all the ω6 fatty acids, esterified and non-esterified, in the extracted lipid, oil, recombinant cell, plant part or seed, as the context determines, expressed as a percentage of the total fatty acid content. These ω6 fatty acids include (if present) LA, GLA, DGLA, ARA, EDA and ω6-DPA, and exclude any ω3 fatty acids and monounsaturated fatty acids.

As used herein, "new ω6 fatty acids" or "new ω6 fatty acid content" or the like refers to the sum of all the ω6 fatty acids excluding LA, esterified and non-esterified, in the extracted lipid, oil, recombinant cell, plant part or seed, as the context determines, expressed as a percentage of the total fatty acid content. These new ω6 fatty acids are the fatty acids that are produced in the cells, plants, plant parts and seeds of the invention by the expression of the genetic constructs (exogenous polynucleotides) introduced into the cells, and include (if present) GLA, DGLA, ARA, EDA and ω6-DPA, but exclude LA and any ω3 fatty acids and monounsaturated fatty acids. Exemplary total ω6 fatty acid contents and new ω6 fatty acid contents are determined by conversion of fatty acids in a sample to FAME and analysis by GC, as described in Example 1.

As used herein, "total ω3 fatty acids" or "total ω3 fatty acid content" or the like refers to the sum of all the ω3 fatty acids, esterified and non-esterified, in the extracted lipid, oil, recombinanat cell, plant part or seed, as the context determines, expressed as a percentage of the total fatty acid content. These ω3 fatty acids include (if present) ALA, SDA, ETrA, ETA, EPA, DPA and DHA, and exclude any ω6 fatty acids and monounsaturated fatty acids.

As used herein, "new ω3 fatty acids" or "new ω3 fatty acid content" or the like refers to the sum of all the ω3 fatty acids excluding ALA, esterified and non-esterified, in the extracted lipid, oil, recombinanat cell, plant part or seed, as the context determines, expressed as a percentage of the total fatty acid content. These new ω3 fatty acids are the fatty acids that are produced in the cells, plants, plant parts and seeds of the invention by the expression of the genetic constructs (exogenous polynucleotides) introduced into the cells, and include (if present) SDA, ETrA, ETA, EPA, DPA and DHA, but exclude ALA and any ω6 fatty acids and monounsaturated fatty acids. Exemplary total ω3 fatty acid contents and new ω3 fatty acid contents are determined by conversion of fatty acids in a sample to FAME and analysis by GC, as described in Example 1.

The desaturase, elongase and acyl transferase proteins and genes encoding them that may be used in the invention are any of those known in the art or homologues or derivatives thereof. Examples of such genes and encoded protein sizes are listed in Table 1. The desaturase enzymes that have been shown to participate in LC-PUFA biosynthesis all belong to the group of so-called “front-end” desaturases.

As used herein, the term “front-end desaturase” refers to a member of a class of enzymes that introduce a double bond between the carboxyl group and a pre-existing unsaturated part of the acyl chain of lipids, which are characterized structurally by the presence of an N-terminal cytochrome b5 domain, along with a typical fatty acid desaturase domain that includes three highly conserved histidine boxes (Napier et al., 1997).

Activity of any of the elongases or desaturases for use in the invention may be tested by expressing a gene encoding the enzyme in a cell such as, for example, a yeast cell, a plant cell or preferably in somatic embryos or transgenic plants, and determining whether the cell, embryo or plant has an increased capacity to produce LC-PUFA compared to a comparable cell, embryo or plant in which the enzyme is not expressed.

In one embodiment one or more of the desaturases and/or elongases for use in the invention can purified from a microalga, i.e. is identical in amino acid sequence to a polypeptide which can be purified from a microalga.

Whilst certain enzymes are specifically described herein as “bifunctional”, the absence of such a term does not necessarily imply that a particular enzyme does not possess an activity other than that specifically defined.

Desaturases

As used herein, the term “desaturase” refers to an enzyme which is capable of introducing a carbon-carbon double bond into the acyl group of a fatty acid substrate which is typically in an esterified form such as, for example, acyl-CoA esters. The acyl group may be esterified to a phospholipid such as phosphatidylcholine (PC), or to acyl carrier protein (ACP), or in a preferred embodiment to CoA. Desaturases generally may be categorized into three groups accordingly. In one embodiment, the desaturase is a front-end desaturase.

As used herein, a “Δ4-desaturase” refers to a protein which performs a desaturase reaction that introduces a carbon-carbon double bond at the $4^{tH}$ carbon-carbon bond from the carboxyl end of a fatty acid substrate. The “Δ4-desaturase” is at least capable of converting DPA to DHA. The desaturation step to produce DHA from DPA is catalysed by a Δ4-desaturase in organisms other than mammals, and a gene encoding this enzyme has been isolated from the freshwater protist species *Euglena gracilis* and the marine species *Thraustochytrium* sp. (Qiu et al., 2001; Meyer et al., 2003). In one embodiment, the Δ4-desaturase comprises amino acids having a sequence as provided in SEQ ID NO:41, or a *Thraustochytrium* sp. Δ4-desaturase, a biologically active fragment thereof, or an amino acid sequence which is at least 80% identical to SEQ ID NO:41.

TABLE 1

Cloned genes involved in LC-PUFA biosynthesis

| Enzyme | Type of organism | Species | Accession Nos. | Protein size (aa's) | References |
|---|---|---|---|---|---|
| Δ4-desaturase | Protist | *Euglena gracilis* | AY278558 | 541 | Meyer et al., 2003 |
| | Algae | *Pavlova lutherii* | AY332747 | 445 | Tonon et al, 2003 |
| | | *Isochrysis galbana* | AAV33631 | 433 | Pereira et al., 2004b |
| | | *Pavlova salina* | AAY15136 | 447 | Zhou et al., 2007 |
| | Thraustochytrid | *Thraustochytrium aureum* | AAN75707<br>AAN75708<br>AAN75709<br>AAN75710 | 515 | N/A |
| | | *Thraustochytrium* sp. ATCC21685 | AAM09688 | 519 | Qiu et al. 2001 |
| Δ5-desaturase | Mammals | *Homo sapiens* | AF199596 | 444 | Cho et al., 1999b<br>Leonard et al., 2000b |
| | Nematode | *Caenorhabditis elegans* | AF11440,<br>NM_069350 | 447 | Michaelson et al., 1998b;<br>Watts and Browse, 1999b |
| | Fungi | *Mortierella alpina* | AF067654 | 446 | Michaelson et al., 1998a;<br>Knutzon et al., 1998 |
| | | *Pythium irregulare* | AF419297 | 456 | Hong et al., 2002a |
| | | *Dictyostelium discoideum* | AB022097 | 467 | Saito et al., 2000 |
| | | *Saprolegnia diclina* | | 470 | WO02081668 |
| | Diatom | *Phaeodactylum tricornutum* | AY082392 | 469 | Domergue et al., 2002 |
| | Algae | *Thraustochytrium* sp | AF489588 | 439 | Qiu et al., 2001 |
| | | *Thraustochytrium aureum* | | 439 | WO02081668 |
| | | *Isochrysis galbana* | | 442 | WO02081668 |
| | Moss | *Marchantia polymorpha* | AY583465 | 484 | Kajikawa et al., 2004 |
| Δ6-desaturase | Mammals | *Homo sapiens* | NM_013402 | 444 | Cho et al., 1999a;<br>Leonard et al., 2000 |
| | | *Mus musculus* | NM_019699 | 444 | Cho et al., 1999a |
| | Nematode | *Caenorhabditis elegans* | Z70271 | 443 | Napier et al., 1998 |
| | Plants | *Borago officinales* | U79010 | 448 | Sayanova et al., 1997 |
| | | *Echium* | AY055117<br>AY055118 | | Garcia-Maroto et al., 2002 |
| | | *Primula vialii* | AY234127 | 453 | Sayanova et al., 2003 |
| | | *Anemone leveillei* | AF536525 | 446 | Whitney et al., 2003 |
| | Mosses | *Ceratodon purpureus* | AJ250735 | 520 | Sperling et al., 2000 |
| | | *Marchantia polymorpha* | AY583463 | 481 | Kajikawa et al., 2004 |
| | | *Physcomitrella patens* | CAA11033 | 525 | Girke et al., 1998 |
| | Fungi | *Mortierella alpina* | AF110510<br>AB020032 | 457 | Huang et al., 1999;<br>Sakuradani et al., 1999 |
| | | *Pythium irregulare* | AF419296 | 459 | Hong et al., 2002a |
| | | *Mucor circinelloides* | AB052086 | 467 | NCBI* |
| | | *Rhizopus* sp. | AY320288 | 458 | Zhang et al., 2004 |
| | | *Saprolegnia diclina* | | 453 | WO02081668 |

TABLE 1-continued

Cloned genes involved in LC-PUFA biosynthesis

| Enzyme | Type of organism | Species | Accession Nos. | Protein size (aa's) | References |
|---|---|---|---|---|---|
| | Diatom | *Phaeodactylum tricornutum* | AY082393 | 477 | Domergue et al., 2002 |
| | Bacteria | *Synechocystis* | L11421 | 359 | Reddy et al., 1993 |
| | Algae | *Thraustochytrium aureum* | | 456 | WO02081668 |
| Bifunctional Δ5/Δ6-desaturase | Fish | *Danio rerio* | AF309556 | 444 | Hastings et al., 2001 |
| C20 Δ8-desaturase | Algae | *Euglena gracilis* | AF139720 | 419 | Wallis and Browse, 1999 |
| | Plants | *Borago officinales* | AAG43277 | 446 | Sperling et al., 2001 |
| Δ6-elongase | Nematode | *Caenorhabditis elegans* | NM_069288 | 288 | Beaudoin et al., 2000 |
| | Mosses | *Physcomitrella patens* | AF428243 | 290 | Zank et al., 2002 |
| | | *Marchantia polymorpha* | AY583464 | 290 | Kajikawa et al., 2004 |
| | Fungi | *Mortierella alpina* | AF206662 | 318 | Parker-Barnes et al., 2000 |
| | Algae | *Pavlova lutheri*** | | 501 | WO 03078639 |
| | | *Thraustochytrium* | AX951565 | 271 | WO 03093482 |
| | | *Thraustochytrium* sp** | AX214454 | 271 | WO 0159128 |
| PUFA-elongase | Mammals | *Homo sapiens* | AF231981 | 299 | Leonard et al., 2000b; Leonard et al., 2002 |
| | | *Rattus norvegicus* | AB071985 | 299 | Inagaki et al., 2002 |
| | | *Rattus norvegicus*** | AB071986 | 267 | Inagaki et al., 2002 |
| | | *Mus musculus* | AF170907 | 279 | Tvrdik et al., 2000 |
| | | *Mus musculus* | AF170908 | 292 | Tvrdik et al., 2000 |
| | Fish | *Danio rerio* | AF532782 | 291 (282) | Agaba et al., 2004 |
| | | *Danio rerio*** | NM_199532 | 266 | Lo et al., 2003 |
| | Worm | *Caenorhabditis elegans* | Z68749 | 309 | Abbott et al., 1998 Beaudoin et al., 2000 |
| | Algae | *Thraustochytrium aureum*** | AX464802 | 272 | WO 0208401-A2 |
| | | *Pavlova lutheri*** | | 320 | WO 03078639 |
| Δ9-elongase | Algae | *Isochrysis galbana* | AF390174 | 263 | Qi et al., 2002 |
| | | *Euglena gracilis* | | 258 | WO 08/128241 |
| Δ5-elongase | Algae | *Ostreococcus tauri* | AAV67798 | 300 | Meyer et al., 2004 |
| | | *Pyramimonas cordata* | | 268 | WO 2010/057246 |
| | | *Pavlova* sp. CCMP459 | AAV33630 | 277 | Pereira et al., 2004b |
| | | *Pavlova salina* | AAY15135 | 302 | Robert et al., 2009 |
| | Diatom | *Thalassiosira pseudonana* | AAV67800 | 358 | Meyer et al., 2004 |
| | Fish | *Oncorhynchus mykiss* | CAM55862 | 295 | WO 06/008099 |
| | Moss | *Marchantia polymorpha* | BAE71129 | 348 | Kajikawa et al., 2006 |

*http://www.ncbi.nlm.nih.gov/

**Function not proven/not demonstrated

As used herein, a "Δ5-desaturase" refers to a protein which performs a desaturase reaction that introduces a carbon-carbon double bond at the $5^{th}$ carbon-carbon bond from the carboxyl end of a fatty acid substrate. Examples of Δ5-desaturases are listed in Ruiz-Lopez et al. (2012) and Petrie et al. (2010a) and in Table 1 herein. In one embodiment, the Δ5-desaturase comprises amino acids having a sequence as provided in SEQ ID NO:30, a biologically active fragment thereof, or an amino acid sequence which is at least 80% identical to SEQ ID NO:30. In another embodiment, the Δ5-desaturase comprises amino acids having a sequence as provided in SEQ ID NO:32, a biologically active fragment thereof, or an amino acid sequence which is at least 53% identical to SEQ ID NO:32. In another embodiment, the Δ5-desaturase is from *Thraustochytrium* sp or *Emiliania huxleyi.*

As used herein, a "Δ6-desaturase" refers to a protein which performs a desaturase reaction that introduces a carbon-carbon double bond at the $6^{th}$ carbon-carbon bond from the carboxyl end of a fatty acid substrate. Examples of Δ6-desaturases are listed in Ruiz-Lopez et al. (2012) and Petrie et al. (2010a) and in Table 1 herein. Preferred Δ6-desaturases are from *Micromonas pusilla, Pythium irregulare* or *Ostreococcus taurii.*

In an embodiment, the Δ6-desaturase is further characterised by having at least two, preferably all three and preferably in a plant cell, of the following: i) greater Δ6-desaturase activity on α-linolenic acid (ALA, 18:3Δ9,12,15, ω3) than linoleic acid (LA, 18:2Δ9,12, ω6) as fatty acid substrate; ii) greater Δ6-desaturase activity on ALA-CoA as fatty acid substrate than on ALA joined to the sn-2 position of PC as fatty acid substrate; and iii) Δ8-desaturase activity on ETrA. Examples of such Δ6-desaturases are provided in Table 2.

In an embodiment the Δ6-desaturase has greater activity on an ω3 substrate than the corresponding ω6 substrate and has activity on ALA to produce octadecatetraenoic acid (stearidonic acid, SDA, 18:4Δ6,9,12, 15, ω3) with an efficiency of at least 30%, more preferably at least 40%, or most preferably at least 50% when expressed from an exogenous polynucleotide in a recombinant cell such as a plant cell, or at least 35% when expressed in a yeast cell. In one embodiment, the Δ6-desaturase has greater activity, for example, at least about a 2-fold greater Δ6-desaturase activity, on ALA than LA as fatty acid substrate. In another embodiment, the Δ6-desaturase has greater activity, for example, at least about 5 fold greater Δ6-desaturase activity or at least 10-fold greater activity, on ALA-CoA as fatty acid substrate than on ALA joined to the sn-2 position of PC as fatty acid substrate. In a further embodiment, the Δ6-desaturase has activity on both fatty acid substrates ALA-CoA and on ALA joined to the sn-2 position of PC.

TABLE 2

| Desaturases demonstrated to have activity on an acyl-CoA substrate | | | | | |
|---|---|---|---|---|---|
| Enzyme | Type of organism | Species | Accession Nos. | Protein size (aa's) | References |
| Δ6-desaturase | Algae | *Mantoniella squamata* | CAQ30479 | 449 | Hoffmann et al., 2008 |
| | | *Ostreococcus tauri* | AAW70159 | 456 | Domergue et al., 2005 |
| | | *Micromonas pusilla* | EEH58637 | | Petrie et al., 2010a (SEQ ID NO: 13) |
| Δ5-desaturase | Algae | *Mantoniella squamata* | CAQ30478 | 482 | Hoffmann et al., 2008 |
| | Plant | *Anemone leveillei* | N/A | | Sayanova et al., 2007 |
| ω3-desaturase | Fungi | *Pythium aphanidermatum* | FW362186.1 | 359 | Xue et al., 2012; WO2008/054565 |
| | Fungi (oomycete) | *Phytophthora sojae* | FW362214.1 | 363 | Xue et al., 2012; WO2008/054565 |
| | Fungi (oomycete) | *Phytophthora ramorum* | FW362213.1 | 361 | Xue et al., 2012; WO2008/054565 |

In one embodiment, the Δ6-desaturase has no detectable Δ5-desaturase activity on ETA. In another embodiment, the Δ6-desaturase comprises amino acids having a sequence as provided in SEQ ID NO:16, SEQ ID NO:19 or SEQ ID NO:20, a biologically active fragment thereof, or an amino acid sequence which is at least 77% identical to SEQ ID NO:16, SEQ ID NO:19 or SEQ ID NO:20. In another embodiment, the Δ6-desaturase comprises amino acids having a sequence as provided in SEQ ID NO:19 or SEQ ID NO:20, a biologically active fragment thereof, or an amino acid sequence which is at least 67% identical to one or both of SEQ ID NO: 19 or SEQ ID NO:20. The Δ6-desaturase may also have Δ8-desaturase activity.

As used herein, a "Δ8-desaturase" refers to a protein which performs a desaturase reaction that introduces a carbon-carbon double bond at the $8^{th}$ carbon-carbon bond from the carboxyl end of a fatty acid substrate. The Δ8-desaturase is at least capable of converting ETrA to ETA. Examples of Δ8-desaturases are listed in Table 1. In one embodiment, the Δ8-desaturase comprises amino acids having a sequence as provided in SEQ ID NO:52, a biologically active fragment thereof, or an amino acid sequence which is at least 80% identical to SEQ ID NO:52.

As used herein, an "ω3-desaturase" refers to a protein which performs a desaturase reaction that introduces a carbon-carbon double bond at the 3rd carbon-carbon bond from the methyl end of a fatty acid substrate. A ω3-desaturase therefore may convert LA to ALA and GLA to SDA (all C18 fatty acids), or DGLA to ETA and/or ARA to EPA (C20 fatty acids). Some ω3-desaturases (group I) have activity only on C18 substrates, such as plant and cyanobacterial ω3-desaturases. Such ω3-desaturases are also Δ15-desaturases. Other ω3-desaturases have activity on C20 substrates with no activity (group II) or some activity (group III) on C18 substrates. Such ω3-desaturases are also Δ17-desaturases. Preferred ω3-desaturases are group III type which convert LA to ALA, GLA to SDA, DGLA to ETA and ARA to EPA, such as the *Pichia pastoris* ω3-desaturase (SEQ ID NO: 12). Examples of ω3-desaturases include those described by Pereira et al. (2004a) (*Saprolegnia diclina* ω3-desaturase, group II), Horiguchi et al. (1998), Berberich et al. (1998) and Spychalla et al. (1997) (*C. elegans* ω3-desaturase, group III). In a preferred embodiment, the ω3-desaturase is a fungal ω3-desaturase. As used herein, a "fungal ω3-desaturase" refers to an ω3-desaturase which is from a fungal source, including an oomycete source, or a variant thereof whose amino acid sequence is at least 95% identical thereto. Genes encoding numerous ω3-desaturases have been isolated from fungal sources such as, for example, from *Phytophthora infestans* (Accession No. CAJ30870, WO2005083053; SEQ ID NO: 70), *Saprolegnia diclina* (Accession No. AAR20444, Pereira et al., 2004a & U.S. Pat. No. 7,211,656), *Pythium irregulare* (WO2008022963, Group II; SEQ ID NO: 72), *Mortierella alpina* (Sakuradani et al., 2005; Accession No. BAD91495; WO2006019192), *Thalassiosira pseudonana* (Armbrust et al., 2004; Accession No. XP_002291057; WO2005012316, SEQ ID NO: 71), *Lachancea kluyveri* (also known as *Saccharomyces kluyveri*; Oura et al., 2004; Accession No. AB118663). Xue et al. (2012) describes ω3-desaturases from the oomycetes *Pythium aphanidermatum, Phytophthora sojae*, and *Phytophthora ramorum* which were able to efficiently convert ω6 fatty acid substrates to the corresponding ω3 fatty acids, with a preference for C20 substrates, i.e. they had stronger Δ17-desaturase activity than Δ15-desaturase activity. These enzymes lacked Δ12-desaturase activity, but could use fatty acids in both acyl-CoA and phospholipid fraction as substrates.

In a more preferred embodiment, the fungal ω3-desaturase is the *Pichia pastoris* (also known as *Komagataella pastoris*) ω3-desaturase/Δ15-desaturase (Zhang et al., 2008; Accession No. EF116884; SEQ ID NO: 12), or a polypeptide which is at least 95% identical thereto.

In an embodiment, the ω3-desaturase is at least capable of converting one of ARA to EPA, DGLA to ETA, GLA to SDA, both ARA to EPA and DGLA to ETA, both ARA to EPA and GLA to SDA, or all three of these.

In one embodiment, the ω3-desaturase has Δ17-desaturase activity on a C20 fatty acid which has at least three carbon-carbon double bonds, preferably ARA. In another embodiment, the ω3-desaturase has Δ15-desaturase activity on a C18 fatty acid which has three carbon-carbon double bonds, preferably GLA. Preferably, both activities are present.

As used herein, a "Δ12-desaturase" refers to a protein which performs a desaturase reaction that introduces a carbon-carbon double bond at the $12^{th}$ carbon-carbon bond from the carboxyl end of a fatty acid substrate. Δ12-desaturases typically convert either oleoyl-phosphatidylcholine or oleoyl-CoA to linoleoyl-phosphatidylcholine (18:1-PC) or linoleoyl-CoA (18:1-CoA), respectively. The subclass using the PC linked substrate are referred to as phospholipid-dependent Δ12-desaturases, the latter sublclass as acyl-CoA dependent Δ12-desaturases. Plant and fungal Δ12-desaturases are generally of the former subclass, whereas animal Δ12-desaturases are of the latter subclass, for example the Δ12-desaturases encoded by genes cloned from insects by Zhou et al. (2008). Many other Δ12-desaturase sequences can be easily identified by searching sequence databases.

As used herein, a "Δ15-desaturase" refers to a protein which performs a desaturase reaction that introduces a carbon-carbon double bond at the 15$^{th}$ carbon-carbon bond from the carboxyl end of a fatty acid substrate. Numerous genes encoding Δ15-desaturases have been cloned from plant and fungal species. For example, U.S. Pat. No. 5,952,544 describes nucleic acids encoding plant Δ15-desaturases (FAD3). These enzymes comprise amino acid motifs that were characteristic of plant Δ15-desaturases. WO200114538 describes a gene encoding soybean FAD3. Many other Δ15-desaturase sequences can be easily identified by searching sequence databases.

As used herein, a "Δ17-desaturase" refers to a protein which performs a desaturase reaction that introduces a carbon-carbon double bond at the 17$^{th}$ carbon-carbon bond from the carboxyl end of a fatty acid substrate. A Δ17-desaturase is also regarded as an ω3-desaturase if it acts on a C20 substrate to introduce a desaturation at the ω3 bond.

In a preferred embodiment, the Δ12-desaturase and/or Δ15-desaturase is a fungal Δ12-desaturase or fungal Δ15-desaturase. As used herein, a "fungal Δ12-desaturase" or "a fungal Δ15-desaturase" refers to a Δ12-desaturase or Δ15-desaturase which is from a fungal source, including an oomycete source, or a variant thereof whose amino acid sequence is at least 95% identical thereto. Genes encoding numerous desaturases have been isolated from fungal sources. U.S. Pat. No. 7,211,656 describes a Δ12 desaturase from *Saprolegnia diclina*. WO2009016202 describes fungal desaturases from *Helobdella robusta, Laccaria bicolor, Lottia gigantea, Microcoleus chthonoplastes, Monosiga brevicollis, Mycosphaerella fijiensis, Mycospaerella graminicola, Naegleria gruben, Nectria haematococca, Nematostella vectensis, Phycomyces blakesleeanus, Trichoderma resii, Physcomitrella patens, Postia placenta, Selaginella moellendorffi and Microdochium nivale*. WO2005/012316 describes a Δ12-desaturase from *Thalassiosira pseudonana* and other fungi. WO2003/099216 describes genes encoding fungal Δ12-desaturases and Δ15-desaturases isolated from *Neurospora crassa, Aspergillus nidulans, Botrytis cinerea* and *Mortierella alpina*. WO2007133425 describes fungal Δ15 desaturases isolated from: *Saccharomyces kluyveri, Mortierella alpina, Aspergillus nidulans, Neurospora crassa, Fusarium graminearum, Fusarium moniliforme* and *Magnaporthe grisea*. A preferred Δ12 desaturase is from *Phytophthora sojae* (Ruiz-Lopez et al., 2012).

A distinct subclass of fungal Δ12-desaturases, and of fungal Δ15-desaturases, are the bifunctional fungal Δ12/Δ15-desaturases. Genes encoding these have been cloned from *Fusarium monoliforme* (Accession No. DQ272516, Damude et al., 2006), *Acanthamoeba castellanii* (Accession No. EF017656, Sayanova et al., 2006), *Perkinsus marinus* (WO2007042510), *Claviceps purpurea* (Accession No. EF536898, Meesapyodsuk et al., 2007) and *Coprinus cinereus* (Accession No. AF269266, Zhang et al., 2007).

In another embodiment, the ω3-desaturase has at least some activity on, preferably greater activity on, an acyl-CoA substrate than a corresponding acyl-PC substrate. As used herein, a "corresponding acyl-PC substrate" refers to the fatty acid esterified at the sn-2 position of phosphatidylcholine (PC) where the fatty acid is the same fatty acid as in the acyl-CoA substrate. For example, the acyl-CoA substrate may be ARA-CoA and the corresponding acyl-PC substrate is sn-2 ARA-PC. In an embodiment, the activity is at least two-fold greater. Preferably, the ω3-desaturase has at least some activity on both an acyl-CoA substrate and its corresponding acyl-PC substrate and has activity on both C18 and C20 substrates. Examples of such ω3-desaturases are known amongst the cloned fungal desaturases listed above.

In a further embodiment, the ω3-desaturase comprises amino acids having a sequence as provided in SEQ ID NO: 12, a biologically active fragment thereof, or an amino acid sequence which is at least 60% identical to SEQ ID NO: 12, preferably at least 90% or at least 95% identical to SEQ ID NO: 12.

In yet a further embodiment, a desaturase for use in the present invention has greater activity on an acyl-CoA substrate than a corresponding acyl-PC substrate. In another embodiment, a desaturase for use in the present invention has greater activity on an acyl-PC substrate than a corresponding acyl-CoA substrate, but has some activity on both substrates. As outlined above, a "corresponding acyl-PC substrate" refers to the fatty acid esterified at the sn-2 position of phosphatidylcholine (PC) where the fatty acid is the same fatty acid as in the acyl-CoA substrate. In an embodiment, the greater activity is at least two-fold greater. In an embodiment, the desaturase is a Δ5 or Δ6-desaturase, or an ω3-desaturase, examples of which are provided, but not limited to, those listed in Table 2. To test which substrate a desaturase acts on, namely an acyl-CoA or an acyl-PC substrate, assays can be carried out in yeast cells as described in Domergue et al. (2003) and (2005). Acyl-CoA substrate capability for a desaturase can also be inferred when an elongase, when expressed together with the desturase, has an enzymatic conversion efficiency in plant cells of at least about 90% where the elongase catalyses the elongation of the product of the desaturase. On this basis, the Δ5-desaturase and Δ4-desaturases expressed from the GA7 construct (Examples 2 and 3) and variants thereof (Example 5) are capable of desaturating their respective acyl-CoA substrates, ETA-CoA and DPA-CoA.

Elongases

Biochemical evidence suggests that the fatty acid elongation consists of 4 steps: condensation, reduction, dehydration and a second reduction. In the context of this invention, an "elongase" refers to the polypeptide that catalyses the condensing step in the presence of the other members of the elongation complex, under suitable physiological conditions. It has been shown that heterologous or homologous expression in a cell of only the condensing component ("elongase") of the elongation protein complex is required for the elongation of the respective acyl chain. Thus, the introduced elongase is able to successfully recruit the reduction and dehydration activities from the transgenic host to carry out successful acyl elongations. The specificity of the elongation reaction with respect to chain length and the degree of desaturation of fatty acid substrates is thought to reside in the condensing component. This component is also thought to be rate limiting in the elongation reaction.

As used herein, a "Δ5-elongase" is at least capable of converting EPA to DPA. Examples of Δ5-elongases include those disclosed in WO2005/103253. In one embodiment, the Δ5-elongase has activity on EPA to produce DPA with an efficiency of at least 60%, more preferably at least 65%, more preferably at least 70% or most preferably at least 80% or 90%. In a further embodiment, the Δ5-elongase comprises an amino acid sequence as provided in SEQ ID NO:37, a biologically active fragment thereof, or an amino acid sequence which is at least 47% identical to SEQ ID NO:37. In a further embodiment, the Δ6-elongase is from *Ostreococcus taurii* or *Ostreococcus lucimarinus* (US2010/088776).

As used herein, a "Δ6-elongase" is at least capable of converting SDA to ETA. Examples of Δ6-elongases include those listed in Table 1. In one embodiment, the elongase comprises amino acids having a sequence as provided in SEQ ID NO:25, a biologically active fragment thereof (such as the fragment provided as SEQ ID NO:26), or an amino acid sequence which is at least 55% identical to one or both of SEQ ID NO:25 or SEQ ID NO:26. In an embodiment, the Δ6-elongase is from *Physcomitrella patens* (Zank et al., 2002; Accession No. AF428243) or *Thalassiosira pseudonana* (Ruiz-Lopez et al., 2012).

As used herein, a "Δ9-elongase" is at least capable of converting ALA to ETrA. Examples of Δ9-elongases include those listed in Table 1. In one embodiment, the Δ9-elongase comprises amino acids having a sequence as provided in SEQ ID NO:43, a biologically active fragment thereof, or an amino acid sequence which is at least 80% identical to SEQ ID NO:43. In another embodiment, the Δ9-elongase comprises amino acids having a sequence as provided in SEQ ID NO:46, a biologically active fragment thereof, or an amino acid sequence which is at least 81% identical to SEQ ID NO:46. In another embodiment, the Δ9-elongase comprises amino acids having a sequence as provided in SEQ ID NO:48, a biologically active fragment thereof, or an amino acid sequence which is at least 50% identical to SEQ ID NO:48. In another embodiment, the Δ9-elongase comprises amino acids having a sequence as provided in SEQ ID NO:50, a biologically active fragment thereof, or an amino acid sequence which is at least 50% identical to SEQ ID NO:50. In a further embodiment, the Δ9-elongase has greater activity on an ω6 substrate than the corresponding ω3 substrate, or the converse.

As used herein, the term "has greater activity on an ω6 substrate than the corresponding ω3 substrate" refers to the relative activity of the enzyme on substrates that differ by the action of an ω3 desaturase. Preferably, the ω6 substrate is LA and the ω3 substrate is ALA.

An elongase with Δ6-elongase and Δ9-elongase activity is at least capable of (i) converting SDA to ETA and (ii) converting ALA to ETrA and has greater Δ6-elongase activity than Δ9-elongase activity. In one embodiment, the elongase has an efficiency of conversion on SDA to produce ETA which is at least 50%, more preferably at least 60%, and/or an efficiency of conversion on ALA to produce ETrA which is at least 6% or more preferably at least 9%. In another embodiment, the elongase has at least about 6.5 fold greater Δ6-elongase activity than Δ9-elongase activity. In a further embodiment, the elongase has no detectable Δ5-elongase activity Other Enzymes As used herein, the term "1-acyl-glycerol-3-phosphate acyltransferase" (LPAAT), also termed lysophosphatidic acid-acyltransferase or acylCoA-lysophosphatidate-acyltransferase, refers to a protein which acylates sn-1-acyl-glycerol-3-phosphate (sn-1 G-3-P) at the sn-2 position to form phosphatidic acid (PA). Thus, the term "1-acyl-glycerol-3-phosphate acyltransferase activity" refers to the acylation of (sn-1 G-3-P) at the sn-2 position to produce PA (EC 2.3.1.51). Preferred LPAATs are those that can use a polyunsaturated C22 acyl-CoA as substrate to transfer the polyunsaturated C22 acyl group to the sn-2 position of LPA, forming PA. Such LPAATs are exemplified in Example 13 and can be tested as described therein. In an embodiment, an LPAAT useful for the invention comprises amino acids having a sequence as provided in any one of SEQ ID NOs: 63 to 69, a biologically active fragment thereof, or an amino acid sequence which is at least 40% identical to any one or more of SEQ ID NOs: 63 to 69. In a preferred embodiment, an LPAAT useful for the invention comprises amino acids having a sequence as provided in any one of SEQ ID NOs: 64, 65 and 67, a biologically active fragment thereof, or an amino acid sequence which is at least 40% identical to any one or more of SEQ ID NOs: 64, 65 and 67.

As used herein, the term "diacylglycerol acyltransferase" (EC 2.3.1.20; DGAT) refers to a protein which transfers a fatty acyl group from acyl-CoA to a diacylglycerol substrate to produce a triacylglycerol. Thus, the term "diacylglycerol acyltransferase activity" refers to the transfer of acyl-CoA to diacylglycerol to produce triacylglycerol. There are three known types of DGAT referred to as DGAT1, DGAT2 and DGAT3 respectively. DGAT1 polypeptides typically have 10 transmembrane domains, DGAT2 typically have 2 transmembrane domains, whilst DGAT3 is typically soluble. Examples of DGAT1 polypeptides include polypeptides encoded by DGAT1 genes from *Aspergillus fumigatus* (Accession No. XP_755172), *Arabidopsis* thaliana (CAB44774), *Ricinus communis* (AAR11479), *Vernicia fordii* (ABC94472), *Vernonia galamensis* (ABV21945, ABV21946), *Euonymus alatus* (AAV31083), *Caenorhabditis elegans* (AAF82410), *Rattus norvegicus* (NP_445889), *Homo sapiens* (NP_036211), as well as variants and/or mutants thereof. Examples of DGAT2 polypeptides include polypeptides encoded by DGAT2 genes from *Arabidopsis thaliana* (Accession No. NP_566952), *Ricinus communis* (AAY 16324), *Vernicia fordii* (ABC94474), *Mortierella ramanniana* (AAK84179), *Homo sapiens* (Q96PD7, Q58HT5), *Bos taurus* (Q70VD8), *Mus musculus* (AAK84175), *Micromonas* CCMP1545, as well as variants and/or mutants thereof. Examples of DGAT3 polypeptides include polypeptides encoded by DGAT3 genes from peanut (*Arachis hypogaea*, Saha, et al., 2006), as well as variants and/or mutants thereof.

Polypeptides/Peptides

The term "recombinant" in the context of a polypeptide refers to the polypeptide when produced by a cell, or in a cell-free expression system, in an altered amount or at an altered rate, compared to its native state if it is produced naturally. In one embodiment the cell is a cell that does not naturally produce the polypeptide. However, the cell may be a cell which comprises a non-endogenous gene that causes an altered amount of the polypeptide to be produced. A recombinant polypeptide of the invention includes polypeptides in the cell, tissue, organ or organism, or cell-free expression system, in which it is produced i.e. a polypeptide which has not been purified or separated from other components of the transgenic (recombinant) cell in which it was produced, and polypeptides produced in such cells or cell-free systems which are subsequently purified away from at least some other components.

The terms "polypeptide" and "protein" are generally used interchangeably.

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length. The polypeptide or class of polypeptides may have the same enzymatic activity as, or a different activity than, or lack the activity of, the reference polypeptide. Preferably, the polypeptide has an enzymatic activity of at least 10%, at least 50%, at least 75% or at least 90%, of the activity of the reference polypeptide.

As used herein a "biologically active" fragment is a portion of a polypeptide defined herein which maintains a defined activity of a full-length reference polypeptide, for example possessing desaturase and/or elongase activity or other enzyme activity. Biologically active fragments as used herein exclude the full-length polypeptide. Biologically active fragments can be any size portion as long as they maintain the defined activity. Preferably, the biologically active fragment maintains at least 10%, at least 50%, at least 75% or at least 90%, of the activity of the full length protein.

With regard to a defined polypeptide or enzyme, it will be appreciated that % identity figures higher than those provided herein will encompass preferred embodiments. Thus, where applicable, in light of the minimum % identity figures, it is preferred that the polypeptidelenzyme comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence variants/mutants of the polypeptides of the defined herein can be prepared by introducing appropriate nucleotide changes into a nucleic acid defined herein, or by in vitro synthesis of the desired polypeptide. Such variants/mutants include, for example, deletions, insertions or substitutions of residues within the amino acid sequence. A combination of deletion, insertion and substitution can be made to arrive at the final construct, provided that the final peptide product possesses the desired enzyme activity.

Mutant (altered) peptides can be prepared using any technique known in the art. For example, a polynucleotide defined herein can be subjected to in vitro mutagenesis or DNA shuffling techniques as broadly described by Harayama (1998). Products derived from mutated/altered DNA can readily be screened using techniques described herein to determine if they possess, for example, desaturase or elongase activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites which are not conserved amongst naturally occurring desaturases or elongases. These sites are preferably substituted in a relatively conservative manner in order to maintain enzyme activity. Such conservative substitutions are shown in Table 3 under the heading of "exemplary substitutions".

In a preferred embodiment a mutant/variant polypeptide has only, or not more than, one or two or three or four conservative amino acid changes when compared to a naturally occurring polypeptide. Details of conservative amino acid changes are provided in Table 3. As the skilled person would be aware, such minor changes can reasonably be predicted not to alter the activity of the polypeptide when expressed in a recombinant cell.

Polypeptides can be produced in a variety of ways, including production and recovery of natural polypeptides or recombinant polypeptides according to methods known in the art. In one embodiment, a recombinant polypeptide is produced by culturing a cell capable of expressing the polypeptide under conditions effective to produce the polypeptide, such as a host cell defined herein. A more preferred cell to produce the polypeptide is a cell in a plant, especially in a seed in a plant.

Polynucleotides

The invention also provides and/or uses polynucleotides which may be, for example, a gene, an isolated polynucleotide, a chimeric genetic construct such as a T-DNA molecule, or a chimeric DNA. It may be DNA or RNA of genomic or synthetic origin, double-stranded or single-stranded, and combined with carbohydrate, lipids, protein or other materials to perform a particular activity defined herein. The term "polynucleotide" is used interchangeably herein with the term "nucleic acid molecule". By "isolated polynucleotide" we mean a polynucleotide which, if obtained from a natural source, has been separated from the polynucleotide sequences with which it is associated or linked in its native state, or a non-naturally occurring polynucleotide. Preferably, the isolated polynucleotide is at least 60% free, more preferably at least 75% free, and more preferably at least 90% free from other components with which it is naturally associated.

TABLE 3

Exemplary substitutions.

| Original Residue | Exemplary Substitutions |
| --- | --- |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |

TABLE 3-continued

| Exemplary substitutions. | |
|---|---|
| Original Residue | Exemplary Substitutions |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In an embodiment, a polynucleotide of the invention is non-naturally occurring. Examples of non-naturally occurring polynucleotides include, but are not limited to, those that have been mutated (such as by using methods described herein), and polynucleotides where an open reading frame encoding a protein is operably linked to a promoter to which it is not naturally associated (such as in the constructs described herein).

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, termination and/or polyadenylation signals that are naturally associated with a given gene, or heterologous control signals in which case the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA). Introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, a "chimeric DNA" or "chimeric genetic construct" refers to any DNA molecule that is not a native DNA molecule in its native location, also referred to herein as a "DNA construct". Typically, a chimeric DNA or chimeric gene comprises regulatory and transcribed or protein coding sequences that are not found operably linked together in nature i.e. that are heterologous with respect to each other. Accordingly, a chimeric DNA or chimeric gene may comprise regulatory sequences and coding sequences that are derived from different sources, or regulatory sequences and coding sequences derived from the same source, but arranged in a manner different than that found in nature.

The term "endogenous" is used herein to refer to a substance that is normally present or produced in, for example, an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. Foreign or exogenous genes may be genes that are inserted into a non-native organism, native genes introduced into a new location within the native host, or chimeric genes. A "transgene" is a gene that has been introduced into the genome by a transformation procedure. The terms "genetically modified", "transgenic" and variations thereof include introducing genes into cells by transformation or transduction, mutating genes in cells and altering or modulating the regulation of a gene in a cell or organisms to which these acts have been done or their progeny. A "genomic region" as used herein refers to a position within the genome where a transgene, or group of transgenes (also referred to herein as a cluster), have been inserted into a cell, or an ancestor thereof. Such regions only comprise nucleotides that have been incorporated by the intervention of man such as by methods described herein.

The term "exogenous" in the context of a polynucleotide refers to the polynucleotide when present in a cell in an altered amount compared to its native state. In one embodiment, the cell is a cell that does not naturally comprise the polynucleotide. However, the cell may be a cell which comprises a non-endogenous polynucleotide resulting in an altered amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

As used herein, the term "different exogenous polynucleotides" or variations thereof means that the nucleotide sequence of each polynucleotide are different by at least one, preferably more, nucleotides. The polynucleotides encode RNAs which may or may not be translated to a protein within the cell. In an example, it is preferred that each polynucleotide encodes a protein with a different activity. In another example, each exogenous polynucleotide is less than 95%, less than 90%, or less than 80% identical to the other exogenous polynuclotides. Preferably, the exogenous polynucleotides encode functional proteins/enzymes. Furthermore, it is preferred that the different exogenous polynucleotides are non-overlapping in that each polynucleotide is a distinct region of the, for example, extrachromosomal transfer nucleic acid which does not overlap with another exogenous polynucleotide. At a minimum, each exogenous polynucleotide has a transcription start and stop site, as well as the designated promoter. An individual exogenous polynucloeotide may or may not comprise introns.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

A polynucleotide of the present invention may selectively hybridise, under stringent conditions, to a polynucleotide that encodes a polypeptide of the present invention. As used herein, stringent conditions are those that (1) employ during hybridisation a denaturing agent such as formamide, for example, 50% (v/v) formamide with 0.1% (w/v) bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (2) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS and/or (3) employ low ionic strength and high temperature for washing, for example, 0.015 M NaCl/0.0015 M sodium citrate/0.1% SDS at 50° C.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above). It is thus apparent that polynucleotides of the invention can be either from a naturally occurring source or recombinant. Preferred polynucleotides are those which have coding regions that are codon-optimised for translation in plant cells, as is known in the art.

Recombinant Vectors

One embodiment of the present invention includes a recombinant vector, which comprises at least one polynucleotide molecule defined herein, inserted into any vector capable of delivering the polynucleotide molecule into a host cell. Recombinant vectors include expression vectors. Recombinant vectors contain heterologous polynucleotide sequences, that is, polynucleotide sequences that are not naturally found adjacent to polynucleotide molecules defined herein that preferably are derived from a species other than the species from which the polynucleotide molecule(s) are derived.

The vector can be either RNA or DNA and typically is a plasmid. Plasmid vectors typically include additional nucleic acid sequences that provide for easy selection, amplification, and transformation of the expression cassette in prokaryotic cells, e.g., pUC-derived vectors, pSK-derived vectors, pGEM-derived vectors, pSP-derived vectors, pBS-derived vectors, or preferably binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells. The recombinant vector may comprise more than one polynucleotide defined herein, for example three, four, five or six polynucleotides defined herein in combination, preferably a chimeric genetic construct of the invention, each polynucleotide being operably linked to expression control sequences that are operable in the cell of interest. More than one polynucleotide defined herein, for example 3, 4, 5 or 6 polynucleotides, are preferably covalently joined together in a single recombinant vector, preferably within a single T-DNA molecule, which may then be introduced as a single molecule into a cell to form a recombinant cell according to the invention, and preferably integrated into the genome of the recombinant cell, for example in a transgenic plant. Thereby, the polynucleotides which are so joined will be inherited together as a single genetic locus in progeny of the recombinant cell or plant. The recombinant vector or plant may comprise two or more such recombinant vectors, each containing multiple polynucleotides, for example wherein each recombinant vector comprises 3, 4, 5 or 6 polynucleotides.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

When there are multiple promoters present, each promoter may independently be the same or different.

Recombinant molecules such as the chimeric DNAs or genetic constructs may also contain (a) one or more secretory signals which encode signal peptide sequences, to enable an expressed polypeptide defined herein to be secreted from the cell that produces the polypeptide or which provide for localisation of the expressed polypeptide, for example for retention of the polypeptide in the endoplasmic reticulum (ER) in the cell or transfer into a plastid, and/or (b) contain fusion sequences which lead to the expression of nucleic acid molecules as fusion proteins. Examples of suitable signal segments include any signal segment capable of directing the secretion or localisation of a polypeptide defined herein. Recombinant molecules may also include intervening and/or untranslated sequences surrounding and/or within the nucleic acid sequences of nucleic acid molecules defined herein.

To facilitate identification of transformants, the nucleic acid construct desirably comprises a selectable or screenable marker gene as, or in addition to, the foreign or exogenous polynucleotide. By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked. The actual choice of a marker is not crucial as long as it is functional (i.e., selective) in combination with the cells of choice such as a plant cell.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of the cell, such as the plant cell. Accordingly, the nucleic acid may comprise appropriate elements which allow the molecule to be incorporated into the genome, preferably the right and left border sequences of a T-DNA molecule, or the construct is placed in an appropriate vector which can be incorporated into a chromosome of the cell.

Expression

As used herein, an expression vector is a DNA vector that is capable of transforming a host cell and of effecting expression of one or more specified polynucleotide molecule(s). Preferred expression vectors of the present invention can direct gene expression in yeast and/or plant cells. Expression vectors useful for the invention contain regulatory sequences such as transcription control sequences, translation control sequences, origins of replication, and other regulatory sequences that are compatible with the recombinant cell and that control the expression of polynucleotide molecules of the present invention. In particular, polynucleotides or vectors useful for the present invention include transcription control sequences. Transcription control sequences are sequences which control the initiation, elongation, and termination of transcription. Particularly important transcription control sequences are those which control transcription initiation, such as promoter and enhancer sequences. Suitable transcription control sequences include any transcription control sequence that can function in at least one of the recombinant cells of the present invention. The choice of the regulatory sequences used depends on the target organism such as a plant and/or target organ or tissue of interest. Such regulatory sequences may be obtained from any eukaryotic organism such as plants or plant viruses, or may be chemically synthesized. A variety of such transcription control sequences are known to those skilled in the art. Particularly preferred transcription control sequences are promoters active in directing transcription in plants, either constitutively or stage and/or tissue specific, depending on the use of the plant or parts thereof.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the *commelina* yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea, the chloroplast fructose-1,6-biphosphatase promoter from wheat, the nuclear photosynthetic ST-LS 1 promoter from potato, the serine/threonine kinase promoter and the glucoamylase (CHS) promoter from *Arabidopsis thaliana*. Also reported to be active in photosynthetically active tissues are ribulose-1,5-bisphosphate carboxylase promoters, and Cab promoters.

A variety of plant gene promoters that are regulated in response to environmental, hormonal, chemical, and/or developmental signals, also can be used for expression of genes in plant cells, including promoters regulated by (1) heat, (2) light (e.g., pea RbcS-3A promoter, maize RbcS promoter); (3) hormones, such as abscisic acid, (4) wounding (e.g., WunI); or (5) chemicals, such as methyl jasmonate, salicylic acid, steroid hormones, alcohol, Safeners (WO97/06269), or it may also be advantageous to employ (6) organ-specific promoters.

As used herein, the term "plant seed specific promoter" or variations thereof refer to a promoter that preferentially, when compared to other plant tissues, directs gene transcription in a developing seed of a plant. In an embodiment, the seed specific promoter is expressed at least 5-fold more strongly in the developing seed of the plant relative to the leaves and/or stems of the plant, and is preferably expressed more strongly in the embryo of the developing seed compared to other plant tissues. Preferably, the promoter only directs expression of a gene of interest in the developing seed, and/or expression of the gene of interest in other parts of the plant such as leaves is not detectable by Northern blot analysis and/or RT-PCR. Typically, the promoter drives expression of genes during growth and development of the seed, in particular during the phase of synthesis and accumulation of storage compounds in the seed. Such promoters may drive gene expression in the entire plant storage organ or only part thereof such as the seedcoat, or cotyledon(s), preferably in the embryos, in seeds of dicotyledonous plants or the endosperm or aleurone layer of a seeds of monocotyledonous plants.

Preferred promoters for seed-specific expression include i) promoters from genes encoding enzymes involved in fatty acid biosynthesis and accumulation in seeds, such as desaturases and elongases, ii) promoters from genes encoding seed storage proteins, and iii) promoters from genes encoding enzymes involved in carbohydrate biosynthesis and accumulation in seeds. Seed specific promoters which are suitable are the oilseed rape napin gene promoter (U.S. Pat. No. 5,608,152), the *Vicia faba* USP promoter (Baumlein et al., 1991), the *Arabidopsis* oleosin promoter (WO98/45461), the *Phaseolus vulgaris* phaseolin promoter (U.S. Pat. No. 5,504,200), the *Brassica* Bce4 promoter (WO91/13980) or the legumin LeB4 promoter from *Vicia faba* (Baumlein et al., 1992), and promoters which lead to the seed-specific expression in monocots such as maize, barley, wheat, rye, rice and the like. Notable promoters which are suitable are the barley lpt2 or lpt1 gene promoter (WO95/15389 and WO95/23230) or the promoters described in WO99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the *sorghum* kasirin gene, the rye secalin gene). Other promoters include those described by Broun et al. (1998), Potenza et al. (2004), US20070192902 and US20030159173. In an embodiment, the seed specific promoter is preferentially expressed in defined parts of the seed such as the embryo, cotyledon(s) or the endosperm. Examples of such specific promoters include, but are not limited to, the FP1 promoter (Ellerstrom et al., 1996), the pea legumin promoter (Perrin et al., 2000), the bean phytohemagglutnin promoter (Perrin et al., 2000), the conlinin 1 and conlinin 2 promoters for the genes encoding the flax 2S storage proteins (Cheng et al., 2010), the promoter of the FAE1 gene from *Arabidopsis thaliana*, the BnGLP promoter of the globulin-like protein gene of *Brassica napus*, the LPXR promoter of the peroxiredoxin gene from *Linum usitatissimum*.

The 5' non-translated leader sequence can be derived from the promoter selected to express the heterologous gene sequence of the polynucleotide of the present invention, or preferably is heterologous with respect to the coding region of the enzyme to be produced, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. No. 5,362,865 and U.S. Pat. No. 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene or a flax conlinin gene are commonly used in this capacity. The 3' transcribed, non-translated regions containing the polyadenylate signal of *Agrobacterium* tumor-inducing (Ti) plasmid genes are also suitable.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules defined herein include, but are not limited to, integration of the polynucleotide molecule into one or more host cell chromosomes, addition of stability sequences to mRNAs, substitutions or modifications of transcription control signals (e.g., promoters, operators, enhancers), substitutions or modifications of translational control signals (e.g., ribosome binding sites, Shine-Dalgarno sequences), modification of polynucleotide molecules to correspond to the codon usage of the host cell, and the deletion of sequences that destabilize transcripts.

Recombinant Cells

The invention also provides a recombinant cell, preferably a recombinant plant cell, which is a host cell transformed with one or more recombinant molecules, such as the polynucleotides, chimeric genetic constructs or recombinant vectors defined herein. The recombinant cell may comprise any combination thereof, such as two or three recombinant vectors, or a recombinant vector and one or more additional polynucleotides or chimeric DNAs. Suitable cells of the invention include any cell that can be transformed with a polynucleotide, chimeric DNA or recombinant vector of the invention, such as for example, a molecule encoding a polypeptide or enzyme described herein. The cell is preferably a cell which is thereby capable of being used for producing LC-PUFA. The recombinant cell may be a cell in culture, a cell in vitro, or in an organism such as for example a plant, or in an organ such as for example a seed or a leaf. Preferably, the cell is in a plant or plant part, more preferably in the seed of a plant.

Host cells into which the polynucleotide(s) are introduced can be either untransformed cells or cells that are already transformed with at least one nucleic acid molecule. Such nucleic acid molecules may be related to LC-PUFA synthesis, or unrelated. Host cells of the present invention either can be endogenously (i.e., naturally) capable of producing proteins defined herein, in which case the recombinant cell derived therefrom has an enhanced capability of producing the polypeptides, or can be capable of producing such proteins only after being transformed with at least one polynucleotide of the invention. In an embodiment, a recombinant cell of the invention has a enhanced capacity to synthesize a long chain polyunsaturated fatty acid. As used herein, the term "cell with an enhanced capacity to synthesize a long chain polyunsaturated fatty acid" is a relative term where the recombinant cell of the invention is compared to the host cell lacking the polynucleotide(s) of the invention, with the recombinant cell producing more long chain polyunsaturated fatty acids, or a greater concentration of LC-PUFA such as DHA (relative to other fatty acids), than the native cell. The cell with an enhanced capacity to synthesize another product, such as for example another fatty acid, a lipid, a carbohydrate such as starch, an RNA molecule, a polypeptide, a pharmaceutical or other product has a corresponding meaning.

Host cells of the present invention can be any cell capable of producing at least one protein described herein, and include bacterial, fungal (including yeast), parasite, arthropod, animal and plant cells. The cells may be prokaryotic or eukaryotic. Preferred host cells are yeast and plant cells. In a preferred embodiment, the plant cell is a seed cell, in particular a cell in a cotyledon or endosperm of a seed. In one embodiment, the cell is an animal cell or an algal cell. The animal cell may be of any type of animal such as, for example, a non-human animal cell, a non-human vertebrate cell, a non-human mammalian cell, or cells of aquatic animals such as, fish or crustacea, invertebrates, insects, etc. The cells may be of an organism suitable for a fermentation process. As used herein, the term the "fermentation process" refers to any fermentation process or any process comprising a fermentation step. Examples of fermenting microorganisms include fungal organisms, such as yeast. As used herein, "yeast" includes *Saccharomyces* spp., *Saccharomyces cerevisiae, Saccharomyces carlbergensis. Candida* spp., *Kluveromyces* spp., *Pichia* spp., *Hansenula* spp., *Trichoderma* spp., *Lipomyces starkey*, and *Yarrowia lipolytica*. Preferred yeast include strains of the *Saccharomyces* spp., and in particular, *Saccharomyces cerevisiae.*

Transgenic Plants

The invention also provides a plant comprising a cell of the invention, such as a transgenic plant comprising one or more polynucleotides of the invention. The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. The term "plant part" refers to all plant parts that comprise the plant DNA, including vegetative structures such as, for example, leaves or stems, roots, floral organs or structures, pollen, seed, seed parts such as an embryo, endosperm, scutellum or seed coat, plant tissue such as, for example, vascular tissue, cells and progeny of the same, as long as the plant part synthesizes lipid according to the invention.

A "transgenic plant", "genetically modified plant" or variations thereof refers to a plant that contains a gene construct ("transgene") not found in a wild-type plant of the same species, variety or cultivar. Transgenic plants as defined in the context of the present invention include plants and their progeny which have been genetically modified using recombinant techniques to cause production of the lipid or at least one polypeptide defined herein in the desired plant or plant organ. Transgenic plant cells and transgenic plant parts have corresponding meanings. A "transgene" as referred to herein has the normal meaning in the art of biotechnology and includes a genetic sequence which has been produced or altered by recombinant DNA or RNA technology and which has been introduced into a cell of the invention, preferably a plant cell. The transgene may include genetic sequences derived from a plant cell which may be of the same species, variety or cultivar as the plant cell into which the transgene is introduced or of a different species, variety or cultivar, or from a cell other than a plant cell. Typically, the transgene has been introduced into the cell, such as a plant, by human manipulation such as, for example, by transformation but any method can be used as one of skill in the art recognizes.

The terms "seed" and "grain" are used interchangeably herein. "Grain" refers to mature grain such as harvested grain or grain which is still on a plant but ready for harvesting, but can also refer to grain after imbibition or germination, according to the context. Mature grain or seed commonly has a moisture content of less than about 18-20%. "Developing seed" as used herein refers to a seed prior to maturity, typically found in the reproductive structures of the plant after fertilisation or anthesis, but can also refer to such seeds prior to maturity which are isolated from a plant.

As used herein, the term "obtaining a plant part" or "obtaining a seed" refers to any means of obtaining a plant part or seed, respectively, including harvesting of the plant parts or seed from plants in the field or in containment such as a greenhouse or growth chamber, or by purchase or receipt from a supplier of the plant parts or seed.

The seed may be suitable for planting i.e. able to germinate and produce progeny plants, or alternatively has been processed in such a way that it is no longer able to germinate, e.g. cracked, polished or milled seed which is useful for food or feed applications, or for extraction of lipid of the invention.

As used herein, the term "plant storage organ" refers to a part of a plant specialized to storage energy in the form of, for example, proteins, carbohydrates, fatty acids and/or oils. Examples of plant storage organs are seed, fruit, tuberous roots, and tubers. A preferred plant storage organ of the invention is seed.

As used herein, the term "phenotypically normal" refers to a genetically modified plant or plant organ, particularly a storage organ such as a seed, tuber or fruit of the invention not having a significantly reduced ability to grow and reproduce when compared to an unmodified plant or plant organ. In an embodiment, the genetically modified plant or plant organ which is phenotypically normal comprises an exogenous polynucleotide encoding a silencing suppressor operably linked to a plant storage organ specific promoter and has an ability to grow or reproduce which is essentially the same as an isogenic plant or organ not comprising said polynucleotide. Preferably, the biomass, growth rate, germination rate, storage organ size, seed size and/or the number of viable seeds produced is not less than 90% of that of a plant lacking said exogenous polynucleotide when grown under identical conditions. This term does not encompass features of the plant which may be different to the wild-type plant but which do not effect the usefulness of the plant for commercial purposes such as, for example, a ballerina phenotype of seedling leaves.

Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, *sorghum*, millet, cassava, barley, or pea), or other legumes. The plants may be grown for production of edible roots, tubers, leaves, stems, flowers or fruit. The plants may be vegetables or ornamental plants. The plants of the invention may be: corn (*Zea mays*), canola (*Brassica napus. Brassica rapa* ssp.), mustard (*Brassica juncea*), flax (*Linum usitatissimum*), alfalfa (*Medicago sativa*), rice (*Oryza sativa*), rye (*Secale cerale*), *sorghum* (*Sorghum bicolour. Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), *papaya* (*Carica papaya*), cashew (*Anacardium occidentale*), *macadamia* (*Macadamia intergrifolia*), almond (*Prunus amygdalus*), sugar beets (*Beta vulgaris*), oats, or barley.

In a preferred embodiment, the plant is an angiosperm.

In an embodiment, the plant is an oilseed plant, preferably an oilseed crop plant. As used herein, an “oilseed plant” is a plant species used for the commercial production of oils from the seeds of the plant. The oilseed plant may be oil-seed rape (such as canola), maize, sunflower, soybean, *sorghum*, flax (linseed) or sugar beet. Furthermore, the oilseed plant may be other *Brassicas*, cotton, peanut, poppy, mustard, castor bean, sesame, safflower, or nut producing plants. The plant may produce high levels of oil in its fruit, such as olive, oil palm or coconut. Horticultural plants to which the present invention may be applied are lettuce, endive, or vegetable *brassicas* including cabbage, broccoli, or cauliflower. The present invention may be applied in tobacco, cucurbits, carrot, strawberry, tomato, or pepper.

In a further preferred embodiment, the non-transgenic plant used to produce a transgenic plant of the invention produces oil, especially in the seed, which has i) less than 20%, less than 10% or less than 5% 18:2 fatty acids and/or ii) less than 10% or less than 5% 18:3 fatty acids.

In a preferred embodiment, the transgenic plant is homozygous for each and every gene that has been introduced (transgene) so that its progeny do not segregate for the desired phenotype. The transgenic plant may also be heterozygous for the introduced transgene(s), preferably uniformly heterozygous for the transgene, such as for example in F1 progeny which have been grown from hybrid seed. Such plants may provide advantages such as hybrid vigour, well known in the art.

Where relevant, the transgenic plants may also comprise additional transgenes encoding enzymes involved in the production of LC-PUFAs such as, but not limited to, a Δ6-desaturase, a Δ9-elongase, a Δ8-desaturase, a Δ6-elongase, a Δ5-desaturase, an ω3-desaturase, a Δ4-desaturase, a Δ5-elongase, diacylglycerol acyltransferase, LPAAT, a Δ17-desaturase, a Δ15-desaturase and/or a Δ12 desaturase. Examples of such enzymes with one of more of these activities are known in the art and include those described herein. In specific examples, the transgenic plant at least comprises exogenous polynucleotides encoding;

a) a Δ4-desaturase, a Δ5-desaturase, a Δ6-desaturase, a Δ5-elongase and a Δ6-elongase,
b) a Δ4-desaturase, a Δ5-desaturase, a Δ8-desaturase, a Δ5-elongase and a Δ9-elongase,
c) a Δ4-desaturase, a Δ5-desaturase, a Δ6-desaturase, a Δ5-elongase, a Δ6-elongase, and a Δ15-desaturase,
d) a Δ4-desaturase, a Δ5-desaturase, a Δ8-desaturase, a Δ5-elongase, a Δ9-elongase, and a Δ15-desaturase,
e) a Δ4-desaturase, a Δ5-desaturase, a Δ6-desaturase, a Δ5-elongase, a Δ6-elongase, and a Δ17-desaturase, or
f) a Δ4-desaturase, a Δ5-desaturase, a Δ8-desaturase, a Δ5-elongase, a Δ9-elongase, and a Δ17-desaturase.

In an embodiment, the exogenous polynucleotides encode set of polypeptides which are a *Pythium irregulare* Δ6-desaturase, a *Thraustochytrid* Δ5-desaturase or an *Emiliana huxleyi* Δ5-desaturase, a *Physcomitrella patens* Δ6-elongase, a *Thraustochytrid* Δ5-elongase or an *Ostreocccus taurii* Δ5-elongase, a *Phytophthora infestans* ω3-desaturase or a *Pythium irregulare* ω3-desaturase, and a *Thraustochytrid* Δ4-desaturase.

In an embodiment, plants of the invention are grown in the field, preferably as a population of at least 1,000 or 1,000,000 plants that are essentially the same, or in an area of at least 1 hectare. Planting densities differ according to the plant species, plant variety, climate, soil conditions, fertiliser rates and other factors as known in the art. For example, canola is typically grown at a planting density of 1.2-1.5 million plants per hectare. Plants are harvested as is known in the art, which may comprise swathing, windrowing and/or reaping of plants, followed by threshing and/or winnowing of the plant material to separate the seed from the remainder of the plant parts often in the form of chaff. Alternatively, seed may be harvested from plants in the field in a single process, namely combining.

Transformation of Plants

Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

As used herein, the terms “stably transforming”, “stably transformed” and variations thereof refer to the integration of the exogenous nucleic acid molecules into the genome of the cell such that they are transferred to progeny cells during cell division without the need for positively selecting for their presence. Stable transformants, or progeny thereof, can be selected by any means known in the art such as Southern blots on chromosomal DNA or in situ hybridization of genomic DNA.

*Agrobacterium*-mediated transfer is a widely applicable system for introducing genes into plant cells because DNA can be introduced into cells in whole plant tissues or plant organs or explants in tissue culture, for either transient expression or for stable integration of the DNA in the plant cell genome. The use of *Agrobacterium*-mediated plant integrating vectors to introduce DNA into plant cells is well known in the art (see, for example, U.S. Pat. No. 5,177,010, U.S. Pat. No. 5,104,310, U.S. Pat. No. 5,004,863 or U.S. Pat. No. 5,159,135) including floral dipping methods using *Agrobacterium* or other bacteria that can transfer DNA into plant cells. The region of DNA to be transferred is defined by the border sequences, and the intervening DNA (T-DNA) is usually inserted into the plant genome. Further, the integration of the T-DNA is a relatively precise process resulting in few rearrangements. In those plant varieties where *Agrobacterium*-mediated transformation is efficient, it is the method of choice because of the facile and defined nature of the gene transfer. Preferred *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required.

In another alternative embodiment, plastids can be stably transformed. Methods disclosed for plastid transformation in higher plants include particle gun delivery of DNA containing a selectable marker and targeting of the DNA to the plastid genome through homologous recombination (U.S. Pat. No. 5,451,513, U.S. Pat. No. 5,545,818, U.S. Pat. No. 5,877,402, U.S. Pat. No. 5,932,479, and WO99/05265).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

A transgenic plant formed using *Agrobacterium* or other transformation methods typically contains a single genetic locus on one chromosome. Such transgenic plants can be referred to as being hemizygous for the added gene(s). More preferred is a transgenic plant that is homozygous for the added gene(s); i.e., a transgenic plant that contains two added genes, one gene at the same locus on each chromosome of a chromosome pair. A homozygous transgenic plant can be obtained by self-fertilising a hemizygous transgenic plant, germinating some of the seed produced and analyzing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both exogenous genes or loci. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Enhancing Exogenous RNA Levels and Stabilized Expression

Silencing Suppressors

In an embodiment, a cell, plant or plant part of the invention comprises an exogenous polynucleotide encoding a silencing suppressor protein.

Post-transcriptional gene silencing (PTGS) is a nucleotide sequence-specific defense mechanism that can target both cellular and viral mRNAs for degradation PTGS occurs in plants or fungi stably or transiently transformed with foreign (heterologous) or endogenous DNA and results in the reduced accumulation of RNA molecules with sequence similarity to the introduced nucleic acid.

It has widely been considered that co-expression of a silencing suppressor with a transgene of interest will increase the levels of RNA present in the cell transcribed from the transgene. Whilst this has proven true for cells in vitro, significant side-effects have been observed in many whole plant co-expression studies. More specifically, as described in Mallory et al. (2002), Chapman et al. (2004), Chen et al. (2004), Dunoyer et al. (2004), Zhang et al. (2006), Lewsey et al. (2007) and Meng et al. (2008) plants expressing silencing suppressors, generally under constitutive promoters, are often phenotypically abnormal to the extent that they are not useful for commercial production.

Recently, it has been found that RNA molecule levels can be increased, and/or RNA molecule levels stabilized over numerous generations, by limiting the expression of the silencing suppressor to a seed of a plant or part thereof (WO2010/057246). As used herein, a "silencing suppressor protein" or SSP is any polypeptide that can be expressed in a plant cell that enhances the level of expression product from a different transgene in the plant cell, particularly over repeated generations from the initially transformed plant. In an embodiment, the SSP is a viral silencing suppressor or mutant thereof. A large number of viral silencing suppressors are known in the art and include, but are not limited to P19, V2, P38, Pe-Po and RPV-P0. In an embodiment, the viral silencing suppressor comprises amino acids having a sequence as provided in any one of SEQ ID NOs 53 to 57, a biologically active fragment thereof, or an amino acid sequence which is at least 50% identical to any one or more of SEQ ID NOs 53 to 57 and which has activity as a silencing suppressor.

As used herein, the terms "stabilising expression", "stably expressed", "stabilised expression" and variations thereof refer to level of the RNA molecule being essentially the same or higher in progeny plants over repeated generations, for example at least three, at least five or at least 10 generations, when compared to isogenic plants lacking the exogenous polynucleotide encoding the silencing suppressor. However, this term(s) does not exclude the possibility that over repeated generations there is some loss of levels of the RNA molecule when compared to a previous generation, for example not less than a 10% loss per generation.

The suppressor can be selected from any source e.g. plant, viral, mammal etc. See WO2010/057246 for a list of viruses from which the suppressor can be obtained and the protein (eg B2, P14 etc) or coding region designation for the suppressor from each particular virus. Multiple copies of a suppressor may be used. Different suppressors may be used together (e. g., in tandem).

RNA Molecules

Essentially any RNA molecule which is desirable to be expressed in a plant seed can be co-expressed with the silencing suppressor. The encoded polypeptides may be involved in metabolism of oil, starch, carbohydrates, nutrients, etc., or may be responsible for the synthesis of proteins, peptides, fatty acids, lipids, waxes, oils, starches, sugars, carbohydrates, flavors, odors, toxins, carotenoids. hormones, polymers, flavonoids, storage proteins, phenolic acids, alkaloids, lignins, tannins, celluloses, glycoproteins, glycolipids, etc, preferably the biosynthesis or assembly of TAG.

In a particular example, the plants produced increased levels of enzymes for oil production in plants such as *Brassicas*, for example canola or sunflower, safflower, flax, cotton, soya bean, *Camelina* or maize.

Levels of LC-PUFA Produced

The levels of the LC-PUFA or combination of LC-PUFAs that are produced in the recombinant cell or plant part such as seed are of importance. The levels may be expressed as a composition (in percent) of the total fatty acid that is a particular LC-PUFA or group of related LC-PUFA, for example the ω3 LC-PUFA or the ω6 LC-PUFA, or the VLC-PUFA, or other which may be determined by methods known in the art. The level may also be expressed as a LC-PUFA content, such as for example the percentage of LC-PUFA in the dry weight of material comprising the recombinant cells, for example the percentage of the weight of seed that is LC-PUFA. It will be appreciated that the LC-PUFA that is produced in an oilseed may be considerably higher in terms of LC-PUFA content than in a vegetable or a grain that is not grown for oil production, yet both may have similar LC-PUFA compositions, and both may be used as sources of LC-PUFA for human or animal consumption.

The levels of LC-PUFA may be determined by any of the methods known in the art. In a preferred method, total lipid is extracted from the cells, tissues or organisms and the fatty acid converted to methyl esters before analysis by gas chromatography (GC). Such techniques are described in Example 1. The peak position in the chromatogram may be used to identify each particular fatty acid, and the area under each peak integrated to determine the amount. As used herein, unless stated to the contrary, the percentage of particular fatty acid in a sample is determined as the area under the peak for that fatty acid as a percentage of the total area for fatty acids in the chromatogram. This corresponds essentially to a weight percentage (w/w). The identity of fatty acids may be confirmed by GC-MS. Total lipid may be separated by techniques known in the art to purify fractions such as the TAG fraction. For example, thin-layer chromatography (TLC) may be performed at an analytical scale to separate TAG from other lipid fractions such as DAG, acyl-CoAs or phospholipid in order to determine the fatty acid composition specifically of TAG.

In one embodiment, the sum total of ARA, EPA, DPA and DHA in the fatty acids in the extracted lipid is between about 7% and about 25% of the total fatty acids in the cell. In a further embodiment, the total fatty acid in the cell has less than 1% C20:1. In preferred embodiments, the extractable TAG in the cell comprises the fatty acids at the levels referred to herein. Each possible combination of the features defining the lipid as described herein is also encompassed.

The level of production of LC-PUFA in the recombinant cell, plant or plant part such as seed may also be expressed as a conversion percentage of a specific substrate fatty acid to one or more product fatty acids, which is also referred to herein as a "conversion efficiency" or "enzymatic efficiency". This parameter is based on the fatty acid composition in the lipid extracted from the cell, plant, plant part or seed, i.e., the amount of the LC-PUFA formed (including other LC-PUFA derived therefrom) as a percentage of one or more substrate fatty acids (including all other fatty acids derived therefrom). The general formula for a conversion percentage is: 100×(the sum of percentages of the product LC-PUFA and all products derived therefrom)/(the sum of the percentages of the substrate fatty acid and all products derived therefrom). With regard to DHA, for example, this may be expressed as the ratio of the level of DHA (as a percentage in the total fatty acid content in the lipid) to the level of a substrate fatty acid (e.g. OA, LA, ALA, SDA, ETA or EPA) and all products other than DHA derived from the substrate. The conversion percentage or efficiency of conversion can be expressed for a single enzymatic step in a pathway, or for part or the whole of a pathway.

Specific conversion efficiencies are calculated herein according to the formulae:

1. OA to DHA=100×(% DHA)/(sum % for OA, LA, GLA, DGLA, ARA, EDA, ALA, SDA, ETrA, ETA, EPA, DPA and DHA).
2. LA to DHA=100×(% DHA)/(sum % for LA, GLA, DGLA, ARA, EDA, ALA, SDA, ETrA, ETA, EPA, DPA and DHA).
3. ALA to DHA=100×(% DHA)/(sum % for ALA, SDA, ETrA, ETA, EPA, DPA and DHA).
4. EPA to DHA=100×(% DHA)/(sum % for EPA, DPA and DHA).

5. DPA to DHA (Δ4-desaturase efficiency)=100×(% DHA)/(sum % for DPA and DHA).
6. Δ12-desaturase efficiency=100×(sum % for LA, GLA, DGLA, ARA, EDA, ALA, SDA, ETrA, ETA, EPA, DPA and DHA)/(sum % for OA, LA, GLA, DGLA, ARA, EDA, ALA, SDA, ETrA, ETA, EPA, DPA and DHA).
7. ω3-desaturase efficiency=100×(sum % for ALA, SDA, ETrA, ETA, EPA, DPA and DHA)/(sum % for LA, GLA, DGLA, ARA, EDA, ALA, SDA, ETrA, ETA, EPA, DPA and DHA).
8. OA to ALA=100×(sum % for ALA, SDA, ETrA, ETA, EPA, DPA and DHA)/(sum % for OA, LA, GLA, DGLA, ARA, EDA, ALA, SDA, ETrA, ETA, EPA, DPA and DHA).
9. Δ6-desaturase efficiency (on ω3 substrate ALA)=100×(sum % for SDA, ETA, EPA, DPA and DHA)/(% ALA, SDA, ETrA, ETA, EPA, DPA and DHA).
10. Δ6-elongase efficiency (on ω3 substrate SDA)=100×(sum % for ETA, EPA, DPA and DHA)/(sum % for SDA, ETA, EPA, DPA and DHA).
11. Δ5-desaturase efficiency (on ω3 substrate ETA)=100×(sum % for EPA, DPA and DHA)/(sum % for ETA, EPA, DPA and DHA).
12. Δ5-elongase efficiency (on ω3 substrate EPA)=100×(sum % for DPA and DHA)/(sum % for EPA, DPA and DHA).

The fatty acid composition of the lipid, preferably seedoil, of the invention, is also characterised by the ratio of ω6 fatty acids:ω3 fatty acids in the total fatty acid content, for either total ω6 fatty acids:total ω3 fatty acids or for new ω6 fatty acids:new ω3 fatty acids. The terms total ω6 fatty acids, total ω3 fatty acids, new ω6 fatty acids and new ω3 fatty acids have the meanings as defined herein. The ratios are calculated from the fatty acid composition in the lipid extracted from the cell, plant, plant part or seed, in the manner as exemplified herein. It is desirable to have a greater level of ω3 than ω6 fatty acids in the lipid, and therefore an ω6:ω3 ratio of less than 1.0 is preferred. A ratio of 0.0 indicates a complete absence of the defined ω6 fatty acids; a ratio of 0.03 was achieved as described in Example 6. Such low ratios can be achieved through the combined use of a Δ6-desaturase which has an ω3 substrate preference together with an ω3-desaturase, particularly a fungal ω3-desaturase such as the *Pichia pastoris* ω3-desaturase as exemplified herein.

The yield of LC-PUFA per weight of seed may also be calculated based on the total oil content in the seed and the % DHA in the oil. For example, if the oil content of canola seed is about 40% (w/w) and about 12% of the total fatty acid content of the oil is DHA, the DHA content of the seed is about 4.8% or about 48 mg per gram of seed. As described in Example 2, the DHA content of *Arabidopsis* seed having about 9% DHA, which has a lower oil content than canola, was about 25 mg/g seed. At a DHA content of about 7%, canola seed or *Camelina sativa* seed has a DHA content of about 28 mg per gram of seed. The present invention therefore provides *Brassica napus. B. juncea* and *Camelina sativa* plants, and seed obtained therefrom, comprising at least about 28 mg DHA per gram seed. The seed has a moisture content as is standard for harvested mature seed after drying down (4-15% moisture). The invention also provides a process for obtaining oil, comprising obtaining the seed and extracting the oil from the seed, and uses of the oil and methods of obtaining the seed comprising harvesting the seeds from the plants according to the invention.

The amount of DHA produced per hectare can also be calculated if the seed yield per hectare is known or can be estimated. For example, canola in Australia typically yields about 2.5 tonnes seed per hectare, which at 40% oil content yields about 1000 kg of oil. At 12% DHA in the total oil, this provides about 120 kg of DHA per hectare. If the oil content is reduced by 50%, this still provides about 60 kg DHA/ha.

Evidence to date suggests that some desaturases expressed heterologously in yeast or plants have relatively low activity in combination with some elongases. This may be alleviated by providing a desaturase with the capacity of to use an acyl-CoA form of the fatty acid as a substrate in LC-PUFA synthesis, and this is thought to be advantageous in recombinant cells particularly in plant cells. A particularly advantageous combination for efficient DHA synthesis is a fungal ω3-desaturase, for example such as the *Pichia pastoris* ω3-desaturase (SEQ ID NO: 12), with a Δ6-desaturase which has a preference for ω3 acyl substrates such as, for example, the *Micromonas pusilla* Δ6-desaturase (SEQ ID NO: 13), or variants thereof which have at least 95% amino acid sequence identity.

As used herein, the term "essentially free" means that the composition (for example lipid or oil) comprises little (for example, less than about 0.5%, less than about 0.25%, less than about 0.1%, or less than about 0.01%) or none of the defined component. In an embodiment, "essentially free" means that the component is undetectable using a routine analytical technique, for example a specific fatty acid (such as ω6-docosapentaenoic acid) cannot be detected using gas chromatography as outlined in Example 1.

Production of Oils

Techniques that are routinely practiced in the art can be used to extract, process, and analyze the oils produced by cells, plants, seeds, etc of the instant invention. Typically, plant seeds are cooked, pressed, and extracted to produce crude oil, which is then degummed, refined, bleached, and deodorized. Generally, techniques for crushing seed are known in the art. For example, oilseeds can be tempered by spraying them with water to raise the moisture content to, e.g., 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the oil droplets, and agglomerates protein particles, all of which facilitate the extraction process.

In an embodiment, the majority of the seed oil is released by passage through a screw press. Cakes expelled from the screw press are then solvent extracted, e.g., with hexane, using a heat traced column. Alternatively, crude oil produced by the pressing operation can be passed through a settling tank with a slotted wire drainage top to remove the solids that are expressed with the oil during the pressing operation. The clarified oil can be passed through a plate and frame filter to remove any remaining fine solid particles. If desired, the oil recovered from the extraction process can be combined with the clarified oil to produce a blended crude oil.

Once the solvent is stripped from the crude oil, the pressed and extracted portions are combined and subjected to normal oil processing procedures. As used herein, the term "purified" when used in connection with lipid or oil of the invention typically means that that the extracted lipid or oil has been subjected to one or more processing steps of increase the purity of the lipid/oil component. For example, a purification step may comprise one or more or all of the group consisting of: degumming, deodorising, decolourising, drying and/or fractionating the extracted oil. However, as used herein, the term "purified" does not include a transesterification process or other process which alters the fatty acid composition of the lipid or oil of the invention so as to increase the DHA content as a percentage of the total fatty acid content. Expressed in other words, the fatty acid composition of the purified lipid or oil is essentially the same as that of the unpurified lipid or oil.

Degumming

Degumming is an early step in the refining of oils and its primary purpose is the removal of most of the phospholipids from the oil, which may be present as approximately 1-2% of the total extracted lipid. Addition of ~2% of water, typically containing phosphoric acid, at 70-80° C. to the crude oil results in the separation of most of the phospholipids accompanied by trace metals and pigments. The insoluble material that is removed is mainly a mixture of phospholipids and triacylglycerols and is also known as lecithin. Degumming can be performed by addition of concentrated phosphoric acid to the crude seedoil to convert non-hydratable phosphatides to a hydratable form, and to chelate minor metals that are present. Gum is separated from the seedoil by centrifugation.

Alkali Refining

Alkali refining is one of the refining processes for treating crude oil, sometimes also referred to as neutralization. It usually follows degumming and precedes bleaching. Following degumming, the seedoil can treated by the addition of a sufficient amount of an alkali solution to titrate all of the fatty acids and phosphoric acids, and removing the soaps thus formed. Suitable alkaline materials include sodium hydroxide, potassium hydroxide, sodium carbonate, lithium hydroxide, calcium hydroxide, calcium carbonate and ammonium hydroxide. This process is typically carried out at room temperature and removes the free fatty acid fraction. Soap is removed by centrifugation or by extraction into a solvent for the soap, and the neutralised oil is washed with water. If required, any excess alkali in the oil may be neutralized with a suitable acid such as hydrochloric acid or sulphuric acid.

Bleaching

Bleaching is a refining process in which oils are heated at 90-120° C. for 10-30 minutes in the presence of a bleaching earth (0.2-2.0%) and in the absence of oxygen by operating with nitrogen or steam or in a vacuum. This step in oil processing is designed to remove unwanted pigments (carotenoids, chlorophyll, gossypol etc), and the process also removes oxidation products, trace metals, sulphur compounds and traces of soap.

Deodorization

Deodorization is a treatment of oils and fats at a high temperature (200-260° C.) and low pressure (0.1-1 mm Hg). This is typically achieved by introducing steam into the seedoil at a rate of about 0.1 ml/minute/100 ml of seedoil. After about 30 minutes of sparging, the seedoil is allowed to cool under vacuum. The seedoil is typically transferred to a glass container and flushed with argon before being stored under refrigeration. This treatment improves the colour of the seedoil and removes a majority of the volatile substances or odorous compounds including any remaining free fatty acids, monoacylglycerols and oxidation products.

Winterisation

Winterization is a process sometimes used in commercial production of oils for the separation of oils and fats into solid (stearin) and liquid (olein) fractions by crystallization at sub-ambient temperatures. It was applied originally to cottonseed oil to produce a solid-free product. It is typically used to decrease the saturated fatty acid content of oils.

Transesterification

Transesterification is a process that exchanges the fatty acids within and between TAGs or transfers the fatty acids to another alcohol to form an ester, initially by releasing fatty acids from the TAGs either as free fatty acids or as fatty acid esters, usually fatty acid methyl esters or ethyl esters. When combined with a fractionation process, transesterification can be used to modify the fatty acid composition of lipids (Marangoni et al., 1995). Transesterification can use either chemical (e.g. strong acid or base catalysed) or enzymatic means, the latter using lipases which may be position-specific (sn-1/3 or sn-2 specific) for the fatty acid on the TAG, or having a preference for some fatty acids over others (Speranza et al, 2012). The fatty acid fractionation to increase the concentration of LC-PUFA in an oil can be achieved by any of the methods known in the art, such as, for example, freezing crystallization, complex formation using urea, molecular distillation, supercritical fluid extraction and silver ion complexing. Complex formation with urea is a preferred method for its simplicity and efficiency in reducing the level of saturated and monounsaturated fatty acids in the oil (Gamez et al., 2003). Initially, the TAGs of the oil are split into their constituent fatty acids, often in the form of fatty acid esters, by hydrolysis under either acid or base catalysed reaction conditions, whereby one mol of TAG is reacted with at least 3 mol of alcohol (e.g. ethanol for ethyl esters or methanol for methyl esters) with excess alcohol used to enable separation of the formed alkyl esters and the glycerol that is also formed, or by lipases. These free fatty acids or fatty acid esters, which are usually unaltered in fatty acid composition by the treatment, may then be mixed with an ethanolic solution of urea for complex formation. The saturated and monounsaturated fatty acids easily complex with urea and crystallize out on cooling and may subsequently be removed by filtration. The non-urea complexed fraction is thereby enriched with LC-PUFA.

Feedstuffs

The present invention includes compositions which can be used as feedstuffs. For purposes of the present invention, “feedstuffs” include any food or preparation for human or animal consumption which when taken into the body (a) serve to nourish or build up tissues or supply energy; and/or (b) maintain, restore or support adequate nutritional status or metabolic function. Feedstuffs of the invention include nutritional compositions for babies and/or young children such as, for example, infant formula, and seedmeal of the invention.

Feedstuffs of the invention comprise, for example, a cell of the invention, a plant of the invention, the plant part of the invention, the seed of the invention, an extract of the invention, the product of the method of the invention, the product of the fermentation process of the invention, or a composition along with a suitable carrier(s). The term “carrier” is used in its broadest sense to encompass any component which may or may not have nutritional value. As the skilled addressee will appreciate, the carrier must be suitable for use (or used in a sufficiently low concentration) in a feedstuff such that it does not have deleterious effect on an organism which consumes the feedstuff.

The feedstuff of the present invention comprises an oil, fatty acid ester, or fatty acid produced directly or indirectly by use of the methods, cells or plants disclosed herein. The composition may either be in a solid or liquid form. Additionally, the composition may include edible macronutrients, protein, carbohydrate, vitamins, and/or minerals in amounts desired for a particular use. The amounts of these ingredients will vary depending on whether the composition is intended for use with normal individuals or for use with individuals having specialized needs, such as individuals suffering from metabolic disorders and the like.

Examples of suitable carriers with nutritional value include, but are not limited to, macronutrients such as edible fats, carbohydrates and proteins. Examples of such edible fats include, but are not limited to, coconut oil, borage oil, fungal oil, black current oil, soy oil, and mono- and diglycerides. Examples of such carbohydrates include (but are not limited to): glucose, edible lactose, and hydrolyzed starch. Additionally, examples of proteins which may be utilized in the nutritional composition of the invention include (but are not limited to) soy proteins, electrodialysed whey, electrodialysed skim milk, milk whey, or the hydrolysates of these proteins.

With respect to vitamins and minerals, the following may be added to the feedstuff compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the feedstuff compositions of the present invention can be of semi-purified or purified origin. By semi-purified or purified is meant a material which has been prepared by purification of a natural material or by de novo synthesis.

A feedstuff composition of the present invention may also be added to food even when supplementation of the diet is not required. For example, the composition may be added to food of any type, including (but not limited to): margarine, modified butter, cheeses, milk, yogurt, chocolate, candy, snacks, salad oils, cooking oils, cooking fats, meats, fish and beverages.

The genus *Saccharomyces* spp is used in both brewing of beer and wine making and also as an agent in baking, particularly bread. Other yeasts such as oleaginous yeast including, for example, *Yarrowia* spp, are also useful in LC-PUFA production. Yeasts may be used as an additive in animal feed, such as in aquaculture. It will be apparent that genetically engineered yeast strains can be provided which are adapted to synthesise LC-PUFA as described herein. These yeast strains, or LC-PUFA produced therein, can then be used in food stuffs and in wine and beer making to provide products which have enhanced fatty acid content.

Additionally, fatty acids produced in accordance with the present invention or host cells transformed to contain and express the subject genes may also be used as animal food supplements to alter an animal's tissue, egg or milk fatty acid composition to one more desirable for human or animal consumption. Examples of such animals include sheep, cattle, horses, poultry such as chickens and the like.

Furthermore, feedstuffs of the invention can be used in aquaculture to increase the levels of fatty acids in fish or crustaceans such as, for example, prawns for human or animal consumption. Preferred fish are salmon.

Preferred feedstuffs of the invention are the plants, seed and other plant parts such as leaves and stems which may be used directly as food or feed for humans or other animals. For example, animals may graze directly on such plants grown in the field or be fed more measured amounts in controlled feeding. The invention includes the use of such plants and plant parts as feed for increasing the LC-PUFA levels in humans and other animals.

Compositions

The present invention also encompasses compositions, particularly pharmaceutical compositions, comprising one or more of the fatty acids and/or resulting oils produced using the methods of the invention.

A pharmaceutical composition may comprise one or more of the fatty acids and/or oils, in combination with a standard, well-known, non-toxic pharmaceutically-acceptable carrier, adjuvant or vehicle such as phosphate-buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride, and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as ethoxylated isostearyl alcohols, polyoxyethylene sorbitol and sorbitan esters, microcrystalline cellulose, aluminum metahydroxide, bentonite, agar-agar, and tragacanth or mixtures of these substances.

Solid dosage forms such as tablets and capsules can be prepared using techniques well known in the art. For example, fatty acids produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant fatty acid(s).

For intravenous administration, the fatty acids produced in accordance with the present invention or derivatives thereof may be incorporated into commercial formulations.

A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses). As known in the art, a minimum of about 300 mg/day of fatty acid, especially LC-PUFA, is desirable. However, it will be appreciated that any amount of fatty acid will be beneficial to the subject.

Possible routes of administration of the pharmaceutical compositions of the present invention include, for example, enteral (e.g., oral and rectal) and parenteral. For example, a liquid preparation may be administered orally or rectally. Additionally, a homogenous mixture can be completely dispersed in water, admixed under sterile conditions with physiologically acceptable diluents, preservatives, buffers or propellants to form a spray or inhalant.

The dosage of the composition to be administered to the patient may be determined by one of ordinary skill in the art and depends upon various factors such as weight of the patient, age of the patient, overall health of the patient, past history of the patient, immune status of the patient, etc.

Additionally, the compositions of the present invention may be utilized for cosmetic purposes. It may be added to pre-existing cosmetic compositions such that a mixture is formed or a fatty acid produced according to the subject invention may be used as the sole "active" ingredient in a cosmetic composition.

EXAMPLES

Example 1. Materials and Methods

Expression of Genes in Plant Cells in a Transient Expression System

Exogenous genetic constructs were expressed in plant cells in a transient expression system essentially as described by Voinnet et al. (2003) and Wood et al. (2009). Plasmids containing a coding region to be expressed from a strong constitutive promoter such as the CaMV 35S promoter were introduced into *Agrobacterium tumefaciens* strain AGL1. A chimeric gene 35S:p19 for expression of the p19 viral silencing suppressor was separately introduced into AGL1, as described in WO 2010/057246. The recombinant *Agrobacterium* cells were grown at 28° C. in LB broth supplemented with 50 mg/L kanamycin and 50 mg/L rifampicin to stationary phase. The bacteria were then pelleted by centrifugation at 5000 g for 15 min at room temperature before being resuspended to OD600=1.0 in an infiltration buffer containing 10 mM MES pH 5.7, 10 mM $MgCl_2$ and 100 μM acetosyringone. The cells were then incubated at 28° C. with shaking for 3 hours before equal volumes of *Agrobacterium* cultures containing 35S:p19 and the test chimeric construct(s) of interest were mixed prior to infiltration into leaf tissue. The plants were typically grown for a further five days after infiltration before leaf discs were taken and freeze-dried for GC analysis of the fatty acids.

Fatty acid methyl esters (FAME) of total leaf lipids in freeze-dried samples were produced by incubating the samples in methanol/HCl/dichloromethane (10/1/1 v/v) solution for 2 hours at 80° C. together with a known amount of hexadecanoic acid as an internal standard. FAMEs were extracted in hexane/DCM, concentrated to a small volume in hexane and injected into a GC. The amount of individual and total fatty acids present in the lipid fractions were quantified on the basis of the known amount of internal standard.

Gas Chromatography (GC) Analysis of Fatty Acids

FAME were analysed by gas chromatography using an Agilent Technologies 7890A GC (Palo Alto, Calif., USA) equipped with a 30 m SGE-BPX70 column (70% cyanopropyl polysilphenylene-siloxane, 0.25 mm inner diameter, 0.25 mm film thickness), an FID, a split/splitless injector and an Agilent Technologies 7693 Series auto sampler and injector. Helium was used as the carrier gas. Samples were injected in split mode (50:1 ratio) at an oven temperature of 150° C. After injection, the oven temperature was held at 150° C. for 1 min then raised to 210° C. at 3° C. $min^{-1}$, again raised to 240° C. at 50° C. $min^{-1}$ and finally holding for 1.4 min at 240° C. Peaks were quantified with Agilent Technologies ChemStation software (Rev B.04.03 (16), Palo Alto, Calif., USA) based on the response of the known amount of the external standard GLC-411 (Nucheck) and C17:0-ME internal standard.

Liquid Chromatography—Mass Spectrometry (LC-MS) Analysis of Lipids

Total lipids were extracted from freeze-dried developing seeds, twelve days after flowering (daf), and mature seeds after adding a known amount oftri-C17:0-TAG as an internal quantitation standard. The extracted lipids were dissolved into 1 mL of 10 mM butylated hydroxytoluene in butanol: methanol (1:1 v/v) per 5 mg dry material and analysed using an Agilent 1200 series LC and 6410b electrospray ionisation triple quadrupole LC-MS. Lipids were chromatographically separated using an Ascentis Express RP-Amide column (50 mm×2.1 mm, 2.7 μm, Supelco) operating a binary gradient with a flow rate of 0.2 mL/min. The mobile phases were: A. 10 mM ammonium formate in $H_2O$:methanol: tetrahydrofuran (50:20:30 v/v/v); B. 10 mM ammonium formate in $H_2O$:methanol: tetrahydrofuran (5:20:75, v/v/v). Multiple reaction monitoring (MRM) lists were based on the following major fatty acids: 16:0, 18:0, 18:1, 18:2, 18:3, 18:4, 20:1, 20:2, 20:3, 20:4, 20:5, 22:4, 22:5, 22:6 using a collision energy of 30 V and fragmentor of 60 V. Individual MRM TAG was identified based on ammoniated precursor ion and product ion from neutral loss of 22:6. TAG was quantified using a 10 μM tristearin external standard.

Determination of Seed Fatty Acid Profile and Oil Content

Where seed oil content was to be determined, seeds were dried in a desiccator for 24 h and approximately 4 mg of seed was transferred to a 2 ml glass vial containing Teflon-lined screw cap. 0.05 mg triheptadecanoin dissolved in 0.1 ml toluene was added to the vial as internal standard.

Seed FAME were prepared by adding 0.7 ml of IN methanolic HCl (Supelco) to the vial containing seed material, vortexed briefly and incubated at 80° C. for 2 h. After cooling to room temperature, 0.3 ml of 0.9% NaCl (w/v) and 0.1 ml hexane was added to the vial and mixed well for 10 min in Heidolph Vibramax 110. The FAME was collected into 0.3 ml glass insert and analysed by GC with a flame ionization detector (FID) as mentioned earlier.

The peak area of individual FAME were first corrected on the basis of the peak area responses of known amount of the same FAMEs present in a commercial standard GLC-411 (NU-CHEK PREP, INC., USA). GLC-411 contains equal amounts of 31 fatty acids (% by wt), ranging from C8:0 to C22:6. In case of fatty acids, which were not present in the standard, the inventors took the peak area responses of the most similar FAME. For example, peak area response of FAMEs of 16:1d9 was used for 16:1d7 and FAME response of C22:6 was used for C22:5. The corrected areas were used to calculate the mass of each FAME in the sample by comparison to the internal standard mass. Oil is stored mainly in the form of TAG and its weight was calculated based on FAME weight. Total moles of glycerol was determined by calculating moles of each FAMES and dividing total moles of FAMEs by three. TAG was calculated as the sum of glycerol and fatty acyl moieties using a relation: % oil by weight=100×((41×total mol FAME/3)+(total g FAME−(15×total mol FAME)))/g seed, where 41 and 15 are molecular weights of glycerol moiety and methyl group, respectively.

Analysis of the Sterol Content of Oil Samples

Samples of approximately 10 mg of oil together with an added aliquot of C24:0 monol as an internal standard were saponified using 4 mL 5% KOH in 80% MeOH and heating for 2 h at 80° C. in a Teflon-lined screw-capped glass tube. After the reaction mixture was cooled, 2 mL of Milli-Q water were added and the sterols were extracted into 2 mL of hexane: dichloromethane (4:1 v/v) by shaking and vortexing. The mixture was centrifuged and the sterol extract was removed and washed with 2 mL of Milli-Q water. The sterol extract was then removed after shaking and centrifugation. The extract was evaporated using a stream of nitrogen gas and the sterols silylated using 200 mL of BSTFA and heating for 2 h at 80° C.

For GC/GC-MS analysis of the sterols, sterol-OTMSi derivatives were dried under a stream of nitrogen gas on a heat block at 40° C. and then re-dissolved in chloroform or hexane immediately prior to GC/GC-MS analysis. The sterol-OTMS derivatives were analysed by gas chromatography (GC) using an Agilent Technologies 6890A GC (Palo Alto, Calif., USA) fitted with an Supelco Equity™-1 fused silica capillary column (15 m×0.1 mm i.d., 0.1 μm film thickness), an FID, a split/splitless injector and an Agilent Technologies 7683B Series auto sampler and injector. Helium was the carrier gas. Samples were injected in splitless mode at an oven temperature of 120° C. After injection, the oven temperature was raised to 270° C. at 10° C. $min^{-1}$ and finally to 300° C. at 5° C. $min^{-1}$. Peaks were quantified with Agilent Technologies ChemStation software (Palo Alto, Calif., USA). GC results are subject to an error of ±5% of individual component areas.

GC-mass spectrometric (GC-MS) analyses were performed on a Finnigan Thermoquest GCQ GC-MS and a Finnigan Thermo Electron Corporation GC-MS; both systems were fitted with an on-column injector and Thermoquest Xcalibur software (Austin, Tex., USA). Each GC was fitted with a capillary column of similar polarity to that described above. Individual components were identified using mass spectral data and by comparing retention time data with those obtained for authentic and laboratory standards. A full procedural blank analysis was performed concurrent to the sample batch.

RT-PCR Conditions

Reverse transcription-PCR (RT-PCR) amplification was typically carried out using the Superscript III One-Step RT-PCR system (Invitrogen) in a volume of 25 μL using 10 pmol of the forward primer and 30 pmol of the reverse primer, $MgSO_4$ to a final concentration of 2.5 mM, 400 ng of total RNA with buffer and nucleotide components according to the manufacturer's instructions. Typical temperature regimes were: 1 cycle of 45° C. for 30 minutes for the reverse transcription to occur; then 1 cycle of 94° C. for 2 minutes followed by 40 cycles of 94° C. for 30 seconds, 52° C. for 30 seconds, 70° C. for 1 minute; then 1 cycle of 72° C. for 2 minutes before cooling the reaction mixtures to 5° C.

Production of *B. napus* Somatic Embryos by Induction with 35S-LEC2

*B. napus* (cv. Oscar) seeds were sterilized using chlorine gas as described by (Attila Kereszt et al., 2007). Sterilized seeds were germinated on ½ strength MS media (Murashige and Skoog, 1962) with 0.8% agar adjusted to pH 5.8, and grown at 24° C. under fluorescent lighting (50 $\mu E/m^2 s$) with a 18/6 h (light/dark) photoperiod for 6-7 days. Cotyledonary petioles with 2-4 mm stalk length were isolated aseptically from these seedlings and used as explants. Cultures of the transformed *A. tumefaciens* strain AGL1, one harbouring a seed specific binary vector and a second with a 35S-LEC2 construct were inoculated from single colonies from fresh plates and grown in 10 mL of LB medium with appropriate antibiotics and grown overnight at 28° C. with agitation at 150 rpm. The bacterial cells were collected by centrifugation at 4000 rpm for 5 minutes, washed with MS media containing 2% sucrose and re-suspended in 10 mL of the same medium and grown with antibiotics for selection as appropriate for 4 hours after the addition of acetosyringone to 100 μM. Two hours before addition to the plant tissues, spermidine was added to a final concentration of 1.5 mM and the final density of the bacteria adjusted to OD 600 nm=0.4 with fresh medium. The two bacterial cultures, one carrying the seed specific construct and other carrying 35S-AtLEC2, were mixed in 1:1 to 1:1.5 ratios.

Freshly-isolated *B. napus* cotyledonary petioles were infected with 20 mL *A. tumefaciens* cultures for 6 minutes. The cotyledonary petioles were blotted on sterile filter paper to remove excess *A. tumefaciens* and then transferred to co-cultivation media (MS media with 1 mg/L TDZ, 0.1 mg/L NAA, 100 μM acetosyringone supplemented with L-cysteine (50 mg/L), ascorbic acid (15 mg/L) and MES (250 mg/1)). The plates were sealed with micro-pore tape and incubated in the dark at 24° C. for 48 hrs. The co-cultivated explants were transferred to pre-selection media (MS containing 1 mg/L TDZ, 0.1 mg/L NAA, 3 mg/L $AgNO_3$, 250 mg/L cefotaxime and 50 mg/L timentin) and cultured for 4-5 days at 24° C. with a 16 h/8 h photoperiod. The explants were then transferred to selection media (MS containing 1 mg/L TDZ, 0.1 mg/L NAA, 3 mg/L $AgNO_3$, 250 mg/L cefotaxime and 50 mg/L timentin) according to the selectable marker gene on the seed specific vector and cultured for 2-3 weeks at 24° C. with a 16 h/8 h photoperiod. Explants with green embryogenic callus were transferred to hormone free MS media (MS with 3 mg/L $AgNO_3$, 250 mg/L cefotaxime, 50 mg/L timentin and the selection agent) and cultured for another 2-3 weeks. Torpedo or cotyledonary stage embryos isolated from surviving explants on the selection medium were analysed for fatty acid composition in their total lipid using GC.

Example 2. Stable Expression of Transgenic DHA Pathways in *Arabidopsis thaliana* Seeds Binary Vector Construction The binary vectors pJP3416-GA7 and pJP3404 each contained seven heterologous fatty acid biosynthesis genes, encoding 5 desaturases and 2 elongases, and a plant selectable marker between the left and right border repeats of the T-DNA present in each vector (FIGS. 2 and 3). SEQ ID NO:1 provides the nucleotide sequence of the T-DNA region of pJP3416-GA7 from the right to left border sequences. Both genetic constructs contained plant codon-optimised genes encoding a *Lachancea kluyveri* Δ12-desaturase (comprising nucleotides 14143-16648 of SEQ ID NO: 1), a *Pichia pastoris* ω3-desaturase (comprising nucleotides 7654-10156 of SEQ ID NO: 1), a *Micromonas pusilla* Δ6-desaturase (comprising nucleotides 226-2309 of SEQ ID NO: 1), *Pavlova salina* Δ5- and Δ4-desaturases (comprising nucleotides 4524-6485 and 10157-14142 of SEQ ID NO:1, respectively) and *Pyramimonas cordata* Δ6- and Δ5-elongases (comprising nucleotides 2310-4523 and 17825-19967 of SEQ ID NO: 1, respectively). The specific regions of the T-DNA (Orientation: right to left border sequences) region of the binary vector pJP3416-GA7 with respect to SEQ ID NO: 1 are as follows:

Nucleotides 1-163: Right border; 480-226, *Agrobacterium tumefaciens* nopaline synthase terminator (TER_NOS); 1883-489, *Micromonas pusilla* Δ6-desaturase; 2309-1952, *Brassica napus* truncated napin promoter (PRO_FP1); 2310-3243, *Arabidopsis thaliana* FAE1 promoter (PRO_FAE1); 3312-4181, *Pyramimonas cordata* Δ6-elongase; 4190-4523, *Glycine max* lectin terminator (TER_Lectin); 4524-4881, PRO_FP1; 4950-6230: *Pavlova salina* Δ5-desaturase; 6231-6485: TER_NOS; 7653-6486, *Nicotiana tabacum* Rb7 matrix attachment region (MAR); 8387-7654, *Linum usitatissimum* conlinin1 terminator (TER_Cnl1); 9638-8388, *Pichia pastoris* ω3-desaturase; 10156-9707, *Linum usitatissimum* conlinin promoter (PRO_Cnl1); 10157-12189, *Linum usitatissimum* conlinin1 promoter; 12258-13604, *Pavlova salina* Δ4-desaturase; 13605-14142, *Linum usitatissimum* conlinin2 terminator; 14143-14592, PRO_Cnl1; 14661-15914, *Lachancea kluyveri* Δ12-desaturase; 15915-16648, TER_Cnl1; 17816-16649, MAR; 17825-18758, PRO_FAE1; 18827-19633, *Pyramimonas cordata* Δ5-elongase; 19634-19967, TER_Lectin; 19990-20527, Cauliflower mosaic virus 35S promoter with duplicated enhancer region; 20537-21088, *Streptomyces viridochromogenes* phosphinothricin-N-acetyltransferase; 21097-21349, TER_NOS; 21367-21527, Left border.

The seven coding regions in the constructs were each under the control of a seed specific promoter-three different promoters were used, namely the truncated *Brassica napus* napin promoter (pBnFP1), the *Arabidopsis thaliana* FAE1 promoter (pAtFAE1) and the *Linum usitatissimum* conlinin 1 promoter (pLuCnl1). The seven fatty acid biosynthesis genes together coded for an entire DHA synthesis pathway that was designed to convert $18{:}1^{\Delta9}$ (oleic acid) through to $22{:}6^{\Delta4,7,10,13,16,19}$ (DHA). Both binary vectors contained a BAR plant selectable marker coding region operably linked to a Cauliflower Mosaic Virus (CaMV) 35S promoter with duplicated enhancer region and *A. tumefaciens* nos3' polyadenylation region-transcription terminator. The plant selectable marker was situated adjacent to the left border of the T-DNA region, therefore distally located on the T-DNA with respect to the orientation of T-DNA transfer into the plant cells. This increased the likelihood that partial transfer of the T-DNA, which would be likely to not include the selectable marker gene, would not be selected. pJP3416-GA7 and pJP3404 each contained an RiA4 origin of replication from *Agrobacterium rhizogenes* (Hamilton, 1997).

pJP3416-GA7 was generated by synthesising the DNA region corresponding to nucleotides 226-19975 of SEQ ID NO: 1 (GA7 region) and inserting this region into the recipient binary vector pJP3416 at the PspOMI site. Each fatty acid biosynthetic gene on GA7 included a Tobacco Mosaic Virus 5' untranslated region (5'UTR) sequence which was operably linked to each coding region, between the promoter and the translation initiation ATG, to maximise translation efficiency of the mRNAs produced from the genes. The GA7 construct also included two *Nicotiana tabacum* Rb7 matrix attachment region (MAR) sequences, as described by Hall et al. (1991). MAR sequences, sometimes termed nuclear attachment regions, are known to bind specifically to the nuclear matrix in vitro and may mediate binding of chromatin to the nuclear matrix in vivo. MARs are thought to function to reduce transgene silencing. In pJP3416-GA7 the MARs were also inserted and positioned within the T-DNA region in order to act as DNA spacers to insulate transgenic expression cassettes. The pJP3416 vector prior to insertion of the GA7 region contained only the plant selectable marker cassette between the borders.

The genetic construct pJP3404 was made by sequential restriction enzyme-based insertions in which gene cassettes were added to the binary vector, pJP3367, which comprised genes for production of SDA in seeds. This construct contained genes encoding the *L. kluyveri* Δ12-desaturase and *P. pastoris* ω3-desaturase, both expressed by the *B. napus* truncated napin promoter (FP1), and the *M. pusilla* Δ6-desaturase expressed by the *A. thaliana* FAE1 promoter (FIG. 4). First, the *A. thaliana* FAD2 intron was flanked by EcoRI sites and cloned into the pJP3367 MfeI site to generate pJP3395. A fragment containing the *P. cordata* Δ6- and Δ5-elongase cassettes driven by the FAE1 and FP1 promoters, respectively, was cloned into the KasI site of pJP3395 to generate pJP3398. pJP3399 was then generated by replacing the RK2 origin of replication in pJP3398 with a RiA4 origin of replication. The final binary vector, pJP3404, was generated by cloning a SbfI-flanked fragment containing the *P. salina* Δ5- and Δ4-desaturase cassettes driven by the FP1 and FAE1 promoters, respectively, into the SbfI site of pJP3399. *A. thaliana* Transformation and Analysis of Fatty Acid Composition The chimeric vectors were introduced into *A. tumefaciens* strain AGL1 and cells from cultures of the transformed *Agrobacterium* used to treat *A. thaliana* (ecotypes Columbia and a fad2 mutant) plants using the floral dip method for transformation (Clough and Bent, 1998). After maturation, the $T_1$ seeds from the treated plants were harvested and plated onto MS plates containing PPT for selection of plants containing the BAR selectable marker gene. Surviving, healthy $T_1$ seedlings were transferred to soil. After growth of the plants to maturity and allowing for self-fertilisation, $T_2$ seeds from these plants were harvested and the fatty acid composition of their seed lipid analysed by GC analysis as described in Example 1.

The data for the DHA level in the seed lipids are shown in FIG. 5 (lanes labelled $T_2$) for 13 transformants using pJP3416-GA7 into the Columbia genetic background, and for six transformants using the fad2 mutant. The pJP3416-GA7 construct resulted in the production of slightly higher levels of DHA, as a percentage of total fatty acid content, on average than the pJP3404 construct. Table 4 shows the fatty acid composition of total seed lipid from the $T_2$ lines with the highest DHA levels. The calculated conversion efficiencies for each enzymatic step in the production of DHA from oleic acid in the same seeds are shown in Table 5. Conversion efficiencies were calculated as (% products×100)/(% remaining substrate+% products), thereby expressed as a percentage.

The highest observed level of DHA produced in the pJP3416-GA7 $T_2$ transformed lines was 6.2%, additionally with 0.5% EPA and 0.2% DPA (line #14). These $T_2$ seeds were still segregating for the transgene i.e. were not yet uniformly homozygous. Compiled data from the total seed lipid profiles from independent transgenic seed (Table 4) are shown in Table 6. The level of ω3 fatty acids produced as a result of the transgenes in these seeds (total new ω3 fatty acids, excluding the level of ALA which was produced endogenously in the Columbia background) was 10.7% while the level of ω6 fatty acids (total new ω6 fatty acids but excluding $18{:}2^{\Delta9,12}$) was 1.5%. This represents an extremely favourable ration of new ω3 fatty acids:new ω6 fatty acids, namely 7.3:1.

$T_2$ seeds of selected lines transformed with pJP3416-GA7, namely for lines designated 7, 10, 14, 22 and 34 in the Columbia background and for lines designated 18, 21 and 25 in the fad2 mutant background, were plated onto MS media containing PPT for selection of transgenic seedlings in vitro. Twenty PPT-resistant seedlings for each line were transferred to soil and grown to maturity after self-fertilisation. These plants were highly likely to be homozygous for the selectable marker gene, and therefore for at least one T-DNA insertion in the genome of the plants. $T_3$ seed from these plants were harvested and analysed for fatty acid composition in their seedoil by GC. The data are shown in Table 7. This analysis revealed that the pJP3416-GA7 construct generated higher levels of the ω3 LC-PUFA DHA in $T_3$ seeds of the homozygous plants than in the segregating $T_2$ seed. Up to about 13.9% DHA was observed in the $T_3$ pJP3416-GA7 transformed line designated 22.2 in the Columbia background, increased from about 5.5% in the hemizygous $T_2$ seed, with a sum level of about 24.3% of new ω3 fatty acids as a percentage of the total fatty acids in the seed lipid content. New ω6 fatty acids were at a level of 1.1% of total fatty acids, representing a very favourable ratio of new ω3 fatty acids:new ω6 fatty acids, namely about 22:1. Similarly, transformants in the fad2 mutant background yielded 20.6% as a sum of new ω3 fatty acids, including 11.5% DHA, as a percentage of the total fatty acids in the seed lipid content.

TABLE 4

Fatty acid composition of total seed lipid from independent transgenic $T_2$ *Arabidopsis* seeds with DHA levels at the higher end of the observed range. 'Col' refers to the Columbia ecotype and 'FAD2' to the fad2 mutant ecotype. 'GA7' refers to transformation with the T-DNA of the pJP3416-GA7 vector, pJP3404 with the T-DNA of the pJP3404 vector. 20:1n-9 and 20:1n-11 fatty acids were not resolved in the GC analysis. "Other minor" fatty acids include 14:0, 16:1n7, 16:1n9, 16:1n13t, 16;2n6, 16:3n3, i18:0, 18:1n5, 20:1n5, 22:0, 22:1n7, 22:1n11/n13, 24:0, 24:1n9.

| | pJP3404_ Col_#1 | pJP3404_ FAD2_#31 | GA7_ Col_ #7 | GA7_ Col_ #34 | GA7_ Col_ #2 | GA7_ Col_ #10 | GA7_ Col_ #22 | GA7_ Col_ #14 | GA7_ FAD2_ #25 | GA7_ FAD2_ #21 | GA7_ FAD2_ #18 |
|---|---|---|---|---|---|---|---|---|---|---|---|
| 16:0 | 9.6 | 7.8 | 8.7 | 8.2 | 8.7 | 8.6 | 8.3 | 9.7 | 7.2 | 8.5 | 7.5 |
| 18:0 | 2.9 | 3.9 | 3.7 | 3.9 | 3.6 | 3.3 | 3.4 | 3.6 | 3.2 | 3.9 | 3.0 |
| 18:1d11 | 2.2 | 1.8 | 2.0 | 1.9 | 2.0 | 2.3 | 2.3 | 2.7 | 1.9 | 2.0 | 1.8 |
| 20:0 | 1.6 | 2.3 | 2.0 | 2.0 | 2.1 | 1.6 | 1.6 | 1.8 | 1.6 | 2.2 | 1.5 |
| 20:1d13 | 2.2 | 1.8 | 1.6 | 1.5 | 1.7 | 1.6 | 1.5 | 1.7 | 1.5 | 1.7 | 1.4 |
| 20:1d9/d11 | 13.0 | 15.9 | 16.1 | 16.1 | 16.3 | 15.0 | 13.9 | 13.5 | 18.3 | 15.9 | 17.0 |
| 22:1d13 | 1.1 | 1.2 | 1.1 | 1.1 | 1.3 | 1.0 | 1.0 | 1.0 | 1.0 | 1.3 | 1.2 |
| Other minor | 1.9 | 1.5 | 1.5 | 1.4 | 1.5 | 1.3 | 1.6 | 1.7 | 1.6 | 1.4 | 1.6 |
| 18:1d9 | 10.8 | 14.0 | 10.6 | 10.6 | 10.1 | 11.1 | 10.0 | 7.7 | 26.0 | 8.2 | 20.9 |
| 18:2ω6 | 28.9 | 28.3 | 16.4 | 16.1 | 18.2 | 13.7 | 13.7 | 11.4 | 6.6 | 16.6 | 4.3 |
| 18:3ω3 | 16.6 | 14.9 | 29.6 | 29.6 | 27.5 | 32.4 | 30.4 | 32.8 | 21.9 | 27.7 | 30.1 |
| 18:3ω6 | 0.7 | 0.5 | 0.1 | 0.1 | 0.1 | 0.1 | 0.2 | 0.1 | 0.1 | 0.2 | 0.1 |
| 20:2ω6 | 1.6 | 1.5 | 1.1 | 1.2 | 1.3 | 1.0 | 1.0 | 1.0 | 0.4 | 1.4 | 0.4 |
| 20:3ω6 | 0.0 | 0.0 | 0.0 | 0.0 | 0.0 | 0.0 | 0.0 | 0.0 | 0.0 | 0.0 | 0.0 |
| 20:4ω6 | 0.0 | 0.0 | 0.0 | 0.0 | 0.0 | 0.0 | 0.0 | 0.0 | 0.0 | 0.0 | 0.0 |
| 22:4ω6 | 1.6 | 0.6 | 0.3 | 0.3 | 0.3 | 0.4 | 0.5 | 0.4 | 0.5 | 0.4 | 0.4 |
| 22:5ω6 | 0.1 | 0.1 | 0.0 | 0.0 | 0.0 | 0.0 | 0.0 | 0.0 | 0.0 | 0.0 | 0.0 |
| 18:4ω3 | 1.0 | 0.5 | 1.2 | 1.1 | 1.1 | 1.3 | 2.7 | 2.7 | 1.9 | 1.8 | 1.7 |
| 20:3ω3 | 0.0 | 0.0 | 0.0 | 0.6 | 0.0 | 0.0 | 0.6 | 0.7 | 0.0 | 0.8 | 0.6 |
| 20:4ω3 | 0.4 | 0.6 | 0.6 | 0.7 | 0.5 | 0.8 | 0.8 | 0.4 | 1.0 | 0.8 | 0.8 |
| 20:5ω3 | 0.2 | 0.2 | 0.3 | 0.3 | 0.3 | 0.3 | 0.7 | 0.5 | 0.6 | 0.4 | 0.5 |
| 22:5ω3 | 0.0 | 0.2 | 0.2 | 0.2 | 0.2 | 0.2 | 0.2 | 0.2 | 0.3 | 0.3 | 0.3 |
| 22:6ω3 | 3.6 | 2.4 | 3.0 | 3.1 | 3.3 | 3.9 | 5.5 | 6.2 | 4.3 | 4.4 | 4.8 |

TABLE 5

Conversion efficiencies of the individual enzymatic steps for production of DHA from oleic acid, observed in total seed lipid from independent transgenic seed as for Table 4.

| | | pJP3404_ Col_#1 | pJP3404_ FAD2_#31 | GA7_ Col_ #7 | GA7_ Col_ #34 | GA7_ Col_ #2 | GA7_ Col_ #10 | GA7_ Col_ #22 | GA7_ Col_ #14 | GA7_ Col_ #25 | GA7_ FAD2_ #21 | GA7_ FAD2_ #18 |
|---|---|---|---|---|---|---|---|---|---|---|---|---|
| | d12-des | 69.6% | 62.5% | 66.4% | 66.6% | 66.7% | 67.5% | 70.2% | 72.7% | 45.9% | 69.5% | 53.7% |
| | d15-des | 39.8% | 37.8% | 66.1% | 66.8% | 62.3% | 72.1% | 72.7% | 77.2% | 79.7% | 66.0% | 88.1% |
| Omega-6 | d6-des | 4.5% | 2.5% | 0.7% | 0.7% | 0.7% | 0.9% | 1.3% | 1.0% | 1.6% | 1.1% | 1.1% |
| | (d9-elo) | 3.1% | 3.1% | 2.2% | 2.3% | 2.4% | 1.8% | 1.8% | 1.7% | 1.2% | 2.7% | 0.9% |
| | d6-elo | 71.4% | 56.9% | 83.3% | 83.4% | 83.0% | 84.7% | 70.3% | 74.5% | 85.5% | 66.1% | 88.0% |
| | d5-des | 100.0% | 100.0% | 100.0% | 100.0% | 100.0% | 100.0% | 100.0% | 100.0% | 100.0% | 100.0% | 100.0% |
| | d5-elo | 100.0% | 97.8% | 100.0% | 100.0% | 100.0% | 100.0% | 100.0% | 100.0% | 100.0% | 100.0% | 100.0% |
| | d4-des | 6.2% | 13.0% | 0.0% | 0.0% | 0.0% | 0.0% | 0.0% | 0.0% | 0.0% | 0.0% | 0.0% |
| Omega-3 | d6-des | 23.9% | 21.0% | 15.2% | 15.4% | 16.4% | 17.1% | 24.7% | 23.6% | 27.1% | 21.9% | 21.0% |
| | (d9-elo) | 0.0% | 0.0% | 0.0% | 1.8% | 0.0% | 0.0% | 2.0% | 2.2% | 0.0% | 2.6% | 2.1% |
| | d6-elo | 80.6% | 86.6% | 77.7% | 79.6% | 79.4% | 77.5% | 72.7% | 73.0% | 76.7% | 77.4% | 79.2% |
| | d5-des | 93.7% | 92.1% | 91.7% | 91.4% | 91.5% | 92.6% | 89.6% | 92.4% | 88.0% | 91.8% | 91.0% |
| | d5-elo | 93.7% | 92.1% | 91.7% | 91.4% | 91.5% | 92.6% | 89.6% | 92.4% | 88.0% | 91.8% | 91.0% |
| | d4-des | 100.0% | 90.6% | 94.8% | 94.0% | 95.3% | 94.4% | 95.8% | 96.9% | 93.1% | 92.9% | 94.2% |

TABLE 6

Compiled data from the total seed lipid profiles from independent transgenic seed shown in Table 2. Calculations do not include the 'minor fatty acids' in Table 4.

| Parameter | pJP3404_ Col_#1 | pJP3404_ FAD2_#31 | GA7_ Col_ #7 | GA7_ Col_ #34 | GA7_ Col_ #2 | GA7_ Col_ #10 | GA7_ Col_ #22 | GA7_ Col_ #14 | GA7_ FAD2_ #25 | GA7_ FAD2_ #21 | GA7_ FAD2_ #18 |
|---|---|---|---|---|---|---|---|---|---|---|---|
| total w3 (% of total FA) | 21.8 | 18.8 | 34.9 | 35.6 | 32.9 | 39.1 | 40.9 | 43.5 | 30.0 | 36.2 | 38.8 |
| total w6 (% of total FA) | 32.9 | 31.0 | 17.9 | 17.7 | 19.9 | 15.2 | 15.4 | 12.9 | 7.6 | 18.6 | 5.2 |
| w3/w6 ratio | 0.66 | 0.61 | 1.95 | 2.01 | 1.65 | 2.57 | 2.66 | 3.37 | 3.95 | 1.95 | 7.46 |

TABLE 6-continued

Compiled data from the total seed lipid profiles from independent transgenic seed shown in Table 2. Calculations do not include the 'minor fatty acids' in Table 4.

| Parameter | pJP3404_Col_#1 | pJP3404_FAD2_#31 | GA7_Col_#7 | GA7_Col_#34 | GA7_Col_#2 | GA7_Col_#10 | GA7_Col_#22 | GA7_Col_#14 | GA7_FAD2_#25 | GA7_FAD2_#21 | GA7_FAD2_#18 |
|---|---|---|---|---|---|---|---|---|---|---|---|
| w6/w3 ratio | 1.51 | 1.65 | 0.51 | 0.50 | 0.60 | 0.39 | 0.38 | 0.30 | 0.25 | 0.51 | 0.13 |
| total novel w3 (% of total FA) | 5.2 | 3.9 | 5.3 | 6.0 | 5.4 | 6.7 | 10.5 | 10.7 | 8.1 | 8.5 | 8.7 |
| total novel w6 (% of total FA) | 4.0 | 2.7 | 1.5 | 1.6 | 1.7 | 1.5 | 1.7 | 1.5 | 1.0 | 2.0 | 0.9 |
| novel w3/w6 ratio | 1.30 | 1.44 | 3.53 | 3.75 | 3.18 | 4.47 | 6.18 | 7.13 | 8.10 | 4.25 | 9.67 |
| novel w6/w3 ratio | 0.77 | 0.69 | 0.28 | 0.27 | 0.31 | 0.22 | 0.16 | 0.14 | 0.12 | 0.24 | 0.10 |
| OA to EPA efficiency | 4.8% | 3.5% | 4.3% | 4.4% | 4.7% | 5.4% | 7.9% | 8.8% | 6.3% | 6.4% | 6.7% |
| OA to DHA efficiency | 4.5% | 3.0% | 3.7% | 3.8% | 4.1% | 4.8% | 6.8% | 7.9% | 5.2% | 5.5% | 5.8% |
| LA to EPA efficiency | 6.9% | 5.6% | 6.6% | 6.8% | 7.2% | 8.1% | 11.4% | 12.2% | 13.8% | 9.3% | 12.7% |
| LA to DHA efficiency | 6.6% | 4.8% | 5.7% | 5.8% | 6.3% | 7.2% | 9.8% | 11.0% | 11.4% | 8.0% | 10.9% |
| ALA to EPA efficiency | 17.4% | 14.9% | 10.0% | 10.1% | 11.6% | 11.3% | 15.6% | 15.9% | 17.3% | 14.1% | 14.4% |
| ALA to DHA efficiency | 16.5% | 12.8% | 8.6% | 8.7% | 10.0% | 10.0% | 13.4% | 14.3% | 14.3% | 12.2% | 12.4% |
| total saturates | 14.1 | 14.0 | 14.4 | 14.1 | 14.4 | 13.5 | 13.3 | 15.1 | 12.0 | 14.6 | 12.0 |
| total monounsaturates | 29.3 | 34.7 | 31.4 | 31.2 | 31.4 | 31.0 | 28.7 | 26.6 | 48.7 | 29.1 | 42.3 |
| total polyunsaturates | 54.7 | 49.8 | 52.8 | 53.3 | 52.8 | 54.3 | 56.3 | 56.4 | 37.6 | 54.8 | 44.0 |
| total C20 | 17.4 | 20 | 19.7 | 20.4 | 20.1 | 18.7 | 18.5 | 17.8 | 21.8 | 21 | 20.7 |
| total C22 | 6.4 | 4.5 | 4.6 | 4.7 | 5.1 | 5.5 | 7.2 | 7.8 | 6.1 | 6.4 | 6.7 |
| C20/C22 ratio | 2.72 | 4.44 | 4.28 | 4.34 | 3.94 | 3.40 | 2.57 | 2.28 | 3.57 | 3.28 | 3.09 |

TABLE 7

Fatty acid composition of total seed lipid from independent transgenic $T_3$ and $T_4$ *Arabidopsis* progeny seeds obtained from plant lines as in Table 3. The error shown in the $T_4$ generation denotes the SD of n = 10.

| | GA7_Col_7.2 | GA7_Col_34.2 | GA7_Col_10.13 | GA7_Col_22.2 | GA7_Col_14.19 | GA7_FAD2-25.10 | GA7_FAD2-21.2 | GA7_FAD2-18.14 | $T_4$ Col_22.2 (mean ± SD) | $T_4$ Col_22.2 best line |
|---|---|---|---|---|---|---|---|---|---|---|
| 16:0 | 9.8 | 9.0 | 9.5 | 11.2 | 10.4 | 8.1 | 10.7 | 7.7 | 10.6 ± 0.9 | 12.2 |
| 18:0 | 4.0 | 3.8 | 4.2 | 3.4 | 3.5 | 3.5 | 3.8 | 3.3 | 3.5 ± 0.4 | 3.6 |
| 18:1n7 | 2.0 | 1.9 | 2.2 | 2.9 | 2.5 | 1.7 | 2.2 | 1.6 | 2.3 ± 0.2 | 2.6 |
| 20:0 | 2.2 | 1.9 | 1.7 | 1.4 | 2.3 | 1.8 | 2.0 | 1.9 | 1.9 ± 0.3 | 2.0 |
| 20:1d13 | 1.4 | 1.3 | 1.2 | 1.6 | 2.5 | 1.2 | 1.4 | 1.3 | 1.6 ± 0.2 | 1.9 |
| 20:1d9/11 | 13.6 | 14.7 | 12.4 | 9.5 | 13.0 | 15.7 | 12.4 | 18.4 | 11.7 ± 1.7 | 9.5 |
| 22:1d13 | 1.2 | 1.2 | 0.8 | 0.6 | 1.6 | 1.0 | 1.1 | 1.5 | 0.9 ± 0.1 | 0.8 |
| Other minor | 1.8 | 1.5 | 1.5 | 2.1 | 2.6 | 1.7 | 1.9 | 1.6 | 1.9 ± 0.1 | 2.3 |
| 18:1d9 | 5.5 | 6.7 | 6.8 | 4.6 | 6.9 | 11.3 | 4.2 | 11.5 | 4.6 ± 1.0 | 3.3 |
| 18:2ω6 | 7.5 | 7.9 | 7.4 | 5.6 | 14.8 | 5.8 | 8.9 | 5.6 | 5.3 ± 0.9 | 4.3 |
| 18:3ω3 | 33.7 | 33.7 | 36.1 | 31.5 | 26.1 | 28.3 | 28.9 | 30.8 | 31.0 ± 1.1 | 29.5 |
| 18:3ω6 | 0.2 | 0.2 | 0.2 | 0.4 | 0.1 | 0.3 | 0.6 | 0.1 | 0.4 ± 0.1 | 0.4 |
| 20:2ω6 | 1.0 | 1.0 | 0.7 | 0.7 | 1.4 | 0.6 | 1.2 | 0.6 | 0.9 ± 0.1 | 0.9 |
| 20:3ω6 | 0 | 0 | 0 | 0 | 0 | 0 | 0 | 0 | | |
| 20:4ω6 | 0 | 0 | 0 | 0 | 0 | 0 | 0 | 0 | | |
| 22:4ω6 | 0 | 0 | 0 | 0 | 0 | 0 | 0 | 0 | 0.1 ± 0.0 | 0.1 |
| 22:5ω6 | 0 | 0 | 0 | 0 | 0 | 0 | 0 | 0 | | |
| 18:4ω3 | 3.1 | 2.6 | 3.0 | 5.3 | 3.3 | 3.7 | 5.2 | 2.6 | 4.8 ± 0.9 | 5.5 |
| 20:3ω3 | 1.4 | 1.3 | 1.2 | 1.3 | 1.2 | 1.1 | 1.3 | 1.3 | 1.5 ± 0.2 | 1.7 |
| 20:4ω3 | 0.7 | 0.6 | 0.6 | 0.9 | 0.2 | 1.7 | 0.9 | 0.9 | 0.8 ± 0.2 | 0.8 |
| **20:5ω3** | **0.9** | **0.9** | **0.7** | **1.9** | **0.8** | **1.2** | **1.0** | **0.8** | **1.5 ± 0.3** | **1.8** |
| **22:5ω3** | **0.7** | **0.6** | **0.6** | **1.0** | **0.4** | **0.8** | **0.6** | **0.5** | **1.1 ± 0.2** | **1.5** |
| **22:6ω3** | **9.5** | **9.2** | **9.4** | **13.9** | **6.6** | **10.3** | **11.5** | **7.9** | **13.3 ± 1.6** | **15.1** |

Enzymatic conversion efficiencies for each enzyme step in the pathway for production of DHA from oleic acid are shown in Table 8 for the $T_3$ seeds with the higher DHA levels. The Δ12-desaturase conversion efficiency in seeds of line 22.2 was 81.6% and the ω3-desaturase efficiency was 89.1%, both of them remarkably high and indicating that these fungal (yeast) enzymes were able to function well in developing seeds. The activities of the other exogenous enzymes in the DHA pathway were similarly high for ω3 substrates with the Δ6-desaturase acting at 42.2% efficiency, Δ6-elongase at 76.8%, Δ5-desaturase at 95.0%, Δ5-elongase at 88.7% and Δ4-desaturase at 93.3% efficiency. The Δ6-desaturase activity on the ω6 substrate LA was much lower, with the Δ6-desaturase acting at only 0.7% conversion efficiency on LA. GLA was present at a level of only 0.4% and was the only new ω6 product aside from 20:2ω6 detected in the $T_3$ seeds with the highest DHA content. Compiled data from the total seed lipid profiles from independent transgenic seed (Table 7) are shown in Table 9. This data for the line with the greatest DHA level included a total ω6 FA (including LA) to total ω3 FA (including ALA) ratio of 0.10. The new ω6 FA (excluding LA) to new ω3 FA (excluding ALA) ratio in the lipid of this line was 0.05. Total polyunsaturated fatty acid levels were more than 50% in these lines, and greater than 60% in at least 4 of the lines. Overall conversion efficiencies were calculated to be: OA to EPA=21.8%, OA to DHA=18.0%, LA to EPA=26.9%, LA to DHA=22.2%, ALA to EPA=30.1%, ALA to DHA=24.9%.

TABLE 8

Conversion efficiencies of the individual enzymatic steps for the production of DHA from oleic acid, observed in total seed lipid from transgenic $T_3$ *Arabidopsis* seeds as in Table 7.

| | | GA7_ Col_ 7.2 | GA7_ Col_ 34.2 | GA7_ Col_ 10.13 | GA7_ Col_ 22.2 | GA7_ Col_ 14.19 | GA7_ FAD2- 25.10 | GA7_ FAD2- 21.2 | GA7_ FAD2- 18.14 | $T_4$ Col_22.2 (mean) | $T_4$ Col_22.2 best line |
|---|---|---|---|---|---|---|---|---|---|---|---|
| | d12-des | 75.4% | 73.1% | 75.7% | 81.6% | 73.4% | 66.6% | 78.5% | 63.1% | 67.6% | 82.7% |
| | d15-des | 85.3% | 84.4% | 86.2% | 89.1% | 70.2% | 87.5% | 82.2% | 87.6% | 81.0% | 90.9% |
| Omega-6 | d6-des | 0.3% | 0.3% | 0.3% | 0.7% | 0.3% | 0.6% | 1.0% | 0.2% | 1.3% | 0.7% |
| | (d9-elo) | 1.7% | 1.7% | 1.2% | 1.2% | 2.6% | 1.1% | 2.0% | 1.3% | 1.6% | 1.5% |
| | d6-elo | | | | | | | | | | |
| | d5-des | | | | | | | | | | |
| | d5-elo | | | | | | | | | | |
| | d4-des | | | | | | | | | | |
| Omega-3 | d6-des | 30.7% | 29.3% | 28.2% | 42.2% | 30.2% | 38.5% | 40.0% | 29.2% | 41.0% | 45.7% |
| | (d9-elo) | 2.7% | 2.7% | 2.3% | 2.4% | 3.0% | 2.3% | 2.7% | 2.9% | 2.8% | 3.1% |
| | d6-elo | 79.0% | 81.1% | 79.0% | 76.8% | 70.9% | 79.2% | 73.2% | 79.1% | 77.5% | 77.7% |
| | d5-des | 94.0% | 94.6% | 94.5% | 95.0% | 97.9% | 87.8% | 93.3% | 91.1% | 95.0% | 95.8% |
| | d5-elo | 91.9% | 91.7% | 93.6% | 88.7% | 89.5% | 89.9% | 92.2% | 91.6% | 90.8% | 90.2% |
| | d4-des | 93.2% | 93.7% | 94.4% | 93.3% | 93.7% | 92.5% | 95.0% | 93.9% | 92.2% | 90.9% |

TABLE 9

Compiled data from the total seed lipid profiles from independent transgenic seed shown in Table 5. Calculations do not include the 'minor fatty acids' in Table 7.

| Parameter | GA7- Col_ 7.2 | GA7- Col_ 34.2 | GA7- Col_ 10.13 | GA7- Col_ 22.2 | GA7- Col_ 14.19 | GA7- FAD2- 25.10 | GA7- FAD2- 21.2 | GA7- FAD2- 18.14 | $T_4$ Col_22.2 (mean ± SD) | $T_4$ Col_22.2 best line |
|---|---|---|---|---|---|---|---|---|---|---|
| total w3 (% of total FA) | 50.0 | 48.9 | 51.6 | 55.8 | 38.6 | 47.1 | 49.4 | 44.8 | 54.0 | 55.9 |
| total w6 (% of total FA) | 8.7 | 9.1 | 8.3 | 6.7 | 16.3 | 6.7 | 10.7 | 6.3 | 6.7 | 5.7 |
| w3/w6 ratio | 5.75 | 5.37 | 6.22 | 8.33 | 2.37 | 7.03 | 4.62 | 7.11 | 8.06 | 9.81 |
| w6/w3 ratio | 0.17 | 0.19 | 0.16 | 0.12 | 0.42 | 0.14 | 0.22 | 0.14 | 0.12 | 0.10 |
| total novel w3 (% of total FA) | 16.3 | 15.2 | 15.5 | 24.3 | 12.5 | 18.8 | 20.5 | 14.0 | 23.0 | 26.4 |
| total novel w6 (% of total FA) | 1.2 | 1.2 | 0.9 | 1.1 | 1.5 | 0.9 | 1.8 | 0.7 | 1.4 | 1.4 |
| novel w3/w6 ratio | 13.58 | 12.67 | 17.22 | 22.09 | 8.33 | 20.89 | 11.39 | 20.00 | 16.43 | 18.86 |
| novel w6/w3 ratio | 0.07 | 0.08 | 0.06 | 0.05 | 0.12 | 0.05 | 0.09 | 0.05 | 0.06 | 0.05 |
| OA to EPA efficiency | 14.1% | 13.3% | 13.4% | 21.8% | 10.2% | 15.0% | 16.8% | 11.2% | 20.4% | 24.5% |
| OA to DHA efficiency | 12.0% | 11.4% | 11.8% | 18.0% | 8.6% | 12.6% | 14.8% | 9.6% | 17.1% | 20.1% |
| LA to EPA efficiency | 18.9% | 18.4% | 17.9% | 26.9% | 14.2% | 22.9% | 21.8% | 18.0% | 26.2% | 29.9% |
| LA to DHA efficiency | 16.2% | 15.9% | 15.7% | 22.2% | 12.0% | 19.1% | 19.1% | 15.5% | 21.9% | 24.5% |
| ALA to EPA efficiency | 22.2% | 21.9% | 20.7% | 30.1% | 20.2% | 26.1% | 26.5% | 20.5% | 29.4% | 32.9% |
| ALA to DHA efficiency | 19.0% | 18.8% | 18.2% | 24.9% | 17.1% | 21.9% | 23.3% | 17.6% | 24.6% | 27.0% |
| total saturates | 16.0 | 14.7 | 15.4 | 16.0 | 16.2 | 13.4 | 16.5 | 12.9 | 16.0 | 17.8 |
| total monounsaturates | 23.7 | 25.8 | 23.4 | 19.2 | 26.5 | 30.9 | 21.3 | 34.3 | 21.1 | 18.1 |
| total polyunsaturates | 58.7 | 58.0 | 59.9 | 62.5 | 54.9 | 53.8 | 60.1 | 51.1 | 60.7 | 61.6 |
| total C20 | 19 | 19.8 | 16.8 | 15.9 | 19.1 | 21.5 | 18.2 | 23.3 | 18 | 16.6 |
| total C22 | 11.4 | 11 | 10.8 | 15.5 | 8.6 | 12.1 | 13.2 | 9.9 | 15.4 | 17.5 |
| C20/C22 ratio | 1.67 | 1.80 | 1.56 | 1.03 | 2.22 | 1.78 | 1.38 | 2.35 | 1.17 | 0.95 |

$T_3$ seeds from the pJP3416-GA7 line 22.2 in the Columbia background, which were progeny from $T_2$ line 22, were sown directly to soil and the fatty acid composition of mature seed from the resultant $T_3$ plants analysed by GC. The average DHA level of these seeds was 13.3%±1.6 (n=10) as a percentage of total fatty acids in the seed lipid. As shown in Table 6 (right hand column), the line with the highest level of DHA contained 15.1% DHA in the total fatty acids of the seed lipid. The enzymatic conversion efficiencies are shown in Table 8 for each step in the production of DHA from oleic acid.

The total ω6 FA (including LA) to ω3 FA (including ALA) ratio in the line with the highest DHA level was 0.102. The new ω6 FA (excluding LA) to new ω3 FA (excluding ALA) ratio in the line with the highest DHA level was 0.053. The level of total saturated fatty acids was about 17.8% and the level of monounsaturated fatty acids was about 18.1%. The level of total ω6-fatty acids was about 5.7% and the level of ω3-fatty acids was about 55.9%. Overall conversion efficiencies were calculated to be: OA to EPA=24.5%, OA to DHA=20.1%, LA to EPA=29.9%, LA to DHA=24.5%, ALA to EPA=32.9%, ALA to DHA=27.0%. Total omega-3 fatty acids were found to accumulate to 55.9% of total fatty acids whereas omega-6 fatty acids were 5.7% of the total profile.

Southern blot hybridisation analysis was performed. The results showed that the high-accumulating DHA lines were either single- or double-copy for the T-DNA from the pJP3416-GA7 construct with the exception of transgenic line Columbia#22, which had three T-DNA insertions in the genome of the *Arabidopsis* plant. The T5 generation seed was also analysed and found to have up to 13.6% DHA in the total seed lipids. The GA7 construct was found to be stable across multiple generations in terms of DHA production capability.

Determination of Oil Content in Transgenic *A. thaliana* DHA Lines

The oil content of transgenic *A. thaliana* seeds with various levels of DHA was determined by GC as described in Example 1. The data are shown in FIG. 6, graphing the oil content (% oil by weight of seed) against the DHA content (as a percentage of total fatty acids). Up to 26.5 mg of DHA per gram of seed was observed (Table 10). The oil content of the transgenic *Arabidopsis* seeds was found to be negatively correlated with DHA content. The amount of DHA per weight of seed was greater in the transformed seeds with a DHA level of about 9% relative to the seeds with about 14% DHA. Whether this would be true for seeds other than *Arabidopsis* has not been determined.

TABLE 10

Proportion and amount of DHA in GA7-transformed *Arabidopsis* seeds.

| | DHA content (% of TFA) | Oil content (% oil per g seeds) | DHA content per weight (mg/g seed) |
|---|---|---|---|
| GA7/col 22.2-1 | 14.2 | 14.89 | 20.2 |
| GA7/col 22.2-2 | 14.3 | 15.02 | 20.5 |
| GA7/col 22.2-3 | 14.0 | 15.92 | 21.2 |
| GA7/col 10.15-1 | 8.7 | 30.23 | 25.06 |
| GA7/col 10.15-2 | 8.6 | 31.25 | 25.77 |
| GA7/col 10.15-3 | 8.8 | 31.70 | 26.49 |

Example 3. Stable Expression of a Transgenic DHA Pathway in *Camelina Sativa* Seeds The binary vector pJP3416-GA7 as described above was introduced into *A. tumefaciens* strain AGL1 and cells from a culture of the transformed *Agrobacterium* used to treat *C. sativa* flowering plants using a floral dip method for transformation (Lu and Kang, 2008). After growth and maturation of the plants, the $T_1$ seeds from the treated plants were harvested, sown onto soil and the resultant plants treated by spraying with the herbicide BASTA to select for plants which were transgenic for, and expressing, the bar selectable marker gene present on the T-DNA of pJP3416-GA7. Surviving $T_1$ plants which were tolerant to the herbicide were grown to maturity after allowing them to self-fertilise, and the resultant $T_2$ seed harvested. Five transgenic plants were obtained, only three of which contained the entire T-DNA.

Lipid was extracted from a pool of approximately twenty seeds from each of the three plants that contained the entire T-DNA. Two of the pooled samples contained very low, barely detectable levels of DHA, but the third pool contained about 4.7% DHA (Table 12). Therefore, lipid was extracted from 10 individual $T_2$ seeds from this plant and the fatty acid composition analysed by GC. The fatty acid composition data of the individual seeds for this transformed line is also shown in Table 11. Compiled data from the total seed lipid profiles (Table 11) are shown in Table 12.

TABLE 11

Fatty acid composition of total seed lipids from transgenic $T_2$ *Camelina sativa* seeds transformed with the T-DNA from pJP3416-GA7. The fatty acid composition is shown for a pooled seed batch (FD5.46) and for 10 single seeds ranked (left to right) from highest to lowest DHA.

| Fatty acid | FD5.46 pooled | #2 | #4 | #8 | #7 | #9 | #1 | #3 | #5 | #6 | #10 |
|---|---|---|---|---|---|---|---|---|---|---|---|
| 14:0 | 0 | 0.2 | 0.2 | 0.1 | 0.2 | 0.2 | 0.2 | 0.2 | 0.1 | 0.2 | 0.2 |
| 16:0 | 11.6 | 12.1 | 12.3 | 12.1 | 13.2 | 12.3 | 12.8 | 11.9 | 11.4 | 11.5 | 11.7 |
| 16:1 | 0.2 | 0.0 | 0.1 | 0.1 | 0.0 | 0.2 | 0.0 | 0.2 | 0.2 | 0.2 | 0.2 |
| 16:3 | 0.3 | 0 | 0.0 | 0.0 | 0.0 | 0.0 | 0.0 | 0.0 | 0.0 | 0.0 | 0.0 |
| 18:0 | 3.7 | 3.3 | 3.2 | 3.2 | 3.0 | 3.1 | 3.2 | 3.3 | 3.1 | 3.2 | 3.2 |
| 18:1 | 10.8 | 8.0 | 8.0 | 8.6 | 8.5 | 9.4 | 11.0 | 10.2 | 8.3 | 9.4 | 8.6 |
| 18:1d11 | 1.7 | 1.3 | 1.4 | 1.4 | 1.7 | 1.4 | 1.5 | 1.3 | 1.3 | 1.3 | 1.3 |
| 18:2 | 24.7 | 18.2 | 19.5 | 19.2 | 18.5 | 20.1 | 23.8 | 32.2 | 30.3 | 29.8 | 31.6 |
| 18:3ω3 | 27.4 | 26.7 | 26.6 | 27.3 | 28.9 | 28.2 | 27.4 | 28.3 | 29.2 | 29.5 | 28.2 |
| 18:3ω6 | 0.2 | 1.4 | 0.3 | 0.3 | 0.4 | 0.2 | 0.5 | 0.0 | 0.5 | 0.4 | 0.6 |
| 20:0 | 1.6 | 1.4 | 1.3 | 1.4 | 1.2 | 1.4 | 1.4 | 1.8 | 2.1 | 1.9 | 2.0 |
| 18:4ω3 | 2.2 | 6.8 | 6.4 | 5.7 | 7.2 | 5.7 | 4.1 | 0.0 | 0.0 | 0.0 | 0.0 |
| 20:1d11 | 5.3 | 4.4 | 4.6 | 4.8 | 3.3 | 4.1 | 3.5 | 4.4 | 6.1 | 5.8 | 5.5 |
| 20:1iso | 0.4 | 0.3 | 0.3 | 0.3 | 0.3 | 0.3 | 0.0 | 0.5 | 0.6 | 0.5 | 0.5 |
| 20:2ω6 | 0.8 | 0.8 | 0.9 | 0.8 | 0.6 | 0.8 | 0.7 | 1.3 | 1.5 | 1.4 | 1.4 |
| 20:3ω3 | 0.6 | 0.8 | 0.8 | 0.8 | 0.7 | 0.8 | 0.7 | 0.6 | 0.7 | 0.7 | 0.6 |
| 22:0 | 0.4 | 0.5 | 0.5 | 0.5 | 0.4 | 0.5 | 0.5 | 0.6 | 0.6 | 0.6 | 0.6 |
| 20:4ω3 | 0.2 | 0.3 | 0.3 | 0.3 | 0.4 | 0.4 | 0.5 | 0.0 | 0.0 | 0.0 | 0.0 |
| 22:1 | 1.1 | 1.1 | 1.2 | 1.1 | 0.5 | 0.9 | 0.8 | 1.6 | 2.2 | 1.9 | 2.0 |
| 20:5ω3 | 0.7 | 1.3 | 1.6 | 1.5 | 1.6 | 1.1 | 1.7 | 0.0 | 0.0 | 0.0 | 0.1 |
| 22:2ω6 | 0.1 | 0.0 | 0.0 | 0.0 | 0.0 | 0.0 | 0.0 | 0.2 | 0.3 | 0.2 | 0.2 |
| 22:4ω6 + 22:3ω3 | 0.3 | 0.2 | 0.3 | 0.3 | 0.0 | 0.3 | 0.0 | 0.4 | 0.6 | 0.5 | 0.5 |
| 24:0 | 0.3 | 0.3 | 0.3 | 0.3 | 0.0 | 0.3 | 0.0 | 0.4 | 0.4 | 0.4 | 0.4 |
| 24:1 | 0.3 | 0.4 | 0.4 | 0.3 | 0.0 | 0.3 | 0.0 | 0.5 | 0.6 | 0.5 | 0.5 |
| 22:5ω3 | 0.3 | 1.1 | 1.2 | 1.1 | 1.1 | 0.9 | 0.8 | 0.0 | 0.0 | 0.0 | 0.0 |
| 22:6ω3 | 4.7 | 9.0 | 8.5 | 8.3 | 8.3 | 7.1 | 4.9 | 0.0 | 0.0 | 0.0 | 0.0 |

TABLE 12

Compiled data from the total seed lipid profiles from transgenic seed shown in Table 11. Calculations do not include the 'minor fatty acids' in Table 11.

| Parameter | FD5.46 pooled | # 2 | # 4 | # 8 | # 7 | # 9 | # 1 | # 3 | # 5 | # 6 | # 10 |
|---|---|---|---|---|---|---|---|---|---|---|---|
| total w3 (% of total FA) | 36.1 | 46 | 45.4 | 45 | 48.2 | 44.2 | 40.1 | 28.9 | 29.9 | 30.2 | 28.9 |
| total w6 (% of total FA) | 25.8 | 20.4 | 20.7 | 20.3 | 19.5 | 21.1 | 25 | 33.7 | 32.6 | 31.8 | 33.8 |
| w3/w6 ratio | 1.40 | 2.25 | 2.19 | 2.22 | 2.47 | 2.09 | 1.60 | 0.86 | 0.92 | 0.95 | 0.86 |
| w6/w3 ratio | 0.71 | 0.44 | 0.46 | 0.45 | 0.40 | 0.48 | 0.62 | 1.17 | 1.09 | 1.05 | 1.17 |
| total novel w3 (% of total FA) | 8.1 | 18.5 | 18 | 16.9 | 18.6 | 15.2 | 12 | 0 | 0 | 0 | 0.1 |
| total novel w6 (% of total FA) | 1.1 | 2.2 | 1.2 | 1.1 | 1 | 1 | 1.2 | 1.5 | 2.3 | 2 | 2.2 |
| novel w3/w6 ratio | 7.36 | 8.41 | 15.00 | 15.36 | 18.60 | 15.20 | 10.00 | | | | 0.05 |
| novel w6/w3 ratio | 0.14 | 0.12 | 0.07 | 0.07 | 0.05 | 0.07 | 0.10 | | | | 22.00 |
| OA to EPA efficiency | 8.2% | 15.6% | 15.5% | 15.1% | 15.1% | 12.8% | 10.5% | 0.0% | 0.0% | 0.0% | 0.1% |
| OA to DHA efficiency | 6.7% | 12.3% | 11.6% | 11.5% | 11.4% | 10.0% | 7.0% | 0.0% | 0.0% | 0.0% | 0.0% |
| LA to EPA efficiency | 9.2% | 17.2% | 17.1% | 16.7% | 16.2% | 13.9% | 11.4% | 0.0% | 0.0% | 0.0% | 0.2% |
| LA to DHA efficiency | 7.6% | 13.6% | 12.9% | 12.7% | 12.3% | 10.9% | 7.5% | 0.0% | 0.0% | 0.0% | 0.0% |
| ALA to EPA efficiency | 15.8% | 24.8% | 24.9% | 24.2% | 22.8% | 20.6% | 18.5% | 0.0% | 0.0% | 0.0% | 0.3% |
| ALA to DHA efficiency | 13.0% | 19.6% | 18.7% | 18.4% | 17.2% | 16.1% | 12.2% | 0.0% | 0.0% | 0.0% | 0.0% |
| total saturates | 17.6 | 17.8 | 17.8 | 17.6 | 18 | 17.8 | 18.1 | 18.2 | 17.7 | 17.8 | 18.1 |
| total monounsaturates | 19.8 | 15.5 | 16 | 16.6 | 14.3 | 16.6 | 16.8 | 18.7 | 19.3 | 19.6 | 18.6 |
| total polyunsaturates | 62.5 | 66.6 | 66.4 | 65.6 | 67.7 | 65.6 | 65.1 | 63 | 63.1 | 62.5 | 63.2 |
| total C20 | 9.6 | 9.3 | 9.8 | 9.9 | 8.1 | 8.9 | 8.5 | 8.6 | 11 | 10.3 | 10.1 |
| total C22 | 5.4 | 10.3 | 10 | 9.7 | 9.4 | 8.3 | 5.7 | 0.6 | 0.9 | 0.7 | 0.7 |
| C20/C22 ratio | 1.78 | 0.90 | 0.98 | 1.02 | 0.86 | 1.07 | 1.49 | 14.33 | 12.22 | 14.71 | 14.43 |

DHA was present in six of the 10 individual seeds. The four other seeds did not have DHA and were presumed to be null segregants which did not have the T-DNA, based on hemizygosity of the T-DNA insertion in the parental plant. Extracted lipid from the single seed with the highest level of DHA had 9.0% DHA while the sum of the percentages for EPA, DPA and DHA was 11.4%. The sum of the percentages for the new ω3 fatty acids produced in this seed as a result of the transformation (SDA, ETrA, ETA, EPA, DPA, DHA) was 19.3% whilst the corresponding sum for the new ω6 fatty acids (GLA, EDA, DGLA, ARA and any ω6 elongation products) was 2.2%-only GLA and EDA were detected as new ω6 fatty acids. The total ω6 FA (including LA) to ω3 FA (including ALA) ratio was found to be 0.44. The new ω6 FA (excluding LA) to new ω3 FA (excluding ALA) ratio in the seed with the highest DHA level was 0.12. The level of total saturated fatty acids was about 17.8% and the level of monounsaturated fatty acids was about 15.5%. The level of total ω6-fatty acids was about 20.4% and the level of ω3-fatty acids was about 46%. Overall conversion efficiencies were calculated to be: OA to EPA=15.6%, OA to DHA=12.3%, LA to EPA=17.2%, LA to DHA=13.6%, ALA to EPA=24.8%, ALA to DHA=19.6%.

Homozygous seed from this line was obtained in the T4 generation. Up to 10.3% DHA was produced in event FD5-46-18-110 with an average of 7.3% DHA observed across the entire T4 generation.

Homozygous seed was planted out across several glasshouses to generate a total of over 600 individual plants. Oil is being extracted from the seed using a variety of methods including soxhlet, acetone and hexane extractions.

Since the number of independently transformed lines of *C. sativa* obtained as described above was low, further experiments to transform *C. sativa* with pJP3416-GA7 are performed. The inventors predict that DHA levels of greater than 10% as a percentage of total fatty acids in seed oil will be achieved in further transformed lines, and plants which are homozygous for the T-DNA to 20% DHA. Twenty *C. sativa* GA7_modH events were generated and seed is being analysed for DHA content. Three GA7_modB events were generated and analysis of the T1 seed from event CMD17.1 revealed a pooled seed DHA content of 9.8%. The highest single seed DHA value was found to be 13.5%.

Example 4. Stable Expression of Transgenic DHA Pathways in *Brassica napus* Seeds

*B. napus* Transformation and Analysis of Fatty Acid Composition Using Single Vector The binary vector pJP3416-GA7 was used to generate transformed *Brassica napus* plants and seeds from the plants. The vector pJP3416-GA7 as described above was introduced into *Agrobacterium tumefaciens* strain AGL1 via standard electroporation procedures. Cultures of the transgenic *Agrobacterium* cells were grown overnight at 28° C. in LB medium with agitation at 150 rpm. The bacterial cells were collected by centrifugation at 4000 rpm for 5 minutes, washed with Winans AB medium (Winans, 1988) and re-suspended in 10 mL of Winans AB medium (pH 5.2) and growth continued overnight in the presence of kanamycin (50 mg/L), rifampicin (25 mg/L) and 100 μM acetosyringone. Two hours before infection of the *Brassica* cells, spermidine (120 mg/L) was added and the final density of the bacteria adjusted to an OD 600 nm of 0.3-0.4 with fresh AB media. Freshly isolated cotyledonary petioles from 8-day old *Brassica napus* seedlings grown on ½ MS (Murashige and Skoog, 1962) or hypocotyl segments preconditioned by 3-4 days on MS media with 1 mg/L thidiazuron (TDZ) and 0.1 mg/L α-naphthaleneacetic acid (NAA) were infected with mL *Agrobacterium* cultures for 5 minutes. The explants infected with *Agrobacterium* were then blotted on sterile filter paper to remove the excess *Agrobacterium* and transferred to co-cultivation media (MS media with 1 mg/L TDZ, 0.1 mg/L NAA and 100 μM acetosyringone) supplemented with or without different antioxidants (L-cysteine 50 mg/L and ascorbic 15 mg/L). All the plates were sealed with parafilm and incubated in the dark at 23-24° C. for 48 hrs.

The treated explants were then washed with sterile distilled water containing 500 mg/L cefotaxime and 50 mg/L timentin for 10 minutes, rinsed in sterile distilled water for 10 minutes, blotted dry on sterile filter paper, transferred to pre-selection media (MS containing 1 mg/L TDZ, 0.1 mg/L NAA, 20 mg/L adenine sulphate (ADS), 1.5 mg/L $AgNO_3$. 250 mg/L cefotaxime and 50 mg/L timentin) and cultured for five days at 24° C. with a 16 h/8 h photoperiod. They were then transferred to selection media (MS containing 1 mg/L TDZ, 0.1 mg/L NAA, 20 mg/L ADS, 1.5 mg/L $AgNO_3$. 250 mg/L cefotaxime and 50 mg/L timentin) with 1.5 mg/L glufosinate ammonium as the agent for selection of transformed cells, and cultured for 4 weeks at 24° C. with 16 h/8 h photoperiod with a biweekly subculture on to the same media. Explants with green callus were transferred to shoot initiation media (MS containing 1 mg/L kinetin, 20 mg/L ADS, 1.5 mg/L $AgNO_3$. 250 mg/L cefotaxime, 50 mg/L timentin and 1.5 mg/L glufosinate ammonium) and cultured for another 2-3 weeks. Shoots emerging from the resistant explants were transferred to shoot elongation media (MS media with 0.1 mg/L gibberelic acid, 20 mg/L ADS, 1.5 mg/L $AgNO_3$. 250 mg/L cefotaxime and 1.5 mg/L glufosinate ammonium) and cultured for another two weeks. Healthy shoots 2-3 cm long were selected and transferred to rooting media (½ MS containing 1 mg/L NAA, 20 mg/L ADS, 1.5 mg/L $AgNO_3$ and 250 mg/L cefotaxime) and cultured for 2-3 weeks. Well established shoots with roots were transferred to pots containing seedling raising mix and grown in a growth cabinet for two weeks and subsequently transferred to a glasshouse. Approximately 40 ($T_0$) plants transformed with the GA7 construct were obtained by this method.

Plants were grown to maturity after being allowed to self-fertilise. Seeds obtained from transformed plants were analysed for fatty acid composition in their seedoil as described in Example 1. Data for a transformed line with the highest DHA level are shown in Table 13. DHA levels on average were significantly lower in the seedoil of the *B. napus* seeds transformed with the T-DNA from pJP3416-GA7 than in *A. thaliana* seeds (Example 2) or *Camelina* seeds (Example 3) transformed with the same construct. The highest level of DHA in approximately 40 lines was found to be 1.52% with the majority of the transgenic lines having detectable DHA. It was noted that there was a substantial accumulation of ALA, about 35% of the total fatty acids, in these seeds which was not being converted efficiently to SDA or following products in the pathway.

Fatty acid profile analysis of single *B. napus* seeds from a $T_1$ event, CT125-2, was performed to better determine the amount of DHA produced in transgenic seeds. Seeds were found to contain between 0% (null seeds) and 8.5% DHA (Table 13).

Some of the seeds from the plant line CT116 as well as other transgenic lines showing DHA production were sown to produce progeny plants. RT-PCR was performed on total RNA isolated from developing embryos from these plants in order to determine why the GA7 construct performed poorly for DHA production relative to transgenic *A. thaliana* and *C. sativa* having the same construct, and poorly relative to the combination of the genes on pJP3115 and pJP3116 (below). RT-PCR was performed on total RNA using a one-step RT-PCR kit (Invitrogen) and gene-specific primers targeting each transgene. This confirmed that each of the genes in the GA7 construct was expressed well in the *B. napus* transformants except for the Δ6-desaturase which was poorly expressed in the majority of transformed seeds. The other genes from this construct functioned well in both *B. napus* and *A. thaliana* seeds, for example the Δ12- and Δ15-desaturases which functioned to produce increased levels of LA and ALA in the seeds whilst decreasing oleic acid levels. A representative RT-PCR gel is shown in FIG. 7 which clearly shows the low expression of the Δ6-desaturase relative to the other transgenes from pJP3416-GA7.

Transgenic plants and seed which are homozygous for the transgenes are generated by planting out progeny from the lines with the highest DHA.

TABLE 13

Fatty acid composition as a percentage of total fatty acids in seedoil from independent $T_1$ *Brassica napus* seed transformed with pJP3416-GA7, lines CT116-11 and CT-125-2 compared to wild-type (untransformed) control. 22:6ω3 is DHA. Data from single CT125-2 *B. napus* seeds is denoted by 'SS'.

| | Control | CT116-11 | CT125-2 | CT125-2 #2 SS | CT125-2 #3 SS | CT125-2 #10 SS |
|---|---|---|---|---|---|---|
| 14:0 | 0.1 | 0.2 | 0.1 | 0.1 | 0.1 | 0.1 |
| 16:0 | 4.3 | 7.2 | 5.2 | 6.5 | 4.7 | 7.7 |
| 16:1 | 0.2 | 0.5 | 0.4 | 0.3 | 0.3 | 0.8 |
| 16:3 | 0.2 | 0.2 | 0.2 | 0.1 | 0.2 | 0.2 |
| 18:0 | 2.1 | 2.2 | 2.4 | 2.3 | 2.3 | 2.8 |
| 18:1d9 | 59.1 | 27.0 | 38.1 | 34.0 | 19.3 | 14.8 |
| 18:1d11 | 3.7 | 6.6 | 4.2 | 4.4 | 4.3 | 9.6 |
| 18:2 | 19.7 | 14.1 | 16.6 | 13.9 | 10.2 | 10.2 |
| 18:3ω3 | 8.3 | 35.2 | 27.7 | 34.1 | 49.5 | 37.9 |
| 20:0 | 0.6 | 0.5 | 0.6 | 0.4 | 0.3 | 0.7 |
| 18:4ω3 | 0.0 | 0.9 | 0.3 | 0.5 | 0.6 | 2.6 |
| 20:1d11 | 1.2 | 1.1 | 1.0 | 1.0 | 0.8 | 0.6 |
| 20:1iso | | 0.2 | | 0.1 | | 0.2 |
| 20:2ω6 | 0.1 | 0.1 | 0.1 | 0.1 | 0.1 | 0.1 |
| 20:3ω3 | | 1.3 | 0.7 | 0.8 | 1.6 | 0.9 |
| 22:0 | 0.3 | 0.4 | 0.3 | 0.1 | 0.1 | 0.4 |
| 20:4ω3 | | 0.1 | 0.3 | 0.4 | 0.6 | 0.5 |
| 22:1 | | | | | | |
| 20:5ω3 | | | | | 0.1 | 0.3 |
| 22:3ω3 | | | | | 0.1 | |
| 24:0 | 0.2 | 0.4 | 0.3 | 0.1 | 0.1 | 0.3 |
| 24:1 | 0.1 | 0.3 | 0.1 | 0.1 | 0.2 | 0.1 |
| 22:5ω3 | | 0.1 | 0.1 | 0.1 | 0.1 | 0.5 |
| 22:6ω3 | | 1.52 | 1.2 | 1.3 | 2.7 | 8.5 |

B. *Napus* Transformation and Analysis of Fatty Acid Composition Using Two Vectors In another experiment in *B. napus* and as an alternative format for introducing the transgenes, the binary vectors pJP3115 and pJP3116 as described in WO 2010/057246 were used to separately generate transformed *B. napus* plants and transformed seeds were obtained from the plants. The T-DNA on pJP3115 comprised chimeric genes encoding the *Crepis palestina* Δ12-desaturase, *Micromonas pusilla* Δ6-desaturase, *Pyramimonas cordata* Δ6-elongase and *Pavlova salina* Δ5-desaturase and the T-DNA on pJP3116 contained chimeric genes encoding *Perilla frutescens* Δ15-desaturase, *Pyramimonas cordata* Δ5-elongase and *Pavlova salina* Δ4-desaturase. The two T-DNAs, when present together and expressed in developing seeds, formed a 7-gene pathway for producing DHA from endogenously produced oleic acid. These vectors were introduced into *Agrobacterium tumefaciens* strain AGL1 via standard electroporation procedures and the transformed cells used independently to transform *B. napus* using the method as described above to generate stably transformed $T_0$ plants. 29 pJP3115 and 19 pJP3116 transformants were obtained and these plants were grown to maturity and seeds obtained after self-fertilisation were analysed for fatty acid composition in their seedoil. Transformation with the T-DNA from pJP3115 was expected to result in EPA production from endogenously produced ALA whilst transformation with the T-DNA from pJP3116 was expected to result in increased ALA production from LA. Several plants were identified which displayed these phenotypes. The majority of events displayed a decreased OA/increased LA phenotype due to Δ12 desaturation with a low level of EPA production. Up to 2.6% EPA was observed in pJP31115 transgenic pooled seed. Similarly, the majority of pJP3116 events were found to have an elevated ALA phenotype due to Δ15-desaturase activity. Up to 18.5% ALA was found in pooled seed transformed with the T-DNA from pJP3116.

$T_1$ plants from the lines with the highest levels of EPA and ALA were crossed and the progeny seed (F1) from 24 recovered events analysed for DHA content. DHA was found in 17 of these events with up to 1.9% DHA found in pooled seed from these events. Single-seed analysis was performed to determine the range of DHA production—the data are shown in Table 14. A large range of DHA levels were observed in the crossed progeny, probably due to the hemizygous nature of the T-DNAs in the parental plants, so that some seeds did not receive both T-DNAs. Up to 6.7% DHA was observed in total seed lipid.

TABLE 14

Fatty acid composition as a percentage of total fatty acids in seedoil from *B. napus* F1 single seeds that were from a cross of plants transgenic for the T-DNA from pJP3115 with plants transgenic for the T-DNA from pJP3116. B1, B2 and B4 designate events.

| | B1.1 | B1.2 | B1.3 | B1.4-g | B1.5-g | B2.1 | B2.2 | B2.3g | B2.4g | B2.5g | B3.1 | B3.2 |
|---|---|---|---|---|---|---|---|---|---|---|---|---|
| 14:0 | 0.1 | 0.1 | 0.1 | 0.2 | 0.2 | 0.1 | 0.1 | 0.2 | 0.2 | 0.1 | 0.1 | 0.1 |
| 16:0 | 6.6 | 6.4 | 4.5 | 12.3 | 7.9 | 5.1 | 5.0 | 10.1 | 8.5 | 6.8 | 5.3 | 7.2 |
| 16:1 | 0.4 | 0.5 | 0.2 | 1.0 | 0.6 | 0.4 | 0.4 | 0.6 | 1.1 | 0.5 | 0.5 | 0.6 |
| 16:3 | 0.1 | 0.1 | 0.1 | 0.1 | 0.1 | 0.1 | 0.1 | 0.1 | 0.2 | 0.1 | 0.1 | 0.2 |
| 18:0 | 2.3 | 2.6 | 2.2 | 1.6 | 2.9 | 2.9 | 3.4 | 2.2 | 1.8 | 2.9 | 3.4 | 2.4 |
| 18:1 | 34.1 | 39.3 | 46.9 | 14.9 | 20.7 | 41.6 | 46.3 | 14.4 | 23.4 | 38.3 | 43.6 | 32.0 |
| 18:1d11 | 4.6 | 5.8 | 2.7 | 6.8 | 6.2 | 3.8 | 4.9 | 5.9 | 8.7 | 4.5 | 5.5 | 5.1 |
| 18:2 | 33.6 | 30.7 | 30.4 | 29.2 | 34.4 | 31.7 | 27.7 | 33.2 | 23.9 | 33.3 | 27.9 | 33.4 |
| 18:3ω6 | 0.2 | 0.3 | 0.1 | 0.4 | 0.4 | 0.2 | 0.2 | 0.7 | 0.1 | 0.2 | 0.2 | 0.3 |
| 18:3ω3 | 10.3 | 7.1 | 7.7 | 18.7 | 14.9 | 8.2 | 5.9 | 14.8 | 28.1 | 6.3 | 7.3 | 10.0 |
| 20:0 | 0.6 | 0.7 | 0.6 | 0.5 | 0.7 | 0.8 | 0.9 | 0.6 | 0.4 | 0.7 | 0.9 | 0.7 |
| 18:4ω3 | 0.2 | 0.1 | 0.1 | 0.8 | 0.5 | 0.2 | 0.2 | 0.8 | 0.0 | 0.2 | 0.2 | 0.2 |
| 20:1d11 | 1.0 | 1.1 | 1.1 | 0.7 | 0.8 | 1.1 | 1.1 | 0.5 | 0.9 | 1.1 | 1.1 | 0.9 |
| 20:1iso | 0.1 | 0.1 | 0.0 | 0.1 | 0.1 | 0.1 | 0.1 | 0.1 | 0.3 | 0.1 | 0.1 | 0.1 |
| 20:2ω6 | 0.4 | 0.3 | 0.2 | 0.5 | 0.5 | 0.4 | 0.3 | 0.4 | 0.5 | 0.5 | 0.3 | 0.5 |
| 20:3ω6 | 0.0 | 0.0 | 0.0 | 0.0 | 0.0 | 0.0 | 0.0 | 0.0 | 0.0 | 0.0 | 0.0 | 0.0 |
| 20:4ω6 | 0.0 | 0.0 | 0.0 | 0.0 | 0.0 | 0.0 | 0.0 | 0.1 | 0.0 | 0.0 | 0.0 | 0.0 |
| 20:3ω3 | 1.8 | 1.6 | 1.1 | 2.8 | 2.1 | 1.1 | 1.0 | 2.7 | 0.7 | 1.4 | 0.9 | 1.6 |
| 22:0 | 0.3 | 0.4 | 0.3 | 0.3 | 0.4 | 0.4 | 0.5 | 0.3 | 0.3 | 0.4 | 0.5 | 0.4 |
| 20:4ω3 | 0.3 | 0.2 | 0.2 | 0.4 | 0.4 | 0.1 | 0.1 | 0.5 | 0.0 | 0.2 | 0.1 | 0.2 |
| 22:1 | 0.0 | 0.0 | 0.0 | 0.0 | 0.0 | 0.0 | 0.0 | 0.0 | 0.0 | 0.0 | 0.0 | 0.0 |
| 20:5ω3 | 0.0 | 0.0 | 0.0 | 0.1 | 0.1 | 0.0 | 0.0 | 0.2 | 0.0 | 0.0 | 0.0 | 0.0 |
| 22:2ω6 | 0.0 | 0.0 | 0.0 | 0.0 | 0.0 | 0.0 | 0.0 | 0.0 | 0.0 | 0.0 | 0.0 | 0.0 |
| 22:4ω6 | 0.1 | 0.2 | 0.1 | 0.2 | 0.2 | 0.1 | 0.1 | 0.4 | 0.2 | 0.2 | 0.1 | 0.2 |
| 24:0 | 0.3 | 0.4 | 0.2 | 0.2 | 0.3 | 0.3 | 0.3 | 0.3 | 0.4 | 0.4 | 0.4 | 0.3 |
| 22:5ω6 | 0.1 | 0.2 | 0.1 | 0.2 | 0.3 | 0.1 | 0.1 | 0.5 | 0.0 | 0.2 | 0.1 | 0.2 |
| 24:1 | 0.2 | 0.2 | 0.2 | 0.3 | 0.3 | 0.2 | 0.2 | 0.3 | 0.3 | 0.2 | 0.2 | 0.2 |
| 22:5ω3 | 0.7 | 0.7 | 0.3 | 2.1 | 1.6 | 0.3 | 0.4 | 3.2 | 0.0 | 0.5 | 0.4 | 1.2 |
| 22:6ω3 | 1.4 | 1.0 | 0.5 | 5.5 | 3.9 | 0.8 | 0.7 | 6.7 | 0.0 | 1.1 | 0.8 | 2.0 |

0.0 = not detectable by the GC method.

TABLE 15

Compiled data from the total seed lipid profiles from transgenic seed shown in Table 14. Calculations do not include the 'minor fatty acids' in Table 14.

| Parameter | B1.1 | B1.2 | B1.3 | B1.4-g | B1.5-g | B2.1 | B2.2 | B2.3g | B2.4g | B2.5g | B3.1 |
|---|---|---|---|---|---|---|---|---|---|---|---|
| total w3 (% of total FA) | 4.6 | 3.9 | 2.3 | 12.1 | 9 | 2.7 | 2.6 | 14.8 | 0.8 | 3.6 | 2.6 |
| total w6 (% of total FA) | 44.5 | 38.5 | 38.5 | 48.8 | 50.3 | 40.5 | 34.1 | 49.4 | 52.7 | 40.5 | 35.7 |
| w3/w6 ratio | 0.10 | 0.10 | 0.06 | 0.25 | 0.18 | 0.07 | 0.08 | 0.30 | 0.02 | 0.09 | 0.07 |
| w6/w3 ratio | 9.67 | 9.87 | 16.74 | 4.03 | 5.59 | 15.00 | 13.12 | 3.34 | 65.88 | 11.25 | 13.73 |
| total novel w3 (% of total FA) | 2.6 | 2 | 1.1 | 8.9 | 6.5 | 1.4 | 1.4 | 11.4 | 0 | 2 | 1.5 |
| total novel w6 (% of total FA) | 10.5 | 7.5 | 7.9 | 19.1 | 15.4 | 8.4 | 6.1 | 15.8 | 28.3 | 6.7 | 7.5 |
| novel w3/w6 ratio | 0.25 | 0.27 | 0.14 | 0.47 | 0.42 | 0.17 | 0.23 | 0.72 | 0.00 | 0.30 | 0.20 |
| novel w6/w3 ratio | 4.04 | 3.75 | 7.18 | 2.15 | 2.37 | 6.00 | 4.36 | 1.39 | | 3.35 | 5.00 |
| OA to EPA efficiency | 2.5% | 2.1% | 0.9% | 10.1% | 6.9% | 1.3% | 1.3% | 12.8% | | 1.9% | 1.4% |
| OA to DHA efficiency | 1.7% | 1.2% | 0.6% | 7.2% | 4.8% | 0.9% | 0.8% | 8.5% | | 1.3% | 1.0% |
| LA to EPA efficiency | 4.3% | 4.0% | 2.0% | 12.6% | 9.4% | 2.5% | 3.0% | 15.7% | | 3.6% | 3.1% |
| LA to DHA efficiency | 2.9% | 2.4% | 1.2% | 9.0% | 6.6% | 1.9% | 1.9% | 10.4% | | 2.5% | 2.1% |
| ALA to EPA efficiency | 47.7% | 44.7% | 36.4% | 68.1% | 65.9% | 44.0% | 45.8% | 72.1% | | 47.1% | 50.0% |
| ALA to DHA efficiency | 31.8% | 26.3% | 22.7% | 48.7% | 45.9% | 32.0% | 29.2% | 47.9% | | 32.4% | 33.3% |
| total saturates | 10.2 | 10.6 | 7.9 | 15.1 | 12.4 | 9.6 | 10.2 | 13.7 | 11.6 | 11.3 | 10.6 |
| total monounsaturates | 40.4 | 47 | 51.1 | 23.8 | 28.7 | 47.2 | 53 | 21.8 | 34.7 | 44.7 | 51 |
| total polyunsaturates | 49.2 | 42.5 | 40.9 | 61 | 59.4 | 43.3 | 36.8 | 64.3 | 53.7 | 44.2 | 38.4 |
| total C20 | 4.2 | 4 | 3.2 | 5.1 | 4.7 | 3.6 | 3.5 | 5.1 | 2.8 | 4 | 3.4 |
| total C22 | 2.6 | 2.5 | 1.3 | 8.3 | 6.4 | 1.7 | 1.8 | 11.1 | 0.5 | 2.4 | 1.9 |
| C20/C22 ratio | 1.62 | 1.60 | 2.46 | 0.61 | 0.73 | 2.12 | 1.94 | 0.46 | 5.60 | 1.67 | 1.79 |

Compiled data from the total lipid profiles (Table 14) are shown in Table 15. From the data in Table 15, the total ω6 FA (including LA) to ω3 FA (including ALA) ratio in the seed with the highest level of DHA was 3.34. The new ω6 FA (excluding LA) to new ω3 FA (excluding ALA) ratio was 1.39. The level of total saturated fatty acids was about 13.7% and the level of monounsaturated fatty acids was about 21.8%. The level of total ω6-fatty acids was about 46.4% and the level of ω3-fatty acids was about 14.8%. Overall conversion efficiencies were calculated to be: OA to EPA=12.8%, OA to DHA=8.5%, LA to EPA=15.7%, LA to DHA=10.4%, ALA to EPA=72.1%, ALA to DHA=47.9%. The reduced efficiency of the ω6 fatty acids to ω3 fatty acids conversion observed in this experiment with the combination of the pJP3115 and pJP3116 was thought to be due to a lower efficiency of the plant Δ15-desaturase compared to the fungal Δ15/ω3 desaturase (Examples 2 and 3) when combined with the genes for conversion of ALA to DHA.

Progeny from DHA-containing lines which are homozygous for all of the introduced transgenes are generated for analysis.

Example 5. Modifications to T-DNAs Encoding DHA Pathways in Plant Seeds

In order to improve the DHA production level in *B. napus* beyond the levels described in Example 4, the binary vectors pJP3416-GA7-modA, pJP3416-GA7-modB, pJP3416-GA7-modC, pJP3416-GA7-modD, pJP3416-GA7-modE and pJP3416-GA7-modF were constructed as follows. These binary vectors were variants of the pJP3416-GA7 construct described in Example 2 and were designed to further increase the synthesis of DHA in plant seeds, particularly by improving Δ6-desaturase and Δ6-elongase functions. SDA had been observed to accumulate in some seed transformed with the GA7 construct due to a relatively low elongation efficiency compared to the Δ5-elongase, so amongst other modifications, the two elongase gene positions were switched in the T-DNA.

The two elongase coding sequences in pJP3416-GA7 were switched in their positions on the T-DNA to yield pJP3416-GA7-modA by first cloning a new *P. cordata* Δ6-elongase cassette between the SbfI sites of pJP3416-GA7 to replace the *P. cordata* Δ5-elongase cassette. This construct was further modified by exchanging the FP1 promoter driving the *M. pusilla* Δ6-desaturase with a conlinin Cnl2 promoter (pLuCnl2) to yield pJP3416-GA7-modB. This modification was made in an attempt to increase the Δ6-desaturase expression and thereby enzyme efficiency. It was thought that the Cnl2 promoter might yield higher expression of the transgene in *B. napus* than the truncated napin promoter. pJP3416-GA7-modC was produced by adding a second *M. pusilla* Δ6-desaturase cassette with slightly different codon usage (SEQ ID NO: 15) and driven by the FP1 promoter, which was inserted at the PmeI site just inside the right border of pJP3416-GA7-modB. The second Δ6-desaturase cassette was added to both pJP3416-GA7-modB and pJP3416-GA7-modF in order to increase the Δ6-desaturase expression level and extend the time period during seed development for expression of Δ6-desaturase by the use of multiple promoters. Different codon usages were used in the two nucleotide sequences to result in the translation of the same protein sequence without risking co-suppression from similar coding regions within the same T-DNA. pJP3416-GA7-modD and pJP3416-GA7-modE were similar variants in which a third MAR sequence, corresponding to nucleotides 16649-17816 of SEQ ID NO: 1, was added to pJP3416-GA7 and pJP3416-GA7-modB, respectively, at the PmeI site. pJP3416-GA7-modF was produced by adding a second *M. pusilla* Δ6-desaturase cassette containing the native Δ6-desaturase nucleotide sequence and driven by the FP1 promoter at the PmeI site at the right border of pJP3416-GA7-modB. pJP3416-GA7-modG was made by first replacing the *M. pusilla* Δ6-desaturase cassette with a Cnl2:*P. cordata* Δ5-elongase cassette by restriction cloning at the AscI-PacI sites. pJP3416-GA7-modG was then made by replacing the original FAE:*P. cordata* Δ5-elongase cassette with a FAE1:*M. pusilla* Δ6-desaturase cassette by restriction cloning at the SbfI sites. The nucleotide sequences of the T-DNAs from each of these genetic constructs are shown as: pJP3416-GA7-modB (SEQ ID NO:2), pJP3416-GA7-modC (SEQ ID NO:3), pJP3416-GA7-modD (SEQ ID NO:4), pJP3416-GA7-modE (SEQ ID NO:5), pJP3416-GA7-modF (SEQ ID NO:6) and pJP3416-GA7-modG (SEQ ID NO:7).

The binary vectors pJP3416-GA7-modB, pJP3416-GA7-modC, pJP3416-GA7-modD, pJP3416-GA7-modE, pJP3416-GA7-modF and pJP3416-GA7-modG are used to generate transformed *Brassica* somatic embryos and *Brassica napus. Camelina sativa* and *Arabidopsis thaliana* plants and progeny seeds. Data for pJP3416-GA7-modB are shown in the next Example.

Eight transgenic pJP3416-GA7-modB *A. thaliana* events and 15 transgenic pJP3416-GA7-modG *A. thaliana* events were generated. Between 3.4% and 7.2% DHA in pooled pJP3416-GA7-modB seed was observed and between 0.6 and 4.1% DHA in pooled T2 pJP3416-GA7-modG seed was observed. Several of the highest pJP3416-GA7-modB events were sown out on selectable media and surviving seedlings taken to the next generation. Seed is being analysed for DHA content. Since the pooled T1 seeds represented populations that were segregating for the transgenes and included any null segregants, it is expected that the homozygous seeds from progeny plants will have increased levels of DHA, up to 20% of the total fatty acid content in the seed oil. The other modified constructs were used to transform *A. thaliana*. Although only a small number of transformed lines were obtained, none yielded higher levels of DHA than the modB construct.

The pJP3416-GA7-modB construct was also used to generate transformed *B. napus* plants of cultivar Oscar and in a breeding line designated NX005. Ten independent transformed plants (T0) were obtained so far for the Oscar transformation, and 20 independent lines for NX005. Seed (T1 seed) was harvested from these transgenic lines. Pools of seed were tested for levels of DHA in the seed oil, and two lines which showed the highest levels were selected, these were designated lines CT132.5 (in cultivar Oscar) and CT133.15 (in NX005). Twenty seeds from CT132.5 and 11 seeds from CT133.15 were imbibed and, after two days, oil was extracted from a half cotyledon from each of the individual seeds. The other half cotyledons with embryonic axes were kept and cultured on media to maintain the specific progeny lines. The fatty acid composition in the oil was determined; the data is shown in Table 16 for CT132.5. The DHA level in ten of the 20 seeds analysed was in the range of 7-20% of the total fatty acid content as determined by the GC analysis. Other seeds had less than 7% DHA and may have contained a partial (incomplete) copy of the T-DNA from pJP3416-GA7-modB. The transgenic line appeared to contain multiple transgene insertions that were genetically unlinked. The seeds of transgenic line CT133.15 exhibited DHA levels in the range 0-5%. Seeds with no DHA were likely to be null segregants. These data confirmed that the modB construct performed well for DHA production in canola seed.

The pJP3416-GA7-modB and pJP3416-GA7-modF constructs were also used to generate transformed *Camelina sativa* plants. At least 24 independent transformed plants (T0) were obtained and examined in more detail by progeny analysis. Seed (T1 seed) was harvested from these transgenic lines. Pools of seed were tested for levels of DHA in the seed oil, and 6 lines which showed the highest levels of DHA (between 6% and 9%) were selected. The DHA levels in 20 T1 seeds from each line were analysed-most seeds exhibited DHA levels in the range of 6-14% of the total fatty acid content as determined by the GC analysis. The fatty acid composition in the oil was determined; the data is shown in Table 17 for several transgenic seeds. These data confirmed that the modB and modF constructs both performed well for DHA production in *Camelina* seed.

TABLE 16

Fatty acid profiles of half cotyledons of germinating T1 transgenic *B. napus* seeds containing the modB construct. Up to 18.1% DHA was observed with numerous samples containing greater than 10% DHA.

| Seed | 14:0 | 16:0 | 16:1d3? | 16:1 | 16:3 | 18:0 | 18:1 | 18:1d11 | 18:2 | 18:3n6 | 18:3n3 | 20:0 | 18:4n3 | C20:1d11 |
|---|---|---|---|---|---|---|---|---|---|---|---|---|---|---|
| 1 | 0.1 | 4.2 | 0.1 | 0.1 | 0.2 | 1.8 | 29.9 | 2.5 | 9.9 | 0.1 | 38.4 | 0.5 | 0.8 | 1.0 |
| 2 | 0.1 | 4.7 | 0.1 | 0.1 | 0.2 | 4.0 | 23.0 | 2.3 | 7.4 | 0.3 | 29.3 | 1.0 | 4.3 | 1.1 |
| 3 | 0.1 | 3.7 | 0.2 | 0.1 | 0.2 | 1.8 | 55.1 | 1.9 | 4.7 | 0.2 | 15.2 | 0.8 | 1.8 | 1.4 |
| 4 | 0.1 | 4.6 | 0.2 | 0.2 | 0.2 | 2.9 | 22.1 | 1.8 | 6.6 | 0.4 | 26.5 | 1.0 | 7.2 | 1.0 |
| 5 | 0.1 | 4.0 | 0.1 | 0.1 | 0.2 | 1.7 | 27.4 | 2.1 | 8.1 | 0.3 | 26.4 | 0.6 | 2.8 | 1.0 |
| 6 | 0.1 | 3.5 | 0.1 | 0.1 | 0.2 | 1.6 | 59.8 | 2.0 | 4.3 | 0.1 | 18.5 | 0.6 | 0.5 | 1.3 |
| 7 | 0.1 | 6.0 | 0.3 | 0.3 | 0.3 | 1.7 | 16.6 | 2.6 | 23.9 | 1.0 | 23.2 | 0.6 | 5.4 | 0.8 |
| 8 | 0.1 | 4.9 | 0.1 | 0.1 | 0.2 | 2.7 | 12.9 | 1.4 | 11.7 | 0.3 | 34.3 | 0.9 | 5.0 | 0.9 |
| 9 | 0.1 | 3.9 | 0.1 | 0.1 | 0.1 | 2.4 | 41.6 | 1.7 | 21.5 | 0.0 | 23.4 | 0.7 | 0.0 | 1.2 |
| 10 | 0.1 | 3.7 | 0.2 | 0.1 | 0.1 | 2.1 | 30.9 | 1.7 | 19.2 | 0.4 | 23.6 | 0.7 | 2.1 | 1.1 |
| 11 | 0.1 | 5.7 | 0.4 | 0.3 | 0.2 | 3.8 | 41.2 | 2.4 | 26.7 | 2.1 | 7.2 | 1.3 | 0.3 | 1.2 |
| 12 | 0.1 | 4.6 | 0.0 | 0.1 | 0.2 | 2.4 | 25.5 | 1.7 | 16.1 | 0.3 | 28.9 | 0.8 | 3.9 | 1.1 |
| 13 | 0.1 | 4.3 | 0.1 | 0.1 | 0.1 | 4.2 | 19.4 | 1.6 | 9.2 | 0.1 | 45.5 | 1.0 | 0.2 | 1.1 |
| 14 | 0.1 | 6.3 | 0.2 | 0.2 | 0.2 | 4.0 | 10.5 | 2.3 | 8.4 | 0.3 | 31.1 | 1.3 | 3.9 | 0.8 |
| 15 | 0.1 | 5.1 | 0.1 | 0.2 | 0.2 | 3.3 | 16.8 | 2.4 | 11.2 | 0.3 | 28.8 | 1.0 | 4.5 | 0.9 |
| 16 | 0.1 | 4.4 | 0.1 | 0.1 | 0.2 | 4.0 | 16.2 | 1.5 | 11.6 | 0.2 | 33.5 | 0.9 | 2.8 | 1.1 |
| 17 | 0.2 | 7.2 | 0.2 | 0.2 | 0.2 | 4.9 | 15.0 | 2.1 | 8.9 | 0.3 | 25.9 | 1.4 | 5.1 | 0.9 |
| 18 | 0.1 | 4.0 | 0.1 | 0.1 | 0.2 | 2.3 | 64.8 | 1.2 | 7.2 | 0.1 | 12.5 | 1.0 | 3.5 | 1.5 |
| 19 | 0.1 | 3.9 | 0.1 | 0.1 | 0.2 | 4.6 | 36.9 | 1.7 | 7.1 | 0.2 | 28.6 | 1.2 | 1.8 | 1.2 |
| 20 | 0.1 | 4.8 | 0.1 | 0.1 | 0.2 | 6.0 | 18.5 | 1.2 | 12.8 | 0.2 | 34.8 | 1.4 | 2.4 | 1.1 |

| Seed | 20:1d13 | C20:2n6 | C20:3n3 | C22:0 | 20:4n3 | 20:5n3 | 22:3n3 | C24:0 | C24:1 | 22:5n3 | C22:6n3 |
|---|---|---|---|---|---|---|---|---|---|---|---|
| 1 | 0.0 | 0.1 | 2.1 | 0.3 | 2.8 | 0.3 | 0.1 | 0.2 | 0.2 | 0.5 | 3.9 |
| 2 | 0.0 | 0.1 | 1.9 | 0.4 | 6.9 | 1.0 | 0.0 | 0.3 | 0.1 | 1.7 | 9.5 |
| 3 | 0.0 | 0.1 | 0.3 | 0.5 | 11.3 | 0.0 | 0.0 | 0.3 | 0.2 | 0.0 | 0.0 |
| 4 | 0.0 | 0.1 | 0.8 | 0.5 | 11.2 | 1.9 | 0.0 | 0.2 | 0.2 | 1.7 | 8.7 |
| 5 | 0.0 | 0.1 | 1.5 | 0.3 | 7.6 | 1.5 | 0.0 | 0.1 | 0.1 | 1.8 | 12.2 |
| 6 | 0.0 | 0.0 | 0.7 | 0.3 | 6.0 | 0.0 | 0.0 | 0.2 | 0.1 | 0.0 | 0.0 |
| 7 | 0.0 | 0.2 | 0.6 | 0.4 | 2.6 | 1.1 | 0.0 | 0.3 | 0.3 | 1.7 | 9.9 |
| 8 | 0.0 | 0.2 | 2.4 | 0.5 | 4.1 | 1.3 | 0.0 | 0.2 | 0.2 | 1.8 | 13.8 |
| 9 | 0.0 | 0.1 | 2.2 | 0.4 | 0.0 | 0.0 | 0.1 | 0.3 | 0.2 | 0.0 | 0.0 |
| 10 | 0.0 | 0.1 | 1.5 | 0.4 | 3.6 | 0.6 | 0.0 | 0.2 | 0.1 | 0.7 | 6.9 |
| 11 | 0.0 | 0.2 | 0.3 | 0.8 | 4.8 | 0.0 | 0.0 | 0.6 | 0.3 | 0.0 | 0.0 |
| 12 | 0.0 | 0.1 | 1.9 | 0.4 | 3.9 | 0.6 | 0.0 | 0.2 | 0.0 | 1.1 | 6.2 |
| 13 | 0.0 | 0.1 | 5.2 | 0.4 | 2.6 | 0.3 | 0.2 | 0.2 | 0.1 | 0.4 | 3.4 |
| 14 | 0.0 | 0.1 | 2.3 | 0.6 | 4.6 | 1.8 | 0.1 | 0.3 | 0.2 | 2.5 | 18.1 |
| 15 | 0.0 | 0.1 | 2.1 | 0.6 | 3.2 | 1.5 | 0.1 | 0.3 | 0.1 | 1.8 | 15.1 |
| 16 | 0.0 | 0.2 | 3.7 | 0.4 | 4.6 | 0.7 | 0.1 | 0.3 | 0.1 | 1.3 | 12.1 |
| 17 | 0.0 | 0.0 | 1.6 | 0.8 | 4.9 | 2.1 | 0.0 | 0.6 | 0.3 | 2.2 | 15.0 |
| 18 | 0.0 | 0.1 | 0.0 | 0.7 | 0.0 | 0.0 | 0.0 | 0.5 | 0.2 | 0.0 | 0.0 |
| 19 | 0.0 | 0.1 | 1.4 | 0.5 | 4.3 | 0.4 | 0.0 | 0.4 | 0.1 | 0.8 | 4.3 |
| 20 | 0.0 | 0.1 | 3.4 | 0.6 | 3.2 | 0.4 | 0.1 | 0.3 | 0.1 | 0.7 | 7.6 |

TABLE 17

Fatty acid profiles of T1 transgenic *C. sativa* seeds containing the modB or modF constructs

| | C14:0 | C16:0 | C16:1 | C18:0 | C18:1 | C18:1d11 | C18:2 | C18:3n6 | C18:3n3 |
|---|---|---|---|---|---|---|---|---|---|
| 123-8 | 0.1 | 7.3 | 0.0 | 5.2 | 7.9 | 1.0 | 7.7 | 0.7 | 29.9 |
| 123-12 | 0.1 | 8.3 | 0.0 | 5.3 | 7.2 | 1.2 | 8.7 | 0.9 | 27.2 |
| 5-8 | 0.1 | 8.3 | 0.1 | 3.5 | 9.4 | 1.3 | 8.1 | 1.1 | 29.0 |
| 5-9 | 0.1 | 8.1 | 0.0 | 3.5 | 9.4 | 1.2 | 8.4 | 1.2 | 29.2 |
| 17-10 | 0.1 | 8.7 | 0.1 | 4.1 | 8.4 | 1.3 | 5.5 | 1.2 | 26.1 |
| 17-26 | 0.1 | 8.8 | 0.1 | 5.5 | 5.0 | 1.3 | 7.6 | 0.9 | 27.8 |

TABLE 17-continued

Fatty acid profiles of T1 transgenic *C. sativa* seeds containing the modB or modF constructs

| | C20:0 | 18:4n3 | C20:1d11 | 20:1d13 | C20:2n6 | C20:3n6 | C20:4n6 | C20:3n3 | C22:0 |
|---|---|---|---|---|---|---|---|---|---|
| 123-8 | 2.3 | 6.0 | 7.1 | 0.4 | 0.7 | 0.0 | 0.0 | 0.9 | 0.4 |
| 123-12 | 2.5 | 5.7 | 6.9 | 0.5 | 0.7 | 0.0 | 0.1 | 0.9 | 0.5 |
| 5-8 | 1.0 | 9.3 | 7.9 | 0.4 | 0.6 | 0.0 | 0.0 | 0.8 | 0.2 |
| 5-9 | 1.0 | 9.0 | 8.1 | 0.3 | 0.6 | 0.0 | 0.0 | 0.8 | 0.2 |
| 17-10 | 1.6 | 11.8 | 7.2 | 0.3 | 0.0 | 0.4 | 0.03 | 0.8 | 0.3 |
| 17-26 | 2.7 | 10.1 | 6.2 | 0.3 | 0.0 | 0.7 | 0.03 | 1.1 | 0.6 |

| | 20:4n3 | C22:1 | 20:5n3 | C22:2n6 | 22:3n3 | C24:0 | C24:1 | 22:5n3 | C22:6n3 |
|---|---|---|---|---|---|---|---|---|---|
| 123-8 | 1.3 | 1.0 | 4.6 | 0.0 | 0.1 | 0.2 | 0.3 | 1.5 | 13.3 |
| 123-12 | 1.5 | 1.2 | 5.0 | 0.0 | 0.1 | 0.2 | 0.4 | 1.5 | 13.2 |
| 5-8 | 0.4 | 0.8 | 3.4 | 0.0 | 0.1 | 0.2 | 0.4 | 0.9 | 12.6 |
| 5-9 | 0.5 | 0.8 | 3.5 | 0.0 | 0.1 | 0.1 | 0.3 | 0.9 | 12.6 |
| 17-10 | 0.4 | 0.7 | 5.5 | 0.0 | 0.0 | 0.2 | 0.3 | 1.3 | 13.5 |
| 17-26 | 0.5 | 1.0 | 4.7 | 0.1 | 0.1 | 0.3 | 0.4 | 1.0 | 13.1 |

The inventors considered that, in general, the efficiency of rate-limiting enzyme activities in the DHA pathway can be greater in multicopy T-DNA transformants compared to single-copy T-DNA transformants, or can be increased by inserting into the T-DNA multiple genes encoding the enzyme which might be limiting in the pathway. Evidence for the possible importance of multi-copy transformants was seen in the *Arabidopsis* seeds transformed with the GA7 construct (Example 2), where the highest yielding DHA event had three T-DNAs inserted into the host genome. The multiple genes can be identical, or preferably are different variants that encode the same polypeptide, or are under the control of different promoters which have overlapping expression patterns. For example, increased expression could be achieved by expression of multiple Δ6-desaturase coding regions, even where the same protein is produced. In pJP3416-GA7-modF and pJP3416-GA7-modC, for instance, two versions of the *M. pusilla* Δ6-desaturase were present and expressed by different promoters. The coding sequences had different codon usage and therefore different nucleotide sequences, to reduce potential silencing or co-suppression effects but resulting in the production of the same protein.

Example 6. Activity of Seed-Specific Constructs in Somatic Embryos

In order to establish a rapid assay system which was predictive of expression of genetic constructs in seeds under the control of seed-specific promoters, a somatic embryo system was set up for *Brassica napus*. This used a vector to express the LEC2 transcription factor which is involved in initiation of somatic embryogenesis. As a demonstration, the binary vectors 35S:LEC2 and pJP107 (Petrie et al., 2010a and b) were introduced into *Agrobacterium tumefaciens* strain AGL1 via standard electroporation and the *Agrobacterium* transformants used to co-transform *Brassica napus* by co-cultivation. The T-DNA region of pJP107 contained genes encoding the *Isochrysis galbana* Δ9-elongase, *P. salina* Δ8-desaturase and *P. salina* Δ5-desaturase with each gene expressed by a seed-specific promoter. A control transformation used the 35S:LEC2 vector alone. 35S:LEC2 expression resulted in the generation of somatic embryos in tissue culture directly from the transformed *B. napus* callus tissue as described in Example 1.

Fatty acid analysis showed that the seed-specific genes on the T-DNA of the construct pJP107 were expressed in the transgenic somatic embryos in the presence of the co-transformed LEC2 gene and functioned to produce ARA ($20:4^{\Delta5,8,11,14}$) from LA and EPA ($20:5^{\Delta5,8,11,14,17}$) from ALA. The data for three co-transformed somatic embryos are shown in Table 18 and the fatty acid composition of each compared to the fatty acid composition of seed oil from *Brassica napus* seed which was transgenic for, and expressing, the T-DNA of pJP107 (Petrie et al., 2010a and b). Similar total percentages of ARA and the intermediate fatty acids EDA (20:2ω6) and DGLA (20:3ω6), as well as conversion efficiencies, were observed in somatic embryo tissue when compared with stably-transformed seed profiles. Similar results were observed in the fatty acid compositions of the stable $T_2$ transgenic seed and somatic embryos: ω6 fatty acids were at a level of 26.6% and 25.6% (on average), respectively, whilst ARA levels were found to be 9.7% and 10.6% (on average), respectively.

When 35S:LEC2 alone was introduced and the somatic embryos analysed in a time-course, the fatty acid profile was found to change to a more embryo-like profile with $18:3^{\Delta9,12,15}$ decreasing and $18:1^{\Delta9}$ increasing in an inversely correlated manner (FIG. 8). These results indicated that the somatic embryos were indeed becoming seed-like in character and the genes on the T-DNA from pJP107 were expressed. This demonstrated that the somatic embryo system allowed a rapid characterisation of transgenic seed-specific constructs in *B. napus* without requiring the full process of producing a transgenic plant and, from that, mature seed.

TABLE 18

Fatty acid composition of lipid obtained from *Brassica napus* somatic embryos generated by co-transforming pJP107 with 35S:LEC2, compared to the control untransformed (WT) and $T_2$ seeds transformed with pJP107. Individual enzymatic conversion efficiencies are shown in brackets after the relevant enzymatic steps. D9-Elo is Δ9-elongase, D8-Des is Δ8-desaturase and D5-Des is Δ5-desaturase.

| | WT | T2 pJP107 transgenic seed | LEC2: #45 | LEC2: #57 | LEC2: #58 |
|---|---|---|---|---|---|
| $18:1^{\Delta 9}$ | 57.2 | 45.7 | 3.8 | 2.5 | 1.9 |
| $18:2^{\Delta 9,12}$ | 19.1 | 8.7 | 10 | 10.6 | 10 |
| $18:3^{\Delta 9,12,15}$ | 10.2 | 4.1 | 22.5 | 27.5 | 24.2 |
| $20:2^{\Delta 11,14}$ | | 7.1 ± 1.9 (67% D9-elo) | 5.2 (61.8% D9-elo) | 3.7 (56.7% D9-elo) | 4.6 (61.8% D9-elo) |
| $20:3^{\Delta 8,11,14}$ | | 1.1 ± 0.2 (60% D8-des) | 0.4 (67% D8-des) | 0.2 (73% D8-des) | 0.4 (73% D8-des) |
| $20:4^{\Delta 5,8,11,14}$ | | 9.7 ± 0.9 (90% D5-des) | 10.6 (98% D5-des) | 10 (96% D5-des) | 11.2 (97% D5-des) |
| $20:3^{\Delta 11,14,17}$ | | 4.0 ± 0.8 | 9.9 | 5.5 | 7.3 |
| $20:4^{\Delta 8,11,14,17}$ | | 0.3 ± 0.1 | 0.4 | 0.3 | 0.4 |
| $20:5^{\Delta 5,8,11,14,17}$ | | 2.4 ± 0.2 | 7.6 | 6.4 | 7.9 |
| Total new | | 24.6 | 34.1 | 26.1 | 31.8 |

Using the same system to generate somatic embryos, *Brassica napus* cells were transformed separately with pJP3416-GA7-modB and pJP3416-GA7-modD. 42 embryos were obtained, 18 for modB and 24 for modD. Total lipid was extracted from the embryos and analysed for fatty acid composition. The embryos contained between 0% and up to 16.9% DHA (Table 19). The results with 0% DHA was presumed to be due to integration of only a partial T-DNA or an insertion into a transcriptionally silent region of the genome. The total Ω3 FA (including ALA) to total ω6 FA (including LA) ratio was found to be 2.3 for embryo #270 and 11.96 for embryo #284. The total ω6 FA (including LA) to total ω3 FA (including ALA) ratio was 0.08 for #284. The new ω6 FA (excluding LA) to new ω3 FA (excluding ALA) ratio was 0.03 for #284. Overall conversion efficiencies were calculated to be: (for embryos #270, #284) OA to EPA=14.0%, 29.8%; OA to DHA=9.7%, 24.2%; LA to EPA=15.4%, 30.7%; LA to DHA=10.7%, 25.0%; ALA to EPA=22.1%, 33.3%; ALA to DHA=15.3%, 27.0%. These efficiencies were similar, or greater than in the case of #284, to those observed for the $T_3$ pJP3416-GA7 *Arabidopsis* lines which indicated that the pJP3416-GA7-modB vector was capable of functioning well in *B. napus* cells. The SDA level was below 3.0%, indicating that the Δ6-elongase was performing even better than the GA7 construct. The individual enzyme efficiencies achieved in #284 were: Δ12-desaturase, 97.4%; ω3-desaturase, 92.3%; Δ6-desaturase, 38.2%; Δ6-elongase, 88.2%; Δ5-desaturase, 98.8%; Δ5-elongase, 94.1%; and Δ4-desaturase, 86.3%. Total saturates were 21.2%, total monounsaturates were 10.2%, total polyunsaturates were 68.6%.

The inventors believe this was the highest level of DHA achieved in *B. napus* cells to date, except for further data described below. This also demonstrated that the modification in pJP3416-GA7-modB relative to pJP3416-GA7 was effective in increasing the level of expression of the Δ6-desaturase gene. The binary vectors pJP3416-GA7, pJP3416-GA7-modA, pJP3416-GA7-modC, pJP3416-GA7-modD, pJP3416-GA7-modE and pJP3416-GA7-modF as described above are co-transformed with 35S:LEC2 to generate transformed *B. napus* somatic embryos. Up to 7.0% DHA was observed in modD embryos, 9.9% in modE embryos, 8.3% in modF embryos and 3.6% in a small number of modG embryos.

TABLE 19

Fatty acid composition of oil from *Brassica napus* somatic embryos #270 and #284 generated by co-transforming the seed-specific DHA acid construct pJP3416-GA7-modB with 35S:LEC2, and #286 and #289 (pJP3416-GA7-modD).

| | #270 | #284 | #286 | #289 |
|---|---|---|---|---|
| 14:0 | 0.3 | 0.2 | 0.2 | 0.2 |
| 16:0 | 14.0 | 15.7 | 17.2 | 16.6 |
| 16:1d9 | 0.7 | 0.4 | 0.8 | 0.8 |
| 16:3 | 0.5 | 0.6 | 1.1 | 1.3 |
| 18:0 | 2.6 | 2.4 | 2.5 | 2.5 |
| 18:1d9 | 6.6 | 1.8 | 1.5 | 1.1 |
| 18:1d11 | 6.3 | 6.8 | 6.5 | 6.7 |
| 18:2 | 18.9 | 4.5 | 10.0 | 9.8 |
| 18:3ω6 | 0.7 | 0.8 | 0.3 | 0.3 |
| 18:3ω3 | 33.0 | 37.2 | 42.0 | 41.5 |
| 20:0 | 0.9 | 0.9 | 0.8 | 0.8 |
| 18:4ω3 | 1.9 | 2.8 | 3.6 | 4.5 |
| 20:1d11 | 0.2 | 0.1 | 0.1 | 0.1 |
| 20:2ω6 | 0.1 | 0.1 | 0.1 | 0.2 |
| 20:3ω3 | 0.5 | 0.0 | 0.5 | 0.6 |
| 22:0 | 0.8 | 1.5 | 0.6 | 0.7 |
| 20:4ω3 | 0.2 | 0.9 | 0.7 | 0.7 |
| 20:5ω3 | 0.7 | 0.2 | 0.3 | 0.3 |
| 22:2ω6 | 0.0 | 1.2 | 0.0 | 0.0 |
| 22:3ω3 | 0.0 | 0.1 | 0.0 | 0.1 |
| 24:0 | 0.8 | 1.0 | 1.0 | 1.0 |
| 24:1 | 0.8 | 1.0 | 0.7 | 0.9 |
| 22:5ω3 | 2.4 | 2.7 | 3.2 | 3.0 |
| 22:6ω3 | 7.0 | 16.9 | 6.1 | 6.4 |

Example 7. Analysis of TAG from Transgenic *A. thaliana* Seeds Producing DHA

The positional distribution of DHA on the TAG from the transformed *A. thaliana* seed was determined by NMR. Total lipid was extracted from approximately 200 mg of seed by first crushing them under hexane before transferring the crushed seed to a glass tube containing 10 mL hexane. The tube was warmed at approximately 55° C. in a water bath and then vortexed and centrifuged. The hexane solution was removed and the procedure repeated with a further 4×10 mL. The extracts were combined, concentrated by rotary evaporation and the TAG in the extracted lipid purified away from polar lipids by passage through a short silica column using 20 mL of 7% diethyl ether in hexane. Acyl group positional distributions on the purified TAG were determined quantitatively as previously described (Petrie et al., 2010a and b).

The analysis showed that the majority of the DHA in the total seed oil was located at the sn-1/3 positions of TAG with little found at the sn-2 position (FIG. 9). This was in contrast to TAG from ARA producing seeds which demonstrated that 50% of the ARA (20:4Δ5,8,11,14) was located at the sn-2 position of transgenic canola oil whereas only 33% would be expected in a random distribution (Petrie et al., 2012).

Positional distribution of DHA in the TAG from the *B. napus* seeds transformed with pJP3416-GA7 or with the combination of pJP3115 and pJP3116 is determined by essentially the same method.

The total lipid from transgenic *A. thaliana* seeds was also analysed by triple quadrupole LC-MS to determine the major DHA-containing triacylglycerol (TAG) species (FIG. 10). The most abundant DHA-containing TAG species was found to be DHA-18:3-18:3 (TAG 58:12; nomenclature not descriptive of positional distribution) with the second-most abundant being DHA-18:3-18:2 (TAG 58:11). Tri-DHA TAG (TAG 66:18) was observed in total seed oil, albeit at low but detectable levels. Other major DHA-containing TAG species included DHA-34:3 (TAG 56:9), DHA-36:3 (TAG 58:9), DHA-36:4 (TAG 58:10), DHA-36:7 (TAG 58:13) and DHA-38:4 (TAG 60:10). The identities of the two major DHA-containing TAG were further confirmed by Q-TOF MS/MS.

Example 8. Predicting DHA Production in *B. nanus* Seeds

Efficient production of DHA in *Arabidopsis* seeds at a 15% level using the GA7 genetic construct was demonstrated in Example 2. The same construct in *Brassica napus* seeds produced only about 1.5% DHA in many (but not all) of the transformants, primarily due to the poor expression of the Δ6-desaturase gene of GA7 in this species (Example 4). Based on the realisation that modifications to the GA7 construct would overcome the Δ6-desaturase gene expression problem (see Example 5, as demonstrated in Example 6), calculations were performed to determine the likely fatty acid profile of *B. napus* transgenic seeds expressing the genes from a variant of pJP3416-GA7, where each transgene-encoded enzyme was performing as efficiently as was observed in *A. thaliana* with the GA7 construct. The predicted fatty acid compositions for three calculations (#1, #2, #3) are shown in Table 20. This was based on a wild-type (non-transformed) fatty acid composition for *B. napus* that included 59% oleic acid, 20% LA and 8% ALA. The three predicted partial fatty acid profiles shown in the lower half of the table were based on the conversion efficiencies for each enzymatic step shown in the upper half of the table. In prediction #2, a combination of Δ12-desaturation at 75% efficiency, Δ15-desaturation at 75%, Δ6-desaturation at 35%, Δ6-elongation at 80%, Δ5-desaturation at 90%, Δ5-elongation at 90% and Δ4-desaturation at 90% would result in the production of approximately 10% DHA in a typical canola transgenic seed. These efficiencies were all lower or about equal to the individual efficiencies seen in *Arabidopsis*, so prediction #2 represented a conservative estimate. The conversion efficiencies listed in #3 were approximations based on the efficient conversions seen in *A. thaliana* transformed with pJP3416-GA7. DHA was predicted to be produced at about 15% of the total fatty acid content in seedoil produced in *B. napus* seed, a result that mirrored the most efficient production levels observed in *A. thaliana*. Insertion of multiple T-DNAs in the homozygous state is expected to raise the DHA level to 20% in *B. napus*.

TABLE 20

Predicted fatty acid composition for selected fatty acids as a percentage of total fatty acid content in seedoil from *Brassica napus* transformed with a DHA pathway construct, based on observed enzymatic efficiencies in transgenic *Arabidopsis*. The enzymes are listed in order in the pathway for producing DHA from oleic acid. des = desaturase, elo = elongase. Predicted fatty acid compositions #1, #2 and #3 are based on the efficiencies in the upper half of the Table.

| Enzyme | #1 | #2 | #3 |
|---|---|---|---|
| d12-des | 70% | 75% | 80% |
| d15-des | 70% | 75% | 80% |
| d6-des (ω3) | 30% | 35% | 40% |
| d6-elo | 80% | 80% | 90% |
| d5-des | 80% | 90% | 90% |
| d5-elo | 80% | 90% | 90% |
| d4-des | 80% | 90% | 90% |

| Fatty acid | WT | #1 | #2 | #3 |
|---|---|---|---|---|
| 18:1d9 | 59% | 26% | 22% | 18% |
| 18:2ω6 | 20% | 19% | 17% | 14% |
| 18:3ω6 | | 1% | 2% | 3% |
| 18:3ω3 | 8% | 30% | 32% | 34% |
| 18:4ω3 | | 3% | 3% | 2% |
| 20:4ω3 | | 2% | 1% | 2% |
| 20:5ω3 | | 2% | 1% | 2% |
| 22:5ω3 | | 1% | 1% | 2% |
| 22:6ω3 | | 5% | 10% | 15% |

Example 9. Stable Expression of a Transgenic EPA Pathway in Plant Leaf

Binary Vector Construction

A binary vector, pORE04+11ABGBEC_Cowpea_EPA_insert (SEQ ID NO:8), was designed for introduction of a T-DNA into plants for the synthesis of EPA in leaf tissues. It contained chimeric genes encoding the enzymes: *M. pusilla* Δ6-desaturase (SEQ ID NO:16), *P. cordata* Δ6-elongase (SEQ ID NO:25) and *P. salina* Δ5-desaturase (SEQ ID NO:30), each under the control of the CaMV 35S and *A. thaliana* rubisco small subunit (SSU) promoters (FIG. 9). The binary vector was constructed by synthesising the region 199-10878 of SEQ ID 2 and cloning this into the recipient binary vector pORE04 (Coutu et al., 1997) at the BsiWI and KasI sites. The three fatty acid biosynthesis genes coded for the enzymes required to convert ALA, $18:3^{\Delta9,12,15}$ to EPA, $20:5^{\Delta5,8,11,14,17}$.

Transient Expression of EPA Construct in *N. benthamiana* Leaf Cells

To test that the construct was correct and would express the genes efficiently in leaf tissues, the chimeric vector pORE04+11ABGBEC_Cowpea_EPA_insert was introduced into *A. tumefaciens* strain AGL1. The chimeric vector 35S:p19 was also introduced into *A. tumefaciens* strain AGL1 as described in Example 1. Cells from cultures of these infiltrated into leaf tissue of *Nicotiana benthamiana* plants in a 24° C. growth room. Several direct comparisons were infiltrated with the samples being compared located on either side of the same leaf. Experiments were performed in triplicate. Following infiltration, the plants were grown for a further five days before leaf discs were taken for fatty acid profile analysis by GC as described in Example 1. GC analysis revealed that the EPA vector was functioning to produce EPA in *Nicotiana benthamiana* leaf (Table 21) with the highest level of EPA found to be 10.7% of total leaf lipids.

Nicotiana tabacum Stable Transformation

The chimeric vector pORE04+11ABGBEC_Cowpea_EPA_insert was used to stably transform *Nicotiana tabacum*. The vector was introduced into *A. tumefaciens* strain AGL1 via standard electroporation procedure. The transformed cells were grown on solid LB media supplemented with kanamycin (50 mg/L) and rifampicin (25 mg/L) and incubated at 28° C. for two days. A single colony was used to initiate fresh culture. Following 48 h vigorous culture, the cells were collected by centrifugation at 2,000×g and the supernatant was removed. The cells were resuspended in fresh solution containing 50% LB and 50% MS medium at the density of $OD_{600}$=0.5.

TABLE 21

Fatty acid composition of total leaf lipid from transgenic *Nicotiana benthamiana* (transient) and *Nicotiana tabacum* (stable primary transformant) events with the highest EPA levels from each experiment.

| | | *N. benthamiana* | *N. tabacum* |
|---|---|---|---|
| | 14:0 | 0.1 | 0.1 |
| | 16:0 | 18.5 | 17.8 |
| | 16:1w13t | 2.2 | 3.8 |
| | 16:1d9 | 0.1 | 0 |
| | 16:3 | 6.2 | 5.7 |
| | 18:0 | 3.4 | 3.2 |
| | 18:1d11 | 0.3 | 0.3 |
| | 20:0 | 0.5 | 0.5 |
| | 22:0 | 0.2 | 0.3 |
| | 24:0 | 0.1 | 0.4 |
| | 18:1 | 2.9 | 1.6 |
| | 18:2ω6 | 12.6 | 14.5 |
| Omega-6 | 18:3ω6 | 2.3 | 2.9 |
| | 20:2ω6 | 0.0 | 0.0 |
| | 20:3ω6 | 0.1 | 0.0 |
| | 20:4ω6 | 0.3 | 0.7 |
| Omega-3 | 18:3ω3 | 37.1 | 32.4 |
| | 18:4ω3 | 1.6 | 1.9 |
| | 20:3ω3 | 0.1 | 0.3 |
| | 20:4ω3 | 0.3 | 1.1 |
| | 20:5ω3 | 10.7 | 12.1 |
| | 22:5ω3 | 0.3 | 0.4 |

Leaf samples of *N. tabacum* cultivar W38 grown in vitro were excised and cut into square sections around 0.5-1 $cm^2$ in size with a sharp scalpel while immersed in the *A. tumefaciens* solution. The wounded *N. tabacum* leaf pieces submerged in *A. tumefaciens* were allowed to stand at room temperature for 10 minutes prior to being blotted dry on a sterile filter paper and transferred onto MS plates without supplement. Following a co-cultivation period of two days at 24° C., the explants were washed three times with sterile, liquid MS medium, then blotted dry with sterile filter paper and placed on the selective MS agar supplemented with 1.0 mg/L benzylaminopurine (BAP), 0.25 mg/L indoleacetic acid (IAA), 50 mg/L kanamycin and 250 mg/L cefotaxime. The plates were incubated at 24° C. for two weeks to allow for shoot development from the transformed *N. tabacum* leaf pieces.

To establish rooted transgenic plants in vitro, healthy green shoots were cut off and transferred into 200 mL tissue culture pots containing MS agar medium supplemented with 25 μg/L IAA, 50 mg/L kanamycin and 250 mg/L cefotaxime. Transgenic shoots were transferred to soil after rooting and grown to maturity in the glasshouse. Sufficiently large leaf discs were taken from 21 mature transgenic plants from and analysed for fatty acid profile as described in Example 1. All transgenic samples were found to contain EPA (Table 21) with the highest level of EPA in a hemizygous primary transformant found to be 12.1% of total leaf lipids. The leaf samples also contained a small amount (<0.5%) of DPA in their lipid, which resulted from elongation of the EPA by a low level of Δ5-elongation activity of the Δ6-elongase. The total ω3 FA (including ALA) to ω6 FA (including LA) ratio was found to be 2.7. Overall conversion efficiencies were calculated to be: OA to EPA=18.4%, LA to EPA=18.9%, ALA to EPA=25.9%. The production of 12.1% EPA is notable especially since the events were hemizygous primary transformants. The ALA to EPA efficiency in particular is close to that observed in stable seed transformants. It is worth noting that the construct did not contain a Δ12 or Δ15-desaturase to increase the conversion of OA and LA to ALA. Increased efficiencies would be expected with addition of these activities.

Seed from hemizygous transformants is being harvested and sown out to generate homozygous plants.

Seed set in the top EPA lines appeared normal and seed from lines #10 and #17 germinated well to establish the $T_2$ generation. The ratio of EPA to null (no EPA) lines indicated that event #28 was single-locus and the $T_3$ generation of this line was therefore also established. Fatty acid profile analysis of the $T_3$ population indicated that the transgenes were homozygous with no null events found and a stable amount of EPA. The average amount of EPA in the total leaf lipids in the entire $T_3$ population was found to be 9.4%+0.3 (Table 22).

TABLE 22

Representative fatty acid profiles of total leaf lipids from wildtype (WT) and independent transgenic or transiently-transformed lines (EPA). Species are *Nicotiana benthamiana* (transient transformation), *N. tabacum* (a stably transformed $T_3$ population), *Vigna unguiculata* (stably transformed $T_1$ event). The errors denote standard deviation of multiple samples. Apparent conversion efficiencies shown at the bottom describe the ω3 pathway and are calculated as the sum of product FAs/sum of substrate + product FAs.

| | | *N. benthamiana* | | *N. tabacum* | | *V. unguiculata* | |
|---|---|---|---|---|---|---|---|
| | | WT | EPA | WT | EPA | WT | EPA |
| | 16:0 | 17.7 ± 0.1 | 18.7 ± 0.2 | 15.0 ± 0.6 | 16.5 ± 0.5 | 18.0 | 18.2 ± 0.2 |
| | 16:1ω13t | 3.2 ± 0.1 | 2.2 ± 0 | 3.5 ± 0.1 | 3.0 ± 0.3 | 3.8 | 2.0 ± 0.9 |
| | 16:3 | 6.8 ± 0.1 | 6.2 ± 0.1 | 5.2 ± 0.5 | 5.4 ± 0.3 | — | — |
| | 18:0 | 3.1 ± 0 | 3.5 ± 0.3 | 2.2 ± 0.2 | 2.6 ± 0.1 | 1.8 | 4.5 ± 0.4 |
| | Minor | 1.4 ± 0 | 1.4 ± 0.1 | 3.1 ± 0.4 | 2.5 ± 0.3 | 2.3 | 2.5 ± 0.4 |
| | OA | 1.7 ± 0.1 | 2.7 ± 0.2 | 1.6 ± 0.3 | 2.1 ± 0.3 | 2.0 | 4.3 ± 1.3 |
| | LA | 12.5 ± 0.4 | 12.7 ± 0.2 | 17.0 ± 1.1 | 18.0 ± 0.9 | 13.4 | 18.2 ± 3.0 |
| | ALA | 53.3 ± 0.2 | 37.2 ± 0.2 | 52.2 ± 1.9 | 34.0 ± 0.6 | 58.6 | 38.2 ± 0 |
| Omega-6 | GLA | — | 2.3 ± 0.1 | — | 2.3 ± 0.3 | — | 0.6 ± 0.2 |
| | 20:2ω6 | 0.1 ± 0 | — | 0.1 ± 0 | 0.1 ± 0 | — | 0.1 ± 0 |

TABLE 22-continued

Representative fatty acid profiles of total leaf lipids from wildtype (WT) and independent transgenic or transiently-transformed lines (EPA). Species are *Nicotiana benthamiana* (transient transformation), *N. tabacum* (a stably transformed $T_3$ population), *Vigna unguiculata* (stably transformed $T_1$ event). The errors denote standard deviation of multiple samples. Apparent conversion efficiencies shown at the bottom describe the ω3 pathway and are calculated as the sum of product FAs/sum of substrate + product FAs.

| | | *N. benthamiana* | | *N. tabacum* | | *V. unguiculata* | |
|---|---|---|---|---|---|---|---|
| | | WT | EPA | WT | EPA | WT | EPA |
| | DGLA | 0.1 ± 0 | 0.1 ± 0 | — | — | — | — |
| | ARA | — | 0.3 ± 0 | — | 0.7 ± 0.1 | — | 0.2 ± 0 |
| Omega-3 | SDA | — | 1.5 ± 0.1 | — | 1.6 ± 0.1 | — | 1.5 ± 0 |
| | 20:3ω3 | 0.1 ± 0 | 0.1 ± 0 | 0.1 ± 0 | 0.3 ± 0 | 0.1 ± 0 | 1.5 ± 0.1 |
| | ETA | — | 0.4 ± 0 | — | 1.1 ± 0.1 | — | 0.3 ± 0.2 |
| | EPA | — | 10.2 ± 0.5 | — | 9.4 ± 0.3 | — | 7.1 ± 0.2 |
| | DPA | — | 0.3 ± 0.1 | — | 0.4 ± 0 | — | 0.8 ± 0.1 |
| Omega-3 | Δ6-des | | 25% | | 27% | | 20% |
| conversion | Δ6-elo | | 88% | | 87% | | 85% |
| | Δ5-des | | 97% | | 90% | | 96% |
| | Δ5-elo | | 3% | | 4% | | 10% |

Leaf samples of homozygous $T_3$ *N. tabacum* plants were subjected to further biochemical analysis. Total lipids were extracted from freeze-dried leaf material and fractionated by thin-layer chromatography (TLC). EPA was found to be present in *N. tabacum* TAG at up to 30.1% as well as in the polar lipids at 6.3% (Table 23). It was interesting to note that the EPA produced by the transgenic pathway was present in all of the lipid fractions assessed including TAG, MGDG, DGDG, SQDG, PG, PC, PE, PI and PS. All lipid pools contained low levels of novel intermediate or ω6 LC-PUFA fatty acids with the TAG ratio of novel ω3 to ω6 fatty acids being 10:1.

Stable Transformation of Cowpea

The chimeric vector pORE04+11ABGBEC-Cowpea-EPA-insert was transformed into cowpea (*Vigna unguiculata*) as follows. Mature dry seeds are the preferred starting material although seeds harvested from immature pods at maximum fresh weight of seeds can also be used. Dry seeds are threshed by hand to avoid cracking of seed coats and thus reduce contamination with microorganisms.

Dry seeds or immature pods are submerged in 70% ethanol for 2 min and then treated for 30 min in 20% commercial bleach (8.4 g/L sodium hypochlorite final concentration). The seeds are then washed several times with sterile water. Immature seeds are removed aseptically from pods while mature seeds are imbibed overnight. Two different explants can be used for multiple shoot production, ie the embryonic axis and the cotyledon itself, preferably the cotyledon with the bisected embryonic axis attached. The shoot and root tips are removed from the axis before wounding at the cotyledonary node, i.e. the point of attachment of the axis to the cotyledon. From an initial comparison of 19 cultivars and lines, it is now clear that most lines of cowpea can be transformed, the only caveat being that different tissue culture conditions need to be optimised for each line.

TABLE 23

Analysis of young and mature (young | mature) leaf lipid fractions triacylglycerol (TAG), total polar lipid (PL), monogalactosyldiacylglycerol (MGDG), digalactosyldiacylglycerol (DGDG), sulfoquinovosyldiacylglycerol (SQDG), phosphatidylglycerol (PG), phosphatidylcholine (PC), phosphatidylethanolamine (PE), phosphatidylinositol (PI) and phosphatidylserine (PS) from transgenic *Nicotiana tabacum* leaf samples. The errors denote standard deviation of multiple samples. Up to 30% EPA was observed in leaf TAG with EPA also distributed throughout the polar lipids. Differences between yound and mature leaf profiles were also observed for several fatty acids.

<table>
<tr><th></th><th></th><th></th><th></th><th colspan="3">Chloroplastidic</th><th colspan="5">Extra-chloroplastic</th></tr>
<tr><th></th><th></th><th>TAG</th><th>PL</th><th>MGDG</th><th>DGDG</th><th>SQDG</th><th>PG</th><th>PC</th><th>PE</th><th>PI</th><th>PS</th></tr>
<tr><td></td><td>16:0</td><td>9.8 | 18.3</td><td>17.8 | 23.8</td><td>3.1 | 3.2</td><td>18.0 | 16.8</td><td>48.3 | 50.0</td><td>21.0 | 26.4</td><td>22.9 | 30.0</td><td>24.0 | 30.5</td><td>38.7 | 43.3</td><td>31.9 | 36.2</td></tr>
<tr><td></td><td>16:1ω13t</td><td>0 | 0</td><td>3.4 | 3.1</td><td>0 | 0</td><td>0 | 0</td><td>0 | 0</td><td>34.0 | 32.0</td><td>0 | 0</td><td>0 | 0</td><td>0 | 0</td><td>1.0 | 1.4</td></tr>
<tr><td></td><td>16:3</td><td>0.2 | 0.9</td><td>5.6 | 6.4</td><td>14.8 | 19.4</td><td>1.2 | 1.8</td><td>0.4 | 1.2</td><td>0 | 0</td><td>0 | 0</td><td>0 | 0</td><td>0 | 0</td><td>0 | 0</td></tr>
<tr><td></td><td>18:0</td><td>7.3 | 3.7</td><td>2.9 | 3.9</td><td>1.1 | 1.2</td><td>3.5 | 3.5</td><td>5.4 | 7.1</td><td>4.7 | 6.9</td><td>6.6 | 9.1</td><td>11.0 | 11.4</td><td>9.4 | 9.3</td><td>20.2 | 19.4</td></tr>
<tr><td></td><td>Minor</td><td>2.5 | 2.9</td><td>1.4 | 2.4</td><td>1.0 | 0.4</td><td>0.8 | 1.0</td><td>1.9 | 2.1</td><td>1.0 | 1.5</td><td>1.4 | 1.6</td><td>4.9 | 4.1</td><td>6.5 | 7.7</td><td>2.5 | 3.7</td></tr>
<tr><td></td><td>OA</td><td>5.5 | 0.8</td><td>2.8 | 1.1</td><td>0.8 | 0.3</td><td>1.8 | 1.0</td><td>2.7 | 1.3</td><td>5.3 | 4.9</td><td>8.1 | 2.9</td><td>2.5 | 1.1</td><td>2.5 | 0.8</td><td>4.9 | 2.3</td></tr>
<tr><td></td><td>LA</td><td>27.7 | 13.7</td><td>17.3 | 12.3</td><td>8.0 | 6.8</td><td>9.2 | 10.5</td><td>11.7 | 8.9</td><td>17.1 | 13.2</td><td>39.2 | 25.2</td><td>37.9 | 28.5</td><td>22.0 | 13.4</td><td>24.4 | 17.1</td></tr>
<tr><td></td><td>ALA</td><td>9.6 | 17.2</td><td>39.0 | 34.4</td><td>60.3 | 51.9</td><td>61.2 | 58.6</td><td>23.7 | 21.5</td><td>15.7 | 14.1</td><td>7.3 | 18.2</td><td>5.5 | 10.5</td><td>7.6 | 10.0</td><td>4.8 | 10.5</td></tr>
<tr><td>Omega-6</td><td>GLA</td><td>2.5 | 3.0</td><td>1.5 | 2.1</td><td>2.1 | 3.0</td><td>1.1 | 1.8</td><td>1.4 | 1.9</td><td>0.2 | 0</td><td>1.8 | 2.5</td><td>1.7 | 2.7</td><td>0.8 | 0.9</td><td>1.1 | 1.3</td></tr>
<tr><td></td><td>20:2ω6</td><td>0 | 0</td><td>0.1 | 1.1</td><td>0 | 0</td><td>0 | 0</td><td>0 | 0</td><td>0 | 0</td><td>0 | 0</td><td>0.5 | 0</td><td>0 | 0</td><td>0 | 03</td></tr>
<tr><td></td><td>DGLA</td><td>0 | 0</td><td>0 | 0</td><td>0 | 0</td><td>0 | 0</td><td>0 | 0</td><td>0 | 0</td><td>0 | 0</td><td>0 | 0</td><td>0 | 0</td><td>0 | 0</td></tr>
<tr><td></td><td>ARA</td><td>0.6 | 0.9</td><td>0.1 | 0.2</td><td>0.2 | 0.4</td><td>0 | 0</td><td>0 | 0</td><td>0 | 0</td><td>0.3 | 0.3</td><td>0.4 | 0.4</td><td>0.4 | 0.6</td><td>0 | 0.2</td></tr>
<tr><td>Omega-3</td><td>SDA</td><td>4.0 | 7.6</td><td>1.6 | 2.0</td><td>1.7 | 2.0</td><td>0.6 | 0.7</td><td>1.2 | 1.2</td><td>0 | 0</td><td>2.1 | 3.6</td><td>1.3 | 2.0</td><td>0.8 | 0.8</td><td>0.9 | 1.6</td></tr>
<tr><td></td><td>20:3ω3</td><td>0.2 | 0.3</td><td>0.1 | 0.2</td><td>0 | 0</td><td>0.2 | 0.3</td><td>0 | 0</td><td>0 | 0.1</td><td>0.2 | 0</td><td>0.3 | 0.4</td><td>0 | 0</td><td>0 | 0</td></tr>
<tr><td></td><td>ETA</td><td>0.9 | 0.2</td><td>0.2 | 0.3</td><td>0 | 0.2</td><td>0 | 0.3</td><td>0 | 0</td><td>0 | 0</td><td>0.2 | 0</td><td>0.4 | 0.2</td><td>0.1 | 0.2</td><td>0 | 0</td></tr>
<tr><td></td><td>EPA</td><td>28.8 | 30.1</td><td>6.1 | 6.3</td><td>6.9 | 11.2</td><td>2.3 | 3.6</td><td>3.4 | 4.6</td><td>1.0 | 0.8</td><td>9.7 | 6.4</td><td>9.1 | 7.8</td><td>11.2 | 12.8</td><td>8.4 | 6.2</td></tr>
<tr><td></td><td>DPA</td><td>0.4 | 0.5</td><td>0 | 0</td><td>0 | 0.1</td><td>0 | 0</td><td>0 | 0</td><td>0 | 0</td><td>0.3 | 0.4</td><td>0.5 | 0.4</td><td>0 | 0.2</td><td>0 | 0.1</td></tr>
</table>

The selectable marker genes, bar or NptII can be used for transformation. The *Agrobacterium tumefaciens* strain AGL1 is the preferred strain for cowpea transformation. *Agrobacterium* containing the pORE04+11ABGBEC-Cowpea-EPA-insert vector is cultured overnight at 28° C. on a shaker at 180 rpm and the suspension is centrifuged at 8000 g for 10 min and re-suspended in Medium 1 (MS-basic medium diluted one in ten and containing 30 g/l sucrose, 20 mM 2-MES, adjusted to pH 5.6 prior to autoclaving, supplemented with filter sterilized MS-vitamins, 100 mg/l myo-inositol, 1.7 mg/l BAP, 0.25 mg/l $GA_3$, 0.2 mM acetosyringone, 250 mg/l Na-thiosulphate, 150 mg/l dithiothreitol and 0.4 g/l L-cysteine). The explants are submerged without shaking in the bacterial suspension for one hour following wounding in the meristematic regions with a scalpel. The treated explants are then blotted on sterile filter paper and transferred to solidified Medium 2 (Medium 1 containing 0.8% agar) overlayed with filter paper. After four days of co-cultivation, explants are transferred to Medium 3 (full strength MS medium, supplemented with 100 mg/l myo-inositol, 150 mg/l timentin, 30 g/L sucrose, 3 mM MES, 1.7 mg/L BAP, 5 mg/L PPT or 25-50 mg/L geneticin or 150 mg/L kanamycin, 0.8 g/L agar and adjusted to pH 5.6) for shoot initiation and selection of transformed shoots. After two weeks the first shoots are visible. The cotyledons are removed from the cotyledonary node region and cultures are transferred to fresh Medium 3. Cultures are transferred to fresh Medium 3 every two weeks following removal of dead and dying tissue. The first four subcultures are on kanamycin selection followed by alternating with geneticin and kanamycin. After six sub-cultures, the surviving green shoots are transferred to Medium 4 (Medium 3 without BAP but supplemented with 0.5 mg/l $GA_3$, 50 mg/l asparagine, 0.1 mg/l 3-indoleacetic acid (IAA), 150 mg/l timentin, and either PPT (10 mg/l), geneticin (50 mg/L) or kanamycin (150 mg/L), for shoot elongation. The shoots are sub-cultured every two weeks until single shoots are more than 1 cm long. These larger shoots are transferred from petri dishes to culture jars (80 mm height) for further growth under selection.

The majority of the regenerated shoots can be rooted in vitro, and the rooted plants are transferred to soil and allowed to establish in a high humidity chamber for 14-21 days before transfer to ambient greenhouse conditions.

To enhance gene transfer to cowpea, co-culture media is supplemented with thiol compounds. The addition of L-cysteine, dithiothreitol, and sodium thiosulfate reduces browning of wounded tissue.

Large numbers of cowpea explants can be processed in a simplified protocol. In brief, the protocol consists of the following steps: imbibition of sterilized mature seeds overnight in water, explants are derived by longitudinally bisecting the seed as a result of which, the split embryonic axis (with shoot and root apices removed) is still attached to the cotyledon, infection with *Agrobacterium* strain AGL1 aided by local wounding in the meristematic regions, co-culture on medium containing thiol compounds over 4 days at 25° C. in light, shoot initiation and elongation on medium containing selective agents, shoots are rooted in vitro and transferred to greenhouse conditions for flowering and seed setting, PCR or enzyme analysis of putative transgenic plants, and screening of next generation progeny by PCR or enzyme activity.

The progeny of transgenic $T_0$ plants are normal in phenotype. The transgenes are transmitted to the progeny and homozygous $T_2$ plants are identified by screening their $T_3$ progeny for enzyme activity or by PCR.

Using this transformation system about 10 transgenic plants are produced per 1000 explants, which is similar to the transformation frequency for other legumes. Depending on the cultivar or line to be transformed, this protocol requires 5-8 months from explant preparation to harvested $T_1$ seeds.

The transformation system is used to introduce the pORE04+11ABGBEC-Cowpea-EPA-insert binary vector into regenerated, transformed cowpea plants.

Modifications to the pORE04+11ABGBEC-Cowpea-EPA-insert binary vector are made in which genes encoding a Δ5-elongase and Δ4-desaturase are added, to provide a genetic construct which confers the ability to further convert the produced EPA to DHA. The construct is transformed into plants for production of DHA in vegetative tissues.

EPA was found to be present in the small number of events surviving chemical selection. The highest line contained 7.1%/0.2 EPA in the total leaf lipids. The rate of transformation was lower than usually experienced for cowpea with only six lines confirmed transgenic. It is, as yet, unknown what caused this effect although it is interesting to note that a larger than usual proportion of transgenic events contained incomplete T-DNA regions. It is possible that the large construct size contributed to the reduced efficiency. The apparent conversion efficiencies of each of the three transgenic enzymes were also calculated (Table 22). Results were broadly similar in all three species with good conversion to EPA after initial Δ6-desaturation of the native ALA. Some Δ5-elongation of EPA to DPA was noted despite the absence of a specific Δ5-elongase. The *P. cordata* Δ6-elongase has previously been shown to have a low level of Δ9-elongase activity (i.e. $18{:}3^{\Delta9,12,15}$ to $20{:}3^{\Delta11,14,17}$ conversion) although no Δ5-elongase activity was detected in a yeast assay.

Example 10. Testing Variations of Δ12-Desaturase Genes

Binary Vector Construction

In an attempt to test and compare a series of chimeric Δ12-desaturase genes, several binary vectors were made which were used to transform *A. thaliana* and *B. napus*. The binary vectors pJP3365, pJP3366, pJP3367, pJP3368 and pJP3369 each contained genes that encoded the *P. pastoris* ω3-desaturase (SEQ ID NO:12) and *M. pusilla* Δ6-desaturase (SEQ ID NO:16) enzymes, and one of a series of Δ12-desaturases. The Δ12-desaturases were from *Cryptococcus neoformans* (Accession No. XP_570226 in pJP3365), a version of the *Cryptococcus neoformans* Δ12-desaturase which contained a L151M mutation in an attempt to increase gene activity (in pJP3366), *Lachancea kluyveri* (SEQ ID NO: 10 in pJP3367), *Synechocystis* PCC6803 (Accession No. BAA18169 in pJP3368) and *Crepis palaestina* (Accession No. CAA76157, Lee et al., 1998, in pJP3369). The *Crepis* desaturase was the only plant desaturase in the series; the others were fungal enzymes. The vectors were made by inserting a plant codon-optimised protein coding region, except for the *Crepis palestina* Δ12-desaturase which was wildtype, for each Δ12-desaturase into the NotI site of the vector pJP3364 (see FIG. 12), in the orientation operably linked to the FP1 promoter to provide for seed-specific expression of each desaturase. The vector pJP3364 already contained the chimeric genes encoding the *P. pastoris* ω3-desaturase and *M. pusilla* Δ6-desaturase, each under the control of seed-specific promoters (FIG. 12). The combination of the three fatty acid biosynthesis enzymes, namely Δ12-desaturase, ω3-desaturase and Δ6-desaturase, was designed to assemble a pathway to convert oleic acid ($18:1^{\Delta 9}$) to SDA ($18:4^{\Delta 6,9,12,15}$). Assays were therefore carried out to measure the level of SDA production in transformed seeds.

*A. thaliana* and *B. Napus* Transformation and Analysis

The chimeric binary vectors were introduced into *A. tumefaciens* strain AGL1 and cells from cultures of the transformed *Agrobacterium* used to transform fad2 mutant *A. thaliana* plants using the floral dip method for transformation (Clough and Bent, 1998). After maturation, the $T_1$ seeds from the treated plants were harvested and plated on MS plates containing kanamycin for selection of plantlets having the NptII selectable marker gene present on the T-DNA of each chimeric vector. Surviving $T_1$ seedlings were transferred to soil. After allowing the plants to self-fertilise and growing them to maturity, the $T_2$ seeds from these plants were harvested and the fatty acid composition of seed lipids analysed by GC.

The chimeric vector pJP3367 was also used to transform *B. napus* by the method described in Example 4 to generate 12 transgenic events. SDA was found to range from 0.6% to 2.2% in pooled seed of the plants, and nine individual seeds from the transgenic plant with the highest SDA transgenic plant were analysed for fatty acid composition. Fatty acid composition data from such analysis is shown in Table 24.

The data showed that the Δ12-desaturase activity expressed from each of the T-DNAs in both *A. thaliana* and *B. napus* were unexpectedly low, providing an enzyme conversion efficiency of about 20% rather than the 70-80% seen with the same expression cassette in the GA7 construct (Examples 2 and 3). The reason for this relatively poor expression of the Δ12-desaturase genes from these vectors is unclear but could be related to the position of the genes in the construct as a whole.

In contrast, RT-PCR expression analysis demonstrated that the *P. pastoris* ω3-desaturase and *M. pusilla* Δ6-desaturase genes on the T-DNAs were relatively well expressed in the transformed seed. Table 24 includes the Δ6-desaturase conversion efficiencies in the transformed seeds, which ranged from about 11% to about 25% in the one *B. napus* transformed line. This was considerably higher than the Δ6-desaturase conversion efficiency of about 7% seen in the *B. napus* seeds transformed with the GA7 construct (Example 4).

TABLE 24

Fatty acid composition as a percentage of total fatty acids in seed oil from single seeds from a $T_1$ *Brassica napus* plant transformed with the T-DNA from pJP3367. SDA (18:4ω3) is shown in bold.

| Sample | CT110-3#1 | CT110-3#2 | CT110-3#3 | CT110-3#4 | CT110-3#5 | CT110-3#6 | CTI10-3#7 | CT110-3#8 | CT110-3#9 |
|---|---|---|---|---|---|---|---|---|---|
| C14:0 | 0.1 | 0.1 | 0.1 | 0.1 | 0.1 | 0.1 | 0.1 | 0.1 | 0.1 |
| C16:0 | 4.3 | 4.2 | 4.1 | 4.5 | 3.8 | 4.3 | 4.0 | 5.0 | 4.7 |
| 16:1d7 | 0.1 | 0.1 | 0.1 | 0.1 | 0.0 | 0.1 | 0.1 | 0.1 | 0.1 |
| C16:1d9 | 0.2 | 0.2 | 0.2 | 0.2 | 0.2 | 0.2 | 0.2 | 0.3 | 0.3 |
| 16:3 | 0.2 | 0.2 | 0.2 | 0.2 | 0.2 | 0.2 | 0.2 | 0.2 | 0.2 |
| C18:0 | 1.9 | 1.9 | 1.3 | 1.8 | 2.1 | 1.8 | 2.4 | 3.1 | 2.2 |
| C18:1 | 58.1 | 59.4 | 55.5 | 59.1 | 62.1 | 56.0 | 57.2 | 52.0 | 53.2 |
| C18:1d11 | 3.5 | 3.6 | 3.0 | 3.2 | 2.9 | 3.6 | 3.2 | 4.4 | 3.5 |
| C18:2 | 18.4 | 17.1 | 19.2 | 17.3 | 17.4 | 18.7 | 19.0 | 20.3 | 20.2 |
| C18:3ω6 | 0.3 | 0.2 | 0.3 | 0.2 | 0.2 | 0.2 | 0.2 | 0.2 | 0.3 |
| C18:3ω3 | 8.2 | 9.0 | 11.1 | 8.6 | 7.5 | 10.2 | 9.8 | 9.3 | 9.8 |
| C20:0 | 0.5 | 0.5 | 0.4 | 0.5 | 0.6 | 0.5 | 0.6 | 0.7 | 0.6 |
| **18:4ω3** | **2.4** | **2.0** | **2.8** | **2.5** | **1.4** | **2.6** | **1.3** | **2.4** | **3.2** |
| C20:1d11 | 1.1 | 1.1 | 1.2 | 1.2 | 1.2 | 1.1 | 1.2 | 1.1 | 1.1 |
| 20:1iso | 0.03 | 0.03 | 0.03 | 0.03 | 0.01 | 0.03 | 0.02 | 0.03 | 0.02 |
| C20:2ω6 | 0.1 | 0.1 | 0.1 | 0.1 | 0.1 | 0.1 | 0.1 | 0.1 | 0.1 |
| C22:0 | 0.2 | 0.2 | 0.2 | 0.2 | 0.2 | 0.2 | 0.2 | 0.3 | 0.2 |
| C24:0 | 0.1 | 0.1 | 0.1 | 0.2 | 0.1 | 0.1 | 0.2 | 0.3 | 0.2 |
| C24:1 | 0.1 | 0.1 | 0.1 | 0.1 | 0.1 | 0.1 | 0.1 | 0.1 | 0.1 |
| Δ6-des % | 22.9 | 17.9 | 20.3 | 22.8 | 15.8 | 20.2 | 11.7 | 20.9 | 24.9 |

Therefore, to take advantage of the higher Δ6-desaturase conversion efficiencies conferred by the T-DNA from pJP3367, *B. napus* plants transformed with this T-DNA were crossed to plants transformed with the T-DNA from pJP3416-GA7 (Example 4) to produce progeny plants and seeds carrying both T-DNAs. The fatty acid composition of oil extracted from F1 seeds is analysed by GC for DHA content and other fatty acid contents. Increased DHA levels are observed as a consequence of increased expression of the Δ6-desaturase. Plants which are homozygous for both T-DNAs are produced and should produce higher levels of DHA.

Example 11. Increasing Accumulation of Fatty Acids by Using Silencing Suppressor Proteins Binary Vector Construction WO 2010/057246 describes the use of silencing suppressor proteins (SSP) to increase transgene expression in the seeds of plants. To demonstrate that the use of such proteins could enhance and stabilise the production of LC-PUFA in oilseeds over several generations, several SSP were selected for testing, namely V2 (Accession No. GU178820.1), p19 (Accession No. AJ288943.1), p38 (Accession No. DQ286869.1) and $P0^{PE}$ (Accession No. L04573.1). $p^{19}$ is a suppressor protein from Tomato Bushy Stunt Virus (TBSV) which binds to 21 nucleotide long siRNAs before they guide Argonaute-guided cleavage of homologous RNA (Voinnet et al., 2003). V2, a suppressor protein from Tomato Yellow Leaf Curl Virus (TYLCV), binds to the plant protein SGS3 (Glick et al., 2008), a protein thought to be required for the production of double stranded RNA intermediates from ssRNA substrates (Beclin et al., 2002), or binds to dsRNA structures that have a 5' overhangs (Fukunaga et al., 2009). p38 is a suppressor protein from Turnip Crinkle Virus (TCV)

which interferes with plant silencing mechanisms by binding to Dicer and Argonaute proteins (Azevedo et al., 2010). P0 proteins such as $P0^{PE}$ and RPV-P0, from poleroviruses, target Argonaut proteins for enhanced degradation (Baumberger et al., 2007; Bortolamiol et al., 2007, Fusaro et al., 2012). Genetic constructs were therefore prepared for expression of these SSP in plant seed in combination with a set of fatty acid biosynthesis genes for production of ARA ($20{:}4^{\Delta5,8,11,14}$) from LA ($18{:}1^{\Delta9,12}$), as follows.

The fatty acid biosynthesis genes encoding the *Isochrysis galbana* Δ9-elongase and the *Pavlova salina* Δ8- and Δ5-desaturases and the bacterial selection marker were obtained on a single DNA fragment from pJP3010 by digestion with PmeI and AvrII giving rise to a 9560 bp fragment. The Δ9-elongase coding region on this fragment was joined to an *A. thaliana* FAE1 promoter (pAtFAE1) and a conlinin transcription termination/polyadenylation region (LuCnl2-3'). The desaturase coding regions were each joined to a truncated napin FP1 promoter (pBnFP1) and a nos3' transcription termination/polyadenylation region. The three fatty acid biosynthesis genes on this fragment were oriented and spaced in the same manner as in pJP107 (Petrie et al., 2012) and encoded the same proteins as pJP107. The DNA fragment also comprised a pFP1:GFiP:nos3' gene from pCW141 (see WO2010/057246) which encoded a green fluorescent protein (GFP). This screenable marker gene was used as a visual seed-specific marker, allowing simple and non-destructive identification and thereby selection of transgenic seed comprising and expressing the gene.

The PmeI-AvrII fragment was inserted into the PmeI-AvrII site of each of a series of five vectors, each containing a different SSP gene (WO2010/057246), resulting in the genetic constructs designated pFN045, pFN046, pFN047, pFN048 and pFN049. These comprise the genes encoding the SSPs $P0^{PE}$, p38, p19, 35S:V2 and V2, respectively. Each of the SSP genes was under the control of the FP1 promoter and ocs3' transcription termination/polyadenylation region except in the construct pFN048 where the V2 coding region was under the control of the constitutive CaMV 35S promoter. The SSP gene in each case was within the T-DNA region of the constructs, adjacent to the right border (RB) of the T-DNA. A sixth construct, pFN050 which lacked any SSP coding sequence, was made by digesting pFN045 with AhdI and NheI followed by recircularisation with DNA ligase to delete the FP1:$P0^{PE}$ gene. Each of the six constructs comprised an NptII selectable marker gene within the T-DNA and adjacent to the left border of the T-DNA. All of the constructs had an RK2 origin of replication for maintenance of the plasmids in *Agrobacterium.*

Transformation of *A. thaliana* with ARA Expression Vectors in Combination with SSPs To transform the genotype MC49 of *Arabidopsis*, which is a fad2/fae1 double mutant with high linoleic acid levels in its seed lipid, plants were treated by the floral dip method (Clough and Bent, 1998) with *A. tumefaciens* strain GV3101 separately transformed with each of the six constructs pFN045-pFN050. The treated plants were grown to maturity and $T_1$ seeds harvested from them were plated on MS media containing kanamycin to select for transformed $T_1$ plants. Screening for GFP expression in the seed was also used as a visual marker for transformed $T_1$ seeds. The seedlings which survived on MS/Kan plates or which were obtained from GFP-positive seeds were transferred to soil and grown to maturity for $T_2$ seeds. The numbers of transformed plants obtained were 5, 14, 32, 8, 23 and 24 for the transformations with pFN045, pFN046, pFN047, pFN048, pFN049 and pFN050, respectively. It was discovered at this stage that the gene encoding p38 in pFN046 was not functional and therefore plants transformed with the vector pFN046 were considered as additional controls i.e. essentially the same as for pFN050.

About 100 pooled $T_2$ seeds were taken from each transformed plant for fatty acid composition determination of seed lipid by FAME preparation and GC analysis. Six $T_2$ seedlings from each transgenic line were also grown to produce $T_3$ seeds.

The fatty acid composition in total lipid extracted from the $T_2$ seeds was determined using GC. The analysis showed a range of levels of ARA and the intermediates EDA (20:2ω6) and DGLA (20:3ω6) in the $T_2$ populations. The data for ARA is shown in FIGS. 13 and 14.

FIG. 13 shows a box-plot analysis of the ARA level in the lipid of the populations of the $T_2$ seeds. It was evident that the median ($50^{th}$ percentile) level of ARA in the populations of seeds which contained the FP1:p19 and 35S:V2 genes in addition to the ARA biosynthetic genes was significantly higher than in seeds containing the defective FP1:p38 gene or the control T-DNA from pFP050 which did not contain an SSP gene. The average ARA levels for seeds transformed with genes encoding p19 and V2 were greater than for seeds transformed with the p38 gene or those without an SSP (FIG. 14). One FP1:p19 and two FP1:V2 lines exhibited about 19%, 20% and 23% ARA, respectively. These were outliers and therefore not included in the calculations for the box-plot analysis. Fewer plants transformed with the T-DNAs comprising the genes FP1:$P0^{PE}$ and 35S:V2 survived compared to the other constructs; it is thought that these genes could be detrimental to plant health in the MC49 background.

Not only were the ARA levels significantly different among the constructs, the levels in seed lipid of the first intermediate of the pathway from LA to ARA, namely EDA (20:2ω6), was observed to be lower in lines expressing either V2 or p19 than in seeds lacking an SSP or containing the p38 construct (FIG. 15). In $T_3$ seeds, one population containing the construct expressing p19 exhibited 38% ARA as a percentage of total fatty acids in the seed lipid.

A range of transgenic $T_3$ lines were progressed to the $T_4$ generation. The levels of ARA in the $T_4$ seeds expressing V2 were either the same as compared to the previous generation, or indeed exhibited increased levels compared to their $T_3$ parents (FIG. 16). The lines expressing p19 showed more varied ARA levels. The ARA level was decreased in some lines while in others it was the same or increased compared to the T3 parents. In contrast, the lines containing the defective p38 gene or lacking an SSP generally showed a decline in the level of ARA and an increase in the levels of intermediates (FIG. 18). In some of these lines, ARA was reduced to about 1% and levels of EDA had increased to about 20%. The mean levels of ARA in $T_4$ seeds were higher for lines expressing p19 and V2 compared to lines expressing p38 or lacking an SSP (FIG. 17).

This experiment showed that the expression of an SSP in seeds of a transgenic plant along with additional genes for a LC-PUFA biosynthetic pathway not only increased the level of production of the desired fatty acid in the first generation of progeny, but also stabilised the level of the fatty acid production in later generations such as the third or fourth generation of progeny. The increased fatty acid production was accompanied by decreased levels of intermediate fatty acids in the biosynthetic pathway. The SSP's p19 and V2 expressed from seed-specific promoters were preferred. The construct designed to express the p38 SSP was defective and no useful data were obtained with this construct. The V2

SSP and its homologs from other viruses are thought to be particularly preferred because they allow maximal expression of the biosynthetic pathway genes and the simultaneous silencing of other genes in the same cells in the developing seed.

Example 12. Assaying Sterol Content and Composition in Oils

The phytosterols from 12 vegetable oil samples purchased from commercial sources in Australia were characterised by GC and GC-MS analysis as O-trimethylsilyl ether (OTMSi-ether) derivatives as described in Example 1. Sterols were identified by retention data, interpretation of mass spectra and comparison with literature and laboratory standard mass spectral data. The sterols were quantified by use of a 5β(H)-Cholan-24-ol internal standard. The basic phytosterol structure and the chemical structures of some of the identified sterols are shown in FIG. 19 and Table 25.

The vegetable oils analysed were from: sesame (*Sesamum indicum*), olive (*Olea europaea*), sunflower (*Helianthus annus*), castor (*Ricinus communis*), canola (*Brassica napus*), safflower (*Carthamus tinctorius*), peanut (*Arachis hypogaea*), flax (*Linum usitatissimum*) and soybean (*Glycine max*). In decreasing relative abundance, across all of the oil samples, the major phytosterols were: J-sitosterol (range 28-55% of total sterol content), Δ5-avenasterol (isofucosterol) (3-24%), campesterol (2-33%), Δ5-stigmasterol (0.7-18%), Δ7-stigmasterol (1-18%) and Δ7-avenasterol (0.1-5%). Several other minor sterols were identified, these were: cholesterol, brassicasterol, chalinasterol, campestanol and eburicol. Four C29:2 and two C30:2 sterols were also detected, but further research is required to complete identification of these minor components. In addition, several other unidentified sterols were present in some of the oils but due to their very low abundance, the mass spectra were not intense enough to enable identification of their structures.

The sterol contents expressed as mg/g of oil in decreasing amount were: canola oil (6.8 mg/g), sesame oil (5.8 mg/g), flax oil (4.8-5.2 mg/g), sunflower oil (3.7-4.1 mg/g), peanut oil (3.2 mg/g), safflower oil (3.0 mg/g), soybean oil (3.0 mg/g), olive oil (2.4 mg/g), castor oil (1.9 mg/g). The % sterol compositions and total sterol content are presented in Table 26.

TABLE 25

IUPAC/systematic names of identified sterols.

| Sterol No. | Common name(s) | IUPAC/Systematic name |
|---|---|---|
| 1 | cholesterol | cholest-5-en-3β-ol |
| 2 | brassicasterol | 24-methylcholesta-5,22E-dien-3β-ol |
| 3 | chalinasterol/24-methylene cholesterol | 24-methylcholesta-5,24(28)E-dien-3β-ol |
| 4 | campesterol/24-methyl-cholesterol | 24-methylcholest-5-en-3β-ol |
| 5 | campestanol/24-methyl-cholestanol | 24-methylcholestan-3β-ol |
| 7 | Δ5-stigmasterol | 24-ethylcholesta-5,22E-dien-3β-ol |
| 9 | ergost-7-en-3β-ol | 24-methylcholest-7-en-3β-ol |
| 11 | eburicol | 4,4,14-trimthylergosta-8,24(28)-dien-3β-ol |
| 12 | β-sitosterol/24-ethylcholesterol | 24-ethylcholest-5-en-3β-ol |
| 13 | D5-avenasterol/isofucosterol | 24-ethylcholesta-5,24(28)Z-dien-3β-ol |
| 19 | D7-stigmasterol/stigmast-7-en-3b-ol | 24-ethylcholest-7-en-3β-ol |
| 20 | D7-avenasterol | 24-ethylcholesta 7,24(28)-dien-3β-ol |

Among all the seed oil samples, the major phytosterol was generally 3-sitosterol (range 30-57% of total sterol content). There was a wide range amongst the oils in the proportions of the other major sterols: campesterol (2-17%), Δ5-stigmasterol (0.7-18%), Δ5-avenasterol (4-23%), Δ7-stigmasterol (1-18%). Oils from different species had a different sterol profile with some having quite distinctive profiles. In the case of canola oil, it had the highest proportion of campesterol (33.6%), while the other species samples generally had lower levels, e.g. up to 17% in peanut oil. Safflower oil had a relatively high proportion of Δ7-stigmasterol (18%), while this sterol was usually low in the other species oils, up to 9% in sunflower oil. Because they were distinctive for each species, sterol profiles can therefore be used to help in the identification of specific vegetable or plant oils and to check their genuineness or adulteration with other oils.

TABLE 26

Sterol content and composition of assayed plant oils.

| Sterol number* | Sterol common name | Sesame | Olive | Sunflower | Sunflower cold-pressed | Castor | Canola | Safflower | Safflower cold-pressed | Peanut | Flax (linseed) | Flax (linseed) | Soybean |
|---|---|---|---|---|---|---|---|---|---|---|---|---|---|
| 1 | cholesterol | 0.2 | 0.8 | 0.2 | 0.0 | 0.1 | 0.3 | 0.2 | 0.1 | 0.2 | 0.4 | 0.4 | 0.2 |
| 2 | brassicasterol | 0.1 | 0.0 | 0.0 | 0.0 | 0.3 | 0.1 | 0.0 | 0.0 | 0.0 | 0.2 | 0.2 | 0.0 |
| 3 | chalinasterol/24-methylene cholesterol | 1.5 | 0.1 | 0.3 | 0.1 | 1.1 | 2.4 | 0.2 | 0.1 | 0.9 | 1.5 | 1.4 | 0.8 |
| 4 | campesterol/24-methylcholesterol | 16.2 | 2.4 | 7.4 | 7.9 | 8.4 | 33.6 | 12.1 | 8.5 | 17.4 | 15.7 | 14.4 | 16.9 |
| 5 | campestanol/24-methylcholestanol | 0.7 | 0.3 | 0.3 | 0.1 | 0.9 | 0.2 | 0.8 | 0.8 | 0.3 | 0.2 | 0.2 | 0.7 |
| 6 | C29:2* | 0.0 | 0.0 | 0.1 | 0.2 | 0.0 | 0.1 | 0.5 | 0.5 | 0.0 | 1.2 | 1.3 | 0.1 |
| 7 | Δ5-stigmasterol | 6.4 | 1.2 | 7.4 | 7.2 | 18.6 | 0.7 | 7.0 | 4.6 | 6.9 | 5.1 | 5.8 | 17.6 |
| 8 | unknown | 0.5 | 1.3 | 0.7 | 0.6 | 0.8 | 0.7 | 0.7 | 1.3 | 0.4 | 0.7 | 0.6 | 1.3 |
| 9 | ergost-7-en-3β-ol | 0.1 | 0.1 | 1.9 | 1.8 | 0.2 | 0.4 | 2.7 | 4.0 | 1.4 | 1.4 | 1.4 | 1.0 |
| 10 | unknown | 0.0 | 1.3 | 0.9 | 0.8 | 1.2 | 0.9 | 1.8 | 0.7 | 1.2 | 0.7 | 0.5 | 0.7 |
| 11 | eburicol | 1.6 | 1.8 | 4.1 | 4.4 | 1.5 | 1.0 | 1.9 | 2.9 | 1.2 | 3.5 | 3.3 | 0.9 |

TABLE 26-continued

Sterol content and composition of assayed plant oils.

| Sterol number* | Sterol common name | Sesame | Olive | Sun-flower | Sun-flower cold-pressed | Castor | Canola | Saf-flower | Saf-flower cold-pressed | Peanut | Flax (linseed) | Flax (linseed) | Soy-bean |
|---|---|---|---|---|---|---|---|---|---|---|---|---|---|
| 12 | β-sitosterol/24-ethylcholesterol | 55.3 | 45.6 | 43.9 | 43.6 | 37.7 | 50.8 | 40.2 | 35.1 | 57.2 | 29.9 | 28.4 | 40.2 |
| 13 | Δ5-avenasterol/isofucosterol | 8.6 | 16.9 | 7.2 | 4.1 | 19.3 | 4.4 | 7.3 | 6.3 | 5.3 | 23.0 | 24.2 | 3.3 |
| 14 | triterpenoid alcohol | 0.0 | 2.4 | 0.9 | 1.1 | 0.0 | 0.0 | 1.6 | 1.9 | 0.0 | 0.0 | 0.0 | 0.9 |
| 15 | triterpenoid alcohol | 0.0 | 0.0 | 0.7 | 0.6 | 0.0 | 0.0 | 2.8 | 1.8 | 0.0 | 0.0 | 0.3 | 0.0 |
| 16 | C29:2* | 0.0 | 0.5 | 0.7 | 0.7 | 1.5 | 1.2 | 2.8 | 1.9 | 2.0 | 1.0 | 0.7 | 0.5 |
| 17 | C29:2* | 1.0 | 0.9 | 2.3 | 2.4 | 0.6 | 0.4 | 1.3 | 1.9 | 0.9 | 1.0 | 1.0 | 1.0 |
| 18 | C30:2* | 0.0 | 0.0 | 0.0 | 0.0 | 1.9 | 0.0 | 0.0 | 0.0 | 0.0 | 0.0 | 0.0 | 0.0 |
| 19 | Δ7-stigmasterol/stigmast-7-en-3β-ol | 2.2 | 7.1 | 9.3 | 10.9 | 2.3 | 0.9 | 10.5 | 18.3 | 1.1 | 7.9 | 8.7 | 5.6 |
| 20 | Δ7-avenasterol | 1.3 | 0.1 | 4.0 | 3.6 | 0.6 | 0.2 | 2.0 | 4.7 | 0.7 | 0.4 | 0.4 | 0.6 |
| 21 | unknown | 0.7 | 7.1 | 0.9 | 0.8 | 0.0 | 0.4 | 0.3 | 0.4 | 0.0 | 3.0 | 3.6 | 0.0 |
| 22 | unknown | 0.3 | 0.0 | 0.3 | 0.9 | 0.0 | 0.0 | 1.2 | 1.3 | 0.2 | 0.1 | 0.0 | 0.3 |
| 23 | unknown | 0.2 | 0.2 | 0.3 | 0.3 | 0.2 | 0.1 | 0.3 | 0.2 | 0.2 | 0.1 | 0.2 | 0.5 |
| 24 | unknown | 0.0 | 3.1 | 0.9 | 1.3 | 0.6 | 0.4 | 0.2 | 0.4 | 0.7 | 1.7 | 1.9 | 0.8 |
| 25 | unknown | 0.9 | 0.4 | 0.3 | 0.5 | 0.3 | 0.1 | 0.5 | 0.7 | 0.3 | 0.1 | 0.1 | 0.6 |
| 26 | C30:2 | 2.2 | 6.0 | 4.6 | 5.7 | 1.4 | 0.6 | 1.0 | 1.2 | 1.2 | 1.2 | 1.1 | 5.2 |
| 27 | unknown | 0.0 | 0.4 | 0.4 | 0.3 | 0.3 | 0.2 | 0.1 | 0.2 | 0.3 | 0.1 | 0.0 | 0.3 |
| | Sum | 100.0 | 100.0 | 100.0 | 100.0 | 100.0 | 100.0 | 100.0 | 100.0 | 100.0 | 100.0 | 100.0 | 100.0 |
| | Total sterol (mg/g oil) | 5.8 | 2.4 | 4.1 | 3.7 | 1.9 | 6.8 | 3.2 | 3.0 | 3.2 | 4.8 | 5.2 | 3.0 |

C29:2* and and C30:2* denotes a C29 sterol with two double bonds and a C30 sterol with two double bonds, respectively Two samples each of sunflower and safflower were compared, in each case one was produced by cold pressing of seeds and unrefined, while the other was not cold-pressed and refined. Although some differences were observed, the two sources of oils had similar sterol compositions and total sterol contents, suggesting that processing and refining had little effect on these two parameters. The sterol content among the samples varied three-fold and ranged from 1.9 mg/g to 6.8 mg/g. Canola oil had the highest and castor oil the lowest sterol content.

Example 13. Increasing Accumulation of DHA at the Sn-2 TAG Position

The present inventors considered that DHA accumulation at the sn-2 position in TAG could be increased by co-expressing an 1-acyl-glycerol-3-phosphate acyltransferase (LPAAT) together with the DHA biosynthesis pathway such as conferred by the GA7 construct or its variants. Preferred LPAATs are those which can act on polyunsaturated C22 fatty acyl-CoA as substrate, resulting in increased insertion of the polyunsaturated C22 chain at the sn-2 position of LPA to form PA, relative to the endogenous LPAAT. Cytoplasmic LPAAT enzymes often display varied substrate preferences, particularly where the species synthesises and accumulates unusual fatty acids in TAG. A LPAAT2 from *Limnanthes douglasii* was shown to use erucoyl-CoA (C22:1-CoA) as a substrate for PA synthesis, in contrast to an LPAAT1 from the same species that could not utilise the C22 substrate (Brown et al., 2002).

Known LPAATs were considered and a number were selected for testing, including some which were not expected to increase DHA incorporation at the sn-2 position, as controls. The known LPAATs included: *Arabidopsis thaliana* LPAAT2: (SEQ ID NO: 63, Accession No. ABG48392, Kim et al., 2005), *Limnanthes alba* LPAAT (SEQ ID NO: 64, Accession No. AAC49185, Lassner et al., 1995), *Saccharomyces cerevisiae* Slc1p (SEQ ID NO: 65, Accession No. NP_010231, Zou et al., 1997), *Mortierella alpina* LPAAT1 (SEQ ID NO: 67, Accession No. AED33305; U.S. Pat. No. 7,879,591) and *Brassica napus* LPAATs (SEQ ID NO: 68 and SEQ ID NO:69, Accession Nos ADC97479 and ADC97478 respectively). These were chosen to cover three groups of LPAAT enzymes: 1) control plant seed LPAATs with typically low activity on unusual long-chain polyunsaturated fatty acids (including the *Arabidopsis* and *Brassica* LPAATs), 2. LPAATs that had previously been demonstrated to act on C22 fatty acids by using C22 acyl-CoA as substrate, in this case erucic acid C22:1 (including the *Limnanthes* and *Saccharomyces* LPAATs), 3. LPAATs which the inventors considered likely to be able to utilise long-chain polyunsaturated fatty acids such as EPA and DHA as substrates (including the *Mortierella* LPAAT).

The *Arabidopsis* LPAAT2 (also designated LPAT2) is an endoplasmic reticulum-localised enzyme shown to have activity on C16 and C18 substrates, however activity on C20 or C22 substrates was not tested (Kim et al., 2005). *Limnanthes alba* LPAAT2 was demonstrated to insert a C22:1 acyl chain into the sn-2 position of PA, although the ability to use DHA as a substrate was not tested (Lassner et al., 1995). The selected *S. cerevisiae* LPAAT Slc1p was shown to have activity using 22:1-CoA in addition to 18:1-CoA as substrates, indicating a broad substrate specificity with respect to chain length (Zou et al., 1997). Again, DHA-CoA and other LC-PUFAs were not tested as substrates. The *Mortierella* LPAAT had previously been shown to have activity on EPA and DHA fatty acid substrates in transgenic *Yarrowia lipolytica* (U.S. Pat. No. 7,879,591).

Additional LPAATs were identified by the inventors. *Micromonas pusilla* is a microalga that produces and accumulates DHA in its oil, although the positional distribution of the DHA on TAG in this species has not been confirmed. The *Micromonas pusilla* LPAAT (SEQ ID NO: 66, Accession No. XP_002501997) was identified by searching the

*Micromonas pusilla* genomic sequence using the *Arabidopsis* LPAAT2 as a BLAST query sequence. Several candidate sequences emerged and the sequence XP_002501997 was synthesised for testing as a likely LPAAT enzyme with activity on C22 LC-PUFA. The *Ricinus communis* LPAAT was annotated as a putative LPAAT in the castor genome sequence (Chan et al., 2010). Four candidate LPAATs from the castor genome were synthesised and tested in crude leaf lysates of infiltrated *N. benthamiana* leaf tissue. The candidate sequence described here showed LPAAT activity.

A number of candidate LPAATs were aligned with known LPAATs on a phylogenetic tree (FIG. 20). It was noted that the putative *Micromonas* LPAAT did not cluster with the putative C22 LPAATs but was a divergent sequence.

As an initial test of various LPAATs for their ability to use DHA-CoA as substrate, chimeric genetic constructs are made for constitutive expression of exogenous LPAATs in *N. benthamiana* leaves, each under the control of the 35S promoter, as follows: 35S:Arath-LPAAT2 (*Arabidopsis* ER LPAAT); 35S:Ricco-LPAAT2; 35S:Limal-LPAAT (*Limnanthes alba* LPAAT); 35S:Sacce-Slc1p (*S. cerevisiae* LPAAT); 35S:Micpu-LPAAT (*Micromonas pusilla* LPAAT); 35S:Moral-LPAAT1 (*Mortierella alpina* LPAAT). A 35S:p19 construct lacking an exogenous LPAAT is used as a control in the experiment. Each of these constructs is introduced via *Agrobacterium* into *N. benthamiana* leaves as described in Example 1, and 5 days after infiltration, the treated leaf zones are excised and ground to make leaf lysates. Each lysate includes the exogenous LPAAT as well as the endogenous enzymes for synthesizing LPA. In vitro reactions are set up by separately adding $^{14}$C-labelled-OA, -LA or -ALA (C18 substrates), -ARA (a C20 substrate) and -DHA (C22) to the lysates, in triplicate. Reactions are incubated at 25° C. and the level of incorporation of the $^{14}$C labelled fatty acids into PA determined by TLC. The ability of each LPAAT to use DHA relative to ARA and the C18 fatty acids is calculated. The meadowfoam, *Mortierella* and *Saccharomyces* LPAATs were found to have activity on DHA substrate, with radiolabelled PA appearing for these but not the other LPAATs. All LPAATs were confirmed active by a similar oleic acid feed.

To test LPAAT activity in seeds, several of the protein coding sequences or LPAATs are inserted into a binary vector under the control of a conlinin (pLuCnl1) promoter. The resultant genetic constructs containing the chimeric genes, Cnl1:Arath-LPAAT (negative control), Cnl1:Limal-LPAAT, Cnl:Sacce-Slc1p, and Cnl1:Moral-LPAAT, respectively, are then used transform *B. napus* and *A. thaliana* plants to generate stable transformants expressing the LPAATs in a seed-specific manner. The transformed plants having the Cnl1:LPAAT constructs are crossed with plants expressing the GA7 construct or its variants (Example 5) which produce DHA in the seed to result in increased incorporation of DHA at the sn-2 position of TAG. The constructs are also used to transform *B. napus, C. sativa* and *A. thaliana* plants that already contain the GA7 construct and variants thereof (Examples 2 to 5) to generate progeny carrying both the parental and LPAAT genetic constructs. Increased incorporation of DHA at the sn-2 position of TAG is expected relative to the incorporation in plants lacking the LPAAT encoding transgenes. Oil content is also improved in the seeds, particularly for seeds producing higher levels of DHA, counteracting the trend seen in *Arabidopsis* seed as described in Example 2.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/660,392 filed 15 Jun. 2012, U.S. 61/663,344 filed 22 Jun. 2012, U.S. 61/697,676 filed 6 Sep. 2012 and U.S. 61/782,680 filed 14 Mar. 2013, the entire contents of each of which are incorporated herein by reference.

All publications discussed and/or referenced herein are incorporated herein in their entirety.

This application incorporates herein by reference U.S. 61/660,392 filed 15 Jun. 2012, U.S. 61/663,344 filed 22 Jun. 2012 and U.S. 61/697,676 filed 6 Sep. 2012.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abbadi et al. (2004) Plant Cell 16: 2734-2748.
Abbott et al. (1998) Science 282:2012-2018.
Abdullah et al. (1986) Biotech. 4:1087.
Agaba et al. (2004) Marine Biotechnol. (NY) 6:251-261.
Alvarez et al. (2000) Theor Appl Genet 100:319-327.
Armbrust et al. (2004) Science 306:79-86.
Attila Kereszt et al. (2007) Nature Protocols 2:948-952.
Baumberger et al. (2007) Curr. Biol. 17:1609-1614.
Baumlein et al. (1991) Mol. Gen. Genet. 225:459-467.
Baumlein et al. (1992) Plant J. 2:233-239.
Beaudoin et al. (2000) Proc. Natl. Acad. Sci. U.S.A. 97:6421-6426.
Beclin et al. (2002) Curr. Biol. 12:684-688.
Berberich. et al. (1998) Plant Mol. Biol. 36:297-306.
Bortolamiol et al. (2007) Curr. Biol. 17:1615-1621.
Broun et al. (1998) Plant J. 13:201-210.
Brown et al. (2002) Biochem J. 364:795-805.
Chapman et al. (2004) Gen. Dev. 18:1179-1186.
Chen et al. (2004) The Plant Cell 16:1302-1313.
Cheng et al. (1996) Plant Cell Rep. 15:653-657.
Cheng et al. (2010) Transgenic Res 19: 221-229.
Chikwamba et al. (2003) Proc. Natl. Acad. Sci. U.S.A. 100:11127-11132.
Cho et al. (1999a) J. Biol. Chem. 274:471-477.
Cho et al. (1999b) J. Biol. Chem. 274:37335-37339.
Clough and Bent (1998) Plant J. 16:735-43.
Coutu et al. (2007) Transgenic Res. 16: 771-781.
Damude et al. (2006). Proc Natl Acad Sci USA 103: 9446-9451.
Denic and Weissman (2007) Cell 130:663-677.
Domergue et al (2002) Eur. J. Biochem. 269:4105-4113.
Domergue et al. (2002) Eur. J. Biochem. 269:4105-4113.
Domergue et al. (2003) J. Biol. Chem. 278: 35115-35126.
Domergue et al. (2005) Biochem. J. 1 389: 483-490.
Dunoyer et al. (2004) The Plant Cell 16:1235-1250.
Ellerstrom et al. (1996) Plant Mol. Biol. 32:1019-1027.
Fujimura et al. (1985) Plant Tissue Culture Lett. 2:74.
Fukunaga (2009) EMBO J. 28:545-55.
Gamez et al. (2003) Food Res International 36: 721-727.
Garcia-Maroto et al. (2002) Lipids 37:417-426.
Girke et al. (1998) Plant J. 15:39-48.
Glick et al. (2008) Proc. Natl. Acad. Sci U.S.A. 105-157-161.

Grant et al. (1995) Plant Cell Rep. 15:254-258.
Hall et al. (1991) Proc. Natl. Acad. Sci. USA 88:9320-9324
Hamilton and Baulcombe (1999) Science 286:950-952.
Hamilton et al. (1997) Gene 200:107-16.
Harayama (1998). Trends Biotechnol. 16: 76-82.
Hastings et al. (2001) Proc. Natl. Acad. Sci. U.S.A. 98:14304-14309.
Hinchee et al. (1988) Biotechnology 6:915-922.
Hoffmann et al. (2008) J Biol. Chem. 283:22352-22362.
Hong et al. (2002a) Lipids 37:863-868.
Horiguchi et al. (1998) Plant Cell Physiol. 39:540-544.
Horvath et al. (2000) Proc. Natl. Acad. Sci. U.S.A. 97:1914-1919.
Huang et al. (1999) Lipids 34:649-659.
Inagaki et al. (2002) Biosci. Biotechnol. Biochem. 66:613-621.
Johansen and Carrington (2001) Plant Physiol. 126-930-938.
Kajikawa et al. (2004) Plant Mol. Biol. 54:335-52.
Kajikawa et al. (2006) FEBS Lett 580:149-154.
Kim et al. (2005) Plant Cell. 2005 1073-89.
Knutzon et al. (1998) J. Biol Chem. 273:29360-6.
Koziel et al. (1996) Plant Mol. Biol. 32:393-405.
Lassner (1995) Plant Physiol. 109:1389-94.
Leonard et al. (2000) Biochem. J. 347:719-724.
Leonard et al. (2000b) Biochem. J. 350:765-770.
Leonard et al. (2002) Lipids 37:733-740.
Lewsey et al. (2007) Plant J. 50:240-252.
Lo et al. (2003) Genome Res. 13:455-466.
Lu and Kang (2008) Plant Cell Rep. 27:273-8.
Mallory et al. (2002) Nat. Biotech. 20:622-625.
Marangoni et al. (1995) Trends in Food Sci. Technol. 6: 329-335.
Meesapyodsuk et al. (2007) J Biol Chem 282: 20191-20199.
Meng et al. (2008) J. Gen. Virol. 89:2349-2358.
Meyer et al. (2003) Biochem. 42:9779-9788.
Meyer et al. (2004) Lipid Res 45:1899-1909.
Michaelson et al. (1998a) J. Biol. Chem. 273:19055-19059.
Michaelson et al. (1998b) FEBS Lett. 439:215-218.
Murashige and Skoog (1962) Physiologia Plantarum 15:473-497.
Napier et al. (1998) Biochem. J. 330:611-614.
Needleman and Wunsch (1970) J. Mol. Biol. 48:443-453.
Niedz et al. (1995) Plant Cell Reports 14:403.
Ow et al. (1986) Science 234:856-859.
Parker-Barnes et al. (2000) Proc. Natl. Acad. Sci. USA 97:8284-8289.
Pereira et al. (2004a) Biochem. J. 378:665-671.
Pereira et al. (2004b) Biochem. J. 384:357-366.
Perrin et al. (2000) Mol Breed 6:345-352.
Petrie et al. (2010a) Metab. Eng. 12:233-240.
Petrie et al. (2010b) Plant Methods 11:6:8.
Petrie et al. (2012) Transgenic Res. 21:139-147.
Potenza et al. (2004) In Vitro Cell Dev Biol—Plant 40:1-22.
Prasher et al (1985) Biochem. Biophys. Res. Commun. 127:31-36.
Qi et al. (2002) FEBS Lett. 510:159-165.
Qi et al. (2004) Nat. Biotech. 22: 739-745.
Qiu et al. (2001) J. Biol. Chem. 276:31561-31566.
Reddy and Thomas (1996) Nat. Biotech. 14:639-642.
Reddy et al. (1993) Plant Mol. Biol. 22:293-300.
Robert et al. (2005) Func. Plant Biol. 32:473-479.
Robert et al. (2009) Marine Biotech 11:410-418.
Ruiz-Lopez et al. (2012) Transgenic Res. 21:139-147.
Saha et al. (2006) Plant Physiol. 141:1533-1543.
Saito et al. (2000) Eur. J. Biochem. 267:1813-1818.
Sakuradani et al. (1999) Gene 238:445-453.
Sato et al. (2004) Crop Sci. 44: 646-652.
Sakuradani et al. (2005) Appl. Microbiol. Biotechnol. 66:648-654.
Sayanova et al. (2006) J Biol Chem 281: 36533-36541.
Sayanova et al. (1997) Proc. Natl. Acad. Sci. U.S.A. 94:4211-4216.
Sayanova et al. (2003) FEBS Lett. 542:100-104.
Sayanova et al. (2006) Planta 224:1269-1277.
Sayanova et al. (2007) Plant Physiol 144:455-467.
Singh et al. (2005) Curr. Opin. in Plant Biol. 8:197-203.
Speranza et al. (2012) Process Biochemistry (In Press).
Sperling et al. (2000) Eur. J. Biochem. 267:3801-3811.
Sperling et al. (2001) Arch. Biochm. Biophys. 388:293-8.
Sprecher et al. (1995) J. Lipid Res. 36:2471-2477.
Spychalla et al. (1997) Proc. Natl. Acad. Sci. U.S.A. 94:1142-1147.
Stalker et al. (1998) J. Biol. Chem. 263:6310-6314.
Thillet et al. (1988) J. Biol. Chem 263:12500-12508.
Tonon et al. (2003) FEBS Lett. 553:440-444.
Toriyama et al. (1986) Theor. Appl. Genet. 205:34.
Trautwein (2001) European J. Lipid Sci. and Tech. 103:45-55.
Tvrdik (2000) J. Cell Biol. 149:707-718.
Venegas-Caleron et al. (2010) Prog. Lipid Res. 49:108-119.
Voinnet et al. (2003) Plant J. 33:949-956.
Wallis and Browse (1999) Arch. Biochem. Biophys. 365: 307-316.
Watts and Browse (1999b) Arch. Biochem. Biophys. 362: 175-182.
Weiss et al. (2003) Int. J. Med. Microbiol. 293:95:106.
Whitney et al. (2003) Planta 217:983-992.
Winans (1988) J. Bacteriol. 170:4047-54.
Wood (2009) Plant Biotechnol J. 7:914-24.
Wu et al. (2005) Nat. Biotech. 23:1013-1017.
Yang et al. (2003) Planta 216:597-603.
Zank et al. (2002) Plant J. 31:255-268.
Zank et al. (2005) WO 2005/012316
Zhang et al. (2004) FEBS Lett. 556:81-85.
Zhang et al. (2006) 20:3255-3268.
Zhang et al. (2007a) FEBS Letters 581: 315-319.
Zhang et al. (2008) Yeast 25: 21-27.
Zhou et al. (2007) Phytochem. 68:785-796.
Zhou et al. (2008) Insect Mol Biol 17: 667-676.
Zou et al. (1997) Plant Cell. 9:909-23.

What is claimed is:

1. A process for producing ethyl esters of polyunsaturated fatty acids, the process comprising transesterifying polyunsaturated fatty acids in triacylglycerols (TAG) in oil extracted from *Brassica napus* seeds or *Arabidopsis thaliana* seeds, wherein the oil comprises a total fatty acid content which comprises a) a total monounsaturated fatty acid content which comprises oleic acid, b) a total saturated fatty acid content which comprises palmitic acid, or palmitic acid and myristic acid (C14:0), c) a total ω6 fatty acid content which comprises linoleic acid (LA) and γ-linolenic acid (GLA), d) a total ω3 fatty acid content which comprises α-linolenic acid (ALA), docosahexaenoic acid (DHA), stearidonic acid (SDA), eicosapentaenoic acid (EPA), docosapentaenoic acid (DPA) and eicosatetraenoic acid (ETA), wherein i) DHA is present in the extracted oil at a level of about 3% of the total fatty acid content, wherein at least 70% of the DHA which is esterified in the form of triacylglycerols (TAG) is esterified at the sn-1 or sn-3 position of the TAG, ii) palmitic acid is present in the extracted oil at a level of between 2% and 15% of the total fatty acid content, iii) oleic acid is present in the extracted oil at a level of between 1% and 30% of the total fatty acid content, iv) LA is present in the extracted oil at a level of between 4% and 35% of the total fatty acid content, v) GLA is present in the extracted oil at a level of less than 4% of the total fatty acid content, vi) ALA is present in the extracted oil at a level of between 4% and 40% of the total fatty acid content, vii) the total saturated fatty acid content of the extracted oil is between 4% and 25% of the total fatty acid content, viii) the ratio of the total ω6 fatty acid content to the total ω3 fatty acid content of the extracted oil is between 0.1 and 3.0, ix) myristic acid, if present, is present at a level of less than 1% of the total fatty acid content, and x) eicosatrienoic acid (ETrA), if present, is present at a level of less than 4% of the total fatty acid content, thereby producing the ethyl esters.

2. The process of claim 1, wherein γ-linolenic acid (GLA) is present in the extracted oil at a level of less than 3% of the total fatty acid content.

3. The process of claim 1, wherein oleic acid is present in the extracted oil at a level of between 6% and 30% of the total fatty acid content.

4. The process of claim 1, wherein the total saturated fatty acid content of the extracted oil is between 6% and 20% of the total fatty acid content.

5. The process of claim 1, wherein the extracted oil comprises new ω3 fatty acids in the total ω3 fatty acid content and new ω6 fatty acids in the total ω6 fatty acid content, wherein the ratio of the new ω6 fatty acids to the new ω3 fatty acids in the extracted canola oil is between 0.1 and 1.

6. The process of claim 1, wherein the extracted oil comprises tri-DHA TAG (TAG 66:18).

7. The process of claim 1, wherein at least 80% of the DHA esterified in the form of TAG in the extracted oil is at the sn-1 or sn-3 position of the TAG.

8. A process for producing ethyl esters of polyunsaturated fatty acids, the process comprising transesterifying polyunsaturated fatty acids in triacylglycerols (TAG) in oil extracted from *Brassica napus* seeds or *Arabidopsis thaliana* seeds, wherein the oil comprises a total fatty acid content which comprises a) a total monounsaturated fatty acid content which comprises oleic acid, b) a total saturated fatty acid content which comprises palmitic acid, or palmitic acid and myristic acid (C14:0), c) a total ω6 fatty acid content which comprises linoleic acid (LA) and γ-linolenic acid (GLA), d) a total ω3 fatty acid content which comprises α-linolenic acid (ALA), docosahexaenoic acid (DHA), stearidonic acid (SDA), eicosapentaenoic acid (EPA), docosapentaenoic acid (DPA) and eicosatetraenoic acid (ETA), wherein i) DHA is present in the extracted oil at a level of about 4% of the total fatty acid content, wherein at least 70% of the DHA which is esterified in the form of triacylglycerols (TAG) is esterified at the sn-1 or sn-3 position of the TAG, ii) palmitic acid is present in the extracted oil at a level of between 2% and 16% of the total fatty acid content, iii) oleic acid is present in the extracted oil at a level of between 1% and 30% of the total fatty acid content, iv) LA is present in the extracted oil at a level of between 4% and 35% of the total fatty acid content, v) GLA is present in the extracted oil at a level of less than 4% of the total fatty acid content, vi) ALA is present in the extracted oil at a level of between 4% and 40% of the total fatty acid content, vii) the total saturated fatty acid content of the extracted oil is between 4% and 250 of the total fatty acid content, viii) the ratio of the total ω6 fatty acid content to the total ω3 fatty acid content of the extracted oil is between 0.1 and 3.0, ix) myristic acid, if present, is present at a level of less than 1% of the total fatty acid content, and x) eicosatrienoic acid (ETrA), if present, is present at a level of less than 4% of the total fatty acid content, thereby producing the ethyl esters.

9. The process of claim 8, wherein γ-linolenic acid (GLA) is present in the extracted oil at a level of less than 3% of the total fatty acid content.

10. The process of claim 8, wherein oleic acid is present in the extracted oil at a level of between 6% and 30% of the total fatty acid content.

11. The process of claim 8, wherein the total saturated fatty acid content of the extracted oil is between 6% and 20% of the total fatty acid content.

12. The process of claim 8, wherein the extracted oil comprises new ω3 fatty acids in the total ω3 fatty acid content and new ω6 fatty acids in the total ω6 fatty acid content, wherein the ratio of the new ω6 fatty acids to the new ω3 fatty acids in the extracted oil is between 0.1 and 1.

13. The process of claim 8, wherein the extracted oil comprises tri-DHA TAG (TAG 66:18).

14. The process of claim 8, wherein at least 80% of the DHA esterified in the form of TAG in the extracted oil is at the sn-1 or sn-3 position of the TAG.

15. A process for producing ethyl esters of polyunsaturated fatty acids, the process comprising transesterifying polyunsaturated fatty acids in triacylglycerols (TAG) in oil extracted from *Brassica napus* seeds or *Arabidopsis thaliana* seeds, wherein the oil comprises a total fatty acid content which comprises a) a total monounsaturated fatty acid content which comprises oleic acid, b) a total saturated fatty acid content which comprises palmitic acid, or palmitic acid and myristic acid (C14:0), c) a total ω6 fatty acid content which comprises linoleic acid (LA) and 7-linolenic acid (GLA), d) a total ω3 fatty acid content which comprises α-linolenic acid (ALA), docosahexaenoic acid (DHA), stearidonic acid (SDA), eicosapentaenoic acid (EPA), docosapentaenoic acid (DPA) and eicosatetraenoic acid (ETA), wherein i) DHA is present in the extracted oil at a level of about 5% of the total fatty acid content, wherein at least 70% of the DHA which is esterified in the form of triacylglycerols (TAG) is esterified at the sn-1 or sn-3 position of the TAG, ii) palmitic acid is present in the extracted oil at a level of between 2% and 16% of the total fatty acid content, iii) oleic acid is present in the extracted oil at a level of between 1% and 30% of the total fatty acid content, iv) LA is present in the extracted oil at a level of between 4% and 35% of the total fatty acid content, v) GLA is present in the extracted oil at a level of less than 4% of the total fatty acid content, vi) ALA is present in the extracted oil at a level of between 4% and 40% of the total fatty acid content, vii) the total saturated fatty acid content of the extracted oil is between 4% and 25% of the total fatty acid content, viii) the ratio of the total ω6 fatty acid content to the total ω3 fatty acid content of the extracted oil is between 0.1 and 3.0, ix) myristic acid, if present, is present at a level of less than 1% of the total fatty acid content, and x) eicosatrienoic acid (ETrA), if present, is present at a level of less than 4% of the total fatty acid content, thereby producing the ethyl esters.

16. The process of claim 15, wherein γ-linolenic acid (GLA) is present in the extracted oil at a level of less than 3% of the total fatty acid content.

17. The process of claim 15, wherein oleic acid is present in the extracted oil at a level of between 6% and 30% of the total fatty acid content.

18. The process of claim 15, wherein the total saturated fatty acid content of the extracted oil is between 6% and 20% of the total fatty acid content.

19. The process of claim 15, wherein the extracted oil comprises new ω3 fatty acids in the total ω3 fatty acid content and new ω6 fatty acids in the total ω6 fatty acid content, wherein the ratio of the new ω6 fatty acids to the new ω3 fatty acids in the extracted oil is between 0.1 and 1.

20. The process of claim 15, wherein the extracted oil comprises tri-DHA TAG (TAG 66:18).

21. The process of claim 15, wherein at least 80% of the DHA esterified in the form of TAG in the extracted oil is at the sn-1 or sn-3 position of the TAG.

22. A process for producing ethyl esters of polyunsaturated fatty acids, the process comprising transesterifying polyunsaturated fatty acids in triacylglycerols (TAG) in oil extracted from *Brassica napus* seeds or *Arabidopsis thaliana* seeds, wherein the oil comprises a total fatty acid content which comprises a) a total monounsaturated fatty acid content which comprises oleic acid, b) a total saturated fatty acid content which comprises palmitic acid, or palmitic acid and myristic acid (C14:0), c) a total ω6 fatty acid content which comprises linoleic acid (LA) and γ-linolenic acid (GLA), d) a total ω3 fatty acid content which comprises α-linolenic acid (ALA), docosahexaenoic acid (DHA), stearidonic acid (SDA), eicosapentaenoic acid (EPA), docosapentaenoic acid (DPA) and eicosatetraenoic acid (ETA), wherein i) DHA is present in the extracted oil at a level of about 6% of the total fatty acid content, wherein at least 70% of the DHA which is esterified in the form of triacylglycerols (TAG) is esterified at the sn-1 or sn-3 position of the TAG, ii) palmitic acid is present in the extracted oil at a level of between 2% and 16% of the total fatty acid content, iii) oleic acid is present in the extracted oil at a level of between 1% and 30% of the total fatty acid content, iv) LA is present in the extracted oil at a level of between 4% and 35% of the total fatty acid content, v) GLA is present in the extracted oil at a level of less than 4% of the total fatty acid content, vi) ALA is present in the extracted oil at a level of between 4% and 40% of the total fatty acid content, vii) the total saturated fatty acid content of the extracted oil is between 4% and 25% of the total fatty acid content, viii) the ratio of the total ω6 fatty acid content to the total ω3 fatty acid content of the extracted oil is between 0.1 and 3.0, ix) myristic acid, if present, is present at a level of less than 1% of the total fatty acid content, and x) eicosatrienoic acid (ETrA), if present, is present at a level of less than 4% of the total fatty acid content, thereby producing the ethyl esters.

23. The process of claim 22, wherein γ-linolenic acid (GLA) is present in the extracted oil at a level of less than 3% of the total fatty acid content.

24. The process of claim 22, wherein oleic acid is present in the extracted oil at a level of between 6% and 30% of the total fatty acid content.

25. The process of claim 22, wherein the total saturated fatty acid content of the extracted oil is between 6% and 20% of the total fatty acid content.

26. The process of claim 22, wherein the extracted oil comprises new ω3 fatty acids in the total ω3 fatty acid content and new ω6 fatty acids in the total ω6 fatty acid content, wherein the ratio of the new ω6 fatty acids to the new ω3 fatty acids in the extracted oil is between 0.1 and 1.

27. The process of claim 22, wherein the extracted oil comprises tri-DHA TAG (TAG 66:18).

28. The process of claim 22, wherein at least 80% of the DHA esterified in the form of TAG in the extracted oil is at the sn-1 or sn-3 position of the TAG.

* * * * *

SEQUENCE LISTING

<160> NUMBER OF SEQ ID NOS: 72

<210> SEQ ID NO 1
<211> LENGTH: 21527
<212> TYPE: DNA
<213> ORGANISM: Artificial Sequence
<220> FEATURE:
<223> OTHER INFORMATION: pJP3416-GA7 nucleotide sequence.

-continued

<400> SEQUENCE: 1

```
tcctgtggtt ggcatgcaca tacaaatgga cgaacggata aacctttca cgccctttta     60
aatatccgat tattctaata aacgctcttt tctcttaggt ttacccgcca atatatcctg    120
tcaaacactg atagtttaaa ctgaaggcgg gaaacgacaa tctgctagtg gatctcccag    180
tcacgacgtt gtaaaacggg cgccccgcgg aaagcttgcg gccgcccgat ctagtaacat    240
agatgacacc gcgcgcgata atttatccta gtttgcgcgc tatattttgt tttctatcgc    300
gtattaaatg tataattgcg ggactctaat cataaaaacc catctcataa ataacgtcat    360
gcattacatg ttaattatta cgtgcttaac gtaattcaac agaaattata tgataatcat    420
cgcaagaccg gcaacaggat tcaatcttaa gaaactttat tgccaaatgt ttgaacgatc    480
ggcgcgcctc attagtgagc cttctcagcc tttccgttaa cgtagtagtg ctgtcccacc    540
ttatcaaggt tagagaaagt agccttccaa gcaccgtagt aagagagcac cttgtagttg    600
agtccccact tcttagcgaa aggaacgaat cttctgctaa cctcaggctg tctgaattga    660
ggcatatcag ggaagaggtg gtggataacc tgacagttaa ggtatcccat aagccagttc    720
acgtatcctc tagaaggatc gatatcaacg gtgtgatcaa cagcgtagtt aacccaagaa    780
aggtgcttat cagatggaac aacagggagg tgagtatgag aagtagagaa gtgagcgaaa    840
aggtacatgt aagcgatcca gtttccgaaa gtgaaccacc agtaagcaac aggccaagag    900
tatccagtag caagcttgat aacagcggtt ctaacaacat gagaaacgag catccaagaa    960
gcctcttcgt agttcttctt acggagaact tgtctagggt ggagaacgta gatccagaaa   1020
gcttgaacaa gaagtccaga ggtaacagga acgaaagtcc aagcttgaag tctagcccaa   1080
gctctagaga atcctctagg tctgttatcc tcaacagcag tgttgaagaa agccacagca   1140
ggagtggtat caagatccat atcgtgtcta accttttgag ggtagcatg gtgcttgtta   1200
tgcatctggt tccacatctc accagaagta gaaagtccga atccacaagt catagcctga   1260
agtctcttgt ccacgtaaac agatccggta agagagttat gtccaccctc atgttgaacc   1320
catccacatc tagctccgaa gaaagcaccg taaacaacag aagcaatgat agggtatcca   1380
gcgtacataa gagcagttcc aagagcgaat gtagcaagaa gctcgagaag tctgtaagcc   1440
acatgggtga tagaaggctt gaagaatcca tctctctcaa gctcagcacg ccatctagcg   1500
aaatcctcaa gcataggagc atcctcagac tcagatctct tgatctcagc aggtctagaa   1560
ggcaaagctc taagcatctt ccaagccttg agagaacgca tgtggaattc tttgaaagcc   1620
tcagtagcat cagcaccagt gttagcaagc atgtagaaga tcacagatcc accagggtgc   1680
ttgaagttag tcacatcgta ctcaacgtcc tcaactctaa cccatctagt ctcgaaagta   1740
gcagcaagct catgaggctc aagagtctta agatcaacag gagcagtaga agcatcctta   1800
gcatcaagag cctcagcaga agatttagac ctggtaagtg gagatctagg agaagatctt   1860
ccatcagtct taggagggca catggtatgg taattgtaaa tgtaattgta atgttgtttg   1920
ttgtttgttg ttgttggtaa ttgttgtaaa agatcctcgt gtatgttttt aatcttgttt   1980
gtatcgatga gttttggttt gagtaaagag tgaagcggat gagttaattt ataggctata   2040
aaggagattt gcatggcgat cacgtgtaat aatgcatgca cgcatgtgat tgtatgtgtg   2100
tgctgtgaga gagaagctct taggtgtttg aagggagtga caagtggcga agaaaaacaa   2160
ttctccgcgg ctgcatgcta tgtgtaacgt gtagctaatg ttctggcatg gcatcttatg   2220
aacgattctt tttaaaaaca aggtaaaaac ttaacttcat aaaattaaaa aaaaaaacgt   2280
```

-continued ttactaagtt ggtttaaaag gggatgagac tagtagattg gttggttggt ttccatgtac 2340
cagaaggctt accctattag ttgaaagttg aaactttgtt ccctactcaa ttcctagttg 2400
tgtaaatgta tgtatatgta atgtgtataa aacgtagtac ttaaatgact aggagtggtt 2460
cttgagaccg atgagagatg ggagcagaac taaagatgat gacataatta agaacgaatt 2520
tgaaaggctc ttaggtttga atcctattcg agaatgtttt tgtcaaagat agtggcgatt 2580
ttgaaccaaa gaaaacattt aaaaaatcag tatccggtta cgttcatgca aatagaaagt 2640
ggtctaggat ctgattgtaa ttttagactt aaagagtctc ttaagattca atcctggctg 2700
tgtacaaaac tacaaataat atattttaga ctatttggcc ttaactaaac ttccactcat 2760
tatttactga ggttagagaa tagacttgcg aataaacaca ttcccgagaa atactcatga 2820
tcccataatt agtcagaggg tatgccaatc agatctaaga acacacattc cctcaaattt 2880
taatgcacat gtaatcatag tttagcacaa ttcaaaaata atgtagtatt aaagacagaa 2940
atttgtagac ttttttttgg cgttaaaaga agactaagtt tatacgtaca ttttatttta 3000
agtggaaaac cgaaattttc catcgaaata tatgaattta gtatatatat ttctgcaatg 3060
tactattttg ctattttggc aactttcagt ggactactac tttattacaa tgtgtatgga 3120
tgcatgagtt tgagtataca catgtctaaa tgcatgcttt gtaaaacgta acggaccaca 3180
aaagaggatc catacaaata catctcatag cttcctccat tattttccga cacaaacaga 3240
gcattttaca acaattacca acaacaacaa acaacaaaca acattacaat tacatttaca 3300
attaccatac catggaattc gcccagcctc ttgttgctat ggctcaagag caatacgctg 3360
ctatcgatgc tgttgttgct cctgctatct tctctgctac tgattctatc ggatggggac 3420
ttaagcctat ctcttctgct actaaggact tgcctcttgt tgagtctcct acacctctca 3480
tcctttcttt gcttgcttac ttcgctatcg ttggatctgg actcgtttac agaaaggttt 3540
tccctagaac cgtgaaggga caagatccat tccttttgaa ggctcttatg cttgctcaca 3600
acgtgttcct tatcggactt tctctttaca tgtgcctcaa gcttgtgtac gaggcttacg 3660
ttaacaagta ctctttctgg ggaaacgctt acaaccctgc tcaaactgag atggctaagg 3720
ttatctggat cttctacgtg agcaagatct acgagttcat ggataccttc atcatgctcc 3780
tcaagggaaa tgttaaccag gttagcttcc ttcacgttta ccatcacgga tctatctctg 3840
gaatctggtg gatgattact tacgctgctc ctggtggtga tgcttacttc tctgctgctc 3900
ttaactcttg ggttcacgtg tgtatgtaca cctactattt tatggctgcc gtgcttccta 3960
aggacgagaa aactaagaga aagtacctct ggtggggaag ataccttact caaatgcaga 4020
tgttccagtt cttcatgaac cttctccagg ctgtttacct tctctactct tcatctcctt 4080
accctaagtt tatcgctcag ctcctcgtgg tgtacatggt tactcttctc atgcttttcg 4140
gaaacttcta ctacatgaag caccacgcta gcaagtgatg aggcgcgccg ggccgccgcc 4200
atgtgacaga tcgaaggaag aaagtgtaat aagacgactc tcactactcg atcgctagtg 4260
attgtcattg ttatatataa taatgttatc tttcacaact tatcgtaatg catgtgaaac 4320
tataacacat taatcctact tgtcatatga taacactctc cccatttaaa actcttgtca 4380
atttaaagat ataagattct ttaaatgatt aaaaaaaata tattataaat tcaatcactc 4440
ctactaataa attattaatt attatttatt gattaaaaaa atacttatac taatttagtc 4500
tgaatagaat aattagattc tagtctcatc cccttttaaa ccaacttagt aaacgttttt 4560
tttttaatt ttatgaagtt aagtttttac cttgttttta aaaagaatcg ttcataagat 4620
gccatgccag aacattagct acacgttaca catagcatgc agccgcggag aattgttttt 4680

-continued

```
cttcgccact tgtcactccc ttcaaacacc taagagcttc tctctcacag cacacacata   4740
caatcacatg cgtgcatgca ttattacacg tgatcgccat gcaaatctcc tttatagcct   4800
ataaattaac tcatccgctt cactctttac tcaaaccaaa actcatcgat acaaacaaga   4860
ttaaaaacat acacgaggat cttttacaac aattaccaac aacaacaaac aacaaacaac   4920
attacaatta catttacaat taccatacca tgcctccaag ggactcttac tcttatgctg   4980
ctcctccttc tgctcaactt cacgaagttg atactcctca agagcacgac aagaaagagc   5040
ttgttatcgg agatagggct tacgatgtta ccaacttcgt taagagacac cctggtggaa   5100
agatcattgc ttaccaagtt ggaactgatg ctaccgatgc ttacaagcag ttccatgtta   5160
gatctgctaa ggctgacaag atgcttaagt ctcttccttc tcgtcctgtt cacaagggat   5220
actctccaag aagggctgat cttatcgctg atttccaaga gttcaccaag caacttgagg   5280
ctgagggaat gttcgagcct tctcttcctc atgttgctta cagacttgct gaggttatcg   5340
ctatgcatgt tgctggtgct gctcttatct ggcatggata cactttcgct ggaatcgcta   5400
tgcttggagt tgttcaggga agatgtggat ggcttatgca tgagggtgga cattactctc   5460
tcactggaaa cattgctttc gacagagcta tccaagttgc ttgttacgga cttggatgtg   5520
gaatgtctgg tgcttggtgg cgtaaccagc ataacaagca ccatgctact cctcaaaagc   5580
ttcagcacga tgttgatctt gatacccttc ctctcgttgc tttccatgag agaatcgctg   5640
ctaaggttaa gtctcctgct atgaaggctt ggctttctat gcaagctaag cttttcgctc   5700
ctgttaccac tcttcttgtt gctcttggat ggcagcttta ccttcatcct agacacatgc   5760
tcaggactaa gcactacgat gagcttgcta tgctcggaat cagatacgga cttgttggat   5820
accttgctgc taactacggt gctggatacg ttctcgcttg ttaccttctt tacgttcagc   5880
ttggagctat gtacatcttc tgcaacttcg ctgtttctca tactcacctc cctgttgttg   5940
agcctaacga gcatgctact tgggttgagt acgctgctaa ccacactact aactgttctc   6000
catcttggtg gtgtgattgg tggatgtctt accttaacta ccagatcgag caccaccttt   6060
acccttctat gcctcaattc agacacccta agatcgctcc tagagttaag cagcttttcg   6120
agaagcacgg acttcactac gatgttagag gatacttcga ggctatggct gatactttcg   6180
ctaaccttga taacgttgcc catgctcctg agaagaaaat gcagtaatga gatcgttcaa   6240
acatttggca ataaagtttc ttaagattga atcctgttgc cggtcttgcg atgattatca   6300
tataatttct gttgaattac gttaagcacg taataattaa catgtaatgc atgacgttat   6360
ttatgagatg ggtttttatg attagagtcc cgcaattata catttaatac gcgatagaaa   6420
acaaaatata gcgcgcaaac taggataaat tatcgcgcgc ggtgtcatct atgttactag   6480
atcggtcgat taaaaatccc aattatattt ggtctaattt agtttggtat tgagtaaaac   6540
aaattcgaac caaaccaaaa tataaatata tagtttttat atatatgcct ttaagacttt   6600
ttatagaatt ttctttaaaa aatatctaga aatatttgcg actcttctgg catgtaatat   6660
ttcgttaaat atgaagtgct ccatttttat taactttaaa taattggttg tacgatcact   6720
ttcttatcaa gtgttactaa aatgcgtcaa tctctttgtt cttccatatt catatgtcaa   6780
aatctatcaa aattcttata tatctttttc gaatttgaag tgaaatttcg ataatttaaa   6840
attaaataga acatatcatt atttaggtat catattgatt tttatactta attactaaat   6900
ttggttaact ttgaaagtgt acatcaacga aaaattagtc aaacgactaa aataaataaa   6960
tatcatgtgt tattaagaaa attctcctat aagaatattt taatagatca tatgtttgta   7020
```

-continued

```
aaaaaaatta atttttacta acacatatat ttacttatca aaaatttgac aaagtaagat   7080
taaaataata ttcatctaac aaaaaaaaaa ccagaaaatg ctgaaaaccc ggcaaaaccg   7140
aaccaatcca aaccgatata gttggtttgg tttgattttg atataaaccg aaccaactcg   7200
gtccatttgc acccctaatc ataatagctt taatatttca agatattatt aagttaacgt   7260
tgtcaatatc ctggaaattt tgcaaaatga atcaagccta tatggctgta atatgaattt   7320
aaaagcagct cgatgtggtg gtaatatgta atttacttga ttctaaaaaa atatcccaag   7380
tattaataat ttctgctagg aagaaggtta gctacgattt acagcaaagc cagaatacaa   7440
agaaccataa agtgattgaa gctcgaaata tacgaaggaa caaatatttt taaaaaaata   7500
cgcaatgact tggaacaaaa gaaagtgata tatttttgt tcttaaacaa gcatcccctc   7560
taaagaatgg cagttttcct ttgcatgtaa ctattatgct cccttcgtta caaaaatttt   7620
ggactactat tgggaacttc ttctgaaaat agtgatagaa cccacacgag catgtgcttt   7680
ccatttaatt ttaaaaacca agaaacatac atacataaca ttccatcagc ctctctctct   7740
ttttattacg gttaatgact taaaacacat cttattatcc catccttaac acctagcagt   7800
gtctttatac gatctcatcg atcaccactt caaaaccatg cagactgctg ctgcccctgg   7860
agctggcatc ggctaggctg ggtgccgcac tgtcccggaa ggtccctagc gacttgttta   7920
gattgatggg accacctctc aacttcctgc tgctgtccct gctgctggat gtcctgcctc   7980
atctggccga ttgcacgctc cagtcccctg catgtgcact cgctcctcaa ttgcttaaga   8040
tcatcgcagc agctatcgaa gtgctggctc tgttgccctc ctccacggcc ttggttgtag   8100
tagtagctgc cgccgccctt ctggactttt tcccacagga accgccgaat aattcgatag   8160
aaccacacga gcatgtgctt tcatttattt taaaaaccaa gaaacataca taacatttca   8220
tcagcctctc tctctctctc tctctctctc tctctctctc tctctctctc tctctcttta   8280
ttacagctgt tacactaact taaaacacat tcatctcatt attattatta ttatccatcc   8340
ttaacaccta gcagtgtctt tgtacgatct cataatcgat caccccttca tcaggtatcc   8400
ttaggcttca ctccaacgtt gttgcagtta cggaacatgt acacaccatc atggttctca   8460
acgaactggc aagatctcca agttttccaa aggctaaccc acatgttctc atcggtgtgt   8520
ctgtagtgct ctcccataac tttcttgatg cactcggtag cttctctagc atggtagaat   8580
gggatccttg aaacgtagtg atggagcaca tgagtctcga tgatgtcatg gaagatgatt   8640
ccgaggattc cgaactctct atcgatagta gcagcagcac ccttagcgaa agtccactct   8700
tgagcatcgt aatgaggcat agaagaatcg gtgtgctgaa ggaaggtaac gaaaacaagc   8760
cagtggttaa caaggatcca aggacagaac catgtgatga aagtaggcca gaatccgaaa   8820
accttgtaag cggtgtaaac agaagtgagg gtagcaagga ttccaagatc agaaagaacg   8880
atgtaccagt agtccttctt atcgaaaaca gggctagaag gccagtagtg agacttgaag   8940
aacttagaaa caccagggta aggttgtcca gtagcgttag tagcaaggta aagagaaagt   9000
cctccaagct gttggaacaa gagagcgaaa acagagtaga taggagtttc ctcagcgata   9060
tcgtgaaggc tggtaacttg gtgcttctct ttgaattcct cggcggtgta aggaacgaaa   9120
accatatctc tggtcatgtg tccagtagcc ttatggtgct tagcatgaga gaacttccag   9180
ctgaagtaag gaaccataac aagagagtgg agaacccatc caacggtatc gttaacccat   9240
ccgtagttag agaaagcaga atgtccacac tcatgtccaa ggatccagat tccgaatccg   9300
aaacaagaga tagagaacac gtaagcagac caagcagcga atctaaggaa ttcgttaggg   9360
agaagaggga tgtaggtaag tccaacgtaa gcgatagcag agatagccac gatatctctc   9420
```

-continued

```
accacgtaag acatagactt cacgagagat ctctcgtaac agtgcttagg gatagcgtca   9480
aggatatcct tgatggtgta atctggcacc ttgaaaacgt ttccgaaggt atcgatagcg   9540
gtcttttgct gcttgaaaga tgcaacgttt ccagaacgcc taacggtctt agtagatccc   9600
tcaaggatct cagatccaga cacggtaacc ttagacatgg tatggtaatt gtaaatgtaa   9660
ttgtaatgtt gtttgttgtt tgttgttgtt ggtaattgtt gtaaaatttt tggtggtgat   9720
tggttcttta aggtgtgaga gtgagttgtg agttgtgtgg tgggtttggt gagattgggg   9780
atggtgggtt tatatagtgg agactgagga atggggtcgt gagtgttaac tttgcatggg   9840
ctacacgtgg gttcttttgg gcttacacgt agtattattc atgcaaatgc agccaataca   9900
tatacggtat tttaataatg tgtgggaata caatatgccg agtattttac taattttggc   9960
aatgacaagt gtacatttgg attatcttac ttggcctctc ttgctttaat ttggattatt  10020
tttattctct taccttggcc gttcatattc acatccctaa aggcaagaca gaattgaatg  10080
gtggccaaaa attaaaacga tggatatgac ctacatagtg taggatcaat taacgtcgaa  10140
ggaaaatact gattctctca agcatacgga caagggtaaa taacatagtc accagaacat  10200
aataaacaaa aagtgcagaa gcaagactaa aaaaattagc tatggacatt caggttcata  10260
ttggaaacat cattatccta gtcttgtgac catccttcct cctgctctag ttgagaggcc  10320
ttgggactaa cgagaggtca gttgggatag cagatcctta tcctggacta gcctttctgg  10380
tgtttcagag tcttcgtgcc gccgtctaca tctatctcca ttaggtctga agatgactct  10440
tcacaccaac gacgtttaag gtctctatcc tactcctagc ttgcaatacc tggcttgcaa  10500
tacctggagc atcgtgcacg atgattggat actgtggagg aggagtgttt gctgatttag  10560
agctcccggt tgggtgattt gacttcgatt tcagtttagg cttgttgaaa tttttcaggt  10620
tccattgtga agcctttaga gcttgagctt ccttccatgt taatgccttg atcgaatact  10680
cctagagaaa agggaagtcg atctctgagt attgaaatcg aagtgcacat tttttttcaa  10740
cgtgtccaat caatccacaa acaaagcaga agacaggtaa tctttcatac ttatactgac  10800
aagtaatagt cttaccgtca tgcataataa cgtctcgttc cttcaagagg ggttttccga  10860
catccataac gacccgaagc ctcatgaaag cattagggaa gaacttttgg ttcttcttgt  10920
catggccttt ataggtgtca gccgagctcg ccaattcccg tccgactggc tccgcaaaat  10980
attcgaacgg caagttatgg acttgcaacc ataactccac ggtattgagc aggacctatt  11040
gtgaagactc atctcatgga gcttcagaat gtggttgtca gcaaaccaat gaccgaaatc  11100
catcacatga cggacgtcca gtgggtgagc gaaacgaaac aggaagcgcc tatctttcag  11160
agtcgtgagc tccacaccgg attccggcaa ctacgtgttg ggcaggcttc gccgtattag  11220
agatatgttg aggcagaccc atctgtgcca ctcgtacaat tacgagagtt gttttttttg  11280
tgattttcct agtttctcgt tgatggtgag ctcatattct acatcgtatg gtctctcaac  11340
gtcgtttcct gtcatctgat atcccgtcat ttgcatccac gtgcgccgcc tcccgtgcca  11400
agtccctagg tgtcatgcac gccaaattgg tggtggtgcg ggctgccctg tgcttcttac  11460
cgatgggtgg aggttgagtt tgggggtctc cgcggcgatg gtagtgggtt gacggtttgg  11520
tgtgggttga cggcattgat caatttactt cttgcttcaa attctttggc agaaaacaat  11580
tcattagatt agaactggaa accagagtga tgagacggat taagtcagat tccaacagag  11640
ttacatctct taagaaataa tgtaacccct ttagacttta tatatttgca attaaaaaaa  11700
taatttaact tttagacttt atatatagtt ttaataacta agtttaacca ctctattatt  11760
```

-continued

```
tatatcgaaa ctatttgtat gtctcccctc taaataaact tggtattgtg tttacagaac  11820
ctataatcaa ataatcaata ctcaactgaa gtttgtgcag ttaattgaag ggattaacgg  11880
ccaaaatgca ctagtattat caaccgaata gattcacact agatggccat ttccatcaat  11940
atcatcgccg ttcttcttct gtccacatat cccctctgaa acttgagaga cacctgcact  12000
tcattgtcct tattacgtgt tacaaaatga aacccatgca tccatgcaaa ctgaagaatg  12060
gcgcaagaac ccttcccctc catttcttat gtggcgacca tccatttcac catctcccgc  12120
tataaaacac ccccatcact tcacctagaa catcatcact acttgcttat ccatccaaaa  12180
gatacccact tttacaacaa ttaccaacaa caacaaacaa caaacaacat tacaattaca  12240
tttacaatta ccataccatg ccacctagcg ctgctaagca aatgggagct tctactggtg  12300
ttcatgctgg tgttactgac tcttctgctt tcaccagaaa ggatgttgct gatagacctg  12360
atctcaccat cgttggagat tctgtttacg atgctaaggc tttcagatct gagcatcctg  12420
gtggtgctca tttcgtttct ttgttcggag gaagagatgc tactgaggct ttcatggaat  12480
accatagaag ggcttggcct aagtctagaa tgtctagatt ccacgttgga tctcttgctt  12540
ctactgagga acctgttgct gctgatgagg gataccttca actttgtgct aggatcgcta  12600
agatggtgcc ttctgtttct tctggattcg ctcctgcttc ttactgggtt aaggctggac  12660
ttatccttgg atctgctatc gctcttgagg cttacatgct ttacgctgga aagagacttc  12720
tcccttctat cgttcttgga tggcttttcg ctcttatcgg tcttaacatc cagcatgatg  12780
ctaaccatgg tgctttgtct aagtctgctt ctgttaacct tgctcttgga ctttgtcagg  12840
attggatcgg aggatctatg atcctttggc ttcaagagca tgttgttatg caccacctcc  12900
acactaacga tgttgataag gatcctgatc aaaaggctca cggtgctctt agactcaagc  12960
ctactgatgc ttggtcacct atgcattggc ttcagcatct ttaccttttg cctggtgaga  13020
ctatgtacgc tttcaagctt ttgttcctcg acatctctga gcttgttatg tggcgttggg  13080
agggtgagcc tatctctaag cttgctggat acctctttat gccttctttg cttctcaagc  13140
ttaccttctg ggctagattc gttgctttgc ctctttacct tgctccttct gttcatactg  13200
ctgtgtgtat cgctgctact gttatgactg gatctttcta cctcgctttc ttcttcttca  13260
tctcccacaa cttcgagggt gttgcttctg ttggacctga tggatctatc acttctatga  13320
ctagaggtgc tagcttcctt aagagacaag ctgagacttc ttctaacgtt ggaggacctc  13380
ttcttgctac tcttaacggt ggactcaact accaaattga gcatcacttg ttccctagag  13440
ttcaccatgg attctaccct agacttgctc ctcttgttaa ggctgagctt gaggctagag  13500
gaatcgagta caagcactac cctactatct ggtctaacct tgcttctacc ctcagacata  13560
tgtacgctct tggaagaagg cctagatcta aggctgagta atgacaagct tatgtgacgt  13620
gaaataataa cggtaaaata tatgtaataa taataataat aaagccacaa agtgagaatg  13680
aggggaaggg gaaatgtgta atgagccagt agccggtggt gctaattttg tatcgtattg  13740
tcaataaatc atgaatttg tggtttttat gtgttttttt aaatcatgaa ttttaaattt  13800
tataaaataa tctccaatcg gaagaacaac attccatatc catgcatgga tgtttcttta  13860
cccaaatcta gttcttgaga ggatgaagca tcaccgaaca gttctgcaac tatccctcaa  13920
aagctttaaa atgaacaaca aggaacagag caacgttcca aagatcccaa acgaaacata  13980
ttatctatac taatactata ttattaatta ctactgcccg gaatcacaat ccctgaatga  14040
ttcctattaa ctacaagcct tgttggcggc ggagaagtga tcggcgcggc gagaagcagc  14100
ggactcggag acgaggcctt ggaagatctg agtcgaacgg gcagaatcag tattttcctt  14160
```

```
cgacgttaat tgatcctaca ctatgtaggt catatccatc gttttaattt ttggccacca  14220
ttcaattctg tcttgccttt agggatgtga atatgaacgg ccaaggtaag agaataaaaa  14280
taatccaaat taaagcaaga gaggccaagt aagataatcc aaatgtacac ttgtcattgc  14340
caaaattagt aaaatactcg gcatattgta ttcccacaca ttattaaaat accgtatatg  14400
tattggctgc atttgcatga ataatactac gtgtaagccc aaaagaaccc acgtgtagcc  14460
catgcaaagt taacactcac gaccccattc ctcagtctcc actatataaa cccaccatcc  14520
ccaatctcac caaacccacc acacaactca caactcactc tcacacctta aagaaccaat  14580
caccaccaaa aattttacaa caattaccaa caacaacaaa caacaaacaa cattacaatt  14640
acatttacaa ttaccatacc atgagcgctg ttaccgttac tggatctgat cctaagaaca  14700
gaggatcttc tagcaacacc gagcaagagg ttccaaaagt tgctatcgat accaacggaa  14760
acgtgttctc tgttcctgat ttcaccatca aggacatcct tggagctatc cctcatgagt  14820
gttacgagag aagattggct acctctctct actacgtgtt cagagatatc ttctgcatgc  14880
ttaccaccgg ataccttacc cataagatcc tttaccctct cctcatctct tacacctcta  14940
acagcatcat caagttcact ttctgggccc tttacactta cgttcaagga cttttcggaa  15000
ccggaatctg ggttctcgct catgagtgtg gacatcaagc tttctctgat tacggaatcg  15060
tgaacgattt cgttggatgg acccttcact cttaccttat ggttccttac ttcagctgga  15120
agtactctca tggaaagcac cataaggcta ctggacacat gaccagagat atggttttcg  15180
ttcctgccac caaagaggaa ttcaagaagt ctaggaactt cttcggtaac ctcgctgagt  15240
actctgagga ttctccactt agaacccttt acgagcttct tgttcaacaa cttggaggat  15300
ggatcgctta cctcttcgtt aacgttacag gacaacctta ccctgatgtt ccttcttgga  15360
aatggaacca cttctggctt acctctccac ttttcgagca aagagatgct ctctacatct  15420
tcctttctga tcttggaatc ctcacccagg gaatcgttct tactctttgg tacaagaaat  15480
tcggaggatg gtccctttc atcaactggt tcgttcctta catctgggtt aaccactggc  15540
tcgttttcat cacattcctt cagcacactg atcctactat gcctcattac aacgctgagg  15600
aatggacttt cgctaagggt gctgctgcta ctatcgatag aaagttcgga ttcatcggac  15660
ctcacatctt ccatgatatc atcgagactc atgtgcttca ccactactgt tctaggatcc  15720
cattctacaa cgctagacct gcttctgagg ctatcaagaa agttatggga aagcactaca  15780
ggtctagcga cgagaacatg tggaagtcac tttggaagtc tttcaggtct tgccaatacg  15840
ttgacggtga taacggtgtt ctcatgttcc gtaacatcaa caactgcgga gttggagctg  15900
ctgagaagta atgaaggggt gatcgattat gagatcgtac aaagacactg ctaggtgtta  15960
aggatggata ataataataa taatgagatg aatgtgtttt aagttagtgt aacagctgta  16020
ataaagagag agagagagag agagagagag agagagagag agagagagag agagaggctg  16080
atgaaatgtt atgtatgttt cttggttttt aaaataaatg aaagcacatg ctcgtgtggt  16140
tctatcgaat tattcggcgg ttcctgtggg aaaaagtcca gaagggccgc cgcagctact  16200
actacaacca aggccgtgga ggagggcaac agagccagca cttcgatagc tgctgcgatg  16260
atcttaagca attgaggagc gagtgcacat gcaggggact ggagcgtgca atcggccaga  16320
tgaggcagga catccagcag cagggacagc agcaggaagt tgagaggtgg tcccatcaat  16380
ctaaacaagt cgctagggac cttccgggac agtgcggcac ccagcctagc cgatgccagc  16440
tccaggggca gcagcagtct gcatggtttt gaagtggtga tcgatgagat cgtataaaga  16500
```

-continued

```
cactgctagg tgttaaggat gggataataa gatgtgtttt aagtcattaa ccgtaataaa  16560
aagagagaga ggctgatgga atgttatgta tgtatgtttc ttggttttta aaattaaatg  16620
gaaagcacat gctcgtgtgg gttctatctc gattaaaaat cccaattata tttggtctaa  16680
tttagtttgg tattgagtaa aacaaattcg aaccaaacca aaatataaat atatagtttt  16740
tatatatatg cctttaagac tttttataga attttcttta aaaaatatct agaaatattt  16800
gcgactcttc tggcatgtaa tatttcgtta aatatgaagt gctccatttt tattaacttt  16860
aaataattgg ttgtacgatc actttcttat caagtgttac taaaatgcgt caatctcttt  16920
gttcttccat attcatatgt caaaatctat caaaattctt atatatcttt ttcgaatttg  16980
aagtgaaatt tcgataattt aaaattaaat agaacatatc attatttagg tatcatattg  17040
atttttatac ttaattacta aatttggtta actttgaaag tgtacatcaa cgaaaaatta  17100
gtcaaacgac taaaataaat aaatatcatg tgttattaag aaaattctcc tataagaata  17160
ttttaataga tcatatgttt gtaaaaaaaa ttaattttta ctaacacata tatttactta  17220
tcaaaaattt gacaaagtaa gattaaaata atattcatct aacaaaaaaa aaaccagaaa  17280
atgctgaaaa cccggcaaaa ccgaaccaat ccaaaccgat atagttggtt tggtttgatt  17340
ttgatataaa ccgaaccaac tcggtccatt tgcacccccta atcataatag ctttaatatt  17400
tcaagatatt attaagttaa cgttgtcaat atcctggaaa ttttgcaaaa tgaatcaagc  17460
ctatatggct gtaatatgaa tttaaaagca gctcgatgtg gtggtaatat gtaatttact  17520
tgattctaaa aaaatatccc aagtattaat aatttctgct aggaagaagg ttagctacga  17580
tttacagcaa agccagaata caaagaacca taaagtgatt gaagctcgaa atatacgaag  17640
gaacaaatat ttttaaaaaa atacgcaatg acttggaaca aaagaaagtg atatattttt  17700
tgttcttaaa caagcatccc ctctaaagaa tggcagtttt cctttgcatg taactattat  17760
gctcccttcg ttacaaaaat tttggactac tattgggaac ttcttctgaa aatagtcctg  17820
caggctagta gattggttgg ttggtttcca tgtaccagaa ggcttaccct attagttgaa  17880
agttgaaact ttgttcccta ctcaattcct agttgtgtaa atgtatgtat atgtaatgtg  17940
tataaaacgt agtacttaaa tgactaggag tggttcttga gaccgatgag agatgggagc  18000
agaactaaag atgatgacat aattaagaac gaatttgaaa ggctcttagg tttgaatcct  18060
attcgagaat gtttttgtca aagatagtgg cgattttgaa ccaaagaaaa catttaaaaa  18120
atcagtatcc ggttacgttc atgcaaatag aaagtggtct aggatctgat tgtaatttta  18180
gacttaaaga gtctcttaag attcaatcct ggctgtgtac aaaactacaa ataatatatt  18240
ttagactatt tggccttaac taaacttcca ctcattattt actgaggtta gagaatagac  18300
ttgcgaataa acacattccc gagaaatact catgatccca taattagtca gagggtatgc  18360
caatcagatc taagaacaca cattccctca aattttaatg cacatgtaat catagtttag  18420
cacaattcaa aaataatgta gtattaaaga cagaaatttg tagactttt tttggcgtta  18480
aaagaagact aagtttatac gtacatttta ttttaagtgg aaaaccgaaa ttttccatcg  18540
aaatatatga atttagtata tatatttctg caatgtacta ttttgctatt ttggcaactt  18600
tcagtggact actactttat tacaatgtgt atggatgcat gagtttgagt atacacatgt  18660
ctaaatgcat gctttgtaaa acgtaacgga ccacaaaaga ggatccatac aaatacatct  18720
catagcttcc tccattattt tccgacacaa acagagcatt ttacaacaat taccaacaac  18780
aacaaacaac aaacaacatt acaattacat ttacaattac cataccatgg cctctatcgc  18840
tatccctgct gctcttgctg gaactcttgg atacgttacc tacaatgtgg ctaaccctga  18900
```

```
tatcccagct tctgagaaag ttcctgctta cttcatgcag gttgagtact ggggacctac  18960
tatcggaact attggatacc tcctcttcat ctacttcgga aagcgtatca tgcagaacag  19020
atctcaacct ttcggactca agaacgctat gctcgtttac aacttctacc agaccttctt  19080
caacagctac tgcatctacc ttttcgttac ttctcatagg gctcagggac ttaaggtttg  19140
gggaaacatc cctgatatga ctgctaactc ttggggaatc tctcaggtta tctggcttca  19200
ctacaacaac aagtacgttg agcttctcga caccttcttc atggtgatga ggaagaagtt  19260
cgaccagctt tctttccttc acatctacca ccacactctt ctcatctggt catggttcgt  19320
tgttatgaag cttgagcctg ttggagattg ctacttcgga tcttctgtta acaccttcgt  19380
gcacgtgatc atgtactctt actacggact tgctgctctt ggagttaact gtttctggaa  19440
gaagtacatc acccagatcc agatgcttca gttctgtatc tgtgcttctc actctatcta  19500
caccgcttac gttcagaata ccgctttctg gcttccttac cttcaactct gggttatggt  19560
gaacatgttc gttctcttcg ccaacttcta ccgtaagagg tacaagtcta agggtgctaa  19620
gaagcagtga taagggccgc cgccatgtga cagatcgaag gaagaaagtg taataagacg  19680
actctcacta ctcgatcgct agtgattgtc attgttatat ataataatgt tatctttcac  19740
aacttatcgt aatgcatgtg aaactataac acattaatcc tacttgtcat atgataacac  19800
tctccccatt taaaactctt gtcaatttaa agatataaga ttctttaaat gattaaaaaa  19860
aatatattat aaattcaatc actcctacta ataaattatt aattattatt tattgattaa  19920
aaaaatactt atactaattt agtctgaata gaataattag attctagcct gcagggcggc  19980
cgcggatccc atggagtcaa agattcaaat agaggaccta acagaactcg ccgtaaagac  20040
tggcgaacag ttcatacaga gtctcttacg actcaatgac aagaagaaaa tcttcgtcaa  20100
catggtggag cacgacacac ttgtctactc caaaaatatc aaagatacag tctcagaaga  20160
ccaaagggca attgagactt ttcaacaaag ggtaatatcc ggaaacctcc tcggattcca  20220
ttgcccagct atctgtcact ttattgtgaa gatagtggaa aaggaaggtg gctcctacaa  20280
atgccatcat tgcgataaag gaaaggccat cgttgaagat gcctctgccg acagtggtcc  20340
caaagatgga cccccaccca cgaggagcat cgtggaaaaa gaagacgttc caaccacgtc  20400
ttcaaagcaa gtggattgat gtgatatctc cactgacgta agggatgacg cacaatccca  20460
ctatccttcg caagaccctt cctctatata aggaagttca tttcatttgg agagaacacg  20520
ggggactgaa ttaaatatga gccctgagag gcgtcctgtt gaaatcagac ctgctactgc  20580
tgctgatatg gctgctgttt gtgatatcgt gaaccactac atcgagactt ctaccgttaa  20640
cttcagaact gagcctcaaa ctcctcaaga gtggatcgat gatcttgaga gactccaaga  20700
tagataccct tggcttgttg ctgaggttga gggtgttgtt gctggaatcg cttacgctgg  20760
accttggaag gctagaaacg cttacgattg gactgttgag tctaccgttt acgtttcaca  20820
cagacatcag agacttggac ttggatctac cctttacact caccttctca agtctatgga  20880
agctcaggga ttcaagtctg ttgttgctgt tatcggactc cctaacgatc cttctgttag  20940
acttcatgag gctcttggat acactgctag aggaactctt agagctgctg gatacaagca  21000
cggtggatgg catgatgttg gattctggca aagagatttc gagcttcctg ctcctcctag  21060
acctgttaga ccagttactc agatctgaat ttgcgtgatc gttcaaacat ttggcaataa  21120
agtttcttaa gattgaatcc tgttgccggt cttgcgatga ttatcatata atttctgttg  21180
aattacgtta agcatgtaat aattaacatg taatgcatga cgttatttat gagatgggtt  21240
```

-continued

```
tttatgatta gagtcccgca attatacatt taatacgcga tagaaaacaa aatatagcgc  21300

gcaaactagg ataaattatc gcgcgcggtg tcatctatgt tactagatca ctagtgatgt  21360

acggttaaaa ccaccccagt acattaaaaa cgtccgcaat gtgttattaa gttgtctaag  21420

cgtcaatttg tttacaccac aatatatcct gccaccagcc agccaacagc tccccgaccg  21480

gcagctcggc acaaaatcac cactcgatac aggcagccca tcagtcc               21527
```

<210> SEQ ID NO 2
<211> LENGTH: 23512
<212> TYPE: DNA
<213> ORGANISM: Artificial Sequence
<220> FEATURE:
<223> OTHER INFORMATION: pGA7- mod_B nucleotide sequence

<400> SEQUENCE: 2

```
tcctgtggtt ggcatgcaca tacaaatgga cgaacggata aaccttttca cgccctttta     60

aatatccgat tattctaata aacgctcttt tctcttaggt ttacccgcca atatatcctg    120

tcaaacactg atagtttaaa ctgaaggcgg gaaacgacaa tctgctagtg gatctcccag    180

tcacgacgtt gtaaaacggg cgccccgcgg aaagcttgcg gccgcggtac cgcccgttcg    240

actcagatct tccaaggcct cgtctccgag tccgctgctt ctcgccgcgc cgatcacttc    300

tccgccgcca acaaggcttg tagttaatag gaatcattca gggattgtga ttccgggcag    360

tagtaattaa taatatagta ttagtataga taatatgttt cgtttgggat ctttggaacg    420

ttgctctgtt ccttgttgtt cattttaaag cttttgaggg atagttgcag aactgttcgg    480

tgatgcttca tcctctcaag aactagattt gggtaaagaa acatccatgc atggatatgg    540

aatgttgttc ttccgattgg agattatttt ataaaattta aaattcatga tttaaaaaaa    600

cacataaaaa ccacaaaatt catgatttat tgacaatacg atacaaaatt agcaccaccg    660

gctactggct cattacacat ttccccttcc cctcattctc actttgtggc tttattatta    720

ttattattac atatatttta ccgttattat ttcacgtcac ataagcttgt taattaatca    780

ttagtgagcc ttctcagcct ttccgttaac gtagtagtgc tgtcccacct tatcaaggtt    840

agagaaagta gccttccaag caccgtagta agagagcacc ttgtagttga gtccccactt    900

cttagcgaaa ggaacgaatc ttctgctaac ctcaggctgt ctgaattgag gcatatcagg    960

gaagaggtgg tggataacct gacagttaag gtatcccata agccagttca cgtatcctct   1020

agaaggatcg atatcaacgg tgtgatcaac agcgtagtta acccaagaaa ggtgcttatc   1080

agatggaaca acagggaggt gagtatgaga agtagagaag tgagcgaaaa ggtacatgta   1140

agcgatccag tttccgaaag tgaaccacca gtaagcaaca ggccaagagt atccagtagc   1200

aagcttgata acagcggttc taacaacatg agaaacgagc atccaagaag cctcttcgta   1260

gttcttctta cggagaactt gtctagggtg gagaacgtag atccagaaag cttgaacaag   1320

aagtccagag gtaacaggaa cgaaagtcca agcttgaagt ctagcccaag ctctagagaa   1380

tcctctaggt ctgttatcct caacagcagt gttgaagaaa gccacagcag gagtggtatc   1440

aagatccata tcgtgtctaa ccttttgagg ggtagcatgg tgcttgttat gcatctggtt   1500

ccacatctca ccagaagtag aaagtccgaa tccacaagtc atagcctgaa gtctcttgtc   1560

cacgtaaaca gatccggtaa gagagttatg tccaccctca tgttgaaccc atccacatct   1620

agctccgaag aaagcaccgt aaacaacaga agcaatgata gggtatccag cgtacataag   1680

agcagttcca agagcgaatg tagcaagaag ctcgagaagt ctgtaagcca catgggtgat   1740

agaaggcttg aagaatccat ctctctcaag ctcagcacgc catctagcga aatcctcaag   1800
```

-continued

```
cataggagca tcctcagact cagatctctt gatctcagca ggtctagaag gcaaagctct   1860
aagcatcttc caagccttga gagaacgcat gtggaattct ttgaaagcct cagtagcatc   1920
agcaccagtg ttagcaagca tgtagaagat cacagatcca ccagggtgct tgaagttagt   1980
cacatcgtac tcaacgtcct caactctaac ccatctagtc tcgaaagtag cagcaagctc   2040
atgaggctca agagtcttaa gatcaacagg agcagtagaa gcatccttag catcaagagc   2100
ctcagcagaa gatttagacc tggtaagtgg agatctagga gaagatcttc catcagtctt   2160
aggagggcac atggtatggt aattgtaaat gtaattgtaa tgttgtttgt tgtttgttgt   2220
tgttggtaat tgttgtaaaa ttaattaagt gggtatcttt tggatggata agcaagtagt   2280
gatgatgttc taggtgaagt gatgggggtg ttttatagcg ggagatggtg aaatggatgg   2340
tcgccacata agaaatggag gggaagggtt cttgcgccat tcttcagttt gcatggatgc   2400
atgggtttca ttttgtaaca cgtaataagg acaatgaagt gcaggtgtct ctcaagtttc   2460
agaggggata tgtggacaga agaagaacgg cgatgatatt gatggaaatg gccatctagt   2520
gtgaatctat tcggttgata atactagtgc attttggccg ttaatccctt caattaactg   2580
cacaaacttc agttgagtat tgattatttg attataggtt ctgtaaacac aataccaagt   2640
ttatttagag gggagacata caaatagttt cgatataaat aatagagtgg ttaaacttag   2700
ttattaaaac tatatataaa gtctaaaagt taaattattt ttttaattgc aaatatataa   2760
agtctaaagg ggttacatta tttcttaaga gatgtaactc tgttggaatc tgacttaatc   2820
cgtctcatca ctctggtttc cagttctaat ctaatgaatt gttttctgcc aaagaatttg   2880
aagcaagaag taaattgatc aatgccgtca acccacacca aaccgtcaac ccactaccat   2940
cgccgcggag acccccaaac tcaacctcca cccatcggta agaagcacag ggcagcccgc   3000
accaccacca atttggcgtg catgacacct agggacttgg cacgggaggc ggcgcacgtg   3060
gatgcaaatg acgggatatc agatgacagg aaacgacgtt gagagaccat acgatgtaga   3120
atatgagctc accatcaacg agaaactagg aaaatcacaa aaaaaacaac tctcgtaatt   3180
gtacgagtgg cacagatggg tctgcctcaa catatctcta atacggcgaa gcctgcccaa   3240
cacgtagttg ccggaatccg gtgtggagct cacgactctg aaagataggc gcttcctgtt   3300
tcgtttcgct cacccactgg acgtccgtca tgtgatggat ttcggtcatt ggtttgctga   3360
caaccacatt ctgaagctcc atgagatgag tcttcacaat aggtcctgct caataccgtg   3420
gagttatggt tgcaagtcca taacttgccg ttcgaatatt ttgcggagcc agtcggacgg   3480
gaattggcga gctcggctga cacctataaa ggccatgaca agaagaacca aaagttcttc   3540
cctaatgctt tcatgaggct tcgggtcgtt atggatgtcg gaaaacccct cttgaaggaa   3600
cgagacgtta ttatgcatga cggtaagact attacttgtc agtataagta tgaaagatta   3660
cctgtcttct gctttgtttg tggattgatt ggacacgttg aaaaaaaatg tgcacttcga   3720
tttcaatact cagagatcga cttccctttt ctctaggagt attcgatcaa ggcattaaca   3780
tggaaggaag ctcaagctct aaaggcttca caatggaacc tgaaaaattt caacaagcct   3840
aaactgaaat cgaagtcaaa tcacccaacc gggagctcta aatcagcaaa cactcctcct   3900
ccacagtatc caatcatcgt gcacgatgct ccaggtattg caagccaggt attgcaagct   3960
aggagtagga tagagacctt aaacgtcgtt ggtgtgaaga gtcatcttca gacctaatgg   4020
agatagatgt agacggcggc acgaagactc tgaaacacca gaaaggctag tccaggataa   4080
ggatctgcta tcccaactga cctctcgtta gtcccaaggc ctctcaacta gagcaggagg   4140
```

-continued

```
aaggatggtc acaagactag gataatgatg tttccaatat gaacctgaat gtccatagct   4200
aattttttta gtcttgcttc tgcacttttt gtttattatg ttctggtgac tatgttattt   4260
acccttgtcc gtatgcttga gggtacccta gtagattggt tggttggttt ccatgtacca   4320
gaaggcttac cctattagtt gaaagttgaa actttgttcc ctactcaatt cctagttgtg   4380
taaatgtatg tatatgtaat gtgtataaaa cgtagtactt aaatgactag gagtggttct   4440
tgagaccgat gagagatggg agcagaacta aagatgatga cataattaag aacgaatttg   4500
aaaggctctt aggtttgaat cctattcgag aatgtttttg tcaaagatag tggcgatttt   4560
gaaccaaaga aaacatttaa aaaatcagta tccggttacg ttcatgcaaa tagaaagtgg   4620
tctaggatct gattgtaatt ttagacttaa agagtctctt aagattcaat cctggctgtg   4680
tacaaaacta caaataatat attttagact atttggcctt aactaaactt ccactcatta   4740
tttactgagg ttagagaata gacttgcgaa taaacacatt cccgagaaat actcatgatc   4800
ccataattag tcagagggta tgccaatcag atctaagaac acacattccc tcaaatttta   4860
atgcacatgt aatcatagtt tagcacaatt caaaaataat gtagtattaa agacagaaat   4920
ttgtagactt ttttttggcg ttaaaagaag actaagttta tacgtacatt ttattttaag   4980
tggaaaaccg aaattttcca tcgaaatata tgaatttagt atatatattt ctgcaatgta   5040
ctattttgct attttggcaa ctttcagtgg actactactt tattacaatg tgtatggatg   5100
catgagtttg agtatacaca tgtctaaatg catgctttgt aaaacgtaac ggaccacaaa   5160
agaggatcca tacaaataca tctcatagct tcctccatta ttttccgaca caaacagagc   5220
attttacaac aattaccaac aacaacaaac aacaaacaac attacaatta catttacaat   5280
taccatacca tggcctctat cgctatccct gctgctcttg ctggaactct tggatacgtt   5340
acctacaatg tggctaaccc tgatatccca gcttctgaga aagttcctgc ttacttcatg   5400
caggttgagt actggggacc tactatcgga actattggat acctcctctt catctacttc   5460
ggaaagcgta tcatgcagaa cagatctcaa cctttcggac tcaagaacgc tatgctcgtt   5520
tacaacttct accagacctt cttcaacagc tactgcatct accttttcgt tacttctcat   5580
agggctcagg gacttaaggt ttggggaaac atccctgata tgactgctaa ctcttgggga   5640
atctctcagg ttatctggct tcactacaac aacaagtacg ttgagcttct cgacaccttc   5700
ttcatggtga tgaggaagaa gttcgaccag ctttctttcc ttcacatcta ccaccacact   5760
cttctcatct ggtcatggtt cgttgttatg aagcttgagc ctgttggaga ttgctacttc   5820
ggatcttctg ttaacacctt cgtgcacgtg atcatgtact cttactacgg acttgctgct   5880
cttggagtta actgtttctg gaagaagtac atcacccaga tccagatgct tcagttctgt   5940
atctgtgctt ctcactctat ctacaccgct tacgttcaga ataccgcttt ctggcttcct   6000
taccttcaac tctgggttat ggtgaacatg ttcgttctct tcgccaactt ctaccgtaag   6060
aggtacaagt ctaagggtgc taagaagcag tgataaggcg cgcggcgcgc cgggccgccg   6120
ccatgtgaca gatcgaagga agaaagtgta ataagacgac tctcactact cgatcgctag   6180
tgattgtcat tgttatatat aataatgtta tctttcacaa cttatcgtaa tgcatgtgaa   6240
actataacac attaatccta cttgtcatat gataacactc tccccattta aaactcttgt   6300
caatttaaag atataagatt ctttaaatga ttaaaaaaaa tatattataa attcaatcac   6360
tcctactaat aaattattaa ttattattta ttgattaaaa aaatacttat actaatttag   6420
tctgaataga ataattagat tctagtctca tccccttta aaccaactta gtaaacgttt   6480
ttttttttaa ttttatgaag ttaagttttt accttgtttt taaaaagaat cgttcataag   6540
```

atgccatgcc agaacattag ctacacgtta cacatagcat gcagccgcgg agaattgttt 6600
ttcttcgcca cttgtcactc ccttcaaaca cctaagagct tctctctcac agcacacaca 6660
tacaatcaca tgcgtgcatg cattattaca cgtgatcgcc atgcaaatct cctttatagc 6720
ctataaatta actcatccgc ttcactcttt actcaaacca aaactcatcg atacaaacaa 6780
gattaaaaac atacacgagg atcttttaca acaattacca acaacaacaa acaacaaaca 6840
acattacaat tacatttaca attaccatac catgcctcca agggactctt actcttatgc 6900
tgctcctcct tctgctcaac ttcacgaagt tgatactcct caagagcacg acaagaaaga 6960
gcttgttatc ggagataggg cttacgatgt taccaacttc gttaagagac accctggtgg 7020
aaagatcatt gcttaccaag ttggaactga tgctaccgat gcttacaagc agttccatgt 7080
tagatctgct aaggctgaca agatgcttaa gtctcttcct tctcgtcctg ttcacaaggg 7140
atactctcca agaagggctg atcttatcgc tgatttccaa gagttcacca agcaacttga 7200
ggctgaggga atgttcgagc cttctcttcc tcatgttgct tacagacttg ctgaggttat 7260
cgctatgcat gttgctggtg ctgctcttat ctggcatgga tacactttcg ctggaatcgc 7320
tatgcttgga gttgttcagg gaagatgtgg atggcttatg catgagggtg gacattactc 7380
tctcactgga aacattgctt tcgacagagc tatccaagtt gcttgttacg gacttggatg 7440
tggaatgtct ggtgcttggt ggcgtaacca gcataacaag caccatgcta ctcctcaaaa 7500
gcttcagcac gatgttgatc ttgataccct tcctctcgtt gctttccatg agagaatcgc 7560
tgctaaggtt aagtctcctg ctatgaaggc ttggctttct atgcaagcta agcttttcgc 7620
tcctgttacc actcttcttg ttgctcttgg atggcagctt taccttcatc ctagacacat 7680
gctcaggact aagcactacg atgagcttgc tatgctcgga atcagatacg gacttgttgg 7740
ataccttgct gctaactacg gtgctggata cgttctcgct tgttaccttc tttacgttca 7800
gcttggagct atgtacatct tctgcaactt cgctgtttct catactcacc tccctgttgt 7860
tgagcctaac gagcatgcta cttgggttga gtacgctgct aaccacacta ctaactgttc 7920
tccatcttgg tggtgtgatt ggtggatgtc ttaccttaac taccagatcg agcaccacct 7980
ttacccttct atgcctcaat tcagacaccc taagatcgct cctagagtta agcagctttt 8040
cgagaagcac ggacttcact acgatgttag aggatacttc gaggctatgg ctgatacttt 8100
cgctaacctt gataacgttg cccatgctcc tgagaagaaa atgcagtaat gagatcgttc 8160
aaacatttgg caataaagtt tcttaagatt gaatcctgtt gccggtcttg cgatgattat 8220
catataattt ctgttgaatt acgttaagca cgtaataatt aacatgtaat gcatgacgtt 8280
atttatgaga tgggttttta tgattagagt cccgcaatta tacatttaat acgcgataga 8340
aaacaaaata tagcgcgcaa actaggataa attatcgcgc gcggtgtcat ctatgttact 8400
agatcggtcg attaaaaatc ccaattatat ttggtctaat ttagtttggt attgagtaaa 8460
acaaattcga accaaaccaa aatataaata tatagttttt atatatatgc ctttaagact 8520
ttttatagaa ttttctttaa aaaatatcta gaaatatttg cgactcttct ggcatgtaat 8580
atttcgttaa atatgaagtg ctccattttt attaacttta aataattggt tgtacgatca 8640
ctttcttatc aagtgttact aaaatgcgtc aatctctttg ttcttccata ttcatatgtc 8700
aaaatctatc aaaattctta tatatctttt tcgaatttga agtgaaattt cgataattta 8760
aaattaaata gaacatatca ttatttaggt atcatattga tttttatact taattactaa 8820
atttggttaa ctttgaaagt gtacatcaac gaaaaattag tcaaacgact aaaataaata 8880

-continued aatatcatgt gttattaaga aaattctcct ataagaatat tttaatagat catatgtttg 8940
taaaaaaaat taatttttac taacacatat atttacttat caaaaatttg acaaagtaag 9000
attaaaataa tattcatcta acaaaaaaaa aaccagaaaa tgctgaaaac ccggcaaaac 9060
cgaaccaatc caaaccgata tagttggttt ggtttgattt tgatataaac cgaaccaact 9120
cggtccattt gcacccctaa tcataatagc tttaatattt caagatatta ttaagttaac 9180
gttgtcaata tcctggaaat tttgcaaaat gaatcaagcc tatatggctg taatatgaat 9240
ttaaaagcag ctcgatgtgg tggtaatatg taatttactt gattctaaaa aaatatccca 9300
agtattaata atttctgcta ggaagaaggt tagctacgat ttacagcaaa gccagaatac 9360
aaagaaccat aaagtgattg aagctcgaaa tatacgaagg aacaaatatt tttaaaaaaa 9420
tacgcaatga cttggaacaa aagaaagtga tatatttttt gttcttaaac aagcatcccc 9480
tctaaagaat ggcagttttc ctttgcatgt aactattatg ctcccttcgt tacaaaaatt 9540
ttggactact attgggaact tcttctgaaa atagtgatag aacccacacg agcatgtgct 9600
ttccatttaa ttttaaaaac caagaaacat acatacataa cattccatca gcctctctct 9660
ctttttatta cggttaatga cttaaaacac atcttattat cccatcctta acacctagca 9720
gtgtctttat acgatctcat cgatcaccac ttcaaaacca tgcagactgc tgctgcccct 9780
ggagctggca tcggctaggc tgggtgccgc actgtcccgg aaggtcccta gcgacttgtt 9840
tagattgatg ggaccacctc tcaacttcct gctgctgtcc ctgctgctgg atgtcctgcc 9900
tcatctggcc gattgcacgc tccagtcccc tgcatgtgca ctcgctcctc aattgcttaa 9960
gatcatcgca gcagctatcg aagtgctggc tctgttgccc tcctccacgg ccttggttgt 10020
agtagtagct gccgccgccc ttctggactt tttcccacag gaaccgccga ataattcgat 10080
agaaccacac gagcatgtgc tttcatttat tttaaaaacc aagaaacata cataacattt 10140
catcagcctc tctctctctc tctctctctc tctctctctc tctctctctc tctctctctt 10200
tattacagct gttacactaa cttaaaacac attcatctca ttattattat tattatccat 10260
ccttaacacc tagcagtgtc tttgtacgat ctcataatcg atcacccctt catcaggtat 10320
ccttaggctt cactccaacg ttgttgcagt tacggaacat gtacacacca tcatggttct 10380
caacgaactg gcaagatctc caagttttcc aaaggctaac ccacatgttc tcatcggtgt 10440
gtctgtagtg ctctcccata actttcttga tgcactcggt agcttctcta gcatggtaga 10500
atgggatcct tgaaacgtag tgatggagca catgagtctc gatgatgtca tggaagatga 10560
ttccgaggat tccgaactct ctatcgatag tagcagcagc acccttagcg aaagtccact 10620
cttgagcatc gtaatgaggc atagaagaat cggtgtgctg aaggaaggta acgaaaacaa 10680
gccagtggtt aacaaggatc caaggacaga accatgtgat gaaagtaggc cagaatccga 10740
aaaccttgta agcggtgtaa acagaagtga gggtagcaag gattccaaga tcagaaagaa 10800
cgatgtacca gtagtccttc ttatcgaaaa cagggctaga aggccagtag tgagacttga 10860
agaacttaga aacaccaggg taaggttgtc cagtagcgtt agtagcaagg taaagagaaa 10920
gtcctccaag ctgttggaac aagagagcga aaacagagta gataggagtt tcctcagcga 10980
tatcgtgaag gctggtaact tggtgcttct ctttgaattc ctcggcggtg taaggaacga 11040
aaaccatatc tctggtcatg tgtccagtag ccttatggtg cttagcatga gagaacttcc 11100
agctgaagta aggaaccata acaagagagt ggagaaccca tccaacggta tcgttaaccc 11160
atccgtagtt agagaaagca gaatgtccac actcatgtcc aaggatccag attccgaatc 11220
cgaaacaaga gatagagaac acgtaagcag accaagcagc gaatctaagg aattcgttag 11280

```
ggagaagagg gatgtaggta agtccaacgt aagcgatagc agagatagcc acgatatctc  11340
tcaccacgta agacatagac ttcacgagag atctctcgta acagtgctta gggatagcgt  11400
caaggatatc cttgatggtg taatctggca ccttgaaaac gtttccgaag gtatcgatag  11460
cggtcttttg ctgcttgaaa gatgcaacgt ttccagaacg cctaacggtc ttagtagatc  11520
cctcaaggat ctcagatcca gacacggtaa ccttagacat ggtatggtaa ttgtaaatgt  11580
aattgtaatg ttgtttgttg tttgttgttg ttggtaattg ttgtaaaatt tttggtggtg  11640
attggttctt taaggtgtga gagtgagttg tgagttgtgt ggtgggtttg gtgagattgg  11700
ggatggtggg tttatatagt ggagactgag gaatggggtc gtgagtgtta actttgcatg  11760
ggctacacgt gggttctttt gggcttacac gtagtattat tcatgcaaat gcagccaata  11820
catatacggt attttaataa tgtgtgggaa tacaatatgc cgagtatttt actaattttg  11880
gcaatgacaa gtgtacattt ggattatctt acttggcctc tcttgcttta atttggatta  11940
tttttattct cttaccttgg ccgttcatat tcacatccct aaaggcaaga cagaattgaa  12000
tggtggccaa aaattaaaac gatggatatg acctacatag tgtaggatca attaacgtcg  12060
aaggaaaata ctgattctct caagcatacg gacaagggta aataacatag tcaccagaac  12120
ataataaaca aaaagtgcag aagcaagact aaaaaaatta gctatggaca ttcaggttca  12180
tattggaaac atcattatcc tagtcttgtg accatccttc ctcctgctct agttgagagg  12240
ccttgggact aacgagaggt cagttgggat agcagatcct tatcctggac tagcctttct  12300
ggtgtttcag agtcttcgtg ccgccgtcta catctatctc cattaggtct gaagatgact  12360
cttcacacca acgacgttta aggtctctat cctactccta gcttgcaata cctggcttgc  12420
aatacctgga gcatcgtgca cgatgattgg atactgtgga ggaggagtgt ttgctgattt  12480
agagctcccg gttgggtgat ttgacttcga tttcagttta ggcttgttga aatttttcag  12540
gttccattgt gaagccttta gagcttgagc ttccttccat gttaatgcct tgatcgaata  12600
ctcctagaga aaagggaagt cgatctctga gtattgaaat cgaagtgcac atttttttc  12660
aacgtgtcca atcaatccac aaacaaagca gaagacaggt aatctttcat acttatactg  12720
acaagtaata gtcttaccgt catgcataat aacgtctcgt tccttcaaga ggggttttcc  12780
gacatccata acgacccgaa gcctcatgaa agcattaggg aagaactttt ggttcttctt  12840
gtcatggcct ttataggtgt cagccgagct cgccaattcc cgtccgactg gctccgcaaa  12900
atattcgaac ggcaagttat ggacttgcaa ccataactcc acggtattga gcaggaccta  12960
ttgtgaagac tcatctcatg gagcttcaga atgtggttgt cagcaaacca atgaccgaaa  13020
tccatcacat gacggacgtc cagtgggtga gcgaaacgaa acaggaagcg cctatctttc  13080
agagtcgtga gctccacacc ggattccggc aactacgtgt tgggcaggct tcgccgtatt  13140
agagatatgt tgaggcagac ccatctgtgc cactcgtaca attacgagag ttgttttttt  13200
tgtgattttc ctagtttctc gttgatggtg agctcatatt ctacatcgta tggtctctca  13260
acgtcgtttc ctgtcatctg atatcccgtc atttgcatcc acgtgcgccg cctcccgtgc  13320
caagtcccta ggtgtcatgc acgccaaatt ggtggtggtg cgggctgccc tgtgcttctt  13380
accgatgggt ggaggttgag tttgggggtc tccgcggcga tggtagtggg ttgacggttt  13440
ggtgtgggtt gacggcattg atcaatttac ttcttgcttc aaattctttg gcagaaaaca  13500
attcattaga ttagaactgg aaaccagagt gatgagacgg attaagtcag attccaacag  13560
agttacatct cttaagaaat aatgtaaccc ctttagactt tatatatttg caattaaaaa  13620
```

-continued

```
aataatttaa cttttagact ttatatatag ttttaataac taagtttaac cactctatta  13680
tttatatcga aactatttgt atgtctcccc tctaaataaa cttggtattg tgtttacaga  13740
acctataatc aaataatcaa tactcaactg aagtttgtgc agttaattga agggattaac  13800
ggccaaaatg cactagtatt atcaaccgaa tagattcaca ctagatggcc atttccatca  13860
atatcatcgc cgttcttctt ctgtccacat atcccctctg aaacttgaga gacacctgca  13920
cttcattgtc cttattacgt gttacaaaat gaaacccatg catccatgca aactgaagaa  13980
tggcgcaaga acccttcccc tccatttctt atgtggcgac catccatttc accatctccc  14040
gctataaaac acccccatca cttcacctag aacatcatca ctacttgctt atccatccaa  14100
aagataccca cttttacaac aattaccaac aacaacaaac aacaaacaac attacaatta  14160
catttacaat taccatacca tgccacctag cgctgctaag caaatgggag cttctactgg  14220
tgttcatgct ggtgttactg actcttctgc tttcaccaga aaggatgttg ctgatagacc  14280
tgatctcacc atcgttggag attctgttta cgatgctaag gctttcagat ctgagcatcc  14340
tggtggtgct catttcgttt ctttgttcgg aggaagagat gctactgagg ctttcatgga  14400
ataccataga agggcttggc ctaagtctag aatgtctaga ttccacgttg gatctcttgc  14460
ttctactgag gaacctgttg ctgctgatga gggatacctt caactttgtg ctaggatcgc  14520
taagatggtg ccttctgttt cttctggatt cgctcctgct tcttactggg ttaaggctgg  14580
acttatcctt ggatctgcta tcgctcttga ggcttacatg ctttacgctg gaaagagact  14640
tctcccttct atcgttcttg gatggctttt cgctcttatc ggtcttaaca tccagcatga  14700
tgctaaccat ggtgctttgt ctaagtctgc ttctgttaac cttgctcttg gactttgtca  14760
ggattggatc ggaggatcta tgatcctttg gcttcaagag catgttgtta tgcaccacct  14820
ccacactaac gatgttgata aggatcctga tcaaaaggct cacggtgctc ttagactcaa  14880
gcctactgat gcttggtcac ctatgcattg gcttcagcat ctttaccttt tgcctggtga  14940
gactatgtac gctttcaagc ttttgttcct cgacatctct gagcttgtta tgtggcgttg  15000
ggagggtgag cctatctcta agcttgctgg atacctcttt atgccttctt tgcttctcaa  15060
gcttaccttc tgggctagat tcgttgcttt gcctctttac cttgctcctt ctgttcatac  15120
tgctgtgtgt atcgctgcta ctgttatgac tggatctttc tacctcgctt tcttcttctt  15180
catctcccac aacttcgagg gtgttgcttc tgttggacct gatggatcta tcacttctat  15240
gactagaggt gctagcttcc ttaagagaca agctgagact tcttctaacg ttggaggacc  15300
tcttcttgct actcttaacg gtggactcaa ctaccaaatt gagcatcact tgttccctag  15360
agttcaccat ggattctacc ctagacttgc tcctcttgtt aaggctgagc ttgaggctag  15420
aggaatcgag tacaagcact accctactat ctggtctaac cttgcttcta ccctcagaca  15480
tatgtacgct cttggaagaa ggcctagatc taaggctgag taatgacaag cttatgtgac  15540
gtgaaataat aacggtaaaa tatatgtaat aataataata ataaagccac aaagtgagaa  15600
tgaggggaag gggaaatgtg taatgagcca gtagccggtg gtgctaattt tgtatcgtat  15660
tgtcaataaa tcatgaattt tgtggttttt atgtgttttt ttaaatcatg aattttaaat  15720
tttataaaat aatctccaat cggaagaaca acattccata tccatgcatg gatgtttctt  15780
tacccaaatc tagttcttga gaggatgaag catcaccgaa cagttctgca actatccctc  15840
aaaagcttta aaatgaacaa caaggaacag agcaacgttc caaagatccc aaacgaaaca  15900
tattatctat actaatacta tattattaat tactactgcc cggaatcaca atccctgaat  15960
gattcctatt aactacaagc cttgttggcg gcggagaagt gatcggcgcg gcgagaagca  16020
```

gcggactcgg agacgaggcc ttggaagatc tgagtcgaac gggcagaatc agtattttcc 16080
ttcgacgtta attgatccta cactatgtag gtcatatcca tcgttttaat ttttggccac 16140
cattcaattc tgtcttgcct ttagggatgt gaatatgaac ggccaaggta agagaataaa 16200
aataatccaa attaaagcaa gagaggccaa gtaagataat ccaaatgtac acttgtcatt 16260
gccaaaatta gtaaaatact cggcatattg tattcccaca cattattaaa ataccgtata 16320
tgtattggct gcatttgcat gaataatact acgtgtaagc ccaaaagaac ccacgtgtag 16380
cccatgcaaa gttaacactc acgaccccat tcctcagtct ccactatata aacccaccat 16440
ccccaatctc accaaaccca ccacacaact cacaactcac tctcacacct taaagaacca 16500
atcaccacca aaaattttac aacaattacc aacaacaaca aacaacaaac aacattacaa 16560
ttacatttac aattaccata ccatgagcgc tgttaccgtt actggatctg atcctaagaa 16620
cagaggatct tctagcaaca ccgagcaaga ggttccaaaa gttgctatcg ataccaacgg 16680
aaacgtgttc tctgttcctg atttcaccat caaggacatc cttggagcta tccctcatga 16740
gtgttacgag agaagattgg ctacctctct ctactacgtg ttcagagata tcttctgcat 16800
gcttaccacc ggatacctta cccataagat cctttaccct ctcctcatct cttacacctc 16860
taacagcatc atcaagttca ctttctgggc cctttacact tacgttcaag gacttttcgg 16920
aaccggaatc tgggttctcg ctcatgagtg tggacatcaa gctttctctg attacggaat 16980
cgtgaacgat ttcgttggat ggacccttca ctcttacctt atggttcctt acttcagctg 17040
gaagtactct catggaaagc accataaggc tactggacac atgaccagag atatggtttt 17100
cgttcctgcc accaaagagg aattcaagaa gtctaggaac ttcttcggta acctcgctga 17160
gtactctgag gattctccac ttagaaccct ttacgagctt cttgttcaac aacttggagg 17220
atggatcgct tacctcttcg ttaacgttac aggacaacct taccctgatg ttccttcttg 17280
gaaatggaac cacttctggc ttacctctcc actttcgag caaagagatg ctctctacat 17340
cttcctttct gatcttggaa tcctcaccca gggaatcgtt cttactcttt ggtacaagaa 17400
attcggagga tggtcccttt tcatcaactg gttcgttcct tacatctggg ttaaccactg 17460
gctcgttttc atcacattcc ttcagcacac tgatcctact atgcctcatt acaacgctga 17520
ggaatggact ttcgctaagg gtgctgctgc tactatcgat agaaagttcg gattcatcgg 17580
acctcacatc ttccatgata tcatcgagac tcatgtgctt caccactact gttctaggat 17640
cccattctac aacgctagac ctgcttctga ggctatcaag aaagttatgg gaaagcacta 17700
caggtctagc gacgagaaca tgtggaagtc actttggaag tctttcaggt cttgccaata 17760
cgttgacggt gataacggtg ttctcatgtt ccgtaacatc aacaactgcg gagttggagc 17820
tgctgagaag taatgaaggg gtgatcgatt atgagatcgt acaaagacac tgctaggtgt 17880
taaggatgga taataataat aataatgaga tgaatgtgtt ttaagttagt gtaacagctg 17940
taataaagag agagagagag agagagagag agagagagag agagagagag agagagaggc 18000
tgatgaaatg ttatgtatgt ttcttggttt ttaaaataaa tgaaagcaca tgctcgtgtg 18060
gttctatcga attattcggc ggttcctgtg ggaaaaagtc cagaagggcc gccgcagcta 18120
ctactacaac caaggccgtg gaggagggca acagagccag cacttcgata gctgctgcga 18180
tgatcttaag caattgagga gcgagtgcac atgcagggga ctggagcgtg caatcggcca 18240
gatgaggcag gacatccagc agcagggaca gcagcaggaa gttgagaggt ggtcccatca 18300
atctaaacaa gtcgctaggg accttccggg acagtgcggc acccagccta gccgatgcca 18360

-continued

```
gctccagggg cagcagcagt ctgcatggtt ttgaagtggt gatcgatgag atcgtataaa  18420
gacactgcta ggtgttaagg atgggataat aagatgtgtt ttaagtcatt aaccgtaata  18480
aaaagagaga gaggctgatg gaatgttatg tatgtatgtt tcttggtttt taaaattaaa  18540
tggaaagcac atgctcgtgt gggttctatc tcgattaaaa atcccaatta tatttggtct  18600
aatttagttt ggtattgagt aaaacaaatt cgaaccaaac caaaatataa atatatagtt  18660
tttatatata tgcctttaag actttttata gaattttctt taaaaaatat ctagaaatat  18720
ttgcgactct tctggcatgt aatatttcgt taaatatgaa gtgctccatt tttattaact  18780
ttaaataatt ggttgtacga tcactttctt atcaagtgtt actaaaatgc gtcaatctct  18840
ttgttcttcc atattcatat gtcaaaatct atcaaaattc ttatatatct ttttcgaatt  18900
tgaagtgaaa tttcgataat ttaaaattaa atagaacata tcattattta ggtatcatat  18960
tgatttttat acttaattac taaatttggt taactttgaa agtgtacatc aacgaaaaat  19020
tagtcaaacg actaaaataa ataaatatca tgtgttatta agaaaattct cctataagaa  19080
tattttaata gatcatatgt ttgtaaaaaa aattaatttt tactaacaca tatatttact  19140
tatcaaaaat ttgacaaagt aagattaaaa taatattcat ctaacaaaaa aaaaaccaga  19200
aaatgctgaa aacccggcaa aaccgaacca atccaaaccg atatagttgg tttggtttga  19260
ttttgatata aaccgaacca actcggtcca tttgcacccc taatcataat agctttaata  19320
tttcaagata ttattaagtt aacgttgtca atatcctgga aattttgcaa aatgaatcaa  19380
gcctatatgg ctgtaatatg aatttaaaag cagctcgatg tggtggtaat atgtaattta  19440
cttgattcta aaaaaatatc ccaagtatta ataatttctg ctaggaagaa ggttagctac  19500
gatttacagc aaagccagaa tacaaagaac cataaagtga ttgaagctcg aaatatacga  19560
aggaacaaat atttttaaaa aaatacgcaa tgacttggaa caaaagaaag tgatatattt  19620
tttgttctta aacaagcatc ccctctaaag aatggcagtt ttcctttgca tgtaactatt  19680
atgctccctt cgttacaaaa attttggact actattggga acttcttctg aaaatagtcc  19740
tgcaggctag tagattggtt ggttggtttc catgtaccag aaggcttacc ctattagttg  19800
aaagttgaaa ctttgttccc tactcaattc ctagttgtgt aaatgtatgt atatgtaatg  19860
tgtataaaac gtagtactta aatgactagg agtggttctt gagaccgatg agagatggga  19920
gcagaactaa agatgatgac ataattaaga acgaatttga aaggctctta ggtttgaatc  19980
ctattcgaga atgtttttgt caaagatagt ggcgattttg aaccaaagaa aacatttaaa  20040
aaatcagtat ccggttacgt tcatgcaaat agaaagtggt ctaggatctg attgtaattt  20100
tagacttaaa gagtctctta agattcaatc ctggctgtgt acaaaactac aaataatata  20160
ttttagacta tttggcctta actaaacttc cactcattat ttactgaggt tagagaatag  20220
acttgcgaat aaacacattc ccgagaaata ctcatgatcc cataattagt cagagggtat  20280
gccaatcaga tctaagaaca cacattccct caaattttaa tgcacatgta atcatagttt  20340
agcacaattc aaaaataatg tagtattaaa gacagaaatt tgtagacttt tttttggcgt  20400
taaaagaaga ctaagtttat acgtacattt tattttaagt ggaaaaccga aattttccat  20460
cgaaatatat gaatttagta tatatatttc tgcaatgtac tattttgcta ttttggcaac  20520
tttcagtgga ctactacttt attacaatgt gtatggatgc atgagtttga gtatacacat  20580
gtctaaatgc atgctttgta aaacgtaacg gaccacaaaa gaggatccat acaaatacat  20640
ctcatagctt cctccattat tttccgacac aaacagagca ttttacaaca attaccaaca  20700
acaacaaaca acaaacaaca ttacaattac atttacaatt accataccat ggaatttgct  20760
```

caacctctcg ttgctatggc tcaagagcag tacgctgcta tcgatgctgt tgttgctcct 20820
gctatcttct ctgctaccga ctctattgga tggggactca agcctatctc ttctgctact 20880
aaggatctcc ctctcgttga atctcctacc cctcttatcc tttctctcct cgcttacttc 20940
gctatcgttg gttctggact cgtttaccgt aaagtgttcc ctagaaccgt taagggacag 21000
gatcctttcc ttctcaaggc tcttatgctc gctcacaacg ttttccttat cggactcagc 21060
ctttacatgt gcctcaagct cgtttacgag gcttacgtga acaagtactc cttctgggga 21120
aacgcttaca accctgctca aaccgagatg gctaaggtga tctggatctt ctacgtgtcc 21180
aagatctacg agttcatgga caccttcatc atgcttctca agggaaacgt taaccaggtt 21240
tccttcctcc atgtttacca ccacggatct atctctggaa tctggtggat gatcacttat 21300
gctgctccag gtggagatgc ttacttctct gctgctctca actcttgggt tcatgtgtgc 21360
atgtacacct actacttcat ggctgctgtt cttcctaagg acgaaaagac caagagaaag 21420
tacctttggt ggggaagata ccttacccag atgcaaatgt tccagttctt catgaacctt 21480
ctccaggctg tttacctcct ctactcttct tctccttacc ctaagttcat tgctcaactc 21540
ctcgttgttt acatggttac cctcctcatg cttttcggaa acttctacta catgaagcac 21600
cacgcttcta agtgataagg gccgccgcca tgtgacagat cgaaggaaga aagtgtaata 21660
agacgactct cactactcga tcgctagtga ttgtcattgt tatatataat aatgttatct 21720
ttcacaactt atcgtaatgc atgtgaaact ataacacatt aatcctactt gtcatatgat 21780
aacactctcc ccatttaaaa ctcttgtcaa tttaaagata taagattctt taaatgatta 21840
aaaaaaatat attataaatt caatcactcc tactaataaa ttattaatta ttatttattg 21900
attaaaaaaa tacttatact aatttagtct gaatagaata attagattct agcctgcagg 21960
gcggccgcgg atcccatgga gtcaaagatt caaatagagg acctaacaga actcgccgta 22020
aagactggcg aacagttcat acagagtctc ttacgactca atgacaagaa gaaaatcttc 22080
gtcaacatgg tggagcacga cacacttgtc tactccaaaa atatcaaaga tacagtctca 22140
gaagaccaaa gggcaattga gacttttcaa caaagggtaa tatccggaaa cctcctcgga 22200
ttccattgcc cagctatctg tcactttatt gtgaagatag tggaaaagga aggtggctcc 22260
tacaaatgcc atcattgcga taaaggaaag gccatcgttg aagatgcctc tgccgacagt 22320
ggtcccaaag atggaccccc acccacgagg agcatcgtgg aaaaagaaga cgttccaacc 22380
acgtcttcaa agcaagtgga ttgatgtgat atctccactg acgtaaggga tgacgcacaa 22440
tcccactatc cttcgcaaga cccttcctct atataaggaa gttcatttca tttggagaga 22500
acacggggga ctgaattaaa tatgagccct gagaggcgtc ctgttgaaat cagacctgct 22560
actgctgctg atatggctgc tgtttgtgat atcgtgaacc actacatcga gacttctacc 22620
gttaacttca gaactgagcc tcaaactcct caagagtgga tcgatgatct tgagagactc 22680
caagatagat acccttggct tgttgctgag gttgagggtg ttgttgctgg aatcgcttac 22740
gctggacctt ggaaggctag aaacgcttac gattggactg ttgagtctac cgtttacgtt 22800
tcacacagac atcagagact tggacttgga tctacccttt acactcacct tctcaagtct 22860
atggaagctc agggattcaa gtctgttgtt gctgttatcg gactccctaa cgatccttct 22920
gttagacttc atgaggctct tggatacact gctagaggaa ctcttagagc tgctggatac 22980
aagcacggtg gatggcatga tgttggattc tggcaaagag atttcgagct tcctgctcct 23040
cctagacctg ttagaccagt tactcagatc tgaatttgcg tgatcgttca aacatttggc 23100

```
aataaagttt cttaagattg aatcctgttg ccggtcttgc gatgattatc atataatttc  23160

tgttgaatta cgttaagcat gtaataatta acatgtaatg catgacgtta tttatgagat  23220

gggtttttat gattagagtc ccgcaattat acatttaata cgcgatagaa aacaaaatat  23280

agcgcgcaaa ctaggataaa ttatcgcgcg cggtgtcatc tatgttacta gatcactagt  23340

gatgtacggt taaaaccacc ccagtacatt aaaaacgtcc gcaatgtgtt attaagttgt  23400

ctaagcgtca atttgtttac accacaatat atcctgccac cagccagcca acagctcccc  23460

gaccggcagc tcggcacaaa atcaccactc gatacaggca gcccatcagt cc          23512


<210> SEQ ID NO 3
<211> LENGTH: 25787
<212> TYPE: DNA
<213> ORGANISM: Artificial Sequence
<220> FEATURE:
<223> OTHER INFORMATION: pGA7- mod_C nucleotide sequence

<400> SEQUENCE: 3

tcctgtggtt ggcatgcaca tacaaatgga cgaacggata aaccttttca cgccctttta     60

aatatccgat tattctaata aacgctcttt tctcttaggt ttacccgcca atatatcctg    120

tcaaacactg atagtttaaa ctgaaggcgg gaaacgacaa tctgctagtg gatctcccag    180

tcacgacgtt gtaaaacggg cgccccgatc tagtaacata gatgacaccg cgcgcgataa    240

tttatcctag tttgcgcgct atattttgtt ttctatcgcg tattaaatgt ataattgcgg    300

gactctaatc ataaaaaccc atctcataaa taacgtcatg cattacatgt taattattac    360

gtgcttaacg taattcaaca gaaattatat gataatcatc gcaagaccgg caacaggatt    420

caatcttaag aaactttatt gccaaatgtt tgaacgatct gcccggaagc ggccaactcg    480

aaaatttaat taatcatcag tgagccttct cagcctttcc gttaacgtag tagtgctgtc    540

caactttgtc gaggttgctg aaagtagcct tccaagcacc gtagtaagag agcaccttgt    600

agttgagtcc ccacttctta gcgaaaggga cgaatcttct tgacacctca ggctgtctga    660

attgaggcat atcagggaag agatggtgga taacctggca gttaaggtat cccataagcc    720

agttaacgta tccacgagaa ggatcgatgt caacggtgtg atcaacagcg tagttaaccc    780

agctaaggtg cttgtcagat ggaacaacag ggaggtgagt gtgagaagta gagaagtgag    840

cgaagaggta catgtaagcg atccagtttc cgaaagtgaa ccaccagtaa gcaacaggcc    900

aagagtatcc ggtagcaagc ttgataacag cggttctaac aacgtgagaa acgagcatcc    960

aagaagcttc ctcgtagttc ttcttcctga gcacctgtct aggatggaga acgtagatcc   1020

agaaagcctg aacgagaagt ccagaagtaa caggaacgaa ggtccaagct tgaagtctag   1080

cccaagctct agagaatccc ctaggtctat tatcctccac agcggtgttg aagaaagcca   1140

cagcaggagt ggtatcaaga tccatgtcgt gtctaacttt ctgaggggta gcatggtgct   1200

tgttatgcat ctggttccac atctctccgc tggtagaaag tccgaatccg caagtcatag   1260

cctgaagtct cttatccacg tacacagatc cggtaagaga gttgtgtcca ccctcatgtt   1320

gaacccatcc acatctagct ccgaagaaag caccgtacac aacgctagca atgatagggt   1380

atccagcgta cataagagcg gttccaagag cgaaagtagc aagaagctcc aaaagacggt   1440

aagcaacatg ggtgatagaa ggcttgaaga atccgtccct ctcaagttca gctctccacc   1500

tagcgaaatc ctcaagcata ggagcatcct cagactcaga tctcttgatc tcagcaggtc   1560

tagaaggcaa agctctaagc atcttccaag ccttgaggct acgcatgtga aattctttga   1620

aagcctcagt agcatcagca ccagtgttag caagcatgta gaagatcacg cttccaccag   1680
```

-continued

```
gatgtttgaa gttggtcacg tcgtactcaa catcctcaac cctaacccat ctagtctcga   1740
aggtagcagc aagttcatga ggctcaaggg tcttaagatc aacaggagcg gtagaagcat   1800
ccttagcatc aagagcctca gcagatgact tagacctggt gagaggagat ctaggagaag   1860
atcttccatc ggtcttagga ggacacatgg cgcgccgatt ttcgagatgg taattgtaaa   1920
tgtaattgta atgttgtttg ttgtttgttg ttgttggtaa ttgttgtaaa attcgagttg   1980
gccgcttccg gggatcctcg tgtatgtttt taatcttgtt tgtatcgatg agttttggtt   2040
tgagtaaaga gtgaagcgga tgagttaatt tataggctat aaaggagatt tgcatggcga   2100
tcacgtgtaa taatgcatgc acgcatgtga ttgtatgtgt gtgctgtgag agagaagctc   2160
ttaggtgttt gaagggagtg acaagtggcg aagaaaaaca attctccgcg gctgcatgct   2220
atgtgtaacg tgtagctaat gttctggcat ggcatcttat gaacgattct ttttaaaaac   2280
aaggtaaaaa cttaacttca taaaattaaa aaaaaaaacg tttactaagt tggtttaaaa   2340
ggggatgaga ggcgccccgc ggaaagcttg ctagccaatt ggggcccaac gttctcgagt   2400
ttttctagaa ggaaactgaa ggcgggaaac gacaatctgc tagtggatct cccagtcacg   2460
acgttgtaaa acgggcgccc cgcggaaagc ttgcggccgc ggtaccgccc gttcgactca   2520
gatcttccaa ggcctcgtct ccgagtccgc tgcttctcgc cgcgccgatc acttctccgc   2580
cgccaacaag gcttgtagtt aataggaatc attcagggat tgtgattccg ggcagtagta   2640
attaataata tagtattagt atagataata tgtttcgttt gggatctttg gaacgttgct   2700
ctgttccttg ttgttcattt taaagctttt gagggatagt tgcagaactg ttcggtgatg   2760
cttcatcctc tcaagaacta gatttgggta aagaaacatc catgcatgga tatggaatgt   2820
tgttcttccg attggagatt attttataaa atttaaaatt catgatttaa aaaaacacat   2880
aaaaaccaca aaattcatga tttattgaca atacgataca aaattagcac caccggctac   2940
tggctcatta cacatttccc cttcccctca ttctcacttt gtggctttat tattattatt   3000
attacatata ttttaccgtt attatttcac gtcacataag cttgttaatt aatcattagt   3060
gagccttctc agcctttccg ttaacgtagt agtgctgtcc caccttatca aggttagaga   3120
aagtagcctt ccaagcaccg tagtaagaga gcaccttgta gttgagtccc cacttcttag   3180
cgaaaggaac gaatcttctg ctaacctcag gctgtctgaa ttgaggcata tcagggaaga   3240
ggtggtggat aacctgacag ttaaggtatc ccataagcca gttcacgtat cctctagaag   3300
gatcgatatc aacggtgtga tcaacagcgt agttaaccca agaaaggtgc ttatcagatg   3360
gaacaacagg gaggtgagta tgagaagtag agaagtgagc gaaaaggtac atgtaagcga   3420
tccagtttcc gaaagtgaac caccagtaag caacaggcca agagtatcca gtagcaagct   3480
tgataacagc ggttctaaca acatgagaaa cgagcatcca agaagcctct tcgtagttct   3540
tcttacggag aacttgtcta gggtggagaa cgtagatcca gaaagcttga acaagaagtc   3600
cagaggtaac aggaacgaaa gtccaagctt gaagtctagc ccaagctcta gagaatcctc   3660
taggtctgtt atcctcaaca gcagtgttga agaaagccac agcaggagtg gtatcaagat   3720
ccatatcgtg tctaaccttt tgaggggtag catggtgctt gttatgcatc tggttccaca   3780
tctcaccaga agtagaaagt ccgaatccac aagtcatagc ctgaagtctc ttgtccacgt   3840
aaacagatcc ggtaagagag ttatgtccac cctcatgttg aacccatcca catctagctc   3900
cgaagaaagc accgtaaaca acagaagcaa tgatagggta tccagcgtac ataagagcag   3960
ttccaagagc gaatgtagca agaagctcga gaagtctgta agccacatgg gtgatagaag   4020
```

```
gcttgaagaa tccatctctc tcaagctcag cacgccatct agcgaaatcc tcaagcatag    4080

gagcatcctc agactcagat ctcttgatct cagcaggtct agaaggcaaa gctctaagca    4140

tcttccaagc cttgagagaa cgcatgtgga attctttgaa agcctcagta gcatcagcac    4200

cagtgttagc aagcatgtag aagatcacag atccaccagg gtgcttgaag ttagtcacat    4260

cgtactcaac gtcctcaact ctaacccatc tagtctcgaa agtagcagca agctcatgag    4320

gctcaagagt cttaagatca acaggagcag tagaagcatc cttagcatca agagcctcag    4380

cagaagattt agacctggta agtggagatc taggagaaga tcttccatca gtcttaggag    4440

ggcacatggt atggtaattg taaatgtaat tgtaatgttg tttgttgttt gttgttgttg    4500

gtaattgttg taaaattaat taagtgggta tcttttggat ggataagcaa gtagtgatga    4560

tgttctaggt gaagtgatgg gggtgtttta tagcgggaga tggtgaaatg gatggtcgcc    4620

acataagaaa tggaggggaa gggttcttgc gccattcttc agtttgcatg gatgcatggg    4680

tttcattttg taacacgtaa taaggacaat gaagtgcagg tgtctctcaa gtttcagagg    4740

ggatatgtgg acagaagaag aacggcgatg atattgatgg aaatggccat ctagtgtgaa    4800

tctattcggt tgataatact agtgcatttt ggccgttaat cccttcaatt aactgcacaa    4860

acttcagttg agtattgatt atttgattat aggttctgta aacacaatac caagtttatt    4920

tagaggggag acatacaaat agtttcgata taaataatag agtggttaaa cttagttatt    4980

aaaactatat ataaagtcta aaagttaaat tattttttta attgcaaata tataaagtct    5040

aaaggggtta cattatttct taagagatgt aactctgttg gaatctgact taatccgtct    5100

catcactctg gtttccagtt ctaatctaat gaattgtttt ctgccaaaga atttgaagca    5160

agaagtaaat tgatcaatgc cgtcaaccca caccaaaccg tcaacccact accatcgccg    5220

cggagacccc caaactcaac ctccacccat cggtaagaag cacagggcag cccgcaccac    5280

caccaatttg gcgtgcatga cacctaggga cttggcacgg gaggcggcgc acgtggatgc    5340

aaatgacggg atatcagatg acaggaaacg acgttgagag accatacgat gtagaatatg    5400

agctcaccat caacgagaaa ctaggaaaat cacaaaaaaa acaactctcg taattgtacg    5460

agtggcacag atgggtctgc ctcaacatat ctctaatacg gcgaagcctg cccaacacgt    5520

agttgccgga atccggtgtg gagctcacga ctctgaaaga taggcgcttc ctgtttcgtt    5580

tcgctcaccc actggacgtc cgtcatgtga tggatttcgg tcattggttt gctgacaacc    5640

acattctgaa gctccatgag atgagtcttc acaataggtc ctgctcaata ccgtggagtt    5700

atggttgcaa gtccataact tgccgttcga atattttgcg gagccagtcg gacgggaatt    5760

ggcgagctcg gctgacacct ataaaggcca tgacaagaag aaccaaaagt tcttccctaa    5820

tgctttcatg aggcttcggg tcgttatgga tgtcggaaaa cccctcttga aggaacgaga    5880

cgttattatg catgacggta agactattac ttgtcagtat aagtatgaaa gattacctgt    5940

cttctgcttt gtttgtggat tgattggaca cgttgaaaaa aaatgtgcac ttcgatttca    6000

atactcagag atcgacttcc cttttctcta ggagtattcg atcaaggcat taacatggaa    6060

ggaagctcaa gctctaaagg cttcacaatg gaacctgaaa aatttcaaca agcctaaact    6120

gaaatcgaag tcaaatcacc caaccgggag ctctaaatca gcaaacactc ctcctccaca    6180

gtatccaatc atcgtgcacg atgctccagg tattgcaagc caggtattgc aagctaggag    6240

taggatagag accttaaacg tcgttggtgt gaagagtcat cttcagacct aatggagata    6300

gatgtagacg gcggcacgaa gactctgaaa caccagaaag gctagtccag gataaggatc    6360

tgctatccca actgacctct cgttagtccc aaggcctctc aactagagca ggaggaagga    6420
```

tggtcacaag actaggataa tgatgtttcc aatatgaacc tgaatgtcca tagctaattt 6480
ttttagtctt gcttctgcac tttttgttta ttatgttctg gtgactatgt tatttaccct 6540
tgtccgtatg cttgagggta ccctagtaga ttggttggtt ggtttccatg taccagaagg 6600
cttaccctat tagttgaaag ttgaaacttt gttccctact caattcctag ttgtgtaaat 6660
gtatgtatat gtaatgtgta taaaacgtag tacttaaatg actaggagtg gttcttgaga 6720
ccgatgagag atgggagcag aactaaagat gatgacataa ttaagaacga atttgaaagg 6780
ctcttaggtt tgaatcctat tcgagaatgt ttttgtcaaa gatagtggcg attttgaacc 6840
aaagaaaaca tttaaaaaat cagtatccgg ttacgttcat gcaaatagaa agtggtctag 6900
gatctgattg taattttaga cttaaagagt ctcttaagat tcaatcctgg ctgtgtacaa 6960
aactacaaat aatatatttt agactatttg gccttaacta aacttccact cattatttac 7020
tgaggttaga gaatagactt gcgaataaac acattcccga gaaatactca tgatcccata 7080
attagtcaga gggtatgcca atcagatcta agaacacaca ttccctcaaa ttttaatgca 7140
catgtaatca tagtttagca caattcaaaa ataatgtagt attaaagaca gaaatttgta 7200
gacttttttt tggcgttaaa agaagactaa gtttatacgt acattttatt ttaagtggaa 7260
aaccgaaatt ttccatcgaa atatatgaat ttagtatata tatttctgca atgtactatt 7320
ttgctatttt ggcaactttc agtggactac tactttatta caatgtgtat ggatgcatga 7380
gtttgagtat acacatgtct aaatgcatgc tttgtaaaac gtaacggacc acaaaagagg 7440
atccatacaa atacatctca tagcttcctc cattattttc cgacacaaac agagcatttt 7500
acaacaatta ccaacaacaa caaacaacaa acaacattac aattacattt acaattacca 7560
taccatggcc tctatcgcta tccctgctgc tcttgctgga actcttggat acgttaccta 7620
caatgtggct aaccctgata tcccagcttc tgagaaagtt cctgcttact tcatgcaggt 7680
tgagtactgg ggacctacta tcggaactat tggatacctc ctcttcatct acttcggaaa 7740
gcgtatcatg cagaacagat ctcaaccttt cggactcaag aacgctatgc tcgtttacaa 7800
cttctaccag accttcttca acagctactg catctacctt ttcgttactt ctcatagggc 7860
tcagggactt aaggtttggg gaaacatccc tgatatgact gctaactctt ggggaatctc 7920
tcaggttatc tggcttcact acaacaacaa gtacgttgag cttctcgaca ccttcttcat 7980
ggtgatgagg aagaagttcg accagctttc tttccttcac atctaccacc acactcttct 8040
catctggtca tggttcgttg ttatgaagct tgagcctgtt ggagattgct acttcggatc 8100
ttctgttaac accttcgtgc acgtgatcat gtactcttac tacggacttg ctgctcttgg 8160
agttaactgt ttctggaaga agtacatcac ccagatccag atgcttcagt tctgtatctg 8220
tgcttctcac tctatctaca ccgcttacgt tcagaatacc gctttctggc ttccttacct 8280
tcaactctgg gttatggtga acatgttcgt tctcttcgcc aacttctacc gtaagaggta 8340
caagtctaag ggtgctaaga agcagtgata aggcgcgcgg cgcgccgggc cgccgccatg 8400
tgacagatcg aaggaagaaa gtgtaataag acgactctca ctactcgatc gctagtgatt 8460
gtcattgtta tatataataa tgttatcttt cacaacttat cgtaatgcat gtgaaactat 8520
aacacattaa tcctacttgt catatgataa cactctcccc atttaaaact cttgtcaatt 8580
taaagatata agattcttta aatgattaaa aaaaatatat tataaattca atcactccta 8640
ctaataaatt attaattatt atttattgat taaaaaaata cttatactaa tttagtctga 8700
atagaataat tagattctag tctcatcccc ttttaaacca acttagtaaa cgtttttttt 8760

-continued

```
tttaatttta tgaagttaag tttttacctt gtttttaaaa agaatcgttc ataagatgcc   8820
atgccagaac attagctaca cgttacacat agcatgcagc cgcggagaat tgtttttctt   8880
cgccacttgt cactcccttc aaacacctaa gagcttctct ctcacagcac acacatacaa   8940
tcacatgcgt gcatgcatta ttacacgtga tcgccatgca aatctccttt atagcctata   9000
aattaactca tccgcttcac tctttactca aaccaaaact catcgataca aacaagatta   9060
aaaacataca cgaggatctt ttacaacaat taccaacaac aacaaacaac aaacaacatt   9120
acaattacat ttacaattac cataccatgc ctccaaggga ctcttactct tatgctgctc   9180
ctccttctgc tcaacttcac gaagttgata ctcctcaaga gcacgacaag aaagagcttg   9240
ttatcggaga tagggcttac gatgttacca acttcgttaa gagacaccct ggtggaaaga   9300
tcattgctta ccaagttgga actgatgcta ccgatgctta caagcagttc catgttagat   9360
ctgctaaggc tgacaagatg cttaagtctc ttccttctcg tcctgttcac aagggatact   9420
ctccaagaag ggctgatctt atcgctgatt tccaagagtt caccaagcaa cttgaggctg   9480
agggaatgtt cgagccttct cttcctcatg ttgcttacag acttgctgag gttatcgcta   9540
tgcatgttgc tggtgctgct cttatctggc atggatacac tttcgctgga atcgctatgc   9600
ttggagttgt tcagggaaga tgtggatggc ttatgcatga gggtggacat tactctctca   9660
ctggaaacat tgctttcgac agagctatcc aagttgcttg ttacggactt ggatgtggaa   9720
tgtctggtgc ttggtggcgt aaccagcata acaagcacca tgctactcct caaaagcttc   9780
agcacgatgt tgatcttgat acccttcctc tcgttgcttt ccatgagaga atcgctgcta   9840
aggttaagtc tcctgctatg aaggcttggc tttctatgca agctaagctt ttcgctcctg   9900
ttaccactct tcttgttgct cttggatggc agctttacct tcatcctaga cacatgctca   9960
ggactaagca ctacgatgag cttgctatgc tcggaatcag atacggactt gttggatacc  10020
ttgctgctaa ctacggtgct ggatacgttc tcgcttgtta ccttctttac gttcagcttg  10080
gagctatgta catcttctgc aacttcgctg tttctcatac tcacctccct gttgttgagc  10140
ctaacgagca tgctacttgg gttgagtacg ctgctaacca cactactaac tgttctccat  10200
cttggtggtg tgattggtgg atgtcttacc ttaactacca gatcgagcac cacctttacc  10260
cttctatgcc tcaattcaga caccctaaga tcgctcctag agttaagcag cttttcgaga  10320
agcacggact tcactacgat gttagaggat acttcgaggc tatggctgat actttcgcta  10380
accttgataa cgttgcccat gctcctgaga agaaaatgca gtaatgagat cgttcaaaca  10440
tttggcaata aagtttctta agattgaatc ctgttgccgg tcttgcgatg attatcatat  10500
aatttctgtt gaattacgtt aagcacgtaa taattaacat gtaatgcatg acgttattta  10560
tgagatgggt ttttatgatt agagtcccgc aattatacat ttaatacgcg atagaaaaca  10620
aaatatagcg cgcaaactag gataaattat cgcgcgcggt gtcatctatg ttactagatc  10680
ggtcgattaa aaatcccaat tatatttggt ctaatttagt ttggtattga gtaaaacaaa  10740
ttcgaaccaa accaaaatat aaatatatag tttttatata tatgccttta agacttttta  10800
tagaattttc tttaaaaaat atctagaaat atttgcgact cttctggcat gtaatatttc  10860
gttaaatatg aagtgctcca tttttattaa ctttaaataa ttggttgtac gatcactttc  10920
ttatcaagtg ttactaaaat gcgtcaatct ctttgttctt ccatattcat atgtcaaaat  10980
ctatcaaaat tcttatatat ctttttcgaa tttgaagtga aatttcgata atttaaaatt  11040
aaatagaaca tatcattatt taggtatcat attgattttt atacttaatt actaaatttg  11100
gttaactttg aaagtgtaca tcaacgaaaa attagtcaaa cgactaaaat aaataaatat  11160
```

```
catgtgttat taagaaaatt ctcctataag aatattttaa tagatcatat gtttgtaaaa  11220
aaaattaatt tttactaaca catatattta cttatcaaaa atttgacaaa gtaagattaa  11280
aataatattc atctaacaaa aaaaaaacca gaaaatgctg aaaacccggc aaaaccgaac  11340
caatccaaac cgatatagtt ggtttggttt gattttgata taaaccgaac caactcggtc  11400
catttgcacc cctaatcata atagctttaa tatttcaaga tattattaag ttaacgttgt  11460
caatatcctg gaaattttgc aaaatgaatc aagcctatat ggctgtaata tgaatttaaa  11520
agcagctcga tgtggtggta atatgtaatt tacttgattc taaaaaaata tcccaagtat  11580
taataatttc tgctaggaag aaggttagct acgatttaca gcaaagccag aatacaaaga  11640
accataaagt gattgaagct cgaaatatac gaaggaacaa atatttttaa aaaaatacgc  11700
aatgacttgg aacaaaagaa agtgatatat tttttgttct taaacaagca tcccctctaa  11760
agaatggcag ttttcctttg catgtaacta ttatgctccc ttcgttacaa aaattttgga  11820
ctactattgg gaacttcttc tgaaaatagt gatagaaccc acacgagcat gtgctttcca  11880
tttaatttta aaaaccaaga aacatacata cataacattc catcagcctc tctctctttt  11940
tattacggtt aatgacttaa aacacatctt attatcccat ccttaacacc tagcagtgtc  12000
tttatacgat ctcatcgatc accacttcaa aaccatgcag actgctgctg cccctggagc  12060
tggcatcggc taggctgggt gccgcactgt cccggaaggt ccctagcgac ttgtttagat  12120
tgatgggacc acctctcaac ttcctgctgc tgtccctgct gctggatgtc ctgcctcatc  12180
tggccgattg cacgctccag tcccctgcat gtgcactcgc tcctcaattg cttaagatca  12240
tcgcagcagc tatcgaagtg ctggctctgt tgccctcctc cacggccttg gttgtagtag  12300
tagctgccgc cgcccttctg gactttttcc cacaggaacc gccgaataat tcgatagaac  12360
cacacgagca tgtgctttca tttattttaa aaaccaagaa acatacataa catttcatca  12420
gcctctctct ctctctctct ctctctctct ctctctctct ctctctctct ctctttatta  12480
cagctgttac actaacttaa aacacattca tctcattatt attattatta tccatcctta  12540
acacctagca gtgtctttgt acgatctcat aatcgatcac cccttcatca ggtatcctta  12600
ggcttcactc caacgttgtt gcagttacgg aacatgtaca caccatcatg gttctcaacg  12660
aactggcaag atctccaagt tttccaaagg ctaacccaca tgttctcatc ggtgtgtctg  12720
tagtgctctc ccataacttt cttgatgcac tcggtagctt ctctagcatg gtagaatggg  12780
atccttgaaa cgtagtgatg gagcacatga gtctcgatga tgtcatggaa gatgattccg  12840
aggattccga actctctatc gatagtagca gcagcaccct tagcgaaagt ccactcttga  12900
gcatcgtaat gaggcataga agaatcggtg tgctgaagga aggtaacgaa aacaagccag  12960
tggttaacaa ggatccaagg acagaaccat gtgatgaaag taggccagaa tccgaaaacc  13020
ttgtaagcgg tgtaaacaga agtgagggta gcaaggattc caagatcaga aagaacgatg  13080
taccagtagt ccttcttatc gaaaacaggg ctagaaggcc agtagtgaga cttgaagaac  13140
ttagaaacac cagggtaagg ttgtccagta gcgttagtag caaggtaaag agaaagtcct  13200
ccaagctgtt ggaacaagag agcgaaaaca gagtagatag gagtttcctc agcgatatcg  13260
tgaaggctgg taacttggtg cttctctttg aattcctcgg cggtgtaagg aacgaaaacc  13320
atatctctgg tcatgtgtcc agtagcctta tggtgcttag catgagagaa cttccagctg  13380
aagtaaggaa ccataacaag agagtggaga acccatccaa cggtatcgtt aacccatccg  13440
tagttagaga aagcagaatg tccacactca tgtccaagga tccagattcc gaatccgaaa  13500
```

-continued

```
caagagatag agaacacgta agcagaccaa gcagcgaatc taaggaattc gttagggaga  13560
agagggatgt aggtaagtcc aacgtaagcg atagcagaga tagccacgat atctctcacc  13620
acgtaagaca tagacttcac gagagatctc tcgtaacagt gcttagggat agcgtcaagg  13680
atatccttga tggtgtaatc tggcaccttg aaaacgtttc cgaaggtatc gatagcggtc  13740
ttttgctgct tgaaagatgc aacgtttcca gaacgcctaa cggtcttagt agatccctca  13800
aggatctcag atccagacac ggtaacctta gacatggtat ggtaattgta aatgtaattg  13860
taatgttgtt tgttgtttgt tgttgttggt aattgttgta aaatttttgg tggtgattgg  13920
ttctttaagg tgtgagagtg agttgtgagt tgtgtggtgg gtttggtgag attggggatg  13980
gtgggtttat atagtggaga ctgaggaatg gggtcgtgag tgttaacttt gcatgggcta  14040
cacgtgggtt cttttgggct tacacgtagt attattcatg caaatgcagc caatacatat  14100
acggtatttt aataatgtgt gggaatacaa tatgccgagt attttactaa ttttggcaat  14160
gacaagtgta catttggatt atcttacttg gcctctcttg ctttaatttg gattattttt  14220
attctcttac cttggccgtt catattcaca tccctaaagg caagacagaa ttgaatggtg  14280
gccaaaaatt aaaacgatgg atatgaccta catagtgtag gatcaattaa cgtcgaagga  14340
aaatactgat tctctcaagc atacggacaa gggtaaataa catagtcacc agaacataat  14400
aaacaaaaag tgcagaagca agactaaaaa aattagctat ggacattcag gttcatattg  14460
gaaacatcat tatcctagtc ttgtgaccat ccttcctcct gctctagttg agaggccttg  14520
ggactaacga gaggtcagtt gggatagcag atccttatcc tggactagcc tttctggtgt  14580
ttcagagtct tcgtgccgcc gtctacatct atctccatta ggtctgaaga tgactcttca  14640
caccaacgac gtttaaggtc tctatcctac tcctagcttg caatacctgg cttgcaatac  14700
ctggagcatc gtgcacgatg attggatact gtggaggagg agtgtttgct gatttagagc  14760
tcccggttgg gtgatttgac ttcgatttca gtttaggctt gttgaaattt ttcaggttcc  14820
attgtgaagc ctttagagct tgagcttcct tccatgttaa tgccttgatc gaatactcct  14880
agagaaaagg gaagtcgatc tctgagtatt gaaatcgaag tgcacatttt ttttcaacgt  14940
gtccaatcaa tccacaaaca aagcagaaga caggtaatct ttcatactta tactgacaag  15000
taatagtctt accgtcatgc ataataacgt ctcgttcctt caagaggggt tttccgacat  15060
ccataacgac ccgaagcctc atgaaagcat tagggaagaa cttttggttc ttcttgtcat  15120
ggcctttata ggtgtcagcc gagctcgcca attcccgtcc gactggctcc gcaaaatatt  15180
cgaacggcaa gttatggact tgcaaccata actccacggt attgagcagg acctattgtg  15240
aagactcatc tcatggagct tcagaatgtg gttgtcagca aaccaatgac cgaaatccat  15300
cacatgacgg acgtccagtg ggtgagcgaa acgaaacagg aagcgcctat ctttcagagt  15360
cgtgagctcc acaccggatt ccggcaacta cgtgttgggc aggcttcgcc gtattagaga  15420
tatgttgagg cagacccatc tgtgccactc gtacaattac gagagttgtt tttttgtga  15480
ttttcctagt ttctcgttga tggtgagctc atattctaca tcgtatggtc tctcaacgtc  15540
gtttcctgtc atctgatatc ccgtcatttg catccacgtg cgccgcctcc cgtgccaagt  15600
ccctaggtgt catgcacgcc aaattggtgg tggtgcgggc tgccctgtgc ttcttaccga  15660
tgggtggagg ttgagtttgg gggtctccgc ggcgatggta gtgggttgac ggtttggtgt  15720
gggttgacgg cattgatcaa tttacttctt gcttcaaatt ctttggcaga aaacaattca  15780
ttagattaga actggaaacc agagtgatga gacggattaa gtcagattcc aacagagtta  15840
catctcttaa gaaataatgt aaccccttta gactttatat atttgcaatt aaaaaaataa  15900
```

-continued

```
tttaactttt agactttata tatagtttta ataactaagt ttaaccactc tattatttat  15960
atcgaaacta tttgtatgtc tcccctctaa ataaacttgg tattgtgttt acagaaccta  16020
taatcaaata atcaatactc aactgaagtt tgtgcagtta attgaaggga ttaacggcca  16080
aaatgcacta gtattatcaa ccgaatagat tcacactaga tggccatttc catcaatatc  16140
atcgccgttc ttcttctgtc cacatatccc ctctgaaact tgagagacac ctgcacttca  16200
ttgtccttat tacgtgttac aaaatgaaac ccatgcatcc atgcaaactg aagaatggcg  16260
caagaaccct tcccctccat ttcttatgtg gcgaccatcc atttcaccat ctcccgctat  16320
aaaacacccc catcacttca cctagaacat catcactact tgcttatcca tccaaaagat  16380
acccactttt acaacaatta ccaacaacaa caaacaacaa acaacattac aattacattt  16440
acaattacca taccatgcca cctagcgctg ctaagcaaat gggagcttct actggtgttc  16500
atgctggtgt tactgactct tctgctttca ccagaaagga tgttgctgat agacctgatc  16560
tcaccatcgt tggagattct gtttacgatg ctaaggcttt cagatctgag catcctggtg  16620
gtgctcattt cgtttctttg ttcggaggaa gagatgctac tgaggctttc atggaatacc  16680
atagaagggc ttggcctaag tctagaatgt ctagattcca cgttggatct cttgcttcta  16740
ctgaggaacc tgttgctgct gatgagggat accttcaact ttgtgctagg atcgctaaga  16800
tggtgccttc tgtttcttct ggattcgctc ctgcttctta ctgggttaag gctggactta  16860
tccttggatc tgctatcgct cttgaggctt acatgcttta cgctggaaag agacttctcc  16920
cttctatcgt tcttggatgg cttttcgctc ttatcggtct taacatccag catgatgcta  16980
accatggtgc tttgtctaag tctgcttctg ttaaccttgc tcttggactt tgtcaggatt  17040
ggatcggagg atctatgatc ctttggcttc aagagcatgt tgttatgcac cacctccaca  17100
ctaacgatgt tgataaggat cctgatcaaa aggctcacgg tgctcttaga ctcaagccta  17160
ctgatgcttg gtcacctatg cattggcttc agcatcttta ccttttgcct ggtgagacta  17220
tgtacgcttt caagcttttg ttcctcgaca tctctgagct tgttatgtgg cgttgggagg  17280
gtgagcctat ctctaagctt gctggatacc tctttatgcc ttctttgctt ctcaagctta  17340
ccttctgggc tagattcgtt gctttgcctc tttaccttgc tccttctgtt catactgctg  17400
tgtgtatcgc tgctactgtt atgactggat ctttctacct cgctttcttc ttcttcatct  17460
cccacaactt cgagggtgtt gcttctgttg gacctgatgg atctatcact tctatgacta  17520
gaggtgctag cttccttaag agacaagctg agacttcttc taacgttgga ggacctcttc  17580
ttgctactct taacggtgga ctcaactacc aaattgagca tcacttgttc cctagagttc  17640
accatggatt ctaccctaga cttgctcctc ttgttaaggc tgagcttgag gctagaggaa  17700
tcgagtacaa gcactaccct actatctggt ctaaccttgc ttctaccctc agacatatgt  17760
acgctcttgg aagaaggcct agatctaagg ctgagtaatg acaagcttat gtgacgtgaa  17820
ataataacgg taaaatatat gtaataataa taataataaa gccacaaagt gagaatgagg  17880
ggaaggggaa atgtgtaatg agccagtagc cggtggtgct aattttgtat cgtattgtca  17940
ataaatcatg aattttgtgg tttttatgtg ttttttaaa tcatgaattt taaattttat  18000
aaaataatct ccaatcggaa gaacaacatt ccatatccat gcatggatgt ttctttaccc  18060
aaatctagtt cttgagagga tgaagcatca ccgaacagtt ctgcaactat ccctcaaaag  18120
ctttaaaatg aacaacaagg aacagagcaa cgttccaaag atcccaaacg aaacatatta  18180
tctatactaa tactatatta ttaattacta ctgcccggaa tcacaatccc tgaatgattc  18240
```

-continued ctattaacta caagccttgt tggcggcgga gaagtgatcg gcgcggcgag aagcagcgga 18300
ctcggagacg aggccttgga agatctgagt cgaacgggca gaatcagtat tttccttcga 18360
cgttaattga tcctacacta tgtaggtcat atccatcgtt ttaatttttg gccaccattc 18420
aattctgtct tgcctttagg gatgtgaata tgaacggcca aggtaagaga ataaaaataa 18480
tccaaattaa agcaagagag gccaagtaag ataatccaaa tgtacacttg tcattgccaa 18540
aattagtaaa atactcggca tattgtattc ccacacatta ttaaaatacc gtatatgtat 18600
tggctgcatt tgcatgaata atactacgtg taagcccaaa agaacccacg tgtagcccat 18660
gcaaagttaa cactcacgac cccattcctc agtctccact atataaaccc accatcccca 18720
atctcaccaa acccaccaca caactcacaa ctcactctca caccttaaag aaccaatcac 18780
caccaaaaat tttacaacaa ttaccaacaa caacaaacaa caaacaacat tacaattaca 18840
tttacaatta ccataccatg agcgctgtta ccgttactgg atctgatcct aagaacagag 18900
gatcttctag caacaccgag caagaggttc caaaagttgc tatcgatacc aacggaaacg 18960
tgttctctgt tcctgatttc accatcaagg acatccttgg agctatccct catgagtgtt 19020
acgagagaag attggctacc tctctctact acgtgttcag agatatcttc tgcatgctta 19080
ccaccggata ccttacccat aagatccttt accctctcct catctcttac acctctaaca 19140
gcatcatcaa gttcactttc tgggcccttt acacttacgt tcaaggactt ttcggaaccg 19200
gaatctgggt tctcgctcat gagtgtggac atcaagcttt ctctgattac ggaatcgtga 19260
acgatttcgt tggatggacc cttcactctt accttatggt tccttacttc agctggaagt 19320
actctcatgg aaagcaccat aaggctactg gacacatgac cagagatatg gttttcgttc 19380
ctgccaccaa agaggaattc aagaagtcta ggaacttctt cggtaacctc gctgagtact 19440
ctgaggattc tccacttaga accctttacg agcttcttgt tcaacaactt ggaggatgga 19500
tcgcttacct cttcgttaac gttacaggac aaccttaccc tgatgttcct tcttggaaat 19560
ggaaccactt ctggcttacc tctccacttt tcgagcaaag agatgctctc tacatcttcc 19620
tttctgatct tggaatcctc acccagggaa tcgttcttac tctttggtac aagaaattcg 19680
gaggatggtc ccttttcatc aactggttcg ttccttacat ctgggttaac cactggctcg 19740
ttttcatcac attccttcag cacactgatc ctactatgcc tcattacaac gctgaggaat 19800
ggactttcgc taagggtgct gctgctacta tcgatagaaa gttcggattc atcggacctc 19860
acatcttcca tgatatcatc gagactcatg tgcttcacca ctactgttct aggatcccat 19920
tctacaacgc tagacctgct tctgaggcta tcaagaaagt tatgggaaag cactacaggt 19980
ctagcgacga gaacatgtgg aagtcacttt ggaagtcttt caggtcttgc caatacgttg 20040
acggtgataa cggtgttctc atgttccgta acatcaacaa ctgcggagtt ggagctgctg 20100
agaagtaatg aaggggtgat cgattatgag atcgtacaaa gacactgcta ggtgttaagg 20160
atggataata ataataataa tgagatgaat gtgttttaag ttagtgtaac agctgtaata 20220
aagagagaga gagagagaga gagagagaga gagagagaga gagagagaga gaggctgatg 20280
aaatgttatg tatgtttctt ggtttttaaa ataaatgaaa gcacatgctc gtgtggttct 20340
atcgaattat tcggcggttc ctgtgggaaa aagtccagaa gggccgccgc agctactact 20400
acaaccaagg ccgtggagga gggcaacaga gccagcactt cgatagctgc tgcgatgatc 20460
ttaagcaatt gaggagcgag tgcacatgca ggggactgga gcgtgcaatc ggccagatga 20520
ggcaggacat ccagcagcag ggacagcagc aggaagttga gaggtggtcc catcaatcta 20580
aacaagtcgc tagggacctt ccgggacagt gcggcaccca gcctagccga tgccagctcc 20640

-continued

```
aggggcagca gcagtctgca tggttttgaa gtggtgatcg atgagatcgt ataaagacac  20700
tgctaggtgt taaggatggg ataataagat gtgttttaag tcattaaccg taataaaaag  20760
agagagaggc tgatggaatg ttatgtatgt atgtttcttg gtttttaaaa ttaaatggaa  20820
agcacatgct cgtgtgggtt ctatctcgat taaaaatccc aattatattt ggtctaattt  20880
agtttggtat tgagtaaaac aaattcgaac caaaccaaaa tataaatata tagtttttat  20940
atatatgcct ttaagacttt ttatagaatt ttctttaaaa aatatctaga aatatttgcg  21000
actcttctgg catgtaatat ttcgttaaat atgaagtgct ccatttttat taactttaaa  21060
taattggttg tacgatcact ttcttatcaa gtgttactaa aatgcgtcaa tctctttgtt  21120
cttccatatt catatgtcaa aatctatcaa aattcttata tatctttttc gaatttgaag  21180
tgaaatttcg ataatttaaa attaaataga acatatcatt atttaggtat catattgatt  21240
tttatactta attactaaat ttggttaact ttgaaagtgt acatcaacga aaaattagtc  21300
aaacgactaa aataaataaa tatcatgtgt tattaagaaa attctcctat aagaatattt  21360
taatagatca tatgtttgta aaaaaaatta atttttacta acacatatat ttacttatca  21420
aaaatttgac aaagtaagat taaaataata ttcatctaac aaaaaaaaaa ccagaaaatg  21480
ctgaaaaccc ggcaaaaccg aaccaatcca aaccgatata gttggtttgg tttgattttg  21540
atataaaccg aaccaactcg gtccatttgc acccctaatc ataatagctt taatatttca  21600
agatattatt aagttaacgt tgtcaatatc ctggaaattt tgcaaaatga atcaagccta  21660
tatggctgta atatgaattt aaaagcagct cgatgtggtg gtaatatgta atttacttga  21720
ttctaaaaaa atatcccaag tattaataat ttctgctagg aagaaggtta gctacgattt  21780
acagcaaagc cagaatacaa agaaccataa agtgattgaa gctcgaaata tacgaaggaa  21840
caaatatttt taaaaaaata cgcaatgact tggaacaaaa gaaagtgata tattttttgt  21900
tcttaaacaa gcatcccctc taaagaatgg cagttttcct ttgcatgtaa ctattatgct  21960
cccttcgtta caaaaatttt ggactactat tgggaacttc ttctgaaaat agtcctgcag  22020
gctagtagat tggttggttg gtttccatgt accagaaggc ttaccctatt agttgaaagt  22080
tgaaactttg ttccctactc aattcctagt tgtgtaaatg tatgtatatg taatgtgtat  22140
aaaacgtagt acttaaatga ctaggagtgg ttcttgagac cgatgagaga tgggagcaga  22200
actaaagatg atgacataat taagaacgaa tttgaaaggc tcttaggttt gaatcctatt  22260
cgagaatgtt tttgtcaaag atagtggcga ttttgaacca aagaaaacat ttaaaaaatc  22320
agtatccggt tacgttcatg caaatagaaa gtggtctagg atctgattgt aattttagac  22380
ttaaagagtc tcttaagatt caatcctggc tgtgtacaaa actacaaata atatatttta  22440
gactatttgg ccttaactaa acttccactc attatttact gaggttagag aatagacttg  22500
cgaataaaca cattcccgag aaatactcat gatcccataa ttagtcagag ggtatgccaa  22560
tcagatctaa gaacacacat tccctcaaat tttaatgcac atgtaatcat agtttagcac  22620
aattcaaaaa taatgtagta ttaaagacag aaatttgtag actttttttt ggcgttaaaa  22680
gaagactaag tttatacgta cattttattt taagtggaaa accgaaattt tccatcgaaa  22740
tatatgaatt tagtatatat atttctgcaa tgtactattt tgctattttg gcaactttca  22800
gtggactact actttattac aatgtgtatg gatgcatgag tttgagtata cacatgtcta  22860
aatgcatgct ttgtaaaacg taacggacca caaaagagga tccatacaaa tacatctcat  22920
agcttcctcc attattttcc gacacaaaca gagcatttta caacaattac caacaacaac  22980
```

-continued

```
aaacaacaaa caacattaca attacattta caattaccat accatggaat ttgctcaacc  23040
tctcgttgct atggctcaag agcagtacgc tgctatcgat gctgttgttg ctcctgctat  23100
cttctctgct accgactcta ttggatgggg actcaagcct atctcttctg ctactaagga  23160
tctccctctc gttgaatctc ctacccctct tatcctttct ctcctcgctt acttcgctat  23220
cgttggttct ggactcgttt accgtaaagt gttccctaga accgttaagg gacaggatcc  23280
tttccttctc aaggctctta tgctcgctca caacgttttc cttatcggac tcagccttta  23340
catgtgcctc aagctcgttt acgaggctta cgtgaacaag tactccttct ggggaaacgc  23400
ttacaaccct gctcaaaccg agatggctaa ggtgatctgg atcttctacg tgtccaagat  23460
ctacgagttc atggacacct tcatcatgct tctcaaggga aacgttaacc aggtttcctt  23520
cctccatgtt taccaccacg gatctatctc tggaatctgg tggatgatca cttatgctgc  23580
tccaggtgga gatgcttact tctctgctgc tctcaactct tgggttcatg tgtgcatgta  23640
cacctactac ttcatggctg ctgttcttcc taaggacgaa aagaccaaga gaaagtacct  23700
ttggtgggga agatacctta cccagatgca aatgttccag ttcttcatga accttctcca  23760
ggctgtttac ctcctctact cttcttctcc ttaccctaag ttcattgctc aactcctcgt  23820
tgtttacatg gttaccctcc tcatgctttt cggaaacttc tactacatga agcaccacgc  23880
ttctaagtga taagggccgc cgccatgtga cagatcgaag gaagaaagtg taataagacg  23940
actctcacta ctcgatcgct agtgattgtc attgttatat ataataatgt tatctttcac  24000
aacttatcgt aatgcatgtg aaactataac acattaatcc tacttgtcat atgataacac  24060
tctccccatt taaaactctt gtcaatttaa agatataaga ttctttaaat gattaaaaaa  24120
aatatattat aaattcaatc actcctacta ataaattatt aattattatt tattgattaa  24180
aaaaatactt atactaattt agtctgaata gaataattag attctagcct gcagggcggc  24240
cgcggatccc atggagtcaa agattcaaat agaggaccta acagaactcg ccgtaaagac  24300
tggcgaacag ttcatacaga gtctcttacg actcaatgac aagaagaaaa tcttcgtcaa  24360
catggtggag cacgacacac ttgtctactc caaaaatatc aaagatacag tctcagaaga  24420
ccaaagggca attgagactt ttcaacaaag ggtaatatcc ggaaacctcc tcggattcca  24480
ttgcccagct atctgtcact ttattgtgaa gatagtggaa aaggaaggtg gctcctacaa  24540
atgccatcat tgcgataaag gaaaggccat cgttgaagat gcctctgccg acagtggtcc  24600
caaagatgga cccccaccca cgaggagcat cgtggaaaaa gaagacgttc caaccacgtc  24660
ttcaaagcaa gtggattgat gtgatatctc cactgacgta agggatgacg cacaatccca  24720
ctatccttcg caagaccctt cctctatata aggaagttca tttcatttgg agagaacacg  24780
ggggactgaa ttaaatatga gccctgagag gcgtcctgtt gaaatcagac ctgctactgc  24840
tgctgatatg gctgctgttt gtgatatcgt gaaccactac atcgagactt ctaccgttaa  24900
cttcagaact gagcctcaaa ctcctcaaga gtggatcgat gatcttgaga gactccaaga  24960
tagataccct tggcttgttg ctgaggttga gggtgttgtt gctggaatcg cttacgctgg  25020
accttggaag gctagaaacg cttacgattg gactgttgag tctaccgttt acgtttcaca  25080
cagacatcag agacttggac ttggatctac cctttacact caccttctca agtctatgga  25140
agctcaggga ttcaagtctg ttgttgctgt tatcggactc cctaacgatc cttctgttag  25200
acttcatgag gctcttggat acactgctag aggaactctt agagctgctg gatacaagca  25260
cggtggatgg catgatgttg gattctggca aagagatttc gagcttcctg ctcctcctag  25320
acctgttaga ccagttactc agatctgaat ttgcgtgatc gttcaaacat ttggcaataa  25380
```

agtttcttaa gattgaatcc tgttgccggt cttgcgatga ttatcatata atttctgttg 25440
aattacgtta agcatgtaat aattaacatg taatgcatga cgttatttat gagatgggtt 25500
tttatgatta gagtcccgca attatacatt taatacgcga tagaaaacaa aatatagcgc 25560
gcaaactagg ataaattatc gcgcgcggtg tcatctatgt tactagatca ctagtgatgt 25620
acggttaaaa ccaccccagt acattaaaaa cgtccgcaat gtgttattaa gttgtctaag 25680
cgtcaatttg tttacaccac aatatatcct gccaccagcc agccaacagc tccccgaccg 25740
gcagctcggc acaaaatcac cactcgatac aggcagccca tcagtcc 25787

<210> SEQ ID NO 4
<211> LENGTH: 22824
<212> TYPE: DNA
<213> ORGANISM: Artificial Sequence
<220> FEATURE:
<223> OTHER INFORMATION: pGA7- mod_D nucleotide sequence

<400> SEQUENCE: 4
tcctgtggtt ggcatgcaca tacaaatgga cgaacggata aaccttttca cgccctttta 60
aatatccgat tattctaata aacgctcttt tctcttaggt ttacccgcca atatatcctg 120
tcaaacactg atagtttaaa ctgaaggcgg gaaacgacaa tctgctagtg gatctcccag 180
tcacgacgtt gtaaaacggg cgcctcgatt aaaaatccca attatatttg gtctaattta 240
gtttggtatt gagtaaaaca aattcgaacc aaaccaaaat ataaatatat agtttttata 300
tatatgcctt taagactttt tatagaattt tctttaaaaa atatctagaa atatttgcga 360
ctcttctggc atgtaatatt tcgttaaata tgaagtgctc catttttatt aactttaaat 420
aattggttgt acgatcactt tcttatcaag tgttactaaa atgcgtcaat ctctttgttc 480
ttccatattc atatgtcaaa atctatcaaa attcttatat atctttttcg aatttgaagt 540
gaaatttcga taatttaaaa ttaaatagaa catatcatta tttaggtatc atattgattt 600
ttatacttaa ttactaaatt tggttaactt tgaaagtgta catcaacgaa aaattagtca 660
aacgactaaa ataaataaat atcatgtgtt attaagaaaa ttctcctata agaatatttt 720
aatagatcat atgtttgtaa aaaaaattaa tttttactaa cacatatatt tacttatcaa 780
aaatttgaca aagtaagatt aaaataatat tcatctaaca aaaaaaaaac cagaaaatgc 840
tgaaaacccg gcaaaaccga accaatccaa accgatatag ttggtttggt ttgattttga 900
tataaaccga accaactcgg tccatttgca cccctaatca taatagcttt aatatttcaa 960
gatattatta agttaacgtt gtcaatatcc tggaaatttt gcaaaatgaa tcaagcctat 1020
atggctgtaa tatgaattta aaagcagctc gatgtggtgg taatatgtaa tttacttgat 1080
tctaaaaaaa tatcccaagt attaataatt tctgctagga agaaggttag ctacgattta 1140
cagcaaagcc agaatacaaa gaaccataaa gtgattgaag ctcgaaatat acgaaggaac 1200
aaatattttt aaaaaaatac gcaatgactt ggaacaaaag aaagtgatat atttttttgtt 1260 cttaaacaag catcccctct aaagaatggc agttttcctt tgcatgtaac tattatgctc 1320
ccttcgttac aaaaatttg gactactatt gggaacttct tctgaaaata gtggcgcccc 1380
gcggaaagct tgctagccaa ttggggccca acgttctcga gtttttctag aaggaaactg 1440
aaggcgggaa acgacaatct gctagtggat ctcccagtca cgacgttgta aaacgggcgc 1500
cccgcggaaa gcttgcggcc gcccgatcta gtaacataga tgacaccgcg cgcgataatt 1560
tatcctagtt tgcgcgctat attttgtttt ctatcgcgta ttaaatgtat aattgcggga 1620

-continued ctctaatcat aaaaacccat ctcataaata acgtcatgca ttacatgtta attattacgt 1680
gcttaacgta attcaacaga aattatatga taatcatcgc aagaccggca acaggattca 1740
atcttaagaa actttattgc caaatgtttg aacgatcggc gcgcctcatt agtgagcctt 1800
ctcagccttt ccgttaacgt agtagtgctg tcccacctta tcaaggttag agaaagtagc 1860
cttccaagca ccgtagtaag agagcacctt gtagttgagt ccccacttct tagcgaaagg 1920
aacgaatctt ctgctaacct caggctgtct gaattgaggc atatcaggga agaggtggtg 1980
gataacctga cagttaaggt atcccataag ccagttcacg tatcctctag aaggatcgat 2040
atcaacggtg tgatcaacag cgtagttaac ccaagaaagg tgcttatcag atggaacaac 2100
agggaggtga gtatgagaag tagagaagtg agcgaaaagg tacatgtaag cgatccagtt 2160
tccgaaagtg aaccaccagt aagcaacagg ccaagagtat ccagtagcaa gcttgataac 2220
agcggttcta acaacatgag aaacgagcat ccaagaagcc tcttcgtagt tcttcttacg 2280
gagaacttgt ctagggtgga gaacgtagat ccagaaagct tgaacaagaa gtccagaggt 2340
aacaggaacg aaagtccaag cttgaagtct agcccaagct ctagagaatc ctctaggtct 2400
gttatcctca acagcagtgt tgaagaaagc cacagcagga gtggtatcaa gatccatatc 2460
gtgtctaacc ttttgagggg tagcatggtg cttgttatgc atctggttcc acatctcacc 2520
agaagtagaa agtccgaatc cacaagtcat agcctgaagt ctcttgtcca cgtaaacaga 2580
tccggtaaga gagttatgtc caccctcatg ttgaacccat ccacatctag ctccgaagaa 2640
agcaccgtaa acaacagaag caatgatagg gtatccagcg tacataagag cagttccaag 2700
agcgaatgta gcaagaagct cgagaagtct gtaagccaca tgggtgatag aaggcttgaa 2760
gaatccatct ctctcaagct cagcacgcca tctagcgaaa tcctcaagca taggagcatc 2820
ctcagactca gatctcttga tctcagcagg tctagaaggc aaagctctaa gcatcttcca 2880
agccttgaga gaacgcatgt ggaattcttt gaaagcctca gtagcatcag caccagtgtt 2940
agcaagcatg tagaagatca cagatccacc agggtgcttg aagttagtca catcgtactc 3000
aacgtcctca actctaaccc atctagtctc gaaagtagca gcaagctcat gaggctcaag 3060
agtcttaaga tcaacaggag cagtagaagc atccttagca tcaagagcct cagcagaaga 3120
tttagacctg gtaagtggag atctaggaga agatcttcca tcagtcttag gagggcacat 3180
ggtatggtaa ttgtaaatgt aattgtaatg ttgtttgttg tttgttgttg ttggtaattg 3240
ttgtaaaaga tcctcgtgta tgtttttaat cttgtttgta tcgatgagtt ttggtttgag 3300
taaagagtga agcggatgag ttaatttata ggctataaag gagatttgca tggcgatcac 3360
gtgtaataat gcatgcacgc atgtgattgt atgtgtgtgc tgtgagagag aagctcttag 3420
gtgtttgaag ggagtgacaa gtggcgaaga aaaacaattc tccgcggctg catgctatgt 3480
gtaacgtgta gctaatgttc tggcatggca tcttatgaac gattcttttt aaaaacaagg 3540
taaaaactta acttcataaa attaaaaaaa aaaacgttta ctaagttggt ttaaaagggg 3600
atgagactag tagattggtt ggttggtttc catgtaccag aaggcttacc ctattagttg 3660
aaagttgaaa ctttgttccc tactcaattc ctagttgtgt aaatgtatgt atatgtaatg 3720
tgtataaaac gtagtactta aatgactagg agtggttctt gagaccgatg agagatggga 3780
gcagaactaa agatgatgac ataattaaga acgaatttga aaggctctta ggtttgaatc 3840
ctattcgaga atgtttttgt caaagatagt ggcgattttg aaccaaagaa aacatttaaa 3900
aaatcagtat ccggttacgt tcatgcaaat agaaagtggt ctaggatctg attgtaattt 3960
tagacttaaa gagtctctta agattcaatc ctggctgtgt acaaaactac aaataatata 4020

```
ttttagacta tttggcctta actaaacttc cactcattat ttactgaggt tagagaatag   4080
acttgcgaat aaacacattc ccgagaaata ctcatgatcc cataattagt cagagggtat   4140
gccaatcaga tctaagaaca cacattccct caaattttaa tgcacatgta atcatagttt   4200
agcacaattc aaaaataatg tagtattaaa gacagaaatt tgtagacttt tttttggcgt   4260
taaaagaaga ctaagtttat acgtacattt tattttaagt ggaaaaccga aattttccat   4320
cgaaatatat gaatttagta tatatatttc tgcaatgtac tattttgcta ttttggcaac   4380
tttcagtgga ctactacttt attacaatgt gtatggatgc atgagtttga gtatacacat   4440
gtctaaatgc atgctttgta aaacgtaacg gaccacaaaa gaggatccat acaaatacat   4500
ctcatagctt cctccattat tttccgacac aaacagagca ttttacaaca attaccaaca   4560
acaacaaaca acaaacaaca ttacaattac atttacaatt accataccat ggaattcgcc   4620
cagcctcttg ttgctatggc tcaagagcaa tacgctgcta tcgatgctgt tgttgctcct   4680
gctatcttct ctgctactga ttctatcgga tggggactta agcctatctc ttctgctact   4740
aaggacttgc ctcttgttga gtctcctaca cctctcatcc tttctttgct tgcttacttc   4800
gctatcgttg gatctggact cgtttacaga aaggttttcc ctagaaccgt gaagggacaa   4860
gatccattcc ttttgaaggc tcttatgctt gctcacaacg tgttccttat cggactttct   4920
ctttacatgt gcctcaagct tgtgtacgag gcttacgtta acaagtactc tttctgggga   4980
aacgcttaca accctgctca aactgagatg gctaaggtta tctggatctt ctacgtgagc   5040
aagatctacg agttcatgga taccttcatc atgctcctca agggaaatgt taaccaggtt   5100
agcttccttc acgtttacca tcacggatct atctctggaa tctggtggat gattacttac   5160
gctgctcctg gtggtgatgc ttacttctct gctgctctta actcttgggt tcacgtgtgt   5220
atgtacacct actattttat ggctgccgtg cttcctaagg acgagaaaac taagagaaag   5280
tacctctggt ggggaagata ccttactcaa atgcagatgt tccagttctt catgaacctt   5340
ctccaggctg tttaccttct ctactcttca tctccttacc ctaagtttat cgctcagctc   5400
ctcgtggtgt acatggttac tcttctcatg cttttcggaa acttctacta catgaagcac   5460
cacgctagca agtgatgagg cgcgccgggc cgccgccatg tgacagatcg aaggaagaaa   5520
gtgtaataag acgactctca ctactcgatc gctagtgatt gtcattgtta tatataataa   5580
tgttatcttt cacaacttat cgtaatgcat gtgaaactat aacacattaa tcctacttgt   5640
catatgataa cactctcccc atttaaaact cttgtcaatt taaagatata agattcttta   5700
aatgattaaa aaaaatatat tataaattca atcactccta ctaataaatt attaattatt   5760
atttattgat taaaaaaata cttatactaa tttagtctga atagaataat tagattctag   5820
tctcatcccc ttttaaacca acttagtaaa cgtttttttt tttaatttta tgaagttaag   5880
tttttacctt gtttttaaaa agaatcgttc ataagatgcc atgccagaac attagctaca   5940
cgttacacat agcatgcagc cgcggagaat tgtttttctt cgccacttgt cactcccttc   6000
aaacacctaa gagcttctct ctcacagcac acacatacaa tcacatgcgt gcatgcatta   6060
ttacacgtga tcgccatgca aatctccttt atagcctata aattaactca tccgcttcac   6120
tctttactca aaccaaaact catcgataca aacaagatta aaaacataca cgaggatctt   6180
ttacaacaat taccaacaac aacaaacaac aaacaacatt acaattacat ttacaattac   6240
cataccatgc ctccaaggga ctcttactct tatgctgctc ctccttctgc tcaacttcac   6300
gaagttgata ctcctcaaga gcacgacaag aaagagcttg ttatcggaga tagggcttac   6360
```

-continued gatgttacca acttcgttaa gagacaccct ggtggaaaga tcattgctta ccaagttgga 6420
actgatgcta ccgatgctta caagcagttc catgttagat ctgctaaggc tgacaagatg 6480
cttaagtctc ttccttctcg tcctgttcac aagggatact ctccaagaag ggctgatctt 6540
atcgctgatt tccaagagtt caccaagcaa cttgaggctg agggaatgtt cgagccttct 6600
cttcctcatg ttgcttacag acttgctgag gttatcgcta tgcatgttgc tggtgctgct 6660
cttatctggc atggatacac tttcgctgga atcgctatgc ttggagttgt tcagggaaga 6720
tgtggatggc ttatgcatga gggtggacat tactctctca ctggaaacat tgctttcgac 6780
agagctatcc aagttgcttg ttacggactt ggatgtggaa tgtctggtgc ttggtggcgt 6840
aaccagcata acaagcacca tgctactcct caaaagcttc agcacgatgt tgatcttgat 6900
acccttcctc tcgttgcttt ccatgagaga atcgctgcta aggttaagtc tcctgctatg 6960
aaggcttggc tttctatgca agctaagctt ttcgctcctg ttaccactct tcttgttgct 7020
cttggatggc agctttacct tcatcctaga cacatgctca ggactaagca ctacgatgag 7080
cttgctatgc tcggaatcag atacggactt gttggatacc ttgctgctaa ctacggtgct 7140
ggatacgttc tcgcttgtta ccttctttac gttcagcttg gagctatgta catcttctgc 7200
aacttcgctg tttctcatac tcacctccct gttgttgagc ctaacgagca tgctacttgg 7260
gttgagtacg ctgctaacca cactactaac tgttctccat cttggtggtg tgattggtgg 7320
atgtcttacc ttaactacca gatcgagcac cacctttacc cttctatgcc tcaattcaga 7380
caccctaaga tcgctcctag agttaagcag cttttcgaga agcacggact tcactacgat 7440
gttagaggat acttcgaggc tatggctgat actttcgcta accttgataa cgttgcccat 7500
gctcctgaga agaaaatgca gtaatgagat cgttcaaaca tttggcaata aagtttctta 7560
agattgaatc ctgttgccgg tcttgcgatg attatcatat aatttctgtt gaattacgtt 7620
aagcacgtaa taattaacat gtaatgcatg acgttattta tgagatgggt ttttatgatt 7680
agagtcccgc aattatacat ttaatacgcg atagaaaaca aaatatagcg cgcaaactag 7740
gataaattat cgcgcgcggt gtcatctatg ttactagatc ggtcgattaa aaatcccaat 7800
tatatttggt ctaatttagt ttggtattga gtaaaacaaa ttcgaaccaa accaaaatat 7860
aaatatatag tttttatata tatgccttta agacttttta tagaattttc tttaaaaaat 7920
atctagaaat atttgcgact cttctggcat gtaatatttc gttaaatatg aagtgctcca 7980
tttttattaa ctttaaataa ttggttgtac gatcactttc ttatcaagtg ttactaaaat 8040
gcgtcaatct ctttgttctt ccatattcat atgtcaaaat ctatcaaaat tcttatatat 8100
ctttttcgaa tttgaagtga aatttcgata atttaaaatt aaatagaaca tatcattatt 8160
taggtatcat attgattttt atacttaatt actaaatttg gttaactttg aaagtgtaca 8220
tcaacgaaaa attagtcaaa cgactaaaat aaataaatat catgtgttat taagaaaatt 8280
ctcctataag aatattttaa tagatcatat gtttgtaaaa aaaattaatt tttactaaca 8340
catatattta cttatcaaaa atttgacaaa gtaagattaa aataatattc atctaacaaa 8400
aaaaaaacca gaaaatgctg aaaacccggc aaaaccgaac caatccaaac cgatatagtt 8460
ggtttggttt gattttgata taaaccgaac caactcggtc catttgcacc cctaatcata 8520
atagctttaa tatttcaaga tattattaag ttaacgttgt caatatcctg gaaattttgc 8580
aaaatgaatc aagcctatat ggctgtaata tgaatttaaa agcagctcga tgtggtggta 8640
atatgtaatt tacttgattc taaaaaaata tcccaagtat taataatttc tgctaggaag 8700
aaggttagct acgatttaca gcaaagccag aatacaaaga accataaagt gattgaagct 8760

```
cgaaatatac gaaggaacaa atatttttaa aaaaatacgc aatgacttgg aacaaaagaa   8820
agtgatatat tttttgttct taaacaagca tcccctctaa agaatggcag ttttcctttg   8880
catgtaacta ttatgctccc ttcgttacaa aaattttgga ctactattgg gaacttcttc   8940
tgaaaatagt gatagaaccc acacgagcat gtgctttcca tttaatttta aaaaccaaga   9000
aacatacata cataacattc catcagcctc tctctctttt tattacggtt aatgacttaa   9060
aacacatctt attatcccat ccttaacacc tagcagtgtc tttatacgat ctcatcgatc   9120
accacttcaa aaccatgcag actgctgctg cccctggagc tggcatcggc taggctgggt   9180
gccgcactgt cccggaaggt ccctagcgac ttgtttagat tgatgggacc acctctcaac   9240
ttcctgctgc tgtccctgct gctggatgtc ctgcctcatc tggccgattg cacgctccag   9300
tcccctgcat gtgcactcgc tcctcaattg cttaagatca tcgcagcagc tatcgaagtg   9360
ctggctctgt tgccctcctc cacggccttg gttgtagtag tagctgccgc cgcccttctg   9420
gactttttcc cacaggaacc gccgaataat tcgatagaac cacacgagca tgtgctttca   9480
tttattttaa aaaccaagaa acatacataa catttcatca gcctctctct ctctctctct   9540
ctctctctct ctctctctct ctctctctct ctctttatta cagctgttac actaacttaa   9600
aacacattca tctcattatt attattatta tccatcctta acacctagca gtgtctttgt   9660
acgatctcat aatcgatcac cccttcatca ggtatcctta ggcttcactc caacgttgtt   9720
gcagttacgg aacatgtaca caccatcatg gttctcaacg aactggcaag atctccaagt   9780
tttccaaagg ctaacccaca tgttctcatc ggtgtgtctg tagtgctctc ccataacttt   9840
cttgatgcac tcggtagctt ctctagcatg gtagaatggg atccttgaaa cgtagtgatg   9900
gagcacatga gtctcgatga tgtcatggaa gatgattccg aggattccga actctctatc   9960
gatagtagca gcagcaccct tagcgaaagt ccactcttga gcatcgtaat gaggcataga  10020
agaatcggtg tgctgaagga aggtaacgaa aacaagccag tggttaacaa ggatccaagg  10080
acagaaccat gtgatgaaag taggccagaa tccgaaaacc ttgtaagcgg tgtaaacaga  10140
agtgagggta gcaaggattc caagatcaga aagaacgatg taccagtagt ccttcttatc  10200
gaaaacaggg ctagaaggcc agtagtgaga cttgaagaac ttagaaacac cagggtaagg  10260
ttgtccagta gcgttagtag caaggtaaag agaaagtcct ccaagctgtt ggaacaagag  10320
agcgaaaaca gagtagatag gagtttcctc agcgatatcg tgaaggctgg taacttggtg  10380
cttctctttg aattcctcgg cggtgtaagg aacgaaaacc atatctctgg tcatgtgtcc  10440
agtagcctta tggtgcttag catgagagaa cttccagctg aagtaaggaa ccataacaag  10500
agagtggaga acccatccaa cggtatcgtt aacccatccg tagttagaga aagcagaatg  10560
tccacactca tgtccaagga tccagattcc gaatccgaaa caagagatag agaacacgta  10620
agcagaccaa gcagcgaatc taaggaattc gttagggaga agagggatgt aggtaagtcc  10680
aacgtaagcg atagcagaga tagccacgat atctctcacc acgtaagaca tagacttcac  10740
gagagatctc tcgtaacagt gcttagggat agcgtcaagg atatccttga tggtgtaatc  10800
tggcaccttg aaaacgtttc cgaaggtatc gatagcggtc ttttgctgct tgaaagatgc  10860
aacgtttcca gaacgcctaa cggtcttagt agatccctca aggatctcag atccagacac  10920
ggtaacctta gacatggtat ggtaattgta aatgtaattg taatgttgtt tgttgtttgt  10980
tgttgttggt aattgttgta aaatttttgg tggtgattgg ttctttaagg tgtgagagtg  11040
agttgtgagt tgtgtggtgg gtttggtgag attggggatg gtgggtttat atagtggaga  11100
```

ctgaggaatg gggtcgtgag tgttaacttt gcatgggcta cacgtgggtt cttttgggct 11160
tacacgtagt attattcatg caaatgcagc caatacatat acggtatttt aataatgtgt 11220
gggaatacaa tatgccgagt attttactaa ttttggcaat gacaagtgta catttggatt 11280
atcttacttg gcctctcttg ctttaatttg gattattttt attctcttac cttggccgtt 11340
catattcaca tccctaaagg caagacagaa ttgaatggtg gccaaaaatt aaaacgatgg 11400
atatgaccta catagtgtag gatcaattaa cgtcgaagga aaatactgat tctctcaagc 11460
atacggacaa gggtaaataa catagtcacc agaacataat aaacaaaaag tgcagaagca 11520
agactaaaaa aattagctat ggacattcag gttcatattg gaaacatcat tatcctagtc 11580
ttgtgaccat ccttcctcct gctctagttg agaggccttg ggactaacga gaggtcagtt 11640
gggatagcag atccttatcc tggactagcc tttctggtgt ttcagagtct tcgtgccgcc 11700
gtctacatct atctccatta ggtctgaaga tgactcttca caccaacgac gtttaaggtc 11760
tctatcctac tcctagcttg caatacctgg cttgcaatac ctggagcatc gtgcacgatg 11820
attggatact gtggaggagg agtgtttgct gatttagagc tcccggttgg gtgatttgac 11880
ttcgatttca gtttaggctt gttgaaattt ttcaggttcc attgtgaagc ctttagagct 11940
tgagcttcct tccatgttaa tgccttgatc gaatactcct agagaaaagg gaagtcgatc 12000
tctgagtatt gaaatcgaag tgcacatttt ttttcaacgt gtccaatcaa tccacaaaca 12060
aagcagaaga caggtaatct ttcatactta tactgacaag taatagtctt accgtcatgc 12120
ataataacgt ctcgttcctt caagaggggt tttccgacat ccataacgac ccgaagcctc 12180
atgaaagcat tagggaagaa cttttggttc ttcttgtcat ggcctttata ggtgtcagcc 12240
gagctcgcca attcccgtcc gactggctcc gcaaaatatt cgaacggcaa gttatggact 12300
tgcaaccata actccacggt attgagcagg acctattgtg aagactcatc tcatggagct 12360
tcagaatgtg gttgtcagca aaccaatgac cgaaatccat cacatgacgg acgtccagtg 12420
ggtgagcgaa acgaaacagg aagcgcctat ctttcagagt cgtgagctcc acaccggatt 12480
ccggcaacta cgtgttgggc aggcttcgcc gtattagaga tatgttgagg cagacccatc 12540
tgtgccactc gtacaattac gagagttgtt tttttgtga ttttcctagt ttctcgttga 12600
tggtgagctc atattctaca tcgtatggtc tctcaacgtc gtttcctgtc atctgatatc 12660
ccgtcatttg catccacgtg cgccgcctcc cgtgccaagt ccctaggtgt catgcacgcc 12720
aaattggtgg tggtgcgggc tgccctgtgc ttcttaccga tgggtggagg ttgagtttgg 12780
gggtctccgc ggcgatggta gtgggttgac ggtttggtgt gggttgacgg cattgatcaa 12840
tttacttctt gcttcaaatt ctttggcaga aaacaattca ttagattaga actggaaacc 12900
agagtgatga gacggattaa gtcagattcc aacagagtta catctcttaa gaaataatgt 12960
aacccctta gactttatat atttgcaatt aaaaaaataa tttaactttt agactttata 13020
tatagtttta ataactaagt ttaaccactc tattatttat atcgaaacta tttgtatgtc 13080
tcccctctaa ataaacttgg tattgtgttt acagaaccta taatcaaata atcaatactc 13140
aactgaagtt tgtgcagtta attgaaggga ttaacggcca aaatgcacta gtattatcaa 13200
ccgaatagat tcacactaga tggccatttc catcaatatc atcgccgttc ttcttctgtc 13260
cacatatccc ctctgaaact tgagagacac ctgcacttca ttgtccttat tacgtgttac 13320
aaaatgaaac ccatgcatcc atgcaaactg aagaatggcg caagaaccct tcccctccat 13380
ttcttatgtg gcgaccatcc atttcaccat ctcccgctat aaaacacccc catcacttca 13440
cctagaacat catcactact tgcttatcca tccaaaagat acccactttt acaacaatta 13500
ccaacaacaa caaacaacaa acaacattac aattacattt acaattacca taccatgcca 13560
cctagcgctg ctaagcaaat gggagcttct actggtgttc atgctggtgt tactgactct 13620
tctgctttca ccagaaagga tgttgctgat agacctgatc tcaccatcgt tggagattct 13680
gtttacgatg ctaaggcttt cagatctgag catcctggtg gtgctcattt cgtttctttg 13740
ttcggaggaa gagatgctac tgaggctttc atggaatacc atagaagggc ttggcctaag 13800
tctagaatgt ctagattcca cgttggatct cttgcttcta ctgaggaacc tgttgctgct 13860
gatgagggat accttcaact ttgtgctagg atcgctaaga tggtgccttc tgtttcttct 13920
ggattcgctc ctgcttctta ctgggttaag gctggactta tccttggatc tgctatcgct 13980
cttgaggctt acatgcttta cgctggaaag agacttctcc cttctatcgt tcttggatgg 14040
cttttcgctc ttatcggtct taacatccag catgatgcta accatggtgc tttgtctaag 14100
tctgcttctg ttaaccttgc tcttggactt tgtcaggatt ggatcggagg atctatgatc 14160
ctttggcttc aagagcatgt tgttatgcac cacctccaca ctaacgatgt tgataaggat 14220
cctgatcaaa aggctcacgg tgctcttaga ctcaagccta ctgatgcttg gtcacctatg 14280
cattggcttc agcatcttta ccttttgcct ggtgagacta tgtacgcttt caagcttttg 14340
ttcctcgaca tctctgagct tgttatgtgg cgttgggagg gtgagcctat ctctaagctt 14400
gctggatacc tctttatgcc ttctttgctt ctcaagctta ccttctgggc tagattcgtt 14460
gctttgcctc tttaccttgc tccttctgtt catactgctg tgtgtatcgc tgctactgtt 14520
atgactggat ctttctacct cgctttcttc ttcttcatct cccacaactt cgagggtgtt 14580
gcttctgttg gacctgatgg atctatcact tctatgacta gaggtgctag cttccttaag 14640
agacaagctg agacttcttc taacgttgga ggacctcttc ttgctactct taacggtgga 14700
ctcaactacc aaattgagca tcacttgttc cctagagttc accatggatt ctaccctaga 14760
cttgctcctc ttgttaaggc tgagcttgag gctagaggaa tcgagtacaa gcactaccct 14820
actatctggt ctaaccttgc ttctaccctc agacatatgt acgctcttgg aagaaggcct 14880
agatctaagg ctgagtaatg acaagcttat gtgacgtgaa ataataacgg taaaatatat 14940
gtaataataa taataataaa gccacaaagt gagaatgagg ggaaggggaa atgtgtaatg 15000
agccagtagc cggtggtgct aattttgtat cgtattgtca ataaatcatg aattttgtgg 15060
tttttatgtg tttttttaaa tcatgaattt taaattttat aaaataatct ccaatcggaa 15120
gaacaacatt ccatatccat gcatggatgt ttctttaccc aaatctagtt cttgagagga 15180
tgaagcatca ccgaacagtt ctgcaactat ccctcaaaag ctttaaaatg aacaacaagg 15240
aacagagcaa cgttccaaag atcccaaacg aaacatatta tctatactaa tactatatta 15300
ttaattacta ctgcccggaa tcacaatccc tgaatgattc ctattaacta caagccttgt 15360
tggcggcgga gaagtgatcg gcgcggcgag aagcagcgga ctcggagacg aggccttgga 15420
agatctgagt cgaacgggca gaatcagtat tttccttcga cgttaattga tcctacacta 15480
tgtaggtcat atccatcgtt ttaatttttg gccaccattc aattctgtct tgcctttagg 15540
gatgtgaata tgaacggcca aggtaagaga ataaaaataa tccaaattaa agcaagagag 15600
gccaagtaag ataatccaaa tgtacacttg tcattgccaa aattagtaaa atactcggca 15660
tattgtattc ccacacatta ttaaaatacc gtatatgtat tggctgcatt tgcatgaata 15720
atactacgtg taagcccaaa agaacccacg tgtagcccat gcaaagttaa cactcacgac 15780
cccattcctc agtctccact atataaaccc accatcccca atctcaccaa acccaccaca 15840
caactcacaa ctcactctca caccttaaag aaccaatcac caccaaaaat tttacaacaa 15900
ttaccaacaa caacaaacaa caaacaacat tacaattaca tttacaatta ccataccatg 15960
agcgctgtta ccgttactgg atctgatcct aagaacagag gatcttctag caacaccgag 16020
caagaggttc caaaagttgc tatcgatacc aacggaaacg tgttctctgt tcctgatttc 16080
accatcaagg acatccttgg agctatccct catgagtgtt acgagagaag attggctacc 16140
tctctctact acgtgttcag agatatcttc tgcatgctta ccaccggata ccttacccat 16200
aagatccttt accctctcct catctcttac acctctaaca gcatcatcaa gttcactttc 16260
tgggcccttt acacttacgt tcaaggactt ttcggaaccg gaatctgggt tctcgctcat 16320
gagtgtggac atcaagcttt ctctgattac ggaatcgtga acgatttcgt tggatggacc 16380
cttcactctt accttatggt tccttacttc agctggaagt actctcatgg aaagcaccat 16440
aaggctactg gacacatgac cagagatatg gttttcgttc ctgccaccaa agaggaattc 16500
aagaagtcta ggaacttctt cggtaacctc gctgagtact ctgaggattc tccacttaga 16560
accctttacg agcttcttgt tcaacaactt ggaggatgga tcgcttacct cttcgttaac 16620
gttacaggac aaccttaccc tgatgttcct tcttggaaat ggaaccactt ctggcttacc 16680
tctccacttt tcgagcaaag agatgctctc tacatcttcc tttctgatct tggaatcctc 16740
acccagggaa tcgttcttac tctttggtac aagaaattcg gaggatggtc ccttttcatc 16800
aactggttcg ttccttacat ctgggttaac cactggctcg ttttcatcac attccttcag 16860
cacactgatc ctactatgcc tcattacaac gctgaggaat ggactttcgc taagggtgct 16920
gctgctacta tcgatagaaa gttcggattc atcggacctc acatcttcca tgatatcatc 16980
gagactcatg tgcttcacca ctactgttct aggatcccat tctacaacgc tagacctgct 17040
tctgaggcta tcaagaaagt tatgggaaag cactacaggt ctagcgacga gaacatgtgg 17100
aagtcacttt ggaagtcttt caggtcttgc caatacgttg acggtgataa cggtgttctc 17160
atgttccgta acatcaacaa ctgcggagtt ggagctgctg agaagtaatg aaggggtgat 17220
cgattatgag atcgtacaaa gacactgcta ggtgttaagg atggataata ataataataa 17280
tgagatgaat gtgttttaag ttagtgtaac agctgtaata aagagagaga gagagagaga 17340
gagagagaga gagagagaga gagagagaga gaggctgatg aaatgttatg tatgtttctt 17400
ggtttttaaa ataaatgaaa gcacatgctc gtgtggttct atcgaattat tcggcggttc 17460
ctgtgggaaa aagtccagaa gggccgccgc agctactact acaaccaagg ccgtggagga 17520
gggcaacaga gccagcactt cgatagctgc tgcgatgatc ttaagcaatt gaggagcgag 17580
tgcacatgca ggggactgga gcgtgcaatc ggccagatga ggcaggacat ccagcagcag 17640
ggacagcagc aggaagttga gaggtggtcc catcaatcta aacaagtcgc tagggacctt 17700
ccgggacagt gcggcaccca gcctagccga tgccagctcc aggggcagca gcagtctgca 17760
tggttttgaa gtggtgatcg atgagatcgt ataaagacac tgctaggtgt taaggatggg 17820
ataataagat gtgttttaag tcattaaccg taataaaaag agagagaggc tgatggaatg 17880
ttatgtatgt atgtttcttg gtttttaaaa ttaaatggaa agcacatgct cgtgtgggtt 17940
ctatctcgat taaaaatccc aattatattt ggtctaattt agtttggtat tgagtaaaac 18000
aaattcgaac caaaccaaaa tataaatata tagtttttat atatatgcct ttaagacttt 18060
ttatagaatt ttctttaaaa aatatctaga aatatttgcg actcttctgg catgtaatat 18120
ttcgttaaat atgaagtgct ccatttttat taactttaaa taattggttg tacgatcact 18180
ttcttatcaa gtgttactaa aatgcgtcaa tctctttgtt cttccatatt catatgtcaa 18240

-continued aatctatcaa aattcttata tatctttttc gaatttgaag tgaaatttcg ataatttaaa 18300
attaaataga acatatcatt atttaggtat catattgatt tttatactta attactaaat 18360
ttggttaact ttgaaagtgt acatcaacga aaaattagtc aaacgactaa aataaataaa 18420
tatcatgtgt tattaagaaa attctcctat aagaatattt taatagatca tatgtttgta 18480
aaaaaaatta atttttacta acacatatat ttacttatca aaaatttgac aaagtaagat 18540
taaaataata ttcatctaac aaaaaaaaaa ccagaaaatg ctgaaaaccc ggcaaaaccg 18600
aaccaatcca aaccgatata gttggtttgg tttgattttg atataaaccg aaccaactcg 18660
gtccatttgc acccctaatc ataatagctt taatatttca agatattatt aagttaacgt 18720
tgtcaatatc ctggaaattt tgcaaaatga atcaagccta tatggctgta atatgaattt 18780
aaaagcagct cgatgtggtg gtaatatgta atttacttga ttctaaaaaa atatcccaag 18840
tattaataat ttctgctagg aagaaggtta gctacgattt acagcaaagc cagaatacaa 18900
agaaccataa agtgattgaa gctcgaaata tacgaaggaa caaatatttt taaaaaaata 18960
cgcaatgact tggaacaaaa gaaagtgata tattttttgt tcttaaacaa gcatcccctc 19020
taaagaatgg cagttttcct ttgcatgtaa ctattatgct cccttcgtta caaaaatttt 19080
ggactactat tgggaacttc ttctgaaaat agtcctgcag gctagtagat tggttggttg 19140
gtttccatgt accagaaggc ttaccctatt agttgaaagt tgaaactttg ttccctactc 19200
aattcctagt tgtgtaaatg tatgtatatg taatgtgtat aaaacgtagt acttaaatga 19260
ctaggagtgg ttcttgagac cgatgagaga tgggagcaga actaaagatg atgacataat 19320
taagaacgaa tttgaaaggc tcttaggttt gaatcctatt cgagaatgtt tttgtcaaag 19380
atagtggcga ttttgaacca aagaaaacat ttaaaaaatc agtatccggt tacgttcatg 19440
caaatagaaa gtggtctagg atctgattgt aattttagac ttaaagagtc tcttaagatt 19500
caatcctggc tgtgtacaaa actacaaata atatatttta gactatttgg ccttaactaa 19560
acttccactc attatttact gaggttagag aatagacttg cgaataaaca cattcccgag 19620
aaatactcat gatcccataa ttagtcagag ggtatgccaa tcagatctaa gaacacacat 19680
tccctcaaat tttaatgcac atgtaatcat agtttagcac aattcaaaaa taatgtagta 19740
ttaaagacag aaatttgtag actttttttt ggcgttaaaa gaagactaag tttatacgta 19800
cattttattt taagtggaaa accgaaattt tccatcgaaa tatatgaatt tagtatatat 19860
atttctgcaa tgtactattt tgctattttg gcaactttca gtggactact actttattac 19920
aatgtgtatg gatgcatgag tttgagtata cacatgtcta aatgcatgct ttgtaaaacg 19980
taacggacca caaaagagga tccatacaaa tacatctcat agcttcctcc attattttcc 20040
gacacaaaca gagcatttta caacaattac caacaacaac aaacaacaaa caacattaca 20100
attacattta caattaccat accatggcct ctatcgctat ccctgctgct cttgctggaa 20160
ctcttggata cgttacctac aatgtggcta accctgatat cccagcttct gagaaagttc 20220
ctgcttactt catgcaggtt gagtactggg gacctactat cggaactatt ggatacctcc 20280
tcttcatcta cttcggaaag cgtatcatgc agaacagatc tcaacctttc ggactcaaga 20340
acgctatgct cgtttacaac ttctaccaga ccttcttcaa cagctactgc atctaccttt 20400
tcgttacttc tcatagggct cagggactta aggtttgggg aaacatccct gatatgactg 20460
ctaactcttg gggaatctct caggttatct ggcttcacta caacaacaag tacgttgagc 20520
ttctcgacac cttcttcatg gtgatgagga agaagttcga ccagctttct ttccttcaca 20580

-continued

```
tctaccacca cactcttctc atctggtcat ggttcgttgt tatgaagctt gagcctgttg  20640
gagattgcta cttcggatct tctgttaaca ccttcgtgca cgtgatcatg tactcttact  20700
acggacttgc tgctcttgga gttaactgtt tctggaagaa gtacatcacc cagatccaga  20760
tgcttcagtt ctgtatctgt gcttctcact ctatctacac cgcttacgtt cagaataccg  20820
ctttctggct tccttacctt caactctggg ttatggtgaa catgttcgtt ctcttcgcca  20880
acttctaccg taagaggtac aagtctaagg gtgctaagaa gcagtgataa gggccgccgc  20940
catgtgacag atcgaaggaa gaaagtgtaa taagacgact ctcactactc gatcgctagt  21000
gattgtcatt gttatatata ataatgttat ctttcacaac ttatcgtaat gcatgtgaaa  21060
ctataacaca ttaatcctac ttgtcatatg ataacactct ccccatttaa aactcttgtc  21120
aatttaaaga tataagattc tttaaatgat taaaaaaaat atattataaa ttcaatcact  21180
cctactaata aattattaat tattatttat tgattaaaaa aatacttata ctaatttagt  21240
ctgaatagaa taattagatt ctagcctgca gggcggccgc ggatcccatg gagtcaaaga  21300
ttcaaataga ggacctaaca gaactcgccg taaagactgg cgaacagttc atacagagtc  21360
tcttacgact caatgacaag aagaaaatct tcgtcaacat ggtggagcac gacacacttg  21420
tctactccaa aaatatcaaa gatacagtct cagaagacca aagggcaatt gagacttttc  21480
aacaaagggt aatatccgga aacctcctcg gattccattg cccagctatc tgtcacttta  21540
ttgtgaagat agtggaaaag gaaggtggct cctacaaatg ccatcattgc gataaaggaa  21600
aggccatcgt tgaagatgcc tctgccgaca gtggtcccaa agatggaccc ccacccacga  21660
ggagcatcgt ggaaaaagaa gacgttccaa ccacgtcttc aaagcaagtg gattgatgtg  21720
atatctccac tgacgtaagg gatgacgcac aatcccacta tccttcgcaa gacccttcct  21780
ctatataagg aagttcattt catttggaga gaacacgggg gactgaatta aatatgagcc  21840
ctgagaggcg tcctgttgaa atcagacctg ctactgctgc tgatatggct gctgtttgtg  21900
atatcgtgaa ccactacatc gagacttcta ccgttaactt cagaactgag cctcaaactc  21960
ctcaagagtg gatcgatgat cttgagagac tccaagatag ataccettgg cttgttgctg  22020
aggttgaggg tgttgttgct ggaatcgctt acgctggacc ttggaaggct agaaacgctt  22080
acgattggac tgttgagtct accgtttacg tttcacacag acatcagaga cttggacttg  22140
gatctaccct ttacactcac cttctcaagt ctatggaagc tcagggattc aagtctgttg  22200
ttgctgttat cggactccct aacgatcctt ctgttagact tcatgaggct cttggataca  22260
ctgctagagg aactcttaga gctgctggat acaagcacgg tggatggcat gatgttggat  22320
tctggcaaag agatttcgag cttcctgctc ctcctagacc tgttagacca gttactcaga  22380
tctgaatttg cgtgatcgtt caaacatttg gcaataaagt ttcttaagat tgaatcctgt  22440
tgccggtctt gcgatgatta tcatataatt tctgttgaat tacgttaagc atgtaataat  22500
taacatgtaa tgcatgacgt tatttatgag atgggttttt atgattagag tcccgcaatt  22560
atacatttaa tacgcgatag aaaacaaaat atagcgcgca aactaggata aattatcgcg  22620
cgcggtgtca tctatgttac tagatcacta gtgatgtacg gttaaaacca ccccagtaca  22680
ttaaaaacgt ccgcaatgtg ttattaagtt gtctaagcgt caatttgttt acaccacaat  22740
atatcctgcc accagccagc caacagctcc ccgaccggca gctcggcaca aaatcaccac  22800
tcgatacagg cagcccatca gtcc                                        22824
```

<210> SEQ ID NO 5
<211> LENGTH: 24809

<212> TYPE: DNA
<213> ORGANISM: Artificial Sequence
<220> FEATURE:
<223> OTHER INFORMATION: pga7- mod_e nucleotide sequence

<400> SEQUENCE: 5
tcctgtggtt ggcatgcaca tacaaatgga cgaacggata aaccttttca cgccctttta 60
aatatccgat tattctaata aacgctcttt tctcttaggt ttacccgcca atatatcctg 120
tcaaacactg atagtttaaa ctgaaggcgg gaaacgacaa tctgctagtg gatctcccag 180
tcacgacgtt gtaaaacggg cgcctcgatt aaaaatccca attatatttg gtctaattta 240
gtttggtatt gagtaaaaca aattcgaacc aaaccaaaat ataaatatat agtttttata 300
tatatgcctt taagactttt tatagaattt tctttaaaaa atatctagaa atatttgcga 360
ctcttctggc atgtaatatt tcgttaaata tgaagtgctc catttttatt aactttaaat 420
aattggttgt acgatcactt tcttatcaag tgttactaaa atgcgtcaat ctctttgttc 480
ttccatattc atatgtcaaa atctatcaaa attcttatat atctttttcg aatttgaagt 540
gaaatttcga taatttaaaa ttaaatagaa catatcatta tttaggtatc atattgattt 600
ttatacttaa ttactaaatt tggttaactt tgaaagtgta catcaacgaa aaattagtca 660
aacgactaaa ataaataaat atcatgtgtt attaagaaaa ttctcctata agaatatttt 720
aatagatcat atgtttgtaa aaaaaattaa tttttactaa cacatatatt tacttatcaa 780
aaatttgaca aagtaagatt aaaataatat tcatctaaca aaaaaaaaac cagaaaatgc 840
tgaaaacccg gcaaaaccga accaatccaa accgatatag ttggtttggt ttgattttga 900
tataaaccga accaactcgg tccatttgca cccctaatca taatagcttt aatatttcaa 960
gatattatta agttaacgtt gtcaatatcc tggaaatttt gcaaaatgaa tcaagcctat 1020
atggctgtaa tatgaattta aaagcagctc gatgtggtgg taatatgtaa tttacttgat 1080
tctaaaaaaa tatcccaagt attaataatt tctgctagga agaaggttag ctacgattta 1140
cagcaaagcc agaatacaaa gaaccataaa gtgattgaag ctcgaaatat acgaaggaac 1200
aaatattttt aaaaaaatac gcaatgactt ggaacaaaag aaagtgatat atttttttgtt 1260 cttaaacaag catcccctct aaagaatggc agttttcctt tgcatgtaac tattatgctc 1320
ccttcgttac aaaaatttg gactactatt gggaacttct tctgaaaata gtggcgcccc 1380
gcggaaagct tgctagccaa ttggggccca acgttctcga gtttttctag aaggaaactg 1440
aaggcgggaa acgacaatct gctagtggat ctcccagtca cgacgttgta aaacgggcgc 1500
cccgcggaaa gcttgcggcc gcggtaccgc ccgttcgact cagatcttcc aaggcctcgt 1560
ctccgagtcc gctgcttctc gccgcgccga tcacttctcc gccgccaaca aggcttgtag 1620
ttaataggaa tcattcaggg attgtgattc cgggcagtag taattaataa tatagtatta 1680
gtatagataa tatgtttcgt ttgggatctt tggaacgttg ctctgttcct tgttgttcat 1740
tttaaagctt ttgagggata gttgcagaac tgttcggtga tgcttcatcc tctcaagaac 1800
tagatttggg taaagaaaca tccatgcatg gatatggaat gttgttcttc cgattggaga 1860
ttattttata aaatttaaaa ttcatgattt aaaaaaacac ataaaaacca caaaattcat 1920
gatttattga caatacgata caaaattagc accaccggct actggctcat tacacatttc 1980
cccttcccct cattctcact ttgtggcttt attattatta ttattacata tattttaccg 2040
ttattatttc acgtcacata agcttgttaa ttaatcatta gtgagccttc tcagcctttc 2100
cgttaacgta gtagtgctgt cccaccttat caaggttaga gaaagtagcc ttccaagcac 2160

-continued

```
cgtagtaaga gagcaccttg tagttgagtc cccacttctt agcgaaagga acgaatcttc   2220
tgctaacctc aggctgtctg aattgaggca tatcagggaa gaggtggtgg ataacctgac   2280
agttaaggta tcccataagc cagttcacgt atcctctaga aggatcgata tcaacggtgt   2340
gatcaacagc gtagttaacc caagaaaggt gcttatcaga tggaacaaca gggaggtgag   2400
tatgagaagt agagaagtga gcgaaaaggt acatgtaagc gatccagttt ccgaaagtga   2460
accaccagta agcaacaggc caagagtatc cagtagcaag cttgataaca gcggttctaa   2520
caacatgaga aacgagcatc caagaagcct cttcgtagtt cttcttacgg agaacttgtc   2580
tagggtggag aacgtagatc cagaaagctt gaacaagaag tccagaggta acaggaacga   2640
aagtccaagc ttgaagtcta gcccaagctc tagagaatcc tctaggtctg ttatcctcaa   2700
cagcagtgtt gaagaaagcc acagcaggag tggtatcaag atccatatcg tgtctaacct   2760
tttgaggggt agcatggtgc ttgttatgca tctggttcca catctcacca gaagtagaaa   2820
gtccgaatcc acaagtcata gcctgaagtc tcttgtccac gtaaacagat ccggtaagag   2880
agttatgtcc accctcatgt tgaacccatc cacatctagc tccgaagaaa gcaccgtaaa   2940
caacagaagc aatgataggg tatccagcgt acataagagc agttccaaga gcgaatgtag   3000
caagaagctc gagaagtctg taagccacat gggtgataga aggcttgaag aatccatctc   3060
tctcaagctc agcacgccat ctagcgaaat cctcaagcat aggagcatcc tcagactcag   3120
atctcttgat ctcagcaggt ctagaaggca aagctctaag catcttccaa gccttgagag   3180
aacgcatgtg gaattctttg aaagcctcag tagcatcagc accagtgtta gcaagcatgt   3240
agaagatcac agatccacca gggtgcttga agttagtcac atcgtactca acgtcctcaa   3300
ctctaaccca tctagtctcg aaagtagcag caagctcatg aggctcaaga gtcttaagat   3360
caacaggagc agtagaagca tccttagcat caagagcctc agcagaagat ttagacctgg   3420
taagtggaga tctaggagaa gatcttccat cagtcttagg agggcacatg gtatggtaat   3480
tgtaaatgta attgtaatgt tgtttgttgt ttgttgttgt tggtaattgt tgtaaaatta   3540
attaagtggg tatcttttgg atggataagc aagtagtgat gatgttctag gtgaagtgat   3600
gggggtgttt tatagcggga gatggtgaaa tggatggtcg ccacataaga aatggagggg   3660
aagggttctt gcgccattct tcagtttgca tggatgcatg ggtttcattt tgtaacacgt   3720
aataaggaca atgaagtgca ggtgtctctc aagtttcaga ggggatatgt ggacagaaga   3780
agaacggcga tgatattgat ggaaatggcc atctagtgtg aatctattcg gttgataata   3840
ctagtgcatt ttggccgtta atcccttcaa ttaactgcac aaacttcagt tgagtattga   3900
ttatttgatt ataggttctg taaacacaat accaagttta tttagagggg agacatacaa   3960
atagtttcga tataaataat agagtggtta aacttagtta ttaaaactat atataaagtc   4020
taaaagttaa attatttttt taattgcaaa tatataaagt ctaaaggggt tacattattt   4080
cttaagagat gtaactctgt tggaatctga cttaatccgt ctcatcactc tggtttccag   4140
ttctaatcta atgaattgtt ttctgccaaa gaatttgaag caagaagtaa attgatcaat   4200
gccgtcaacc cacaccaaac cgtcaaccca ctaccatcgc cgcggagacc cccaaactca   4260
acctccaccc atcggtaaga agcacagggc agcccgcacc accaccaatt tggcgtgcat   4320
gacacctagg gacttggcac gggaggcggc gcacgtggat gcaaatgacg ggatatcaga   4380
tgacaggaaa cgacgttgag agaccatacg atgtagaata tgagctcacc atcaacgaga   4440
aactaggaaa atcacaaaaa aaacaactct cgtaattgta cgagtggcac agatgggtct   4500
gcctcaacat atctctaata cggcgaagcc tgcccaacac gtagttgccg gaatccggtg   4560
```

-continued

```
tggagctcac gactctgaaa gataggcgct tcctgtttcg tttcgctcac ccactggacg   4620
tccgtcatgt gatggatttc ggtcattggt ttgctgacaa ccacattctg aagctccatg   4680
agatgagtct tcacaatagg tcctgctcaa taccgtggag ttatggttgc aagtccataa   4740
cttgccgttc gaatattttg cggagccagt cggacgggaa ttggcgagct cggctgacac   4800
ctataaaggc catgacaaga agaaccaaaa gttcttccct aatgctttca tgaggcttcg   4860
ggtcgttatg gatgtcggaa aacccctctt gaaggaacga gacgttatta tgcatgacgg   4920
taagactatt acttgtcagt ataagtatga aagattacct gtcttctgct ttgtttgtgg   4980
attgattgga cacgttgaaa aaaaatgtgc acttcgattt caatactcag agatcgactt   5040
ccctttctc taggagtatt cgatcaaggc attaacatgg aaggaagctc aagctctaaa   5100
ggcttcacaa tggaacctga aaaatttcaa caagcctaaa ctgaaatcga agtcaaatca   5160
cccaaccggg agctctaaat cagcaaacac tcctcctcca cagtatccaa tcatcgtgca   5220
cgatgctcca ggtattgcaa gccaggtatt gcaagctagg agtaggatag agaccttaaa   5280
cgtcgttggt gtgaagagtc atcttcagac ctaatggaga tagatgtaga cggcggcacg   5340
aagactctga aacaccagaa aggctagtcc aggataagga tctgctatcc caactgacct   5400
ctcgttagtc ccaaggcctc tcaactagag caggaggaag gatggtcaca agactaggat   5460
aatgatgttt ccaatatgaa cctgaatgtc catagctaat ttttttagtc ttgcttctgc   5520
actttttgtt tattatgttc tggtgactat gttatttacc cttgtccgta tgcttgaggg   5580
taccctagta gattggttgg ttggtttcca tgtaccagaa ggcttaccct attagttgaa   5640
agttgaaact ttgttcccta ctcaattcct agttgtgtaa atgtatgtat atgtaatgtg   5700
tataaaacgt agtacttaaa tgactaggag tggttcttga gaccgatgag agatgggagc   5760
agaactaaag atgatgacat aattaagaac gaatttgaaa ggctcttagg tttgaatcct   5820
attcgagaat gtttttgtca aagatagtgg cgattttgaa ccaaagaaaa catttaaaaa   5880
atcagtatcc ggttacgttc atgcaaatag aaagtggtct aggatctgat tgtaatttta   5940
gacttaaaga gtctcttaag attcaatcct ggctgtgtac aaaactacaa ataatatatt   6000
ttagactatt tggccttaac taaacttcca ctcattattt actgaggtta gagaatagac   6060
ttgcgaataa acacattccc gagaaatact catgatccca taattagtca gagggtatgc   6120
caatcagatc taagaacaca cattccctca aattttaatg cacatgtaat catagtttag   6180
cacaattcaa aaataatgta gtattaaaga cagaaatttg tagacttttt tttggcgtta   6240
aaagaagact aagtttatac gtacatttta ttttaagtgg aaaaccgaaa ttttccatcg   6300
aaatatatga atttagtata tatatttctg caatgtacta ttttgctatt ttggcaactt   6360
tcagtggact actactttat tacaatgtgt atggatgcat gagtttgagt atacacatgt   6420
ctaaatgcat gctttgtaaa acgtaacgga ccacaaaaga ggatccatac aaatacatct   6480
catagcttcc tccattattt tccgacacaa acagagcatt ttacaacaat taccaacaac   6540
aacaaacaac aaacaacatt acaattacat ttacaattac cataccatgg cctctatcgc   6600
tatccctgct gctcttgctg gaactcttgg atacgttacc tacaatgtgg ctaaccctga   6660
tatcccagct tctgagaaag ttcctgctta cttcatgcag gttgagtact ggggacctac   6720
tatcggaact attggatacc tcctcttcat ctacttcgga aagcgtatca tgcagaacag   6780
atctcaacct ttcggactca agaacgctat gctcgtttac aacttctacc agaccttctt   6840
caacagctac tgcatctacc ttttcgttac ttctcatagg gctcagggac ttaaggtttg   6900
```

-continued

```
gggaaacatc cctgatatga ctgctaactc ttggggaatc tctcaggtta tctggcttca   6960
ctacaacaac aagtacgttg agcttctcga caccttcttc atggtgatga ggaagaagtt   7020
cgaccagctt tctttccttc acatctacca ccacactctt ctcatctggt catggttcgt   7080
tgttatgaag cttgagcctg ttggagattg ctacttcgga tcttctgtta acaccttcgt   7140
gcacgtgatc atgtactctt actacggact tgctgctctt ggagttaact gtttctggaa   7200
gaagtacatc acccagatcc agatgcttca gttctgtatc tgtgcttctc actctatcta   7260
caccgcttac gttcagaata ccgctttctg gcttccttac cttcaactct gggttatggt   7320
gaacatgttc gttctcttcg ccaacttcta ccgtaagagg tacaagtcta agggtgctaa   7380
gaagcagtga taaggcgcgc ggcgcgccgg gccgccgcca tgtgacagat cgaaggaaga   7440
aagtgtaata agacgactct cactactcga tcgctagtga ttgtcattgt tatatataat   7500
aatgttatct ttcacaactt atcgtaatgc atgtgaaact ataacacatt aatcctactt   7560
gtcatatgat aacactctcc ccatttaaaa ctcttgtcaa tttaaagata taagattctt   7620
taaatgatta aaaaaaatat attataaatt caatcactcc tactaataaa ttattaatta   7680
ttatttattg attaaaaaaa tacttatact aatttagtct gaatagaata attagattct   7740
agtctcatcc ccttttaaac caacttagta aacgtttttt tttttaattt tatgaagtta   7800
agtttttacc ttgtttttaa aaagaatcgt tcataagatg ccatgccaga acattagcta   7860
cacgttacac atagcatgca gccgcggaga attgtttttc ttcgccactt gtcactccct   7920
tcaaacacct aagagcttct ctctcacagc acacacatac aatcacatgc gtgcatgcat   7980
tattacacgt gatcgccatg caaatctcct ttatagccta taaattaact catccgcttc   8040
actctttact caaaccaaaa ctcatcgata caaacaagat taaaaacata cacgaggatc   8100
ttttacaaca attaccaaca acaacaaaca acaaacaaca ttacaattac atttacaatt   8160
accataccat gcctccaagg gactcttact cttatgctgc tcctccttct gctcaacttc   8220
acgaagttga tactcctcaa gagcacgaca agaaagagct tgttatcgga gatagggctt   8280
acgatgttac caacttcgtt aagagacacc ctggtggaaa gatcattgct taccaagttg   8340
gaactgatgc taccgatgct tacaagcagt tccatgttag atctgctaag gctgacaaga   8400
tgcttaagtc tcttccttct cgtcctgttc acaagggata ctctccaaga agggctgatc   8460
ttatcgctga tttccaagag ttcaccaagc aacttgaggc tgagggaatg ttcgagcctt   8520
ctcttcctca tgttgcttac agacttgctg aggttatcgc tatgcatgtt gctggtgctg   8580
ctcttatctg gcatggatac actttcgctg gaatcgctat gcttggagtt gttcagggaa   8640
gatgtggatg gcttatgcat gagggtggac attactctct cactggaaac attgctttcg   8700
acagagctat ccaagttgct tgttacggac ttggatgtgg aatgtctggt gcttggtggc   8760
gtaaccagca taacaagcac catgctactc ctcaaaagct tcagcacgat gttgatcttg   8820
ataccctttcc tctcgttgct ttccatgaga gaatcgctgc taaggttaag tctcctgcta   8880
tgaaggcttg gctttctatg caagctaagc ttttcgctcc tgttaccact cttcttgttg   8940
ctcttggatg gcagctttac cttcatccta gacacatgct caggactaag cactacgatg   9000
agcttgctat gctcggaatc agatacggac ttgttggata ccttgctgct aactacggtg   9060
ctggatacgt tctcgcttgt taccttcttt acgttcagct tggagctatg tacatcttct   9120
gcaacttcgc tgtttctcat actcacctcc ctgttgttga gcctaacgag catgctactt   9180
gggttgagta cgctgctaac cacactacta actgttctcc atcttggtgg tgtgattggt   9240
ggatgtctta ccttaactac cagatcgagc accaccttta cccttctatg cctcaattca   9300
```

gacaccctaa gatcgctcct agagttaagc agcttttcga gaagcacgga cttcactacg 9360
atgttagagg atacttcgag gctatggctg atactttcgc taaccttgat aacgttgccc 9420
atgctcctga gaagaaaatg cagtaatgag atcgttcaaa catttggcaa taaagtttct 9480
taagattgaa tcctgttgcc ggtcttgcga tgattatcat ataatttctg ttgaattacg 9540
ttaagcacgt aataattaac atgtaatgca tgacgttatt tatgagatgg gtttttatga 9600
ttagagtccc gcaattatac atttaatacg cgatagaaaa caaaatatag cgcgcaaact 9660
aggataaatt atcgcgcgcg gtgtcatcta tgttactaga tcggtcgatt aaaaatccca 9720
attatatttg gtctaattta gtttggtatt gagtaaaaca aattcgaacc aaaccaaaat 9780
ataaatatat agtttttata tatatgcctt taagactttt tatagaattt tctttaaaaa 9840
atatctagaa atatttgcga ctcttctggc atgtaatatt tcgttaaata tgaagtgctc 9900
catttttatt aactttaaat aattggttgt acgatcactt tcttatcaag tgttactaaa 9960
atgcgtcaat ctctttgttc ttccatattc atatgtcaaa atctatcaaa attcttatat 10020
atctttttcg aatttgaagt gaaatttcga taatttaaaa ttaaatagaa catatcatta 10080
tttaggtatc atattgattt ttatacttaa ttactaaatt tggttaactt tgaaagtgta 10140
catcaacgaa aaattagtca aacgactaaa ataaataaat atcatgtgtt attaagaaaa 10200
ttctcctata agaatatttt aatagatcat atgtttgtaa aaaaaattaa tttttactaa 10260
cacatatatt tacttatcaa aaatttgaca aagtaagatt aaaataatat tcatctaaca 10320
aaaaaaaaac cagaaaatgc tgaaaacccg gcaaaaccga accaatccaa accgatatag 10380
ttggtttggt ttgattttga tataaaccga accaactcgg tccatttgca cccctaatca 10440
taatagcttt aatatttcaa gatattatta agttaacgtt gtcaatatcc tggaaatttt 10500
gcaaaatgaa tcaagcctat atggctgtaa tatgaattta aaagcagctc gatgtggtgg 10560
taatatgtaa tttacttgat tctaaaaaaa tatcccaagt attaataatt tctgctagga 10620
agaaggttag ctacgattta cagcaaagcc agaatacaaa gaaccataaa gtgattgaag 10680
ctcgaaatat acgaaggaac aaatattttt aaaaaaatac gcaatgactt ggaacaaaag 10740
aaagtgatat attttttgtt cttaaacaag catcccctct aaagaatggc agttttcctt 10800
tgcatgtaac tattatgctc ccttcgttac aaaaattttg gactactatt gggaacttct 10860
tctgaaaata gtgatagaac ccacacgagc atgtgctttc catttaattt taaaaaccaa 10920
gaaacataca tacataacat tccatcagcc tctctctctt tttattacgg ttaatgactt 10980
aaaacacatc ttattatccc atccttaaca cctagcagtg tctttatacg atctcatcga 11040
tcaccacttc aaaaccatgc agactgctgc tgcccctgga gctggcatcg gctaggctgg 11100
gtgccgcact gtcccggaag gtccctagcg acttgtttag attgatggga ccacctctca 11160
acttcctgct gctgtccctg ctgctggatg tcctgcctca tctggccgat tgcacgctcc 11220
agtcccctgc atgtgcactc gctcctcaat tgcttaagat catcgcagca gctatcgaag 11280
tgctggctct gttgccctcc tccacggcct tggttgtagt agtagctgcc gccgcccttc 11340
tggacttttt cccacaggaa ccgccgaata attcgataga accacacgag catgtgcttt 11400
catttatttt aaaaaccaag aaacatacat aacatttcat cagcctctct ctctctctct 11460
ctctctctct ctctctctct ctctctctct ctctctttat tacagctgtt acactaactt 11520
aaaacacatt catctcatta ttattattat tatccatcct taacacctag cagtgtcttt 11580
gtacgatctc ataatcgatc accccttcat caggtatcct taggcttcac tccaacgttg 11640
ttgcagttac ggaacatgta cacaccatca tggttctcaa cgaactggca agatctccaa 11700
gttttccaaa ggctaaccca catgttctca tcggtgtgtc tgtagtgctc tcccataact 11760
ttcttgatgc actcggtagc ttctctagca tggtagaatg ggatccttga aacgtagtga 11820
tggagcacat gagtctcgat gatgtcatgg aagatgattc cgaggattcc gaactctcta 11880
tcgatagtag cagcagcacc cttagcgaaa gtccactctt gagcatcgta atgaggcata 11940
gaagaatcgg tgtgctgaag gaaggtaacg aaaacaagcc agtggttaac aaggatccaa 12000
ggacagaacc atgtgatgaa agtaggccag aatccgaaaa ccttgtaagc ggtgtaaaca 12060
gaagtgaggg tagcaaggat tccaagatca gaaagaacga tgtaccagta gtccttctta 12120
tcgaaaacag ggctagaagg ccagtagtga gacttgaaga acttagaaac accagggtaa 12180
ggttgtccag tagcgttagt agcaaggtaa agagaaagtc ctccaagctg ttggaacaag 12240
agagcgaaaa cagagtagat aggagtttcc tcagcgatat cgtgaaggct ggtaacttgg 12300
tgcttctctt tgaattcctc ggcggtgtaa ggaacgaaaa ccatatctct ggtcatgtgt 12360
ccagtagcct tatggtgctt agcatgagag aacttccagc tgaagtaagg aaccataaca 12420
agagagtgga gaacccatcc aacggtatcg ttaacccatc cgtagttaga gaaagcagaa 12480
tgtccacact catgtccaag gatccagatt ccgaatccga aacaagagat agagaacacg 12540
taagcagacc aagcagcgaa tctaaggaat tcgttaggga gaagagggat gtaggtaagt 12600
ccaacgtaag cgatagcaga gatagccacg atatctctca ccacgtaaga catagacttc 12660
acgagagatc tctcgtaaca gtgcttaggg atagcgtcaa ggatatcctt gatggtgtaa 12720
tctggcacct tgaaaacgtt tccgaaggta tcgatagcgg tcttttgctg cttgaaagat 12780
gcaacgtttc cagaacgcct aacggtctta gtagatccct caaggatctc agatccagac 12840
acggtaacct tagacatggt atggtaattg taaatgtaat tgtaatgttg tttgttgttt 12900
gttgttgttg gtaattgttg taaaattttt ggtggtgatt ggttctttaa ggtgtgagag 12960
tgagttgtga gttgtgtggt gggtttggtg agattgggga tggtgggttt atatagtgga 13020
gactgaggaa tggggtcgtg agtgttaact ttgcatgggc tacacgtggg ttcttttggg 13080
cttacacgta gtattattca tgcaaatgca gccaatacat atacggtatt ttaataatgt 13140
gtgggaatac aatatgccga gtattttact aattttggca atgacaagtg tacatttgga 13200
ttatcttact tggcctctct tgctttaatt tggattattt ttattctctt accttggccg 13260
ttcatattca catccctaaa ggcaagacag aattgaatgg tggccaaaaa ttaaaacgat 13320
ggatatgacc tacatagtgt aggatcaatt aacgtcgaag gaaaatactg attctctcaa 13380
gcatacggac aagggtaaat aacatagtca ccagaacata ataaacaaaa agtgcagaag 13440
caagactaaa aaaattagct atggacattc aggttcatat tggaaacatc attatcctag 13500
tcttgtgacc atccttcctc ctgctctagt tgagaggcct tgggactaac gagaggtcag 13560
ttgggatagc agatccttat cctggactag cctttctggt gtttcagagt cttcgtgccg 13620
ccgtctacat ctatctccat taggtctgaa gatgactctt cacaccaacg acgtttaagg 13680
tctctatcct actcctagct tgcaatacct ggcttgcaat acctggagca tcgtgcacga 13740
tgattggata ctgtggagga ggagtgtttg ctgatttaga gctcccggtt gggtgatttg 13800
acttcgattt cagtttaggc ttgttgaaat ttttcaggtt ccattgtgaa gcctttagag 13860
cttgagcttc cttccatgtt aatgccttga tcgaatactc ctagagaaaa gggaagtcga 13920
tctctgagta ttgaaatcga agtgcacatt ttttttcaac gtgtccaatc aatccacaaa 13980
caaagcagaa gacaggtaat ctttcatact tatactgaca agtaatagtc ttaccgtcat 14040

-continued

```
gcataataac gtctcgttcc ttcaagaggg gttttccgac atccataacg acccgaagcc  14100
tcatgaaagc attagggaag aacttttggt tcttcttgtc atggccttta taggtgtcag  14160
ccgagctcgc caattcccgt ccgactggct ccgcaaaata ttcgaacggc aagttatgga  14220
cttgcaacca taactccacg gtattgagca ggacctattg tgaagactca tctcatggag  14280
cttcagaatg tggttgtcag caaaccaatg accgaaatcc atcacatgac ggacgtccag  14340
tgggtgagcg aaacgaaaca ggaagcgcct atctttcaga gtcgtgagct ccacaccgga  14400
ttccggcaac tacgtgttgg gcaggcttcg ccgtattaga gatatgttga ggcagaccca  14460
tctgtgccac tcgtacaatt acgagagttg tttttttgt gattttccta gtttctcgtt  14520
gatggtgagc tcatattcta catcgtatgg tctctcaacg tcgtttcctg tcatctgata  14580
tcccgtcatt tgcatccacg tgcgccgcct cccgtgccaa gtccctaggt gtcatgcacg  14640
ccaaattggt ggtggtgcgg gctgccctgt gcttcttacc gatgggtgga ggttgagttt  14700
gggggtctcc gcggcgatgg tagtgggttg acggtttggt gtgggttgac ggcattgatc  14760
aatttacttc ttgcttcaaa ttctttggca gaaaacaatt cattagatta gaactggaaa  14820
ccagagtgat gagacggatt aagtcagatt ccaacagagt tacatctctt aagaaataat  14880
gtaacccctt tagactttat atatttgcaa ttaaaaaaat aatttaactt ttagacttta  14940
tatatagttt taataactaa gtttaaccac tctattattt atatcgaaac tatttgtatg  15000
tctcccctct aaataaactt ggtattgtgt ttacagaacc tataatcaaa taatcaatac  15060
tcaactgaag tttgtgcagt taattgaagg gattaacggc caaaatgcac tagtattatc  15120
aaccgaatag attcacacta gatggccatt tccatcaata tcatcgccgt tcttcttctg  15180
tccacatatc ccctctgaaa cttgagagac acctgcactt cattgtcctt attacgtgtt  15240
acaaaatgaa acccatgcat ccatgcaaac tgaagaatgg cgcaagaacc cttcccctcc  15300
atttcttatg tggcgaccat ccatttcacc atctcccgct ataaaacacc cccatcactt  15360
cacctagaac atcatcacta cttgcttatc catccaaaag atacccactt ttacaacaat  15420
taccaacaac aacaaacaac aaacaacatt acaattacat ttacaattac cataccatgc  15480
cacctagcgc tgctaagcaa atgggagctt ctactggtgt tcatgctggt gttactgact  15540
cttctgcttt caccagaaag gatgttgctg atagacctga tctcaccatc gttggagatt  15600
ctgtttacga tgctaaggct ttcagatctg agcatcctgg tggtgctcat ttcgtttctt  15660
tgttcggagg aagagatgct actgaggctt tcatggaata ccatagaagg gcttggccta  15720
agtctagaat gtctagattc cacgttggat ctcttgcttc tactgaggaa cctgttgctg  15780
ctgatgaggg ataccttcaa ctttgtgcta ggatcgctaa gatggtgcct tctgtttctt  15840
ctggattcgc tcctgcttct tactgggtta aggctggact tatccttgga tctgctatcg  15900
ctcttgaggc ttacatgctt tacgctggaa agagacttct cccttctatc gttcttggat  15960
ggcttttcgc tcttatcggt cttaacatcc agcatgatgc taaccatggt gctttgtcta  16020
agtctgcttc tgttaacctt gctcttggac tttgtcagga ttggatcgga ggatctatga  16080
tcctttggct tcaagagcat gttgttatgc accacctcca cactaacgat gttgataagg  16140
atcctgatca aaaggctcac ggtgctctta gactcaagcc tactgatgct tggtcaccta  16200
tgcattggct tcagcatctt taccttttgc ctggtgagac tatgtacgct ttcaagcttt  16260
tgttcctcga catctctgag cttgttatgt ggcgttggga gggtgagcct atctctaagc  16320
ttgctggata cctctttatg ccttctttgc ttctcaagct taccttctgg gctagattcg  16380
```

-continued

```
ttgctttgcc tctttacctt gctccttctg ttcatactgc tgtgtgtatc gctgctactg  16440
ttatgactgg atctttctac ctcgctttct tcttcttcat ctcccacaac ttcgagggtg  16500
ttgcttctgt tggacctgat ggatctatca cttctatgac tagaggtgct agcttcctta  16560
agagacaagc tgagacttct tctaacgttg gaggacctct tcttgctact cttaacggtg  16620
gactcaacta ccaaattgag catcacttgt tccctagagt tcaccatgga ttctacccta  16680
gacttgctcc tcttgttaag gctgagcttg aggctagagg aatcgagtac aagcactacc  16740
ctactatctg gtctaacctt gcttctaccc tcagacatat gtacgctctt ggaagaaggc  16800
ctagatctaa ggctgagtaa tgacaagctt atgtgacgtg aaataataac ggtaaaatat  16860
atgtaataat aataataata aagccacaaa gtgagaatga ggggaagggg aaatgtgtaa  16920
tgagccagta gccggtggtg ctaattttgt atcgtattgt caataaatca tgaattttgt  16980
ggtttttatg tgttttttta aatcatgaat tttaaatttt ataaaataat ctccaatcgg  17040
aagaacaaca ttccatatcc atgcatggat gtttctttac ccaaatctag ttcttgagag  17100
gatgaagcat caccgaacag ttctgcaact atccctcaaa agctttaaaa tgaacaacaa  17160
ggaacagagc aacgttccaa agatcccaaa cgaaacatat tatctatact aatactatat  17220
tattaattac tactgcccgg aatcacaatc cctgaatgat tcctattaac tacaagcctt  17280
gttggcggcg gagaagtgat cggcgcggcg agaagcagcg gactcggaga cgaggccttg  17340
gaagatctga gtcgaacggg cagaatcagt attttccttc gacgttaatt gatcctacac  17400
tatgtaggtc atatccatcg ttttaatttt tggccaccat tcaattctgt cttgccttta  17460
gggatgtgaa tatgaacggc caaggtaaga gaataaaaat aatccaaatt aaagcaagag  17520
aggccaagta agataatcca aatgtacact tgtcattgcc aaaattagta aaatactcgg  17580
catattgtat tcccacacat tattaaaata ccgtatatgt attggctgca tttgcatgaa  17640
taatactacg tgtaagccca aaagaaccca cgtgtagccc atgcaaagtt aacactcacg  17700
accccattcc tcagtctcca ctatataaac ccaccatccc caatctcacc aaacccacca  17760
cacaactcac aactcactct cacaccttaa agaaccaatc accaccaaaa atttacaac   17820
aattaccaac aacaacaaac aacaaacaac attacaatta catttacaat taccatacca  17880
tgagcgctgt taccgttact ggatctgatc ctaagaacag aggatcttct agcaacaccg  17940
agcaagaggt tccaaaagtt gctatcgata ccaacggaaa cgtgttctct gttcctgatt  18000
tcaccatcaa ggacatcctt ggagctatcc ctcatgagtg ttacgagaga agattggcta  18060
cctctctcta ctacgtgttc agagatatct tctgcatgct taccaccgga taccttaccc  18120
ataagatcct ttaccctctc ctcatctctt acacctctaa cagcatcatc aagttcactt  18180
tctgggccct ttacacttac gttcaaggac ttttcggaac cggaatctgg gttctcgctc  18240
atgagtgtgg acatcaagct ttctctgatt acggaatcgt gaacgatttc gttggatgga  18300
cccttcactc ttaccttatg gttccttact tcagctggaa gtactctcat ggaaagcacc  18360
ataaggctac tggacacatg accagagata tggttttcgt tcctgccacc aaagaggaat  18420
tcaagaagtc taggaacttc ttcggtaacc tcgctgagta ctctgaggat tctccactta  18480
gaacccttta cgagcttctt gttcaacaac ttggaggatg gatcgcttac ctcttcgtta  18540
acgttacagg acaaccttac cctgatgttc cttcttggaa atggaaccac ttctggctta  18600
cctctccact tttcgagcaa agagatgctc tctacatctt cctttctgat cttggaatcc  18660
tcacccaggg aatcgttctt actctttggt acaagaaatt cggaggatgg tcccttttca  18720
tcaactggtt cgttccttac atctgggtta accactggct cgttttcatc acattccttc  18780
```

-continued

```
agcacactga tcctactatg cctcattaca acgctgagga atggactttc gctaagggtg  18840
ctgctgctac tatcgataga aagttcggat tcatcggacc tcacatcttc catgatatca  18900
tcgagactca tgtgcttcac cactactgtt ctaggatccc attctacaac gctagacctg  18960
cttctgaggc tatcaagaaa gttatgggaa agcactacag gtctagcgac gagaacatgt  19020
ggaagtcact ttggaagtct ttcaggtctt gccaatacgt tgacggtgat aacggtgttc  19080
tcatgttccg taacatcaac aactgcggag ttggagctgc tgagaagtaa tgaaggggtg  19140
atcgattatg agatcgtaca aagacactgc taggtgttaa ggatggataa taataataat  19200
aatgagatga atgtgtttta agttagtgta acagctgtaa taaagagaga gagagagaga  19260
gagagagaga gagagagaga gagagagaga gagaggctga tgaaatgtta tgtatgtttc  19320
ttggttttta aaataaatga aagcacatgc tcgtgtggtt ctatcgaatt attcggcggt  19380
tcctgtggga aaaagtccag aagggccgcc gcagctacta ctacaaccaa ggccgtggag  19440
gagggcaaca gagccagcac ttcgatagct gctgcgatga tcttaagcaa ttgaggagcg  19500
agtgcacatg caggggactg gagcgtgcaa tcggccagat gaggcaggac atccagcagc  19560
agggacagca gcaggaagtt gagaggtggt cccatcaatc taaacaagtc gctagggacc  19620
ttccgggaca gtgcggcacc cagcctagcc gatgccagct ccaggggcag cagcagtctg  19680
catggttttg aagtggtgat cgatgagatc gtataaagac actgctaggt gttaaggatg  19740
ggataataag atgtgtttta agtcattaac cgtaataaaa agagagagag gctgatggaa  19800
tgttatgtat gtatgtttct tggtttttaa aattaaatgg aaagcacatg ctcgtgtggg  19860
ttctatctcg attaaaaatc ccaattatat ttggtctaat ttagtttggt attgagtaaa  19920
acaaattcga accaaaccaa aatataaata tatagttttt atatatatgc ctttaagact  19980
ttttatagaa ttttctttaa aaaatatcta gaaatatttg cgactcttct ggcatgtaat  20040
atttcgttaa atatgaagtg ctccattttt attaacttta aataattggt tgtacgatca  20100
ctttcttatc aagtgttact aaaatgcgtc aatctctttg ttcttccata ttcatatgtc  20160
aaaatctatc aaaattctta tatatctttt tcgaatttga agtgaaattt cgataattta  20220
aaattaaata gaacatatca ttatttaggt atcatattga tttttatact taattactaa  20280
atttggttaa ctttgaaagt gtacatcaac gaaaaaattag tcaaacgact aaaataaata  20340
aatatcatgt gttattaaga aaattctcct ataagaatat tttaatagat catatgtttg  20400
taaaaaaaat taatttttac taacacatat atttacttat caaaaatttg acaaagtaag  20460
attaaaataa tattcatcta acaaaaaaaa aaccagaaaa tgctgaaaac ccggcaaaac  20520
cgaaccaatc caaaccgata tagttggttt ggtttgattt tgatataaac cgaaccaact  20580
cggtccattt gcacccctaa tcataatagc tttaatattt caagatatta ttaagttaac  20640
gttgtcaata tcctggaaat tttgcaaaat gaatcaagcc tatatggctg taatatgaat  20700
ttaaaagcag ctcgatgtgg tggtaatatg taatttactt gattctaaaa aaatatccca  20760
agtattaata atttctgcta ggaagaaggt tagctacgat ttacagcaaa gccagaatac  20820
aaagaaccat aaagtgattg aagctcgaaa tatacgaagg aacaaatatt tttaaaaaaa  20880
tacgcaatga cttggaacaa aagaaagtga tatatttttt gttcttaaac aagcatcccc  20940
tctaaagaat ggcagttttc ctttgcatgt aactattatg ctcccttcgt tacaaaaatt  21000
ttggactact attgggaact tcttctgaaa atagtcctgc aggctagtag attggttggt  21060
tggtttccat gtaccagaag gcttacccta ttagttgaaa gttgaaactt tgttccctac  21120
```

```
tcaattccta gttgtgtaaa tgtatgtata tgtaatgtgt ataaaacgta gtacttaaat  21180
gactaggagt ggttcttgag accgatgaga gatgggagca gaactaaaga tgatgacata  21240
attaagaacg aatttgaaag gctcttaggt ttgaatccta ttcgagaatg tttttgtcaa  21300
agatagtggc gattttgaac caaagaaaac atttaaaaaa tcagtatccg gttacgttca  21360
tgcaaataga aagtggtcta ggatctgatt gtaattttag acttaaagag tctcttaaga  21420
ttcaatcctg gctgtgtaca aaactacaaa taatatattt tagactattt ggccttaact  21480
aaacttccac tcattattta ctgaggttag agaatagact tgcgaataaa cacattcccg  21540
agaaatactc atgatcccat aattagtcag agggtatgcc aatcagatct aagaacacac  21600
attccctcaa attttaatgc acatgtaatc atagtttagc acaattcaaa aataatgtag  21660
tattaaagac agaaatttgt agactttttt ttggcgttaa aagaagacta agtttatacg  21720
tacattttat tttaagtgga aaaccgaaat tttccatcga aatatatgaa tttagtatat  21780
atatttctgc aatgtactat tttgctattt tggcaacttt cagtggacta ctactttatt  21840
acaatgtgta tggatgcatg agtttgagta tacacatgtc taaatgcatg ctttgtaaaa  21900
cgtaacggac cacaaaagag gatccataca aatacatctc atagcttcct ccattatttt  21960
ccgacacaaa cagagcattt tacaacaatt accaacaaca acaaacaaca aacaacatta  22020
caattacatt tacaattacc ataccatgga atttgctcaa cctctcgttg ctatggctca  22080
agagcagtac gctgctatcg atgctgttgt tgctcctgct atcttctctg ctaccgactc  22140
tattggatgg ggactcaagc ctatctcttc tgctactaag gatctccctc tcgttgaatc  22200
tcctacccct cttatccttt ctctcctcgc ttacttcgct atcgttggtt ctggactcgt  22260
ttaccgtaaa gtgttcccta gaaccgttaa gggacaggat cctttccttc tcaaggctct  22320
tatgctcgct cacaacgttt tccttatcgg actcagcctt tacatgtgcc tcaagctcgt  22380
ttacgaggct tacgtgaaca agtactcctt ctggggaaac gcttacaacc ctgctcaaac  22440
cgagatggct aaggtgatct ggatcttcta cgtgtccaag atctacgagt tcatggacac  22500
cttcatcatg cttctcaagg gaaacgttaa ccaggtttcc ttcctccatg tttaccacca  22560
cggatctatc tctggaatct ggtggatgat cacttatgct gctccaggtg gagatgctta  22620
cttctctgct gctctcaact cttgggttca tgtgtgcatg tacacctact acttcatggc  22680
tgctgttctt cctaaggacg aaaagaccaa gagaaagtac ctttggtggg gaagatacct  22740
tacccagatg caaatgttcc agttcttcat gaaccttctc caggctgttt acctcctcta  22800
ctcttcttct ccttacccta agttcattgc tcaactcctc gttgtttaca tggttaccct  22860
cctcatgctt ttcggaaact tctactacat gaagcaccac gcttctaagt gataagggcc  22920
gccgccatgt gacagatcga aggaagaaag tgtaataaga cgactctcac tactcgatcg  22980
ctagtgattg tcattgttat atataataat gttatctttc acaacttatc gtaatgcatg  23040
tgaaactata acacattaat cctacttgtc atatgataac actctcccca tttaaaactc  23100
ttgtcaattt aaagatataa gattctttaa atgattaaaa aaaatatatt ataaattcaa  23160
tcactcctac taataaatta ttaattatta tttattgatt aaaaaaatac ttatactaat  23220
ttagtctgaa tagaataatt agattctagc ctgcagggcg gccgcggatc ccatggagtc  23280
aaagattcaa atagaggacc taacagaact cgccgtaaag actggcgaac agttcataca  23340
gagtctctta cgactcaatg acaagaagaa aatcttcgtc aacatggtgg agcacgacac  23400
acttgtctac tccaaaaata tcaaagatac agtctcagaa gaccaaaggg caattgagac  23460
ttttcaacaa agggtaatat ccggaaacct cctcggattc cattgcccag ctatctgtca  23520
```

```
ctttattgtg aagatagtgg aaaaggaagg tggctcctac aaatgccatc attgcgataa  23580
aggaaaggcc atcgttgaag atgcctctgc cgacagtggt cccaaagatg gacccccacc  23640
cacgaggagc atcgtggaaa aagaagacgt tccaaccacg tcttcaaagc aagtggattg  23700
atgtgatatc tccactgacg taagggatga cgcacaatcc cactatcctt cgcaagaccc  23760
ttcctctata taaggaagtt catttcattt ggagagaaca cgggggactg aattaaatat  23820
gagccctgag aggcgtcctg ttgaaatcag acctgctact gctgctgata tggctgctgt  23880
ttgtgatatc gtgaaccact acatcgagac ttctaccgtt aacttcagaa ctgagcctca  23940
aactcctcaa gagtggatcg atgatcttga gagactccaa gatagatacc cttggcttgt  24000
tgctgaggtt gagggtgttg ttgctggaat cgcttacgct ggaccttgga aggctagaaa  24060
cgcttacgat tggactgttg agtctaccgt ttacgtttca cacagacatc agagacttgg  24120
acttggatct accctttaca ctcaccttct caagtctatg gaagctcagg gattcaagtc  24180
tgttgttgct gttatcggac tccctaacga tccttctgtt agacttcatg aggctcttgg  24240
atacactgct agaggaactc ttagagctgc tggatacaag cacggtggat ggcatgatgt  24300
tggattctgg caaagagatt tcgagcttcc tgctcctcct agacctgtta gaccagttac  24360
tcagatctga atttgcgtga tcgttcaaac atttggcaat aaagtttctt aagattgaat  24420
cctgttgccg gtcttgcgat gattatcata taatttctgt tgaattacgt taagcatgta  24480
ataattaaca tgtaatgcat gacgttattt atgagatggg tttttatgat tagagtcccg  24540
caattataca tttaatacgc gatagaaaac aaaatatagc gcgcaaacta ggataaatta  24600
tcgcgcgcgg tgtcatctat gttactagat cactagtgat gtacggttaa aaccacccca  24660
gtacattaaa aacgtccgca atgtgttatt aagttgtcta agcgtcaatt tgtttacacc  24720
acaatatatc ctgccaccag ccagccaaca gctccccgac cggcagctcg gcacaaaatc  24780
accactcgat acaggcagcc catcagtcc                                    24809
```

<210> SEQ ID NO 6
<211> LENGTH: 26543
<212> TYPE: DNA
<213> ORGANISM: Artificial Sequence
<220> FEATURE:
<223> OTHER INFORMATION: pGA7- mod_F nucleotide sequence

<400> SEQUENCE: 6

```
tcctgtggtt ggcatgcaca tacaaatgga cgaacggata aaccttttca cgccctttta     60
aatatccgat tattctaata aacgctcttt tctcttaggt ttacccgcca atatatcctg    120
tcaaacactg atagtttaaa ctgaaggcgg gaaacgacaa tctgctagtg gatctcccag    180
tcacgacgtt gtaaaacggg cgggcggccg cctagaatct aattattcta ttcagactaa    240
attagtataa gtattttttt aatcaataaa tattaattaa taatttatta gtaggagtga    300
ttgaatttat aatatatttt ttttaatcat ttaaagaatc ttatatcttt aaattgacaa    360
gagttttaaa tggggagagt gttatcatat gacaagtagg attaatgtgt tatagtttca    420
catgcattac gataagttgt gaaagataac attattatat ataacaatga caatcactag    480
cgatcgagta gtgagagtcg tcttattaca ctttcttcct tcgatctgtc acatggcggc    540
ggcccgcgat cgcgataatt ctcagtgcgc cttctccgcc ttgccgttga cgtagtagtg    600
ctgcccgacc ttatccaagt tcgagaacgt cgccttccag gcgccgtaat aggacagcac    660
cttgtagttc agcccccact tcttcgcgaa cgggacgaac cgccggctca cctccggctg    720
```

-continued

```
gcgaaactgc ggcatgtccg ggaacaggtg atgaatgacc tggcagttca gatatcccat    780
caaccagttc acgtacccgc gcgacgggtc gatgtccacg gtgtgatcga ccgcgtagtt    840
cacccagctc aggtgcttat ccgagggcac gaccgggagg tgcgtgtggc tcgtggagaa    900
gtgcgcgaag aggtacatgt acgcgatcca gttgccgaag gtgaaccacc agtacgcgac    960
gggccacgag taccccgtcg cgagtttaat caccgcggtc ctgacgacgt gagagacgag   1020
catccacgac gcctcctcgt agttcttctt tcgcaacacc tgccgcgggt gcaggacgta   1080
gatccagaac gcctggacga gcagcccgga ggtcaccggg acgaacgtcc acgcctgaag   1140
ccgagcccac gcgcgggaga accccctcgg ccggttgtcc tccacggcgg tgttaaaaaa   1200
cgccaccgcg gggtcgtgt ccaggtccat gtcgtgcctc actttctgcg gcgtcgcgtg   1260
gtgcttattg tgcatctggt tccacatctc cccgctcgtg gacagcccga acccgcacgt   1320
catcgcttgg aggcgcttgt cgacgtagac ggaccccgtg agcgagttgt gcccgccctc   1380
gtgctggacc caaccgcacc gagcgccgaa gaacgcgccg tacacgacgg acgcgatgat   1440
cgggtacccg gcgtacatga gggcggtgcc gagggcgaag gtcgcgagga gctcgagtaa   1500
ccgatacgcg acgtgcgtta tcgagggctt aaagaacccg tcgcgttcga gctccgcgcg   1560
ccaccgcgcg aaatcctcca acatcggcgc gtcctcgctc tcgctgcgtt tgatctccgc   1620
ggggcgcgac ggcagcgctc tgagcatctt ccacgcctta agcgatcgca tgtggaactc   1680
cttgaacgcc tccgtggcgt ccgcgcccgt gttcgcgagc atgtagaata tcacgctgcc   1740
tcccgggtgt ttgaagtttg tgacgtcgta ctcgacgtcc tccacgcgca cccatcgcgt   1800
ctcgaacgtc gccgcgagct cgtgcggctc gagcgttttg agatcgacgg gcgcggtcga   1860
cgcgtccttg gcgtcgagcg cctccgcgga ggatttgctg cgcgtcagcg gcgatcgcgg   1920
ggacgatcgg ccgtccgtct tcggcgggca catcgtcgcg cgcgcgactt aaaccgacga   1980
cggacggacg aacctgcaac ggcgaattat caattgacgc gttgctctgt ttgtgtcgga   2040
aaataatgga ggaagctatg agatgtattt gcatggatcc tcttttgtgg tccgttacgt   2100
tttgcaaagc atgcatttag acatgtgtat actcaaactc atgcatccat acacattgta   2160
ataaagtagt agtccactga aagttgccaa aatagcaaaa tagtacattg cagaaatata   2220
tatactaaat tcatatattt cgatggaaaa tttcggtttt ccacttaaaa taaaatgtac   2280
gtataaactt agtcttcctt taacgccaaa aaaaagtcta caaatttctg tctttaatac   2340
tacattattt ttgaattgtg ctaaactatg attacatgtg cattaaaatt tgagggaatg   2400
tgtgttctta gatctgattg gcataccctc tgactaatta tgggatcatg agtatttctc   2460
gggaatgtgt ttattcgcaa gtctattctc taacctcagt aaataatgag tggaagttta   2520
gttaaggcca aatagtctaa aatatattat ttgtagtttt gtacacagcc aggattgaat   2580
cttaagagac tctttaagtc taaaattaca atcagatcct agaccacttt ctatttgcat   2640
gaacgtaacc ggatactgat tttttaaatg ttttctttgg ttcaaaatcg ccactatctt   2700
tgacaaaaac attctcgaat aggattcaaa cctaagagcc tttcaaattc gttcttaatt   2760
atgtcatcat ctttagttct gctcccatct ctcatcggtc tcaagaacca ctcctagtca   2820
tttaagtact acgttttata cgcattacat atacatacat ttacacaact aggaattgag   2880
tagggaacaa agtttcaact ttcaactaat agggtaagcc ttctggtaca tggaaaccaa   2940
ccaaccaatc tactaggcgg ccgcccgtcg ggatcttctg caagcatctc tatttcctga   3000
aggtctaacc tcgaagattt aagatttaat tacgtttata attacaaaat tgattctagt   3060
atctttaatt taatgcttat acattattaa ttaatttagt actttcaatt tgttttcaga   3120
```

-continued

```
aattatttta ctatttttta taaaataaaa gggagaaaat ggctatttaa actgaaggcg   3180
ggaaacgaca atctgctagt ggatctccca gtcacgacgt tgtaaaacgg gcgccccgcg   3240
gaaagcttgc ggccgcggta ccgcccgttc gactcagatc ttccaaggcc tcgtctccga   3300
gtccgctgct tctcgccgcg ccgatcactt ctccgccgcc aacaaggctt gtagttaata   3360
ggaatcattc agggattgtg attccgggca gtagtaatta ataatatagt attagtatag   3420
ataatatgtt tcgtttggga tctttggaac gttgctctgt tccttgttgt tcattttaaa   3480
gcttttgagg gatagttgca gaactgttcg gtgatgcttc atcctctcaa gaactagatt   3540
tgggtaaaga aacatccatg catggatatg gaatgttgtt cttccgattg gagattattt   3600
tataaaattt aaaattcatg atttaaaaaa acacataaaa accacaaaat tcatgattta   3660
ttgacaatac gatacaaaat tagcaccacc ggctactggc tcattacaca tttccccttc   3720
ccctcattct cactttgtgg ctttattatt attattatta catatatttt accgttatta   3780
tttcacgtca cataagcttg ttaattaatc attagtgagc cttctcagcc tttccgttaa   3840
cgtagtagtg ctgtcccacc ttatcaaggt tagagaaagt agccttccaa gcaccgtagt   3900
aagagagcac cttgtagttg agtccccact tcttagcgaa aggaacgaat cttctgctaa   3960
cctcaggctg tctgaattga ggcatatcag ggaagaggtg gtggataacc tgacagttaa   4020
ggtatcccat aagccagttc acgtatcctc tagaaggatc gatatcaacg gtgtgatcaa   4080
cagcgtagtt aacccaagaa aggtgcttat cagatggaac aacagggagg tgagtatgag   4140
aagtagagaa gtgagcgaaa aggtacatgt aagcgatcca gtttccgaaa gtgaaccacc   4200
agtaagcaac aggccaagag tatccagtag caagcttgat aacagcggtt ctaacaacat   4260
gagaaacgag catccaagaa gcctcttcgt agttcttctt acggagaact tgtctagggt   4320
ggagaacgta gatccagaaa gcttgaacaa gaagtccaga ggtaacagga acgaaagtcc   4380
aagcttgaag tctagcccaa gctctagaga atcctctagg tctgttatcc tcaacagcag   4440
tgttgaagaa agccacagca ggagtggtat caagatccat atcgtgtcta accttttgag   4500
gggtagcatg gtgcttgtta tgcatctggt tccacatctc accagaagta gaaagtccga   4560
atccacaagt catagcctga agtctcttgt ccacgtaaac agatccggta agagagttat   4620
gtccaccctc atgttgaacc catccacatc tagctccgaa gaaagcaccg taaacaacag   4680
aagcaatgat agggtatcca gcgtacataa gagcagttcc aagagcgaat gtagcaagaa   4740
gctcgagaag tctgtaagcc acatgggtga tagaaggctt gaagaatcca tctctctcaa   4800
gctcagcacg ccatctagcg aaatcctcaa gcataggagc atcctcagac tcagatctct   4860
tgatctcagc aggtctagaa ggcaaagctc taagcatctt ccaagccttg agagaacgca   4920
tgtggaattc tttgaaagcc tcagtagcat cagcaccagt gttagcaagc atgtagaaga   4980
tcacagatcc accagggtgc ttgaagttag tcacatcgta ctcaacgtcc tcaactctaa   5040
cccatctagt ctcgaaagta gcagcaagct catgaggctc aagagtctta agatcaacag   5100
gagcagtaga agcatcctta gcatcaagag cctcagcaga agatttagac ctggtaagtg   5160
gagatctagg agaagatctt ccatcagtct taggagggca catggtatgg taattgtaaa   5220
tgtaattgta atgttgtttg ttgtttgttg ttgttggtaa ttgttgtaaa attaattaag   5280
tgggtatctt ttggatggat aagcaagtag tgatgatgtt ctaggtgaag tgatgggggt   5340
gttttatagc gggagatggt gaaatggatg gtcgccacat aagaaatgga ggggaagggt   5400
tcttgcgcca ttcttcagtt tgcatggatg catgggtttc attttgtaac acgtaataag   5460
```

-continued

```
gacaatgaag tgcaggtgtc tctcaagttt cagaggggat atgtggacag aagaagaacg   5520
gcgatgatat tgatggaaat ggccatctag tgtgaatcta ttcggttgat aatactagtg   5580
cattttggcc gttaatccct tcaattaact gcacaaactt cagttgagta ttgattattt   5640
gattataggt tctgtaaaca caataccaag tttatttaga ggggagacat acaaatagtt   5700
tcgatataaa taatagagtg gttaaactta gttattaaaa ctatatataa agtctaaaag   5760
ttaaattatt tttttaattg caaatatata aagtctaaag gggttacatt atttcttaag   5820
agatgtaact ctgttggaat ctgacttaat ccgtctcatc actctggttt ccagttctaa   5880
tctaatgaat tgttttctgc caaagaattt gaagcaagaa gtaaattgat caatgccgtc   5940
aacccacacc aaaccgtcaa cccactacca tcgccgcgga gacccccaaa ctcaacctcc   6000
acccatcggt aagaagcaca gggcagcccg caccaccacc aatttggcgt gcatgacacc   6060
tagggacttg gcacgggagg cggcgcacgt ggatgcaaat gacgggatat cagatgacag   6120
gaaacgacgt tgagagacca tacgatgtag aatatgagct caccatcaac gagaaactag   6180
gaaaatcaca aaaaaaacaa ctctcgtaat tgtacgagtg gcacagatgg gtctgcctca   6240
acatatctct aatacggcga agcctgccca acacgtagtt gccggaatcc ggtgtggagc   6300
tcacgactct gaaagatagg cgcttcctgt ttcgtttcgc tcacccactg gacgtccgtc   6360
atgtgatgga tttcggtcat tggtttgctg acaaccacat tctgaagctc catgagatga   6420
gtcttcacaa taggtcctgc tcaataccgt ggagttatgg ttgcaagtcc ataacttgcc   6480
gttcgaatat tttgcggagc cagtcggacg ggaattggcg agctcggctg acacctataa   6540
aggccatgac aagaagaacc aaaagttctt ccctaatgct ttcatgaggc ttcgggtcgt   6600
tatggatgtc ggaaaacccc tcttgaagga acgagacgtt attatgcatg acggtaagac   6660
tattacttgt cagtataagt atgaaagatt acctgtcttc tgctttgttt gtggattgat   6720
tggacacgtt gaaaaaaaat gtgcacttcg atttcaatac tcagagatcg acttcccttt   6780
tctctaggag tattcgatca aggcattaac atggaaggaa gctcaagctc taaaggcttc   6840
acaatggaac ctgaaaaatt tcaacaagcc taaactgaaa tcgaagtcaa atcacccaac   6900
cgggagctct aaatcagcaa acactcctcc tccacagtat ccaatcatcg tgcacgatgc   6960
tccaggtatt gcaagccagg tattgcaagc taggagtagg atagagacct taaacgtcgt   7020
tggtgtgaag agtcatcttc agacctaatg gagatagatg tagacggcgg cacgaagact   7080
ctgaaacacc agaaaggcta gtccaggata aggatctgct atcccaactg acctctcgtt   7140
agtcccaagg cctctcaact agagcaggag gaaggatggt cacaagacta ggataatgat   7200
gtttccaata tgaacctgaa tgtccatagc taattttttt agtcttgctt ctgcactttt   7260
tgtttattat gttctggtga ctatgttatt taccettgtc cgtatgcttg agggtaccct   7320
agtagattgg ttggttggtt tccatgtacc agaaggctta ccctattagt tgaaagttga   7380
aactttgttc cctactcaat tcctagttgt gtaaatgtat gtatatgtaa tgtgtataaa   7440
acgtagtact taaatgacta ggagtggttc ttgagaccga tgagagatgg gagcagaact   7500
aaagatgatg acataattaa gaacgaattt gaaaggctct taggtttgaa tcctattcga   7560
gaatgttttt gtcaaagata gtggcgattt tgaaccaaag aaaacattta aaaaatcagt   7620
atccggttac gttcatgcaa atagaaagtg gtctaggatc tgattgtaat tttagactta   7680
aagagtctct taagattcaa tcctggctgt gtacaaaact acaaataata tattttagac   7740
tatttggcct taactaaact tccactcatt atttactgag gttagagaat agacttgcga   7800
ataaacacat tcccgagaaa tactcatgat cccataatta gtcagagggt atgccaatca   7860
```

-continued

```
gatctaagaa cacacattcc ctcaaatttt aatgcacatg taatcatagt ttagcacaat   7920
tcaaaaataa tgtagtatta aagacagaaa tttgtagact tttttttggc gttaaaagaa   7980
gactaagttt atacgtacat tttattttaa gtggaaaacc gaaattttcc atcgaaatat   8040
atgaatttag tatatatatt tctgcaatgt actattttgc tattttggca actttcagtg   8100
gactactact ttattacaat gtgtatggat gcatgagttt gagtatacac atgtctaaat   8160
gcatgctttg taaaacgtaa cggaccacaa aagaggatcc atacaaatac atctcatagc   8220
ttcctccatt attttccgac acaaacagag cattttacaa caattaccaa caacaacaaa   8280
caacaaacaa cattacaatt acatttacaa ttaccatacc atggcctcta tcgctatccc   8340
tgctgctctt gctggaactc ttggatacgt tacctacaat gtggctaacc ctgatatccc   8400
agcttctgag aaagttcctg cttacttcat gcaggttgag tactggggac ctactatcgg   8460
aactattgga tacctcctct tcatctactt cggaaagcgt atcatgcaga acagatctca   8520
acctttcgga ctcaagaacg ctatgctcgt ttacaacttc taccagacct tcttcaacag   8580
ctactgcatc taccttttcg ttacttctca tagggctcag ggacttaagg tttggggaaa   8640
catccctgat atgactgcta actcttgggg aatctctcag gttatctggc ttcactacaa   8700
caacaagtac gttgagcttc tcgacacctt cttcatggtg atgaggaaga agttcgacca   8760
gctttctttc cttcacatct accaccacac tcttctcatc tggtcatggt tcgttgttat   8820
gaagcttgag cctgttggag attgctactt cggatcttct gttaacacct tcgtgcacgt   8880
gatcatgtac tcttactacg gacttgctgc tcttggagtt aactgtttct ggaagaagta   8940
catcacccag atccagatgc ttcagttctg tatctgtgct tctcactcta tctacaccgc   9000
ttacgttcag aataccgctt tctggcttcc ttaccttcaa ctctgggtta tggtgaacat   9060
gttcgttctc ttcgccaact tctaccgtaa gaggtacaag tctaagggtg ctaagaagca   9120
gtgataaggc gcgcggcgcg ccgggccgcc gccatgtgac agatcgaagg aagaaagtgt   9180
aataagacga ctctcactac tcgatcgcta gtgattgtca ttgttatata taataatgtt   9240
atctttcaca acttatcgta atgcatgtga aactataaca cattaatcct acttgtcata   9300
tgataacact ctccccattt aaaactcttg tcaatttaaa gatataagat tctttaaatg   9360
attaaaaaaa atatattata aattcaatca ctcctactaa taaattatta attattattt   9420
attgattaaa aaaatactta tactaattta gtctgaatag aataattaga ttctagtctc   9480
atccccttttt aaaccaactt agtaaacgtt ttttttttta attttatgaa gttaagtttt   9540
taccttgttt ttaaaaagaa tcgttcataa gatgccatgc cagaacatta gctacacgtt   9600
acacatagca tgcagccgcg gagaattgtt tttcttcgcc acttgtcact cccttcaaac   9660
acctaagagc ttctctctca cagcacacac atacaatcac atgcgtgcat gcattattac   9720
acgtgatcgc catgcaaatc tcctttatag cctataaatt aactcatccg cttcactctt   9780
tactcaaacc aaaactcatc gatacaaaca agattaaaaa catacacgag gatcttttac   9840
aacaattacc aacaacaaca aacaacaaac aacattacaa ttacatttac aattaccata   9900
ccatgcctcc aagggactct tactcttatg ctgctcctcc ttctgctcaa cttcacgaag   9960
ttgatactcc tcaagagcac gacaagaaag agcttgttat cggagatagg gcttacgatg  10020
ttaccaactt cgttaagaga caccctggtg gaaagatcat tgcttaccaa gttggaactg  10080
atgctaccga tgcttacaag cagttccatg ttagatctgc taaggctgac aagatgctta  10140
agtctcttcc ttctcgtcct gttcacaagg gatactctcc aagaagggct gatcttatcg  10200
```

```
ctgatttcca agagttcacc aagcaacttg aggctgaggg aatgttcgag ccttctcttc  10260
ctcatgttgc ttacagactt gctgaggtta tcgctatgca tgttgctggt gctgctctta  10320
tctggcatgg atacactttc gctggaatcg ctatgcttgg agttgttcag ggaagatgtg  10380
gatggcttat gcatgagggt ggacattact ctctcactgg aaacattgct ttcgacagag  10440
ctatccaagt tgcttgttac ggacttggat gtggaatgtc tggtgcttgg tggcgtaacc  10500
agcataacaa gcaccatgct actcctcaaa agcttcagca cgatgttgat cttgataccc  10560
ttcctctcgt tgctttccat gagagaatcg ctgctaaggt taagtctcct gctatgaagg  10620
cttggctttc tatgcaagct aagcttttcg ctcctgttac cactcttctt gttgctcttg  10680
gatggcagct ttaccttcat cctagacaca tgctcaggac taagcactac gatgagcttg  10740
ctatgctcgg aatcagatac ggacttgttg gataccttgc tgctaactac ggtgctggat  10800
acgttctcgc ttgttacctt ctttacgttc agcttggagc tatgtacatc ttctgcaact  10860
tcgctgtttc tcatactcac ctccctgttg ttgagcctaa cgagcatgct acttgggttg  10920
agtacgctgc taaccacact actaactgtt ctccatcttg gtggtgtgat tggtggatgt  10980
cttaccttaa ctaccagatc gagcaccacc tttacccttc tatgcctcaa ttcagacacc  11040
ctaagatcgc tcctagagtt aagcagcttt tcgagaagca cggacttcac tacgatgtta  11100
gaggatactt cgaggctatg gctgatactt tcgctaacct tgataacgtt gcccatgctc  11160
ctgagaagaa aatgcagtaa tgagatcgtt caaacatttg gcaataaagt ttcttaagat  11220
tgaatcctgt tgccggtctt gcgatgatta tcatataatt tctgttgaat tacgttaagc  11280
acgtaataat taacatgtaa tgcatgacgt tatttatgag atgggttttt atgattagag  11340
tcccgcaatt atacatttaa tacgcgatag aaaacaaaat atagcgcgca aactaggata  11400
aattatcgcg cgcggtgtca tctatgttac tagatcggtc gattaaaaat cccaattata  11460
tttggtctaa tttagtttgg tattgagtaa aacaaattcg aaccaaacca aaatataaat  11520
atatagtttt tatatatatg cctttaagac tttttataga attttcttta aaaaatatct  11580
agaaatattt gcgactcttc tggcatgtaa tatttcgtta aatatgaagt gctccatttt  11640
tattaacttt aaataattgg ttgtacgatc actttcttat caagtgttac taaaatgcgt  11700
caatctcttt gttcttccat attcatatgt caaaatctat caaaattctt atatatcttt  11760
ttcgaatttg aagtgaaatt tcgataattt aaaattaaat agaacatatc attatttagg  11820
tatcatattg atttttatac ttaattacta aatttggtta actttgaaag tgtacatcaa  11880
cgaaaaatta gtcaaacgac taaaataaat aaatatcatg tgttattaag aaaattctcc  11940
tataagaata ttttaataga tcatatgttt gtaaaaaaaa ttaattttta ctaacacata  12000
tatttactta tcaaaaattt gacaaagtaa gattaaaata atattcatct aacaaaaaaa  12060
aaaccagaaa atgctgaaaa cccggcaaaa ccgaaccaat ccaaaccgat atagttggtt  12120
tggtttgatt ttgatataaa ccgaaccaac tcggtccatt tgcaccccta atcataatag  12180
ctttaatatt tcaagatatt attaagttaa cgttgtcaat atcctggaaa ttttgcaaaa  12240
tgaatcaagc ctatatggct gtaatatgaa tttaaaagca gctcgatgtg gtggtaatat  12300
gtaatttact tgattctaaa aaaatatccc aagtattaat aatttctgct aggaagaagg  12360
ttagctacga tttacagcaa agccagaata caaagaacca taaagtgatt gaagctcgaa  12420
atatacgaag gaacaaatat ttttaaaaaa atacgcaatg acttggaaca aaagaaagtg  12480
atatattttt tgttcttaaa caagcatccc ctctaaagaa tggcagtttt cctttgcatg  12540
taactattat gctcccttcg ttacaaaaat tttggactac tattgggaac ttcttctgaa  12600
```

aatagtgata gaacccacac gagcatgtgc tttccattta attttaaaaa ccaagaaaca 12660
tacatacata acattccatc agcctctctc tctttttatt acggttaatg acttaaaaca 12720
catcttatta tcccatcctt aacacctagc agtgtcttta tacgatctca tcgatcacca 12780
cttcaaaacc atgcagactg ctgctgcccc tggagctggc atcggctagg ctgggtgccg 12840
cactgtcccg gaaggtccct agcgacttgt ttagattgat gggaccacct ctcaacttcc 12900
tgctgctgtc cctgctgctg gatgtcctgc ctcatctggc cgattgcacg ctccagtccc 12960
ctgcatgtgc actcgctcct caattgctta agatcatcgc agcagctatc gaagtgctgg 13020
ctctgttgcc ctcctccacg gccttggttg tagtagtagc tgccgccgcc cttctggact 13080
ttttcccaca ggaaccgccg aataattcga tagaaccaca cgagcatgtg ctttcattta 13140
ttttaaaaac caagaaacat acataacatt tcatcagcct ctctctctct ctctctctct 13200
ctctctctct ctctctctct ctctctctct ttattacagc tgttacacta acttaaaaca 13260
cattcatctc attattatta ttattatcca tccttaacac ctagcagtgt ctttgtacga 13320
tctcataatc gatcacccct tcatcaggta tccttaggct tcactccaac gttgttgcag 13380
ttacggaaca tgtacacacc atcatggttc tcaacgaact ggcaagatct ccaagttttc 13440
caaaggctaa cccacatgtt ctcatcggtg tgtctgtagt gctctcccat aactttcttg 13500
atgcactcgg tagcttctct agcatggtag aatgggatcc ttgaaacgta gtgatggagc 13560
acatgagtct cgatgatgtc atggaagatg attccgagga ttccgaactc tctatcgata 13620
gtagcagcag cacccttagc gaaagtccac tcttgagcat cgtaatgagg catagaagaa 13680
tcggtgtgct gaaggaaggt aacgaaaaca agccagtggt taacaaggat ccaaggacag 13740
aaccatgtga tgaaagtagg ccagaatccg aaaaccttgt aagcggtgta aacagaagtg 13800
agggtagcaa ggattccaag atcagaaaga acgatgtacc agtagtcctt cttatcgaaa 13860
acagggctag aaggccagta gtgagacttg aagaacttag aaacaccagg gtaaggttgt 13920
ccagtagcgt tagtagcaag gtaaagagaa agtcctccaa gctgttggaa caagagagcg 13980
aaaacagagt agataggagt ttcctcagcg atatcgtgaa ggctggtaac ttggtgcttc 14040
tctttgaatt cctcggcggt gtaaggaacg aaaaccatat ctctggtcat gtgtccagta 14100
gccttatggt gcttagcatg agagaacttc cagctgaagt aaggaaccat aacaagagag 14160
tggagaaccc atccaacggt atcgttaacc catccgtagt tagagaaagc agaatgtcca 14220
cactcatgtc caaggatcca gattccgaat ccgaaacaag agatagagaa cacgtaagca 14280
gaccaagcag cgaatctaag gaattcgtta gggagaagag ggatgtaggt aagtccaacg 14340
taagcgatag cagagatagc cacgatatct ctcaccacgt aagacataga cttcacgaga 14400
gatctctcgt aacagtgctt agggatagcg tcaaggatat ccttgatggt gtaatctggc 14460
accttgaaaa cgtttccgaa ggtatcgata gcggtctttt gctgcttgaa agatgcaacg 14520
tttccagaac gcctaacggt cttagtagat ccctcaagga tctcagatcc agacacggta 14580
accttagaca tggtatggta attgtaaatg taattgtaat gttgtttgtt gtttgttgtt 14640
gttggtaatt gttgtaaaat ttttggtggt gattggttct ttaaggtgtg agagtgagtt 14700
gtgagttgtg tggtgggttt ggtgagattg gggatggtgg gtttatatag tggagactga 14760
ggaatggggt cgtgagtgtt aactttgcat gggctacacg tgggttcttt tgggcttaca 14820
cgtagtatta ttcatgcaaa tgcagccaat acatatacgg tattttaata atgtgtggga 14880
atacaatatg ccgagtattt tactaatttt ggcaatgaca agtgtacatt tggattatct 14940

```
tacttggcct ctcttgcttt aatttggatt atttttattc tcttaccttg gccgttcata  15000
ttcacatccc taaaggcaag acagaattga atggtggcca aaaattaaaa cgatggatat  15060
gacctacata gtgtaggatc aattaacgtc gaaggaaaat actgattctc tcaagcatac  15120
ggacaagggt aaataacata gtcaccagaa cataataaac aaaaagtgca gaagcaagac  15180
taaaaaaatt agctatggac attcaggttc atattggaaa catcattatc ctagtcttgt  15240
gaccatcctt cctcctgctc tagttgagag gccttgggac taacgagagg tcagttggga  15300
tagcagatcc ttatcctgga ctagcctttc tggtgtttca gagtcttcgt gccgccgtct  15360
acatctatct ccattaggtc tgaagatgac tcttcacacc aacgacgttt aaggtctcta  15420
tcctactcct agcttgcaat acctggcttg caatacctgg agcatcgtgc acgatgattg  15480
gatactgtgg aggaggagtg tttgctgatt tagagctccc ggttgggtga tttgacttcg  15540
atttcagttt aggcttgttg aaatttttca ggttccattg tgaagccttt agagcttgag  15600
cttccttcca tgttaatgcc ttgatcgaat actcctagag aaaagggaag tcgatctctg  15660
agtattgaaa tcgaagtgca catttttttt caacgtgtcc aatcaatcca caaacaaagc  15720
agaagacagg taatctttca tacttatact gacaagtaat agtcttaccg tcatgcataa  15780
taacgtctcg ttccttcaag aggggttttc cgacatccat aacgacccga agcctcatga  15840
aagcattagg gaagaacttt tggttcttct tgtcatggcc tttataggtg tcagccgagc  15900
tcgccaattc ccgtccgact ggctccgcaa aatattcgaa cggcaagtta tggacttgca  15960
accataactc cacggtattg agcaggacct attgtgaaga ctcatctcat ggagcttcag  16020
aatgtggttg tcagcaaacc aatgaccgaa atccatcaca tgacggacgt ccagtgggtg  16080
agcgaaacga aacaggaagc gcctatcttt cagagtcgtg agctccacac cggattccgg  16140
caactacgtg ttgggcaggc ttcgccgtat tagagatatg ttgaggcaga cccatctgtg  16200
ccactcgtac aattacgaga gttgtttttt ttgtgatttt cctagtttct cgttgatggt  16260
gagctcatat tctacatcgt atggtctctc aacgtcgttt cctgtcatct gatatcccgt  16320
catttgcatc cacgtgcgcc gcctcccgtg ccaagtccct aggtgtcatg cacgccaaat  16380
tggtggtggt gcgggctgcc ctgtgcttct taccgatggg tggaggttga gtttgggggt  16440
ctccgcggcg atggtagtgg gttgacggtt tggtgtgggt tgacggcatt gatcaattta  16500
cttcttgctt caaattcttt ggcagaaaac aattcattag attagaactg gaaaccagag  16560
tgatgagacg gattaagtca gattccaaca gagttacatc tcttaagaaa taatgtaacc  16620
cctttagact ttatatattt gcaattaaaa aaataattta acttttagac tttatatata  16680
gttttaataa ctaagtttaa ccactctatt atttatatcg aaactatttg tatgtctccc  16740
ctctaaataa acttggtatt gtgtttacag aacctataat caaataatca atactcaact  16800
gaagtttgtg cagttaattg aagggattaa cggccaaaat gcactagtat tatcaaccga  16860
atagattcac actagatggc catttccatc aatatcatcg ccgttcttct tctgtccaca  16920
tatcccctct gaaacttgag agacacctgc acttcattgt ccttattacg tgttacaaaa  16980
tgaaacccat gcatccatgc aaactgaaga atggcgcaag aacccttccc ctccatttct  17040
tatgtggcga ccatccattt caccatctcc cgctataaaa cacccccatc acttcaccta  17100
gaacatcatc actacttgct tatccatcca aaagataccc acttttacaa caattaccaa  17160
caacaacaaa caacaaacaa cattacaatt acatttacaa ttaccatacc atgccaccta  17220
gcgctgctaa gcaaatggga gcttctactg gtgttcatgc tggtgttact gactcttctg  17280
ctttcaccag aaaggatgtt gctgatagac ctgatctcac catcgttgga gattctgttt  17340
```

-continued

```
acgatgctaa ggctttcaga tctgagcatc ctggtggtgc tcatttcgtt tctttgttcg  17400
gaggaagaga tgctactgag gctttcatgg aataccatag aagggcttgg cctaagtcta  17460
gaatgtctag attccacgtt ggatctcttg cttctactga ggaacctgtt gctgctgatg  17520
agggatacct tcaactttgt gctaggatcg ctaagatggt gccttctgtt tcttctggat  17580
tcgctcctgc ttcttactgg gttaaggctg gacttatcct tggatctgct atcgctcttg  17640
aggcttacat gctttacgct ggaaagagac ttctcccttc tatcgttctt ggatggcttt  17700
tcgctcttat cggtcttaac atccagcatg atgctaacca tggtgctttg tctaagtctg  17760
cttctgttaa ccttgctctt ggactttgtc aggattggat cggaggatct atgatccttt  17820
ggcttcaaga gcatgttgtt atgcaccacc tccacactaa cgatgttgat aaggatcctg  17880
atcaaaaggc tcacggtgct cttagactca agcctactga tgcttggtca cctatgcatt  17940
ggcttcagca tctttacctt ttgcctggtg agactatgta cgctttcaag cttttgttcc  18000
tcgacatctc tgagcttgtt atgtggcgtt gggagggtga gcctatctct aagcttgctg  18060
gatacctctt tatgccttct ttgcttctca agcttacctt ctgggctaga ttcgttgctt  18120
tgcctcttta ccttgctcct tctgttcata ctgctgtgtg tatcgctgct actgttatga  18180
ctggatcttt ctacctcgct ttcttcttct tcatctccca caacttcgag ggtgttgctt  18240
ctgttggacc tgatggatct atcacttcta tgactagagg tgctagcttc cttaagagac  18300
aagctgagac ttcttctaac gttggaggac ctcttcttgc tactcttaac ggtggactca  18360
actaccaaat tgagcatcac ttgttcccta gagttcacca tggattctac cctagacttg  18420
ctcctcttgt taaggctgag cttgaggcta gaggaatcga gtacaagcac taccctacta  18480
tctggtctaa ccttgcttct accctcagac atatgtacgc tcttggaaga aggcctagat  18540
ctaaggctga gtaatgacaa gcttatgtga cgtgaaataa taacggtaaa atatatgtaa  18600
taataataat aataaagcca caaagtgaga atgaggggaa ggggaaatgt gtaatgagcc  18660
agtagccggt ggtgctaatt ttgtatcgta ttgtcaataa atcatgaatt ttgtggtttt  18720
tatgtgtttt tttaaatcat gaattttaaa ttttataaaa taatctccaa tcggaagaac  18780
aacattccat atccatgcat ggatgtttct ttacccaaat ctagttcttg agaggatgaa  18840
gcatcaccga acagttctgc aactatccct caaaagcttt aaaatgaaca acaaggaaca  18900
gagcaacgtt ccaaagatcc caaacgaaac atattatcta tactaatact atattattaa  18960
ttactactgc ccggaatcac aatccctgaa tgattcctat taactacaag ccttgttggc  19020
ggcggagaag tgatcggcgc ggcgagaagc agcggactcg gagacgaggc cttggaagat  19080
ctgagtcgaa cgggcagaat cagtattttc cttcgacgtt aattgatcct acactatgta  19140
ggtcatatcc atcgttttaa tttttggcca ccattcaatt ctgtcttgcc tttagggatg  19200
tgaatatgaa cggccaaggt aagagaataa aaataatcca aattaaagca agagaggcca  19260
agtaagataa tccaaatgta cacttgtcat tgccaaaatt agtaaaatac tcggcatatt  19320
gtattcccac acattattaa aataccgtat atgtattggc tgcatttgca tgaataatac  19380
tacgtgtaag cccaaaagaa cccacgtgta gcccatgcaa agttaacact cacgacccca  19440
ttcctcagtc tccactatat aaacccacca tccccaatct caccaaaccc accacacaac  19500
tcacaactca ctctcacacc ttaaagaacc aatcaccacc aaaaatttta caacaattac  19560
caacaacaac aaacaacaaa caacattaca attacattta caattaccat accatgagcg  19620
ctgttaccgt tactggatct gatcctaaga acagaggatc ttctagcaac accgagcaag  19680
```

aggttccaaa agttgctatc gataccaacg gaaacgtgtt ctctgttcct gatttcacca 19740
tcaaggacat ccttggagct atccctcatg agtgttacga gagaagattg gctacctctc 19800
tctactacgt gttcagagat atcttctgca tgcttaccac cggatacctt acccataaga 19860
tcctttaccc tctcctcatc tcttacacct ctaacagcat catcaagttc actttctggg 19920
ccctttacac ttacgttcaa ggacttttcg gaaccggaat ctgggttctc gctcatgagt 19980
gtggacatca agctttctct gattacggaa tcgtgaacga tttcgttgga tggacccttc 20040
actcttacct tatggttcct tacttcagct ggaagtactc tcatggaaag caccataagg 20100
ctactggaca catgaccaga gatatggttt tcgttcctgc caccaaagag gaattcaaga 20160
agtctaggaa cttcttcggt aacctcgctg agtactctga ggattctcca cttagaaccc 20220
tttacgagct tcttgttcaa caacttggag gatggatcgc ttacctcttc gttaacgtta 20280
caggacaacc ttaccctgat gttccttctt ggaaatggaa ccacttctgg cttacctctc 20340
cacttttcga gcaaagagat gctctctaca tcttcctttc tgatcttgga atcctcaccc 20400
agggaatcgt tcttactctt tggtacaaga aattcggagg atggtccctt ttcatcaact 20460
ggttcgttcc ttacatctgg gttaaccact ggctcgtttt catcacattc cttcagcaca 20520
ctgatcctac tatgcctcat tacaacgctg aggaatggac tttcgctaag ggtgctgctg 20580
ctactatcga tagaaagttc ggattcatcg gacctcacat cttccatgat atcatcgaga 20640
ctcatgtgct tcaccactac tgttctagga tcccattcta caacgctaga cctgcttctg 20700
aggctatcaa gaaagttatg ggaaagcact acaggtctag cgacgagaac atgtggaagt 20760
cactttggaa gtctttcagg tcttgccaat acgttgacgg tgataacggt gttctcatgt 20820
tccgtaacat caacaactgc ggagttggag ctgctgagaa gtaatgaagg ggtgatcgat 20880
tatgagatcg tacaaagaca ctgctaggtg ttaaggatgg ataataataa taataatgag 20940
atgaatgtgt tttaagttag tgtaacagct gtaataaaga gagagagaga gagagagaga 21000
gagagagaga gagagagaga gagagagagg ctgatgaaat gttatgtatg tttcttggtt 21060
tttaaaataa atgaaagcac atgctcgtgt ggttctatcg aattattcgg cggttcctgt 21120
gggaaaaagt ccagaagggc cgccgcagct actactacaa ccaaggccgt ggaggagggc 21180
aacagagcca gcacttcgat agctgctgcg atgatcttaa gcaattgagg agcgagtgca 21240
catgcagggg actggagcgt gcaatcggcc agatgaggca ggacatccag cagcagggac 21300
agcagcagga agttgagagg tggtcccatc aatctaaaca agtcgctagg gaccttccgg 21360
gacagtgcgg cacccagcct agccgatgcc agctccaggg gcagcagcag tctgcatggt 21420
tttgaagtgg tgatcgatga gatcgtataa agacactgct aggtgttaag gatgggataa 21480
taagatgtgt tttaagtcat taaccgtaat aaaaagagag agaggctgat ggaatgttat 21540
gtatgtatgt ttcttggttt ttaaaattaa atggaaagca catgctcgtg tgggttctat 21600
ctcgattaaa aatcccaatt atatttggtc taatttagtt tggtattgag taaaacaaat 21660
tcgaaccaaa ccaaaatata aatatatagt ttttatatat atgcctttaa gactttttat 21720
agaattttct ttaaaaaata tctagaaata tttgcgactc ttctggcatg taatatttcg 21780
ttaaatatga agtgctccat ttttattaac tttaaataat tggttgtacg atcactttct 21840
tatcaagtgt tactaaaatg cgtcaatctc tttgttcttc catattcata tgtcaaaatc 21900
tatcaaaatt cttatatatc tttttcgaat ttgaagtgaa atttcgataa tttaaaatta 21960
aatagaacat atcattattt aggtatcata ttgattttta tacttaatta ctaaatttgg 22020
ttaactttga aagtgtacat caacgaaaaa ttagtcaaac gactaaaata aataaatatc 22080
atgtgttatt aagaaaattc tcctataaga atattttaat agatcatatg tttgtaaaaa 22140
aaattaattt ttactaacac atatatttac ttatcaaaaa tttgacaaag taagattaaa 22200
ataatattca tctaacaaaa aaaaaaccag aaaatgctga aaacccggca aaaccgaacc 22260
aatccaaacc gatatagttg gtttggtttg attttgatat aaaccgaacc aactcggtcc 22320
atttgcaccc ctaatcataa tagctttaat atttcaagat attattaagt taacgttgtc 22380
aatatcctgg aaattttgca aaatgaatca agcctatatg gctgtaatat gaatttaaaa 22440
gcagctcgat gtggtggtaa tatgtaattt acttgattct aaaaaaatat cccaagtatt 22500
aataatttct gctaggaaga aggttagcta cgatttacag caaagccaga atacaaagaa 22560
ccataaagtg attgaagctc gaaatatacg aaggaacaaa tatttttaaa aaaatacgca 22620
atgacttgga acaaaagaaa gtgatatatt ttttgttctt aaacaagcat cccctctaaa 22680
gaatggcagt tttcctttgc atgtaactat tatgctccct tcgttacaaa aattttggac 22740
tactattggg aacttcttct gaaaatagtc ctgcaggcta gtagattggt tggttggttt 22800
ccatgtacca gaaggcttac cctattagtt gaaagttgaa actttgttcc ctactcaatt 22860
cctagttgtg taaatgtatg tatatgtaat gtgtataaaa cgtagtactt aaatgactag 22920
gagtggttct tgagaccgat gagagatggg agcagaacta aagatgatga cataattaag 22980
aacgaatttg aaaggctctt aggtttgaat cctattcgag aatgtttttg tcaaagatag 23040
tggcgatttt gaaccaaaga aaacatttaa aaaatcagta tccggttacg ttcatgcaaa 23100
tagaaagtgg tctaggatct gattgtaatt ttagacttaa agagtctctt aagattcaat 23160
cctggctgtg tacaaaacta caaataatat attttagact atttggcctt aactaaactt 23220
ccactcatta tttactgagg ttagagaata gacttgcgaa taaacacatt cccgagaaat 23280
actcatgatc ccataattag tcagagggta tgccaatcag atctaagaac acacattccc 23340
tcaaatttta atgcacatgt aatcatagtt tagcacaatt caaaaataat gtagtattaa 23400
agacagaaat ttgtagactt ttttttggcg ttaaaagaag actaagttta tacgtacatt 23460
ttattttaag tggaaaaccg aaattttcca tcgaaatata tgaatttagt atatatattt 23520
ctgcaatgta ctattttgct attttggcaa ctttcagtgg actactactt tattacaatg 23580
tgtatggatg catgagtttg agtatacaca tgtctaaatg catgctttgt aaaacgtaac 23640
ggaccacaaa agaggatcca tacaaataca tctcatagct tcctccatta ttttccgaca 23700
caaacagagc attttacaac aattaccaac aacaacaaac aacaaacaac attacaatta 23760
catttacaat taccatacca tggaatttgc tcaacctctc gttgctatgg ctcaagagca 23820
gtacgctgct atcgatgctg ttgttgctcc tgctatcttc tctgctaccg actctattgg 23880
atggggactc aagcctatct cttctgctac taaggatctc cctctcgttg aatctcctac 23940
ccctcttatc ctttctctcc tcgcttactt cgctatcgtt ggttctggac tcgtttaccg 24000
taaagtgttc cctagaaccg ttaagggaca ggatcctttc cttctcaagg ctcttatgct 24060
cgctcacaac gttttcctta tcggactcag cctttacatg tgcctcaagc tcgtttacga 24120
ggcttacgtg aacaagtact ccttctgggg aaacgcttac aaccctgctc aaaccgagat 24180
ggctaaggtg atctggatct tctacgtgtc caagatctac gagttcatgg acaccttcat 24240
catgcttctc aagggaaacg ttaaccaggt ttccttcctc catgtttacc accacggatc 24300
tatctctgga atctggtgga tgatcactta tgctgctcca ggtggagatg cttacttctc 24360
tgctgctctc aactcttggg ttcatgtgtg catgtacacc tactacttca tggctgctgt 24420

```
tcttcctaag gacgaaaaga ccaagagaaa gtacctttgg tggggaagat accttaccca  24480
gatgcaaatg ttccagttct tcatgaacct tctccaggct gtttacctcc tctactcttc  24540
ttctccttac cctaagttca ttgctcaact cctcgttgtt tacatggtta ccctcctcat  24600
gcttttcgga aacttctact acatgaagca ccacgcttct aagtgataag ggccgccgcc  24660
atgtgacaga tcgaaggaag aaagtgtaat aagacgactc tcactactcg atcgctagtg  24720
attgtcattg ttatatataa taatgttatc tttcacaact tatcgtaatg catgtgaaac  24780
tataacacat taatcctact tgtcatatga taacactctc cccatttaaa actcttgtca  24840
atttaaagat ataagattct ttaaatgatt aaaaaaaata tattataaat tcaatcactc  24900
ctactaataa attattaatt attatttatt gattaaaaaa atacttatac taatttagtc  24960
tgaatagaat aattagattc tagcctgcag ggcggccgcg gatcccatgg agtcaaagat  25020
tcaaatagag gacctaacag aactcgccgt aaagactggc gaacagttca tacagagtct  25080
cttacgactc aatgacaaga agaaaatctt cgtcaacatg gtggagcacg acacacttgt  25140
ctactccaaa aatatcaaag atacagtctc agaagaccaa agggcaattg agacttttca  25200
acaaagggta atatccggaa acctcctcgg attccattgc ccagctatct gtcactttat  25260
tgtgaagata gtggaaaagg aaggtggctc ctacaaatgc catcattgcg ataaaggaaa  25320
ggccatcgtt gaagatgcct ctgccgacag tggtcccaaa gatggacccc cacccacgag  25380
gagcatcgtg gaaaaagaag acgttccaac cacgtcttca aagcaagtgg attgatgtga  25440
tatctccact gacgtaaggg atgacgcaca atcccactat ccttcgcaag acccttcctc  25500
tatataagga agttcatttc atttggagag aacacggggg actgaattaa atatgagccc  25560
tgagaggcgt cctgttgaaa tcagacctgc tactgctgct gatatggctg ctgtttgtga  25620
tatcgtgaac cactacatcg agacttctac cgttaacttc agaactgagc ctcaaactcc  25680
tcaagagtgg atcgatgatc ttgagagact ccaagataga tacccttggc ttgttgctga  25740
ggttgagggt gttgttgctg gaatcgctta cgctggacct tggaaggcta gaaacgctta  25800
cgattggact gttgagtcta ccgtttacgt ttcacacaga catcagagac ttggacttgg  25860
atctaccctt tacactcacc ttctcaagtc tatggaagct cagggattca agtctgttgt  25920
tgctgttatc ggactcccta acgatccttc tgttagactt catgaggctc ttggatacac  25980
tgctagagga actcttagag ctgctggata caagcacggt ggatggcatg atgttggatt  26040
ctggcaaaga gatttcgagc ttcctgctcc tcctagacct gttagaccag ttactcagat  26100
ctgaatttgc gtgatcgttc aaacatttgg caataaagtt tcttaagatt gaatcctgtt  26160
gccggtcttg cgatgattat catataattt ctgttgaatt acgttaagca tgtaataatt  26220
aacatgtaat gcatgacgtt atttatgaga tgggttttta tgattagagt cccgcaatta  26280
tacatttaat acgcgataga aaacaaaata tagcgcgcaa actaggataa attatcgcgc  26340
gcggtgtcat ctatgttact agatcactag tgatgtacgg ttaaaaccac cccagtacat  26400
taaaaacgtc cgcaatgtgt tattaagttg tctaagcgtc aatttgttta caccacaata  26460
tatcctgcca ccagccagcc aacagctccc cgaccggcag ctcggcacaa aatcaccact  26520
cgatacaggc agcccatcag tcc                                          26543
```

<210> SEQ ID NO 7
<211> LENGTH: 23760
<212> TYPE: DNA
<213> ORGANISM: Artificial Sequence
<220> FEATURE:
<223> OTHER INFORMATION: pGA7- mod_G nucleotide sequence -continued

<400> SEQUENCE: 7
tcctgtggtt ggcatgcaca tacaaatgga cgaacggata aacctttca cgccctttta 60
aatatccgat tattctaata aacgctcttt tctcttaggt ttacccgcca atatatcctg 120
tcaaacactg atagtttaaa ctgaaggcgg gaaacgacaa tctgctagtg gatctcccag 180
tcacgacgtt gtaaaacggg cgccccgcgg aaagcttgcg gccgcggtac cgcccgttcg 240
actcagatct tccaaggcct cgtctccgag tccgctgctt ctcgccgcgc cgatcacttc 300
tccgccgcca acaaggcttg tagttaatag gaatcattca gggattgtga ttccgggcag 360
tagtaattaa taatatagta ttagtataga taatatgttt cgtttgggat ctttggaacg 420
ttgctctgtt ccttgttgtt cattttaaag cttttgaggg atagttgcag aactgttcgg 480
tgatgcttca tcctctcaag aactagattt gggtaaagaa acatccatgc atggatatgg 540
aatgttgttc ttccgattgg agattatttt ataaaattta aaattcatga tttaaaaaaa 600
cacataaaaa ccacaaaatt catgatttat tgacaatacg atacaaaatt agcaccaccg 660
gctactggct cattacacat ttccccttcc cctcattctc actttgtggc tttattatta 720
ttattattac atatatttta ccgttattat ttcacgtcac ataagcttgt taattaatta 780
tcactgcttc ttagcaccct tagacttgta cctcttacgg tagaagttgg cgaagagaac 840
gaacatgttc accataaccc agagttgaag gtaaggaagc cagaaagcgg tattctgaac 900
gtaagcggtg tagatagagt gagaagcaca gatacagaac tgaagcatct ggatctgggt 960
gatgtacttc ttccagaaac agttaactcc aagagcagca agtccgtagt aagagtacat 1020
gatcacgtgc acgaaggtgt taacagaaga tccgaagtag caatctccaa caggctcaag 1080
cttcataaca acgaaccatg accagatgag aagagtgtgg tggtagatgt gaaggaaaga 1140
aagctggtcg aacttcttcc tcatcaccat gaagaaggtg tcgagaagct caacgtactt 1200
gttgttgtag tgaagccaga taacctgaga gattccccaa gagttagcag tcatatcagg 1260
gatgtttccc caaaccttaa gtccctgagc cctatgagaa gtaacgaaaa ggtagatgca 1320
gtagctgttg aagaaggtct ggtagaagtt gtaaacgagc atagcgttct tgagtccgaa 1380
aggttgagat ctgttctgca tgatacgctt tccgaagtag atgaagagga ggtatccaat 1440
agttccgata gtaggtcccc agtactcaac ctgcatgaag taagcaggaa ctttctcaga 1500
agctgggata tcagggttag ccacattgta ggtaacgtat ccaagagttc cagcaagagc 1560
agcagggata gcgatagagg ccatggtatg gtaattgtaa atgtaattgt aatgttgttt 1620
gttgtttgtt gttgttggta attgttgtaa aattaattaa gtgggtatct tttggatgga 1680
taagcaagta gtgatgatgt tctaggtgaa gtgatggggg tgttttatag cgggagatgg 1740
tgaaatggat ggtcgccaca taagaaatgg aggggaaggg ttcttgcgcc attcttcagt 1800
ttgcatggat gcatgggttt cattttgtaa cacgtaataa ggacaatgaa gtgcaggtgt 1860
ctctcaagtt tcagagggga tatgtggaca gaagaagaac ggcgatgata ttgatggaaa 1920
tggccatcta gtgtgaatct attcggttga taatactagt gcattttggc cgttaatccc 1980
ttcaattaac tgcacaaact tcagttgagt attgattatt tgattatagg ttctgtaaac 2040
acaataccaa gtttatttag aggggagaca tacaaatagt ttcgatataa ataatagagt 2100
ggttaaactt agttattaaa actatatata aagtctaaaa gttaaattat ttttttaatt 2160
gcaaatatat aaagtctaaa ggggttacat tatttcttaa gagatgtaac tctgttggaa 2220
tctgacttaa tccgtctcat cactctggtt tccagttcta atctaatgaa ttgttttctg 2280

-continued

```
ccaaagaatt tgaagcaaga agtaaattga tcaatgccgt caacccacac caaaccgtca   2340
acccactacc atcgccgcgg agacccccaa actcaacctc cacccatcgg taagaagcac   2400
agggcagccc gcaccaccac caatttggcg tgcatgacac ctagggactt ggcacgggag   2460
gcggcgcacg tggatgcaaa tgacgggata tcagatgaca ggaaacgacg ttgagagacc   2520
atacgatgta gaatatgagc tcaccatcaa cgagaaacta ggaaaatcac aaaaaaaaca   2580
actctcgtaa ttgtacgagt ggcacagatg ggtctgcctc aacatatctc taatacggcg   2640
aagcctgccc aacacgtagt tgccggaatc cggtgtggag ctcacgactc tgaaagatag   2700
gcgcttcctg tttcgtttcg ctcacccact ggacgtccgt catgtgatgg atttcggtca   2760
ttggtttgct gacaaccaca ttctgaagct ccatgagatg agtcttcaca ataggtcctg   2820
ctcaataccg tggagttatg gttgcaagtc cataacttgc cgttcgaata ttttgcggag   2880
ccagtcggac gggaattggc gagctcggct gacacctata aaggccatga caagaagaac   2940
caaaagttct tccctaatgc tttcatgagg cttcgggtcg ttatggatgt cggaaaaccc   3000
ctcttgaagg aacgagacgt tattatgcat gacggtaaga ctattacttg tcagtataag   3060
tatgaaagat tacctgtctt ctgctttgtt tgtggattga ttggacacgt tgaaaaaaaa   3120
tgtgcacttc gatttcaata ctcagagatc gacttccctt ttctctagga gtattcgatc   3180
aaggcattaa catggaagga agctcaagct ctaaaggctt cacaatggaa cctgaaaaat   3240
ttcaacaagc ctaaactgaa atcgaagtca aatcacccaa ccgggagctc taaatcagca   3300
aacactcctc ctccacagta tccaatcatc gtgcacgatg ctccaggtat tgcaagccag   3360
gtattgcaag ctaggagtag gatagagacc ttaaacgtcg ttggtgtgaa gagtcatctt   3420
cagacctaat ggagatagat gtagacggcg gcacgaagac tctgaaacac cagaaaggct   3480
agtccaggat aaggatctgc tatcccaact gacctctcgt tagtcccaag gcctctcaac   3540
tagagcagga ggaaggatgg tcacaagact aggataatga tgtttccaat atgaacctga   3600
atgtccatag ctaatttttt tagtcttgct tctgcacttt ttgtttatta tgttctggtg   3660
actatgttat ttacccttgt ccgtatgctt gagggtaccc tagtagattg gttggttggt   3720
ttccatgtac cagaaggctt accctattag ttgaaagttg aaactttgtt ccctactcaa   3780
ttcctagttg tgtaaatgta tgtatatgta atgtgtataa aacgtagtac ttaaatgact   3840
aggagtggtt cttgagaccg atgagagatg ggagcagaac taaagatgat gacataatta   3900
agaacgaatt tgaaaggctc ttaggtttga atcctattcg agaatgtttt tgtcaaagat   3960
agtggcgatt ttgaaccaaa gaaaacattt aaaaaatcag tatccggtta cgttcatgca   4020
aatagaaagt ggtctaggat ctgattgtaa ttttagactt aaagagtctc ttaagattca   4080
atcctggctg tgtacaaaac tacaaataat atattttaga ctatttggcc ttaactaaac   4140
ttccactcat tatttactga ggttagagaa tagacttgcg aataaacaca ttcccgagaa   4200
atactcatga tcccataatt agtcagaggg tatgccaatc agatctaaga acacacattc   4260
cctcaaattt taatgcacat gtaatcatag tttagcacaa ttcaaaaata atgtagtatt   4320
aaagacagaa atttgtagac ttttttttgg cgttaaaaga agactaagtt tatacgtaca   4380
ttttatttta agtggaaaac cgaaattttc catcgaaata tatgaattta gtatatatat   4440
ttctgcaatg tactattttg ctattttggc aactttcagt ggactactac tttattacaa   4500
tgtgtatgga tgcatgagtt tgagtataca catgtctaaa tgcatgcttt gtaaaacgta   4560
acggaccaca aaagaggatc catacaaata catctcatag cttcctccat tattttccga   4620
cacaaacaga gcattttaca acaattacca acaacaacaa acaacaaaca acattacaat   4680
```

-continued tacatttaca attaccatac catggaattc gcccagcctc ttgttgctat ggctcaagag 4740
caatacgctg ctatcgatgc tgttgttgct cctgctatct tctctgctac tgattctatc 4800
ggatggggac ttaagcctat ctcttctgct actaaggact tgcctcttgt tgagtctcct 4860
acacctctca tcctttcttt gcttgcttac ttcgctatcg ttggatctgg actcgtttac 4920
agaaaggttt tccctagaac cgtgaaggga caagatccat tccttttgaa ggctcttatg 4980
cttgctcaca acgtgttcct tatcggactt tctctttaca tgtgcctcaa gcttgtgtac 5040
gaggcttacg ttaacaagta ctctttctgg ggaaacgctt acaaccctgc tcaaactgag 5100
atggctaagg ttatctggat cttctacgtg agcaagatct acgagttcat ggataccttc 5160
atcatgctcc tcaagggaaa tgttaaccag gttagcttcc ttcacgttta ccatcacgga 5220
tctatctctg gaatctggtg gatgattact tacgctgctc ctggtggtga tgcttacttc 5280
tctgctgctc ttaactcttg ggttcacgtg tgtatgtaca cctactattt tatggctgcc 5340
gtgcttccta aggacgagaa aactaagaga aagtacctct ggtggggaag ataccttact 5400
caaatgcaga tgttccagtt cttcatgaac cttctccagg ctgtttacct tctctactct 5460
tcatctcctt accctaagtt tatcgctcag ctcctcgtgg tgtacatggt tactcttctc 5520
atgcttttcg gaaacttcta ctacatgaag caccacgcta gcaagtgatg aggcgcgccg 5580
ggccgccgcc atgtgacaga tcgaaggaag aaagtgtaat aagacgactc tcactactcg 5640
atcgctagtg attgtcattg ttatatataa taatgttatc tttcacaact tatcgtaatg 5700
catgtgaaac tataacacat taatcctact tgtcatatga taacactctc cccatttaaa 5760
actcttgtca atttaaagat ataagattct ttaaatgatt aaaaaaaata tattataaat 5820
tcaatcactc ctactaataa attattaatt attatttatt gattaaaaaa atacttatac 5880
taatttagtc tgaatagaat aattagattc tagtctcatc cccttttaaa ccaacttagt 5940
aaacgttttt ttttttaatt ttatgaagtt aagtttttac cttgttttta aaaagaatcg 6000
ttcataagat gccatgccag aacattagct acacgttaca catagcatgc agccgcggag 6060
aattgttttt cttcgccact tgtcactccc ttcaaacacc taagagcttc tctctcacag 6120
cacacacata caatcacatg cgtgcatgca ttattacacg tgatcgccat gcaaatctcc 6180
tttatagcct ataaattaac tcatccgctt cactctttac tcaaaccaaa actcatcgat 6240
acaaacaaga ttaaaaacat acacgaggat cttttacaac aattaccaac aacaacaaac 6300
aacaaacaac attacaatta catttacaat taccatacca tgcctccaag ggactcttac 6360
tcttatgctg ctcctccttc tgctcaactt cacgaagttg atactcctca agagcacgac 6420
aagaaagagc ttgttatcgg agatagggct tacgatgtta ccaacttcgt taagagacac 6480
cctggtggaa agatcattgc ttaccaagtt ggaactgatg ctaccgatgc ttacaagcag 6540
ttccatgtta gatctgctaa ggctgacaag atgcttaagt ctcttccttc tcgtcctgtt 6600
cacaagggat actctccaag aagggctgat cttatcgctg atttccaaga gttcaccaag 6660
caacttgagg ctgagggaat gttcgagcct tctcttcctc atgttgctta cagacttgct 6720
gaggttatcg ctatgcatgt tgctggtgct gctcttatct ggcatggata cactttcgct 6780
ggaatcgcta tgcttggagt tgttcaggga agatgtggat ggcttatgca tgagggtgga 6840
cattactctc tcactggaaa cattgctttc gacagagcta tccaagttgc ttgttacgga 6900
cttggatgtg gaatgtctgg tgcttggtgg cgtaaccagc ataacaagca ccatgctact 6960
cctcaaaagc ttcagcacga tgttgatctt gataccctc ctctcgttgc tttccatgag 7020

-continued agaatcgctg ctaaggttaa gtctcctgct atgaaggctt ggctttctat gcaagctaag 7080
cttttcgctc ctgttaccac tcttcttgtt gctcttggat ggcagcttta ccttcatcct 7140
agacacatgc tcaggactaa gcactacgat gagcttgcta tgctcggaat cagatacgga 7200
cttgttggat accttgctgc taactacggt gctggatacg ttctcgcttg ttaccttctt 7260
tacgttcagc ttggagctat gtacatcttc tgcaacttcg ctgtttctca tactcacctc 7320
cctgttgttg agcctaacga gcatgctact tgggttgagt acgctgctaa ccacactact 7380
aactgttctc catcttggtg gtgtgattgg tggatgtctt accttaacta ccagatcgag 7440
caccaccttt acccttctat gcctcaattc agacacccta agatcgctcc tagagttaag 7500
cagcttttcg agaagcacgg acttcactac gatgttagag gatacttcga ggctatggct 7560
gatactttcg ctaaccttga taacgttgcc catgctcctg agaagaaaat gcagtaatga 7620
gatcgttcaa acatttggca ataaagtttc ttaagattga atcctgttgc cggtcttgcg 7680
atgattatca tataatttct gttgaattac gttaagcacg taataattaa catgtaatgc 7740
atgacgttat ttatgagatg ggtttttatg attagagtcc cgcaattata catttaatac 7800
gcgatagaaa acaaaatata gcgcgcaaac taggataaat tatcgcgcgc ggtgtcatct 7860
atgttactag atcggtcgat taaaaatccc aattatattt ggtctaattt agtttggtat 7920
tgagtaaaac aaattcgaac caaaccaaaa tataaatata tagtttttat atatatgcct 7980
ttaagacttt ttatagaatt ttctttaaaa aatatctaga aatatttgcg actcttctgg 8040
catgtaatat ttcgttaaat atgaagtgct ccatttttat taactttaaa taattggttg 8100
tacgatcact ttcttatcaa gtgttactaa aatgcgtcaa tctctttgtt cttccatatt 8160
catatgtcaa aatctatcaa aattcttata tatctttttc gaatttgaag tgaaatttcg 8220
ataatttaaa attaaataga acatatcatt atttaggtat catattgatt tttatactta 8280
attactaaat ttggttaact ttgaaagtgt acatcaacga aaaattagtc aaacgactaa 8340
aataaataaa tatcatgtgt tattaagaaa attctcctat aagaatattt taatagatca 8400
tatgtttgta aaaaaaatta atttttacta acacatatat ttacttatca aaaatttgac 8460
aaagtaagat taaaataata ttcatctaac aaaaaaaaaa ccagaaaatg ctgaaaaccc 8520
ggcaaaaccg aaccaatcca aaccgatata gttggtttgg tttgattttg atataaaccg 8580
aaccaactcg gtccatttgc acccctaatc ataatagctt taatatttca agatattatt 8640
aagttaacgt tgtcaatatc ctggaaattt tgcaaaatga atcaagccta tatggctgta 8700
atatgaattt aaaagcagct cgatgtggtg gtaatatgta atttacttga ttctaaaaaa 8760
atatcccaag tattaataat ttctgctagg aagaaggtta gctacgattt acagcaaagc 8820
cagaatacaa agaaccataa agtgattgaa gctcgaaata tacgaaggaa caaatatttt 8880
taaaaaaata cgcaatgact tggaacaaaa gaaagtgata tattttttgt tcttaaacaa 8940
gcatcccctc taaagaatgg cagttttcct ttgcatgtaa ctattatgct ccccttcgtta 9000
caaaaatttt ggactactat tgggaacttc ttctgaaaat agtgatagaa cccacacgag 9060
catgtgcttt ccatttaatt ttaaaaacca agaaacatac atacataaca ttccatcagc 9120
ctctctctct ttttattacg gttaatgact taaaacacat cttattatcc catccttaac 9180
acctagcagt gtctttatac gatctcatcg atcaccactt caaaaccatg cagactgctg 9240
ctgcccctgg agctggcatc ggctaggctg ggtgccgcac tgtcccggaa ggtccctagc 9300
gacttgttta gattgatggg accacctctc aacttcctgc tgctgtccct gctgctggat 9360
gtcctgcctc atctggccga ttgcacgctc cagtcccctg catgtgcact cgctcctcaa 9420

-continued

```
ttgcttaaga tcatcgcagc agctatcgaa gtgctggctc tgttgccctc ctccacggcc   9480
ttggttgtag tagtagctgc cgccgccctt ctggactttt tcccacagga accgccgaat   9540
aattcgatag aaccacacga gcatgtgctt tcatttattt taaaaaccaa gaaacataca   9600
taacatttca tcagcctctc tctctctctc tctctctctc tctctctctc tctctctctc   9660
tctctcttta ttacagctgt tacactaact taaaacacat tcatctcatt attattatta   9720
ttatccatcc ttaacaccta gcagtgtctt tgtacgatct cataatcgat caccccttca   9780
tcaggtatcc ttaggcttca ctccaacgtt gttgcagtta cggaacatgt acacaccatc   9840
atggttctca acgaactggc aagatctcca agttttccaa aggctaaccc acatgttctc   9900
atcggtgtgt ctgtagtgct ctcccataac tttcttgatg cactcggtag cttctctagc   9960
atggtagaat gggatccttg aaacgtagtg atggagcaca tgagtctcga tgatgtcatg  10020
gaagatgatt ccgaggattc cgaactctct atcgatagta gcagcagcac ccttagcgaa  10080
agtccactct tgagcatcgt aatgaggcat agaagaatcg gtgtgctgaa ggaaggtaac  10140
gaaaacaagc cagtggttaa caaggatcca aggacagaac catgtgatga aagtaggcca  10200
gaatccgaaa accttgtaag cggtgtaaac agaagtgagg gtagcaagga ttccaagatc  10260
agaaagaacg atgtaccagt agtccttctt atcgaaaaca gggctagaag gccagtagtg  10320
agacttgaag aacttagaaa caccagggta aggttgtcca gtagcgttag tagcaaggta  10380
aagagaaagt cctccaagct gttggaacaa gagagcgaaa acagagtaga taggagtttc  10440
ctcagcgata tcgtgaaggc tggtaacttg gtgcttctct ttgaattcct cggcggtgta  10500
aggaacgaaa accatatctc tggtcatgtg tccagtagcc ttatggtgct tagcatgaga  10560
gaacttccag ctgaagtaag gaaccataac aagagagtgg agaacccatc caacggtatc  10620
gttaacccat ccgtagttag agaaagcaga atgtccacac tcatgtccaa ggatccagat  10680
tccgaatccg aaacaagaga tagagaacac gtaagcagac caagcagcga atctaaggaa  10740
ttcgttaggg agaagaggga tgtaggtaag tccaacgtaa gcgatagcag agatagccac  10800
gatatctctc accacgtaag acatagactt cacgagagat ctctcgtaac agtgcttagg  10860
gatagcgtca aggatatcct tgatggtgta atctggcacc ttgaaaacgt ttccgaaggt  10920
atcgatagcg gtcttttgct gcttgaaaga tgcaacgttt ccagaacgcc taacggtctt  10980
agtagatccc tcaaggatct cagatccaga cacggtaacc ttagacatgg tatggtaatt  11040
gtaaatgtaa ttgtaatgtt gtttgttgtt tgttgttgtt ggtaattgtt gtaaaatttt  11100
tggtggtgat tggttcttta aggtgtgaga gtgagttgtg agttgtgtgg tgggtttggt  11160
gagattgggg atggtgggtt tatatagtgg agactgagga atggggtcgt gagtgttaac  11220
tttgcatggg ctacacgtgg gttcttttgg gcttacacgt agtattattc atgcaaatgc  11280
agccaataca tatacggtat tttaataatg tgtgggaata caatatgccg agtattttac  11340
taattttggc aatgacaagt gtacatttgg attatcttac ttggcctctc ttgctttaat  11400
ttggattatt tttattctct taccttggcc gttcatattc acatccctaa aggcaagaca  11460
gaattgaatg gtggccaaaa attaaaacga tggatatgac ctacatagtg taggatcaat  11520
taacgtcgaa ggaaaatact gattctctca agcatacgga caagggtaaa taacatagtc  11580
accagaacat aataaacaaa aagtgcagaa gcaagactaa aaaaattagc tatggacatt  11640
caggttcata ttggaaacat cattatccta gtcttgtgac catccttcct cctgctctag  11700
ttgagaggcc ttgggactaa cgagaggtca gttgggatag cagatcctta tcctggacta  11760
```

gcctttctgg tgtttcagag tcttcgtgcc gccgtctaca tctatctcca ttaggtctga 11820
agatgactct tcacaccaac gacgtttaag gtctctatcc tactcctagc ttgcaatacc 11880
tggcttgcaa tacctggagc atcgtgcacg atgattggat actgtggagg aggagtgttt 11940
gctgatttag agctcccggt tgggtgattt gacttcgatt tcagtttagg cttgttgaaa 12000
tttttcaggt tccattgtga agcctttaga gcttgagctt ccttccatgt taatgccttg 12060
atcgaatact cctagagaaa agggaagtcg atctctgagt attgaaatcg aagtgcacat 12120
ttttttcaa cgtgtccaat caatccacaa acaaagcaga agacaggtaa tctttcatac 12180
ttatactgac aagtaatagt cttaccgtca tgcataataa cgtctcgttc cttcaagagg 12240
ggttttccga catccataac gacccgaagc ctcatgaaag cattagggaa gaacttttgg 12300
ttcttcttgt catggccttt ataggtgtca gccgagctcg ccaattcccg tccgactggc 12360
tccgcaaaat attcgaacgg caagttatgg acttgcaacc ataactccac ggtattgagc 12420
aggacctatt gtgaagactc atctcatgga gcttcagaat gtggttgtca gcaaaccaat 12480
gaccgaaatc catcacatga cggacgtcca gtgggtgagc gaaacgaaac aggaagcgcc 12540
tatctttcag agtcgtgagc tccacaccgg attccggcaa ctacgtgttg ggcaggcttc 12600
gccgtattag agatatgttg aggcagaccc atctgtgcca ctcgtacaat tacgagagtt 12660
gttttttttg tgattttcct agtttctcgt tgatggtgag ctcatattct acatcgtatg 12720
gtctctcaac gtcgtttcct gtcatctgat atcccgtcat ttgcatccac gtgcgccgcc 12780
tcccgtgcca agtccctagg tgtcatgcac gccaaattgg tggtggtgcg ggctgccctg 12840
tgcttcttac cgatgggtgg aggttgagtt tgggggtctc cgcggcgatg gtagtgggtt 12900
gacggtttgg tgtgggttga cggcattgat caatttactt cttgcttcaa attctttggc 12960
agaaaacaat tcattagatt agaactggaa accagagtga tgagacggat taagtcagat 13020
tccaacagag ttacatctct taagaaataa tgtaacccct ttagacttta tatatttgca 13080
attaaaaaaa taatttaact tttagacttt atatatagtt ttaataacta agtttaacca 13140
ctctattatt tatatcgaaa ctatttgtat gtctcccctc taaataaact tggtattgtg 13200
tttacagaac ctataatcaa ataatcaata ctcaactgaa gtttgtgcag ttaattgaag 13260
ggattaacgg ccaaaatgca ctagtattat caaccgaata gattcacact agatggccat 13320
ttccatcaat atcatcgccg ttcttcttct gtccacatat cccctctgaa acttgagaga 13380
cacctgcact tcattgtcct tattacgtgt tacaaaatga aacccatgca tccatgcaaa 13440
ctgaagaatg gcgcaagaac ccttcccctc catttcttat gtggcgacca tccatttcac 13500
catctcccgc tataaaacac ccccatcact tcacctagaa catcatcact acttgcttat 13560
ccatccaaaa gatacccact tttacaacaa ttaccaacaa caacaaacaa caaacaacat 13620
tacaattaca tttacaatta ccataccatg ccacctagcg ctgctaagca aatgggagct 13680
tctactggtg ttcatgctgg tgttactgac tcttctgctt tcaccagaaa ggatgttgct 13740
gatagacctg atctcaccat cgttggagat tctgtttacg atgctaaggc tttcagatct 13800
gagcatcctg gtggtgctca tttcgtttct ttgttcggag gaagagatgc tactgaggct 13860
ttcatggaat accatagaag ggcttggcct aagtctagaa tgtctagatt ccacgttgga 13920
tctcttgctt ctactgagga acctgttgct gctgatgagg gataccttca actttgtgct 13980
aggatcgcta agatggtgcc ttctgtttct tctggattcg ctcctgcttc ttactgggtt 14040
aaggctggac ttatccttgg atctgctatc gctcttgagg cttacatgct ttacgctgga 14100
aagagacttc tcccttctat cgttcttgga tggcttttcg ctcttatcgg tcttaacatc 14160
cagcatgatg ctaaccatgg tgctttgtct aagtctgctt ctgttaacct tgctcttgga 14220
ctttgtcagg attggatcgg aggatctatg atcctttggc ttcaagagca tgttgttatg 14280
caccacctcc acactaacga tgttgataag gatcctgatc aaaaggctca cggtgctctt 14340
agactcaagc ctactgatgc ttggtcacct atgcattggc ttcagcatct ttacctttttg 14400
cctggtgaga ctatgtacgc tttcaagctt ttgttcctcg acatctctga gcttgttatg 14460
tggcgttggg agggtgagcc tatctctaag cttgctggat acctctttat gccttctttg 14520
cttctcaagc ttaccttctg ggctagattc gttgctttgc ctctttacct tgctccttct 14580
gttcatactg ctgtgtgtat cgctgctact gttatgactg gatctttcta cctcgctttc 14640
ttcttcttca tctcccacaa cttcgagggt gttgcttctg ttggacctga tggatctatc 14700
acttctatga ctagaggtgc tagcttcctt aagagacaag ctgagacttc ttctaacgtt 14760
ggaggacctc ttcttgctac tcttaacggt ggactcaact accaaattga gcatcacttg 14820
ttccctagag ttcaccatgg attctaccct agacttgctc ctcttgttaa ggctgagctt 14880
gaggctagag gaatcgagta caagcactac cctactatct ggtctaacct tgcttctacc 14940
ctcagacata tgtacgctct tggaagaagg cctagatcta aggctgagta atgacaagct 15000
tatgtgacgt gaaataataa cggtaaaata tatgtaataa taataataat aaagccacaa 15060
agtgagaatg aggggaaggg gaaatgtgta atgagccagt agccggtggt gctaattttg 15120
tatcgtattg tcaataaatc atgaattttg tggtttttat gtgttttttt aaatcatgaa 15180
ttttaaattt tataaaataa tctccaatcg gaagaacaac attccatatc catgcatgga 15240
tgtttcttta cccaaatcta gttcttgaga ggatgaagca tcaccgaaca gttctgcaac 15300
tatccctcaa aagctttaaa atgaacaaca aggaacagag caacgttcca aagatcccaa 15360
acgaaacata ttatctatac taatactata ttattaatta ctactgcccg gaatcacaat 15420
ccctgaatga ttcctattaa ctacaagcct tgttggcggc ggagaagtga tcggcgcggc 15480
gagaagcagc ggactcggag acgaggcctt ggaagatctg agtcgaacgg gcagaatcag 15540
tattttcctt cgacgttaat tgatcctaca ctatgtaggt catatccatc gttttaattt 15600
ttggccacca ttcaattctg tcttgccttt agggatgtga atatgaacgg ccaaggtaag 15660
agaataaaaa taatccaaat taaagcaaga gaggccaagt aagataatcc aaatgtacac 15720
ttgtcattgc caaaattagt aaaatactcg gcatattgta ttcccacaca ttattaaaat 15780
accgtatatg tattggctgc atttgcatga ataatactac gtgtaagccc aaaagaaccc 15840
acgtgtagcc catgcaaagt taacactcac gaccccattc ctcagtctcc actatataaa 15900
cccaccatcc ccaatctcac caaacccacc acacaactca caactcactc tcacacctta 15960
aagaaccaat caccaccaaa aattttacaa caattaccaa caacaacaaa caacaaacaa 16020
cattacaatt acatttacaa ttaccatacc atgagcgctg ttaccgttac tggatctgat 16080
cctaagaaca gaggatcttc tagcaacacc gagcaagagg ttccaaaagt tgctatcgat 16140
accaacggaa acgtgttctc tgttcctgat ttcaccatca aggacatcct tggagctatc 16200
cctcatgagt gttacgagag aagattggct acctctctct actacgtgtt cagagatatc 16260
ttctgcatgc ttaccaccgg ataccttacc cataagatcc tttaccctct cctcatctct 16320
tacacctcta acagcatcat caagttcact ttctgggccc tttacactta cgttcaagga 16380
cttttcggaa ccggaatctg ggttctcgct catgagtgtg gacatcaagc tttctctgat 16440
tacggaatcg tgaacgattt cgttggatgg acccttcact cttaccttat ggttccttac 16500

-continued

```
ttcagctgga agtactctca tggaaagcac cataaggcta ctggacacat gaccagagat  16560
atggttttcg ttcctgccac caaagaggaa ttcaagaagt ctaggaactt cttcggtaac  16620
ctcgctgagt actctgagga ttctccactt agaacccttt acgagcttct tgttcaacaa  16680
cttggaggat ggatcgctta cctcttcgtt aacgttacag gacaacctta ccctgatgtt  16740
ccttcttgga aatggaacca cttctggctt acctctccac ttttcgagca aagagatgct  16800
ctctacatct tcctttctga tcttggaatc ctcacccagg gaatcgttct tactctttgg  16860
tacaagaaat tcggaggatg gtccctttc atcaactggt tcgttcctta catctgggtt  16920
aaccactggc tcgttttcat cacattcctt cagcacactg atcctactat gcctcattac  16980
aacgctgagg aatggacttt cgctaagggt gctgctgcta ctatcgatag aaagttcgga  17040
ttcatcggac ctcacatctt ccatgatatc atcgagactc atgtgcttca ccactactgt  17100
tctaggatcc cattctacaa cgctagacct gcttctgagg ctatcaagaa agttatggga  17160
aagcactaca ggtctagcga cgagaacatg tggaagtcac tttggaagtc tttcaggtct  17220
tgccaatacg ttgacggtga taacggtgtt ctcatgttcc gtaacatcaa caactgcgga  17280
gttggagctg ctgagaagta atgaaggggt gatcgattat gagatcgtac aaagacactg  17340
ctaggtgtta aggatggata ataataataa taatgagatg aatgtgtttt aagttagtgt  17400
aacagctgta ataaagagag agagagagag agagagagag agagagagag agagagagag  17460
agagaggctg atgaaatgtt atgtatgttt cttggttttt aaaataaatg aaagcacatg  17520
ctcgtgtggt tctatcgaat tattcggcgg ttcctgtggg aaaaagtcca gaagggccgc  17580
cgcagctact actacaacca aggccgtgga ggagggcaac agagccagca cttcgatagc  17640
tgctgcgatg atcttaagca attgaggagc gagtgcacat gcaggggact ggagcgtgca  17700
atcggccaga tgaggcagga catccagcag cagggacagc agcaggaagt tgagaggtgg  17760
tcccatcaat ctaaacaagt cgctagggac cttccgggac agtgcggcac ccagcctagc  17820
cgatgccagc tccaggggca gcagcagtct gcatggtttt gaagtggtga tcgatgagat  17880
cgtataaaga cactgctagg tgttaaggat gggataataa gatgtgtttt aagtcattaa  17940
ccgtaataaa aagagagaga ggctgatgga atgttatgta tgtatgtttc ttggttttta  18000
aaattaaatg gaaagcacat gctcgtgtgg gttctatctc gattaaaaat cccaattata  18060
tttggtctaa tttagtttgg tattgagtaa aacaaattcg aaccaaacca aaatataaat  18120
atatagtttt tatatatatg cctttaagac tttttataga attttcttta aaaaatatct  18180
agaaatattt gcgactcttc tggcatgtaa tatttcgtta aatatgaagt gctccatttt  18240
tattaacttt aaataattgg ttgtacgatc actttcttat caagtgttac taaaatgcgt  18300
caatctcttt gttcttccat attcatatgt caaaatctat caaaattctt atatatcttt  18360
ttcgaatttg aagtgaaatt tcgataattt aaaattaaat agaacatatc attatttagg  18420
tatcatattg atttttatac ttaattacta aatttggtta actttgaaag tgtacatcaa  18480
cgaaaaatta gtcaaacgac taaaataaat aaatatcatg tgttattaag aaaattctcc  18540
tataagaata ttttaataga tcatatgttt gtaaaaaaaa ttaattttta ctaacacata  18600
tatttactta tcaaaaattt gacaaagtaa gattaaaata atattcatct aacaaaaaaa  18660
aaaccagaaa atgctgaaaa cccggcaaaa ccgaaccaat ccaaaccgat atagttggtt  18720
tggtttgatt ttgatataaa ccgaaccaac tcggtccatt tgcaccccta atcataatag  18780
ctttaatatt tcaagatatt attaagttaa cgttgtcaat atcctggaaa ttttgcaaaa  18840
tgaatcaagc ctatatggct gtaatatgaa tttaaaagca gctcgatgtg gtggtaatat  18900
```

gtaatttact tgattctaaa aaaatatccc aagtattaat aatttctgct aggaagaagg 18960
ttagctacga tttacagcaa agccagaata caaagaacca taaagtgatt gaagctcgaa 19020
atatacgaag gaacaaatat ttttaaaaaa atacgcaatg acttggaaca aaagaaagtg 19080
atatattttt tgttcttaaa caagcatccc ctctaaagaa tggcagtttt cctttgcatg 19140
taactattat gctcccttcg ttacaaaaat tttggactac tattgggaac ttcttctgaa 19200
aatagtcctg caggctagta gattggttgg ttggtttcca tgtaccagaa ggcttaccct 19260
attagttgaa agttgaaact ttgttcccta ctcaattcct agttgtgtaa atgtatgtat 19320
atgtaatgcg tataaaacgt agtacttaaa tgactaggag tggttcttga gaccgatgag 19380
agatgggagc agaactaaag atgatgacat aattaagaac gaatttgaaa ggctcttagg 19440
tttgaatcct attcgagaat gtttttgtca aagatagtgg cgatttttgaa ccaaagaaaa 19500 catttaaaaa atcagtatcc ggttacgttc atgcaaatag aaagtggtct aggatctgat 19560
tgtaatttta gacttaaaga gtctcttaag attcaatcct ggctgtgtac aaaactacaa 19620
ataatatatt ttagactatt tggccttaac taaacttcca ctcattattt actgaggtta 19680
gagaatagac ttgcgaataa acacattccc gagaaatact catgatccca taattagtca 19740
gagggtatgc caatcagatc taagaacaca cattccctca aattttaatg cacatgtaat 19800
catagtttag cacaattcaa aaataatgta gtattaaaga cagaaatttg tagacttttt 19860
tttggcgtta aaggaagact aagtttatac gtacatttta ttttaagtgg aaaaccgaaa 19920
ttttccatcg aaatatatga atttagtata tatatttctg caatgtacta ttttgctatt 19980
ttggcaactt tcagtggact actactttat tacaatgtgt atggatgcat gagtttgagt 20040
atacacatgt ctaaatgcat gctttgcaaa acgtaacgga ccacaaaaga ggatccatgc 20100
aaatacatct catagcttcc tccattattt tccgacacaa acagagcaga ctctagagga 20160
tccccccgtt ttacaacaat taccaacaac aacaaacaac aaacaacatt acaattacat 20220
ttacaattac catcccaaat cggcgcgcca tgtgtcctcc taagaccgat ggaagatctt 20280
ctcctagatc tcctctcacc aggtctaagt catctgctga ggctcttgat gctaaggatg 20340
cttctaccgc tcctgttgat cttaagaccc ttgagcctca tgaacttgct gctaccttcg 20400
agactagatg ggttagggtt gaggatgttg agtacgacgt gaccaacttc aaacatcctg 20460
gtggaagcgt gatcttctac atgcttgcta acactggtgc tgatgctact gaggctttca 20520
aagaatttca catgcgtagc ctcaaggctt ggaagatgct tagagctttg ccttctagac 20580
ctgctgagat caagagatct gagtctgagg atgctcctat gcttgaggat ttcgctaggt 20640
ggagagctga acttgagagg gacggattct tcaagccttc tatcacccat gttgcttacc 20700
gtcttttgga gcttcttgct actttcgctc ttggaaccgc tcttatgtac gctggatacc 20760
ctatcattgc tagcgttgtg tacggtgctt tcttcggagc tagatgtgga tgggttcaac 20820
atgagggtgg acacaactct cttaccggat ctgtgtacgt ggataagaga cttcaggcta 20880
tgacttgcgg attcggactt tctaccagcg gagagatgtg gaaccagatg cataacaagc 20940
accatgctac ccctcagaaa gttagacacg acatggatct tgataccact cctgctgtgg 21000
ctttcttcaa caccgctgtg gaggataata gacctagggg attctctaga gcttgggcta 21060
gacttcaagc ttggaccttc gttcctgtta cttctggact tctcgttcag gctttctgga 21120
tctacgttct ccatcctaga caggtgctca ggaagaagaa ctacgaggaa gcttcttgga 21180
tgctcgtttc tcacgttgtt agaaccgctg ttatcaagct tgctaccgga tactcttggc 21240

-continued

```
ctgttgctta ctggtggttc actttcggaa actggatcgc ttacatgtac ctcttcgctc  21300
acttctctac ttctcacact cacctccctg ttgttccatc tgacaagcac cttagctggg  21360
ttaactacgc tgttgatcac accgttgaca tcgatccttc tcgtggatac gttaactggc  21420
ttatgggata ccttaactgc caggttatcc accatctctt ccctgatatg cctcaattca  21480
gacagcctga ggtgtcaaga agattcgtcc ctttcgctaa gaagtgggga ctcaactaca  21540
aggtgctctc ttactacggt gcttggaagg ctactttcag caacctcgac aaagttggac  21600
agcactacta cgttaacgga aaggctgaga aggctcactg atgattaatt aaatttgggc  21660
tcgaaccggt tcgagcaagc ttatgtgacg tgaaataata acggtaaaat atatgtaata  21720
ataataataa taaagccaca aagtgagaat gaggggaagg ggaaatgtgt aatgagccag  21780
tagccggtgg tgctaatttt gtatcgtatt gtcaataaat catgaatttt gtggttttta  21840
tgtgtttttt taaatcatga attttaaatt ttataaaata atctccaatc ggaagaacaa  21900
cattccatat ccatgcatgg atgtttcttt acccaaatct agttcttgag aggatgaagc  21960
atcaccgaac agttctgcaa ctatccctca aaagctttaa aatgaacaac aaggaacaga  22020
gcaacgttcc aaagatccca aacgaaacat attatctata ctaatactat attattaatt  22080
actactgccc ggaatcacaa tccctgaatg attcctatta actacaagcc ttgttggcgg  22140
cggagaagtg atcggcgcgg cgagaagcag cggactcgga gacgaggcct tggaagatct  22200
cctgcagggc ggccgcggat cccatggagt caaagattca aatagaggac ctaacagaac  22260
tcgccgtaaa gactggcgaa cagttcatac agagtctctt acgactcaat gacaagaaga  22320
aaatcttcgt caacatggtg gagcacgaca cacttgtcta ctccaaaaat atcaaagata  22380
cagtctcaga agaccaaagg gcaattgaga cttttcaaca aagggtaata tccggaaacc  22440
tcctcggatt ccattgccca gctatctgtc actttattgt gaagatagtg gaaaaggaag  22500
gtggctccta caaatgccat cattgcgata aaggaaaggc catcgttgaa gatgcctctg  22560
ccgacagtgg tcccaaagat ggacccccac ccacgaggag catcgtggaa aaagaagacg  22620
ttccaaccac gtcttcaaag caagtggatt gatgtgatat ctccactgac gtaagggatg  22680
acgcacaatc ccactatcct tcgcaagacc cttcctctat ataaggaagt tcatttcatt  22740
tggagagaac acgggggact gaattaaata tgagccctga gaggcgtcct gttgaaatca  22800
gacctgctac tgctgctgat atggctgctg tttgtgatat cgtgaaccac tacatcgaga  22860
cttctaccgt taacttcaga actgagcctc aaactcctca agagtggatc gatgatcttg  22920
agagactcca agatagatac ccttggcttg ttgctgaggt tgagggtgtt gttgctggaa  22980
tcgcttacgc tggaccttgg aaggctagaa acgcttacga ttggactgtt gagtctaccg  23040
tttacgtttc acacagacat cagagacttg gacttggatc taccctttac actcaccttc  23100
tcaagtctat ggaagctcag ggattcaagt ctgttgttgc tgttatcgga ctccctaacg  23160
atccttctgt tagacttcat gaggctcttg gatacactgc tagaggaact cttagagctg  23220
ctggatacaa gcacggtgga tggcatgatg ttggattctg gcaaagagat ttcgagcttc  23280
ctgctcctcc tagacctgtt agaccagtta ctcagatctg aatttgcgtg atcgttcaaa  23340
catttggcaa taaagtttct taagattgaa tcctgttgcc ggtcttgcga tgattatcat  23400
ataatttctg ttgaattacg ttaagcatgt aataattaac atgtaatgca tgacgttatt  23460
tatgagatgg gtttttatga ttagagtccc gcaattatac atttaatacg cgatagaaaa  23520
caaaatatag cgcgcaaact aggataaatt atcgcgcgcg gtgtcatcta tgttactaga  23580
tcactagtga tgtacggtta aaaccacccc agtacattaa aaacgtccgc aatgtgttat  23640
```

```
taagttgtct aagcgtcaat ttgtttacac cacaatatat cctgccacca gccagccaac  23700

agctccccga ccggcagctc ggcacaaaat caccactcga tacaggcagc ccatcagtcc  23760


<210> SEQ ID NO 8
<211> LENGTH: 11042
<212> TYPE: DNA
<213> ORGANISM: Artificial Sequence
<220> FEATURE:
<223> OTHER INFORMATION: pORE04+11ABGBEC_Cowpea_EPA_insert nucleotide
      sequence

<400> SEQUENCE: 8

tcctgtggtt ggcatgcaca tacaaatgga cgaacggata aaccttttca cgccctttta     60

aatatccgat tattctaata aacgctcttt tctcttaggt ttacccgcca atatatcctg    120

tcaaacactg atagtttaaa ctgaaggcgg gaaacgacaa tctgctagtg gatctcccag    180

tcacgacgtt gtaaaacggg cgccctagaa tctaattatt ctattcagac taaattagta    240

taagtatttt tttaatcaat aaataataat taataattta ttagtaggag tgattgaatt    300

tataatatat ttttttaat catttaaaga atcttatatc tttaaattga caagagtttt    360

aaatggggag agtgttatca tatcacaagt aggattaatg tgttatagtt tcacatgcat    420

tacgataagt tgtgaaagat aacattatta tatataacaa tgacaatcac tagcgatcga    480

gtagtgagag tcgtcttatt acactttctt ccttcgatct gtcacatggc ggcggcccga    540

attctcatca cttagaagcg tggtgcttca tgtagtagaa gtttccgaaa agcatgagaa    600

gagtcaccat gtacaccacg aggagctgag cgataaactt agggtaaggt gaagaagagt    660

agaggaggta cacagcctgg agaaggttca tgaagaactg gaacatttgc atctgggtga    720

ggtatcttcc ccaccagagg tactttctct tagttttctc atccttaggg agcacagcag    780

ccataaagta gtaggtgtac atgcacacgt gcacccaaga gttgagagca gcagagaaat    840

aagcatcacc acctggagca gcgtaggtga tcatccacca gattccagag atagatccgt    900

gatggtacac gtggaggaat gacacctggt tcacatttcc cttgaggagc atgatgaagg    960

tatccatgaa ctcgtagatc tttgacacgt agaaaatcca gatcacctta gccatctcgg   1020

tctgagcagg gttgtaagcg tttccccaga aagagtactt gttcacgtaa gcctcgtaca   1080

cgagcttgag gcacatgtag agtgagagtc cgatgaggaa cacgttatga gcgagcatga   1140

gagccttgag caagaatgga tcctgtccct tcacagttct agggaacacc tttctgtaca   1200

cgagtccaga tcccacgata gcgaagtaag cgaggagaga caagataaga ggggtaggag   1260

attccacgag agggagatcc ttagtagcag aagagatagg cttgagtccc catccgatag   1320

aatcggtagc agagaagata gcaggagcca caacagcatc gatagcagcg tattgttctt   1380

gagccatagc cacgagaggc tgagcaaatt ccatgaattc tgttcttctt tactctttgt   1440

gtgactgagg tttggtctag tgctttggtc atctatatat aatgataaca acaatgagaa   1500

caagctttgg agtgatcgga gggtctagga tacatgagat tcaagtggac taggatctac   1560

accgttggat tttgagtgtg gatatgtgtg aggttaattt tacttggtaa cggccacaaa   1620

ggcctaagga gaggtgttga gacccttatc ggcttgaacc gctggaataa tgccacgtgg   1680

aagataattc catgaatctt atcgttatct atgagtgaaa ttgtgtgatg gtggagtggt   1740

gcttgctcat tttacttgcc tggtggactt ggccctttcc ttatggggaa tttatatttt   1800

acttactata gagctttcat acctttttt taccttggat ttagttaata tataatggta   1860

tgattcatga ataaaaatgg gaaatttttg aatttgtact gctaaatgca taagattagg   1920
```

-continued tgaaactgtg gaatatatat ttttttcatt taaaagcaaa atttgccttt tactagaatt 1980
ataaatatag aaaaatatat aacattcaaa taaaaatgaa aataagaact ttcaaaaaac 2040
agaactatgt ttaatgtgta aagattagtc gcacatcaag tcatctgtta caatatgtta 2100
caacaagtca taagcccaac aaagttagca cgtctaaata aactaaagag tccacgaaaa 2160
tattacaaat cataagccca acaaagttat tgatcaaaaa aaaaaaacgc ccaacaaagc 2220
taaacaaagt ccaaaaaaaa cttctcaagt ctccatcttc ctttatgaac attgaaaact 2280
atacacaaaa caagtcagat aaatctcttt ctgggcctgt cttcccaacc tcctacatca 2340
cttccctatc ggattgaatg ttttacttgt accttttccg ttgcaatgat attgatagta 2400
tgtttgtgaa aactaatagg gttaacaatc gaagtcatgg aatatggatt tggtccaaga 2460
ttttccgaga gctttctagt agaaagccca tcaccagaaa tttactagta aaataaatca 2520
ccaattaggt ttcttattat gtgccaaatt caatataatt atagaggata tttcaaatga 2580
aaacgtatga atgttattag taaatggtca ggtaagacat taaaaaaatc ctacgtcaga 2640
tattcaactt taaaaattcg atcagtgtgg aattgtacaa aaatttggga tctactatat 2700
atatataatg ctttacaaca cttggatttt tttttggagg ctggaatttt taatctacat 2760
atttgttttg gccatgcacc aactcattgt ttagtgtaat actttgattt tgtcaaatat 2820
atgtgttcgt gtatatttgt ataagaattt ctttgaccat atacacacac acatatatat 2880
atatatatat atattatata tcatgcactt ttaattgaaa aaataaatata tatatatata 2940 gtgcattttt tctaacaacc atatatgttg cgattgatct gcaaaaatac tgctagagta 3000
atgaaaaata taatctattg ctgaaattat ctcagatgtt aagattttct taaagtaaat 3060
tctttcaaat tttagctaaa agtcttgtaa taactaaaga ataatacaca atctcgacca 3120
cggaaaaaaa acacataata aatttggggc ccctagaatc taattattct attcagacta 3180
aattagtata agtatttttt taatcaataa ataataatta ataatttatt agtaggagtg 3240
attgaattta taatatattt tttttaatca tttaaagaat cttatatctt taaattgaca 3300
agagttttaa atggggagag tgttatcata tcacaagtag gattaatgtg ttatagtttc 3360
acatgcatta cgataagttg tgaaagataa cattattata tataacaatg acaatcacta 3420
gcgatcgagt agtgagagtc gtcttattac actttcttcc ttcgatctgt cacatggcgg 3480
cggcccgcgg ccgctcatca gtgagccttc tcagcctttc cgttcacgta gtagtgctgt 3540
cccaccttat cgaggtttga gaaggtagcc ttccaagcac cgtagtaaga gagcaccttg 3600
tagttgagtc cccacttctt agcgaaagga acgaatcttc ttgacacctc aggctgtctg 3660
aactgtggca tatctgggaa gaggtgatgg atcacctggc agttgaggta tcccatgagc 3720
cagttcacgt aacccctaga aggatcgata tccacggtgt gatccacagc gtagttcacc 3780
caagaaaggt gcttatcaga tggcaccact gggagatggg tatgagaggt agagaagtga 3840
gcgaagaggt acatgtaagc gatccagttt ccgaaggtga accaccaata agcaacaggc 3900
caagagtatc cggtagcgag cttgataaca gcggttctca caacgtgaga cacgagcatc 3960
caagaagcct cttcgtagtt cttctttctg agcacctgtc taggatggag aacgtagatc 4020
cagaaagcct gcacgagaag tccagaagtc acaggaacga aagtccaagc ctgaagtcta 4080
gcccaagctc tagaaaatcc cctaggcctg ttatcctcaa cagcggtgtt gaagaaagcc 4140
acagcaggag tggtatcgag atccatatca tgcctcacct tttgtggggt tgcgtggtgc 4200
ttgttgtgca tctggttcca catctcacca gaggtagaaa gtccgaatcc gcaagtcata 4260
gcctggagcc tcttatccac atacacagat ccggtgagag agttatgacc accctcgtgt 4320
tgaacccatc cacatctagc tccgaagaaa gcaccgtaca ccacagaagc gataataggg 4380
tatccagcat acatgagagc agttccgaga gcgaaagtag caagaagctc gagaagtctg 4440
tatgccacgt gggtgataga aggcttgaag aatccatccc tctcaagctc agctctccac 4500
ctagcgaaat cttcgagcat aggagcatcc tcagactcag acctcttgat ctcagctggt 4560
ctagaaggca aagccctaag catcttccaa gccttgagag atctcatgtg aaattctttg 4620
aaagcctcag tagcatcagc accggtgtta gcgagcatgt agaagatcac agaaccacca 4680
gggtgcttga agttagtaac atcgtactca acatcctcaa ctctcaccca tctagtctcg 4740
aaggtagcag ccaactcatg aggctcaaga gtcttgagat ccacaggagc agtagaagca 4800
tccttagcat cgagagcctc agcagatgac ttagacctgg taagaggtga cctaggagaa 4860
gatcttccat cagtctttgg agggcacatg cggccgctgt tcttctttac tctttgtgtg 4920
actgaggttt ggtctagtgc tttggtcatc tatatataat gataacaaca atgagaacaa 4980
gctttggagt gatcggaggg tctaggatac atgagattca agtggactag gatctacacc 5040
gttggatttt gagtgtggat atgtgtgagg ttaattttac ttggtaacgg ccacaaaggc 5100
ctaaggagag gtgttgagac ccttatcggc ttgaaccgct ggaataatgc cacgtggaag 5160
ataattccat gaatcttatc gttatctatg agtgaaattg tgtgatggtg gagtggtgct 5220
tgctcatttt acttgcctgg tggacttggc cctttcctta tggggaattt atattttact 5280
tactatagag ctttcatacc ttttttttac cttggattta gttaatatat aatggtatga 5340
ttcatgaata aaaatgggaa atttttgaat ttgtactgct aaatgcataa gattaggtga 5400
aactgtggaa tatatatttt tttcatttaa aagcaaaatt tgccttttac tagaattata 5460
aatatagaaa aatatataac attcaaataa aaatgaaaat aagaactttc aaaaaacaga 5520
actatgttta atgtgtaaag attagtcgca catcaagtca tctgttacaa tatgttacaa 5580
caagtcataa gcccaacaaa gttagcacgt ctaaataaac taaagagtcc acgaaaatat 5640
tacaaatcat aagcccaaca aagttattga tcaaaaaaaa aaaacgccca acaaagctaa 5700
acaaagtcca aaaaaaactt ctcaagtctc catcttcctt tatgaacatt gaaaactata 5760
cacaaaacaa gtcagataaa tctctttctg ggcctgtctt cccaacctcc tacatcactt 5820
ccctatcgga ttgaatgttt tacttgtacc ttttccgttg caatgatatt gatagtatgt 5880
ttgtgaaaac taatagggtt aacaatcgaa gtcatggaat atggatttgg tccaagattt 5940
tccgagagct ttctagtaga aagcccatca ccagaaattt actagtaaaa taaatcacca 6000
attaggtttc ttattatgtg ccaaattcaa tataattata gaggatattt caaatgaaaa 6060
cgtatgaatg ttattagtaa atggtcaggt aagacattaa aaaaatccta cgtcagatat 6120
tcaactttaa aaattcgatc agtgtggaat tgtacaaaaa tttgggatct actatatata 6180
tataatgctt tacaacactt ggattttttt ttggaggctg gaatttttaa tctacatatt 6240
tgttttggcc atgcaccaac tcattgttta gtgtaatact ttgattttgt caaatatatg 6300
tgttcgtgta tatttgtata agaatttctt tgaccatata cacacacaca tatatatata 6360
tatatatata ttatatatca tgcactttta attgaaaaaa taatatatat atatatagtg 6420
catttttttct aacaaccata tatgttgcga ttgatctgca aaaatactgc tagagtaatg 6480
aaaaatataa tctattgctg aaattatctc agatgttaag attttcttaa agtaaattct 6540
ttcaaatttt agctaaaagt cttgtaataa ctaaagaata atacacaatc tcgaccacgg 6600
aaaaaaaaca cataataaat ttgggcgcgc cgcgtattgg ctagagcagc ttgccaacat 6660
ggtggagcac gacactctcg tctactccaa gaatatcaaa gatacagtct cagaagacca 6720
aagggctatt gagacttttc aacaaagggt aatatcggga aacctcctcg gattccattg 6780
cccagctatc tgtcacttca tcaaaaggac agtagaaaag gaaggtggca cctacaaatg 6840
ccatcattgc gataaaggaa aggctatcgt tcaagatgcc tctgccgaca gtggtcccaa 6900
agatggaccc ccacccacga ggagcatcgt ggaaaaagaa gacgttccaa ccacgtcttc 6960
aaagcaagtg gattgatgtg ataacatggt ggagcacgac actctcgtct actccaagaa 7020
tatcaaagat acagtctcag aagaccaaag ggctattgag acttttcaac aaagggtaat 7080
atcgggaaac ctcctcggat tccattgccc agctatctgt cacttcatca aaaggacagt 7140
agaaaaggaa ggtggcacct acaaatgcca tcattgcgat aaaggaaagg ctatcgttca 7200
agatgcctct gccgacagtg gtcccaaaga tggaccccca cccacgagga gcatcgtgga 7260
aaaagaagac gttccaacca cgtcttcaaa gcaagtggat tgatgtgata tctccactga 7320
cgtaagggat gacgcacaat cccactatcc ttcgcaagac cttcctctat ataaggaagt 7380
tcatttcatt tggagaggac acgctgaaat caccagtctc tctctacaaa tctatctctg 7440
cgatcgcatg cctcctaggg attcttactc ttacgctgct cctccatctg ctcagctcca 7500
tgaagttgat actcctcaag agcacgataa gaaagaactc gtgatcggag atagggctta 7560
cgatgtgacc aacttcgtga agagacaccc tggtggaaag attatcgctt accaggttgg 7620
aactgatgct accgatgctt acaagcagtt ccacgtgaga tctgctaagg ctgataagat 7680
gctcaagtct ctcccatcta ggcctgtgca caagggatat tctccaagaa gggctgatct 7740
tatcgctgat ttccaagagt tcaccaagca gcttgaggct gagggaatgt tcgaaccttc 7800
tctccctcat gtggcttaca gactcgctga ggttatcgct atgcatgttg ctggtgctgc 7860
tctcatctgg cacggatata ctttcgctgg aatcgctatg ctcggagtgg ttcagggaag 7920
atgtggatgg cttatgcatg agggtggaca ctactctctc accggaaaca ttgctttcga 7980
tagggctatc caggtggcat gctatggact tggatgtgga atgtctggtg cttggtggag 8040
aaaccagcat aacaagcacc atgctacccc tcaaaagctc cagcatgatg tggatctcga 8100
tactctccct ctcgtggctt tccatgagag aatcgctgct aaggtgaagt ctcctgctat 8160
gaaggcttgg ctctctatgc aggctaagct tttcgctcct gtgactactc ttctcgttgc 8220
tcttggatgg cagctctacc tccatcctag acacatgctc aggaccaagc actacgatga 8280
gcttgctatg ctcggtatca gatacggact cgttggatac ctcgctgcta attacggtgc 8340
tggatacgtt ctcgcttgct accttcttta cgttcagctc ggagctatgt acatcttctg 8400
caacttcgct gtgtctcaca ctcatctccc tgtggttgaa cctaacgagc atgctacttg 8460
ggttgagtac gctgctaacc acactaccaa ctgctctcca tcttggtggt gtgattggtg 8520
gatgtcttac ctcaactacc agatcgagca ccacctctac ccttctatgc ctcagttcag 8580
acaccctaag atcgctccta gagtgaagca gcttttcgag aagcacggac tccactacga 8640
tgtgagagga tactttgagg ctatggctga taccttcgct aacctcgata atgtggctca 8700
cgctcctgag aagaaaatgc agtgatgagc gatcgcgatc gttcaaacat ttggcaataa 8760
agtttcttaa gattgaatcc tgttgccggt cttgcgatga ttatcatata atttctgttg 8820
aattacgtta agcatgtaat aattaacatg taatgcatga cgttatttat gagatgggtt 8880
tttatgatta gagtcccgca attatacatt taatacgcga tagaaaacaa aatatagcgc 8940
gcaaactagg ataaattatc gcgcgcggtg tcatctatgt tactagatcc ctgcagggcg 9000

-continued

```
tattggctag agcagcttgc caacatggtg gagcacgaca ctctcgtcta ctccaagaat    9060
atcaaagata cagtctcaga agaccaaagg gctattgaga cttttcaaca aagggtaata    9120
tcgggaaacc tcctcggatt ccattgccca gctatctgtc acttcatcaa aaggacagta    9180
gaaaaggaag gtggcaccta caaatgccat cattgcgata aaggaaaggc tatcgttcaa    9240
gatgcctctg ccgacagtgg tcccaaagat ggacccccac ccacgaggag catcgtggaa    9300
aaagaagacg ttccaaccac gtcttcaaag caagtggatt gatgtgataa catggtggag    9360
cacgacactc tcgtctactc caagaatatc aaagatacag tctcagaaga ccaaagggct    9420
attgagactt ttcaacaaag ggtaatatcg ggaaacctcc tcggattcca ttgcccagct    9480
atctgtcact tcatcaaaag gacagtagaa aaggaaggtg gcacctacaa atgccatcat    9540
tgcgataaag gaaaggctat cgttcaagat gcctctgccg acagtggtcc caaagatgga    9600
cccccaccca cgaggagcat cgtggaaaaa gaagacgttc caaccacgtc ttcaaagcaa    9660
gtggattgat gtgatatctc cactgacgta agggatgacg cacaatccca ctatccttcg    9720
caagaccttc ctctatataa ggaagttcat ttcatttgga gaggacacgc tgaaatcacc    9780
agtctctctc tacaaatcta tctctctcga gatgattgaa caagatggat tgcacgcagg    9840
ttctccggcc gcttgggtgg agaggctatt cggctatgac tgggcacaac agacaatcgg    9900
ctgctctgat gccgccgtgt tccggctgtc agcgcagggg aggccggttc tttttgtcaa    9960
gaccgacctg tccggtgccc tgaatgaact tcaagacgag gcagcgcggc tatcgtggct   10020
ggccacgacg ggcgttcctt gcgcagctgt gctcgacgtt gtcactgaag cgggaaggga   10080
ctggctgcta ttgggcgaag tgccggggca ggatctcctg tcatctcacc ttgctcctgc   10140
cgagaaagta tccatcatgg ctgatgcaat gcggcggctg catacgcttg atccggctac   10200
ctgcccattc gaccaccaag cgaaacatcg catcgagcga gcacgtactc ggatggaagc   10260
cggtcttgtc gatcaggatg atctggacga agagcatcag gggctcgcgc cagccgaact   10320
gttcgccagg ctcaaggcgc gcatgcccga cggcgaggat ctcgtcgtga ctcatggcga   10380
tgcctgcttg ccgaatatca tggtggaaaa tggccgcttt tctggattca tcgactgtgg   10440
ccggctgggt gtggcggacc gctatcagga catagcgttg gctacccgtg atattgctga   10500
agagcttggc ggcgaatggg ctgaccgctt cctcgtgctt tacggtatcg ccgctcccga   10560
ttcgcagcgc atcgccttct atcgccttct tgacgagttc ttctgaaacg cgtgatcgtt   10620
caaacatttg gcaataaagt ttcttaagat tgaatcctgt tgccggtctt gcgatgatta   10680
tcatataatt tctgttgaat tacgttaagc atgtaataat taacatgtaa tgcatgacgt   10740
tatttatgag atgggttttt atgattagag tcccgcaatt atacatttaa tacgcgatag   10800
aaaacaaaat atagcgcgca aactaggata aattatcgcg cgcggtgtca tctatgttac   10860
tagatcgacg tccgtacggt taaaaccacc ccagtacatt aaaaacgtcc gcaatgtgtt   10920
attaagttgt ctaagcgtca atttgtttac accacaatat atcctgccac cagccagcca   10980
acagctcccc gaccggcagc tcggcacaaa atcaccactc gatacaggca gcccatcagt   11040
cc                                                                  11042
```

<210> SEQ ID NO 9
<211> LENGTH: 1254
<212> TYPE: DNA
<213> ORGANISM: Artificial Sequence
<220> FEATURE:
<223> OTHER INFORMATION: Codon-optimized open reading frame for
      expression of Lachancea kluyveri 12 desaturase in plants

<400> SEQUENCE: 9

```
atgagcgctg ttaccgttac tggatctgat cctaagaaca gaggatcttc tagcaacacc     60
gagcaagagg ttccaaaagt tgctatcgat accaacggaa acgtgttctc tgttcctgat    120
ttcaccatca aggacatcct tggagctatc cctcatgagt gttacgagag aagattggct    180
acctctctct actacgtgtt cagagatatc ttctgcatgc ttaccaccgg ataccttacc    240
cataagatcc tttaccctct cctcatctct tacacctcta acagcatcat caagttcact    300
ttctgggccc tttacactta cgttcaagga cttttcggaa ccggaatctg ggttctcgct    360
catgagtgtg gacatcaagc tttctctgat tacggaatcg tgaacgattt cgttggatgg    420
acccttcact cttaccttat ggttccttac ttcagctgga agtactctca tggaaagcac    480
cataaggcta ctggacacat gaccagagat atggttttcg ttcctgccac caaagaggaa    540
ttcaagaagt ctaggaactt cttcggtaac ctcgctgagt actctgagga ttctccactt    600
agaacccttt acgagcttct tgttcaacaa cttggaggat ggatcgctta cctcttcgtt    660
aacgttacag gacaacctta ccctgatgtt ccttcttgga aatggaacca cttctggctt    720
acctctccac ttttcgagca aagagatgct ctctacatct tcctttctga tcttggaatc    780
ctcacccagg gaatcgttct tactctttgg tacaagaaat tcggaggatg gtcccttttc    840
atcaactggt tcgttcctta catctgggtt aaccactggc tcgttttcat cacattcctt    900
cagcacactg atcctactat gcctcattac aacgctgagg aatggacttt cgctaagggt    960
gctgctgcta ctatcgatag aaagttcgga ttcatcggac ctcacatctt ccatgatatc   1020
atcgagactc atgtgcttca ccactactgt tctaggatcc cattctacaa cgctagacct   1080
gcttctgagg ctatcaagaa agttatggga aagcactaca ggtctagcga cgagaacatg   1140
tggaagtcac tttggaagtc tttcaggtct tgccaatacg ttgacggtga taacggtgtt   1200
ctcatgttcc gtaacatcaa caactgcgga gttggagctg ctgagaagta atga         1254
```

<210> SEQ ID NO 10
<211> LENGTH: 416
<212> TYPE: PRT
<213> ORGANISM: Lachancea kluyveri

<400> SEQUENCE: 10

```
Met Ser Ala Val Thr Val Thr Gly Ser Asp Pro Lys Asn Arg Gly Ser
1               5                   10                  15

Ser Ser Asn Thr Glu Gln Glu Val Pro Lys Val Ala Ile Asp Thr Asn
            20                  25                  30

Gly Asn Val Phe Ser Val Pro Asp Phe Thr Ile Lys Asp Ile Leu Gly
        35                  40                  45

Ala Ile Pro His Glu Cys Tyr Glu Arg Arg Leu Ala Thr Ser Leu Tyr
    50                  55                  60

Tyr Val Phe Arg Asp Ile Phe Cys Met Leu Thr Thr Gly Tyr Leu Thr
65                  70                  75                  80

His Lys Ile Leu Tyr Pro Leu Leu Ile Ser Tyr Thr Ser Asn Ser Ile
                85                  90                  95

Ile Lys Phe Thr Phe Trp Ala Leu Tyr Thr Tyr Val Gln Gly Leu Phe
            100                 105                 110

Gly Thr Gly Ile Trp Val Leu Ala His Glu Cys Gly His Gln Ala Phe
        115                 120                 125

Ser Asp Tyr Gly Ile Val Asn Asp Phe Val Gly Trp Thr Leu His Ser
    130                 135                 140
```

-continued

Tyr Leu Met Val Pro Tyr Phe Ser Trp Lys Tyr Ser His Gly Lys His
145 150 155 160

His Lys Ala Thr Gly His Met Thr Arg Asp Met Val Phe Val Pro Ala
165 170 175

Thr Lys Glu Glu Phe Lys Lys Ser Arg Asn Phe Phe Gly Asn Leu Ala
180 185 190

Glu Tyr Ser Glu Asp Ser Pro Leu Arg Thr Leu Tyr Glu Leu Leu Val
195 200 205

Gln Gln Leu Gly Gly Trp Ile Ala Tyr Leu Phe Val Asn Val Thr Gly
210 215 220

Gln Pro Tyr Pro Asp Val Pro Ser Trp Lys Trp Asn His Phe Trp Leu
225 230 235 240

Thr Ser Pro Leu Phe Glu Gln Arg Asp Ala Leu Tyr Ile Phe Leu Ser
245 250 255

Asp Leu Gly Ile Leu Thr Gln Gly Ile Val Leu Thr Leu Trp Tyr Lys
260 265 270

Lys Phe Gly Gly Trp Ser Leu Phe Ile Asn Trp Phe Val Pro Tyr Ile
275 280 285

Trp Val Asn His Trp Leu Val Phe Ile Thr Phe Leu Gln His Thr Asp
290 295 300

Pro Thr Met Pro His Tyr Asn Ala Glu Glu Trp Thr Phe Ala Lys Gly
305 310 315 320

Ala Ala Ala Thr Ile Asp Arg Lys Phe Gly Phe Ile Gly Pro His Ile
325 330 335

Phe His Asp Ile Ile Glu Thr His Val Leu His His Tyr Cys Ser Arg
340 345 350

Ile Pro Phe Tyr Asn Ala Arg Pro Ala Ser Glu Ala Ile Lys Lys Val
355 360 365

Met Gly Lys His Tyr Arg Ser Ser Asp Glu Asn Met Trp Lys Ser Leu
370 375 380

Trp Lys Ser Phe Arg Ser Cys Gln Tyr Val Asp Gly Asp Asn Gly Val
385 390 395 400

Leu Met Phe Arg Asn Ile Asn Asn Cys Gly Val Gly Ala Ala Glu Lys
405 410 415

<210> SEQ ID NO 11
<211> LENGTH: 1251
<212> TYPE: DNA
<213> ORGANISM: Pichia pastoris

<400> SEQUENCE: 11
atgtctaagg ttaccgtgtc tggatctgag atccttgagg gatctactaa gaccgttagg 60
cgttctggaa acgttgcatc tttcaagcag caaaagaccg ctatcgatac cttcggaaac 120
gttttcaagg tgccagatta caccatcaag gatatccttg acgctatccc taagcactgt 180
tacgagagat ctctcgtgaa gtctatgtct tacgtggtga gagatatcgt ggctatctct 240
gctatcgctt acgttggact tacctacatc cctcttctcc ctaacgaatt ccttagattc 300
gctgcttggt ctgcttacgt gttctctatc tcttgtttcg gattcggaat ctggatcctt 360
ggacatgagt gtggacattc tgctttctct aactacggat gggttaacga taccgttgga 420
tgggttctcc actctcttgt tatggttcct tacttcagct ggaagttctc tcatgctaag 480
caccataagg ctactggaca catgaccaga gatatggttt tcgttcctta caccgccgag 540
gaattcaaag agaagcacca agttaccagc cttcacgata tcgctgagga aactcctatc 600

-continued

```
tactctgttt tcgctctctt gttccaacag cttggaggac tttctcttta ccttgctact    660

aacgctactg gacaacctta ccctggtgtt tctaagttct tcaagtctca ctactggcct    720

tctagccctg ttttcgataa gaaggactac tggtacatcg ttctttctga tcttggaatc    780

cttgctaccc tcacttctgt ttacaccgct tacaaggttt tcggattctg gcctactttc    840

atcacatggt tctgtccttg gatccttgtt aaccactggc ttgttttcgt taccttcctt    900

cagcacaccg attcttctat gcctcattac gatgctcaag agtggacttt cgctaagggt    960

gctgctgcta ctatcgatag agagttcgga atcctcggaa tcatcttcca tgacatcatc   1020

gagactcatg tgctccatca ctacgtttca aggatcccat tctaccatgc tagagaagct   1080

accgagtgca tcaagaaagt tatgggagag cactacagac acaccgatga gaacatgtgg   1140

gttagccttt ggaaaacttg gagatcttgc cagttcgttg agaaccatga tggtgtgtac   1200

atgttccgta actgcaacaa cgttggagtg aagcctaagg atacctgatg a            1251
```

<210> SEQ ID NO 12
<211> LENGTH: 415
<212> TYPE: PRT
<213> ORGANISM: Pichia pastoris

<400> SEQUENCE: 12

```
Met Ser Lys Val Thr Val Ser Gly Ser Glu Ile Leu Glu Gly Ser Thr
1               5                   10                  15

Lys Thr Val Arg Arg Ser Gly Asn Val Ala Ser Phe Lys Gln Gln Lys
            20                  25                  30

Thr Ala Ile Asp Thr Phe Gly Asn Val Phe Lys Val Pro Asp Tyr Thr
        35                  40                  45

Ile Lys Asp Ile Leu Asp Ala Ile Pro Lys His Cys Tyr Glu Arg Ser
    50                  55                  60

Leu Val Lys Ser Met Ser Tyr Val Val Arg Asp Ile Val Ala Ile Ser
65                  70                  75                  80

Ala Ile Ala Tyr Val Gly Leu Thr Tyr Ile Pro Leu Leu Pro Asn Glu
                85                  90                  95

Phe Leu Arg Phe Ala Ala Trp Ser Ala Tyr Val Phe Ser Ile Ser Cys
            100                 105                 110

Phe Gly Phe Gly Ile Trp Ile Leu Gly His Glu Cys Gly His Ser Ala
        115                 120                 125

Phe Ser Asn Tyr Gly Trp Val Asn Asp Thr Val Gly Trp Val Leu His
    130                 135                 140

Ser Leu Val Met Val Pro Tyr Phe Ser Trp Lys Phe Ser His Ala Lys
145                 150                 155                 160

His His Lys Ala Thr Gly His Met Thr Arg Asp Met Val Phe Val Pro
                165                 170                 175

Tyr Thr Ala Glu Glu Phe Lys Glu Lys His Gln Val Thr Ser Leu His
            180                 185                 190

Asp Ile Ala Glu Glu Thr Pro Ile Tyr Ser Val Phe Ala Leu Leu Phe
        195                 200                 205

Gln Gln Leu Gly Gly Leu Ser Leu Tyr Leu Ala Thr Asn Ala Thr Gly
    210                 215                 220

Gln Pro Tyr Pro Gly Val Ser Lys Phe Phe Lys Ser His Tyr Trp Pro
225                 230                 235                 240

Ser Ser Pro Val Phe Asp Lys Lys Asp Tyr Trp Tyr Ile Val Leu Ser
                245                 250                 255

Asp Leu Gly Ile Leu Ala Thr Leu Thr Ser Val Tyr Thr Ala Tyr Lys
```

```
            260                 265                 270

Val Phe Gly Phe Trp Pro Thr Phe Ile Thr Trp Phe Cys Pro Trp Ile
        275                 280                 285

Leu Val Asn His Trp Leu Val Phe Val Thr Phe Leu Gln His Thr Asp
    290                 295                 300

Ser Ser Met Pro His Tyr Asp Ala Gln Glu Trp Thr Phe Ala Lys Gly
305                 310                 315                 320

Ala Ala Ala Thr Ile Asp Arg Glu Phe Gly Ile Leu Gly Ile Ile Phe
                325                 330                 335

His Asp Ile Ile Glu Thr His Val Leu His His Tyr Val Ser Arg Ile
            340                 345                 350

Pro Phe Tyr His Ala Arg Glu Ala Thr Glu Cys Ile Lys Lys Val Met
        355                 360                 365

Gly Glu His Tyr Arg His Thr Asp Glu Asn Met Trp Val Ser Leu Trp
    370                 375                 380

Lys Thr Trp Arg Ser Cys Gln Phe Val Glu Asn His Asp Gly Val Tyr
385                 390                 395                 400

Met Phe Arg Asn Cys Asn Asn Val Gly Val Lys Pro Lys Asp Thr
                405                 410                 415
```

<210> SEQ ID NO 13
<211> LENGTH: 1392
<212> TYPE: DNA
<213> ORGANISM: Micromonas pusilla

<400> SEQUENCE: 13

```
atgtgcccgc cgaagacgga cggccgatcg tccccgcgat cgccgctgac gcgcagcaaa      60

tcctccgcgg aggcgctcga cgccaaggac gcgtcgaccg cgcccgtcga tctcaaaacg     120

ctcgagccgc acgagctcgc ggcgacgttc gagacgcgat gggtgcgcgt ggaggacgtc     180

gagtacgacg tcacaaactt caaacacccg ggaggcagcg tgatattcta catgctcgcg     240

aacacgggcg cggacgccac ggaggcgttc aaggagttcc acatgcgatc gcttaaggcg     300

tggaagatgc tcagagcgct gccgtcgcgc cccgcggaga tcaaacgcag cgagagcgag     360

gacgcgccga tgttggagga tttcgcgcgg tggcgcgcgg agctcgaacg cgacgggttc     420

tttaagccct cgataacgca cgtcgcgtat cggttactcg agctcctcgc gaccttcgcc     480

ctcggcaccg ccctcatgta cgccgggtac ccgatcatcg cgtccgtcgt gtacggcgcg     540

ttcttcggcg ctcggtgcgg ttgggtccag cacgagggcg ggcacaactc gctcacgggg     600

tccgtctacg tcgacaagcg cctccaagcg atgacgtgcg ggttcgggct gtccacgagc     660

ggggagatgt ggaaccagat gcacaataag caccacgcga cgccgcagaa agtgaggcac     720

gacatggacc tggacacgac ccccgcggtg gcgtttttta acaccgccgt ggaggacaac     780

cggccgaggg ggttctcccg cgcgtgggct cggcttcagg cgtggacgtt cgtcccggtg     840

acctccgggc tgctcgtcca ggcgttctgg atctacgtcc tgcacccgcg gcaggtgttg     900

cgaaagaaga actacgagga ggcgtcgtgg atgctcgtct ctcacgtcgt caggaccgcg     960

gtgattaaac tcgcgacggg gtactcgtgg cccgtcgcgt actggtggtt caccttcggc    1020

aactggatcg cgtacatgta cctcttcgcg cacttctcca cgagccacac gcacctcccg    1080

gtcgtgccct cggataagca cctgagctgg gtgaactacg cggtcgatca caccgtggac    1140

atcgacccgt cgcgcgggta cgtgaactgg ttgatgggat atctgaactg ccaggtcatt    1200

catcacctgt tcccggacat gccgcagttt cgccagccgg aggtgagccg gcggttcgtc    1260
```

-continued

```
ccgttcgcga agaagtgggg gctgaactac aaggtgctgt cctattacgg cgcctggaag   1320

gcgacgttct cgaacttgga taaggtcggg cagcactact acgtcaacgg caaggcggag   1380

aaggcgcact ga                                                       1392
```

<210> SEQ ID NO 14
<211> LENGTH: 1395
<212> TYPE: DNA
<213> ORGANISM: Artificial Sequence
<220> FEATURE:
<223> OTHER INFORMATION: Codon-optimized open reading frame for expression of Micromonas pusilla 6-desaturase in plants (version 1)

<400> SEQUENCE: 14

```
atgtgccctc ctaagactga tggaagatct tctcctagat ctccacttac caggtctaaa     60

tcttctgctg aggctcttga tgctaaggat gcttctactg ctcctgttga tcttaagact    120

cttgagcctc atgagcttgc tgctactttc gagactagat gggttagagt tgaggacgtt    180

gagtacgatg tgactaactt caagcaccct ggtggatctg tgatcttcta catgcttgct    240

aacactggtg ctgatgctac tgaggctttc aaagaattcc acatgcgttc tctcaaggct    300

tggaagatgc ttagagcttt gccttctaga cctgctgaga tcaagagatc tgagtctgag    360

gatgctccta tgcttgagga tttcgctaga tggcgtgctg agcttgagag agatggattc    420

ttcaagcctt ctatcaccca tgtggcttac agacttctcg agcttcttgc tacattcgct    480

cttggaactg ctcttatgta cgctggatac cctatcattg cttctgttgt ttacggtgct    540

ttcttcggag ctagatgtgg atgggttcaa catgagggtg gacataactc tcttaccgga    600

tctgtttacg tggacaagag acttcaggct atgacttgtg gattcggact ttctacttct    660

ggtgagatgt ggaaccagat gcataacaag caccatgcta cccctcaaaa ggttagacac    720

gatatggatc ttgataccac tcctgctgtg gctttcttca acactgctgt tgaggataac    780

agacctagag gattctctag agcttgggct agacttcaag cttggacttt cgttcctgtt    840

acctctggac ttcttgttca agctttctgg atctacgttc tccaccctag acaagttctc    900

cgtaagaaga actacgaaga ggcttcttgg atgctcgttt ctcatgttgt tagaaccgct    960

gttatcaagc ttgctactgg atactcttgg cctgttgctt actggtggtt cactttcgga   1020

aactggatcg cttacatgta ccttttcgct cacttctcta cttctcatac tcacctccct   1080

gttgttccat ctgataagca cctttcttgg gttaactacg ctgttgatca caccgttgat   1140

atcgatcctt ctagaggata cgtgaactgg cttatgggat accttaactg tcaggttatc   1200

caccacctct tccctgatat gcctcaattc agacagcctg aggttagcag aagattcgtt   1260

cctttcgcta agaagtgggg actcaactac aaggtgctct cttactacgg tgcttggaag   1320

gctactttct ctaaccttga taaggtggga cagcactact acgttaacgg aaaggctgag   1380

aaggctcact aatga                                                    1395
```

<210> SEQ ID NO 15
<211> LENGTH: 1395
<212> TYPE: DNA
<213> ORGANISM: Artificial Sequence
<220> FEATURE:
<223> OTHER INFORMATION: Codon-optimized open reading frame for expression of Micromonas pusilla 6-desaturase in plants (version 2)

<400> SEQUENCE: 15

```
atgtgtcctc ctaagaccga tggaagatct tctcctagat ctcctctcac caggtctaag     60
```

```
tcatctgctg aggctcttga tgctaaggat gcttctaccg ctcctgttga tcttaagacc    120
cttgagcctc atgaacttgc tgctaccttc gagactagat gggttagggt tgaggatgtt    180
gagtacgacg tgaccaactt caaacatcct ggtggaagcg tgatcttcta catgcttgct    240
aacactggtg ctgatgctac tgaggctttc aaagaatttc acatgcgtag cctcaaggct    300
tggaagatgc ttagagcttt gccttctaga cctgctgaga tcaagagatc tgagtctgag    360
gatgctccta tgcttgagga tttcgctagg tggagagctg aacttgagag ggacggattc    420
ttcaagcctt ctatcaccca tgttgcttac cgtcttttgg agcttcttgc tactttcgct    480
cttggaaccg ctcttatgta cgctggatac cctatcattg ctagcgttgt gtacggtgct    540
ttcttcggag ctagatgtgg atgggttcaa catgagggtg gacacaactc tcttaccgga    600
tctgtgtacg tggataagag acttcaggct atgacttgcg gattcggact ttctaccagc    660
ggagagatgt ggaaccagat gcataacaag caccatgcta cccctcagaa agttagacac    720
gacatggatc ttgataccac tcctgctgtg gctttcttca acaccgctgt ggaggataat    780
agacctaggg gattctctag agcttgggct agacttcaag cttggacctt cgttcctgtt    840
acttctggac ttctcgttca ggctttctgg atctacgttc tccatcctag acaggtgctc    900
aggaagaaga actacgagga agcttcttgg atgctcgttt ctcacgttgt tagaaccgct    960
gttatcaagc ttgctaccgg atactcttgg cctgttgctt actggtggtt cactttcgga   1020
aactggatcg cttacatgta cctcttcgct cacttctcta cttctcacac tcacctccct   1080
gttgttccat ctgacaagca ccttagctgg gttaactacg ctgttgatca caccgttgac   1140
atcgatcctt ctcgtggata cgttaactgg cttatgggat accttaactg ccaggttatc   1200
caccatctct tccctgatat gcctcaattc agacagcctg aggtgtcaag aagattcgtc   1260
cctttcgcta agaagtgggg actcaactac aaggtgctct cttactacgg tgcttggaag   1320
gctactttca gcaacctcga caaagttgga cagcactact acgttaacgg aaaggctgag   1380
aaggctcact gatga                                                     1395
```

```
<210> SEQ ID NO 16
<211> LENGTH: 463
<212> TYPE: PRT
<213> ORGANISM: Micromonas pusilla

<400> SEQUENCE: 16

Met Cys Pro Pro Lys Thr Asp Gly Arg Ser Ser Pro Arg Ser Pro Leu
1               5                   10                  15

Thr Arg Ser Lys Ser Ser Ala Glu Ala Leu Asp Ala Lys Asp Ala Ser
            20                  25                  30

Thr Ala Pro Val Asp Leu Lys Thr Leu Glu Pro His Glu Leu Ala Ala
        35                  40                  45

Thr Phe Glu Thr Arg Trp Val Arg Val Glu Asp Val Glu Tyr Asp Val
    50                  55                  60

Thr Asn Phe Lys His Pro Gly Gly Ser Val Ile Phe Tyr Met Leu Ala
65                  70                  75                  80

Asn Thr Gly Ala Asp Ala Thr Glu Ala Phe Lys Glu Phe His Met Arg
                85                  90                  95

Ser Leu Lys Ala Trp Lys Met Leu Arg Ala Leu Pro Ser Arg Pro Ala
            100                 105                 110

Glu Ile Lys Arg Ser Glu Ser Glu Asp Ala Pro Met Leu Glu Asp Phe
        115                 120                 125
```

```
Ala Arg Trp Arg Ala Glu Leu Glu Arg Asp Gly Phe Phe Lys Pro Ser
    130                 135                 140

Ile Thr His Val Ala Tyr Arg Leu Leu Glu Leu Leu Ala Thr Phe Ala
145                 150                 155                 160

Leu Gly Thr Ala Leu Met Tyr Ala Gly Tyr Pro Ile Ile Ala Ser Val
                165                 170                 175

Val Tyr Gly Ala Phe Phe Gly Ala Arg Cys Gly Trp Val Gln His Glu
            180                 185                 190

Gly Gly His Asn Ser Leu Thr Gly Ser Val Tyr Val Asp Lys Arg Leu
        195                 200                 205

Gln Ala Met Thr Cys Gly Phe Gly Leu Ser Thr Ser Gly Glu Met Trp
    210                 215                 220

Asn Gln Met His Asn Lys His His Ala Thr Pro Gln Lys Val Arg His
225                 230                 235                 240

Asp Met Asp Leu Asp Thr Thr Pro Ala Val Ala Phe Phe Asn Thr Ala
                245                 250                 255

Val Glu Asp Asn Arg Pro Arg Gly Phe Ser Arg Ala Trp Ala Arg Leu
            260                 265                 270

Gln Ala Trp Thr Phe Val Pro Val Thr Ser Gly Leu Leu Val Gln Ala
        275                 280                 285

Phe Trp Ile Tyr Val Leu His Pro Arg Gln Val Leu Arg Lys Lys Asn
    290                 295                 300

Tyr Glu Glu Ala Ser Trp Met Leu Val Ser His Val Val Arg Thr Ala
305                 310                 315                 320

Val Ile Lys Leu Ala Thr Gly Tyr Ser Trp Pro Val Ala Tyr Trp Trp
                325                 330                 335

Phe Thr Phe Gly Asn Trp Ile Ala Tyr Met Tyr Leu Phe Ala His Phe
            340                 345                 350

Ser Thr Ser His Thr His Leu Pro Val Val Pro Ser Asp Lys His Leu
        355                 360                 365

Ser Trp Val Asn Tyr Ala Val Asp His Thr Val Asp Ile Asp Pro Ser
    370                 375                 380

Arg Gly Tyr Val Asn Trp Leu Met Gly Tyr Leu Asn Cys Gln Val Ile
385                 390                 395                 400

His His Leu Phe Pro Asp Met Pro Gln Phe Arg Gln Pro Glu Val Ser
                405                 410                 415

Arg Arg Phe Val Pro Phe Ala Lys Lys Trp Gly Leu Asn Tyr Lys Val
            420                 425                 430

Leu Ser Tyr Tyr Gly Ala Trp Lys Ala Thr Phe Ser Asn Leu Asp Lys
        435                 440                 445

Val Gly Gln His Tyr Tyr Val Asn Gly Lys Ala Glu Lys Ala His
    450                 455                 460
```

<210> SEQ ID NO 17
<211> LENGTH: 1449
<212> TYPE: DNA
<213> ORGANISM: Ostreococcus lucimarinus

<400> SEQUENCE: 17

```
atgtgcgtcg aaacgaccga aggcacatcg cgaacgatgg cgaacgaacg cacgagctcg      60

tcgtcgtcgc tgagcgaagg cggaacgccg acggtgacgg tcgggatggg aagcgaagac     120

gcggggaaga agactcgaaa cgcgagcgtc acggcgtgga cgaaagagtt ggagccgcac     180

gcgatcgcga agacgttcga acggcggtac gtgacgatcg aaggcgtgga atacgatgtg     240
```

```
acggatttta agcatcccgg aggatcggtt atttattaca tgctgtcgaa cacgggagcg    300
gacgcgacgg aggcttttaa agagtttcat tatcggtcga aaaaggcgcg caaggcgttg    360
gcggcgttgc cgcataagcc agtggacgcg gcgacgcggg aaccgatcga agatgaggcg    420
atgctgaagg atttcgcgca gtggcgcaag gaattggagc gtgagggatt ttttaagccc    480
tcgccggcgc acgtggcgta tcgattcgcc gagctcgcgg cgatgttcgc gctcggcacg    540
gcgttgatgc acgcgcgttg gcacgtcgct tccgtgatcg tgtactcgtg tttcttcggc    600
gcgcgatgcg gttgggtgca gcacgagggt gggcacaatt cgttgactgg aaacatttgg    660
tgggacaagc gaatccaagc cttcgccgcg gggttcggct tggcgtcgag tggcgacatg    720
tggaacaaca tgcacaacaa gcatcacgcg acgccccaaa aggtgcgaca cgatatggat    780
ctcgacacca ctcccacggt ggcgttcttc aactccgcgg ttgaagaaaa tcgcccgcgg    840
ggattcagta agttgtggtt gcgccttcaa gcgtggacct tcgtgcccgt gacgtccggt    900
atggttttgt tcttctggat gttcgtcttg cacccgcgta acgcgctgcg acgcaaaagc    960
ttcgaagaag cggcttggat gttttccgcg cacgtcattc gcacggcggt tatcaaagcc   1020
gtcaccggct actcctggat cgcctcgtac ggcttgttcg cggcgacgat gtgggcgagc   1080
ggatgttact tgttcgcgca cttttccacg tctcacacgc acttggatgt cgtgccgagc   1140
gataaacacc tctcgtgggt gcgatacgcc gtcgatcaca cgatcgacat caatccgaac   1200
aacagcgtcg tcaactggtt gatgggctac ttgaactgcc aagtcatcca tcacctgttc   1260
ccggatatgc ctcagttccg ccaacccgaa gtctcccgcc gattcgtccc gtttgcgaag   1320
aagtggaact taaactacaa ggtcttgacg tattatgggg cctggaaggc gacgttcggc   1380
aacttgaacg acgtcgggaa gcactattac gtgcacggat ctcagcgcgt caaatcaaag   1440
tcggcgtga                                                           1449
```

<210> SEQ ID NO 18
<211> LENGTH: 1449
<212> TYPE: DNA
<213> ORGANISM: Artificial Sequence
<220> FEATURE:
<223> OTHER INFORMATION: Codon-optimized open reading frame for expression of Ostreococcus lucimarinus 6-desaturase in plants

<400> SEQUENCE: 18

```
atgtgtgttg agactactga gggaacctct agaactatgg ctaacgagag gacctcttct     60
tcttcttcac tctctgaggg tggaactcct actgttactg tgggaatggg atctgaggat    120
gctggaaaga aaaccagaaa cgcttctgtt actgcttgga ccaaagagct tgagcctcac    180
gctatcgcta agaccttcga gagaagatac gttaccatcg agggtgttga gtacgatgtg    240
accgatttca aacaccctgg tggatctgtg atctactaca tgctctctaa cactggtgct    300
gatgctactg aggctttcaa agagttccac taccgttcta agaaggctag aaaggctctt    360
gctgctcttc ctcacaagcc tgttgatgct gctactagag agcctattga ggacgaggct    420
atgcttaagg atttcgctca gtggagaaaa gagttggaga gagagggatt cttcaagcct    480
tctcctgctc atgttgctta ccgtttcgct gaactcgctg ctatgttcgc tcttggaacc    540
gctcttatgc atgctagatg gcacgttgct agcgttatcg tgtactcctg tttcttcgga    600
gctagatgtg gatgggttca acatgagggt ggacacaact ctcttaccgg aaacatctgg    660
tgggataaga gaatccaagc tttcgctgct ggattcggac ttgcttcttc tggtgacatg    720
tggaacaaca tgcacaacaa gcaccatgct actcctcaga aagtgagaca cgatatggat    780
```

-continued

```
cttgatacca cccctaccgt tgctttcttc aactctgctg tggaggaaaa cagacctagg    840

ggattctcta agctttggct cagacttcaa gcttggacct tcgttcctgt tacctctgga    900

atggtgctct tcttctggat gttcgttctc catcctagaa acgctctccg tcgtaagtct    960

ttcgaagagg ctgcttggat gttctctgct cacgttatca gaaccgctgt tatcaaggct   1020

gttaccggat actcttggat cgctagctac ggacttttcg ctgctactat gtgggcttct   1080

ggatgctacc ttttcgctca cttctctact tctcacaccc acctcgatgt tgttccatct   1140

gataagcacc ttagctgggt taggtacgct gttgatcaca ccatcgacat caaccctaac   1200

aactctgttg tgaactggct tatgggatac cttaactgcc aggttatcca ccatctcttc   1260

cctgatatgc ctcaattcag acagcctgag gtgtcaagaa gattcgtccc tttcgctaag   1320

aagtggaacc tcaactacaa ggtgctcact tactacggtg cttggaaggc tactttcgga   1380

aacctcaacg atgttggaaa gcactactac gttcacggat ctcagagagt gaagagcaag   1440

agcgcttga                                                           1449
```

```
<210> SEQ ID NO 19
<211> LENGTH: 482
<212> TYPE: PRT
<213> ORGANISM: Ostreococcus lucimarinus

<400> SEQUENCE: 19

Met Cys Val Glu Thr Thr Glu Gly Thr Ser Arg Thr Met Ala Asn Glu
1               5                   10                  15

Arg Thr Ser Ser Ser Ser Ser Leu Ser Glu Gly Gly Thr Pro Thr Val
            20                  25                  30

Thr Val Gly Met Gly Ser Glu Asp Ala Gly Lys Lys Thr Arg Asn Ala
        35                  40                  45

Ser Val Thr Ala Trp Thr Lys Glu Leu Glu Pro His Ala Ile Ala Lys
    50                  55                  60

Thr Phe Glu Arg Arg Tyr Val Thr Ile Glu Gly Val Glu Tyr Asp Val
65                  70                  75                  80

Thr Asp Phe Lys His Pro Gly Gly Ser Val Ile Tyr Tyr Met Leu Ser
                85                  90                  95

Asn Thr Gly Ala Asp Ala Thr Glu Ala Phe Lys Glu Phe His Tyr Arg
            100                 105                 110

Ser Lys Lys Ala Arg Lys Ala Leu Ala Ala Leu Pro His Lys Pro Val
        115                 120                 125

Asp Ala Ala Thr Arg Glu Pro Ile Glu Asp Glu Ala Met Leu Lys Asp
    130                 135                 140

Phe Ala Gln Trp Arg Lys Glu Leu Glu Arg Glu Gly Phe Phe Lys Pro
145                 150                 155                 160

Ser Pro Ala His Val Ala Tyr Arg Phe Ala Glu Leu Ala Ala Met Phe
                165                 170                 175

Ala Leu Gly Thr Ala Leu Met His Ala Arg Trp His Val Ala Ser Val
            180                 185                 190

Ile Val Tyr Ser Cys Phe Phe Gly Ala Arg Cys Gly Trp Val Gln His
        195                 200                 205

Glu Gly Gly His Asn Ser Leu Thr Gly Asn Ile Trp Trp Asp Lys Arg
    210                 215                 220

Ile Gln Ala Phe Ala Ala Gly Phe Gly Leu Ala Ser Ser Gly Asp Met
225                 230                 235                 240

Trp Asn Asn Met His Asn Lys His His Ala Thr Pro Gln Lys Val Arg
                245                 250                 255
```

```
His Asp Met Asp Leu Asp Thr Thr Pro Thr Val Ala Phe Phe Asn Ser
            260                 265                 270

Ala Val Glu Glu Asn Arg Pro Arg Gly Phe Ser Lys Leu Trp Leu Arg
        275                 280                 285

Leu Gln Ala Trp Thr Phe Val Pro Val Thr Ser Gly Met Val Leu Phe
    290                 295                 300

Phe Trp Met Phe Val Leu His Pro Arg Asn Ala Leu Arg Arg Lys Ser
305                 310                 315                 320

Phe Glu Glu Ala Ala Trp Met Phe Ser Ala His Val Ile Arg Thr Ala
                325                 330                 335

Val Ile Lys Ala Val Thr Gly Tyr Ser Trp Ile Ala Ser Tyr Gly Leu
            340                 345                 350

Phe Ala Ala Thr Met Trp Ala Ser Gly Cys Tyr Leu Phe Ala His Phe
        355                 360                 365

Ser Thr Ser His Thr His Leu Asp Val Val Pro Ser Asp Lys His Leu
    370                 375                 380

Ser Trp Val Arg Tyr Ala Val Asp His Thr Ile Asp Ile Asn Pro Asn
385                 390                 395                 400

Asn Ser Val Val Asn Trp Leu Met Gly Tyr Leu Asn Cys Gln Val Ile
                405                 410                 415

His His Leu Phe Pro Asp Met Pro Gln Phe Arg Gln Pro Glu Val Ser
            420                 425                 430

Arg Arg Phe Val Pro Phe Ala Lys Lys Trp Asn Leu Asn Tyr Lys Val
        435                 440                 445

Leu Thr Tyr Tyr Gly Ala Trp Lys Ala Thr Phe Gly Asn Leu Asn Asp
    450                 455                 460

Val Gly Lys His Tyr Tyr Val His Gly Ser Gln Arg Val Lys Ser Lys
465                 470                 475                 480

Ser Ala


<210> SEQ ID NO 20
<211> LENGTH: 456
<212> TYPE: PRT
<213> ORGANISM: Ostreococcus lucimarinus

<400> SEQUENCE: 20

Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140
```

```
Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285

Ser Lys Ala Leu Lys Gly Gly Lys Tyr Glu Glu Leu Val Trp Met Leu
    290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
        355                 360                 365

His Thr Ile Asp Ile Asp Pro Ser Gln Gly Trp Val Asn Trp Leu Met
    370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
            420                 425                 430

Ala Thr Leu Gly Asn Leu Asp Asn Val Gly Lys His Tyr Tyr Val His
        435                 440                 445

Gly Gln His Ser Gly Lys Thr Ala
    450                 455
```

<210> SEQ ID NO 21
<211> LENGTH: 894
<212> TYPE: DNA
<213> ORGANISM: Pyramimonas cordata

<400> SEQUENCE: 21

```
atggagttcg ctcagcctct tgtggctatg gcacaggagc agtatgccgc aattgacgcg      60

gtggtagccc ctgcaatttt ctcagctacc gacagcatcg gttggggtct taagcccatt     120

agcagcgcga caaaggatct tcctctcgtt gagagtccga cgccgctcat actgagcctg     180

ttggcctatt ttgcgatcgt cggctctggg ctggtgtacc gcaaagtatt ccctcgcaca     240

gtaaaggggc aagacccctt cctgctgaag gcgctcatgc ttgcgcacaa cgtgttcctc     300
```

-continued

```
attggcctca gtctatacat gtgcttgaag cttgtctacg aggcttacgt caacaagtac    360

tccttctggg gaaacgccta caaccccgca cagaccgaga tggcgaaggt catctggatt    420

ttctacgtct ccaagatcta tgagttcatg gacacgttca tcatgctctt gaagggcaac    480

gtcaaccagg tctctttcct gcatgtgtac catcatggct ccatctctgg tatctggtgg    540

atgatcacct acgctgcccc tggcggtgac gcgtacttct cggcggcgct caactcgtgg    600

gtgcacgtgt gcatgtacac gtactacttc atggcggcgg tgctgcccaa ggacgagaag    660

accaagcgca agtacctctg gtggggccgc tacctgaccc agatgcagat gttccagttc    720

ttcatgaacc tgctccaggc ggtctacctc ctctactcct ctagccccta ccccaagttc    780

atcgcccagc tgctggtggt gtacatggtc acgctgctga tgctcttcgg caacttctac    840

tacatgaagc accacgcgag caagaagcag aagctggcca gcaagaagca gtag          894
```

<210> SEQ ID NO 22
<211> LENGTH: 870
<212> TYPE: DNA
<213> ORGANISM: Artificial Sequence
<220> FEATURE:
<223> OTHER INFORMATION: Codon-optimized open reading frame for expression of Pyramimonas cordata 6-elongase in plants (truncated at 3' end and encoding functional elongase) (version 1)

<400> SEQUENCE: 22

```
atggaattcg cccagcctct tgttgctatg gctcaagagc aatacgctgc tatcgatgct     60

gttgttgctc ctgctatctt ctctgctact gattctatcg gatggggact taagcctatc    120

tcttctgcta ctaaggactt gcctcttgtt gagtctccta cacctctcat cctttctttg    180

cttgcttact tcgctatcgt tggatctgga ctcgtttaca gaaaggtttt ccctagaacc    240

gtgaagggac aagatccatt ccttttgaag gctcttatgc ttgctcacaa cgtgttcctt    300

atcggacttt ctctttacat gtgcctcaag cttgtgtacg aggcttacgt taacaagtac    360

tctttctggg gaaacgctta caaccctgct caaactgaga tggctaaggt tatctggatc    420

ttctacgtga gcaagatcta cgagttcatg gataccttca tcatgctcct caagggaaat    480

gttaaccagg ttagcttcct tcacgtttac catcacggat ctatctctgg aatctggtgg    540

atgattactt acgctgctcc tggtggtgat gcttacttct ctgctgctct taactcttgg    600

gttcacgtgt gtatgtacac ctactatttt atggctgccg tgcttcctaa ggacgagaaa    660

actaagagaa agtacctctg gtggggaaga taccttactc aaatgcagat gttccagttc    720

ttcatgaacc ttctccaggc tgtttacctt ctctactctt catctcctta ccctaagttt    780

atcgctcagc tcctcgtggt gtacatggtt actcttctca tgcttttcgg aaacttctac    840

tacatgaagc accacgctag caagtgatga                                     870
```

<210> SEQ ID NO 23
<211> LENGTH: 870
<212> TYPE: DNA
<213> ORGANISM: Artificial Sequence
<220> FEATURE:
<223> OTHER INFORMATION: Codon-optimized open reading frame for expression of Pyramimonas cordata 6-elongase in plants (truncated at 3' end and encoding functional elongase) (version 2)

<400> SEQUENCE: 23

```
atggaattcg cccagcctct tgttgctatg gctcaagagc aatacgctgc tatcgatgct     60

gttgttgctc ctgctatctt ctctgctact gattctatcg gatggggact taagcctatc    120

tcttctgcta ctaaggactt gcctcttgtt gagtctccta cacctctcat cctttctttg    180
```

cttgcttact tcgctatcgt tggatctgga ctcgtttaca gaaaggtttt ccctagaacc 240
gtgaagggac aagatccatt ccttttgaag gctcttatgc ttgctcacaa cgtgttcctt 300
atcggacttt ctctttacat gtgcctcaag cttgtgtacg aggcttacgt taacaagtac 360
tctttctggg gaaacgctta caaccctgct caaactgaga tggctaaggt tatctggatc 420
ttctacgtga gcaagatcta cgagttcatg gataccttca tcatgctcct caagggaaat 480
gttaaccagg ttagcttcct tcacgtttac catcacggat ctatctctgg aatctggtgg 540
atgattactt acgctgctcc tggtggtgat gcttacttct ctgctgctct taactcttgg 600
gttcacgtgt gtatgtacac ctactatttt atggctgccg tgcttcctaa ggacgagaaa 660
actaagagaa agtacctctg gtggggaaga taccttactc aaatgcagat gttccagttc 720
ttcatgaacc ttctccaggc tgtttacctt ctctactctt catctcctta ccctaagttt 780
atcgctcagc tcctcgtggt gtacatggtt actcttctca tgcttttcgg aaacttctac 840
tacatgaagc accacgctag caagtgatga 870

<210> SEQ ID NO 24
<211> LENGTH: 870
<212> TYPE: DNA
<213> ORGANISM: Artificial Sequence
<220> FEATURE:
<223> OTHER INFORMATION: Codon-optimized open reading frame for expression of Pyramimonas cordata 6-elongase in plants (truncated at 3' end and encoding functional elongase) (version 3)

<400> SEQUENCE: 24
atggaatttg ctcaacctct cgttgctatg gctcaagagc agtacgctgc tatcgatgct 60
gttgttgctc ctgctatctt ctctgctacc gactctattg gatggggact caagcctatc 120
tcttctgcta ctaaggatct ccctctcgtt gaatctccta cccctcttat cctttctctc 180
ctcgcttact tcgctatcgt tggttctgga ctcgtttacc gtaaagtgtt ccctagaacc 240
gttaagggac aggatccttt ccttctcaag gctcttatgc tcgctcacaa cgttttcctt 300
atcggactca gcctttacat gtgcctcaag ctcgtttacg aggcttacgt gaacaagtac 360
tccttctggg gaaacgctta caaccctgct caaaccgaga tggctaaggt gatctggatc 420
ttctacgtgt ccaagatcta cgagttcatg gacaccttca tcatgcttct caagggaaac 480
gttaaccagg tttccttcct ccatgtttac caccacggat ctatctctgg aatctggtgg 540
atgatcactt atgctgctcc aggtggagat gcttacttct ctgctgctct caactcttgg 600
gttcatgtgt gcatgtacac ctactacttc atggctgctg ttcttcctaa ggacgaaaag 660
accaagagaa agtacctttg gtggggaaga taccttaccc agatgcaaat gttccagttc 720
ttcatgaacc ttctccaggc tgtttacctc ctctactctt cttctcctta ccctaagttc 780
attgctcaac tcctcgttgt ttacatggtt accctcctca tgcttttcgg aaacttctac 840
tacatgaagc accacgcttc taagtgataa 870

<210> SEQ ID NO 25
<211> LENGTH: 297
<212> TYPE: PRT
<213> ORGANISM: Pyramimonas cordata

<400> SEQUENCE: 25

Met Glu Phe Ala Gln Pro Leu Val Ala Met Ala Gln Glu Gln Tyr Ala
1 5 10 15

Ala Ile Asp Ala Val Val Ala Pro Ala Ile Phe Ser Ala Thr Asp Ser

```
            20                  25                  30

Ile Gly Trp Gly Leu Lys Pro Ile Ser Ser Ala Thr Lys Asp Leu Pro
        35                  40                  45

Leu Val Glu Ser Pro Thr Pro Leu Ile Leu Ser Leu Leu Ala Tyr Phe
    50                  55                  60

Ala Ile Val Gly Ser Gly Leu Val Tyr Arg Lys Val Phe Pro Arg Thr
65                  70                  75                  80

Val Lys Gly Gln Asp Pro Phe Leu Leu Lys Ala Leu Met Leu Ala His
                85                  90                  95

Asn Val Phe Leu Ile Gly Leu Ser Leu Tyr Met Cys Leu Lys Leu Val
            100                 105                 110

Tyr Glu Ala Tyr Val Asn Lys Tyr Ser Phe Trp Gly Asn Ala Tyr Asn
        115                 120                 125

Pro Ala Gln Thr Glu Met Ala Lys Val Ile Trp Ile Phe Tyr Val Ser
    130                 135                 140

Lys Ile Tyr Glu Phe Met Asp Thr Phe Ile Met Leu Leu Lys Gly Asn
145                 150                 155                 160

Val Asn Gln Val Ser Phe Leu His Val Tyr His His Gly Ser Ile Ser
                165                 170                 175

Gly Ile Trp Trp Met Ile Thr Tyr Ala Ala Pro Gly Gly Asp Ala Tyr
            180                 185                 190

Phe Ser Ala Ala Leu Asn Ser Trp Val His Val Cys Met Tyr Thr Tyr
        195                 200                 205

Tyr Phe Met Ala Ala Val Leu Pro Lys Asp Glu Lys Thr Lys Arg Lys
    210                 215                 220

Tyr Leu Trp Trp Gly Arg Tyr Leu Thr Gln Met Gln Met Phe Gln Phe
225                 230                 235                 240

Phe Met Asn Leu Leu Gln Ala Val Tyr Leu Leu Tyr Ser Ser Ser Pro
                245                 250                 255

Tyr Pro Lys Phe Ile Ala Gln Leu Leu Val Val Tyr Met Val Thr Leu
            260                 265                 270

Leu Met Leu Phe Gly Asn Phe Tyr Tyr Met Lys His His Ala Ser Lys
        275                 280                 285

Lys Gln Lys Leu Ala Ser Lys Lys Gln
    290                 295


<210> SEQ ID NO 26
<211> LENGTH: 288
<212> TYPE: PRT
<213> ORGANISM: Pyramimonas cordata

<400> SEQUENCE: 26

Met Glu Phe Ala Gln Pro Leu Val Ala Met Ala Gln Glu Gln Tyr Ala
1               5                   10                  15

Ala Ile Asp Ala Val Val Ala Pro Ala Ile Phe Ser Ala Thr Asp Ser
            20                  25                  30

Ile Gly Trp Gly Leu Lys Pro Ile Ser Ser Ala Thr Lys Asp Leu Pro
        35                  40                  45

Leu Val Glu Ser Pro Thr Pro Leu Ile Leu Ser Leu Leu Ala Tyr Phe
    50                  55                  60

Ala Ile Val Gly Ser Gly Leu Val Tyr Arg Lys Val Phe Pro Arg Thr
65                  70                  75                  80

Val Lys Gly Gln Asp Pro Phe Leu Leu Lys Ala Leu Met Leu Ala His
                85                  90                  95
```

```
Asn Val Phe Leu Ile Gly Leu Ser Leu Tyr Met Cys Leu Lys Leu Val
            100                 105                 110

Tyr Glu Ala Tyr Val Asn Lys Tyr Ser Phe Trp Gly Asn Ala Tyr Asn
        115                 120                 125

Pro Ala Gln Thr Glu Met Ala Lys Val Ile Trp Ile Phe Tyr Val Ser
    130                 135                 140

Lys Ile Tyr Glu Phe Met Asp Thr Phe Ile Met Leu Leu Lys Gly Asn
145                 150                 155                 160

Val Asn Gln Val Ser Phe Leu His Val Tyr His His Gly Ser Ile Ser
                165                 170                 175

Gly Ile Trp Trp Met Ile Thr Tyr Ala Ala Pro Gly Gly Asp Ala Tyr
            180                 185                 190

Phe Ser Ala Ala Leu Asn Ser Trp Val His Val Cys Met Tyr Thr Tyr
        195                 200                 205

Tyr Phe Met Ala Ala Val Leu Pro Lys Asp Glu Lys Thr Lys Arg Lys
    210                 215                 220

Tyr Leu Trp Trp Gly Arg Tyr Leu Thr Gln Met Gln Met Phe Gln Phe
225                 230                 235                 240

Phe Met Asn Leu Leu Gln Ala Val Tyr Leu Leu Tyr Ser Ser Ser Pro
                245                 250                 255

Tyr Pro Lys Phe Ile Ala Gln Leu Leu Val Val Tyr Met Val Thr Leu
            260                 265                 270

Leu Met Leu Phe Gly Asn Phe Tyr Tyr Met Lys His His Ala Ser Lys
        275                 280                 285


<210> SEQ ID NO 27
<211> LENGTH: 1278
<212> TYPE: DNA
<213> ORGANISM: Pavlova salina

<400> SEQUENCE: 27

atgccgccgc gcgatagcta ctcgtacgcc gccccgccgt cggcccagct gcacgaggtc      60

gataccccgc aggagcatga taagaaggag ctcgtcatcg gtgaccgcgc gtacgacgtg     120

accaactttg tgaagcgcca cccgggtggc aagatcatcg cataccaggt tggcacagat     180

gcgacggacg cgtacaagca gttccatgtg cggtctgcca aggcggacaa gatgctcaag     240

tcgctgcctt cgcgcccggt gcacaagggc tactcgcccc gccgcgctga cctcattgcc     300

gacttccagg agttcaccaa gcagctggag gcggagggca tgtttgagcc gtcgctgccg     360

cacgtggcat accgcctggc ggaggtgatc gcgatgcacg tggccggcgc cgcgctcatc     420

tggcacgggt acaccttcgc gggcattgcc atgctcggcg ttgtgcaggg ccgctgcggc     480

tggctcatgc acgagggcgg ccactactcg ctcacgggca acattgcttt tgaccgtgcc     540

atccaagtcg cgtgctacgg ccttggctgc ggcatgtcgg gcgcgtggtg gcgcaaccag     600

cacaacaagc accacgcgac gccgcagaag ttgcagcacg acgtcgacct cgacaccctc     660

ccgctcgtcg ccttccacga gcggatagcc gccaaggtga agagccccgc gatgaaggcg     720

tggcttagta tgcaggcgaa gctcttcgcg ccagtgacca cgctgctggt cgcgctgggc     780

tggcagctgt acctgcaccc gcgccatatg ctgcgcacca agcactacga cgagctcgcg     840

atgctcggca ttcgctacgg ccttgtcggc tacctcgcgg cgaactacgg cgcggggtac     900

gtgctcgcgt gctacctgct gtacgtgcag ctcggcgcca tgtacatctt ctgcaacttt     960

gccgtgtcgc acacacacct gccggttgtc gagcctaacg agcacgcaac gtgggtggag    1020

tacgccgcga accacacgac caactgctcg ccctcgtggt ggtgcgactg gtggatgtcg    1080
```

```
taccttcaact accagatcga gcaccacctc tacccgtcca tgccgcagtt ccgccacccg   1140

aagattgcgc cgcgggtgaa gcagctcttc gagaagcacg gcctgcacta cgacgtgcgt   1200

ggctacttcg aggccatggc ggacacgttt gccaaccttg acaacgtcgc gcacgcgccg   1260

gagaagaaga tgcagtga                                                 1278


<210> SEQ ID NO 28
<211> LENGTH: 1281
<212> TYPE: DNA
<213> ORGANISM: Artificial Sequence
<220> FEATURE:
<223> OTHER INFORMATION: Codon-optimized open reading frame for
      expression of Pavlova salina 5-desaturase in plants (version 1)

<400> SEQUENCE: 28

atgcctccaa gggactctta ctcttatgct gctcctcctt ctgctcaact tcacgaagtt     60

gatactcctc aagagcacga caagaaagag cttgttatcg gagatagggc ttacgatgtt    120

accaacttcg ttaagagaca ccctggtgga aagatcattg cttaccaagt tggaactgat    180

gctaccgatg cttacaagca gttccatgtt agatctgcta aggctgacaa gatgcttaag    240

tctcttcctt ctcgtcctgt tcacaaggga tactctccaa gaagggctga tcttatcgct    300

gatttccaag agttcaccaa gcaacttgag gctgagggaa tgttcgagcc ttctcttcct    360

catgttgctt acagacttgc tgaggttatc gctatgcatg ttgctggtgc tgctcttatc    420

tggcatggat acactttcgc tggaatcgct atgcttggag ttgttcaggg aagatgtgga    480

tggcttatgc atgagggtgg acattactct ctcactggaa acattgcttt cgacagagct    540

atccaagttg cttgttacgg acttggatgt ggaatgtctg gtgcttggtg gcgtaaccag    600

cataacaagc accatgctac tcctcaaaag cttcagcacg atgttgatct tgataccctt    660

cctctcgttg ctttccatga gagaatcgct gctaaggtta agtctcctgc tatgaaggct    720

tggctttcta tgcaagctaa gcttttcgct cctgttacca ctcttcttgt tgctcttgga    780

tggcagcttt accttcatcc tagacacatg ctcaggacta agcactacga tgagcttgct    840

atgctcggaa tcagatacgg acttgttgga taccttgctg ctaactacgg tgctggatac    900

gttctcgctt gttaccttct ttacgttcag cttggagcta tgtacatctt ctgcaacttc    960

gctgtttctc atactcacct ccctgttgtt gagcctaacg agcatgctac ttgggttgag   1020

tacgctgcta accacactac taactgttct ccatcttggt ggtgtgattg gtggatgtct   1080

taccttaact accagatcga gcaccacctt taccctcta tgcctcaatt cagacaccct   1140

aagatcgctc ctagagttaa gcagcttttc gagaagcacg gacttcacta cgatgttaga   1200

ggatacttcg aggctatggc tgatactttc gctaaccttg ataacgttgc ccatgctcct   1260

gagaagaaaa tgcagtaatg a                                             1281


<210> SEQ ID NO 29
<211> LENGTH: 1281
<212> TYPE: DNA
<213> ORGANISM: Artificial Sequence
<220> FEATURE:
<223> OTHER INFORMATION: Codon-optimized open reading frame for
      expression of Pavlova salina 5-desaturase in plants (version 2)

<400> SEQUENCE: 29

atgcctccta gggactctta ctcttacgct gctcctcctt ctgctcaact tcacgaggtt     60

gacactcctc aagagcacga caagaaagag cttgttatcg gagatagggc ttacgatgtg    120
```

-continued

```
accaacttcg ttaagagaca ccctggtgga aagatcattg cttaccaagt gggaactgat    180

gctaccgatg cttacaagca gttccatgtg agatctgcta aggctgacaa gatgctcaag    240

tctctccctt ctagacctgt tcacaaggga tactctccta gaagagctga tcttatcgct    300

gacttccaag agttcactaa gcaacttgag gctgagggaa tgttcgaacc ttctctccct    360

catgttgctt accgtcttgc tgaggttatc gctatgcatg ttgctggtgc tgctcttatc    420

tggcacggat acactttcgc tggaatcgct atgcttggag ttgttcaggg aagatgcgga    480

tggcttatgc atgagggtgg acactactct cttaccggaa acattgcttt cgatagggct    540

atccaagttg cttgttacgg acttggatgc ggaatgtctg gtgcttggtg gagaaaccag    600

cataacaagc accatgctac tcctcaaaag ctccagcacg atgttgatct tgataccctc    660

cctctcgttg ctttccatga gagaatcgct gctaaggtta agtctcctgc tatgaaggct    720

tggctctcca tgcaagctaa actcttcgct cctgttacca ctcttcttgt tgctcttgga    780

tggcagcttt accttcaccc tagacacatg ctcagaacta agcactacga cgagcttgct    840

atgcttggta tcagatacgg acttgtggga taccttgctg ctaactacgg tgctggatac    900

gttcttgctt gctaccttct ctacgttcag cttggagcta tgtacatctt ctgcaacttc    960

gctgtttctc acactcatct ccctgttgtt gagcctaacg agcatgctac ttgggttgag   1020

tacgctgcta accacactac taactgctct ccatcttggt ggtgtgattg gtggatgagc   1080

tacctcaact accagatcga gcatcacctt taccctteta tgcctcagtt caggcatcct   1140

aagatcgctc ctagagtgaa gcaactcttc gagaagcacg gacttcacta cgatgtgcgt   1200

ggatacttcg aggctatggc tgatactttc gctaacctcg ataacgttgc tcatgctcct   1260

gagaagaaaa tgcaatgatg a                                             1281
```

<210> SEQ ID NO 30
<211> LENGTH: 425
<212> TYPE: PRT
<213> ORGANISM: Pavlova salina

<400> SEQUENCE: 30

```
Met Pro Pro Arg Asp Ser Tyr Ser Tyr Ala Ala Pro Pro Ser Ala Gln
1               5                   10                  15

Leu His Glu Val Asp Thr Pro Gln Glu His Asp Lys Lys Glu Leu Val
            20                  25                  30

Ile Gly Asp Arg Ala Tyr Asp Val Thr Asn Phe Val Lys Arg His Pro
        35                  40                  45

Gly Gly Lys Ile Ile Ala Tyr Gln Val Gly Thr Asp Ala Thr Asp Ala
    50                  55                  60

Tyr Lys Gln Phe His Val Arg Ser Ala Lys Ala Asp Lys Met Leu Lys
65                  70                  75                  80

Ser Leu Pro Ser Arg Pro Val His Lys Gly Tyr Ser Pro Arg Arg Ala
                85                  90                  95

Asp Leu Ile Ala Asp Phe Gln Glu Phe Thr Lys Gln Leu Glu Ala Glu
            100                 105                 110

Gly Met Phe Glu Pro Ser Leu Pro His Val Ala Tyr Arg Leu Ala Glu
        115                 120                 125

Val Ile Ala Met His Val Ala Gly Ala Ala Leu Ile Trp His Gly Tyr
    130                 135                 140

Thr Phe Ala Gly Ile Ala Met Leu Gly Val Val Gln Gly Arg Cys Gly
145                 150                 155                 160

Trp Leu Met His Glu Gly Gly His Tyr Ser Leu Thr Gly Asn Ile Ala
```

-continued

```
                165                 170                 175

Phe Asp Arg Ala Ile Gln Val Ala Cys Tyr Gly Leu Gly Cys Gly Met
            180                 185                 190

Ser Gly Ala Trp Trp Arg Asn Gln His Asn Lys His His Ala Thr Pro
        195                 200                 205

Gln Lys Leu Gln His Asp Val Asp Leu Asp Thr Leu Pro Leu Val Ala
    210                 215                 220

Phe His Glu Arg Ile Ala Ala Lys Val Lys Ser Pro Ala Met Lys Ala
225                 230                 235                 240

Trp Leu Ser Met Gln Ala Lys Leu Phe Ala Pro Val Thr Thr Leu Leu
                245                 250                 255

Val Ala Leu Gly Trp Gln Leu Tyr Leu His Pro Arg His Met Leu Arg
            260                 265                 270

Thr Lys His Tyr Asp Glu Leu Ala Met Leu Gly Ile Arg Tyr Gly Leu
        275                 280                 285

Val Gly Tyr Leu Ala Ala Asn Tyr Gly Ala Gly Tyr Val Leu Ala Cys
    290                 295                 300

Tyr Leu Leu Tyr Val Gln Leu Gly Ala Met Tyr Ile Phe Cys Asn Phe
305                 310                 315                 320

Ala Val Ser His Thr His Leu Pro Val Val Glu Pro Asn Glu His Ala
                325                 330                 335

Thr Trp Val Glu Tyr Ala Ala Asn His Thr Thr Asn Cys Ser Pro Ser
            340                 345                 350

Trp Trp Cys Asp Trp Trp Met Ser Tyr Leu Asn Tyr Gln Ile Glu His
        355                 360                 365

His Leu Tyr Pro Ser Met Pro Gln Phe Arg His Pro Lys Ile Ala Pro
    370                 375                 380

Arg Val Lys Gln Leu Phe Glu Lys His Gly Leu His Tyr Asp Val Arg
385                 390                 395                 400

Gly Tyr Phe Glu Ala Met Ala Asp Thr Phe Ala Asn Leu Asp Asn Val
                405                 410                 415

Ala His Ala Pro Glu Lys Lys Met Gln
            420                 425
```

<210> SEQ ID NO 31
<211> LENGTH: 1329
<212> TYPE: DNA
<213> ORGANISM: Pyramimonas cordata

<400> SEQUENCE: 31

```
atgggaaagg gaggcaatgc tagcgctcct actgcgaaga aggaggtgtt gatcgagggg      60

aagttttacg atgtcaccga cttcaggcac cccggtggtt cgatcatcaa gtttctctcg     120

ggttctggtg ctgacgccac cgcttcctac cgcgagttcc acgttaggtc agcgaaggca     180

gacaagttct tgaagacgct gccctcccgc gaagccactc cccaggagct gaagcaggcg     240

gttgagttct ccaagctcaa cccgccctcc gcggagagtg cctctgctcc cctgaccgac     300

cttgccaagg tggaagcgct gaacaaggac ttcgaggctt tccgtgagca gctcattcag     360

gagggcttct ttaagcccaa tatcccgcat gtggtcaagc gcatcacgga agtcgtggcg     420

atgatggccg tagcctcctg gatgatggtg cagaccaacg ctcttgttgt gaccctcgga     480

gttctgatcc gcggcattgc acagggccgg tgcggttggc ttatgcacga gggcggccac     540

tatagtctta ctgggaagat ctccattgat aggcgtctgc aggagtcaat ttacggattc     600

ggctgtggaa tgtccggcgc ctggtggcgc aaccagcaca acaagcacca cgcaacccca     660
```

```
cagaagctgc agcatgacgt cgacctggag acccttcctc tgatggcttt caacaacgct    720

gttaccgata gacgcaaggt gaagcctggt agtctccagg ctctgtggct caagtaccag    780

gccttcctct tcttccccgt gacctccctt ctggtcggcc tcggttggac caccgtcctc    840

caccccaggc acagcttgcg caccaagcac tatttcgagc tgctctgcat ggctgctcgt    900

tacgcgagtt tcgctgctct tttcgctccc aagtacggac ttgcaggagc tgccgggctc    960

tacctcgcca ccttcgctgt cgggtgcaac tatattttca tcaacttctc ggtctctcac   1020

actcacctgc ccgtgagcgg tgcgagcgag tacctgcatt gggtcgtgta ttcggccatc   1080

cacaccacta acatcaaatc cagcatgctg tgcgattggt ggatgtcatt cctcaacttc   1140

cagatcgagc atcacctgtt cccttcaatg ccccagttcc gccacaagat tatctccccg   1200

cgtgtaaagg ccttgtttga gaagcacggt cttgtgtatg atgtgcgccc ctattggggg   1260

gccatggctg acaccttcaa gaacttgaat gacgttggca ctcacgcatc tcactccaag   1320

gcgcactag                                                           1329


<210> SEQ ID NO 32
<211> LENGTH: 442
<212> TYPE: PRT
<213> ORGANISM: Pyramimonas cordata

<400> SEQUENCE: 32

Met Gly Lys Gly Gly Asn Ala Ser Ala Pro Thr Ala Lys Lys Glu Val
1               5                   10                  15

Leu Ile Glu Gly Lys Phe Tyr Asp Val Thr Asp Phe Arg His Pro Gly
            20                  25                  30

Gly Ser Ile Ile Lys Phe Leu Ser Gly Ser Gly Ala Asp Ala Thr Ala
        35                  40                  45

Ser Tyr Arg Glu Phe His Val Arg Ser Ala Lys Ala Asp Lys Phe Leu
    50                  55                  60

Lys Thr Leu Pro Ser Arg Glu Ala Thr Pro Gln Glu Leu Lys Gln Ala
65                  70                  75                  80

Val Glu Phe Ser Lys Leu Asn Pro Pro Ser Ala Glu Ser Ala Ser Ala
                85                  90                  95

Pro Leu Thr Asp Leu Ala Lys Val Glu Ala Leu Asn Lys Asp Phe Glu
            100                 105                 110

Ala Phe Arg Glu Gln Leu Ile Gln Glu Gly Phe Phe Lys Pro Asn Ile
        115                 120                 125

Pro His Val Val Lys Arg Ile Thr Glu Val Val Ala Met Met Ala Val
    130                 135                 140

Ala Ser Trp Met Met Val Gln Thr Asn Ala Leu Val Val Thr Leu Gly
145                 150                 155                 160

Val Leu Ile Arg Gly Ile Ala Gln Gly Arg Cys Gly Trp Leu Met His
                165                 170                 175

Glu Gly Gly His Tyr Ser Leu Thr Gly Lys Ile Ser Ile Asp Arg Arg
            180                 185                 190

Leu Gln Glu Ser Ile Tyr Gly Phe Gly Cys Gly Met Ser Gly Ala Trp
        195                 200                 205

Trp Arg Asn Gln His Asn Lys His His Ala Thr Pro Gln Lys Leu Gln
    210                 215                 220

His Asp Val Asp Leu Glu Thr Leu Pro Leu Met Ala Phe Asn Asn Ala
225                 230                 235                 240

Val Thr Asp Arg Arg Lys Val Lys Pro Gly Ser Leu Gln Ala Leu Trp
```

```
                245                 250                 255

Leu Lys Tyr Gln Ala Phe Leu Phe Phe Pro Val Thr Ser Leu Leu Val
            260                 265                 270

Gly Leu Gly Trp Thr Thr Val Leu His Pro Arg His Ser Leu Arg Thr
        275                 280                 285

Lys His Tyr Phe Glu Leu Leu Cys Met Ala Ala Arg Tyr Ala Ser Phe
    290                 295                 300

Ala Ala Leu Phe Ala Pro Lys Tyr Gly Leu Ala Gly Ala Ala Gly Leu
305                 310                 315                 320

Tyr Leu Ala Thr Phe Ala Val Gly Cys Asn Tyr Ile Phe Ile Asn Phe
                325                 330                 335

Ser Val Ser His Thr His Leu Pro Val Ser Gly Ala Ser Glu Tyr Leu
            340                 345                 350

His Trp Val Val Tyr Ser Ala Ile His Thr Thr Asn Ile Lys Ser Ser
        355                 360                 365

Met Leu Cys Asp Trp Trp Met Ser Phe Leu Asn Phe Gln Ile Glu His
    370                 375                 380

His Leu Phe Pro Ser Met Pro Gln Phe Arg His Lys Ile Ile Ser Pro
385                 390                 395                 400

Arg Val Lys Ala Leu Phe Glu Lys His Gly Leu Val Tyr Asp Val Arg
                405                 410                 415

Pro Tyr Trp Gly Ala Met Ala Asp Thr Phe Lys Asn Leu Asn Asp Val
            420                 425                 430

Gly Thr His Ala Ser His Ser Lys Ala His
        435                 440
```

<210> SEQ ID NO 33
<211> LENGTH: 804
<212> TYPE: DNA
<213> ORGANISM: Pyramimonas cordata

<400> SEQUENCE: 33

```
atggcgtcta ttgcgattcc ggctgcgctg gcagggactc ttggttatgt gacgtacaat      60

gtcgcaaacc cagatattcc tgcatccgag aaggtgcctg cttactttat gcaggtcgag     120

tattgggggc caacgattgg gaccatcggt tatcttctgt tcatctactt tggtaaacgg     180

attatgcaaa acaggagcca gccgtttggc ctgaagaacg ctatgctggt gtacaacttc     240

tatcagactt tcttcaactc gtactgcata tacctttttg tcacgtcgca ccgcgctcag     300

gggctgaaag tttggggaaa catccccgat atgactgcca acagctgggg gatctcacag     360

gtgatctggc tgcactacaa caacaagtac gttgagctgc tggacacgtt cttcatggtc     420

atgcgcaaga agtttgacca gctttcgttc ctgcacattt accatcatac cctgttgatc     480

tggtcttggt tcgtggtgat gaaattggag cccgttgggg actgctactt tggctctagc     540

gtcaacacgt ttgtgcacgt cattatgtac tcgtactatg gccttgccgc gctcggggtg     600

aattgcttct ggaagaagta cattacgcag attcagatgc tgcagttctg tatctgcgct     660

tcgcactcga tttataccgc ctatgtgcag aacaccgcgt tctggttgcc ttacttgcag     720

ctgtgggtga tggtgaacat gttcgtgttg ttcgccaact tctatcgcaa gcgctacaag     780

agcaagggtg ccaagaagca gtaa                                            804
```

<210> SEQ ID NO 34
<211> LENGTH: 807
<212> TYPE: DNA
<213> ORGANISM: Artificial Sequence
<220> FEATURE:
<223> OTHER INFORMATION: Codon-optimized open reading frame for
expression of Pyramimonas cordata 5-elongase in plants (version 1)

<400> SEQUENCE: 34

```
atggcctcta tcgctatccc tgctgctctt gctggaactc ttggatacgt tacctacaat     60

gtggctaacc ctgatatccc agcttctgag aaagttcctg cttacttcat gcaggttgag    120

tactggggac ctactatcgg aactattgga tacctcctct tcatctactt cggaaagcgt    180

atcatgcaga acagatctca acctttcgga ctcaagaacg ctatgctcgt ttacaacttc    240

taccagacct tcttcaacag ctactgcatc tacctttcg ttacttctca tagggctcag     300

ggacttaagg tttggggaaa catccctgat atgactgcta actcttgggg aatctctcag    360

gttatctggc ttcactacaa caacaagtac gttgagcttc tcgacacctt cttcatggtg    420

atgaggaaga agttcgacca gctttctttc cttcacatct accaccacac tcttctcatc    480

tggtcatggt tcgttgttat gaagcttgag cctgttggag attgctactt cggatcttct    540

gttaacacct tcgtgcacgt gatcatgtac tcttactacg gacttgctgc tcttggagtt    600

aactgtttct ggaagaagta catcacccag atccagatgc ttcagttctg tatctgtgct    660

tctcactcta tctacaccgc ttacgttcag aataccgctt tctggcttcc ttaccttcaa    720

ctctgggtta tggtgaacat gttcgttctc ttcgccaact tctaccgtaa gaggtacaag    780

tctaagggtg ctaagaagca gtgataa                                        807
```

<210> SEQ ID NO 35
<211> LENGTH: 867
<212> TYPE: DNA
<213> ORGANISM: Artificial Sequence
<220> FEATURE:
<223> OTHER INFORMATION: Codon-optimized open reading frame for
expression of Pyramimonas cordata 5-elongase in plants (version 2)

<400> SEQUENCE: 35

```
atggaatttg ctcaacctct cgttgctatg gctcaagagc agtacgctgc tatcgatgct     60

gttgttgctc ctgctatctt ctctgctacc gactctattg gatggggact caagcctatc    120

tcttctgcta ctaaggatct ccctctcgtt gaatctccta cccctcttat cctttctctc    180

ctcgcttact tcgctatcgt tggttctgga ctcgtttacc gtaaagtgtt ccctagaacc    240

gttaagggac aggatccttt ccttctcaag gctcttatgc tcgctcacaa cgttttcctt    300

atcggactca gcctttacat gtgcctcaag ctcgtttacg aggcttacgt gaacaagtac    360

tccttctggg gaaacgctta caaccctgct caaaccgaga tggctaaggt gatctggatc    420

ttctacgtgt ccaagatcta cgagttcatg gacaccttca tcatgcttct caagggaaac    480

gttaaccagg tttccttcct ccatgtttac caccacggat ctatctctgg aatctggtgg    540

atgatcactt atgctgctcc aggtggagat gcttacttct ctgctgctct caactcttgg    600

gttcatgtgt gcatgtacac ctactacttc atggctgctg ttcttcctaa ggacgaaaag    660

accaagagaa agtacctttg gtggggaaga taccttaccc agatgcaaat gttccagttc    720

ttcatgaacc ttctccaggc tgtttacctc ctctactctt cttctcctta ccctaagttc    780

attgctcaac tcctcgttgt ttacatggtt accctcctca tgcttttcgg aaacttctac    840

tacatgaagc accacgcttc taagtga                                        867
```

<210> SEQ ID NO 36
<211> LENGTH: 807
<212> TYPE: DNA

```
<213> ORGANISM: Artificial Sequence
<220> FEATURE:
<223> OTHER INFORMATION: Codon-optimized open reading frame for
      expression of Pyramimonas cordata 5-elongase in plants (version 3)

<400> SEQUENCE: 36

atggcttcta tcgctatccc tgctgctctt gctggaactc ttggatacgt gacctacaac     60

gtggctaacc ctgatattcc tgcttctgag aaggttccag cttacttcat gcaagtggag    120

tactggggac ctactatcgg aactatcggt tacctcctct tcatctactt cggaaagcgt    180

atcatgcaaa acagaagcca gcctttcgga cttaagaacg ctatgctcgt gtacaacttc    240

taccagacct tcttcaacag ctactgcatc tacctcttcg ttacctctca tagggctcag    300

ggacttaaag tttggggaaa catccctgat atgaccgcta actcttgggg aatctctcag    360

gttatctggc tccactacaa caacaagtac gtggagcttc tcgatacctt cttcatggtg    420

atgaggaaga agttcgacca gctttctttc cttcacatct accaccacac tcttctcatc    480

tggtcatggt tcgtggttat gaagctcgag cctgttggag attgctactt cggatctagc    540

gttaacacct tcgtgcacgt gatcatgtac tcttactacg gacttgctgc tcttggagtt    600

aactgcttct ggaagaagta catcacccag atccagatgc ttcagttctg tatctgcgct    660

tctcactcta tctacaccgc ttacgttcag aacactgctt tctggcttcc ttaccttcag    720

ctctgggtga tggttaacat gttcgtgctc ttcgctaact tctaccgtaa aaggtacaag    780

agcaagggtg ctaagaagca gtgataa                                         807


<210> SEQ ID NO 37
<211> LENGTH: 267
<212> TYPE: PRT
<213> ORGANISM: Pyramimonas cordata

<400> SEQUENCE: 37

Met Ala Ser Ile Ala Ile Pro Ala Ala Leu Ala Gly Thr Leu Gly Tyr
1               5                   10                  15

Val Thr Tyr Asn Val Ala Asn Pro Asp Ile Pro Ala Ser Glu Lys Val
            20                  25                  30

Pro Ala Tyr Phe Met Gln Val Glu Tyr Trp Gly Pro Thr Ile Gly Thr
        35                  40                  45

Ile Gly Tyr Leu Leu Phe Ile Tyr Phe Gly Lys Arg Ile Met Gln Asn
    50                  55                  60

Arg Ser Gln Pro Phe Gly Leu Lys Asn Ala Met Leu Val Tyr Asn Phe
65                  70                  75                  80

Tyr Gln Thr Phe Phe Asn Ser Tyr Cys Ile Tyr Leu Phe Val Thr Ser
                85                  90                  95

His Arg Ala Gln Gly Leu Lys Val Trp Gly Asn Ile Pro Asp Met Thr
            100                 105                 110

Ala Asn Ser Trp Gly Ile Ser Gln Val Ile Trp Leu His Tyr Asn Asn
        115                 120                 125

Lys Tyr Val Glu Leu Leu Asp Thr Phe Phe Met Val Met Arg Lys Lys
    130                 135                 140

Phe Asp Gln Leu Ser Phe Leu His Ile Tyr His His Thr Leu Leu Ile
145                 150                 155                 160

Trp Ser Trp Phe Val Val Met Lys Leu Glu Pro Val Gly Asp Cys Tyr
                165                 170                 175

Phe Gly Ser Ser Val Asn Thr Phe Val His Val Ile Met Tyr Ser Tyr
            180                 185                 190
```

-continued

```
Tyr Gly Leu Ala Ala Leu Gly Val Asn Cys Phe Trp Lys Lys Tyr Ile
        195                 200                 205

Thr Gln Ile Gln Met Leu Gln Phe Cys Ile Cys Ala Ser His Ser Ile
    210                 215                 220

Tyr Thr Ala Tyr Val Gln Asn Thr Ala Phe Trp Leu Pro Tyr Leu Gln
225                 230                 235                 240

Leu Trp Val Met Val Asn Met Phe Val Leu Phe Ala Asn Phe Tyr Arg
                245                 250                 255

Lys Arg Tyr Lys Ser Lys Gly Ala Lys Lys Gln
            260                 265


<210> SEQ ID NO 38
<211> LENGTH: 1344
<212> TYPE: DNA
<213> ORGANISM: Pavlova salina

<400> SEQUENCE: 38

atgcctccga gcgcggcgaa gcagatgggc gcgagcacgg gcgtgcatgc gggcgtcaca     60

gattcgtcgg ccttcacgcg caaggatgtc gccgacaggc cggacctcac gatcgtgggt    120

gacagcgtgt acgatgcgaa ggcgttccgc tccgagcatc cgggtggcgc gcactttgtg    180

tcgctgttcg gcgggcgcga tgccacggag gcgttcatgg agtaccaccg gcgcgcctgg    240

cccaagtcgc gcatgtcgcg cttccacgtc ggctctctgg catcgaccga ggagcccgtc    300

gccgccgatg agggctacct ccagctgtgc gctcgcatcg ccaagatggt gccgtcggtc    360

agcagcgggt tcgcgccggc gtcgtactgg gtgaaggccg ggctgatcct cggctccgcg    420

atcgcgctcg aggcgtacat gctgtacgcg ggcaagcgcc tgctcccgtc gatcgtgctc    480

gggtggctgt ttgcgctgat tggcctgaac atccagcacg atgccaacca cggcgcgctc    540

tccaagtcgg cctcggtcaa cctggcgctc gggttgtgcc aggactggat cggcgggagc    600

atgatcctct ggctgcagga gcacgttgtc atgcaccact tgcacaccaa cgacgttgac    660

aaggacccgg accagaaggc gcacggcgcc ctgcggctca agccgaccga cgcgtggagc    720

ccgatgcact ggctgcagca cctctacctg ctgcctgggg agacgatgta cgccttcaag    780

ctgctgtttc tcgacatcag cgagctggtg atgtggcggt gggagggcga gcccatcagc    840

aagctggccg ggtacctctt catgccctcg ctgctcctca agctcacctt ctgggcgcgc    900

tttgtcgcgc tgccgctgta cctcgcgccc agcgtgcaca cggcggtgtg catcgcggcg    960

acggtaatga cggggagctt ctacctcgcc ttcttcttct tcatctcgca caacttcgag   1020

ggcgtggcga gcgtcggacc ggacggcagc atcaccagca tgacgcgcgg cgcatccttc   1080

ctcaagcggc aggccgagac ctcgtccaac gtgggcggcc cgctgctcgc cacgctcaac   1140

ggcggcctca actaccaaat cgagcaccac ctcttcccca gggtgcacca cggcttctac   1200

cctcgcctcg cgccgttggt caaggcggag ctcgaggcgc gcggcattga gtacaagcac   1260

taccccacca tatggagcaa cctggcatcc acgctgaggc acatgtacgc gctcggccgc   1320

aggccgcgca gcaaggcgga gtga                                          1344


<210> SEQ ID NO 39
<211> LENGTH: 1347
<212> TYPE: DNA
<213> ORGANISM: Artificial Sequence
<220> FEATURE:
<223> OTHER INFORMATION: Codon-optimized open reading frame for
      expression of Pavlova salina 4-desaturase in plants (version 1)

<400> SEQUENCE: 39
```

```
atgccaccta gcgctgctaa gcaaatggga gcttctactg gtgttcatgc tggtgttact     60
gactcttctg ctttcaccag aaaggatgtt gctgatagac ctgatctcac catcgttgga    120
gattctgttt acgatgctaa ggctttcaga tctgagcatc ctggtggtgc tcatttcgtt    180
tctttgttcg gaggaagaga tgctactgag gctttcatgg aataccatag aagggcttgg    240
cctaagtcta gaatgtctag attccacgtt ggatctcttg cttctactga ggaacctgtt    300
gctgctgatg agggatacct tcaactttgt gctaggatcg ctaagatggt gccttctgtt    360
tcttctggat tcgctcctgc ttcttactgg gttaaggctg gacttatcct tggatctgct    420
atcgctcttg aggcttacat gctttacgct ggaaagagac ttctcccttc tatcgttctt    480
ggatggcttt tcgctcttat cggtcttaac atccagcatg atgctaacca tggtgctttg    540
tctaagtctg cttctgttaa ccttgctctt ggactttgtc aggattggat cggaggatct    600
atgatccttt ggcttcaaga gcatgttgtt atgcaccacc tccacactaa cgatgttgat    660
aaggatcctg atcaaaaggc tcacggtgct cttagactca agcctactga tgcttggtca    720
cctatgcatt ggcttcagca tctttacctt ttgcctggtg agactatgta cgctttcaag    780
cttttgttcc tcgacatctc tgagcttgtt atgtggcgtt gggagggtga gcctatctct    840
aagcttgctg gatacctctt tatgccttct ttgcttctca agcttacctt ctgggctaga    900
ttcgttgctt tgcctcttta ccttgctcct tctgttcata ctgctgtgtg tatcgctgct    960
actgttatga ctggatcttt ctacctcgct ttcttcttct tcatctccca caacttcgag   1020
ggtgttgctt ctgttggacc tgatggatct atcacttcta tgactagagg tgctagcttc   1080
cttaagagac aagctgagac ttcttctaac gttggaggac ctcttcttgc tactcttaac   1140
ggtggactca actaccaaat tgagcatcac ttgttcccta gagttcacca tggattctac   1200
cctagacttg ctcctcttgt taaggctgag cttgaggcta gaggaatcga gtacaagcac   1260
taccctacta tctggtctaa ccttgcttct accctcagac atatgtacgc tcttggaaga   1320
aggcctagat ctaaggctga gtaatga                                       1347
```

<210> SEQ ID NO 40
<211> LENGTH: 1347
<212> TYPE: DNA
<213> ORGANISM: Artificial Sequence
<220> FEATURE:
<223> OTHER INFORMATION: Codon-optimized open reading frame for
expression of Pavlova salina 4-desaturase in plants (version 2)

<400> SEQUENCE: 40

```
atgcctccat ctgctgctaa acagatggga gcttctactg gtgttcacgc tggtgttacc     60
gattcttctg ctttcaccag aaaggatgtg gctgatagac ctgatcttac catcgttggt    120
gactctgtgt acgatgctaa ggctttcaga tctgagcatc ctggtggtgc tcatttcgtt    180
tcactcttcg gaggaagaga tgctactgag gctttcatgg aataccacag aagagcttgg    240
cctaagtcta ggatgtctag gttccatgtt ggatctcttg cttctaccga ggaacctgtt    300
gctgctgatg agggatacct tcagctttgt gctaggatcg ctaagatggt gccttctgtg    360
tcatctggat tcgctccagc ttcttactgg gttaaggctg gacttatcct cggatctgct    420
atcgctcttg aggcttacat gctctacgct ggaaagagac ttctcccttc tatcgttctt    480
ggatggctct tcgctcttat cggacttaac atccagcatg acgctaacca tggtgctttg    540
tctaagtctg ctagcgttaa ccttgctctt ggactttgtc aggattggat cggaggatct    600
atgatccttt ggctccaaga gcatgttgtt atgcaccacc tccacaccaa cgatgttgat    660
```

aaggaccctg atcaaaaggc tcatggtgct cttagactca agcctaccga tgcttggtca 720
cctatgcatt ggcttcagca cctttacctt ctccctggtg aaactatgta cgctttcaag 780
ctcctcttcc tcgatatctc tgagcttgtg atgtggagat gggagggtga acctatctct 840
aagctcgctg gatacctctt catgccttct cttctcctca agcttacctt ctgggctaga 900
ttcgttgctc ttcctcttta cctcgctcct tctgttcata ctgctgtgtg tatcgctgct 960
actgttatga ccggaagctt ctaccttgct ttcttcttct tcatcagcca caacttcgag 1020
ggtgttgctt ctgttggacc tgatggatct atcacctcta tgaccagggg agcttctttc 1080
cttaagaggc aggctgagac ttcttctaat gtgggaggac ctcttcttgc tactcttaac 1140
ggtggactca actaccaaat cgagcaccac cttttcccta gagttcacca cggattctac 1200
cctagacttg ctcctcttgt gaaggctgaa cttgaggcta gaggaatcga gtacaagcac 1260
taccctacca tctggtctaa cctcgcttct accctcagac atatgtacgc tcttggaaga 1320
aggcctagat ctaaggctga gtgatga 1347

<210> SEQ ID NO 41
<211> LENGTH: 447
<212> TYPE: PRT
<213> ORGANISM: Pavlova salina

<400> SEQUENCE: 41

Met Pro Pro Ser Ala Ala Lys Gln Met Gly Ala Ser Thr Gly Val His
1               5                   10                  15

Ala Gly Val Thr Asp Ser Ser Ala Phe Thr Arg Lys Asp Val Ala Asp
            20                  25                  30

Arg Pro Asp Leu Thr Ile Val Gly Asp Ser Val Tyr Asp Ala Lys Ala
        35                  40                  45

Phe Arg Ser Glu His Pro Gly Gly Ala His Phe Val Ser Leu Phe Gly
    50                  55                  60

Gly Arg Asp Ala Thr Glu Ala Phe Met Glu Tyr His Arg Arg Ala Trp
65                  70                  75                  80

Pro Lys Ser Arg Met Ser Arg Phe His Val Gly Ser Leu Ala Ser Thr
                85                  90                  95

Glu Glu Pro Val Ala Ala Asp Glu Gly Tyr Leu Gln Leu Cys Ala Arg
            100                 105                 110

Ile Ala Lys Met Val Pro Ser Val Ser Ser Gly Phe Ala Pro Ala Ser
        115                 120                 125

Tyr Trp Val Lys Ala Gly Leu Ile Leu Gly Ser Ala Ile Ala Leu Glu
    130                 135                 140

Ala Tyr Met Leu Tyr Ala Gly Lys Arg Leu Leu Pro Ser Ile Val Leu
145                 150                 155                 160

Gly Trp Leu Phe Ala Leu Ile Gly Leu Asn Ile Gln His Asp Ala Asn
                165                 170                 175

His Gly Ala Leu Ser Lys Ser Ala Ser Val Asn Leu Ala Leu Gly Leu
            180                 185                 190

Cys Gln Asp Trp Ile Gly Gly Ser Met Ile Leu Trp Leu Gln Glu His
        195                 200                 205

Val Val Met His His Leu His Thr Asn Asp Val Asp Lys Asp Pro Asp
    210                 215                 220

Gln Lys Ala His Gly Ala Leu Arg Leu Lys Pro Thr Asp Ala Trp Ser
225                 230                 235                 240

Pro Met His Trp Leu Gln His Leu Tyr Leu Leu Pro Gly Glu Thr Met

```
                245                 250                 255

Tyr Ala Phe Lys Leu Leu Phe Leu Asp Ile Ser Glu Leu Val Met Trp
            260                 265                 270

Arg Trp Glu Gly Glu Pro Ile Ser Lys Leu Ala Gly Tyr Leu Phe Met
        275                 280                 285

Pro Ser Leu Leu Leu Lys Leu Thr Phe Trp Ala Arg Phe Val Ala Leu
    290                 295                 300

Pro Leu Tyr Leu Ala Pro Ser Val His Thr Ala Val Cys Ile Ala Ala
305                 310                 315                 320

Thr Val Met Thr Gly Ser Phe Tyr Leu Ala Phe Phe Phe Phe Ile Ser
                325                 330                 335

His Asn Phe Glu Gly Val Ala Ser Val Gly Pro Asp Gly Ser Ile Thr
            340                 345                 350

Ser Met Thr Arg Gly Ala Ser Phe Leu Lys Arg Gln Ala Glu Thr Ser
        355                 360                 365

Ser Asn Val Gly Gly Pro Leu Leu Ala Thr Leu Asn Gly Gly Leu Asn
    370                 375                 380

Tyr Gln Ile Glu His His Leu Phe Pro Arg Val His His Gly Phe Tyr
385                 390                 395                 400

Pro Arg Leu Ala Pro Leu Val Lys Ala Glu Leu Glu Ala Arg Gly Ile
                405                 410                 415

Glu Tyr Lys His Tyr Pro Thr Ile Trp Ser Asn Leu Ala Ser Thr Leu
            420                 425                 430

Arg His Met Tyr Ala Leu Gly Arg Arg Pro Arg Ser Lys Ala Glu
        435                 440                 445
```

<210> SEQ ID NO 42
<211> LENGTH: 792
<212> TYPE: DNA
<213> ORGANISM: Isochrysis galbana

<400> SEQUENCE: 42

```
atggccctcg caaacgacgc gggagagcgc atctgggcgg ctgtgaccga cccggaaatc      60

ctcattggca ccttctcgta cttgctactc aaaccgctgc tccgcaattc cgggctggtg     120

gatgagaaga agggcgcata caggacgtcc atgatctggt acaacgttct gctggcgctc     180

ttctctgcgc tgagcttcta cgtgacggcg accgccctcg gctgggacta tggtacgggc     240

gcgtggctgc gcaggcaaac cggcgacaca ccgcagccgc tcttccagtg cccgtccccg     300

gtttgggact cgaagctctt cacatggacc gccaaggcat tctattactc caagtacgtg     360

gagtacctcg acacggcctg gctggtgctc aagggcaaga gggtctcctt tctccaggcc     420

ttccaccact ttggcgcgcc gtgggatgtg tacctcggca ttcggctgca caacgagggc     480

gtatggatct tcatgttttt caactcgttc attcacacca tcatgtacac ctactacggc     540

ctcaccgccg ccgggtataa gttcaaggcc aagccgctca tcaccgcgat gcagatctgc     600

cagttcgtgg gcggcttcct gttggtctgg gactacatca acgtcccctg cttcaactcg     660

gacaaaggga agttgttcag ctgggctttc aactatgcat acgtcggctc ggtcttcttg     720

ctcttctgcc actttttcta ccaggacaac ttggcaacga agaaatcggc caaggcgggc     780

aagcagctct ag                                                         792
```

<210> SEQ ID NO 43
<211> LENGTH: 263
<212> TYPE: PRT
<213> ORGANISM: Isochrysis galbana

<400> SEQUENCE: 43

```
Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260
```

<210> SEQ ID NO 44
<211> LENGTH: 801
<212> TYPE: DNA
<213> ORGANISM: Emiliania huxleyi

<400> SEQUENCE: 44

```
atgctcgatc gcgcctcgtc cgacgcggcc atctggtctg cggtgtccga tccggaaatc      60

ctgatcggca ctttctccta cctgctgctc aagccgctgc tacgcaactc agggctcgtg     120

gacgagcgga aaggcgccta ccggacctcg atgatctggt acaacgtggt gctcgcgctc     180

ttctccgcga cgagcttcta cgtgactgcg accgcgctcg ggtgggacaa gggcaccggc     240

gagtggctcc gcagtctcac gggcgacagc ccgcagcagc tgtggcaatg cccgtcgagg     300

gtatgggact ccaagctgtt cctgtggacg gccaaggcct tctactactc aaagtacgtg     360

gagtacctcg acacggcgtg gctcgtcctc aaggggaaga aggtctcctt cctgcagggc     420

ttccaccact ttggcgcgcc gtgggacgtg tacctgggca ttcggctgaa gaacgagggc     480

gtgtggatct tcatgttctt caactcgttc atccacacgg tcatgtacac gtactacggc     540
```

-continued

```
ctcaccgccg cgggctacaa gatccgcggc aagccgatca tcaccgcgat gcaaataagc    600

cagttcgtcg gcggctttgt cctagtgtgg gactacatca acgtgccgtg cttccacgcc    660

gacgccgggc aggtcttcag ctgggtcttt aactatgctt acgtcggctc cgtctttctg    720

ctgttctgcc acttcttcta catggacaac atcgcgaagg ccaaggccaa gaaggccgtc    780

gctacccgca aggcgctgtg a                                              801
```

```
<210> SEQ ID NO 45
<211> LENGTH: 801
<212> TYPE: DNA
<213> ORGANISM: Artificial Sequence
<220> FEATURE:
<223> OTHER INFORMATION: Codon-optimized open reading frame for
      expression of Emiliania huxleyi 9-elongase in plants

<400> SEQUENCE: 45

atgcttgata gagcttcatc tgatgctgct atttggagcg ctgtttctga tcctgagatc     60

cttatcggaa ccttctctta ccttttgctt aagcctctcc tcagaaactc tggacttgtg    120

gatgagagaa agggagctta ccgtacttct atgatctggt acaacgttgt tcttgctctt    180

ttctctgcta cctctttcta cgttactgct actgctcttg gatgggataa gggaactggt    240

gagtggctta gatctcttac tggtgattct cctcaacaac tttggcagtg cccttctaga    300

gtttgggaca gcaaactctt cttgtggact gctaaagcct tctactactc caagtacgtt    360

gagtaccttg atactgcttg gcttgttctc aagggaaaga aggtttcatt cctccaggga    420

ttccatcatt tcggtgctcc atgggatgtt taccttggaa tcaggcttaa gaacgaggga    480

gtttggatct tcatgttctt caacagcttc atccacactg ttatgtacac ttactacgga    540

cttactgctg ctggatacaa gatcagagga aagcctatca tcaccgctat gcaaatctct    600

caattcgttg gtggattcgt tcttgtgtgg gactacatca acgttccttg tttccatgct    660

gatgctggac aagttttctc ttgggtgttc aactacgctt atgtgggatc tgttttcctt    720

cttttctgcc acttcttcta catggacaac attgctaagg ctaaggctaa aaaggctgtt    780

gctaccagaa aggctctttg a                                              801


<210> SEQ ID NO 46
<211> LENGTH: 266
<212> TYPE: PRT
<213> ORGANISM: Emiliania huxleyi

<400> SEQUENCE: 46

Met Leu Asp Arg Ala Ser Ser Asp Ala Ala Ile Trp Ser Ala Val Ser
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Arg Lys Gly Ala Tyr Arg
        35                  40                  45

Thr Ser Met Ile Trp Tyr Asn Val Val Leu Ala Leu Phe Ser Ala Thr
    50                  55                  60

Ser Phe Tyr Val Thr Ala Thr Ala Leu Gly Trp Asp Lys Gly Thr Gly
65                  70                  75                  80

Glu Trp Leu Arg Ser Leu Thr Gly Asp Ser Pro Gln Gln Leu Trp Gln
                85                  90                  95

Cys Pro Ser Arg Val Trp Asp Ser Lys Leu Phe Leu Trp Thr Ala Lys
            100                 105                 110
```

```
Ala Phe Tyr Tyr Ser Lys Tyr Val Glu Tyr Leu Asp Thr Ala Trp Leu
        115                 120                 125

Val Leu Lys Gly Lys Lys Val Ser Phe Leu Gln Gly Phe His His Phe
    130                 135                 140

Gly Ala Pro Trp Asp Val Tyr Leu Gly Ile Arg Leu Lys Asn Glu Gly
145                 150                 155                 160

Val Trp Ile Phe Met Phe Phe Asn Ser Phe Ile His Thr Val Met Tyr
                165                 170                 175

Thr Tyr Tyr Gly Leu Thr Ala Ala Gly Tyr Lys Ile Arg Gly Lys Pro
            180                 185                 190

Ile Ile Thr Ala Met Gln Ile Ser Gln Phe Val Gly Gly Phe Val Leu
        195                 200                 205

Val Trp Asp Tyr Ile Asn Val Pro Cys Phe His Ala Asp Ala Gly Gln
    210                 215                 220

Val Phe Ser Trp Val Phe Asn Tyr Ala Tyr Val Gly Ser Val Phe Leu
225                 230                 235                 240

Leu Phe Cys His Phe Phe Tyr Met Asp Asn Ile Ala Lys Ala Lys Ala
                245                 250                 255

Lys Lys Ala Val Ala Thr Arg Lys Ala Leu
            260                 265
```

<210> SEQ ID NO 47
<211> LENGTH: 819
<212> TYPE: DNA
<213> ORGANISM: Pavlova pinguis

<400> SEQUENCE: 47

```
atggttgcgc cacccatcac gctcgagtgg ctgctttcgc cgaagctcaa ggatgcagtg     60

ttcggtgggg aggtgctcta cttctccatt gcctacctgt ttcttgcgcc cattttgaag    120

cgcaccccgt tggtggacac gcggaagggc gcgtataaga gtggtatgat cgcgtacaac    180

gtgatcatgt gcgtgttctc gctggtgtgc ttcatctgcc agctcgcagc cctgggctat    240

gacatgggct acttgcagtg ggtgcgtgac ctcacagggg acgagattgt cccccctctac    300

caggacgtgt ccccgtcccc cgccttctcc aacaagctct tcaagtattc gtctattgcc    360

ttccactact ccaagtatgt tgagtacatg gacaccgcat ggctggtgat gaagggcaag    420

cccgtgtcct tgctccaggg cttccaccac tttggcgccg cctgggacac ctactttggc    480

atcaccttcc agaacgaggg catctacgtg ttcgtggtgc tcaacgcctt catccacacg    540

atcatgtacg catactacgc ggccactgcg gcgggtctca agttctcact gaagttcgtc    600

atcacgctca tgcagatcac ccaattcaac gtgggcttcg taatggtgta tcactacatc    660

accctggagt acttccgcaa ctcaccggag ctcgtcttct cctacctttt caactatgcg    720

tacgtctgca cggttctcct cctcttcatg cagttcttct acatggacaa ctttggcaag    780

aagaaggccg ctgccgccgc gggcaagaag aagaagtag                            819
```

<210> SEQ ID NO 48
<211> LENGTH: 272
<212> TYPE: PRT
<213> ORGANISM: Pavlova pinguis

<400> SEQUENCE: 48

```
Met Val Ala Pro Pro Ile Thr Leu Glu Trp Leu Leu Ser Pro Lys Leu
1               5                   10                  15

Lys Asp Ala Val Phe Gly Gly Glu Val Leu Tyr Phe Ser Ile Ala Tyr
            20                  25                  30
```

```
Leu Phe Leu Ala Pro Ile Leu Lys Arg Thr Pro Leu Val Asp Thr Arg
        35                  40                  45

Lys Gly Ala Tyr Lys Ser Gly Met Ile Ala Tyr Asn Val Ile Met Cys
    50                  55                  60

Val Phe Ser Leu Val Cys Phe Ile Cys Gln Leu Ala Ala Leu Gly Tyr
65                  70                  75                  80

Asp Met Gly Tyr Leu Gln Trp Val Arg Asp Leu Thr Gly Asp Glu Ile
                85                  90                  95

Val Pro Leu Tyr Gln Asp Val Ser Pro Ser Pro Ala Phe Ser Asn Lys
            100                 105                 110

Leu Phe Lys Tyr Ser Ser Ile Ala Phe His Tyr Ser Lys Tyr Val Glu
        115                 120                 125

Tyr Met Asp Thr Ala Trp Leu Val Met Lys Gly Lys Pro Val Ser Leu
    130                 135                 140

Leu Gln Gly Phe His His Phe Gly Ala Ala Trp Asp Thr Tyr Phe Gly
145                 150                 155                 160

Ile Thr Phe Gln Asn Glu Gly Ile Tyr Val Phe Val Val Leu Asn Ala
                165                 170                 175

Phe Ile His Thr Ile Met Tyr Ala Tyr Tyr Ala Ala Thr Ala Ala Gly
            180                 185                 190

Leu Lys Phe Ser Leu Lys Phe Val Ile Thr Leu Met Gln Ile Thr Gln
        195                 200                 205

Phe Asn Val Gly Phe Val Met Val Tyr His Tyr Ile Thr Leu Glu Tyr
    210                 215                 220

Phe Arg Asn Ser Pro Glu Leu Val Phe Ser Tyr Leu Phe Asn Tyr Ala
225                 230                 235                 240

Tyr Val Cys Thr Val Leu Leu Leu Phe Met Gln Phe Phe Tyr Met Asp
                245                 250                 255

Asn Phe Gly Lys Lys Lys Ala Ala Ala Ala Ala Gly Lys Lys Lys Lys
            260                 265                 270


<210> SEQ ID NO 49
<211> LENGTH: 840
<212> TYPE: DNA
<213> ORGANISM: Pavlova salina

<400> SEQUENCE: 49

atggcgactg aagggatgcc ggcgataacg ctggactggc tgctctcgcc cgggctgaag     60

gatgccgtaa ttggcgggga ggtgctctac ttttcgcttg ggtatctgct gctcgagccc    120

atcctcaagc gctcaccgtt tgtggacaag cgcaagggcg cataccgcaa cggcatgatc    180

gcgtacaaca tcctcatgtg cggtttctcg ctggtatgct tcgtgtgcca gatggcggcg    240

ctcggccttg atcgcggcca cctgcagttt gtccgcgacc tcacgggcga cagcgtggtg    300

cagctctacc aggacgtgag cccatcccct gcattcgcga acaagctctt ccggtactca    360

gcggtggcgt tccactactc aaagtacgtg gagtacatgg acacagcgtg gcttgtgctg    420

aagggcaagc ccgtctcgtt cctgcagggc ttccaccact tcggcgccgc gtgggacacc    480

tactttggca tcacgtttca gaacgagggc acctacgtct ttgtgctgct caacgcattc    540

atccacacaa tcatgtacac ctactacggc gcgacggcag cgggcatcaa aatctcgatg    600

aagccgctga tcaccctcat gcagatcacg cagttcctgc tgggcttcgc gctcgtctac    660

ccgtacattg acctcggcta cttccgtgcg tcgcccgagc tcgtgtggag ctacctgttc    720

aactatgcgt acgtactcat ggtgctcttc ctcttcatgc gcttcttcta ccacgacaac    780
```

```
tttagcaagc acaagccaat ctcgcgcatc gactccagca accgcatgaa aaccgagtag    840


<210> SEQ ID NO 50
<211> LENGTH: 279
<212> TYPE: PRT
<213> ORGANISM: Pavlova salina

<400> SEQUENCE: 50

Met Ala Thr Glu Gly Met Pro Ala Ile Thr Leu Asp Trp Leu Leu Ser
1               5                   10                  15

Pro Gly Leu Lys Asp Ala Val Ile Gly Gly Glu Val Leu Tyr Phe Ser
            20                  25                  30

Leu Gly Tyr Leu Leu Leu Glu Pro Ile Leu Lys Arg Ser Pro Phe Val
        35                  40                  45

Asp Lys Arg Lys Gly Ala Tyr Arg Asn Gly Met Ile Ala Tyr Asn Ile
    50                  55                  60

Leu Met Cys Gly Phe Ser Leu Val Cys Phe Val Cys Gln Met Ala Ala
65                  70                  75                  80

Leu Gly Leu Asp Arg Gly His Leu Gln Phe Val Arg Asp Leu Thr Gly
                85                  90                  95

Asp Ser Val Val Gln Leu Tyr Gln Asp Val Ser Pro Ser Pro Ala Phe
            100                 105                 110

Ala Asn Lys Leu Phe Arg Tyr Ser Ala Val Ala Phe His Tyr Ser Lys
        115                 120                 125

Tyr Val Glu Tyr Met Asp Thr Ala Trp Leu Val Leu Lys Gly Lys Pro
    130                 135                 140

Val Ser Phe Leu Gln Gly Phe His His Phe Gly Ala Ala Trp Asp Thr
145                 150                 155                 160

Tyr Phe Gly Ile Thr Phe Gln Asn Glu Gly Thr Tyr Val Phe Val Leu
                165                 170                 175

Leu Asn Ala Phe Ile His Thr Ile Met Tyr Thr Tyr Tyr Gly Ala Thr
            180                 185                 190

Ala Ala Gly Ile Lys Ile Ser Met Lys Pro Leu Ile Thr Leu Met Gln
        195                 200                 205

Ile Thr Gln Phe Leu Leu Gly Phe Ala Leu Val Tyr Pro Tyr Ile Asp
    210                 215                 220

Leu Gly Tyr Phe Arg Ala Ser Pro Glu Leu Val Trp Ser Tyr Leu Phe
225                 230                 235                 240

Asn Tyr Ala Tyr Val Leu Met Val Leu Phe Leu Phe Met Arg Phe Phe
                245                 250                 255

Tyr His Asp Asn Phe Ser Lys His Lys Pro Ile Ser Arg Ile Asp Ser
            260                 265                 270

Ser Asn Arg Met Lys Thr Glu
        275


<210> SEQ ID NO 51
<211> LENGTH: 1284
<212> TYPE: DNA
<213> ORGANISM: Pavlova salina

<400> SEQUENCE: 51

atgggacgcg gcggagacag cagtgggcag gcgcatccgg cggcggagct ggcggtcccg     60

agcgaccgcg cggaggtgag caacgctgac agcaaagcgc tgcacatcgt gctgtatggc    120

aagcgcgtgg atgtgaccaa gttccaacgc acgcacccgg gtggtagcaa ggtcttccgg    180
```

-continued

```
atcttccagg accgcgatgc gacggagcag ttcgagtcct accactcgaa gcgcgcgatc    240

aagatgatgg agggcatgct caagaagtct gaggatgctc ccgccgacac gcccttgccc    300

tcccagtcac cgatggggaa ggacttcaag gcgatgatcg agcggcacgt tgcagcgggt    360

tactacgatc catgcccgct cgatgagctg ttcaagctca gcctcgtgct cctcccgacc    420

tttgcgggca tgtacatgct caaggcgggc gtcggctccc cgctctgcgg cgccctcatg    480

gtgagctttg gctggtacct cgatggctgg ctcgcgcacg actatctgca ccactccgtc    540

ttcaaggggt ccgtcgcacg caccgtcggg tggaacaacg cggcgggcta cttcctcggc    600

ttcgtgcagg ggtatgcggt cgagtggtgg cgcgcgcggc ataacacgca ccacgtgtgc    660

accaatgagg acggctcgga ccccgacatc aaaacggcgc cgctgctcat atacgtgcgc    720

aacaagccga gcatcgccaa gcgcctgaac gccttccagc gctaccagca gtactactat    780

gtgccggtga tggcaatcct cgacctgtac tggcggctcg agtcgatcgc ctacgtcgcg    840

atgcgcctgc cgaagatgct gccgcaggcc ctcgcactcg tcgcgcacta cgccatcgtc    900

gcgtgggtct ttgcgggcaa ctaccacctg ctcccgctcg tgacggttct gcgcgggttt    960

ggcactggga tcaccgtttt cgcgacgcac tacggtgagg acattctcga cgcggaccag   1020

gtgcgtcaca tgacgctcgt cgagcagacg gcactcacct cgcgcaacat ctcgggcggc   1080

tggctcgtga acgtgctcac cggcttcatc tcactgcaga cggagcacca cctgttcccg   1140

atgatgccaa ccggcaacct catgactatc cagcccgagg tgcgcgcctt cttcaagaag   1200

cacggacttg agtaccgcga gggcaacctc attgagtgcg tgcggcagaa catccgtgcg   1260

cttgcattcg agcacctgct ttga                                           1284


<210> SEQ ID NO 52
<211> LENGTH: 427
<212> TYPE: PRT
<213> ORGANISM: Pavlova salina

<400> SEQUENCE: 52

Met Gly Arg Gly Gly Asp Ser Ser Gly Gln Ala His Pro Ala Ala Glu
1               5                   10                  15

Leu Ala Val Pro Ser Asp Arg Ala Glu Val Ser Asn Ala Asp Ser Lys
            20                  25                  30

Ala Leu His Ile Val Leu Tyr Gly Lys Arg Val Asp Val Thr Lys Phe
        35                  40                  45

Gln Arg Thr His Pro Gly Gly Ser Lys Val Phe Arg Ile Phe Gln Asp
    50                  55                  60

Arg Asp Ala Thr Glu Gln Phe Glu Ser Tyr His Ser Lys Arg Ala Ile
65                  70                  75                  80

Lys Met Met Glu Gly Met Leu Lys Lys Ser Glu Asp Ala Pro Ala Asp
                85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
        115                 120                 125

Glu Leu Phe Lys Leu Ser Leu Val Leu Leu Pro Thr Phe Ala Gly Met
    130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                165                 170                 175
```

```
His His Ser Val Phe Lys Gly Ser Val Ala Arg Thr Val Gly Trp Asn
            180                 185                 190

Asn Ala Ala Gly Tyr Phe Leu Gly Phe Val Gln Gly Tyr Ala Val Glu
        195                 200                 205

Trp Trp Arg Ala Arg His Asn Thr His His Val Cys Thr Asn Glu Asp
    210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
                245                 250                 255

Gln Tyr Tyr Tyr Val Pro Val Met Ala Ile Leu Asp Leu Tyr Trp Arg
            260                 265                 270

Leu Glu Ser Ile Ala Tyr Val Ala Met Arg Leu Pro Lys Met Leu Pro
        275                 280                 285

Gln Ala Leu Ala Leu Val Ala His Tyr Ala Ile Val Ala Trp Val Phe
    290                 295                 300

Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
                325                 330                 335

Asp Ala Asp Gln Val Arg His Met Thr Leu Val Glu Gln Thr Ala Leu
            340                 345                 350

Thr Ser Arg Asn Ile Ser Gly Gly Trp Leu Val Asn Val Leu Thr Gly
        355                 360                 365

Phe Ile Ser Leu Gln Thr Glu His His Leu Phe Pro Met Met Pro Thr
    370                 375                 380

Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
                405                 410                 415

Asn Ile Arg Ala Leu Ala Phe Glu His Leu Leu
            420                 425


<210> SEQ ID NO 53
<211> LENGTH: 172
<212> TYPE: PRT
<213> ORGANISM: Tomato bushy stunt virus

<400> SEQUENCE: 53

Met Glu Arg Ala Ile Gln Gly Asn Asp Ala Arg Glu Gln Ala Asn Ser
1               5                   10                  15

Glu Arg Trp Asp Gly Gly Ser Gly Gly Thr Thr Ser Pro Phe Lys Leu
            20                  25                  30

Pro Asp Glu Ser Pro Ser Trp Thr Glu Trp Arg Leu His Asn Asp Glu
        35                  40                  45

Thr Asn Ser Asn Gln Asp Asn Pro Leu Gly Phe Lys Glu Ser Trp Gly
    50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
                85                  90                  95

Tyr Ala Ala Ser Arg Phe Phe Gly Phe Asp Gln Ile Gly Cys Thr Tyr
            100                 105                 110

Ser Ile Arg Phe Arg Gly Val Ser Ile Thr Val Ser Gly Gly Ser Arg
        115                 120                 125
```

```
Thr Leu Gln His Leu Cys Glu Met Ala Ile Arg Ser Lys Gln Glu Leu
    130                 135                 140

Leu Gln Leu Ala Pro Ile Glu Val Glu Ser Asn Val Ser Arg Gly Cys
145                 150                 155                 160

Pro Glu Gly Thr Glu Thr Phe Glu Lys Glu Ser Glu
                165                 170


<210> SEQ ID NO 54
<211> LENGTH: 116
<212> TYPE: PRT
<213> ORGANISM: Tomato yellow leaf curl virus

<400> SEQUENCE: 54

Met Trp Asp Pro Leu Leu Asn Glu Phe Pro Glu Ser Val His Gly Phe
1               5                   10                  15

Arg Cys Met Leu Ala Ile Lys Tyr Leu Gln Ser Val Glu Glu Thr Tyr
            20                  25                  30

Glu Pro Asn Thr Leu Gly His Asp Leu Ile Arg Asp Leu Ile Ser Val
        35                  40                  45

Val Arg Ala Arg Asp Tyr Val Glu Ala Thr Arg Arg Tyr Asn His Phe
    50                  55                  60

His Ala Arg Leu Glu Gly Ser Pro Lys Ala Glu Leu Arg Gln Pro Ile
65                  70                  75                  80

Gln Gln Pro Cys Cys Cys Pro His Cys Pro Arg His Lys Gln Ala Thr
                85                  90                  95

Ile Met Asp Val Gln Ala His Val Pro Glu Ala Gln Asn Ile Gln Asn
            100                 105                 110

Val Ser Lys Pro
        115


<210> SEQ ID NO 55
<211> LENGTH: 351
<212> TYPE: PRT
<213> ORGANISM: Turnip crinkle virus

<400> SEQUENCE: 55

Met Glu Asn Asp Pro Arg Val Arg Lys Phe Ala Ser Glu Gly Ala Gln
1               5                   10                  15

Trp Ala Ile Lys Trp Gln Lys Lys Gly Trp Ser Ser Leu Thr Ser Arg
            20                  25                  30

Gln Lys Gln Thr Ala Arg Ala Ala Met Gly Ile Lys Leu Ser Pro Val
        35                  40                  45

Ala Gln Pro Val Gln Lys Val Thr Arg Leu Ser Ala Pro Val Ala Leu
    50                  55                  60

Ala Tyr Arg Glu Val Ser Thr Gln Pro Arg Val Ser Thr Ala Arg Asp
65                  70                  75                  80

Gly Ile Thr Arg Ser Gly Ser Glu Leu Ile Thr Thr Leu Lys Lys Asn
                85                  90                  95

Thr Asp Thr Glu Pro Lys Tyr Thr Thr Ala Val Leu Asn Pro Ser Glu
            100                 105                 110

Pro Gly Thr Phe Asn Gln Leu Ile Lys Glu Ala Ala Gln Tyr Glu Lys
        115                 120                 125

Tyr Arg Phe Thr Ser Leu Arg Phe Arg Tyr Ser Pro Met Ser Pro Ser
    130                 135                 140

Thr Thr Gly Gly Lys Val Ala Leu Ala Phe Asp Arg Asp Ala Ala Lys
145                 150                 155                 160
```

```
Pro Pro Pro Asn Asp Leu Ala Ser Leu Tyr Asn Ile Glu Gly Cys Val
                165                 170                 175

Ser Ser Val Pro Trp Thr Gly Phe Ile Leu Thr Val Pro Thr Asp Ser
            180                 185                 190

Thr Asp Arg Phe Val Ala Asp Gly Ile Ser Asp Pro Lys Leu Val Asn
        195                 200                 205

Phe Gly Lys Leu Ile Met Ala Thr Tyr Gly Gln Gly Ala Asn Asp Ala
    210                 215                 220

Ala Gln Leu Gly Glu Val Arg Val Glu Tyr Thr Val Gln Leu Lys Asn
225                 230                 235                 240

Arg Thr Gly Ser Thr Ser Asp Ala Gln Ile Gly Asp Phe Ala Gly Val
                245                 250                 255

Lys Asp Gly Pro Arg Leu Val Ser Trp Ser Lys Thr Lys Gly Thr Ala
            260                 265                 270

Gly Trp Glu His Asp Cys His Phe Leu Gly Thr Gly Asn Phe Ser Leu
        275                 280                 285

Thr Leu Phe Tyr Glu Lys Ala Pro Val Ser Gly Leu Glu Asn Ala Asp
    290                 295                 300

Ala Ser Asp Phe Ser Val Leu Gly Glu Ala Ala Ala Gly Ser Val Gln
305                 310                 315                 320

Trp Ala Gly Val Lys Val Ala Glu Arg Gly Gln Ser Val Lys Met Val
                325                 330                 335

Thr Thr Glu Glu Gln Pro Arg Gly Lys Trp Gln Ala Leu Arg Ile
            340                 345                 350


<210> SEQ ID NO 56
<211> LENGTH: 303
<212> TYPE: PRT
<213> ORGANISM: Pea mosaic virus

<400> SEQUENCE: 56

Met His Gly Ile Glu Gln Pro Gln Leu Pro Leu Asp Tyr Val His Arg
1               5                   10                  15

Cys Ala Ser Thr Ser Phe Leu Leu Ala Ser Leu Asp Gly Leu Leu Ser
            20                  25                  30

Glu Ala Arg Glu Leu Ser Gly Pro Leu Ala Leu Ile Thr Ser Ser Tyr
        35                  40                  45

Tyr Leu Leu Val Ser Ile Ala Leu Cys Trp Ala Ile Pro Gly Ser Phe
    50                  55                  60

Trp Tyr Arg Pro Gly Cys Trp Leu Gln Pro Val Ser Gly Arg Asn Leu
65                  70                  75                  80

Ile Phe Cys Gly Pro Thr Glu Ala Leu Gln Arg Phe Arg Leu Tyr Ala
                85                  90                  95

Ala Arg Leu Gly Leu Val Leu Ser Glu Asn Cys Pro Arg His Gly Gln
            100                 105                 110

Ser Ala Ala Ile Thr Leu Gln Ser Tyr Trp Ala Leu Pro Asn Asn Ile
        115                 120                 125

Trp Met Asp Met Ala Gln Leu Asp Leu Leu Thr Phe Ser Met Pro Ile
    130                 135                 140

Ala Asn Thr Phe Ala Tyr Leu Ala Asp Cys Glu Ala Arg Phe Pro Pro
145                 150                 155                 160

Ile Val Glu Gly Val Gly Ser Ala Tyr Tyr Val Pro Thr Leu Leu Gly
                165                 170                 175

Leu Thr His Gln Asp Pro Arg Leu Tyr Leu Ala Leu Arg Arg Arg Asn
```

```
            180                 185                 190

Leu Asp Leu Ser Gly Glu Pro His Arg Val Arg Pro Gly Val Leu Glu
        195                 200                 205

Ser Met Ala Leu Leu Cys Ser Ser Val Arg Ser Thr Ser Arg Ser Arg
    210                 215                 220

Gln Ile Pro Pro Leu Tyr Gly Ser Val Leu His His Val Leu Gly Leu
225                 230                 235                 240

Ala Glu Arg Asp Cys Ile Leu Phe Asp Thr Asp Ser Asn Tyr Ser Ser
                245                 250                 255

Tyr Thr His Arg Val Leu Glu Gln Asp Arg Asn Arg Ala Asp Gln Ser
            260                 265                 270

Leu Phe Ser Ile Asp Leu Glu Tyr Val His Asp Leu Glu Leu Ile Ala
        275                 280                 285

Leu Gly Tyr Ser Asp Glu Asp Asp Glu Asp Leu Asp Asn Phe Phe
    290                 295                 300


<210> SEQ ID NO 57
<211> LENGTH: 256
<212> TYPE: PRT
<213> ORGANISM: Cereal yellow dwarf virus

<400> SEQUENCE: 57

Met Phe Ile Ala Gln Pro Cys Gly Arg Val Leu Val Phe Asp Val Ala
1               5                   10                  15

Ser Arg Thr Pro Ser Phe Phe Thr Arg Tyr Ser Val Glu Leu Ser Leu
            20                  25                  30

Arg Val Leu Asp Pro Phe Phe Thr Arg Ala Val Thr Asp Phe Arg Tyr
        35                  40                  45

Thr Gln Asn Glu Ile Asp Leu Phe Cys Val Ser Leu Gly Phe Leu Leu
    50                  55                  60

Pro Ile Leu Leu Thr Gly Glu Ser Tyr Ser Trp Arg Gly His Leu Asn
65                  70                  75                  80

Leu Pro Leu Ser Tyr Thr Glu Leu Leu Val Arg Trp Gly Leu Ala Val
                85                  90                  95

Gly Tyr Phe Pro Thr Phe Ser Thr Asp Gly Asp Ile Arg Gln Asn Pro
            100                 105                 110

Glu Leu Arg Ile Asp Leu Ser Thr Met Ser Thr Arg Ser Phe Tyr Glu
        115                 120                 125

Gln Phe Leu Leu Arg Tyr Asn Thr Ser Gly Leu Ala Lys Ala Ile Val
    130                 135                 140

Gly Gln Gln Glu Cys Phe Gln Ser Gly Met Glu Ser Phe Lys Arg Phe
145                 150                 155                 160

Leu His Tyr Arg Leu Thr Cys Phe Glu Ser Cys Leu Pro Arg Pro Arg
                165                 170                 175

Trp Glu Ser Pro Leu Ala Pro Gly Pro Tyr Leu Asp Arg Ala Phe Glu
            180                 185                 190

Ala Thr Leu Leu Gly Arg Met Val Gly His Asn Gln Leu Leu Phe Thr
        195                 200                 205

Gly Leu Ser Ser Asp Ile Thr Arg Tyr Tyr Asn Glu Leu Val Val Glu
    210                 215                 220

Gly Val Pro Val Ala Phe Trp Asp Ala Ala Gly Ile Thr Leu His His
225                 230                 235                 240

Ala Gly Glu Glu Tyr Phe Ser Asn Ser Tyr Ile Gln Lys Ile Leu Gln
                245                 250                 255
```

<210> SEQ ID NO 58
<211> LENGTH: 519
<212> TYPE: DNA
<213> ORGANISM: Tomato bushy stunt virus

<400> SEQUENCE: 58
atggaacgag ctatacaagg aaacgacgct agggaacaag ctaacagtga acgttgggat 60
ggaggatcag gaggtaccac ttctcccttc aaacttcctg acgaaagtcc gagttggact 120
gagtggcggc tacataacga tgagacgaat tcgaatcaag ataatcccct tggtttcaag 180
gaaagctggg gtttcgggaa agttgtattt aagagatatc tcagatacga caggacggaa 240
gcttcactgc acagagtcct tggatcttgg acgggagatt cggttaacta tgcagcatct 300
cgatttttcg gtttcgacca gatcggatgt acctatagta ttcggtttcg aggagttagt 360
atcaccgttt ctggagggtc gcgaactctt cagcatctct gtgagatggc aattcggtct 420
aagcaagaac tgctacagct tgccccaatc gaagtggaaa gtaatgtatc aagaggatgc 480
cctgaaggta ctgagacctt cgaaaaagaa agcgagtaa 519

<210> SEQ ID NO 59
<211> LENGTH: 351
<212> TYPE: DNA
<213> ORGANISM: Tomato yellow leaf curl virus

<400> SEQUENCE: 59
atgtgggatc cacttctaaa tgaatttcct gaatctgttc acggatttcg ttgtatgtta 60
gctattaaat atttgcagtc cgttgaggaa acttacgagc ccaatacatt gggccacgat 120
ttaattaggg atcttatatc tgttgtaagg gcccgtgact atgtcgaagc gaccaggcga 180
tataatcatt tccacgcccg cctcgaaggt tcgccgaagg ctgaacttcg acagcccata 240
cagcagccgt gctgctgtcc ccattgtcca aggcacaaac aagcgacgat catggacgta 300
caggcccatg taccggaagc ccagaatata cagaatgtat cgaagccctg a 351

<210> SEQ ID NO 60
<211> LENGTH: 1056
<212> TYPE: DNA
<213> ORGANISM: Turnip crinkle virus

<400> SEQUENCE: 60
atggaaaatg atcctagagt ccgaaagttc gcatccgagg gcgcccaatg ggcgataaag 60
tggcagaaga agggctggtc atccctaacc agcagacaga aacagaccgc ccgcgcagcg 120
atggggatca agctctcccc tgtggcgcaa cctgtgcaga aagtgactcg actgagtgct 180
ccggtggctc tcgcctaccg cgaggtttcc acccagcctc gggtttctac tgccagggac 240
ggcataacca gaagcggttc tgaactgatc acaaccctga agaagaacac tgacactgaa 300
cctaagtaca ccacagctgt gcttaaccca agcgaacccg gaacattcaa ccaactcatc 360
aaggaggcgg cccagtatga aaaataccga ttcacgtcac tcagatttag gtactctccc 420
atgagccctt caaccaccgg gggcaaggtg gctctggcat tcgaccgaga cgctgccaaa 480
cctccgccca acgacctcgc ttccctctac aacatagagg gttgtgtatc tagcgtgccc 540
tggacagggt ttattttgac cgtcccaaca gattctactg accgctttgt ggcggatggt 600
atcagcgatc caaagcttgt caatttcggc aagctcatca tggccaccta tggccaagga 660
gccaatgatg ccgcccaact cggtgaagtg cgagtcgagt acaccgtgca gctcaagaac 720
agaactggct caaccagcga cgcccagatt ggggacttcg cgggtgttaa ggacggaccc 780

```
aggttggtct cgtggtccaa gaccaaggga acagctgggt gggagcacga ttgtcatttt    840

ctcggaaccg gaaacttctc gttgacactg ttctacgaga aggcgcccgt ttcggggcta    900

gaaaacgcag acgcctctga cttctcggtc ctgggagaag ccgcagcagg tagtgtccaa    960

tgggctggag tgaaggtagc agaaagggga caaagcgtga aaatggtcac aactgaggag   1020

cagccaaggg gaaaatggca agcactcagg atttag                             1056
```

<210> SEQ ID NO 61
<211> LENGTH: 912
<212> TYPE: DNA
<213> ORGANISM: Pea mosaic virus

<400> SEQUENCE: 61

```
atgcacggaa ttgagcagcc tcaactaccg ctagattacg ttcaccgttg cgcatcaacc     60

tccttcttgc tcgcatcact agatggcctc ctttctgaag cccgtgaact ctcagggcct    120

ctggctctca ttacttctag ctattactta cttgtttcta ttgccctctg ctgggcaatc    180

cctggatcct tctggtatag gcctggctgc tggttgcagc cagtctcagg gcggaatctc    240

atcttttgcg gccctaccga ggccttgcaa cgattccgtc tgtacgctgc cagacttggg    300

ttggtcctgt cagagaactg cccaagacac ggccaatcag cagcaatcac ccttcaatca    360

tactgggcac ttcctaacaa catctggatg gacatggccc aattggactt gctcaccttc    420

tcaatgccaa ttgctaatac atttgcctac ttggcagatt gtgaagcaag atttcctcct    480

attgttgaag gagtgggatc tgcttactat gtgccaacgc tgctcggact tactcaccaa    540

gaccccaggc tttatcttgc gcttcgcagg agaaaccttg atcttagtgg cgaacctcat    600

agagttcgtc ctggtgtcct ggagtctatg gctttgctct gttctagtgt acgtagcaca    660

agccgttcca ggcaaattcc tcctttatat ggcagcgttt tgcaccacgt tttgggcctg    720

gccgagagag actgcatcct ctttgatacg gatagtaact actcctctta cactcatcgg    780

gttcttgaac aagaccggaa tcgggctgat cagtcattgt ttagcattga cttggaatat    840

gttcatgacc tggagcttat tgccctgggt tactctgatg aagatgatga agatcttgat    900

aacttcttct ag                                                        912
```

<210> SEQ ID NO 62
<211> LENGTH: 771
<212> TYPE: DNA
<213> ORGANISM: Cereal yellow dwarf virus

<400> SEQUENCE: 62

```
atgttcatcg cccaaccttg cgggcgagtt cttgtgttcg acgtcgcctc ccgcacgcca     60

tcgttcttca ctcgttatag tgttgaactc tcgctccgtg ttctagaccc attcttcacg    120

cgagcagtaa cagatttccg atacacccaa aatgaaatcg atttattttg tgtgtctctt    180

ggctttctgt tgccaattct cctcacagga gaatcttact cttggcgcgg tcacctcaac    240

ctcccccttt cttacaccga attacttgtt cgatgggggc tcgcagtggg gtacttccct    300

accttctcca ctgatggtga cattcgacag aacccagaac tccgcatcga cctgtccacc    360

atgtcaaccc gctctttcta cgagcagttc ctactcagat ataacacgag tgggttggca    420

aaagctatcg tcggacagca agagtgcttt caaagcggca tggagtcttt taaaagattc    480

ctacactacc gcctcacgtg ctttgaaagc tgccttccac gacctcgttg ggaaagtcct    540

ttggctcctg gtccttatct ggacagggct tttgaggcaa ctcttctcgg ccgtatggtc    600
```

```
ggtcataacc aactactctt taccggtttg tcttctgata tcactaggta ttataacgag    660

ttggttgtgg aaggcgtgcc ggtggctttt tgggacgctg ccggcattac tttgcatcac    720

gctggtgaag aatatttttc gaattcttac attcaaaaga ttcttcaatg a             771


<210> SEQ ID NO 63
<211> LENGTH: 389
<212> TYPE: PRT
<213> ORGANISM: Arabidopsis thaliana

<400> SEQUENCE: 63

Met Val Ile Ala Ala Ala Val Ile Val Pro Leu Gly Leu Leu Phe Phe
1               5                   10                  15

Ile Ser Gly Leu Ala Val Asn Leu Phe Gln Ala Val Cys Tyr Val Leu
            20                  25                  30

Ile Arg Pro Leu Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
    50                  55                  60

Gly Val Lys Ile Gln Val Phe Ala Asp Asn Glu Thr Phe Asn Arg Met
65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
            100                 105                 110

Ala Leu Ala Val Met Lys Lys Ser Ser Lys Phe Leu Pro Val Ile Gly
        115                 120                 125

Trp Ser Met Trp Phe Ser Glu Tyr Leu Phe Leu Glu Arg Asn Trp Ala
    130                 135                 140

Lys Asp Glu Ser Thr Leu Lys Ser Gly Leu Gln Arg Leu Ser Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Ile Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
    210                 215                 220

Val Thr Ile Pro Lys Thr Ser Pro Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Ser Asp Asp Ala Ile Ala Gln Trp Cys Arg Asp
            260                 265                 270

Gln Phe Val Ala Lys Asp Ala Leu Leu Asp Lys His Ile Ala Ala Asp
        275                 280                 285

Thr Phe Pro Gly Gln Gln Glu Gln Asn Ile Gly Arg Pro Ile Lys Ser
    290                 295                 300

Leu Ala Val Val Leu Ser Trp Ala Cys Val Leu Thr Leu Gly Ala Ile
305                 310                 315                 320

Lys Phe Leu His Trp Ala Gln Leu Phe Ser Ser Trp Lys Gly Ile Thr
                325                 330                 335

Ile Ser Ala Leu Gly Leu Gly Ile Ile Thr Leu Cys Met Gln Ile Leu
            340                 345                 350
```

```
Ile Arg Ser Ser Gln Ser Glu Arg Ser Thr Pro Ala Lys Val Val Pro
        355                 360                 365

Ala Lys Pro Lys Asp Asn His His Pro Glu Ser Ser Ser Gln Thr Glu
    370                 375                 380

Thr Glu Lys Glu Lys
385


<210> SEQ ID NO 64
<211> LENGTH: 281
<212> TYPE: PRT
<213> ORGANISM: Limnanthes alba

<400> SEQUENCE: 64

Met Ala Lys Thr Arg Thr Ser Ser Leu Arg Asn Arg Arg Gln Leu Lys
1               5                   10                  15

Thr Ala Val Ala Ala Thr Ala Asp Asp Asp Lys Asp Gly Ile Phe Met
            20                  25                  30

Val Leu Leu Ser Cys Phe Lys Ile Phe Val Cys Phe Ala Ile Val Leu
        35                  40                  45

Ile Thr Ala Val Ala Trp Gly Leu Ile Met Val Leu Leu Leu Pro Trp
    50                  55                  60

Pro Tyr Met Arg Ile Arg Leu Gly Asn Leu Tyr Gly His Ile Ile Gly
65                  70                  75                  80

Gly Leu Val Ile Trp Leu Tyr Gly Ile Pro Ile Glu Ile Gln Gly Ser
                85                  90                  95

Glu His Thr Lys Lys Arg Ala Ile Tyr Ile Ser Asn His Ala Ser Pro
            100                 105                 110

Ile Asp Ala Phe Phe Val Met Trp Leu Ala Pro Ile Gly Thr Val Gly
        115                 120                 125

Val Ala Lys Lys Glu Val Ile Trp Tyr Pro Leu Leu Gly Gln Leu Tyr
    130                 135                 140

Thr Leu Ala His His Ile Arg Ile Asp Arg Ser Asn Pro Ala Ala Ala
145                 150                 155                 160

Ile Gln Ser Met Lys Glu Ala Val Arg Val Ile Thr Glu Lys Asn Leu
                165                 170                 175

Ser Leu Ile Met Phe Pro Glu Gly Thr Arg Ser Gly Asp Gly Arg Leu
            180                 185                 190

Leu Pro Phe Lys Lys Gly Phe Val His Leu Ala Leu Gln Ser His Leu
        195                 200                 205

Pro Ile Val Pro Met Ile Leu Thr Gly Thr His Leu Ala Trp Arg Lys
    210                 215                 220

Gly Thr Phe Arg Val Arg Pro Val Pro Ile Thr Val Lys Tyr Leu Pro
225                 230                 235                 240

Pro Ile Asn Thr Asp Asp Trp Thr Val Asp Lys Ile Asp Asp Tyr Val
                245                 250                 255

Lys Met Ile His Asp Ile Tyr Val Arg Asn Leu Pro Ala Ser Gln Lys
            260                 265                 270

Pro Leu Gly Ser Thr Asn Arg Ser Lys
        275                 280


<210> SEQ ID NO 65
<211> LENGTH: 303
<212> TYPE: PRT
<213> ORGANISM: Saccharomyces cerevisiae

<400> SEQUENCE: 65
```

```
Met Ser Val Ile Gly Arg Phe Leu Tyr Tyr Leu Arg Ser Val Leu Val
1               5                   10                  15

Val Leu Ala Leu Ala Gly Cys Gly Phe Tyr Gly Val Ile Ala Ser Ile
            20                  25                  30

Leu Cys Thr Leu Ile Gly Lys Gln His Leu Ala Gln Trp Ile Thr Ala
        35                  40                  45

Arg Cys Phe Tyr His Val Met Lys Leu Met Leu Gly Leu Asp Val Lys
    50                  55                  60

Val Val Gly Glu Glu Asn Leu Ala Lys Lys Pro Tyr Ile Met Ile Ala
65                  70                  75                  80

Asn His Gln Ser Thr Leu Asp Ile Phe Met Leu Gly Arg Ile Phe Pro
                85                  90                  95

Pro Gly Cys Thr Val Thr Ala Lys Lys Ser Leu Lys Tyr Val Pro Phe
            100                 105                 110

Leu Gly Trp Phe Met Ala Leu Ser Gly Thr Tyr Phe Leu Asp Arg Ser
        115                 120                 125

Lys Arg Gln Glu Ala Ile Asp Thr Leu Asn Lys Gly Leu Glu Asn Val
    130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
                165                 170                 175

Leu Ala Gln Gln Gly Lys Ile Pro Ile Val Pro Val Val Val Ser Asn
            180                 185                 190

Thr Ser Thr Leu Val Ser Pro Lys Tyr Gly Val Phe Asn Arg Gly Cys
        195                 200                 205

Met Ile Val Arg Ile Leu Lys Pro Ile Ser Thr Glu Asn Leu Thr Lys
    210                 215                 220

Asp Lys Ile Gly Glu Phe Ala Glu Lys Val Arg Asp Gln Met Val Asp
225                 230                 235                 240

Thr Leu Lys Glu Ile Gly Tyr Ser Pro Ala Ile Asn Asp Thr Thr Leu
                245                 250                 255

Pro Pro Gln Ala Ile Glu Tyr Ala Ala Leu Gln His Asp Lys Lys Val
            260                 265                 270

Asn Lys Lys Ile Lys Asn Glu Pro Val Pro Ser Val Ser Ile Ser Asn
        275                 280                 285

Asp Val Asn Thr His Asn Glu Gly Ser Ser Val Lys Lys Met His
    290                 295                 300
```

<210> SEQ ID NO 66
<211> LENGTH: 373
<212> TYPE: PRT
<213> ORGANISM: Micromonas pusilla

<400> SEQUENCE: 66

```
Met Thr Pro Tyr Gln Trp Phe Asn Val Val Ser Ser Leu Gly Tyr Val
1               5                   10                  15

Leu Phe Thr Ala Thr Thr Ser Thr Val Thr Met Leu Val Pro Ala Ile
            20                  25                  30

Ile Leu Leu Arg Pro Val Ser Ala Asn Leu Tyr Ala Arg Cys Thr Ser
        35                  40                  45

Trp Ile Phe Ala Cys Trp Trp Thr Ser Cys Leu Phe Ile Thr Glu Arg
    50                  55                  60

Leu Asn Gly Val Lys Val Arg Val Thr Gly Asp Ala Leu Pro Leu Asn
```

-continued

```
65                  70                  75                  80

Ala Pro Leu Leu Ile Met Ser Asn His Lys Cys Asn Leu Asp Trp Met
                85                  90                  95

Phe Leu Trp Ser Ser Ala Ile Arg Thr Gly Ser Met Phe His Val Gly
            100                 105                 110

Val Phe Lys Ala Val Ala Lys Ser Glu Ile Arg Val Ile Pro Ile Phe
        115                 120                 125

Gly Trp Gly Cys Lys Leu Asn Gly Phe Ala Tyr Val Arg Arg Arg Trp
    130                 135                 140

Ser Ser Asp Ala Ser His Leu Thr Ser Trp Ile Gln Ser Gln Ile Arg
145                 150                 155                 160

Arg Arg Leu Asn Ala Asn Trp Thr Leu Ile Phe Pro Glu Gly Thr Arg
                165                 170                 175

Tyr Thr Asp Arg Asn Lys Glu Arg Ser Asp Leu Ser Cys Ala Lys Asp
            180                 185                 190

Gly Leu Glu Pro Met Ala Gly Glu Ile Leu Arg Pro Arg Thr Lys Gly
        195                 200                 205

Leu Ala Leu Leu Leu Arg Glu Ser Ala Lys Gly Gly Gly Tyr Tyr Arg
    210                 215                 220

Lys Ile Val Asp Met Thr Ile Gln Tyr Thr Asp Ala Asp Gly Lys Pro
225                 230                 235                 240

Leu Lys Gly Ala Ala Leu Gly Thr Arg Cys Phe Gly Gln Leu Ala Lys
                245                 250                 255

Gly Gln Leu Pro Val Ala Thr Cys His Val His Phe Asp Val Phe Ser
            260                 265                 270

His Lys Asp Val Pro Ala Gly Glu Asp Glu Asp Glu Val Glu Ala Trp
        275                 280                 285

Val Trp Lys Arg Trp Arg Lys Lys Ala Asn Met Leu Glu Ala Cys Ala
    290                 295                 300

Ser Ala Gly Gln Phe Glu Gly Val Arg Glu Trp Ser Thr Ser Gly Thr
305                 310                 315                 320

Ala Val Pro Leu Lys Thr Gln Thr Ala Leu Arg Cys Phe Phe Val Leu
                325                 330                 335

Gln Gly Leu Val Cys Val Gly Val Ala Cys Ser Ser Thr Ala Phe Leu
            340                 345                 350

Ala Tyr Val Ala Cys Ala Ala Val Gly Ala Ala Val Ile Ala Gln Thr
        355                 360                 365

Asp Pro Ala Trp Trp
    370


<210> SEQ ID NO 67
<211> LENGTH: 314
<212> TYPE: PRT
<213> ORGANISM: Mortierella alpina

<400> SEQUENCE: 67

Met Ser Ile Gly Ser Ser Asn Pro Val Leu Leu Ala Ala Ile Pro Phe
1               5                   10                  15

Val Tyr Leu Phe Val Leu Pro Arg Val Leu Ala Phe Leu Pro Gln Lys
            20                  25                  30

Ala Gln Phe Leu Ala Lys Cys Ile Val Val Leu Ile Ala Thr Leu Ile
        35                  40                  45

Met Ser Val Ala Gly Cys Phe Ile Ser Ile Val Cys Ala Leu Leu Asp
    50                  55                  60
```

```
Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu Glu His
                85                  90                  95

Leu Asp Lys Tyr Pro Ala Ile Val Val Cys Asn His Gln Ser Ser Met
            100                 105                 110

Asp Met Met Val Leu Gly Arg Val Phe Pro Lys His Cys Val Val Met
        115                 120                 125

Ala Lys Lys Glu Leu Leu Tyr Phe Pro Phe Leu Gly Met Phe Met Lys
    130                 135                 140

Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
                165                 170                 175

Ile Trp Ile Phe Pro Glu Gly Thr Arg Ser Arg Leu Asp Lys Ala Asp
            180                 185                 190

Leu Leu Pro Phe Lys Lys Gly Ala Phe His Leu Ala Ile Gln Ala Gln
        195                 200                 205

Leu Pro Ile Leu Pro Ile Ile Ser Gln Gly Tyr Ser His Ile Tyr Asp
    210                 215                 220

Ser Ser Lys Arg Tyr Phe Pro Gly Gly Glu Leu Glu Ile Arg Val Leu
225                 230                 235                 240

Glu Pro Ile Pro Thr Thr Gly Leu Thr Thr Asp Asp Val Asn Asp Leu
                245                 250                 255

Met Asp Lys Thr Arg Asn Leu Met Leu Lys His Leu Lys Glu Met Asp
            260                 265                 270

Ser Gln Tyr Ser Ser Ser Thr Ala Glu Asn Gly Ser Thr His Ile Asp
        275                 280                 285

Ala Asp Ile Ala Lys Ser Thr Ala Thr Ser Ile Gly Asn Thr Asp Asp
    290                 295                 300

Ala Ile Thr Lys Arg Arg Thr Pro Lys Glu
305                 310


<210> SEQ ID NO 68
<211> LENGTH: 391
<212> TYPE: PRT
<213> ORGANISM: Braccisa napus

<400> SEQUENCE: 68

Met Ala Met Ala Ala Ala Ala Val Ile Val Pro Leu Gly Ile Leu Phe
1               5                   10                  15

Phe Ile Ser Gly Leu Val Val Asn Leu Leu Gln Ala Val Cys Tyr Val
            20                  25                  30

Leu Ile Arg Pro Leu Ser Lys Asn Thr Tyr Arg Lys Ile Asn Arg Val
        35                  40                  45

Val Ala Glu Thr Leu Trp Leu Glu Leu Val Trp Ile Val Asp Trp Trp
    50                  55                  60

Ala Gly Val Lys Ile Gln Val Phe Ala Asp Asp Glu Thr Phe Asn Arg
65                  70                  75                  80

Met Gly Lys Glu His Ala Leu Val Val Cys Asn His Arg Ser Asp Ile
                85                  90                  95

Asp Trp Leu Val Gly Trp Ile Leu Ala Gln Arg Ser Gly Cys Leu Gly
            100                 105                 110

Ser Ala Leu Ala Val Met Lys Lys Ser Ser Lys Phe Leu Pro Val Ile
        115                 120                 125
```

```
Gly Trp Ser Met Trp Phe Ser Glu Tyr Leu Phe Leu Glu Arg Asn Trp
    130                 135                 140

Ala Lys Asp Glu Ser Thr Leu Lys Ser Gly Leu Gln Arg Leu Asn Asp
145                 150                 155                 160

Phe Pro Arg Pro Phe Trp Leu Ala Leu Phe Val Glu Gly Thr Arg Phe
                165                 170                 175

Thr Glu Ala Lys Leu Lys Ala Ala Gln Glu Tyr Ala Ala Ser Ser Gln
            180                 185                 190

Leu Pro Val Pro Arg Asn Val Leu Ile Pro Arg Thr Lys Gly Phe Val
        195                 200                 205

Ser Ala Val Ser Asn Met Arg Ser Phe Val Pro Ala Ile Tyr Asp Met
    210                 215                 220

Thr Val Ala Ile Pro Lys Thr Ser Pro Pro Pro Thr Met Leu Arg Leu
225                 230                 235                 240

Phe Lys Gly Gln Pro Ser Val Val His Val His Ile Lys Cys His Ser
                245                 250                 255

Met Lys Asp Leu Pro Glu Ser Asp Asp Ala Ile Ala Gln Trp Cys Arg
            260                 265                 270

Asp Gln Phe Val Ala Lys Asp Ala Leu Leu Asp Lys His Ile Ala Ala
        275                 280                 285

Asp Thr Phe Pro Gly Gln Lys Glu His Asn Ile Gly Arg Pro Ile Lys
    290                 295                 300

Ser Leu Ala Val Val Val Ser Trp Ala Cys Leu Leu Thr Leu Gly Ala
305                 310                 315                 320

Met Lys Phe Leu His Trp Ser Asn Leu Phe Ser Ser Leu Lys Gly Ile
                325                 330                 335

Ala Leu Ser Ala Leu Gly Leu Gly Ile Ile Thr Leu Cys Met Gln Ile
            340                 345                 350

Leu Ile Arg Ser Ser Gln Ser Glu Arg Ser Thr Pro Ala Lys Val Ala
        355                 360                 365

Pro Ala Lys Pro Lys Asp Lys His Gln Ser Gly Ser Ser Ser Gln Thr
    370                 375                 380

Glu Val Glu Glu Lys Gln Lys
385                 390
```

<210> SEQ ID NO 69
<211> LENGTH: 390
<212> TYPE: PRT
<213> ORGANISM: Braccisa napus

<400> SEQUENCE: 69

```
Met Ala Met Ala Ala Ala Val Ile Val Pro Leu Gly Ile Leu Phe Phe
1               5                   10                  15

Ile Ser Gly Leu Val Val Asn Leu Leu Gln Ala Ile Cys Tyr Val Leu
            20                  25                  30

Ile Arg Pro Leu Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
    50                  55                  60

Gly Val Lys Ile Gln Val Phe Ala Asp Asn Glu Thr Phe Asn Arg Met
65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
```

```
            100                 105                 110

Ala Leu Ala Val Met Lys Lys Ser Ser Lys Phe Leu Pro Val Ile Gly
        115                 120                 125

Trp Ser Met Trp Phe Ser Glu Tyr Leu Phe Leu Glu Arg Asn Trp Ala
    130                 135                 140

Lys Asp Glu Ser Thr Leu Lys Ser Gly Leu Gln Arg Leu Asn Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Val Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
    210                 215                 220

Val Ala Ile Pro Lys Thr Ser Pro Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Ser Asp Asp Ala Ile Ala Gln Trp Cys Arg Asp
            260                 265                 270

Gln Phe Val Ala Lys Asp Ala Leu Leu Asp Lys His Ile Ala Ala Asp
        275                 280                 285

Thr Phe Pro Gly Gln Gln Glu Gln Asn Ile Gly Arg Pro Ile Lys Ser
    290                 295                 300

Leu Ala Val Val Leu Ser Trp Ser Cys Leu Leu Ile Leu Gly Ala Met
305                 310                 315                 320

Lys Phe Leu His Trp Ser Asn Leu Phe Ser Ser Trp Lys Gly Ile Ala
                325                 330                 335

Phe Ser Ala Leu Gly Leu Gly Ile Ile Thr Leu Cys Met Gln Ile Leu
            340                 345                 350

Ile Arg Ser Ser Gln Ser Glu Arg Ser Thr Pro Ala Lys Val Val Pro
        355                 360                 365

Ala Lys Pro Lys Asp Asn His Asn Asp Ser Gly Ser Ser Ser Gln Thr
    370                 375                 380

Glu Val Glu Lys Gln Lys
385                 390


<210> SEQ ID NO 70
<211> LENGTH: 361
<212> TYPE: PRT
<213> ORGANISM: Phytophthora infestans

<400> SEQUENCE: 70

Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80
```

Trp Gly Phe Phe Thr Val Gly His Asp Ala Gly His Gly Ala Phe Ser
85 90 95

Arg Tyr His Leu Leu Asn Phe Val Val Gly Thr Phe Met His Ser Leu
100 105 110

Ile Leu Thr Pro Phe Glu Ser Trp Lys Leu Thr His Arg His His His
115 120 125

Lys Asn Thr Gly Asn Ile Asp Arg Asp Glu Val Phe Tyr Pro Gln Arg
130 135 140

Lys Ala Asp Asp His Pro Leu Ser Arg Asn Leu Ile Leu Ala Leu Gly
145 150 155 160

Ala Ala Trp Leu Ala Tyr Leu Val Glu Gly Phe Pro Pro Arg Lys Val
165 170 175

Asn His Phe Asn Pro Phe Glu Pro Leu Phe Val Arg Gln Val Ser Ala
180 185 190

Val Val Ile Ser Leu Leu Ala His Phe Phe Val Ala Gly Leu Ser Ile
195 200 205

Tyr Leu Ser Leu Gln Leu Gly Leu Lys Thr Met Ala Ile Tyr Tyr Tyr
210 215 220

Gly Pro Val Phe Val Phe Gly Ser Met Leu Val Ile Thr Thr Phe Leu
225 230 235 240

His His Asn Asp Glu Glu Thr Pro Trp Tyr Ala Asp Ser Glu Trp Thr
245 250 255

Tyr Val Lys Gly Asn Leu Ser Ser Val Asp Arg Ser Tyr Gly Ala Leu
260 265 270

Ile Asp Asn Leu Ser His Asn Ile Gly Thr His Gln Ile His His Leu
275 280 285

Phe Pro Ile Ile Pro His Tyr Lys Leu Lys Lys Ala Thr Ala Ala Phe
290 295 300

His Gln Ala Phe Pro Glu Leu Val Arg Lys Ser Asp Glu Pro Ile Ile
305 310 315 320

Lys Ala Phe Phe Arg Val Gly Arg Leu Tyr Ala Asn Tyr Gly Val Val
325 330 335

Asp Gln Glu Ala Lys Leu Phe Thr Leu Lys Glu Ala Lys Ala Ala Thr
340 345 350

Glu Ala Ala Ala Lys Thr Lys Ser Thr
355 360

<210> SEQ ID NO 71
<211> LENGTH: 418
<212> TYPE: PRT
<213> ORGANISM: Thalassiosira pseudonana

<400> SEQUENCE: 71

Met Tyr Arg Leu Thr Ser Thr Phe Leu Ile Ala Leu Ala Phe Ser Ser
1 5 10 15

Ser Ile Asn Ala Phe Ser Pro Gln Arg Pro Pro Arg Thr Ile Thr Lys
20 25 30

Ser Lys Val Gln Ser Thr Val Leu Pro Ile Pro Thr Lys Asp Asp Leu
35 40 45

Asn Phe Leu Gln Pro Gln Leu Asp Glu Asn Asp Leu Tyr Leu Asp Asp
50 55 60

Val Asn Thr Pro Pro Arg Ala Gly Thr Ile Met Lys Met Leu Pro Lys
65 70 75 80

Glu Thr Phe Asn Ile Asp Thr Ala Thr Ser Leu Gly Tyr Phe Gly Met
85 90 95

```
Asp Met Ala Ala Val Val Ser Ser Met Thr Leu Leu Asn Ala Ile Val
            100                 105                 110

Thr Ser Asp Gln Tyr His Ala Leu Pro Leu Pro Leu Gln Ala Ala Thr
        115                 120                 125

Val Ile Pro Phe Gln Leu Leu Ala Gly Phe Ala Met Trp Cys Met Trp
    130                 135                 140

Cys Ile Gly His Asp Ala Gly His Ser Thr Val Ser Lys Thr Lys Trp
145                 150                 155                 160

Ile Asn Arg Val Val Gly Glu Val Ala His Ser Val Val Cys Leu Thr
                165                 170                 175

Pro Phe Val Pro Trp Gln Met Ser His Arg Lys His His Leu Asn His
            180                 185                 190

Asn His Ile Glu Lys Asp Tyr Ser His Lys Trp Tyr Ser Arg Asp Glu
        195                 200                 205

Phe Asp Asp Ile Pro Gln Leu Tyr Lys Thr Phe Gly Tyr Asn Pro Arg
    210                 215                 220

Met Met Gln Leu Pro Phe Leu Tyr Phe Met Tyr Leu Ala Leu Gly Ile
225                 230                 235                 240

Pro Asp Gly Gly His Val Val Phe Tyr Gly Arg Met Trp Glu Gly Val
                245                 250                 255

Ser Leu Gln Lys Lys Phe Asp Ala Ala Ile Ser Val Ala Val Ser Cys
            260                 265                 270

Ala Thr Ala Gly Ser Leu Trp Met Asn Met Gly Thr Ala Asp Phe Thr
        275                 280                 285

Val Val Cys Met Val Pro Trp Leu Val Leu Ser Trp Trp Leu Phe Met
    290                 295                 300

Val Thr Tyr Leu Gln His His Ser Glu Asp Gly Lys Leu Tyr Thr Asp
305                 310                 315                 320

Glu Thr Phe Thr Phe Glu Lys Gly Ala Phe Glu Thr Val Asp Arg Ser
                325                 330                 335

Tyr Gly Lys Leu Ile Asn Arg Met Ser His His Met Met Asp Gly His
            340                 345                 350

Val Val His His Leu Phe Phe Glu Arg Val Pro His Tyr Arg Leu Glu
        355                 360                 365

Ala Ala Thr Glu Ala Leu Val Lys Gly Met Asp Glu Thr Gly Gln Lys
    370                 375                 380

His Leu Tyr Lys Tyr Ile Asp Thr Pro Asp Phe Asn Ala Glu Ile Val
385                 390                 395                 400

Asn Gly Phe Arg Asp Asn Trp Phe Leu Val Glu Glu Glu Asn Ile Lys
                405                 410                 415

Arg Glu
```

<210> SEQ ID NO 72
<211> LENGTH: 363
<212> TYPE: PRT
<213> ORGANISM: Pythium irregulare

<400> SEQUENCE: 72

```
Met Ala Ser Thr Ser Ala Ala Gln Asp Ala Ala Pro Tyr Glu Phe Pro
1               5                   10                  15

Ser Leu Thr Glu Ile Lys Arg Ala Leu Pro Ser Glu Cys Phe Glu Ala
            20                  25                  30

Ser Val Pro Leu Ser Leu Tyr Tyr Thr Ala Arg Ser Leu Ala Leu Ala
        35                  40                  45
```

-continued

```
Gly Ser Leu Ala Val Ala Leu Ser Tyr Ala Arg Ala Leu Pro Leu Val
    50                  55                  60

Gln Ala Asn Ala Leu Leu Asp Ala Thr Leu Cys Thr Gly Tyr Val Leu
65                  70                  75                  80

Leu Gln Gly Ile Val Phe Trp Gly Phe Phe Thr Val Gly His Asp Cys
                85                  90                  95

Gly His Gly Ala Phe Ser Arg Ser His Val Leu Asn Phe Ser Val Gly
            100                 105                 110

Thr Leu Met His Ser Ile Ile Leu Thr Pro Phe Glu Ser Trp Lys Leu
        115                 120                 125

Ser His Arg His His His Lys Asn Thr Gly Asn Ile Asp Lys Asp Glu
    130                 135                 140

Ile Phe Tyr Pro Gln Arg Glu Ala Asp Ser His Pro Val Ser Arg His
145                 150                 155                 160

Leu Val Met Ser Leu Gly Ser Ala Trp Phe Ala Tyr Leu Phe Ala Gly
                165                 170                 175

Phe Pro Pro Arg Thr Met Asn His Phe Asn Pro Trp Glu Ala Met Tyr
            180                 185                 190

Val Arg Arg Val Ala Ala Val Ile Ile Ser Leu Gly Val Leu Phe Ala
        195                 200                 205

Phe Ala Gly Leu Tyr Ser Tyr Leu Thr Phe Val Leu Gly Phe Thr Thr
    210                 215                 220

Met Ala Ile Tyr Tyr Phe Gly Pro Leu Phe Ile Phe Ala Thr Met Leu
225                 230                 235                 240

Val Val Thr Thr Phe Leu His His Asn Asp Glu Glu Thr Pro Trp Tyr
                245                 250                 255

Ala Asp Ser Glu Trp Thr Tyr Val Lys Gly Asn Leu Ser Ser Val Asp
            260                 265                 270

Arg Ser Tyr Gly Ala Leu Ile Asp Asn Leu Ser His Asn Ile Gly Thr
        275                 280                 285

His Gln Ile His His Leu Phe Pro Ile Ile Pro His Tyr Lys Leu Asn
    290                 295                 300

Asp Ala Thr Ala Ala Phe Ala Lys Ala Phe Pro Glu Leu Val Arg Lys
305                 310                 315                 320

Asn Ala Ala Pro Ile Ile Pro Thr Phe Phe Arg Met Ala Ala Met Tyr
                325                 330                 335

Ala Lys Tyr Gly Val Val Asp Thr Asp Ala Lys Thr Phe Thr Leu Lys
            340                 345                 350

Glu Ala Lys Ala Ala Ala Lys Thr Lys Ser Ser
        355                 360
```